(12) United States Patent
Kania et al.

(10) Patent No.: US 6,884,890 B2
(45) Date of Patent: Apr. 26, 2005

(54) INDAZOLE COMPOUNDS AND PHARMACEUTICAL COMPOSITIONS FOR INHIBITING PROTEIN KINASES, AND METHODS FOR THEIR USE

(75) Inventors: Robert Steven Kania, San Diego, CA (US); Steven Lee Bender, Oceanside, CA (US); Allen J. Borchardt, San Diego, CA (US); Stephan James Cripps, San Diego, CA (US); Ye Hua, La Jolla, CA (US); Michael David Johnson, San Diego, CA (US); Theodore Otto Johnson, Jr., San Diego, CA (US); Hiep The Luu, San Diego, CA (US); Cynthia Louise Palmer, San Diego, CA (US); Siegfried Heinz Reich, Solana Beach, CA (US); Anna Marie Tempczyk-Russell, Ramona, CA (US); Min Teng, San Diego, CA (US); Christine Thomas, West Borough, MA (US); Michael David Varney, Solana Beach, CA (US); Michael Brennan Wallace, San Diego, CA (US); Michael Raymond Collins, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/326,755

(22) Filed: Feb. 13, 2003

(65) Prior Publication Data

US 2004/0171634 A1 Sep. 2, 2004

Related U.S. Application Data

(62) Division of application No. 09/983,786, filed on Oct. 25, 2001, now Pat. No. 6,531,491, which is a division of application No. 09/609,335, filed on Jun. 30, 2000, now abandoned.
(60) Provisional application No. 60/142,130, filed on Jul. 2, 1999.

(51) Int. Cl.[7] ............................................. C07D 401/02
(52) U.S. Cl. ................................. 546/275.7; 548/362.5
(58) Field of Search ................................. 514/338, 403; 546/275.7; 548/361, 1, 362.5

(56) References Cited

U.S. PATENT DOCUMENTS

| 5,621,082 A | 4/1997 | Xiong et al. |
| 5,705,499 A | 1/1998 | Cywin et al. |
| 5,760,028 A | 6/1998 | Jadhav et al. |
| 5,861,414 A | 1/1999 | Allen et al. |
| 5,886,195 A | 3/1999 | Tang et al. |

FOREIGN PATENT DOCUMENTS

| DD | DD 273 062 | 11/1989 |
| EP | 0 066 270 | 8/1982 |
| EP | 0 816 357 | 1/1998 |
| WO | WO 86/05779 | 10/1986 |
| WO | WO 93/19052 | 9/1993 |
| WO | WO 96/14843 | 5/1996 |
| WO | WO 96/23783 | 8/1996 |
| WO | WO 97/03967 | 2/1997 |
| WO | WO 97/16447 | 5/1997 |
| WO | WO 97/34876 | 9/1997 |
| WO | WO 97/48697 | 12/1997 |
| WO | WO 98/09961 | 3/1998 |
| WO | WO 98/144851 | 4/1998 |
| WO | WO 99/21845 | 5/1999 |
| WO | WO 99/23076 | 5/1999 |
| WO | WO 99/23077 | 5/1999 |
| WO | WO 00/18761 | 4/2000 |

OTHER PUBLICATIONS

Al–Khodairy et al., *Molec. Biol. Cell*, 5, 147–160 (1994).
Alon et al, *Nat. Med.*, 1, 1024 (1995).
Bolen, *Oncogene*, 8, 2025–2031 (1993).
Bunz et al., *Science*, 282, 1497 (1998).
Castro et al., *J. Med Chem*, 39:842–849 (1996).
Cohen, *Curr. Op. Chem. Biol.*, 3, 459–65 (1999).
Folkman, *Nature Med.*, 1, 27–31 (1995).
Hartwell et al., *Science*, 266, 1821–1828 (1994).
Hartwell et al., *Science*, 246, 629–634 (1989).
Holash et al., *Oncogene*, 18, 5356–62 (1999).
Jeffrey et al., *Nature*, 376, 313–320 (Jul. 27, 1995).
Kamb, *Trends in Genetics*, 11, 136–140 (1995).
Kamb et al., *Science*, 264, 436–440 (1994).
Katsura et al., *Chem Pharm Biol*, 40(8), 2062–2074–140 (1992).
Klohs et al., *Curr. Op. Chem. Biol.*, 10, 544–49 (1999).
Klunder et al., *J. Med. Chem*, 41, 2960–2971 (1998).
Lee et al., *Biochem*, 23, 4255 (1984).
Lin et al., *J Med Chem.*, 15(6), 615 (1972).
Lutty and McLeod, *Arch. Ophthalmol.*, 110, 267 (1992.
Maisonpierre et al., *Science*, 277, 55–60 (1997).
Matsuoka, *Science*, 282, 1893–1897 (1998).
McMahon et al., *Current Opinion in Drug Discovery & Development*, 1, 131–146 (1998).
McMahon et al, *Oncologist*, 5, 3–10 (2000).

(Continued)

Primary Examiner—Zinna Northington Davis
(74) Attorney, Agent, or Firm—Stephen D. Prodnuk; Bryan C. Zielinski; Peter C. Richardson

(57) ABSTRACT

Indazole compounds that modulate and/or inhibit the activity of certain protein kinases are described. These compounds and pharmaceutical compositions containing them are capable of mediating tyrosine kinase signal transduction and thereby modulate and/or inhibit unwanted cell proliferation. The invention is also directed to the therapeutic or prophylactic use of pharmaceutical compositions containing such compounds, and to methods of treating cancer and other disease states associated with unwanted angiogenesis and/or cellular proliferation, such as diabetic retinopathy, neovascular glaucoma, rheumatoid arthritis, and psoriasis, by administering effective amounts of such compounds.

32 Claims, No Drawings

OTHER PUBLICATIONS

Merenmines et al., *Cell Growth & Differentiation*, 8, 3–10 (1997).
Millauer et al., *Cancer Research*, 56, 1615–1620 (1996).
Mohammadi et al., *EMBO Journal*, 17, 5896–5904 (1998.
Mohammadi et al., *Mol. Cell. Biol.*, 16, 977–989 (1996).
Mylari et al., *J. Med. Chem.*, 35, 457–465 (1992).
Nurse, *Cell*, 91, 865–867 (1997).
O'Connor, *Cancer Surveys*, 29, 151–182 (1997).
Parast et al., *BioChemistry*, 37, 16788–16801 (1998).
Peng et al., *Science*, 277, 1501–1505 (1997).
Penn et al, *Invest. Ophthalmol. Vis. Sci.*, 36, 2063, (1995).
Rosenblatt et al., *J. Mol. Biol.*, 230, 1317–1319 (1993).
Rosowsky et al, *J. Med Chem.*, 31, 763–768 (1988).
Sanchez et al., *Science*, 277, 1497–1501 (1997).
Sarodnick et al, *J. Prakt Chem.* 339. 714–720 (1997).
Still et al., *J. Org. Chem.*, 43, 2923 (1978).
Stone et al, *J. Neurosci.*, 15, 4738 (1995).
Strawn et al., *Exp. Opin. Invest. Drugs*, 7, 553–573 (1998).
Thomas et al., *J. Biol. Chem.*, 274, 36684–92 (1999).
Thompson, *Oncogene*, 15, 3025–3035 (1997).
Walworth et al., *Nature*, 363, 368–371 (1993).
Weinert, *Science*, 277, 1450–1451 (1997).
Whitney et al., DNA Cell Biol 9, 823–830, 1993.
Winters et al., *Oncogene*, 17, 673–684 (1998).
Yoshiji et al., *Cancer Research*, 57, 3924–3928 (1997).
Zeng et al., *Nature*, 395, 504–510 (1998).

INDAZOLE COMPOUNDS AND PHARMACEUTICAL COMPOSITIONS FOR INHIBITING PROTEIN KINASES, AND METHODS FOR THEIR USE

CROSS-REFERENCE TO RELATED APPLICATIONS

This application is a Divisional of U.S. application Ser. No. 09/983,786, filed Oct. 25, 2001, now U.S. Pat. No. 6,531,491 which is a divisional of U.S. application Ser. No. 09/609,335, filed Jun. 30, 2000, now abandoned, which claims the benefit of U.S. Provisional Application No. 60/142,130, filed Jul. 2, 1999, hereby incorporated by reference in their entireties for all purposes.

FIELD OF THE INVENTION

This invention is directed to indazole compounds that mediate and/or inhibit the activity of certain protein kinases, and to pharmaceutical compositions containing such compounds. The invention is also directed to the therapeutic or prophylactic use of such compounds and compositions, and to methods of treating cancer as well as other disease states associated with unwanted angiogenesis and/or cellular proliferation, by administering effective amounts of such compounds.

BACKGROUND OF THE INVENTION

Protein kinases are a family of enzymes that catalyze phosphorylation of the hydroxyl group of specific tyrosine, serine, or threonine residues in proteins. Typically, such phosphorylation dramatically perturbs the function of the protein, and thus protein kinases are pivotal in the regulation of a wide variety of cellular processes, including metabolisim, cell proliferation, cell differentiation, and cell survival. Of the many different cellular functions in which the activity of protein kinases is known to be required, some processes represent attractive targets for therapeutic intervention for certain disease states. Two examples are angiogenesis and cell-cycle control, in which protein kinases play a pivotal role; these processes are essential for the growth of solid tumors as well as for other diseases.

Angiogenesis is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. See Merenmies et al., *Cell Growth & Differentiation*, 8, 3–10 (1997). On the other hand, unwanted angiogenesis is a hallmark of several diseases, such as retinopathies, psoriasis, rheumatoid arthritis, age-related macular degeneration (AMD), and cancer (solid tumors). Folkman, *Nature Med.*, 1, 27–31 (1995). Protein kinases which have been shown to be involved in the angiogenic process include three members of the growth factor receptor tyrosine kinase family: VEGF-R2 (vascular endothelial growth factor receptor 2, also known as KDR (kinase insert domain receptor) and as FLK-1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al., *Cancer Research*, 56, 3540–3545 (1996)), as has been shown with mutants of VEGF-R2 which fail to mediate signal transduction. Millauer et al., *Cancer Research*, 56, 1615–1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly, FGF-R binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji et al., *Cancer Research*, 57, 39243928 (1997). Unlike VEGF-R2, however, FGF-R is expressed in a number of different cell types throughout the body and may or may not play important roles in other normal physiological processes in the adult. Nonetheless, systemic administration of a small-molecule inhibitor of the kinase activity of FGF-R has been reported to block bFGF-induced angiogenesis in mice without apparent toxicity. Mohammad et al., *EMBO Journal*, 17, 5996–5904 (1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., *Science*, 277, 55–60 (1997).

As a result of the above-described developments, it has been proposed to treat angiogenesis by the use of compounds inhibiting the kinase activity of VEGF-R2, FGF-R, and/or TEK. For example, WIPO International Publication No. WO 97/34876 discloses certain cinnoline derivatives that are inhibitors of VEGF-R2, which may be used for the treatment of disease states associated with abnormal angiogenesis and/or increased vascular permeability such as cancer, diabetes, psoriasis, rheumatoid arthritis, Kaposi's sarcoma, haemangioma, acute and chronic nephropathies, atheroma, arterial restinosis, autoimmune diseases, acute inflammation, and ocular diseases with retinal vessel proliferation.

Phosphorylase kinase activates glycogen phosphorylase, thus increasing glycogen breakdown and hepatic glucose release. Hepatic glucose production is disregulated in type 2 diabetes, and is the primary cause of fasting hyperglycemia, which results in many of the secondary complications afflicting these patients. Thus, reduction in glucose release from the liver would lower elevated plasma glucose levels. Inhibitors of phosphorylase kinase should therefore decrease phosphorylase activity and glycogenolysis, thus reducing hyperglycemia in patients.

Another physiological response to VEGF is vascular hyperpermeability, which has been proposed to play a role in the early stages of angiogenesis. In ischemic tissues, such as those occurring in the brain of stroke victims, hypoxia trigger VEGF expression, leading to increased vascular permeability and ultimately edema in the surrounding tissues. In a rat model for stroke, it has been shown by van Bruggen et al., *J. Clinical Invest.*, 104, 1613–20 (1999) that administration of a monoclonal antibody to VEGF reduces the infarct volume. Thus, inhibitors of VEGFR are anticipated to be useful for the treatment of stroke.

In addition to its role in angiogenesis, protein kinases also play a crucial role in cell-cycle control. Uncontrolled cell proliferation is the insignia of cancer. Cell proliferation in response to various stimuli is manifested by a de-regulation of the cell division cycle, the process by which cells multiply and divide. Tumor cells typically have damage to the genes that directly or indirectly regulate progression through the cell division cycle.

Cyclin-dependent kinases (CDKs) are serine-threonine protein kinases that play critical roles in regulating the transitions between different phases of the cell cycle. See, e.g., the articles compiled in *Science*, 274, 1643–1677 (1996). CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific phases of the cell cycle.

It is CDK4 complexed to the D cyclins that plays a critical part in initiating the cell-division cycle from a resting or quiescent stage to one in which cells become committed to cell division. This progression is subject to a variety of growth regulatory mechanisms, both negative and positive. Aberrations in this control system, particularly those that affect the function of CDK4, have been implicated in the advancement of cells to the highly proliferative state characteristic of malignancies, particularly familial melanomas, esophageal carcinomas, and pancreatic cancers. See, e.g., Kamb, *Trends in Genetics*, 11, 136–140 (1995); Kamb et al., *Science*, 264, 436440 (1994).

Myriad publications describe a variety of chemical compounds useful against a variety of therapeutic targets. For example. WIPO International Publication Nos. WO 99/23077 and WO 99/23076 describe indazole-containing compounds having phosphodiesterase type IV inhibitory activity produced by an indazole-for-catechol bioisostere replacement. U.S. Pat. No. 5,760,028 discloses heterocycles including 3-[1-[3-(imidazolin-2-ylamino)propyl]indazol-5-ylcarbonylamino]-2-(benzyloxycarbonylamino)propionic acid, which are useful as antagonists of the $\alpha_v\beta_3$ integrin and related cell surface adhesive protein receptors. WIPO International Publication No. WO 98/09961 discloses certain indazole derivatives and their use as inhibitors of phosphodiesterase (PDE) type IV or the production of tumor necrosis factor (TNF) in a mammal. Recent additions to the virtual library of known compounds include those described as being anti-proliferative therapeutic agents that inhibit CDKs. For example, U.S. Pat. No. 5,621,082 to Xiong et al. discloses nucleic acid encoding an inhibitor of CDK6, and European Patent Publication No. 0 666 270 A2 describes peptides and peptide mimetics that act as inhibitors of CDK1 and CDK2. WIPO International Publication No. WO 97/16447 discloses certain analogs of chromones that are inhibitors of cyclin-dependent kinases, in particular of CDK/cyclin complexes such as CDK4/cyclin D1, which may be used for inhibiting excessive or abnormal cell proliferation, and therefore for treating cancer. WIPO International Publication No. WO 99/21845 describes 4-aminothiazole derivatives that are useful as CDK inhibitors.

There is still a need, however, for small-molecule compounds that may be readily synthesized and are effective in inhibiting one or more CDKs or CDK/cyclin complexes. Because CDK4 may serve as a general activator of cell division in most cells, and complexes of CDK4 and D-type cyclins govern the early $G_1$ phase of the cell cycle, there is a need for effective inhibitors of CDK4, and D-type cyclin complexes thereof, for treating one or more types of tumors. Also, the pivotal roles of cyclin E/CDK2 and cyclin B/CDK1 kinases in the $G_1$/S phase and $G_2$/M transitions, respectively, offer additional targets for therapeutic intervention in suppressing deregulated cell-cycle progression in cancer.

Another protein kinase, CHK1, plays an important role as a checkpoint in cell-cycle progression. Checkpoints are control systems that coordinate cell-cycle progression by influencing the formation, activation and subsequent inactivation of the cyclin-dependent kinases. Checkpoints prevent cell-cycle progression at inappropriate times, maintain the metabolic balance of cells while the cell is arrested, and in some instances can induce apoptosis (programmed cell death) when the requirements of the checkpoint have not been met. See, e.g., O'Connor, *Cancer Surveys*, 29, 151–182 (1997); Nurse, *Cell*, 91, 865–867 (1997); Hartwell et al., *Science*, 266, 1821–1828 (1994); Hartwell et al., *Science*, 246, 629–634 (1989).

One series of checkpoints monitors the integrity of the genome and, upon sensing DNA damage, these "DNA damage checkpoints" block cell-cycle progression in $G_1$ and $G_2$ phases, and slow progression through S phase. O'Connor, *Cancer Surveys*, 29, 151–182 (1997); Hartwell et al., *Science*, 266, 1821–1828 (1994). This action enables DNA repair processes to complete their tasks before replication of the genome and subsequent separation of this genetic material into new daughter cells takes place. Importantly, the most commonly mutated gene in human cancer, the p53 tumor suppressor gene, produces a DNA damage checkpoint protein that blocks cell-cycle progression in $G_1$ phase and/or induces apoptosis (programmed cell death) following DNA damage. Hartwell et al., *Science*, 266, 1821–1828 (1994). The p53 tumor suppressor has also been shown to strengthen the action of a DNA damage checkpoint in $G_2$ phase of the cell cycle. See, e.g., Bunz et al., *Science*, 28, 1497–1501 (1998); Winters et al., *Oncogene*, 17, 673–684 (1998); Thompson, *Oncogene*, 15, 3025–3035 (1997).

Given the pivotal nature of the p53 tumor suppressor pathway in human cancer, therapeutic interventions that exploit vulnerabilities in p53-defective cancer have been actively sought. One emerging vulnerability lies in the operation of the $G_2$ checkpoint in p53 defective cancer cells. Cancer cells, because they lack $G_1$ checkpoint control, are particularly vulnerable to abrogation of the last remaining barrier protecting them from the cancer-killing effects of DNA-damaging agents: the $G_2$ checkpoint. The $G_2$ checkpoint is regulated by a control system that has been conserved from yeast to humans. Important in this conserved system is a kinase, CHK1, which transduces signals from the DNA-damage sensory complex to inhibit activation of the cyclin B/Cdc2 kinase, which promotes mitotic entry. See, e.g., Peng et al., *Science*, 277, 1501–1505 (1997); Sanchez et al., *Science*, 277, 1497–1501 (1997). Inactivation of CHK1 has been shown to both abrogate $G_2$ arrest induced by DNA damage inflicted by either anticancer agents or endogenous DNA damage, as well as result in preferential killing of the resulting checkpoint defective cells. See, e.g., Nurse, *Cell*, 91, 865–867 (1997); Weinert, *Science*, 277, 1450–1451 (1997); Walworth et al., *Nature*, 363, 368–371 (1993); and Al-Khodairy et al., *Molec. Biol. Cell*, 5, 147–160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK1 as a pivotal target in DNA-damage checkpoint control. The elucidation of inhibitors of this and functionally related kinases such as Cds1/CHK2, a kinase recently discovered to cooperate with CHK1 in regulating S phase progression (see Zeng et al., Nature, 395, 507–510 (1998); Matsuoka, Science, 282, 1893–1897 (1998)), could provide valuable new therapeutic entities for the treatment of cancer.

Integrin receptor binding to ECM initiates intracellular signals mediated by FAK (Focal Adhesion Kinase) that are involved in cell motility, cellular proliferation, and survival. In human cancers, FAK overexpression is implicated in tumorigenesis and metastatic potential through its role in integrin mediated signaling pathways.

Tyrosine kinases can be of the receptor type (having extracellular, transmembrane and intracellular domains) or the non-receptor type (being wholly intracellular). At least one of the non-receptor protein tyrosine kinases, namely, LCK, is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, Oncogene, 8, 2025–2031 (1993), which is incorporated herein by reference.

In addition to the protein kinases identified above, many other protein kinases have been considered to be therapeutic targets, and numerous publications disclose inhibitors of kinase activity, as reviewed in the following: McMahon et al, Oncologist, 5, 3–10 (2000); Holash et al., Oncogene, 18, 5356–62 (1999); Thomas et al., J. Biol. Chem., 274, 3668492 (1999); Cohen, Curr. Op. Chem Biol., 3, 459–65 (1999); Klohs et al., Curr. Op. Chem Biol., 10, 54449 (1999); McMahon et al., Current Opinion in Drug Discovery & Development, 1, 131–146 (1998); Strawn et al., Exp. Opin. Invest. Drugs, 7, 553–573 (1998). WIPO International Publication WO 00/18761 discloses certain substituted 3-cyanoquinolines as protein kinase inhibitors.

There is still a need, however, for effective inhibitors of protein kinases. Moreover, as is understood by those skilled in the art, it is desirable for kinase inhibitors to possess both high affinity for the target kinase or kinases as well as high selectivity versus other protein kinases.

SUMMARY OF THE INVENTION

Thus, an objective of the invention is to discover potent inhibitors of protein kinases. Another objective of the invention is to discover effective kinase inhibitors having a strong and selective affinity for one or more particular kinases.

These and other objectives of the invention, which will become apparent from the following description, have been achieved by the discovery of the indazole compounds, pharmaceutically acceptable prodrugs, pharmaceutically active metabolites, and pharmaceutically acceptable salts thereof (such compounds, prodrugs, metabolites and salts are collectively referred to as "agents") described below, which modulate and/or inhibit the activity of protein kinases. Pharmaceutical compositions containing such agents are useful in treating diseases mediated by kinase activity, such as cancer, as well as other disease states associated with unwanted angiogenesis and/or cellular proliferation, such as diabetic retinopathy, neovascular glaucoma, rheumatoid arthritis, and psoriasis. Further, the agents have advantageous properties relating to the modulation and/or inhibition of the kinase activity associated with VEGF-R, FGF-R, CDK complexes, CHK1, LCK, TEK, FAK, and/or phosphorylase kinase.

In a general aspect, the invention relates to compounds of the Formula I:

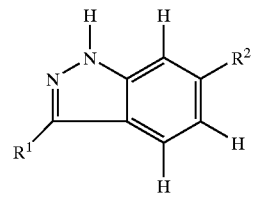

wherein:
R$^1$ is a substituted or unsubstituted aryl or heteroaryl, or a group of the formula CH=CH—R$^3$ or CH=N—R$^3$ where R$^3$ is a substituted or unsubstituted alkyl, alkenyl, cycloalkyl, heterocycloalkyl, aryl, or heteroaryl; and R$^2$ is a substituted or unsubstituted aryl, heteroaryl, or Y—X, where Y is O, S, C=CH$_2$, C=O, S=O, SO$_2$, alkylidene, NH, or N-(C$_1$-C$_8$ alkyl), and X is substituted or unsubstituted Ar, heteroaryl, NH-(alkyl), NH-(cycloalkyl), NH-(heterocycloalkyl), NH(aryl), NH(heteroaryl), NH-(alkoxyl), or NH-(dialkylamide), where Ar is aryl;

The invention is also directed to pharmaceutically acceptable prodrugs, pharmaceutically active metabolites, and pharmaceutically acceptable salts of the compounds of Formula I. Advantageous methods of making the compounds of the Formula I are also described.

In another general aspect, the invention relates to compounds of the Formula 1(a):

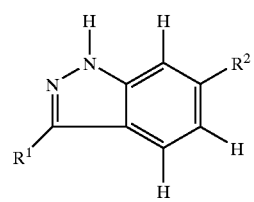

wherein:
R$^1$ is a substituted or unsubstituted aryl or heteroaryl, or a group of the formula CH=CH—R$^3$ or CH=N—R$^3$ where R$^3$ is a substituted or unsubstituted alkyl, alkenyl, cycloalkyl, heterocycloalkyl, aryl, or heteroaryl; and R$^2$ is a substituted or unsubstituted aryl or Y—Ar, where Y is O, S, C=CH$_2$, C=O, S=O, SO$_2$, CH$_2$, CHCH$_3$, NH, or N-(C$_1$-C$_8$ alkyl), and Ar is a substituted or unsubstituted aryl.

The invention is also directed to pharmaceutically acceptable prodrugs, pharmaceutically active metabolites, and pharmaceutically acceptable salts of the compounds of Formula I(a). Advantageous methods of making the compounds of the Formula I(a) are also described.

In one preferred general embodiment, the invention relates to compounds having the Formula II:

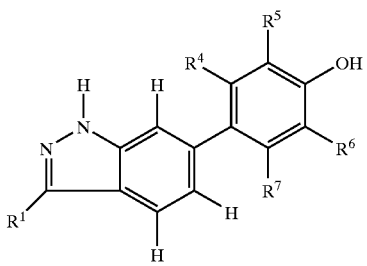

wherein:
R¹ is a substituted or unsubstituted aryl or heteroaryl, or a group of the formula CH=H—R³ or CH=N—R³, where R³ is a substituted or unsubstituted alkyl, cycloalkyl, heterocycloalkyl, aryl, or heteroaryl;

R⁴ and R⁷ are each independently hydrogen, OH, halo, $C_1$–$C_8$ alkyl, $C_1$–$C_8$ alkoxy, $C_1$–$C_8$ alkenyl, aryloxy, thioaryl, $CH_2$—OH, $CH_2$—O—($C_1$–$C_8$ alkyl), $CH_2$—O-aryl, $CH_2$—S—($C_1$–$C_8$ alkyl), or $CH_2$—S-aryl;

R⁵ and R⁶ are each independently hydrogen, OH, halo, Z-alkyl, Z-aryl, or Z-$CH_2$CH=$CH_2$, where Z is O, S, NH, or $CH_2$, and the alkyl and aryl moieties of Z-alkyl and Z-aryl are each optionally substituted;

and pharmaceutically acceptable prodrugs, pharmaceutically active metabolites, and pharmaceutically acceptable salts thereof.

In a preferred embodiment of Formula H: R¹ is a substituted or unsubstituted bicyclic heteroaryl, or a group of the formula CH=CH—R³ where R³ is a substituted or unsubstituted aryl or heteroaryl; R⁴ and R⁷ are each independently hydrogen or $C_1$–$C_8$ alkyl; and R⁵ and R⁶ are each independently halo, Z-alkyl, or Z-$CH_2$CH=$CH_2$, where Z is O or S.

In another preferred general embodiment, compounds of the invention are of Formula m:

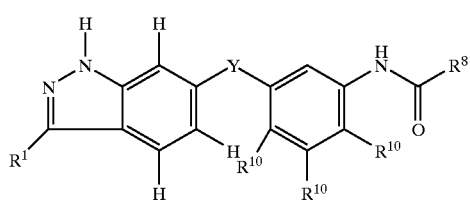

wherein:
R¹ is a substituted or unsubstituted aryl or heteroaryl, or a group of the formula CH=CH—R³ or CH=N—R³, where R³ is a substituted or unsubstituted alkyl, cycloalkyl, heterocycloalkyl, aryl, or heteroaryl;

Y is O, S, C=$CH_2$, C=O, S=O, $SO_2$, $CH_2$, $CHCH_3$, NH, or N-($C_1$–$C_8$ alkyl);

R⁸ is a substituted or unsubstituted alkyl, alkenyl, cycloalkyl, heterocycloalkyl, aryl, heteroaryl, alkoxyl, or aryloxyl;

R¹⁰ is independently selected from hydrogen, halogen, and lower-alkyl;

and pharmaceutically acceptable prodrugs, pharmaceutically acceptable metabolites, and pharmaceutically acceptable salts thereof.

More preferably, in Formula m: R¹ is a substituted or unsubstituted bicyclic heteroaryl, or a group of the formula CH=CH—R³ where R³ is a substituted or unsubstituted aryl or heteroaryl; Y is O, S, C=$CH_2$, C=O, NH, or N—($C_1$–$C_8$ alkyl); R⁸ is a substituted or unsubstituted aryl, heteroaryl, alkyl, and alkenyl, and R¹⁰ is hydrogen or halogen.

In another preferred general embodiment, compounds of the invention are of Formula [(a):

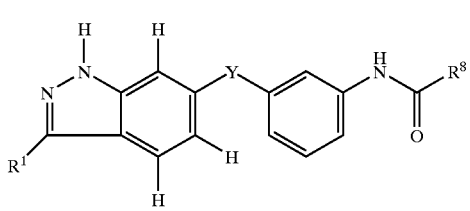

wherein:
R¹ is a substituted or unsubstituted aryl or heteroaryl, or a group of the formula CH=CH—R³ or CH=N—R³, where R³ is a substituted or unsubstituted alkyl, cycloalkyl, heterocycloalkyl, aryl, or heteroaryl;

Y is O, S, C=$CH_2$, C=O, S=O, $SO_2$, $CH_2$, $CHCH_3$, NH, or N-($C_1$–$C_8$ alkyl);

R⁸ is a substituted or unsubstituted alkyl, alkenyl, cycloalkyl, heterocycloalkyl, aryl, heteroaryl, alkoxyl, or aryloxyl;

and pharmaceutically acceptable prodrugs, pharmaceutically acceptable metabolites, and pharmaceutically acceptable salts thereof.

More preferably, in Formula III(a): R¹ is a substituted or unsubstituted bicyclic heteroaryl, or a group of the formula CH=CH—R³ where R³ is a substituted or unsubstituted aryl or heteroaryl; Y is O, S, C=$CH_2$, C=O, NH, or N-($C_1$–$C_8$ alkyl); and R⁸ is a substituted or unsubstituted aryl or heteroaryl.

In another preferred general embodiment, compounds of the invention are of Formula IV:

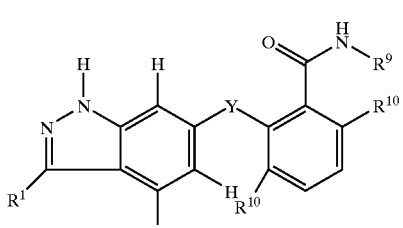

wherein:
R¹ is a substituted or unsubstituted aryl or heteroaryl, or a group of the formula CH=CH—R³ or CH=N—R³, where R³ is a substituted or unsubstituted alkyl, cycloalkyl, heterocycloalkyl, aryl, or heteroaryl;

Y is O, S, C=$CH_2$, C=O, S=O, $SO_2$, $CH_2$, $CHCH_3$, NH, or N—($C_1$–$C_8$ alkyl);

R⁹ is a substituted or unsubstituted alkyl, cycloalkyl, heterocycloalkyl, aryl, heteroaryl, alkoxyl, aryloxyl, cycloalkoxyl, NH-($C_1$–$C_8$ alkyl), NH-(aryl), NH-(heteroaryl), N=CH-(alkyl), NH(C=O)R¹¹, or $NH_2$, where R¹¹ is independently selected from hydrogen, substituted or unsubstituted alkyl, cycloalkyl, heterocycloalkyl, aryl, and heteroaryl; and R¹⁰ is independently selected from hydrogen, halogen, and lower-alkyl;

and pharmaceutically acceptable prodrugs, pharmaceutically acceptable metabolites, and pharmaceutically acceptable salts thereof.

More preferably, in Formula IV: $R^1$ is a group of the formula CH=CH—$R^3$ where $R^3$ is a substituted or unsubstituted aryl or heteroaryl; Y is S or NH, and $R^9$ is a substituted or unsubstituted alkyl, alkoxyl, or NH-(heteroaryl).
Most preferred are compounds of the invention selected from:
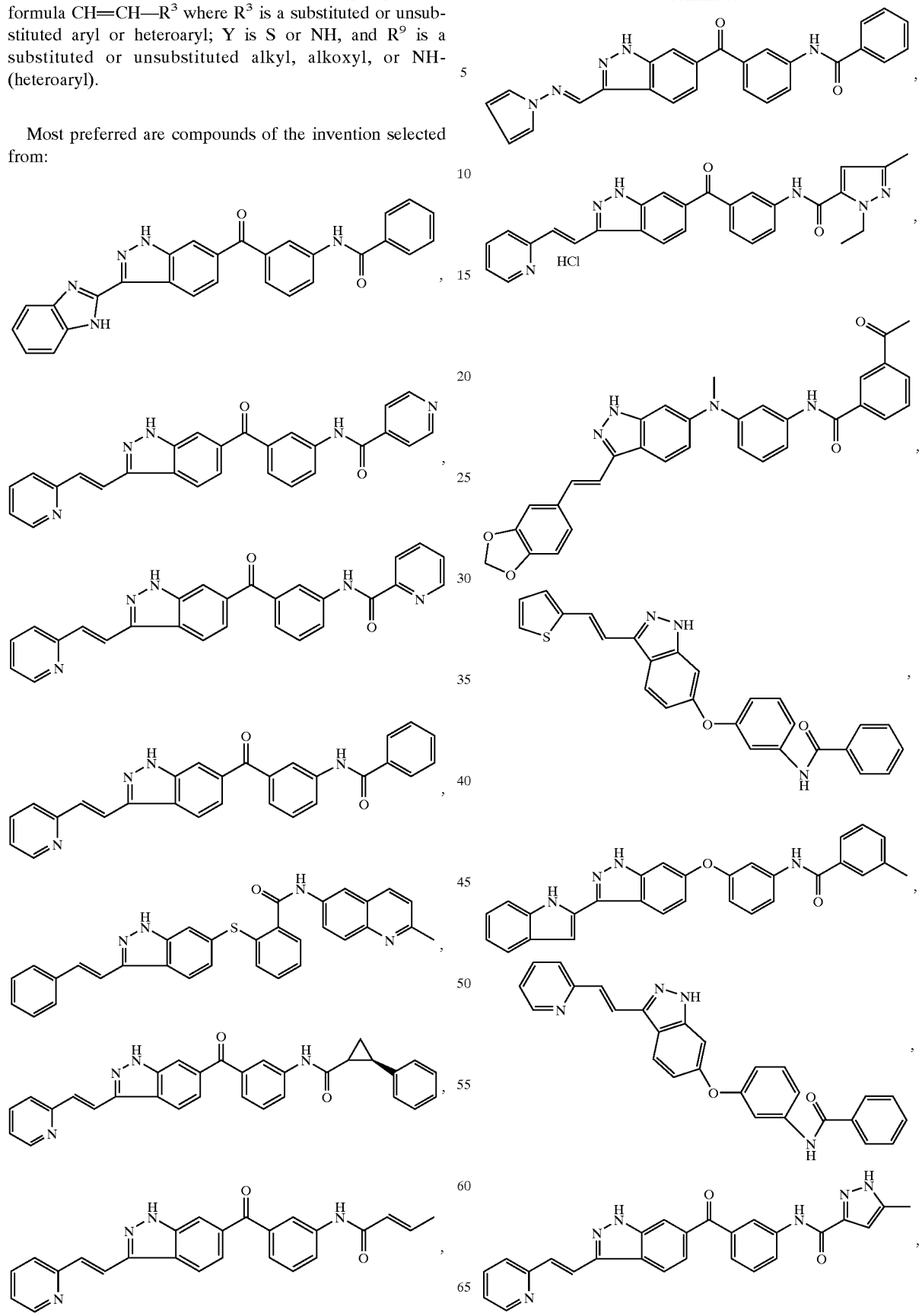

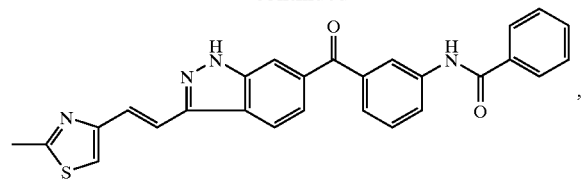
,
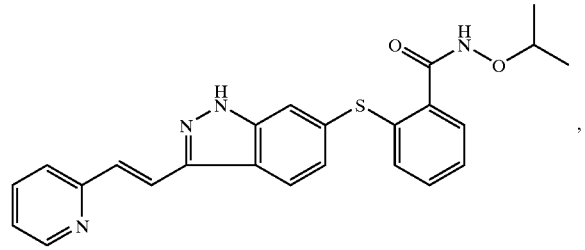
,
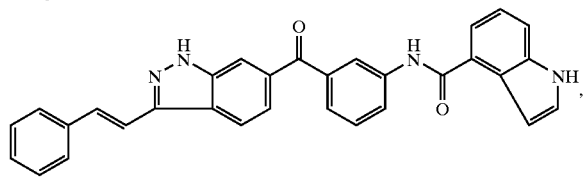
,

,
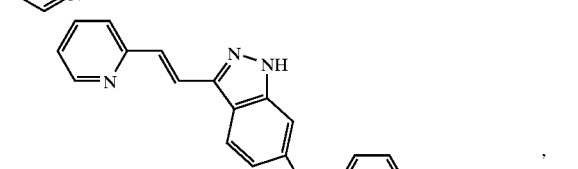
,

,
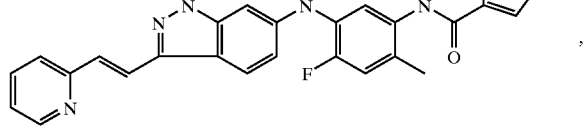
,
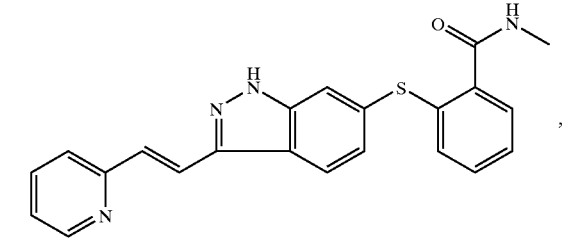
,
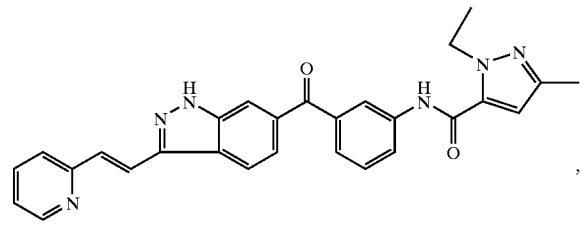
,
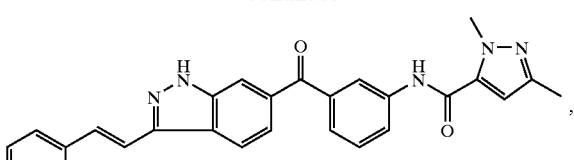
,
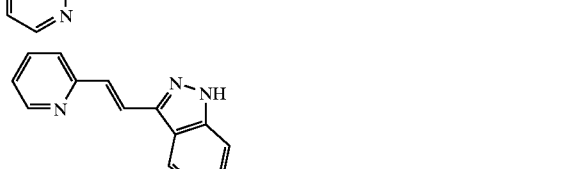
,
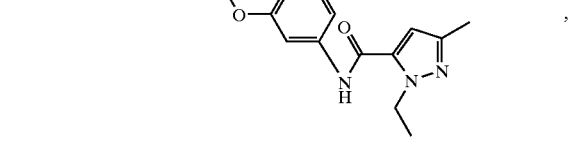
,
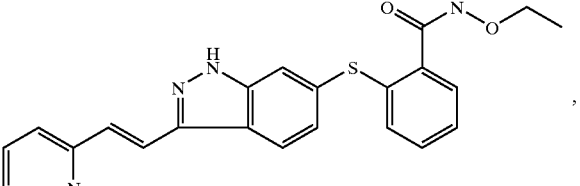
,
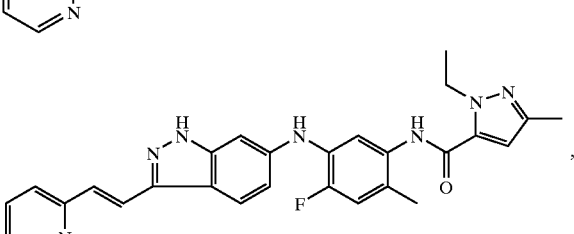
,
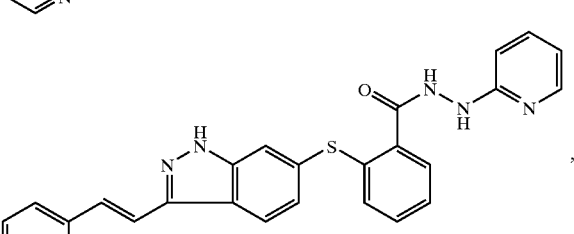
,
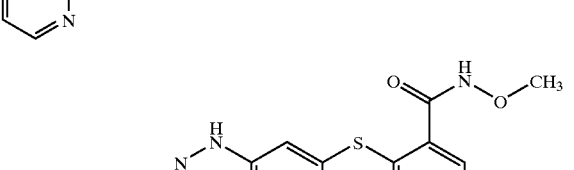
,
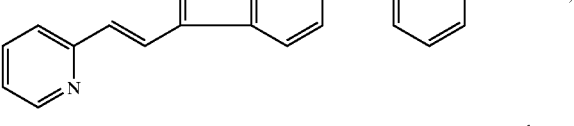
,
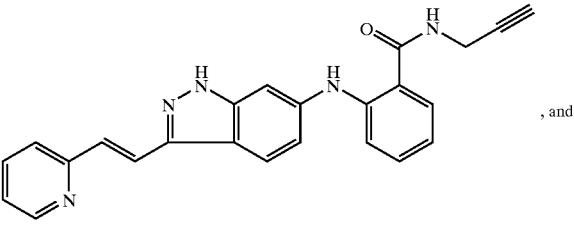
, and -continued

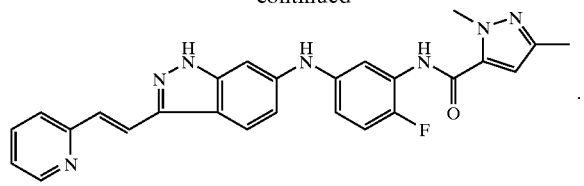

The invention also relates to a method of modulating and/or inhibiting the kinase activity of VEGF-R, FGF-R, a CDK complex, CHK1, LCK, TEK, FAK, and/or phosphorylase kinase by administering a compound of the Formula I, II, III, or IV, or a pharmaceutically acceptable prodrug, pharmaceutically active metabolite, or pharmaceutically acceptable salt thereof. Preferred compounds of the present invention that have selective kinase activity-i.e., they possess significant activity against one or more specific kinases while possessing less or minimal activity against one or more different kinases. In one preferred embodiment of the invention, compounds of the present invention are those of Formula I possessing substantially higher potency against VEGF receptor tyrosine kinase than against FGF-R1 receptor tyrosine kinase. The invention is also directed to methods of modulating VEGF receptor tyrosine kinase activity without significantly modulating FGF receptor tyrosine kinase activity.

The inventive compounds may be used advantageously in combination with other known therapeutic agents. For example, compounds of Formula I, II, III, or IV which possess antiangiogenic activity may be co-administered with cytotoxic chemotherapeutic agents, such as taxol, taxotere, vinblastine, cis-platin, doxorubicin, adriamycin, and the like, to produce an enhanced antitumor effect. Additive or synergistic enhancement of therapeutic effect may also be obtained by co-administration of compounds of Formula I, II, m, or IV which possess antiangiogenic activity with other antiangiogenic agents, such as combretastatin A-4, endostatin, prinomastat, celecoxib, rofocoxib, EMD121974, IM862, anti-VEGF monoclonal antibodies, and anti-KDR monoclonal antibodies.

The invention also relates pharmaceutical compositions, each comprising an effective amount of an agent selected from compounds of Formula I and pharmaceutically acceptable salts, pharmaceutically active metabolites, and pharmaceutically acceptable prodrugs thereof; and a pharmaceutically acceptable carrier or vehicle for such agent. The invention further provides methods of treating cancer as well as other disease states associated with unwanted angiogenesis and/or cellular proliferation, comprising administering effective amounts of such an agent to a patient in need of such treatment.

DETAILED DESCRIPTION OF INVENTION AND PREFERRED EMBODIMENTS

The inventive compounds of the Formula I, II, III, and IV are useful for mediating the activity of protein kinases. More particularly, the compounds are useful as anti-angiogenesis agents and as agents for modulating and/or inhibiting the activity of protein kinases, thus providing treatments for cancer or other diseases associated with cellular proliferation mediated by protein kinases.

The term "alkyl" as used herein refers to straight- and branched-chain alkyl groups having one to twelve carbon atoms. Exemplary alkyl groups include methyl (Me), ethyl (Et), n-propyl, isopropyl, butyl, isobutyl, sec-butyl, tert-butyl (t-Bu), pentyl, isopentyl, tert-pentyl, hexyl, isohexyl, and the like. The term "lower alkyl" designates an alkyl having from 1 to 8 carbon atoms (a $C_{1-4}$-alkyl). Suitable substituted alkyls include fluoromethyl, difluoromethyl, trifluoromethyl, 2-fluoroethyl, 3-fluoropropyl, hydroxymethyl, 2-hydroxyethyl, 3-hydroxypropyl, and the like.

The term "alkylidene" refers to a divalent radical having one to twelve carbon atoms. Illustrative alkylidene groups include $CH_2$, $CHCH_3$, $(CH_3)_2$, and the like.

The term "alkenyl" refers to straight- and branched-chain alkenyl groups having from two to twelve carbon atoms. Illustrative alkenyl groups include prop-2-enyl, but-2-enyl, but-3-enyl, 2-methylprop-2-enyl, hex-2-enyl, and the like.

The term "alkynyl" refers to straight- and branched-chain alkynyl groups having from two to twelve carbon atoms.

The term "cycloalkyl" refers to saturated or partially unsaturated carbocycles having from three to twelve carbon atoms, including bicyclic and tricyclic cycloalkyl structures. Suitable cycloalkyls include cyclopropyl, cyclobutyl, cyclopentyl, cyclohexyl, cycloheptyl, and the like.

A "heterocycloalkyl" group is intended to mean a saturated or partially unsaturated monocyclic radical containing carbon atoms, preferably 4 or 5 ring carbon atoms, and at least one heteroatom selected from nitrogen, oxygen and sulfur.

The terms "aryl" and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like. Such moieties may be optionally substituted by a fused-ring structure or bridge, for example $OCH_2$—O.

The term "alkoxy" is intended to mean the radical —O-alkyl. Illustrative examples include methoxy, ethoxy, propoxy, and the like.

The term "aryloxy" respresents —O-aryl, wherein aryl is defined above.

The term "cycloalkoxyl" represents —O-cycloalkyl, wherein cycloalkyl is defined above.

The term "halogen" represents chlorine, fluorine, bromine or iodine. The term "halo" represents chloro, fluoro, bromo or iodo.

In general, the various moieties or functional groups for variables in the formulae may be optionally substituted by one or more suitable substituents. Exemplary substituents include a halogen (F, Cl, Br, or I), lower alkyl, —OH, —$NO_2$, —CN, —$CO_2H$, —O-lower alkyl, -aryl, -aryl-lower alkyl, —$CO_2CH_3$, —$CONH_2$, —$OCH_2CONH_2$, —$NH_2$, —$SO_2NH_2$, haloalkyl (e.g., —$CF_3$, —$CH_2CF_3$), —O-haloalkyl (e.g., —$OCF_3$, —$OCHF_2$), and the like.

The terms "comprising" and "including" are used in an open, non-limiting sense.

It is understood that while a compound of Formula I may exhibit the phenomenon of tautomerism, the formula drawings within this specification expressly depict only one of the possible tautomeric forms. It is therefore to be understood that within the invention the formulae are intended to represent any tautomeric form of the depicted compound and is not to be limited merely to a specific tautomeric form depicted by the formula drawings.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the formulas are intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of the Formula I, II, III, and IV, the invention includes pharmaceutically acceptable prodrugs, pharmaceutically active metabolites, and pharmaceutically acceptable salts of such compounds.

"A pharmaceutically acceptable prodrug" is a compound that may be converted under physiological conditions or by solvolysis to the specified compound or to a pharmaceutically acceptable salt of such compound.

"A pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art See, e.g., Bertolini, G. et al., *J. Med. Chem.*, 40, 2011–2016 (1997); Shan, D. et al., *J. Pharm. Sci.*, 86 (7), 765–767; Bagshawe K., *Drug Dev. Res.*, 34, 220–230 (1995); Bodor, N., *Advances in Drug Res.*, 13, 224–331 (1984); Bundgaard, H., *Design of Prodrugs* (Elsevier Press 1985); and Larsen, I. K., *Design and Application of Prodrugs*, Drug Design and Development (Krogsgaard-Larsen et al., eds., Harwood Academic Publishers, 1991).

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the agents of the invention may be used to treat diseases mediated by modulation or regulation of protein kinases. An "effective amount" is intended to mean that amount of an agent that, when administered to a mammal in need of such treatment, is sufficient to effect treatment for a disease mediated by the activity of one or more protein kinases, such as tryosine kinases. Thus, e.g., a therapeutically effective amount of a compound of the Formula I, salt, active metabolite or prodrug thereof is a quantity sufficient to modulate, regulate, or inhibit the activity of one or more protein kinases such that a disease condition which is mediated by that activity is reduced or alleviated.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of one or more protein kinases, such as tyrosine kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

The inventive agents may be prepared using the reaction routes and synthesis schemes as described below, employing the techniques available in the art using starting materials that are readily available.

In one general synthetic process, compounds of Formula I are prepared according to the following reaction scheme:

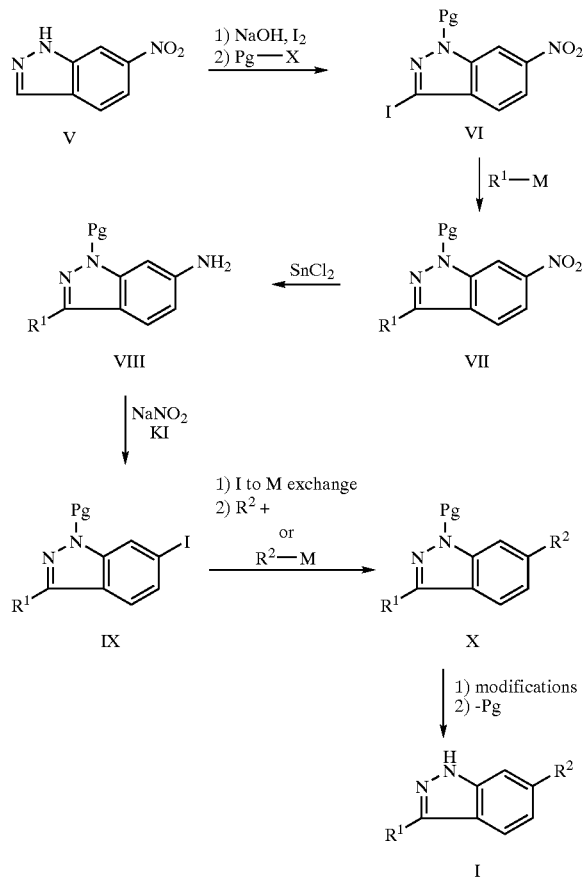

6-Nitroindazole (compound V) is treated with iodine and base, e.g., NaOH, in an aqueous/organic mixture, preferably with dioxane. The mixture is acidified and the product isolated by filtration. To the resulting 3-iodo-6-nitroindazole in dichloromethane-50% aqueous KOH at 0° C. is added a protecting group ("Pg") reagent (wherein X=halo), preferably trimethylsilylethoxymethyl chloride (SEM-Cl), and a phase transfer catalyst, e.g., tetrabutylammonium bromide (TBABr). After 1–4 hours, the two phases are diluted, the organics are separated, dried with sodium sulfate, filtered and concentrated. The crude product is purified by silica gel chromatography to give compounds of formula VI. Treatment of compounds of formula VI in a suitable organic solvent with a suitable $R^1$-organometallic reagent, preferably an $R^1$-boronic acid, in the presence of aqueous base, e.g., sodium carbonate, and a suitable catalyst, preferably Pd(PPh$_3$)$_4$ gives, after extractive work-up and silica gel chromatography, compounds of formula VII. The $R^1$ substituent may be exchanged within compounds of formula VII or later intermediates throughout this scheme by oxidative cleavage (e.g., ozonolysis) followed by additions to the resulting aldehyde functionality with Wittig or condensation transformations (typified in Example 42(a–e)). Treatment of compounds of formula VII with a reducing agent, preferably SnCl$_2$, provides, after conventional aqueous work up and purification, compounds of formula VIII. For the series of derivatives where Y=NH or N-lower alkyl, compounds of formula VIII may be treated with aryl or heteroaryl chlorides, bromides, iodides or triflates in the presence of a base, preferably Cs$_2$CO$_3$, and catalyst, preferably Pd-BINAP, (and where Y N-lower alkyl, with a subsequent alkylation step) to provide compounds of formula X. To produce other Y linkages, sodium nitrite is added to compounds of formula VIII under chilled standard aqueous acidic conditions followed by the addition of potassium iodide and gentle warming. Standard work-up and purification produces iodide compounds of formula IX.

Treatment of compounds of formula Ex with an organometallic reagent, e.g., butyllithium, promotes lithium halogen exchange. This intermediate is then reacted with an $R^2$ electrophile, e.g., a carbonyl or triflate, through the possible mediation of additional metals and catalysts, preferably zinc chloride and Pd(PPh$_3$)$_4$ to provide compounds of formula X. Alternatively, compounds of formula IX may be treated with an organometallic reagent such as an organoboronic acid in the presence of a catalyst, e.g., Pd(PPh$_3$)$_4$, under a carbon monoxide atmosphere to give compounds of formula X. Alternatively, for derivatives where Y=NH or S, compounds of formula IX may be treated with appropriate amines or thiols in the presence of base, preferably Cs$_2$CO$_3$ or K$_3$PO$_4$ and a catalyst, preferably Pd-BINAP or Pd-(bis-cyclohexyl)biphenylphosphine to provide compounds of formula X. Conventional functional group interchanges, such as oxidations, reductions, alkylations, acylations, condensations, and deprotections may then be employed to further derivatize this series giving final compounds of Formula I.

The inventive compounds of Formula I may also be prepared according general procedure shown in the following scheme:

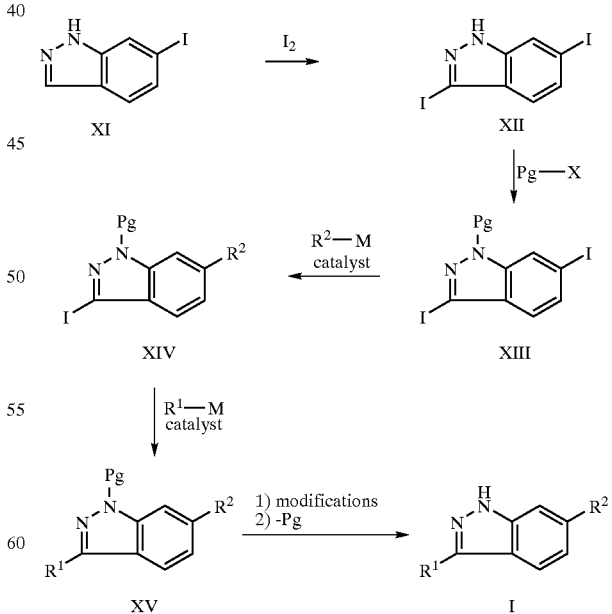

6-Iodoindazole (XI) is treated with iodine and base, e.g., NaOH, in an aqueous/organic mixture, preferably with dioxane. The mixture is acidified and the product XII is isolated by filtration. To the resulting 3,6 di-iodoindazole in dichloromethane-50% aqueous KOH at 0° C. is added a protecting group reagent, preferably SEM-Cl, and a phase transfer catalyst, e.g., TBABr. The two phases are diluted, the organics separated, dried with sodium sulfate, filtered and concentrated. The crude product is purified by silica gel chromatography to give compounds of the formula XIII. Treatment of compounds of formula XIII in a suitable organic solvent with a suitable $R^2$-organometallic reagent, e.g., $R^2$-ZnCl or boron $R^2$-boron reagent and a suitable catalyst, preferably $Pd(PPh_3)_4$ gives, after extractive work-up and silica gel chromatography, compounds of formula XIV. Treatment of compounds of formula XIV in a suitable organic solvent with a suitable $R^1$-organometallic reagent (e.g., boron $R^1$-boron reagent or $R^1$-ZnCl), in the presence of aqueous base, sodium carbonate, and a suitable catalyst, preferably $Pd(PPh_3)_4$ gives, after extractive work-up and silica gel chromatography, compounds of formula XV. Conventional functional group interchanges, such as oxidations, reductions, alkylations, acylations, condensations and deprotections may then be employed to further derivatize this series giving final compounds of Formula I.

Alternatively, compounds of Formula I where $R^2$ is a substituted or unsubstituted Y—Ar, where Y is O or S may be prepared according to the following general scheme:

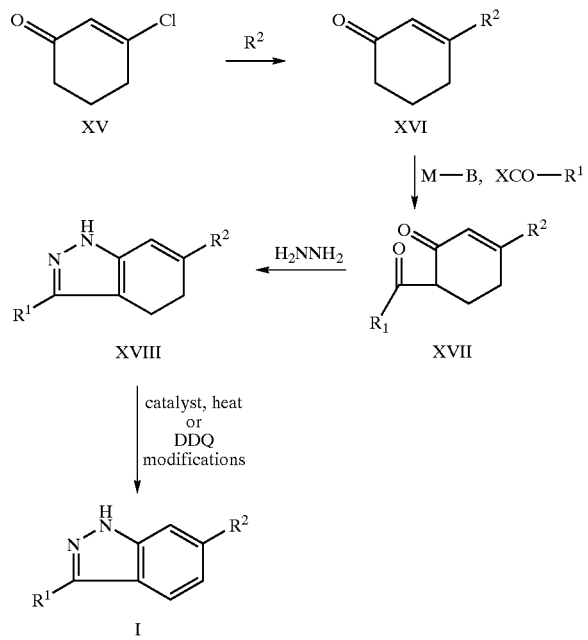

A stirred acetone solution of 3-chloro-cyclohex-2-enone (XV), H—$R^2$, and anhydrous potassium carbonate is refluxed for 15–24 hours, cooled, and filtered. Concentrating and chromatographing the filtrate on silica gel gives 3-$R^2$-cyclohex-2-enone (XVI).

The ketones of formula XVI may be reacted with a suitable base (M-B), preferably lithium bis(trimethylsily)amide, and reacted with $R^1$—CO—X (where X=halogen), which after standard acid work up and purification provides compounds of the formula XVII. This product, in HOAc/EtOH, combined with hydrazine monohydrate, is heated at a suitable temperature for an appropriate time period, preferably at 60–80° C. for 24 hours. After cooling, the mixture is poured into saturated sodium bicarbonate solution, extracted with an organic solvent, concentrated, and purified on silica gel to give compounds of formula XVIII. Compounds of formula XVIII may be oxidized using a variety of known methods to give compounds of the Formula I.

Other compounds of Formula I may be prepared in manners analogous to the general procedures described above or the detailed procedures described in the examples herein. The affinity of the compounds of the invention for a receptor may be enhanced by providing multiple copies of the ligand in close proximity, preferably using a scaffolding provided by a carrier moiety. It has been shown that provision of such multiple valence compounds with optimal spacing between the moieties dramatically improves binding to a receptor. See, e.g, Lee et al., *Biochem*, 23, 4255 (1984). The multivalency and spacing can be controlled by selection of a suitable carrier moiety or linker units. Such moieties include molecular supports which contain a multiplicity of functional groups that can be reacted with functional groups associated with the compounds of the invention. Of course, a variety of carriers can be used, including proteins such as BSA or HAS, a multiplicity of peptides including, for example, pentapeptides, decapeptides, pentadecapeptides, and the like. The peptides or proteins can contain the desired number of amino acid residues having free amino groups in their side chains; however, other functional groups, such as sulfhydryl groups or hydroxyl groups, can also be used to obtain stable linkages.

Compounds that potently regulate, modulate, or inhibit the protein kinase activity associated with receptors VEGF, FGF, CDK complexes, TEK, CHK1, LCK, FAK, and phosphorylase kinase among others, and which inhibit angiogenesis and/or cellular profileration is desirable and is one preferred embodiment of the present invention. The present invention is further directed to methods of modulating or inhibiting protein kinase activity, for example in mammalian tissue, by administering an inventive agent. The activity of the inventive compounds as modulators of protein kinase activity, such as the activity of kinases, may be measured by any of the methods available to those skilled in the art, including in vivo and/or in vitro assays. Examples of suitable assays for activity measurements include those described in Parast C. et al., *BioChemistry*, 37, 16788–16801 (1998); Jeffrey et al., *Nature*, 376, 313–320 (1995); WIPO International Publication No. WO 97/34876; and WIPO International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I, II, III, or IV and an inert, pharmaceutically acceptable carrier or diluent. In one embodiment of the pharmaceutical compositions, efficacious levels of the inventive agents are provided so as to provide therapeutic benefits involving modulation of protein kinases. By "efficacious levels" is meant levels in which the effects of protein kinases are, at a minimum, regulated. These compositions are prepared in unit-dosage form appropriate for the mode of administration, e.g., parenteral or oral administration.

An inventive agent is administered in conventional dosage form prepared by combining a therapeutically effective amount of an agent (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, gylcerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage-determination tests in view of the experimental data for an agent. For oral administration, an exemplary daily dose generally employed is from about 0.001 to about 1000 mg/kg of body weight, more preferably from about 0.001 to about 50 mg/kg body weight, with courses of treatment repeated at appropriate intervals. Administration of prodrugs are typically dosed at weight levels which are chemically equivalent to the weight levels of the fully active form.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, odium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention are conveniently delivered in the form of an aerosol pray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For administration to the eye, a compound of the Formula I, II, III, or IV is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD cosolvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The preparation of preferred compounds of the present invention is described in detail in the following examples, but the artisan will recognize that the chemical reactions described may be readily adapted to prepare a number of other protein kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

EXAMPLES

In the examples described below, unless otherwise indicated all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF), N,N-dimethylformamide (DMF), dichloromethane, toluene, and dioxane were purchased from Aldrich in Sure seal bottles and used as received. All solvents were purified using standard methods readily known to those skilled in the art, unless otherwise indicated.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F. 254 plates Analtech (0.25 mm) and eluted with the appropriate solvent ratios (v/v), and are denoted where appropriate. The reactions were assayed by TLC and terminated as judged by the consumption of starting material.

Visualization of the TLC plates was done with a p-anisaldehyde spray reagent or phosphomolybdic acid reagent (Aldrich Chemical 20 wt % in ethanol) and activated with heal Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ prior to filtration and evaporation of the solvents under reduced pressure on a rotary evaporator and noted as solvents removed in vacuo. Flash column chromatography (Still et al., *J. Org. Chem.*, 43, 2923 (1978)) was done using Baker grade flash silica gel (47–61 µm) and a silica gel: crude material ratio of about 20:1 to 50:1 unless otherwise stated. Hydrogenolysis was done at the pressure indicated in the examples or at ambient pressure.

$^1$H-NMR spectra were recorded on a Bruker instrument operating at 300 MHz and "$^{13}$C-NMR spectra were recorded operating at 75 MHz. NMR spectra were obtained as $CDCl_3$ solutions (reported in ppm), using chloroform as the reference standard (7.25 ppm and 77.00 ppm) or $CD_3OD$ (3.4 and 4.8 ppm and 49.3 ppm), or internally tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Infrared (IR) spectra were recorded on a Perkin-Elmer FT-IR Spectrometer as neat oils, as KBr pellets, or as $CDCl_3$ solutions, and when given are reported in wave numbers ($cm^{-1}$). The mass spectra were obtained using LSIMS or electrospray. All melting points (mp) are uncorrected.

Example 1(a)

3-[E-2-(3,4-Dimethoxy-phenyl)vinyl]-6-(3-methoxy-4-hydroxy-phenyl)-1H-indazole

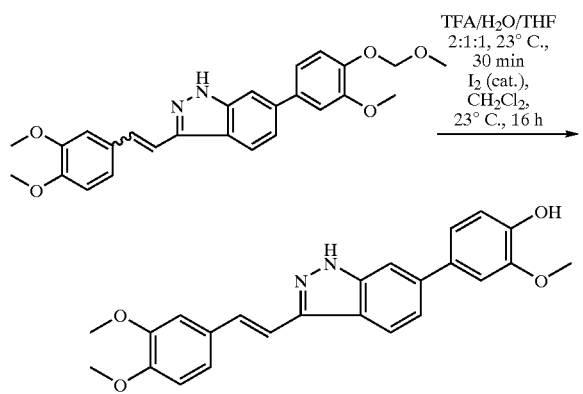

The 3-[E/Z-2-(3,4-dimethoxy-phenyl)vinyl]-6-[3-methoxy-4-(methoxymethoxy)phenyl]-1H-indazole (~205 mg, 0.461 mmol (theoretical)) was dissolved in tetrahydrofuran (THF, 10 mL) and was treated with water (10 mL) and trifluoroacetic acid (TFA, 20 mL). The reaction mixture was allowed to stir at 23° C. for 30 minutes (min.). The mixture was diluted with toluene (100 µl) and the volatile materials were removed under reduced pressure (30 mm Hg, 35° C.) to give a concentrated volume of ~5 mL. Again, toluene (100 mL) was added and the mixture was concentrated under reduced pressure to give crude material which still contained some acid. The material was partitioned between ethyl acetate and saturated sodium bicarbonate, the organic material was separated, dried over sodium sulfate, decanted, and concentrated under reduced pressure. The residue, a mixture of olefin isomers, (~185 mg, 0.461 mmol (theoretical)) was taken up in dichloromethane (50 mL) at 23° C. and was treated with iodine (80 mg). The mixture was allowed to stir at 23° C. for 12 hours (h). The mixture was treated with saturated sodium bicarbonate (10 mL) and 5% aqueous sodium bisulfite (10 mL). The mixture was diluted with ethyl acetate (200 mL) and the organic material was washed with saturated sodium bicarbonate (100 mL), dried over sodium sulfate, decanted, and concentrated under reduced pressure to give crude product. The crude was purified on silica (40 mL, 6:4->7:3 ethyl acetate/hexane) and all fractions containing desired were combined, concentrated and precipitated from a dichloromethane/hexane bilayer (1:3) to give 3-E-2-(3,4-Dimethoxy-phenyl)vinyl]-6-(3-methoxy hydroxy-phenyl)-1H-indazole as a white solid (93 mg combined crops): $R_f$ sm 0.42, p 0.35 (ethyl acetate-hexane 7:3); FTIR (thin film) 3324, 1600, 1514, 1463, 1422, 1264, 1137, 1024, 959, 852 $cm^{-1}$; $^1$H NMR ($CDCl_3$) δ 10.0 (s, 1H), 8.08 (d, 1H, J=8.4 Hz), 7.59 (s, 1H), 7.49 (d, 1H, J=16.6 Hz), 7.45 (dd, 1H, J=1.4, 8.4 Hz), 7.34 (d, 1H, J=16.6 Hz), 7.20–7.12 (m, 4H), 7.03 (d, 1H, J=8.0 Hz), 6.91 (d, 1H, J=8.2 Hz), 5.68 (bs, 1H), 3.99 (s, 3H), 3.97 (s, 3H), 3.93 (s, 3H); $^{13}$C NMR ($CDCl_3$) δ 149.6, 149.5, 146.0, 144.0, 142.6, 140.8, 133.9, 131.4, 130.7, 121.7, 121.4, 120.9, 120.4, 120.2, 118.6, 115.4, 111.7, 110.8, 109.1, 108.2, 56.4, 56.3, 56.2. HRMS (ES) [m+H]/z Calc'd 403.1658, found 403.1658. [m–H]/z Calc'd 401. Found 401.

The starting material was prepared as follows:

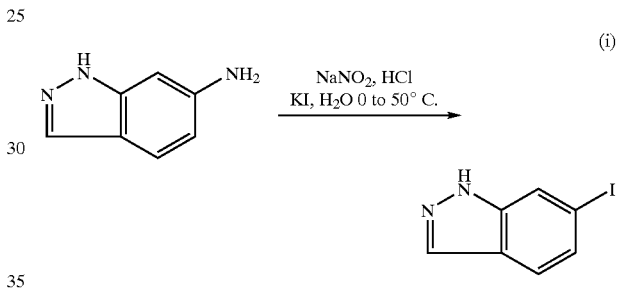

(i)

To 6-aminoindazole (40.8 g. 0.3065 mol, 1 equiv) in a 2-liter (2-L) round-bottom flask containing a large magnetic stir bar was added ice (256 g), followed by water (128 mL) and the reaction vessel was lowered into an ice bath. To this stirring slurry at 0° C. was added concentrated aqueous HCl (128 mL, 1.53 mol, 5 equiv). Immediately after, a solution of $NaNO_2$ (23.3 g, 0.338 mol, 1.1 equiv) in water (96 mL) was added. After 10 min of stirring at 0° C., KI (61 g, 0.368 mol, 1.2 equiv) was added very slowly at first (~100 mg at a time because the first small bits of KI cause an abrupt evolution of gas) then more rapidly (5 min total time). The cold bath was removed and the reaction mixture was warmed to 40° C. (gas evolved). When the rate of gas evolution decreased (~30 min) the reaction mixture was warmed to 50° C. for 30 min. The mix was then cooled to 23° C., and 3N NaOH (320 mL) was added to neutralize followed by 50% saturated $NaHCO_3$ (320 mL). The slurry was then filtered through a Buchner funnel to give a dark reddish-brown solid. The solid was taken up in warm THF (800 mL) and silica (600 mL dry) was added with stirring. To this slurry was added hexane (1.2 L) and the mix was vacuum filtered through a pad of silica (300 mL) in a large fritted filter. The silica was further washed with 2 L of 40% THF in hexane. The filtrates were combined and concentrated under reduced pressure to give a solid. The solid was further triturated with ethyl acetate (~100 mL), filtered and dried under reduced pressure to give 6-iodo-1H-indazole as a light brown solid (36.1 g, 48% yield): $R_f$ sm 0.12, p 0.48 (Hex-EtOAc 1:1); $^1$H NMR (300 MHz, $CDCl_3$) 7.9 (s, 1H), 7.8 (s, 1H), 7.42 (d, 1H), 7.33 (d, 1H); MS (ES) [m+H]/z Calc'd 245, Found 245, [m–H]/z Calc'd 243, Found 243.

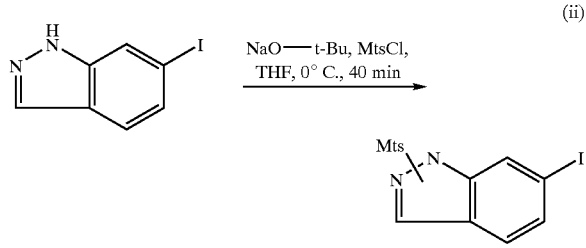

(ii)

To a solution of 6-iodo-1H-indazole (7.35 g, 30.1 mmol, 1 equiv) in THF (100 mL) cooled to 0° C. under argon, was added sodium t-butoxide (2.89 g, 30.1 mmol, 1 equiv). A color change from orange to red was observed. Mesitylenesulfonyl chloride (6.60 g, 30.1 mmol, 1 equiv) was added in one portion and the ice bath was removed allowing the reaction mixture to warm to 23° C. After 40 min the mixture was quenched with saturated ammonium chloride and partitioned between water and ethyl acetate. The aqueous was extracted a total of 3 times with ethyl acetate. The combined organic material was washed with brine, dried over sodium sulfate and concentrated under reduced pressure to give 6-iodo-1-(2,4,6-trimethyl-benzenesulfonyl)-1H-indazole as an orange solid (12.8 g, 100% yield, 2:1 mixture). $^1$H NMR (CDCl$_3$) 8.51 (s, 1H), 7.95 (s, 0.66H, major isomer), 7.91 (s, 0.33H, minor isomer), 7.47 (d, 0.33H, J=8.4 Hz), 7.29 (d, 0.33H, J=8.4 Hz), 7.26 (d, 0.66H, J=8.9 Hz), 7.18 (d, 0.66H, 8.9 Hz), 6.84 (s, 2H), 2.51 (s, 6H), 2.15 (s, 3H).

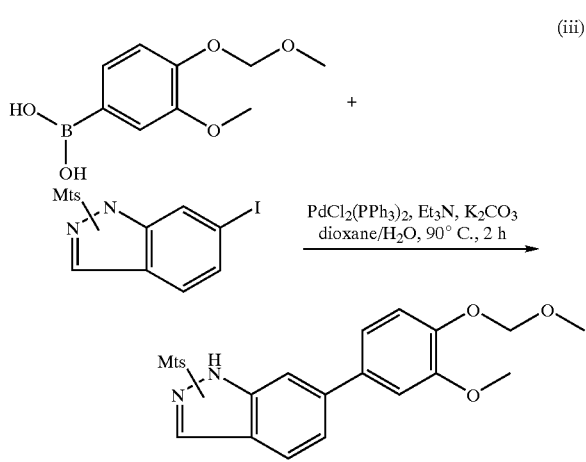

(iii)

A mixture of 6-iodo-1-(2,4,6-trimethyl-benzenesulfonyl)-1H-indazole (5.78 g, 13.56 mmol, 1.00 equiv) and 3-methoxy-4-(methoxymethoxy)benzene-boronic acid (3.45 g, 16.27 mmol, 1.20 equiv) under argon was dissolved in dioxane (15 mL) and water (2.0 mL). To this solution was added triethylamine (2.83 mL, 20.3 mmol, 1.5 equiv), potassium carbonate (2.8 g. 20.3 mmol, 1.5 equiv) and dichlorobis(triphenylphosphine)palladium (476 mg, 0.678 mmol, 0.05 equiv). The reaction mixture was heated to 90° C. for 2 h and then was cooled to 23° C. The mixture was separated between ethyl acetate (250 mL) and saturated sodium bicarbonate (150 mL). The organic material was dried over sodium sulfate, decanted and concentrated under reduced pressure to give crude 6-(3-methoxy-4-methoxymethoxy-phenyl)1-(2,4,6-triethyl-benzenesulfonyl)-1H-indazole that was dried under high vacuum for 15 h and was used without further purification.

3-Methoxy-4-(methoxymethoxy)benzeneboronic acid was prepared as follows: In a 100 mL flask a mixture of 50% KOH in water (20 g KOH, 7 equiv, 20 g ice) was prepared under argon. To this rapidly stirring mixture at 0° C. (maintained with an ice bath) was added dichloromethane (50 mL) followed by 4-bromo-2-methoxyphenol (10.1 g, 50 mmol, 1.00 equiv), methoxymethylchloride (MOMCl) (4.00 mL, 42.5 mmol, 1.05 equiv) and tetrabutylammonium bromide (322 mg, 1 mmol, 0.02 equiv). The bath was removed and the mixture was slowly allowed to warm to 23° C. with rapid stirring for 2 h. The mixture is transferred to a separatory funnel and diluted with dichloromethane (350 mL) and water (300 mL) which are used to aid the transfer. The organic material (now the bottom layer) are separated, dried over sodium sulfate, decanted and concentrated under reduced pressure to give 4-bromo-2-methoxy-1-(methoxymethoxy)benzene as a yellow liquid which is pure by $^1$H NMR (11.9 g, 97%): $^1$H NMR (CDCl$_3$) δ 7.0 (s, 3H), 5.13 (s, 2H), 3.84 (s, 3H), 3.47 (s, 3H). MS (EI) [m+H]/z Calc'd 235, found 235. In a 50 mL round-bottom flask, 4-bromo-2-methoxy-1-(methoxymethoxy)benzene (4.80 g, 19.4 mmol, 1.00 equiv) was taken up in THF (35 mL) and was cooled to −78° C. (20 min for this volume). To this was added n-BuLi (12.75 mL, 1.6 M in hexane, 20.4 mmol. 1.05 equiv) and the mixture was allowed to stir at −78° C. for 40 min. This was then added via cannula to a second flask containing B(OMe)$_3$ (22 mL, 194 mmol, 10 equiv) in THF (50 mL) at −78° C. After 20 min, the cold bath was removed. After 15 min of warming (~0° C., ice on the side of the flask begins to melt) water (50 mL) was added to the reaction mixture which was stirred for 45 min. The mixture was concentrated under reduced pressure to remove most THF and was then partitioned between ethyl acetate (300 mL) and water (150 mL) which was made acidic by addition of a small amount of 20% citric acid (~10 mL). The organic material was dried over sodium sulfate and concentrated under reduced pressure to give a solid. Trituration with ethyl acetate (10 mL) and hexane (5 mL) followed by filtering gave 3-methoxy-4-(methoxymethoxy)benzene-boronic acid as a white solid (3.15 g, 77%): R$_f$ sm 0.59, p 0.18 (ethyl acetate-hexane 1:1); $^1$H NMR (CDCl$_3$) δ 7.85 (d, 1H, J=8 Hz), 7.72 (s, 1H), 7.22 (d, 1H, J=8 Hz), 5.30 (s, 2H), 4.00 (s, 3H), 3.55 (s, 3H).

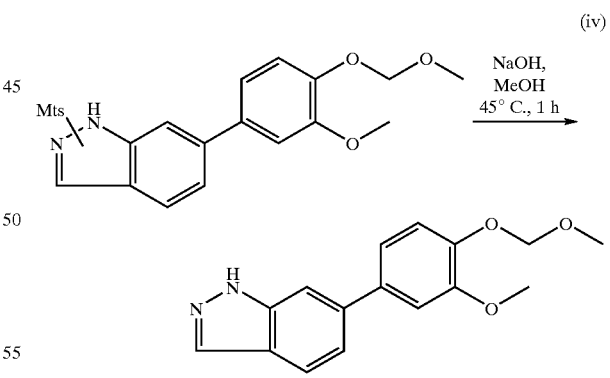

(iv)

Unpurified 6-(3-methoxy-4-methoxymethoxy-phenyl)-1-(2,4,6-trimethyl-benzenesulfonyl)-1H-indazole (under argon) was dissolved in THF (20 mL) and was treated with 1N NaOH in MeOH (70 mL degassed by bubbling through argon for 3 to 5 min). The mixture was heated to 45° C. for 1 h and allowed to cool. The mixture was neutralized by addition of 1N HCl (50 mL) followed by saturated sodium bicarbonate (200 mL). The product was extracted into ethyl acetate (350 mL), dried over sodium sulfate and concentrated under reduced pressure to give crude 6-(3-methoxy- 4-methoxymethoxy-phenyl)-1H-indazole. Purification by silica gel chromatography (500 mL silica, 20% ethyl acetate in benzene (1.8 L), 30% ethyl acetate in benzene (1.8 L)) gave 6-(3-methoxy-4-methoxymethoxy-phenyl)-1H-indazole (1.19 g, 31%): $^1$H NMR (CDCl$_3$) δ 7.80 (s, 1H), 7.69 (d, 1H, J=8.5 Hz), 7.52 (s, 1H), 7.29 (d, 1H, J=8.5 Hz), 7.16 (s, 1H), 7.13 (s, 1H), 7.08 (s, 1H). MS (ES) [m+Na]/z Calc'd 337, found 337; [m+H]/z Calc'd 349, found 349.

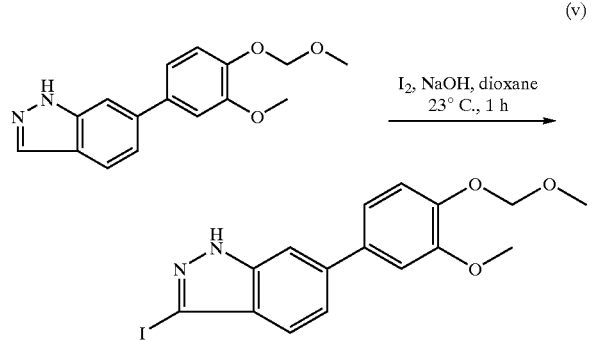

(v)

In a 100-mL round-bottom flask under argon, 6-(3-methoxy-4-methoxymethoxy-phenyl)-1H-indazole (1.19 g, 4.18 mmol, 1 equiv) was dissolved in dioxane (25 mL) and 3N NaOH (14 mL). This mixture was treated with iodine (1.17 g, 14.60 mmol, 1.10 equiv) added in ~5 portions (~10 min). Several (~4) additional portions of iodine (50 mg each) were added until the reaction was complete as visualized by TLC (3:7 ethyl acetate/hexane). The mixture was acidified with 20% citric acid (25 mL) and 5% NaHSO3 (20 mL) was added. The mixture was partitioned between ethyl acetate (150 mL) and water (100 mL). The organic material was washed with saturated sodium bicarbonate (80 mL) and brine (50 mL) and were dried over sodium sulfate and concentrated under reduced pressure. Purification by crystallization from ethyl acetate (3 mL) then hexane (7 mL) gave pure 3-iodo-6-(3-methoxy-4-methoxymethoxy-phenyl)-1H-indazole as a solid (1.33 g, 78%): $^1$H NMR (CDCl$_3$) δ 10.48 (bs, 1H), 7.62 (s, 1H), 7.57 (d, 1H, J=8.5 Hz), 7.47 (dd, 1H, J=1.3, 8.5 Hz), 7.18 (m, 3H), 5.29 (s, 2H), 3.99 (s, 3H), 3.55 (s, 3H).

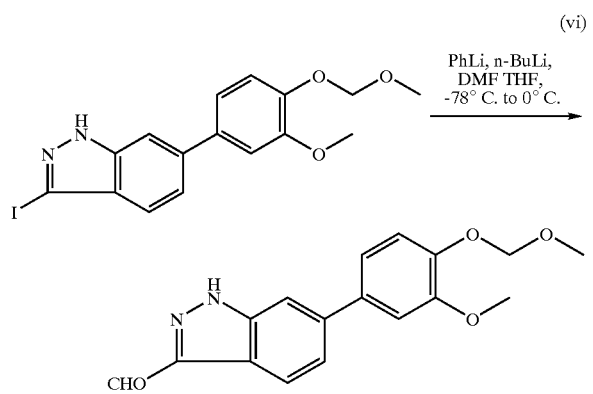

(vi)

In a 100 mL round-bottom flask, 3-iodo-6-(3-methoxy-4-methoxymethoxy-phenyl)-1H-indazole (921 mg, 2.245 mmol, 1.00 equiv) was dissolved in THF (36 mL) and cooled to −78° C. (allow 8 min at this scale). A solution of PhLi (25 mL 1.8 M, 4.49 mmol, 2.00 equiv) was added and the mixture was allowed to stir for 30 min. A solution of s-BuLi (3.63 mL, 4.71 mmol, 2.1 equiv) was added and the reaction mixture was allowed to stir for 1 h at −78° C. Neat DMF (1.4 mL, 18 mmol, 8.0 equiv) was added. The cold bath was removed and the reaction was allowed to slowly warm to 0° C. in the air. As the ice melted saturated sodium bicarbonate (20 mL) was added. The product was extracted into ethyl acetate (200 mL) from saturated sodium bicarbonate (75 mL more), dried over sodium sulfate, decanted and concentrated under reduced pressure. Purification by silica gel chromatography (450 mL silica, 4:6 ethyl acetate/hexane) gave 6-(3-methoxy-4-methoxymethoxy-phenyl)-1H-indazole-3-carbaldehyde (498 mg, 71%)): R$_f$ sm 0.30, p 0.14 (ethyl acetate-hexane 4:6); $^1$H NMR (CDCl$_3$) δ 10.85 (bs, 1H), 10.25 (s, 1H), 8.37 (d, 1H, J=8.4 Hz), 7.67 (s, 1H), 7.60 (d, 1H, J=8.4 Hz), 6.26 (d, 1H, J=8.7 Hz), 7.19 (m, 2H), 5.30 (s, 2H), 3.99 (s, 3H), 3.55 (s, 3H).

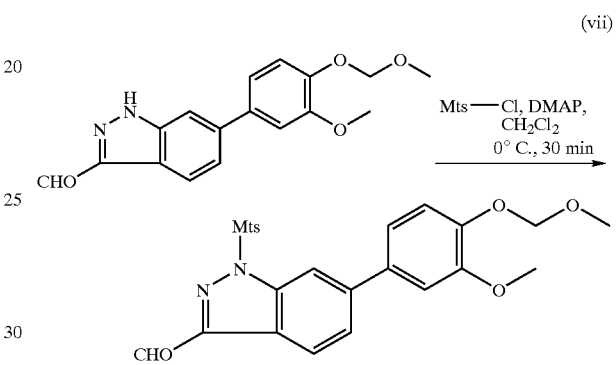

(vii)

6-(3-methoxy-4-methoxymethoxy-phenyl)-1H-indazole-3-carbaldehyde (441 mg, 1.41 mmol, 1.0 equiv) was taken up as a suspension in dichloromethane (15 mL) and was cooled to 0° C. This mixture was treated with mesitylene sulfonyl chloride (324 mg, 1.48 mmol, 1.05 equiv) and dimethylamino pyridine (DMAP) (181 mg, 1.48 mmol, 1.05 equiv). The mixture was allowed to stir for 1 h at 0° C. and was quenched with the addition of water. The mixture was partitioned between water and a 1:1 ethyl acetate/hexane organic layer. The organic material was dried over sodium sulfate, decanted and concentrated under reduced pressure to give crude material which was purified by silica gel chromatography (50 mL silica, 3:7 ethyl acetate/hexane) to give 6-(3-methoxy-4-methoxymethoxy-phenyl)-1-(2,4,6-trimethyl-benzenesulfonyl)-1H-indazole-3-carbaldehyde (374 mg, 54%): R$_f$ sm 0.17, p 0.53 (ethyl acetate-hexane 4:6); $^1$H NMR (CDCl$_3$) δ 10.20 (s, 1H), 8.41 (s, 1H), 8.37 (d, 1H, J=8.5 Hz), 7.73 (dd, 1H, J=1.4, 8.4 Hz), 7.3 (m, 3H), 7.08 (s, 2H), 5.36 (s, 2H), 4.08 (s, 3H), 3.71 (s, 3H), 2.74 (s, 6H), 2.40 (s, 3H).

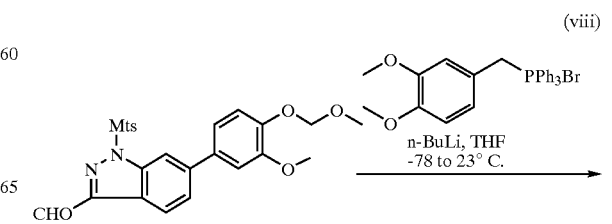

(viii)

-continued

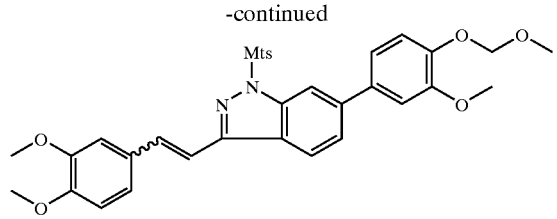

Finely ground triphenyl(3,4-dimthoxybenzyl) phosphonium bromide (1.09 g, 2.22 mmol, 4.0 equiv) was taken up as a slurry in THF (15 mL) and was cooled to −78° C. To this mixture was added n-BuLi (1.04 mL, 1.6 M, 1.66 mmol, 3.0 equiv) which gave a red/orange solution. The mixture was allowed to warm to 23° C. for 1 h. This mixture was then added to a 0° C. solution of 6-(3-methoxy-4-methoxymethoxy-phenyl)-1-(2,4,6-trimethyl-benzenesulfonyl)-1H-indazole-3-carbaldehyde (274 mg, 0.554 mmol, 1.0 equiv) in THF (5 mL) via cannula. The resulting mixture was allowed to stir at 0° C. for 10 min and was quenched with saturated sodium bicarbonate. The resulting mixture was partitioned between saturated sodium bicarbonate and ethyl acetate. The organic material was concentrated under reduced pressure and the residue was purified by silica gel chromatography (50 mL silica. 3:7->4:6 ethyl acetate/hexane) to give a 2.5:1 mixture of cis/trans 3-[2-(3,4-dimethoxy-phenyl)vinyl]-6-(3-methoxy-4-methoxymethoxy-phenyl)-1-(2,4,6-trimethyl-benzenesulfonyl)-1H-indazole (289 mg, 83%): $R_f$ sm 0.53, p 0.32 (ethyl acetate-hexane 4:6); $^1$H NMR (CDCl$_3$) δ 8.35 (s, 0.3H), 8.32 (s, 0.7H), 8.03 (d, 0.3H, J=8.4 Hz), 7.60–6.85 (m, H), 6.65 (d, 0.7H, J=8.4 Hz), 6.60 (d, 0.7H, J=12.5 Hz), 5.30 (s, 0.6H), 5.29 (s, 1.4H), 4.00–3.50 (8 singlets, 12H), 2.72 (s, 1.8H), 2.67 (s. 4.2H), 2.34 (s, 3H); MS (ES) [m+H]/z Calc'd 629, found 629, [m−H]/z Calc'd 627, found 627.

(ix)

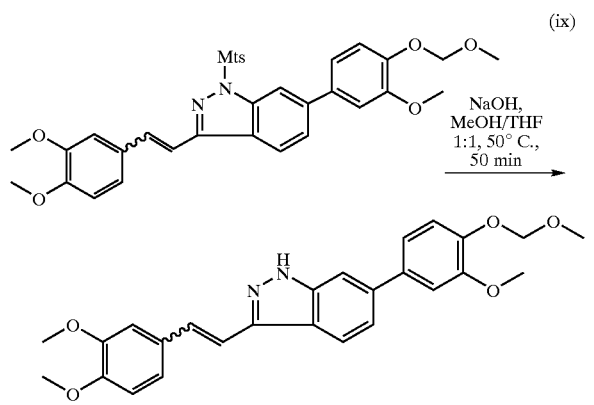

A 1M solution of KOH (1.0 g, 17.8 mmol) in 1:1 water/MeOH (18 mL total) was prepared under argon and was degassed by vacuum/purge cycles with argon (5 times). In a separate flask, 3-[2-(3,4-dimethoxy-phenyl)-vinyl]-6-(3-methoxy-4-methoxymethoxy-phenyl)-1-(2,4,6-trimethyl-benzenesulfonyl)-1H-indazole (289 mg, 0.461 mmol, 1.0 equiv) was dissolved in THF (8 mL) under argon. To this solution was added the above 1M KOH solution (10 mL, 1:1 water/MeOH). The reaction was warmed to 30° C. and was allowed to stir for 7 h. The reaction mix was neutralized by the addition of 20% citric acid (7 mL). The resulting mix was partitioned between ethyl acetate (150 mL) and water (100 mL). The organic material was separated, dried over sodium sulfate, decanted, and concentrated under reduced pressure to give cis and trans 3-[2-(3,4-dimethoxy-phenyl)vinyl]-6-(3-methoxy-4-methoxymethoxy-phenyl) 1H-indazole (used crude): $R_f$ sm 0.46, p1 0.17, p2 0.23 (ethyl acetate-hexane 1:1); $^1$H NMR cis isomer (CDCl$_3$) δ 7.55 (s, 1H), 7.3–7.1 (m, 6H), 7.02 (dd, 1H, J=1.9, 8.3 Hz), 6.85 (d, 1H, J=12.5 Hz), 6.78 (d, 1H, J=12.5 Hz), 6.74 (d, 1H, 3=8.3 Hz), 5.21 (s, 2H), 3.88 (s, 3H), 3.70 (s, 3H), 3.43 (s, 3H), 3.42 (s, 3H). MS (ES) [m+H]/z Calc'd 447, found 447, [m−H]/z Calc'd 445, found 445.

Example 1(b)

3-(E-styryl)-6-(3-benzyloxy-4-hydroxy-phenyl)-1H-indazole

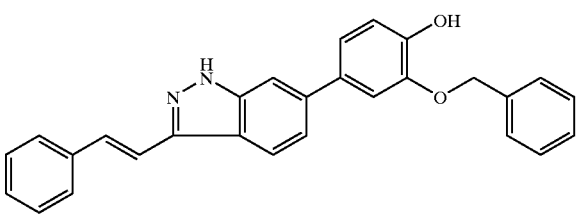

Example 1(b) was prepared in a similar manner to that described for Example 1(a), except that 4-bromo-2-benzyloxy-phenol was used in step(iii) in place of 4-bromo-2-methoxy-phenol. $R_f$ sm 0.35, p 0.30 (ethyl acetate-hexane 4:6); $^1$H NMR (CDCl$_3$) δ 8.06 (d, 1H, J=8.6 Hz), 7.63–7.18 (m, 17H), 7.05 (d, 1H, J=8.2 Hz), 5.19 (s, 2H). MS (CI) [m+H]/z Calc'd 419, found 419, [m−H]/z Calc'd 417, found 417.

Example 1(c)

3-[E-2-(3,4-Dimethoxy-phenyl)vinyl]-6-(3-allyloxy-4-hydroxy-phenyl)-1H-indazole

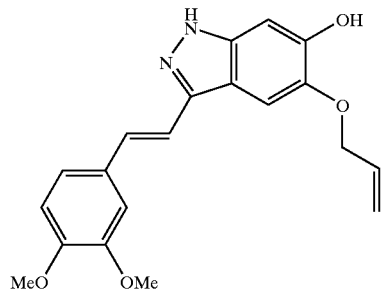

Example 1(c) was prepared in a similar manner to that described for Example 1(a), except that 3-allyloxy4-(methoxymethoxy)benzene-boronic acid was used instead of 3-methoxy 4(methoxymethoxy)benzene-boronic acid in step (iii). MS (ESI) [M+H]/z Calc'd 429, found 429; MS (ESI) [M−H]/z Calc'd 427, found 427.

Example 2(a)

3-(Naphthalen-2-yl)(3-methoxy-4-hydroxy-phenyl)-1H-indazole

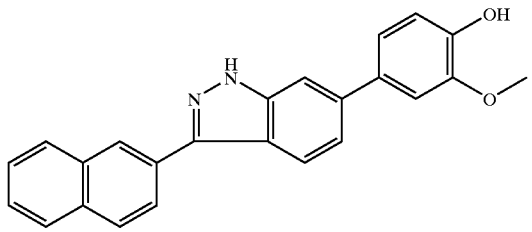

6-(4-Benzyloxy-3-methoxy-phenyl)-3-naphthalen-2-yl-H-indazole (25 mg, 0.055 mmol) was dissolved in a mixture of ethyl acetate (2 mL), benzene (2 mL) and methanol (2 mL). To this solution was added palladium on carbon (25 mg, 10% wt) and the reaction vessel was vacuum/purged with hydrogen gas for five cycles. The reaction mixture was allowed to stir for 3 days (d) at 23° C. and was filtered through a plug of Celite. Concentration and purification by silica gel chromatography afforded 3-(Naphthalen-2-yl)-6-(3-methoxy-4-hydroxy-phenyl)-1H-indazole (8 mg, 40%): $^1$H NMR (CDCl$_3$) δ 10.3 (bs, 1H), 8.50 (s, 1H), 8.20 (d, 1H, J=8 Hz), 7.98 (d, 1H, J=8 Hz), 7.90 (m, 1H), 7.7–6.8 (m, 9H), 3.98 (s, 3H). MS (ES) [m+H]/z Calc'd 367, found 367, [m−H]/z Calc'd 365, found 365.

The starting material was prepared as follows:

(i)

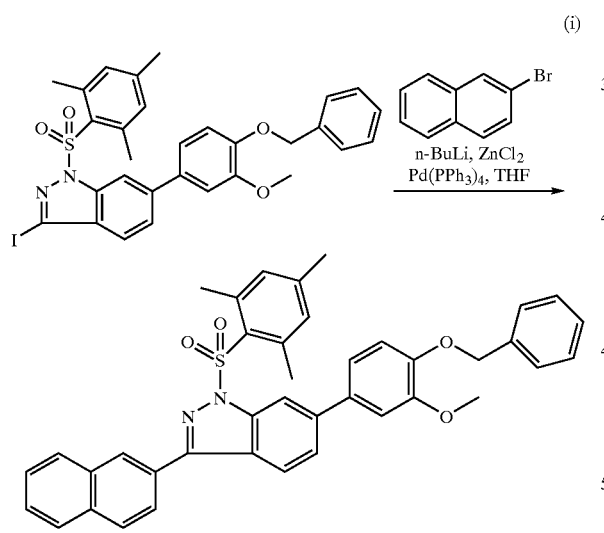

2-Bromonaphthalene (117 mg, 0.564 mmol, 6.0 equiv) was dissolved in TH (0.75 mL) and cooled to −78° C. The mixture was treated with n-BuLi (226 μL, 2.5 M, 6.0 equiv) and was allowed to stir at −78° C. for 30 min. The mixture was then added to freshly dried ZnCl$_2$ solid (139 mg, 0.80 mmol, 8.5 equiv) via cannula and the resulting mix was allowed to warm to 23° C. (during the addition the yellow color disappears). After 30 min at 23° C. the mixture is added to a mixture of 6-(4-benzyloxy-3-methoxy-phenyl)-3-iodo-1-(2,4,6-trimethyl-benzenesulfonyl)-1H-indazole (60 mg, 0.094 mmol, 1 equiv) and Pd(PPh$_3$)$_4$ (6 mg, 0.005 mmol, 0.05 equiv) via cannula The resulting solution was allowed to stir for 16 h. Saturated sodium bicarbonate was added and the mixture was partitioned between saturated sodium bicarbonate (15 mL) and ethyl acetate (15 mL). The organic material was dried over sodium sulfate, decanted and concentrated. Purification by silica gel chromatography (1:9–2:8 ethyl acetate-hexane) gave 6-(4-benzyloxy-3-methoxy-phenyl)-3-naphthalen-2-yl-1-(2,4,6-trimethyl-benzenesulfonyl)-1H-indazole as a solid (42 mg, 70%): R$_f$ sm 0.4, p 0.4 (ethyl acetate-hexane 3:7); $^1$H NMR (CDCl$_3$) δ 8.44 (s, 1H), 8.41 (s, 1H), 8.12 (d, 1H, J=8 Hz), 8.05–7.00 (m, 17H), 5.30 (s, 2H), 4.02 (s, 3H), 2.80 (s, 3H), 2.34 (s, 3H).

6-(4-benzyloxy-3-methoxy-phenyl)-3-iodo-1-(2,4,6-trimethyl-benzenesulfonyl)-1H-indazole was prepared in a similar manner as described in Example 1(a), steps (i) to (v).

(ii)

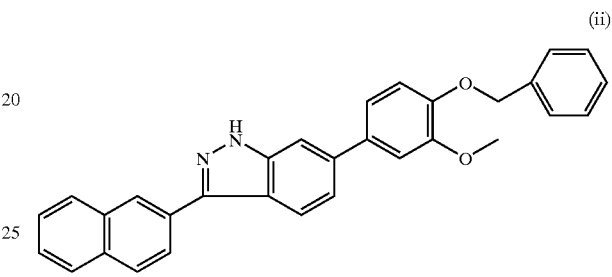

6-(4-Benzyloxy-3-methoxy-phenyl)-3-naphthalen-2-yl-1-(2,4,6-trimethyl-benzenesulfonyl)-1H-indazole was converted to 6-(4-benzyloxy-3-methoxy-phenyl)-3-naphthalen-2-yl-1H-indazole as described in Example 1(a), step (ix). R$_f$ sm 0.40, p 0.17 (ethyl acetate-hexane 3:7); $^1$H NMR (CDCl$_3$) δ 8.40 (s, 1H), 8.12 (d, 1H, J=8.5 Hz), 8.10 (dd, 1H, J=1.6, 8.4 Hz), 7.93 (d, 1H, J=8.3 Hz), 7.88 (m, 2H), 7.61 (m, 1H) 7.56 (s, 1H), 7.43 (m, 5H), 7.30 (m 3H), 7.15 (d, 1H, J=2.0 Hz), 7.08 (dd, 1H, J=2.1, 8.3 Hz), 6.91 (d, 1H, J=8.3 Hz), 5.16 (s, 2H), 3.91 (s, 3H).

Example 2(b)

3-phenyl-6-(3-methoxy-4-hydroxy-phenyl)-1H-indazole

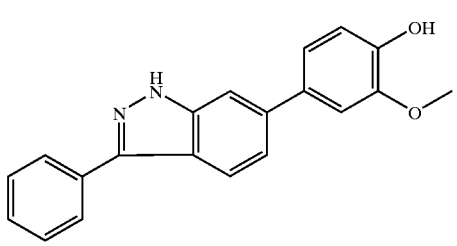

Example 2(b) was prepared in a similar manner to that described for Example 2(a), except that phenyllithium was used in place of 2-napthyllitium generated from 2-bromonaphthylene in step (i). $^1$H NMR (300 MHz, CDCl$_3$) δ 7.87 (d, 1H), 7.83 (d, 2H), 755–7.27 (m, 5H), 7.01 (m, 2H), 6.80 (d, 1H), 3.83 (s, 3H). MS (ES) [m+H]/z Calc'd 317, Found 317, [m−H]/z Calc'd 315, found 315.

Example 2(c)

3-(3,4,5-trimethoxyphenyl)-6-(3-methoxy-4-hydroxy-phenyl)-1H-indazole

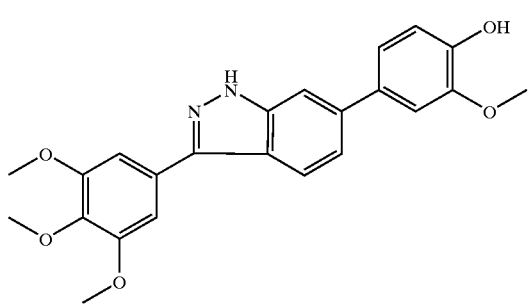

Example 2(c) was prepared in a similar manner to that described for Example 2(a), except that 3,4,5-trimethoxyphenyl bromide was used in step (i) in place of 2-bromonaphthylene. $R_f$ sm 0.67, p 0.38 (ethyl acetate-hexane 8:2); $^1$H NMR (CDCl$_3$) δ 7.93 (d, 1H, J=8 Hz), 7.58 (s, 1H), 7.39 (d, 1H, J=8 Hz), 7.10 (m, 4H), 6.92 (d, 1H, J=8 Hz), 3.90 (s, 9H), 3.85 (s, 3H); MS (ES) [m+H]/z Calc'd 407, Found 407, [m–H]/z Calc'd 405, Found 405.

Example 2(d)

3-(1H-Indol-2-yl)-6-(3-methoxy-4-hydroxy-phenyl)-1H-indazole

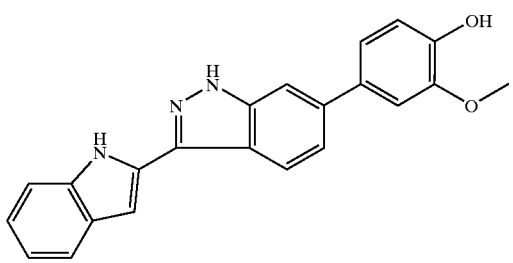

Example 2(d) was prepared in a similar manner to that described for Example 2(a) above, except that 1-phenylsulfonyl-indazole was used in place of 2-bromonaphthylene in step (i). $R_f$ sm 0.20, p 0.15 (ethyl acetate-hexane 4:6); $^1$H NMR (CDCl$_3$) δ 10.0 (bs, 1H), 9.05 (bs, 1H), 8.01 (d, 1H, J=8.0 Hz), 7.55 (d, 1H, J=8.0 Hz), 7.49 (s, 1H), 7.37 (d, 1H, J=8 Hz), 7.29 (d, 1H, J=8 Hz), 7.2–7.1 (m, 5H), 6.92 (d, 1H, J=8 Hz), 5.63 (bs, 1H); MS (ES) [m+H]/z Calc'd 356, Found 356; [m–H]/z Calc'd 354, found 354.

Example 2(e)

3-(Benzofuran-2-yl)-6-(3-benzyloxy-4-hydroxy-phenyl)-1H-indazole

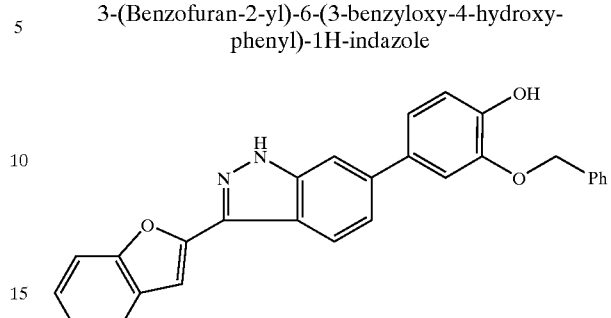

Example 2(e) was prepared in a similar manner to that described for Example 2(a) above, except that benzofuran was used in place of 2-bromonaphthylene in step (i). $^1$H NMR (CDCl$_3$) δ 8.21 (d, 1H, J=8.0 Hz), 7.60 (m, 3H), 7.30.7.10 (m, 12H), 7.01 (d, 1H. J=8 Hz), 5.82 (bs, 1H), 5.15 (s, 3H).

Example 3

3-(1H-Indol-2-yl)-6-(3-methoxy-4-hydroxy-phenyl)-1H-indazole

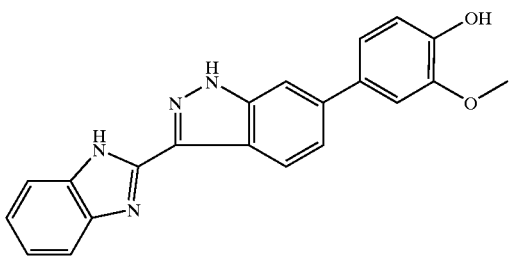

3-(1H-Benzoimidazol-2-yl)-6-(3-methoxy-4-methoxymethoxy-phenyl)-1H-indazole was converted to 4-[3-(1H-benzoimidazol-2-yl)-1H-indazol-6-yl]-2-methoxy-phenol according to the procedure described in Example 1(a) (3.5 mg, 28%). HRMS (FAB) [m+H]/z Calc'd 357.1351, Found 357.1349.

The starting material was prepared as follows:

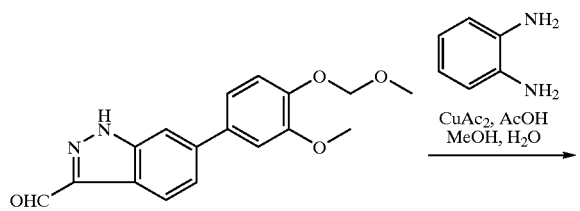

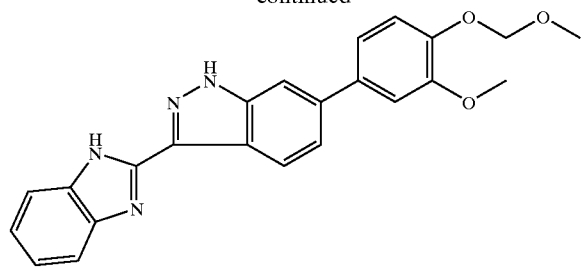

6-(3-Methoxy-4-methoxymethoxy-phenyl)1H-indazole-3-carbaldehyde (from Example 1(a), step (vi)) (20 mg, 0.064 mmol, 1 equiv) was dissolved in degassed 1:1 MeOH-water (0.7 mL) and was treated with acetic acid (19 μL 5 equiv), 1,2-diaminobenzene (8.3 mg, 1.2 equiv) and copper(II) acetate (18 mg, 1.4 equiv) at 23° C. The mixture stirred for 30 min, was diluted with ethanol (3 mL) and water (2 mL) and was treated with a bubbling stream of $SH_2$ for 3 min, which gave a black precipitate. The mixture was allowed to stir for 12 h. The mixture was filtered and concentrated. Purification by silica gel chromatography (6:4 ethyl acetate-hexane) gave 3-(1H-benzoimidazol-2-yl)-6-(3-methoxy-4-methoxymethoxy-phenyl)-1H-indazole as a solid (14 mg, 54%); $R_f$ sm 0.39, p 0.24 (ethyl acetate-hexane 6:4); $^1$H NMR (CDCl$_3$) δ 8.69 d, 1H, J=8 Hz), 7.70 (bs, 2H), 7.58 (s, 1H), 7.53 (d, 1H, J=8 Hz), 7.30–7.15 (m, 7H), 5.30 (s, 2H), 3.97 (s, 3H), 3.58 (s, 3H); MS (ES) [m+H]/z Calc'd 401, found 401, [m–H]/z Calc'd 399, found 399.

Example 4(a)

N-[3-(3-Styryl-1H-indazol-6-yloxy)-phenyl]-benzamide

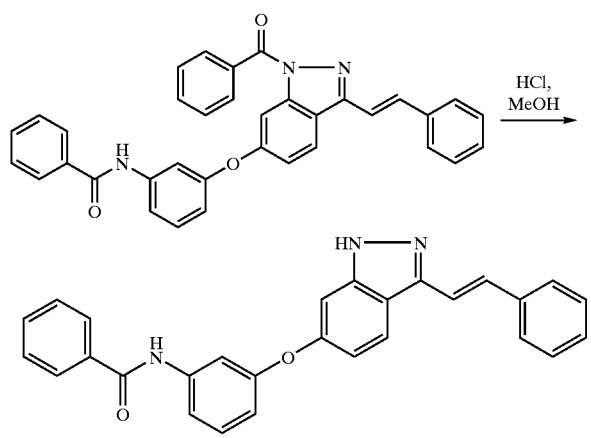

A solution of N-[3-(2-benzoyl-3-styrl-1H-indazol-6-yloxy)phenyl]-benzamide (0.09 g, 0.17 mmol) in 2 mL of 6N HCl (aqueous) and 3 mL of MeOH was heated at 65° C. for about 4 h. The cooled solution was poured cautiously into saturated sodium bicarbonate solution. The precipitate was filtered, collected and chromatographed on silica gel eluting hexanes/EtOAc (1:1). N-(3-(3-Styryl-1H-indazol-6-yloxy)-phenyl]-benzamide was obtained as a beige solid (32 mg, 50%): $^1$H NMR (DMSO-d$_6$) δ 13.50 (s, 1H), 10.32 (s, 1H), 8.23 (d, 1H, J=8.7 Hz), 7.92 (d, 2H, J=6.8 Hz), 7.72 (d, 2H, J=7.3 Hz), 7.71–7.51 (m, 7H), 7.51–7.47 (m, 3H), 7.30 (t, 1H, J=7.2 Hz), 7.05 (s, 1H), 7.01 (d, 1H, J=8.7 Hz), 6.86 (dd, 1H, J=8.2, 2.3 Hz). Anal. Calc. for $C_{28}H_{21}N_3O_2 \cdot 0.3H_2O$: C, 76.97; H, 4.98: N, 9.62. Found: C, 76.94; H, 5.13; N, 9.40.

The starting material was prepared as follows:

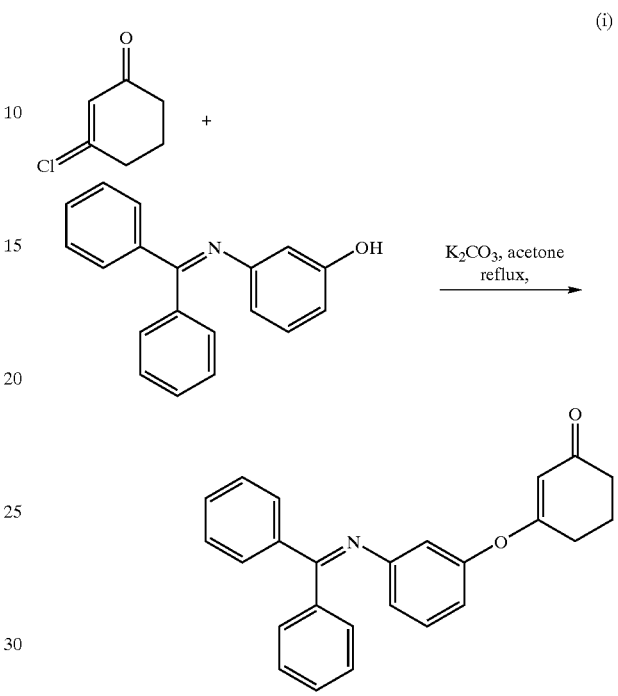

(i)

A suspension of the (benzhydrylidene-amino)-phenol (10.47 g, 38.3 mmol), 3-chloro-cyclohex-2-enone (5.00 g, 38.3 mmol) and potassium carbonate (5.82, 42.1 mmol) in 150 mL of acetone was heated at reflux overnight. The cooled reaction mixture was filtered and concentrated under reduced pressure. The residue was chromatographed on silica gel eluting hexanes/EtOAc (2:1). In this manner, 3-[3-(benzhydrylidene-amino)phenoxy]-cyclohex-2-enone was obtained as a yellow solid, (8.82 g, 63%): $^1$H NMR (CDCl$_3$) δ 7.78 (d, 2H, J=7.0 Hz), 7.50 (d, 1H, J=7.1 Hz), 7.45 (d, 2H, J=7.7 Hz), 7.347.10 (m, 6H), 6.69 (d, 1H, J=8.0 Hz), 6.61 (d, 1H, J=8.0 Hz), 6.38 (s, 1H), 4.89 (s, 1H), 2.55 (t, 2H, J=6.2 Hz), 2.34 (t, 2H, J=6.2 Hz), 2.06 (m, 2H). Anal. Calc. for $C_{25}H_{21}NO_2$ $0.2H_2O$: C, 80.92; H, 5.81; N, 3.78. Found: C, 81.12; H, 5.81; N, 3.72.

3-(Benzhydrylidene-amino)-phenol was prepared as follows: A stirred solution of benzophenone imine (15.0 g, 82.8 mmol) and 3-aminophenol (9.03 g, 82.8 mmol) in 25 mL toluene was heated at reflux with removal of $H_2O$ with a Dean-Stark trap for 3.5 h. The crystals that formed from the cooled reaction mixture were collected by vacuum filtration, washed with hexanes and air dried. In this manner, 3-(benzhydrylidene-amino)phenol was obtained as a light yellow solid (17.3 g, 76%): $^1$H NMR (CDCl$_3$) & 7.64 (d, 2H, J=7.1 Hz), 7.38 (d, 1H, J=7.1 Hz), 7.34–7.15 (m, 7H), 7.04 (d, 2H, J=7.2 Hz), 6.88 (t, 1H, J=8.1 Hz), 6.82 (d, 1H, J=8.2 Hz), 6.23 (s, 1H), 6.21 (d, 1H, J=7.8 Hz). Anal. Calc. for $C_{19}H_{15}NO$: C, 83.49; H, 5.53; N, 5.12. Found: C, 83.51; H, 5.65; N, 5.03.

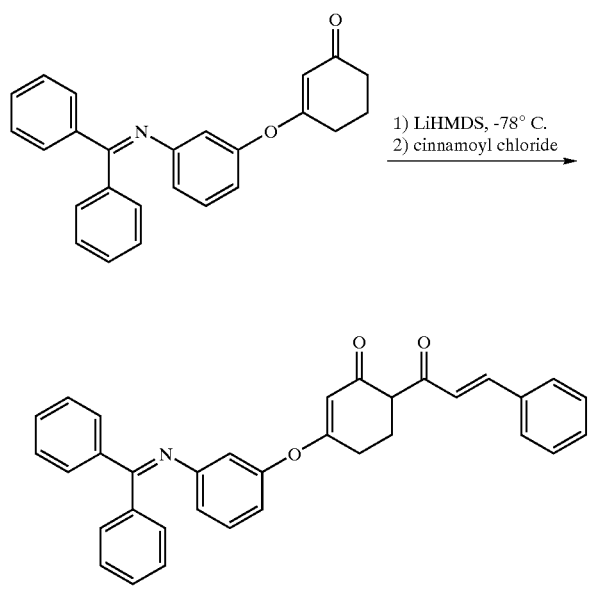

A solution of 3-[3-(benzhydrylidene-amino)phenoxy]-cyclohex-2-enone (4.37 g, 11.89 mmol) in 20 mL of THF was added slowly to a solution of LiHMDS (25.0 mL of 1.0 M solution in THF) in 10 mL of THF at −78° C. Five minutes after the addition was complete trans-cinnamoyl chloride (1.98 g, 11.89 mmol) was added all at once, and stirring was continued at −78° C. for 30 min. The reaction was quenched with saturated NH$_4$Cl solution. And extracted with EtOAc (2×). The combined organic layers were washed with saturated NaCl solution, dried (MgSO$_4$) and concentrated under reduced pressure. The residue was chromatographed on silica gel eluting hexanes/EtOAc (5:1). In this manner, 3-[3-(benzhydrylidene-amino) phenol]-6-(3-phenyl-acryloyl)cyclohex-2-enone was obtained as a yellow-orange solid (3.34 g, 56%): $^1$H NMR(CDCl$_3$) o: 15.69 (s, 1H), 7.80 (d, 2H, J=7.1 Hz), 7.63–7.01 (m, 15H), 6.93 (d, 1H, J=15.6 Hz), 6.75 (d, 1H, J=7.6 Hz), 6.66 (d, 1H, J=8.0 Hz), 6.46 (s, 1H), 4.92 (s, 1H), 2.85 (t, 2H. J=7.2 Hz), 2.62 (t, 2H, J=7.2 Hz). Anal. Calc. for C$_{34}$H$_{27}$NO$_3$: C, 82.07; H, 5.47; N, 2.82. Found: C, 81.88; H, 5.53; N, 2.81.

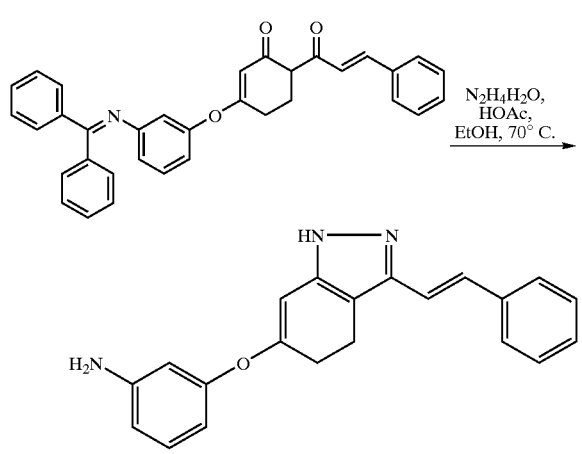

To a stirred solution of 3-[3(benzhydrylidene-amino)-phenol]-6-(3-phenyl-acryloyl)cyclohex-2-enone (1.81 g, 3.64 mmol) dissolved in 10 mL of HOAc/EtOH(1:1) was added hydrazine hydrate (2.0 mL, 41.23 mmol). The solution was heated at 75° C. for 25 min. After cooling, the reaction mixture was cautiously poured into saturated sodium bicarbonate solution and extracted with EtOAc (2×). The combined organic layer was washed with saturated NaCl solution, dried (MgSO$_4$) and concentrated under reduced pressure. The residue was chromatographed on silica gel eluting hexanes/EtOAc (1:1). 3-(3-Styryl-4,5-dihydro-1H-indazol-6-yloxy)-phenylamine was obtained as a yellow solid (539 mg, 45%). $^1$H NMR (DMSO-d$_6$) δ 7.55 (d, 2H, J=7.2 Hz), 7.38 (t, 2H, J=7.2 Hz), 7.27 (t, 1H, J=7.2 Hz), 7.05 (m, 3H), 6.38 (d, 1H, J=8.0 Hz), 6.31 (s, 1H), 6.23 (d, 1H, J=7.9 Hz), 5.52 (s, 1H), 5.26 (s, 2H), 2.92 (t, 2H, J=8.0 Hz), 2.58 (t, 2H, J=8.1 Hz). Anal. Calc. for C$_{21}$H$_{19}$N$_3$O.0.3H$_2$O: C, 75.33; H, 5.90; N, 1255. Found: C, 75.46; H, 5.96; N, 12.35.

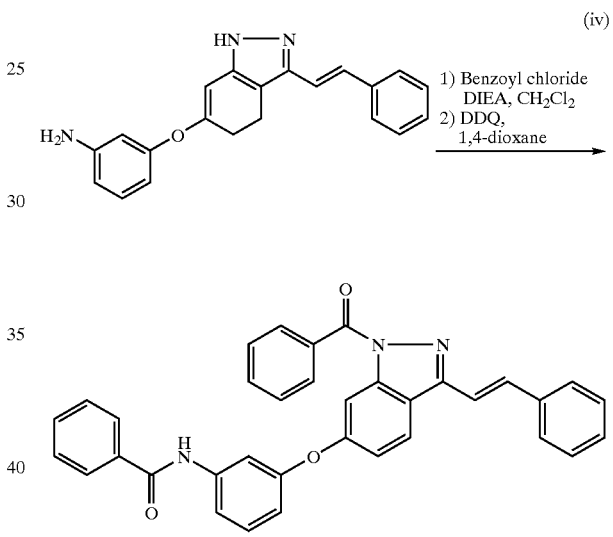

To a stirred solution of 3-(3-styryl-4,5-dihydro-1H-indazol-6-yloxy) phenylamine (50 mg, 0.15 mmol) and N,N-diisopropylethylamine (54 gi, 0.31 mmol) in 5 mL of CH$_2$Cl$_2$, was added benzoyl chloride (36 W, 0.31 mmol). After 15 mini, the reaction mixture was diluted with CH$_2$Cl$_2$ and washed sequentially with 0.5N HCl, saturated sodium bicarbonate solution and brine, dried (MgSO$_4$) and concentrated under reduced pressure. To a stirred solution of the residue in 1,4-dioxane was added 2,3-dichloro-5,6-dicyano-1,4-benzoquinone (DDQ) (35 mg, 0.15 mmol). After 1 h, the reaction mixture was concentrated under reduced pressure and the residue was chromatographed on silica gel eluting hexanes/EtOAc (2:1). In this manner, N-[3-(2-benzoyl-3-styrl-1H-indazol-6-yloxy)-phenyl]-benzamide was prepared as a rust colored solid (90 mg, quantitative): $^1$H NMR (CDCl$_3$) δ 8.13 (s, 1H), 8.02 (d, 2H, J=7.0 Hz), 7.94 (d, 1H, J=8.7 Hz), 7.74 (d, 2H, J=6.8 Hz), 7.57–7.19 (m, 17H), 6.84 (d, 1H, J=8.3 Hz).

Example 4(b)

N-[3-(3-Styryl-1H-indazol-6-yloxy)-phenyl]-acetamide

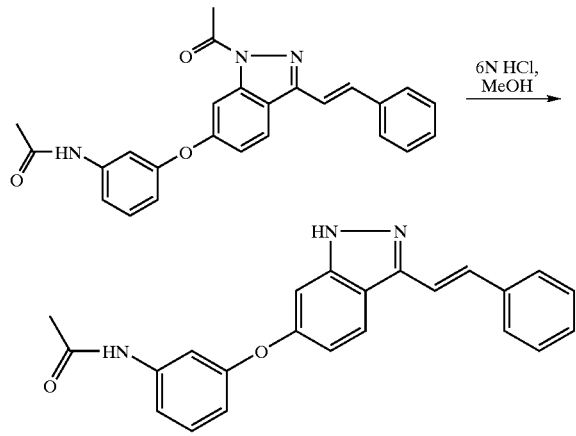

Example 4(b) was prepared in a similar manner to that described for Example 4(a) above, except that acetic anhydride was used instead of benzoyl chloride in step (iv). $^1$H NMR(DMSO-d$_6$) δ 13.08 (bs, 1H), 10.03 (s, 1H), 8.22 (d, 1H, J=8.7 Hz), 7.72(d, 2H, J=7.3 Hz), 7.52 (s, 2H), 7.447.27 (m, 6H), 7.01 (s, 1H), 6.96 (dd, 1H, J=8.7, 2.1 Hz), 6.78 (d, 1H, J=6.9 Hz), 2.01 (s, 3H). Anal. Calc. for C$_{23}$H$_{19}$N$_3$O$_2$.0.25H$_2$O: C, 73.88; H, 5.26; N. 11.24. Found: C, 74.20; H, 5.57; N, 10.82.

Example 5(a)

5-Methyl-thiazole-2-carboxylic acid {3-(3-styryl-1H-indazol-6-yloxy)-phenyl]-amide

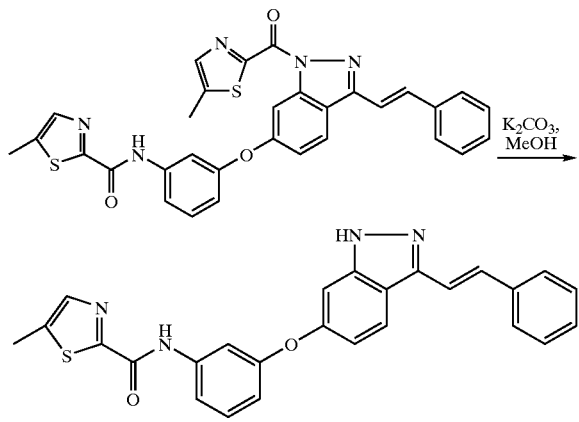

A suspension of S-methyl-thiazole-2-carboxylic acid {3-[1-(5-methyl-thiazole-2-carbonyl)-3-styryl-H-indazol-6-yloxyl-phenyl}amide (57 mg, 0.10 mmol) and potassium carbonate (50 mg, 0.36 mmol) in MeOH was stirred at 23° C. for 20 nm. The solution was filtered, diluted with EtOAc and washed with brine (2×). The organic layer was dried (MgSO$_4$) and concentrated under reduced pressure. In this manner, 5-methyl-thiazole-2-carboxylic acid {3-(3-styryl-1H-indazol-6-yloxy)-phenyl]-amide was prepared as a tan solid in 47% yield: $^1$H NMR (DMSO-d$_6$) δ 13.00 (s, 1H), 10.80 (s, 1H), 8.23 (d, 1H, J=8.8 Hz), 7.79 (s, 2H), 7.71 (t, 2H, J=8.6 Hz), 7.53 (s, 2H), 7.41–7.27 (m. 5H), 7.04 (s. 1H), 7.00 (d, 1H, J=8.7 Hz), 6.89 (d, 1H. J=8.5 Hz), 2.54 (s, 3H). Anal. Calc. for C$_{26}$H$_{20}$N$_4$O$_2$S 1.15H$_2$O: C, 65.98; H. 4.75; N, 11.84; S. 6.78. Found: C, 65.99; H. 4.71; N, 11.58; S, 6.76.

The starting material was prepared as follows:

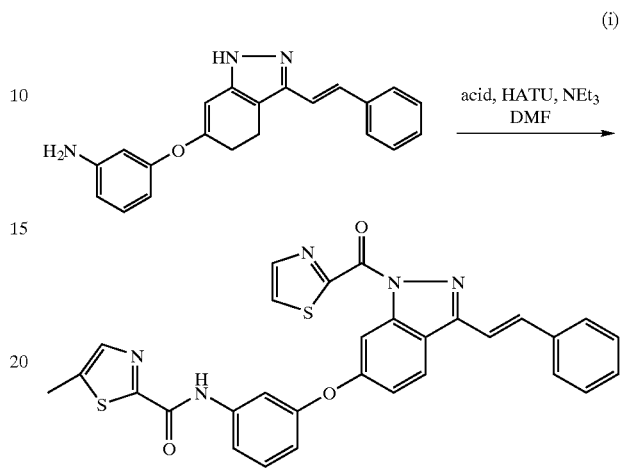

3-(3-Styryl-4,5-dihydro-1H-indazol-6-yloxy)-phenylamine was converted to 5-methyl-thiazole-2-carboxylic acid (3-[1-(5-methyl-thiazole-2-carbonyl)-3-styryl-1H-indazol-6-yloxy]-phenyl amide by treatment with 5-methyl-thiazole-2-carboxylic acid and HATU (o-(2-azabenzotriazol-1-yl)-N,N,N',N'-tetramethyluronium hexafluorophosphate) in DMF and analogous work-up, DDQ treatment and isolation to Example 4(a), step (iv) (50% yield): $^1$H NMR(DMSO-d$_6$) δ 10.85 (s, 1H), 8.45 (d, 1H, J=9.8 Hz), 8.24 (m, 3H), 7.99–7.62 (m, 6H), 7547.34 (m, 5H), 6.96 (d, 1H, J=8.5 Hz), 2.64 (s, 3H), 2.54 (s, 3H).

Example 5(b)

3-Methyl-N-[3-(3-styryl-1h-indazol-6-yloxy)-phenyl)-benzamide

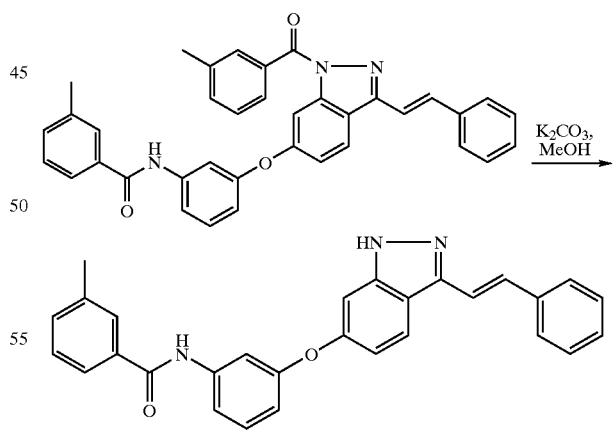

Example 5(b) was prepared in a similar manner to that described for Example 5(a) above, except that m-tolylchloride was used in place of 5-methyl-thiazole-2-carboxylic acid and HATU in step (i). $^1$H NMR (DMSO-d$_6$) δ 13.04 (s, 1H), 10.28 (s, 1H), 8.23 (d, 1H, J=8.8 Hz), 7.73–7.30 (m, 14H), 7.05 (s, 1H), 6.99 (d, 1H, J=8.5 Hz), 6.87 (d, 1H, J=7.7 Hz), 2.38 (s, 3H). Anal. Calc. for $C_{29}H_{23}N_3O_2 \cdot 0.2H_2O \cdot 0.2$ hexanes: C, 77.78; H, 5.66; N, 9.01. Found: C, 77.80; H, 5.84; N, 8.93.

Example 6(a)

N-(3-(3-[2-(4-Chloro-phenyl)-vinyl]-1H-indazol-6-yloxy)-phenyl)-benzamide

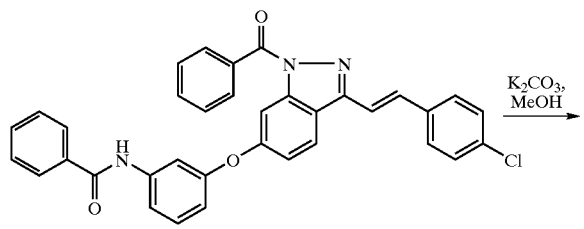

Starting from N-(3-{1-benzoyl-3-[2-(4-chlorophenyl)-vinyl]-1H-indazol-6-yloxyl}-phenyl)-benzamide, the general procedure for example 5(a) was used to prepare the title compound as an off-white solid in 72% yield: $^1$H NMR (DMSO-$d_6$) δ 3.07 (s, 1H), 10.32 (s, 1H), 8.24 (d, 1H, J=8.8 Hz), 7.92 (d, 2H, J=7.1 Hz), 7.76 (d, H, 1=8.5 Hz), 7.59–740 (m, 10H), 7.05 (s, 1H), 7.00 (d, 1H, J=8.7 Hz), 6.87 (d, 1H, J=7.9 Hz). Anal. Calc. for $C_{28}H_{20}ClN_3O_2 \cdot 0.4H_2O \cdot 0.15$ hexanes; C, 71.41; H, 4.75; N, 8.65. Found: C, 71.62; H, 14.83; N, 8.45.

The starting material was prepared as follows:

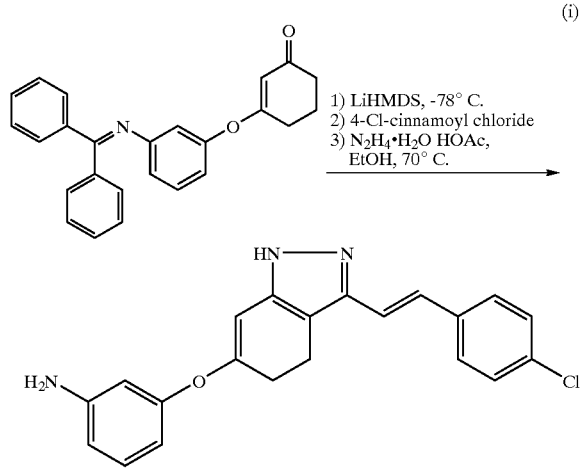

Starting with 3-[3-(benzhydrylidene-amino)phenoxy]-cyclohex-2-enone and 3-(4-chloro-phenyl)acryloyl chloride (prepared as described below), the general procedure for Example 4(a), step (ii) was employed. The product was used without purification in the hydrazine cyclization procedure, Example 4(a) step (iii), to give 3-{3-[2-(4-chloro-phenyl)vinyl]4,5-dihydro-1H-indazol-6-yloxyl}-phenylamine as a yellow solid in 30% yield. $^1$H NMR (DMSO-$d_6$) δ 12.45 (s, 1H), 7.58 (d, 2H, J=8.5 Hz), 7.43 (d, 2H, J=8.5 Hz), 5.52 (s, 1H), 5.26 (s, 2H), 2.92 (t, 2H, J=8.0 Hz), 2.58 (t, 2H, J=8.0 Hz). Anal. Calc. for $C_{21}H_{18}ClN_3O \cdot 0.75H_2O$: C, 66.84; H, 5.21; N, 11.14. Found: C, 66.73; H, 4.89; N, 11.01.

3-(4-chloro-phenyl)-acryloyl chloride was prepared as follows: To a stirred suspension of 4-chloro-trans-cinnamic acid (251 g, 13.77 mmol) in benzene was added thionyl chloride (1.1 mL, 15.14 mmol) and a catalytic amount of DMAP. The reaction mixture was heated at reflux for 1.5 h. The volatile materials were removed under reduced pressure. The white residue was dissolved in Et$_2$O and concentrated again under reduced pressure, to give 3-(4-chloro-phenyl)-acryloyl chloride (2.78 g, quantitative) as a white solid: $^1$H NMR (CDCl$_3$) δ 7.81 (d, 1H, 1=15.6 Hz), 7.54 (d, 2H, J=8.6 Hz), 7.44 (d, 2H, J=8.6 Hz), 6.65 (d, 1H, J=15.6 Hz).

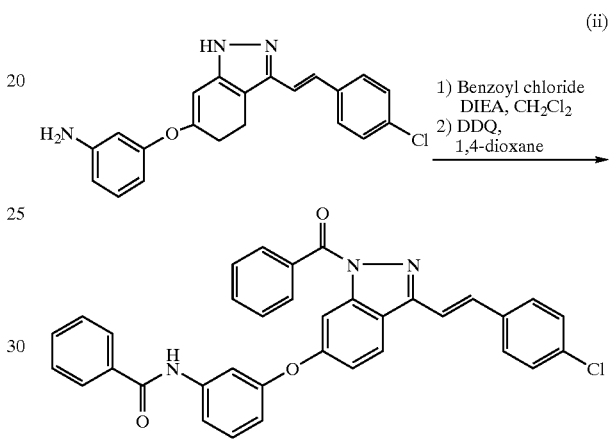

3-{3-[2-(4-Chloro-phenyl)-vinyl]4,5-dihydro-1H-indazol-6-yloxyl}-phenylamine was converted into N-(3-{1-benzoyl-3-[2-(4-chloro-phenyl)-vinyl]-1H-indazol-6-yloxyl}-phenyl)-benzamide by the procedure described in Example 4(a), step (iv) (85% yield). $^1$H NMR (DMSO-$d_6$) δ 10.37 (s, 1H), 8.43 (d, 1H, J=8.8 Hz), 8.00–7.39 (m, 21H), 7.34 (d. 1H, J=8.8 Hz), 6.93 (d, 1H, J=8.8 Hz).

Example 6(b)

N-[3-[3-(2-Indolyl)-1H-indazol-6-yloxy]-phenyl)-3-methyl-benzamide

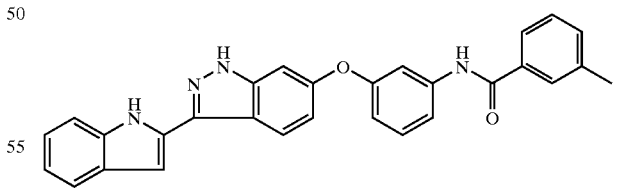

Example 6(b) was prepared in a similar manner to that described for Example 6(a) above, except that 1-SEM-indazole-2-carboxylic acid was used in step (i) in place of 4-chlor-trans-cinnamic acid. $^1$H NM (DMSO-$d_6$) δ 13.19 (s, 1H), 11.59 (s, 1H), 10.29 (s, 1H), 8.23 (d, 1H, J=8.7 Hz), 7.73–7.38 (m. 9H), 7.12 (s, 1H), 7.03 (d, 2H, J=7.3 Hz), 6.88 (d, 1H, J=7.8 Hz), 2.38 (s, 1H). HRMS [m+H]/z Calc'd: 459:1821, found 459.1836.

Example 7

3-(Styryl-1H-indazol-6-yloxy)-phenylamine

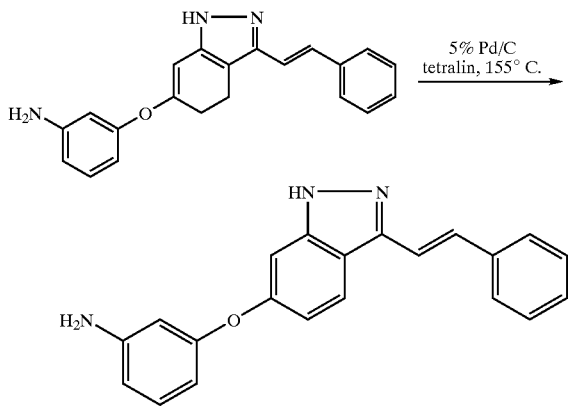

A suspension of 3-(3-styryl-4,5-dihydro-1H-indazol-6-yloxy)-phenylamine (75 mg, 0.23 mmol) and 90 mg of 5% palladium on carbon (Pd/C) was heated at 155° C. After 4 h, more 5% Pd/C (39 mg) was added. After 22 h, more 5% Pd/C (30 mg) was added. The reaction mixture was filtered while hot after 26 h. The catalyst was washed and the filtrate concentrated under reduced pressure. The residue was chromatographed on silica eluting hexanes/EtOAc (1:1). The appropriate fractions were concentrated and triturated with $CH_2Cl_2$/hexanes to give the title compound as an off-white solid (20 mg, 27%): $^1$H NMR (DMSO-$d_6$) δ 8.16 (d, 1H, J=85 Hz), 7.71 (d, 2H, J=6.7 Hz), 7.50 (s, 2H), 7.40 (t, 2H, J=7.0 Hz), 7.30 (d, H, J=6.5 Hz), 7.060.92 (m, 3H), 6.35 (d, 1H, J=8.3 Hz), 6.23 (s, 2H), 5.26 (s, 2H). Anal. Calc. for $C_{21}H_{17}N_3O \cdot 0.15CH_2Cl_2$: C, 74.69; H, 5.13; N, 12.36. Found: C, 74.64; H, 5.23; N, 12.25.

Example 8(a)

3-(E-styryl)-6-phenoxy-1H-indazole

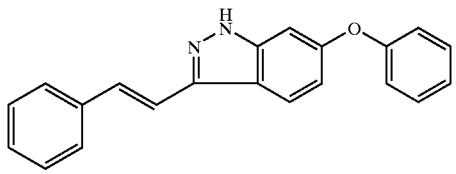

A suspension of 3-(E-styryl)-6-phenoxy-4,5-dihydro-1H-indazole (200 mg. 0.64 mmol) and 5% Pd/C (200 mg) in 10 mL of tetralin was heated at 155° C. for 18 h. The catalyst was removed by filtering the hot solution and washed with THF, EtOAc and MeOH. The filtrate was concentrated under reduced pressure and the residue was chromatographed on silica gel eluting hexanes/EtOAc (2:1) to provide 3-(E-styryl)& phenoxy-1H-indazole as an off-white solid (110 mg, 55%). $^1$H NMR (DMSO-$d_6$) δ 6.96 (s, 2H), 7.10 (d, 2H, J=7.7 Hz), 7.20 (t, 1H, J=7.1 Hz), 7.30 (t, 1H, J=7.1 Hz), 7.44 (m, 6H), 7.71 (d, 2H, J=7.5 Hz), 8.20 (d, 1H, J=9.2 Hz), 12.90 (s, 1H). Anal. Calc. for $C_{21}H_{16}N_2O \cdot 0.1H_2O$: C, 80.28; H, 5.20; N, 8.92. Found: C, 80.20; H, 5.21; N, 8.93.

The starting material was prepared as follows:

(i) To a stirred solution of 3-chloro-cyclohex-2-enone (3.00 g, 23.0 mmol) and phenol (2.16 g, 23.0 mmol) in 25 mL of acetone was added powdered, anhydrous $K_2CO_3$ (3.81 g, 27.6 mmol). After refluxing for 18 h, the mixture was cooled and filtered. The filtrate was concentrated under reduced pressure and chromatographed on silica gel eluting with hexanes/EtOAc (4:1) to give 3-phenoxy-cyclohex-2-enone as a white solid: $^1$H NMR (CDCl$_3$) δ 2.10 (quint, 2H, J=6.3 Hz), 2.40 (t, 2H, 1=6.2 Hz), 2.68 (t, 2H, J=6.3 Hz), 5.14 (s, 1H), 7.05 (d, 2H, J=7.5 Hz), 7.26 (t, 1H, J=7.3 Hz), 7.41 (t, 2H, J=7.6 Hz).

(ii) A solution of 3-phenoxy-cyclohex-2-enone (301 mg, 1.6 mmol) in 1 mL of THF was added to a stirred solution of 1.0 M solution of lithium bis(trimethylsilyl)amide in THF (3.2 mL) at −78° C. After 15 min, cinnamoyl chloride (266 mg, 1.6 mmol) was added all at once. After 15 min, the reaction mixture was poured into 0.5 N HCl and extracted with EtOAc (2×). The combined organic layers were washed with saturated NaCl solution, dried (MgSO$_4$), filtered, and concentrated under reduced pressure. Chromatography of the residue with 4:1 hexanes/ethyl acetate as eluant provided 220 mg (43%) of 3-phenoxy-6-(3-phenyl-acryloyl)-cyclohex-2-none as a yellow solid (220 mg, 43%): $^1$H NMR (CDCl$_3$) (enol form) δ 2.66 (t, 2H, J=7.2 Hz), 2.84 (t, 2H, J=7.1 Hz), 5.11 (s, 1H), 6.86 (d, 1H, J=15.6 Hz), 7.02 (d, 2H, J=8.1 Hz), 7.20 (m, 2H), 7.28–7.38 (m, 3H). HRMS M+H$^+$ calc: 319.1334, found 319.1340.

(iii) To a stirred solution of 3-phenoxy-6-(3-phenyl-acryloyl)-cyclohex-2-enone (1.13 g, 3.55 mmol) in 20 mL of HOAc/EtOH(1:1) was added hydrazine monohydrate (0.21 mL, 4.3 mmol). The reaction was heated at 70° C. for 3 h, cooled and poured cautiously into saturated Na HCO$_3$ solution and extracted with EtOAc (2×). The combined organic layers were washed with saturated NaCl solution, dried (MgSO$_4$) and concentrated under reduced pressure. The residue was chromatographed on silica gel eluting hexanes/EtOAc (2:1) to give 6-phenoxy-3-styryl-4,5-dihydro-1H-indazole (3) as an off-white solid (406 mg, 36%): $^1$H NMR (DMSO $d_6$) δ 2.64 (t, 2H J=8.0 Hz), 2.95 (t, 2H, J=8.0 Hz), 5.46 (s, 1H), 7.04 (AB, 2H, J=16.8 Hz), 7.15 (d, 2H, J=8.1 Hz), 7.25 (m, 2H), 7.42 (m, 4H), 7.55 (d, 2H, J=7.7 Hz), 12.44 (s, 1H). Anal. Calc. for $C_2H_{18}N_2O \cdot 0.2H_2O$: C, 79.32; H, 5.83, N, 8.81. Found: C, 79.36; H, 5.85; N, 8.84.

Example 8(b)

3-(E-styryl)-6-[4-(methoxymethoxy)phenoxy]-1H-indazole

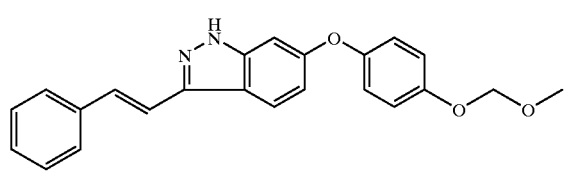

Example 8(b) was prepared in a similar manner to that described for Example 8(a) above, except that 4(methoxymethoxy)phenol was used in place of phenol in step (i). $^1$H NMR (DMSO-$d_6$) δ 12.90 (s, 1H), 8.17 (d, 1H, J=8.8 Hz), 7.71 (d, 2H, J=7.6 Hz), 7.50 (s, 3H), 7.41 (t, 2H, J=7.6 Hz), 7.31 (d, 1H, J=7.4 Hz), 7.10 (s, 3H), 6.95 (dd, 1H, J=8.8, 1.9 Hz), 6.84 (s, 1H), 5.20 (s, 2H), 3.42 (s, 3H). Anal. Calc. for $C_{23}H_{20}N_2O_3$: C, 74.17; H, 5.41, N. 7.52. Found: C, 74.21; H, 5.59; N, 7.46.

Example 8(c)

3-(E-styryl)-6-phenylsulfanyl-1H-indazole

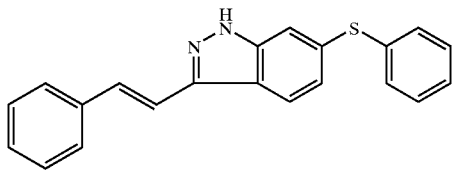

Example 8(c) was prepared in a similar manner to that described for Example 8(a) above, except that thiophenol was used in step (i) in place of phenol. $^1$H NMR (DMSO-$d_6$) δ 7.29 (d, 1H, J=8.5 Hz), 7.45–7.59 (m, 9H), 7.67 (s, 2H), 7.86 (d, 2H, J=7.2 Hz), 8.35 (d, 1H, J=8.5 Hz), 13.30 (s, 1H). Anal. Calc. For $C_{21}H_{16}N_2S$, $0.25H_2O$: C, 75.76; H. 5.00; N, 8.41; S, 9.63. Found: C, 75.79; H. 4.99; N, 8.16; S, 9.63.

Example 8(d)

6-(3-Bromo-phenoxy)-3-styryl-1H-indazole

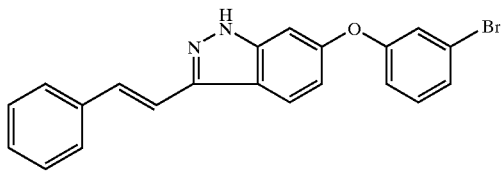

Example 8(d) was prepared in an analogous manner to that described for Example 8(a) above, except that 3-bromophenol was used in step (i) in place of phenol. $^1$H NMR (DMSO d) δ 13.08 (s, 1H), 8.23 (d, 1H, J=8.8 Hz), 7.72 (d, 2H, J=7.3 Hz), 7.53 (s, 2H), 7.43–7.35 (m, 4H), 7.30 (t, 2H, J=7.2 Hz), 7.11 (d, 1H, J=7.2 Hz), 7.09 (s, 1H), 6.98 (d, 1H, J=8.8 Hz). Anal. Calc. for $C_{21}H_{15}BrN_2O$: C, 64.46; H, 3.86; Br, 20.42; N, 7.16. Found: C, 64.31; H, 3.99; Br, 20.52; N, 7.11.

Example 9(a)

3-(E-styryl)-6-[3-hydroxyphenoxy]-1H-indazole

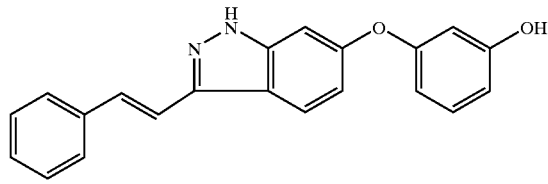

To a stirred solution of 3-(E-styryl)-6-[3-(methoxymethoxy)phenoxy]-1H-indazole (50 mg, 0.13 mmol) in 5 mL $CH_2Cl_2$ at −25° C. was added trimethylsilylbromide (75 μl, 0.57 mmol). After 1.5 h, saturated $NaHCO_3$ solution was added and the product was extract with EtOAc (2×). The combined organic layers were washed with saturated NaCl solution, dried ($MgSO_4$) and concentrated under reduced pressure. The residue was chromatographed on silica gel eluting hexanes/EtOAc (1:1) to give, after trituration with $CH_2Cl_2$/hexanes, 3-(E-styryl)-6-(3-hydroxyphenoxy]-1H-as an off-white solid (22 mg, 50%): $^1$H NMR (DMSO-$d_6$) δ 6.37 (s, 1H), 6.43 (d, 1H, J=8.1 Hz), 6.50 (d, 1H, J=8.1 Hz), 6.88 (d, 1H, J=8.8 Hz), 6.92 (s, 1H), 7.12 (t, 1H, J=8.1 Hz), 7.24 (t, 1H, J=7.3 Hz), 7.31 (t, 2H, J=7.6 Hz), 7.44 (s, 2H), 7.64 (d, 2H, J=7.5 Hz), 8.12 (d, 1H. J=8.7 Hz), 9.54 (s, 1H), 12.92 (s, 1H). Anal. Calc. For $C_{21}H16N_2O_2.0.3H_2O$: C, 75.57; H. 5.01; N. 8.39. Found: C, 75.74; H, 5.11; N. 8.25.

The starting material, 3-(E-styryl)-6-[3-(methoxymethoxy)phenoxy]-1H-indazole, was prepared as described in Example 8(b).

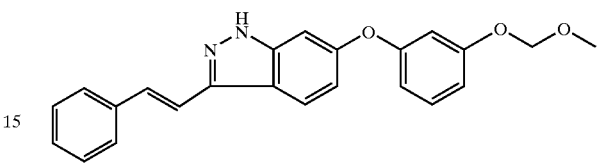

$^1$H NMR (CDCl$_3$) δ 3.42 (s, 3H), 5.10 (s, 2H), 6.64 (d, 1H, J=8.2 Hz), 6.72 (s, 1H), 6.80 (d, 1H, J=8.3 Hz), 6.98 (s, 1H), 7.00 (d, 1H. J=8.8 Hz), 7.19–7.38 (m, 5H), 7.53 (m, 3H), 7.92 (d, 1H, J=8.9 Hz). Anal. Calc. For $C_{23}H_{20}N_2O_3$: M+H$^+$: 373.1552, found 73.1546

Example 9(b)

3-(E-styryl)-6-[4-hydroxyphenoxy]-1H-indazole

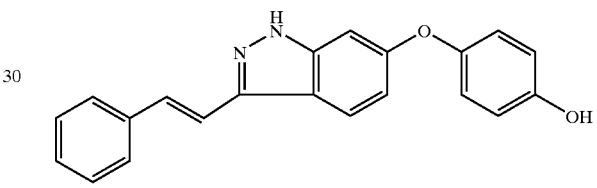

Example 9(b) was prepared like Example 9(a) above, except that 3-(E-styryl) 6[4(methoxymethoxy)phenoxy]-1H-indazole was used in place of 3(E-styryl)-6-[3-(methoxymethoxy)phenoxy]-1H-indazole. $^1$H NMR (DMSO-$d_6$) δ 12.95 (s, 1H), 9.58 (s, 1H), 8.33 (d, 1H, J=9.0 Hz), 7.89 (d, 2H, J=7.1 Hz), 7.68 (s, 1H), 758 (t, 1H, J=7.3 Hz), 7.48 (d, 1H, J=7.3 Hz), 7.24 (s, 1H), 7.13 (m, 3H), 6.99 (d, 2H, J=8.8 Hz). HRMS [m+H]/z Calc'd: 329.1290. Found: 329.1293. Anal. Calc. for $C_{21}H_{16}N_2O_2.0.35H_2O$: C, 75.36; H, 5.03; N, 8.37. Found: C, 75.35; H, 5.22; N, 8.24.

Example 10

6-(1-Phenyl-vinyl)-3-styryl-1H-indazole

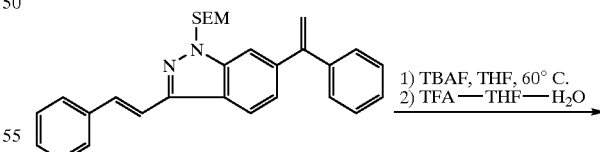

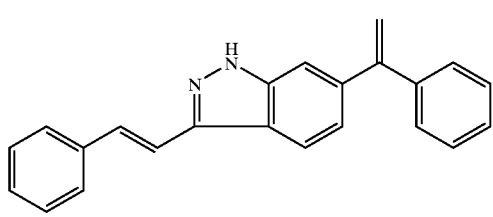

6-(1-Phenyl-vinyl)-3-styryl-1-[2-(trimethyl-silanyl)-ethoxymethyl]-1H-indazole (16.2 mg, 0.0358 mmol) was dissolved in THF (0.6 mL) and was treated with tetrabutylammonium fluoride (TBAF, 1M in THF, 0.6 mL). The mixture was heated to 60° C. under argon for 4 h. The mix was cooled, neutralized with excess saturated sodium bicarbonate and the organic material was extracted into ethyl acetate and concentrated. This mix of 3 compounds (by TLC visualization) was treated with THF-water-TFA (1:1:2, 4 mL) for 30 min. The mix was diluted with toluene (20 mL), concentrated, neutralized with excess saturated sodium bicarbonate, and the organic material was extracted into ethyl acetate. The organic material was dried over sodium sulfate, decanted and concentrated. Purification by silica gel chromatography (2:8 ethyl acetate-hexane) gave 6-(1-Phenyl-vinyl)-3-styryl-1H-indazole (4.6 mg, 40%): $R_f$ sm 0.62, p 0.24 (ethyl acetate-hexane 3:7); $^1$H NMR (300 MHz, CDCl$_3$) δ 7.99 (d, 1H, J=8.5 Hz), 7.60–7.25 (m, 14H), 5.58 (d, 1H, J=1.1 Hz), 5.56 (d, 1H, J=1.1 Hz); HRMS (FAB) [m+H]/z Calc'd 323.1548, Found 323.1545.

The starting material was prepared as follows:

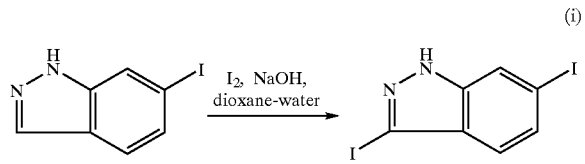

(i)

6-Iodoindazole was converted to 3,6-diiodoindazole (82%) as described in Example 1(a), step (v): $^1$H NMR (300 MHz, CDCl$_3$) δ 10.3 (bs, 1H), 7.90 (s, 1H), 7.52 (dd, 1H, J 1.2, 8.5 Hz), 7.24 (d, 1H, J=8.5 Hz).

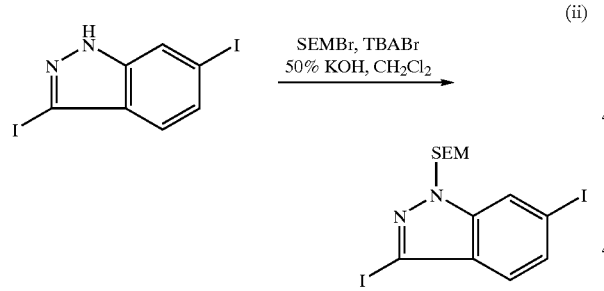

(ii)

3,6-Diiodoindazole (755 mg, 2.04 mmol) was added to 50% KOH (2.5 g in 2.5 mL water) at 0° C. and dichloromethane (4 mL) was added. To this mixture was added tetrabutylammonium bromide (TBABr, 6.6 mg, 0.02 mmol, 0.01 equiv) and 2-(trimethyl-silanyl)ethoxymethyl chloride (SEM-Cl, 397 μL, 2.24 mmol, 1.10 equiv) was added dropwise over a 3 min period. The mixture was stirred rapidly at 0° C. for 1.5 h. Water (20 mL) and dichloromethane (20 mL) were added and the organic material was separated, dried over sodium sulfate and concentrated. Silica gel chromatography (5% ethyl acetate in hexane; 150 mL silica) gave 2 isomeric compounds (1-SEM, 763 mg, 75%; and 2-SEM, 105 mg, 10%): $R_f$ sm 0.08, p 0.34 and 0.27 (ethyl acetate-hexane 1:9); $^1$H NMR (300 MHz, CDCl$_3$) δ 8.0 (s, 1H), 755 (d, 1H, J=8.5 Hz), 7.24 (d, 1H, J=8.5 Hz), 5.69 (s, 2H), 3.58 (t, 2H J=8.2 Hz), 0.90 (t, 2H, =8.2 Hz), 0.1 (s, 9H).

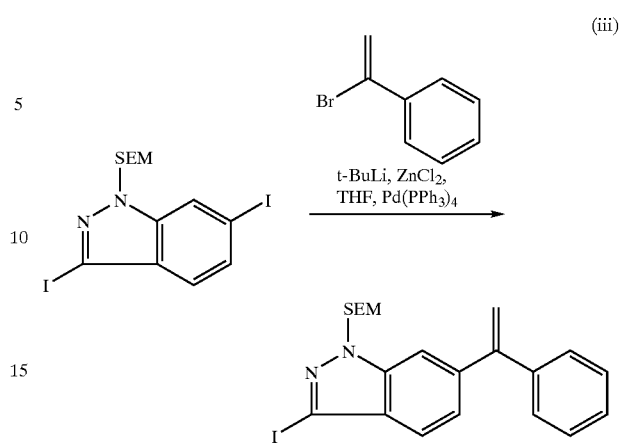

(iii)

1-Bromostyrene (26 μL, 0.20 mmol, 2.0 equiv) was dissolved in THF (0.75 mL), cooled to −78° C. and was treated with t-BuLi (235 μL, 0.40 mmol, 1.70 M, 4.0 equiv). The mixture was allowed to warm to −42° C. for 10 min and was added to freshly dried zinc chloride (34 mg, 0.25 mmol, 2.5 equiv). The resulting solution was allowed to warm to 23° C. with stirring for 25 min. This mix was added to a mixture of neat 3,6-Diiodo-1-[2-(trimethyl-silanyl)-ethoxymethyl]-1H-indazole (50 mg, 0.10 mmol, 1 equiv) and Pd(PPh$_3$)$_4$ (5 mg, 0.004 mmol, 0.04 equiv). After 10 min the reaction was determined to be complete by TLC monitoring and was quenched with saturated sodium bicarbonate. Organic material was extracted into ethyl acetate, dried over sodium sulfate and concentrated under reduced pressure. Silica gel chromatography (5:95 ethyl acetate-hexane) provided 3-Iodo-&6-(1-phenyl-vinyl)-1-[2-(trimethyl-silanyl)-ethoxymethyl]-1H-indazole (33.1 mg, 70%): $R_f$ sm 0.39, p 0.36 (ethyl acetate-hexane 1:9); $^1$H NMR (300 MHz, CDCl$_3$) δ 7.50 (s, 1H), 7.42 (d, 1H, J=8.4 Hz), 7.33 (m, 5H), 7.22 (dd, 1H, J=1.2, 8.4 Hz), 5.68 (s, 2H), 5.59 (d, 1H, J=1.0 Hz), 5.57 (d, 1H, J=1.0 Hz), 3.58 (t, 2H, J=8.2 Hz), 0.88 (t, 2H, J=8.2 Hz), −0.09 (s, 9H); HRMS (FAB) [m+H]/z Calc'd 477.0859, found 477.0866.

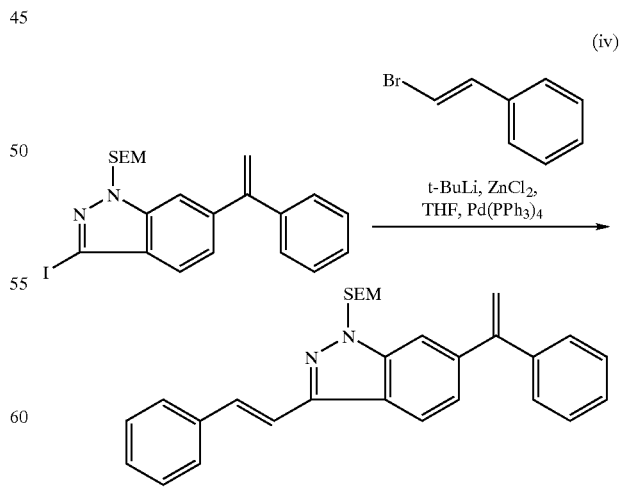

(iv)

Preparation of 6-(1-Phenyl-vinyl)-3-styryl 1-[2-(triethyl-silanyl)-ethoxymethyl]-1H-indazole: E-2-Bromostyrene (23 μL, 0.174 mmol, 2.5 equiv) was dissolved in THF (1.0 mL)

and was cooled to −78° C. t-BuLi (205 μL, 0.348 mmol, 5.00 equiv) was added and the mixture was warmed to 42° C. for 7 min to give a deep red mixture. The solution was added to freshly dried zinc chloride (29 mg, 0.209 mmol, 3.00 equiv) via cannula and the mix was allowed to warm to 23° C. with stirring for 20 min. This solution was added to a neat mixture of 3-Iodo-6-1-phenyl-vinyl)-1-[2-(trimethyl-silanyl)-ethoxymethyl]-1H-indazole (33.1 mg, 0.0696 mmol, 1.0 equiv) and Pd(PPh$_3$)$_4$ (4 mg, 0.0035 mmol, 0.05 equiv) at 23° C. via cannula. This solution was allowed to stir for 15 min and was treated with saturated sodium bicarbonate and extracted with ethyl acetate. The organic material was dried over sodium sulfate, decanted and concentrated. Purification by silica gel chromatography using two columns (5:95 ethyl acetate-hexane; 12 ml silica: and 1:99 ethyl acetate-benzene; 12 mL silica) gave 6-(1-Phenyl-vinyl)-3-styryl-1-[2-(trimethyl-silanyl)-ethoxymethyl]-1H-indazole (16.2 mg, 51%): R$_f$ sm 0.38, p 0.29 (ethyl acetate-hexane 1:9); $^1$H NMR (300 MHz, CDCl$_3$) δ 7.98 (d, 1H, J=8.4 Hz), 7.62–7.22 (m, 14H), 5.71 (s, 2H), 5.57 (s, 2H), 3.60 (t, 2H, J=8.2 Hz), 0.90 (t, 2H, J=8.2 Hz), −0.08 (s, 9H); HRMS (FAB) [m+H]/z Calc'd 453.2362, Found 453.2354.

Example 11

N-Methyl-N-(3-styryl-1H-indazol-6-yl)-benzene-1,3-diamine

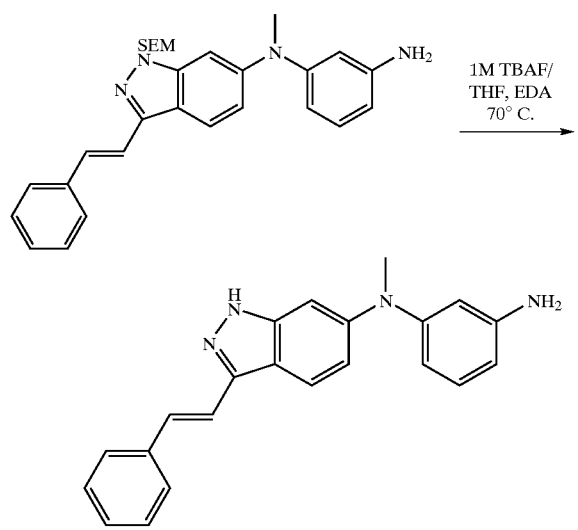

To N-methyl-N-(3-styryl-1-[2-(trimethyl-silanyl) ethoxymethyl]-1H-indazol-6-yl)-benzene-1,3-diamine (237 mg, 0.5 mmol) was added 1M TBAF in THF (10.1 mL, 10.1 mmol), followed by ethylenediamine (0.34 mL, 5.04 mmol, 10 equiv). The resulting mixture was heated to 70° C. for 5 h. The reaction was then quenched with saturated NaHCO$_3$ (10 mL) and extracted 3×35 mL EtOAc. The pooled EtOAc phase was washed 5×20 mL H$_2$O, then brine (20 mL), dried with Na$_2$SO$_4$, decanted and concentrated under reduced pressure to a foam. The crude material was purified by silica gel chromatography (9; 1 dichloromethane/ethyl acetate) to give N-methyl-N-3-styryl-1H-indazolyl)-benzene-1,3-diamine as a foam (120 mg, 70% yield). Rf sm 0.73, Rf p 0.27 (dichloromethane:ethylacetate 7:3); $^{13}$C NMR (75 MHz, CDCl$_3$) δ 150.3, 148.8, 147.5, 147.5, 143.9, 143.4, 137.5, 131.1, 130.3, 129.3, 128.9, 128.2, 127.9, 126.7, 121.0, 120.5, 117.0, 116.0, 112.6, 109.8, 109.0, 98.3, 40.7; LCMS (ESI) [M+H]/z Calc'd 341, Found 341. Anal. Calc'd: C, 77.62; H, 5.92; N, 16.46. Found: C, 76.16; FL 5.88; N, 15.95.

Starting material prepared as follows:

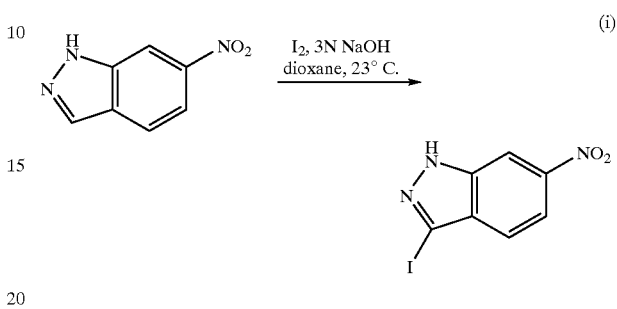

(i)

6-nitro-1H-indazole was converted to 3-Iodo-6-nitro-1H-indazole as described in Example 1(a), step (v) (50.6 g, 87%): FTIR (KBr) 3376, 3076, 2964, 2120, 1739, 1626, 1526, 1439, 1294, 1128, 954 cm$^{-1}$; $^1$H NMR (300 MHz, CDCl$_3$) δ 8.28 (s, 1H), 8.05 (s, 1H), 7.66 (d, 1H, J=8.13 Hz), 7.45 (dd, 1H, J=8.33, 1.38 Hz), 7.17 (d, 1H, J=1.01 Hz), 7.14 (s, 1H), 7.03 (d, 1H, J=8.04 Hz), 6.89 (s, 2H), 3.82 (s, 3H), 2.55 (s, 6H), 2.21 (s, 3H) 1.32 (s, 9H). MS (FAB) [M+H]/z Calc'd 311, Found 311. Anal. Calc'd: C, 69.66; H, 5.85; N, 9.03. Found: C, 69.41; H, 5.98; N, 8.79.

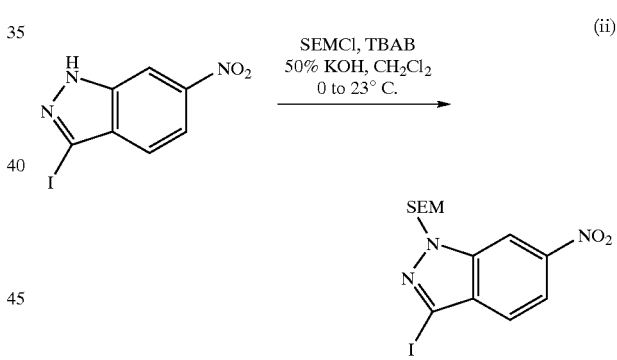

(ii)

3-Iodo-6-nitro-1H-indazole was converted to 6-Nitro-3-iodo-[2-(trimethyl-silanyl)-ethoxymethyl]-1H-indazole as described in Example 10, step (ii) (10.2 g, 81% yield): mp 58° C. Anal. Calc'd: C, 37.24; H, 4.33; N, 10.02. Found: C, 37.21; H, 4.38; N, 10.00.

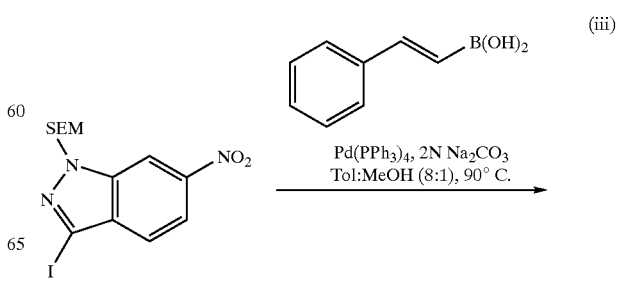

(iii)

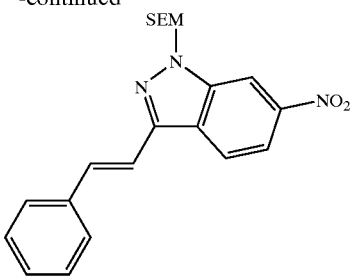

To 6-nitro-3-iodo-[2-(trimethyl-silanyl)-ethoxymethyl]-1H-indazole (11.0 g, 26.1 mmol), styryl boronic acid (4.64, 31.4 mmol), and Pd(PPh$_3$)$_4$ (1.25 g, 1.08 mmol) under an atmosphere of argon was added toluene (192 mL), MeOH (4 mL) and 2N NaOH (aq) (32.6 mL, 65.3 mmol). The resulting heterogeneous mixture was heated to 90° C. After 8 h the reaction was diluted with EtOAc (150 mL) and water (50 mL), the phases were separated and the organic was extracted 2×50 mL EtOAc. The pooled organic phase was washed with brine (50 mL), then dried with Na$_2$SO$_4$, filtered and concentrated under reduced pressure. The crude reaction was purified by silica gel chromatography (1:9 EtOAc:hexane) to give 6-nitro-3-styryl-1-[2-(trimethyl-silanyl) ethoxymethyl]-1H-indazole as a yellow solid (7.65 g, 74%): $^{13}$C NMR (75 MHz, CDCl$_3$) δ 148.3, 145.0, 141.3, 138.1, 134.2, 130.5, 129.9, 129.8, 129.5, 128.1, 127.4, 123.2, 119.8, 117.8, 108.2, 79.7, 68.5, 19.2, 0.0; MS (FAB) [M+Na]/z Calc'd 418, found 418. Anal. Calc'd: C, 63.77; H. 6.37; N. 10.62. Found: C, 64.04; H, 6.29; N, 10.56.

(iv)

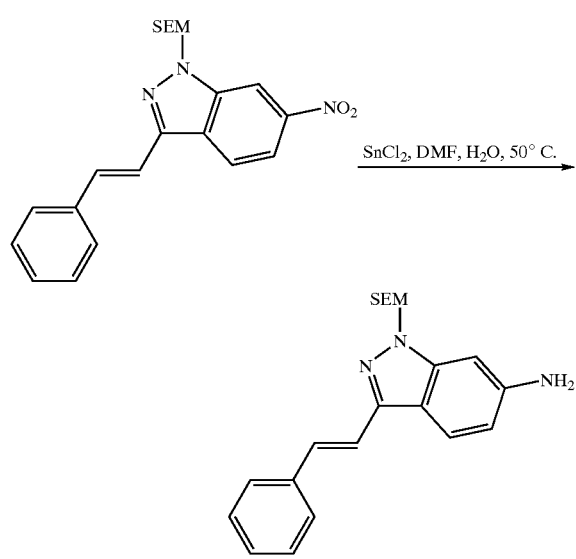

6-Nitro-3-styryl-1-[2-(trimethyl-silanyl)-ethoxymethyl]-1H-indazole (8.1 g, 205 mmol) was dissolved in DMF (75 mL) at 23° C. under an atmosphere of argon. SnCl$_2$ (12.9 g, 67.7 mmol) was added followed by water (1.7 mL, 92.2 mmol) and the resulting mixture was heated to 50° C. After 4 h, 3N NaOH (45 mL, 135 mmol) was added followed by EtOAc (100 m]L). The resulting emulsion was filtered hot through Celite and the bed of Celite was washed with hot EtOAc (3×100 mL). The filtrate was concentrated under reduced pressure, the residue was dissolved in EtOAc, washed with brine, dried with Na$_2$SO$_4$, filtered and concentrated under reduced pressure to give a solid. The crude material was purified by silica gel chromatography (2:8→7:3 ethyl acetate:hexane), to give 3-styryl-1-[2-(trimethyl-silanyl)-ethoxymethyl]-1H-indazol-6-ylamine as a yellow solid (5.1 g, 68% yield). MS (FAB) [M+H]/z Calc'd 366, found 366.

(v)

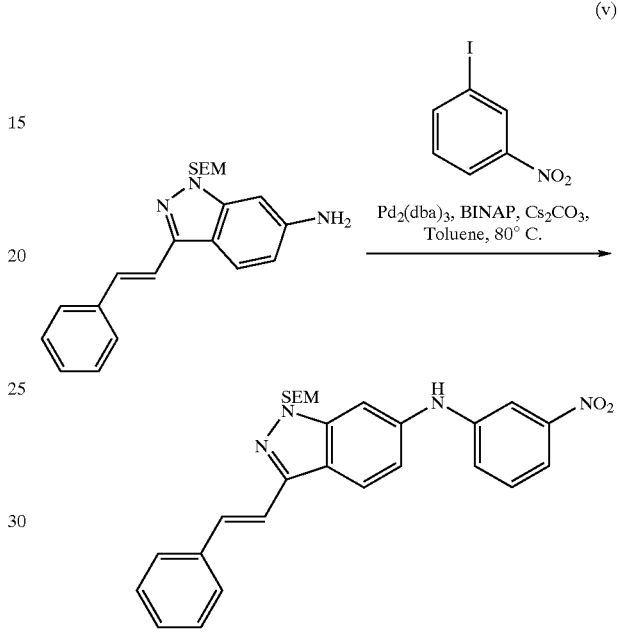

To 3-styryl-1-[2-(trimethyl-silanyl)-ethoxymethyl]-1H-indazol-6-ylamine (1.1 g, 3 mmol, m-nitro-iodobenzene (0.9 g, 3.6 mmol), BINAP (0.07 g, 0.133 mmol), Pd$_2$(dba)$_3$ (34 mg, 0.0375 mmol) and Cs$_2$CO$_3$ (1.37 g, 4.2 mmol) under an atmosphere of argon was added toluene (6 mL). The resulting heterogeneous mixture was heated to 80° C. After 46 h the reaction was cooled to 23° C. diluted with ethyl acetate (EtOAc) (20 mL) and filtered. Water (5 mL) was added, the phases were separated, and the organic was extracted 2×50 mL EtOAc. The pooled organic material was washed with brine, then dried with Na$_2$SO$_4$, filtered and concentrated under reduced pressure. The crude reaction was purified by silica gel chromatography (eluting with 9:1 hexane:EtOAc) to give (3-nitro-phenyl)-{3-styryl-1-[2-(trimethyl-silanyl)-ethoxymethyl]-1H-indazol-6-yl}-amine as a yellow solid (7.65 g, 74%): TLC (Hexane:EtOAc 7:3) Rf sm 0.16, Rf p 0.30 (ethyl acetate:hexane 3:7); FTIR (KBr) 3391, 3059, 2952, 2894, 1614, 1530, 1483, 1346, 1248, 1076, 836, 734 cm$^{-1}$; $^1$H NMR (300 MHz, CDCl$_3$) δ 7.86 (s, 1H), 7.83 (s. 1H), 7.65 (dt, 1H, J=2.21, 5.13 Hz), 7.15–7.41 (m, 5H), 6.93 (dd, 1H, J=1.87, 8.67 Hz), 5.56 (s, 2H), 3.51 (t, 2H, J=8.17 Hz), 0.81 (t, 2H, J=7.96 Hz), −0.15 (s, 9H); $^{13}$C NMR (75 MHz, CDCl$_3$) δ 149.6, 144.8, 143.5, 142.4, 140.9, 137.3, 131.8, 130.3, 129.0, 128.2, 126.7, 122.8, 122.6, 120.1, 119.3, 116.1, 115.6, 111.4, 98.5, 77.9, 66.7, 18.0, −1.2; MS (ESI) [M+H]/z Calc'd 487, found 487. Anal. Calc'd: C, 66.64; H, 6.21; N, 11.51. Found: C, 66.91; H, 6.21; N, 11.44.

(vi)

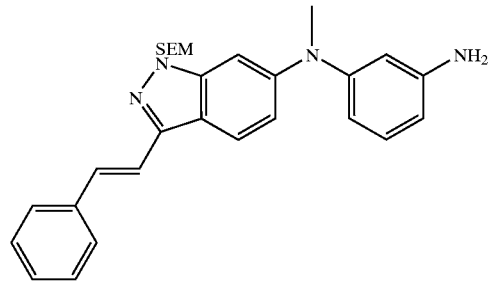

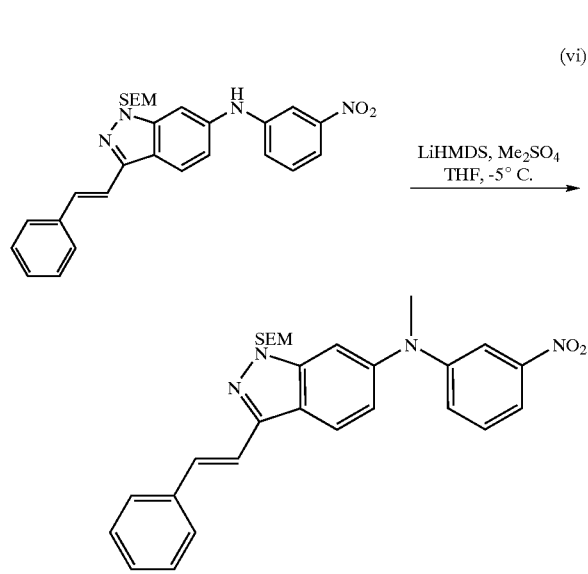

To (3-nitro-phenyl)-(3-styryl-1-[2-(trimethyl-silanyl)-ethoxymethyl]-1H-indazolyl)-amine (434 mg, 0.89 mmol) in THF (5 mL) cooled to −5° C. under an atmosphere of argon, was added dimethylsulfate (0.42 mL, 4.5 mmol) followed by LiHMDS (1M in THF) (1.8 mL, 1.8 mmol). After 20 min the reaction was quenched with saturated NH$_4$Cl(aq) (2 mL), then extracted 3×20 mL EtOAc. The pooled organic material was washed with brine (10 mL), dried with Na$_2$SO$_4$, decanted and concentrated under reduced pressure. Purification by silica gel chromatography (eluting with hexane:EtOAc 9:1) gave methyl-(3-nitro-phenyl)-{3-styryl-1-[2-(trimethyl-silanyl)ethoxymethyl]-1H-indazol-6-yl}-amine, as an oil (367 mg, 82%): TLC (Hexane:EtOAc 7:3) Rf sm 0.29, Rf p 0.39 (ethyl acetate:hexane 3:7); FTIR (KBr) 2951, 2894, 1611, 1528, 1485, 1348, 1248, 1077 cm$^{-1}$; $^1$H NMR (300 MHz, CDCl$_3$) δ 7.99 (d, 1H, J=8.67 Hz) 7.77 (t, 1H, J=2.25 Hz), 7.72 (dd, 1H, J=0.79, 2.09 Hz), 7.60, (d, 2H, J=7.22 Hz), 7.26–7.54 (m, 7H), 7.19 (dd, 1H, J=0.78, 2.41 Hz) 7.07 (dd, 1H, J=1.85, 8.69 Hz), 5.70 (s, 2H), 3.63 (t, 2H, J=8.10 Hz), 3.48 (s, 3H), 0.92 (t, 2H, J=8.10 Hz), −0.04 (s, 9H); $^{13}$C NMR (75 MHz, CDCl$_3$) δ 150.2, 149.6, 147.1, 143.5, 142.5, 137.3, 131.9, 129.8, 129.0, 128.2, 126.8, 123.1, 122.6, 120.2, 120.0, 119.7, 114.4, 111.4, 104.5, 78.0, 66.8, 41.1, 18.0, −1.2; LCMS (ESI) [M+H]/z Calc'd 501, Found 510.

(vii)

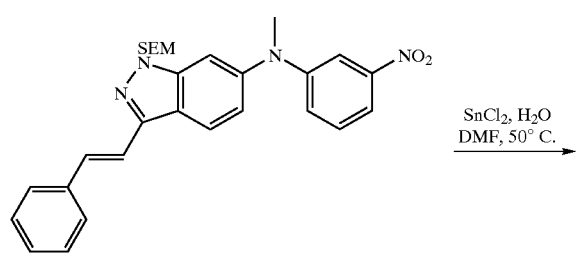

Methyl-(3-nitro-phenyl) {3-styryl-1-[2-(trimethylsilanyl)-ethoxymethyl]-1H-indazol-6-yl}-amine was converted to N-methyl-N-{3-styryl-1-[2-(trimethyl-silanyl)ethoxymethyl]-1H-indazol-6-yl)-benzene-1,3-diamine as described in Example 11, step (iv). Rf sm 0.55, Rf p 0.31 (ethyl acetate:hexane 3:7); FTIR (thin film) 3455, 3360, 2951, 2893, 1621, 1601, 1494, 1449, 1249, 1074 cm$^{-1}$; $^1$H NMR (300 MHz, CDCl$_3$) δ 7.81 (d, 1H, J=8.8 Hz) 7.58 (d, 2H, J=7.21 Hz), 7.26–7.50 (m 5H), 7.12 (t, 1H, J=7.93 Hz), 7.01 (d, 1H, J=1.73 Hz), 6.95 (dd, 1H, J=1.99, 8.85 Hz), 5.67 (s, 2H), 3.63 (t, 2H, J=8.12 Hz), 3.38 (s, 3H), 0.93 (t, 2H, J=8.13 Hz), −0.04 (s, 9H); $^{13}$C NMR (75 MHz, CDCl$_3$) δ 150.3, 149.0, 147.7, 143.4, 143.0, 137.6, 131.3, 130.4, 128.9, 128.0, 126.7, 121.2, 120.6, 117.3, 117.0, 113.1, 110.1, 109.3, 97.5, 77.8, 66.6, 41.0, 18.0, −1.2; LCMS (ESI) [M+H]/z Calc'd 471, Found 471.

Example 12(a)

N-(3-[Methyl-(3-styryl-1H-indazol-6-yl)-amino]-phenyl)-acetamide

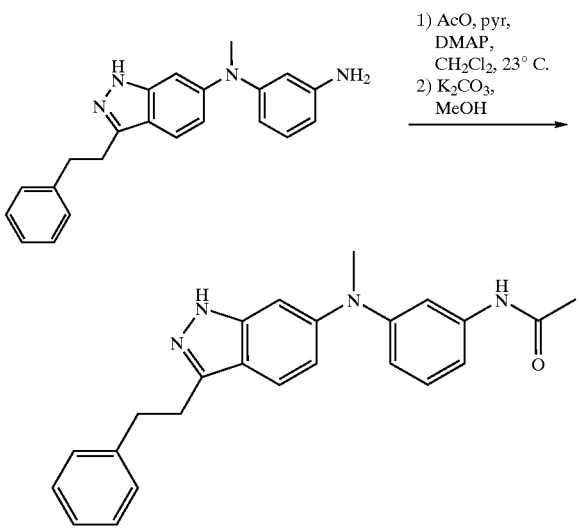

N-Methyl-N-3-styryl-1-[2-(trimethyl-silanyl)-ethoxymethyl]-1H-indazol-6-yl-benzene-1,3-diamine, prepared in Example 11 (34 mg, 0.041 mmol) was suspended in CH$_2$Cl$_2$ (0.5 mL) at 23° C. under an atmosphere of argon. Pyridine (81 μl, 1.0 mmol), Ac$_2$O (94 μl, 1.0 mmol) and DMAP (cat.) were added. The reaction became homogeneous immediately. After 1 h, TLC analysis (CH$_2$Cl$_2$:EtOAc 4:1) indicated no starting material. The reaction was quenched with saturated NaHCO$_3$(aq) (2 mL) then diluted with EtOAc (15 mL) and the organic phase was washed with brine (3 mL), decanted and concentrated under reduced pressure to an oil. The oil was suspended in MeOH (2 mL) and K₂CO₃ (83 mg, 0.6 mmol) was added. The resulting mixture was stirred at 23° C. under an atmosphere of argon. After 1 h, the reaction was diluted with EtOAc (15 mL) and the organic phase was washed with brine (3 mL), decanted and concentrated under reduced pressure. The crude material was purified by semi-prep HPLC to give N-{3-[methyl-(3-styryl-1H-indazol-6-yl)-amino]-phenyl}-acetamide (8.4 mg, 22%). $^1$H NMR (300 MHz, CDCl₃) δ 7.86 (d, 1H, J=8.68 Hz), 7.58 (d, 1H, J=7.17 Hz), 7.16–7.45 (m, 7H), 7.15 (d, 1H, J=8.29 Hz), 6.98 (m, 1H), 6.95 (d, 1H, J=1.92 Hz), 6.8 (dd, 1H, J=1.16, 8.05 Hz), 3.37 (s, 3H), 2.14 (s, 3H). LCMS (ESI) [M+H]/z Calc'd 383, Found 383. Anal. Calc'd: C, 75.37; H, 5.80; N. 14.65. Found: C, 73.53; H, 6.01; N, 13.73.

Example 12(b)

N-(3-[Methyl-(3-styryl-1H-indazol-6-yl)-amino]-phenyl)-benzamide

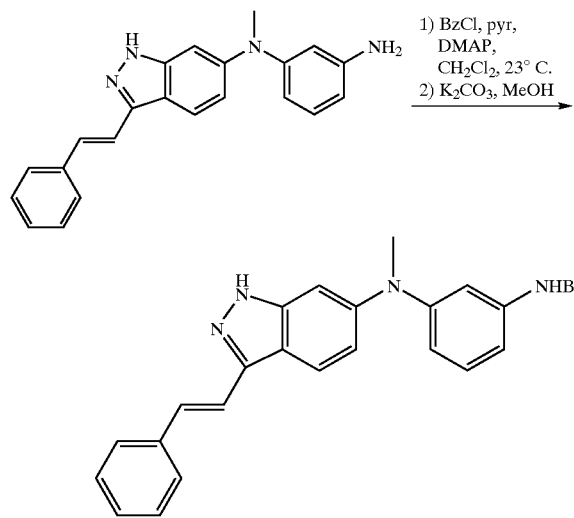

Example 12(b) was prepared in a similar manner to that described for Example 1012(a) above, except that benzoyl chloride was used instead of acetic anhydride. LCMS (ESI) [M+H]/z Calc'd 475, found 475. Anal. Calc'd C (78.36), H (5.44), N (12.60). Found: C (76.57), H (5.0), N (12.12).

Example 12(c)

{3-[Methyl-(3-styryl-1H-indazol-6-yl)-amino)-phenyl}-carbamic acid benzyl ester

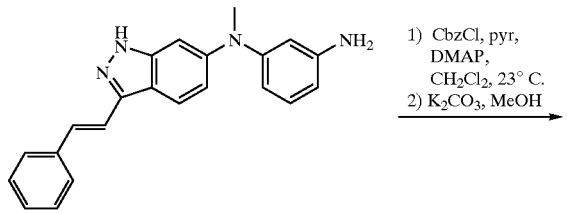

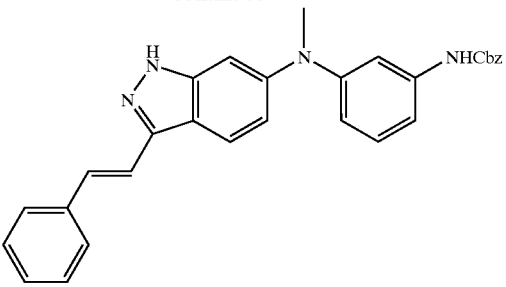

Example 12(c) was prepared in a similar manner to that described for Example 12(a) above, except that carbobenzyloxy chloride was used instead of acetic anhydride. Rf sm 0.30, Rf p 0.57 (CH₂Cl₂:EtOAc 8:2); LCMS (ESI+) [M+H]/z Calc'd 475 Found 475; Anal. Calc'd C (75.93), H (5.52), N (11.81) Found, C (75.60), H (5.96), N (10.75).

Example 12(d)

5-Methyl-thiazole-2-carboxylic acid (3-[methyl-(3-styryl-1H-indazolyl)-6-yl)-amino]-phenyl}-amide

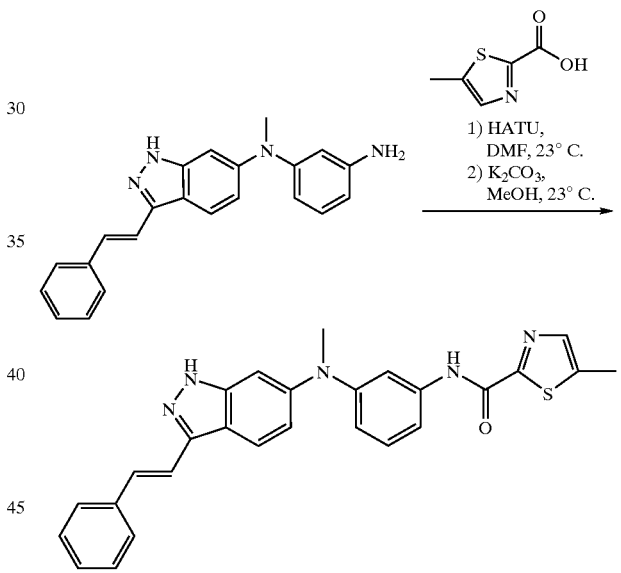

To a solution of N-methyl-N-(3-styryl-1H-indazol-6-yl)-benzene-1,3-diamine, prepared in Example 11, (26 mg, 0.075 mmol) and 5-methyl-thiazole-2-carboxylic acid (64 mg, 0.45 mmol) in DMF (0.375 mL) at 23° C. under an atmosphere of argon was added HATU (171 mg, 0.45 mmol). After 1 h, TLC analysis (CH₂Cl₂:EtOAc 8:2) indicated no starting material. The reaction was quenched with saturated NaHCO₃(aq) (2 mL) then diluted with EtOAc (15 mL) and the organic phase was washed with brine (3 mL), decanted and concentrated under reduced pressure. The oil was suspended in MeOH (2 mL) and K₂CO₃ (62 mg, 0.45 mmol) was added. The resulting mixture was stirred at 23° C. under an atmosphere of argon. After 1 h TLC analysis (CH₂Cl₂:EtOAc 8:2) indicated no starting material. The reaction was diluted with EtOAc (15 mL) and the organic phase was washed with brine (3 mL), decanted and concentrated under reduced pressure to a solid. The crude material was purified by silica gel chromatography (eluting with CH$_2$Cl$_2$:EtOAc 85:15) to give the title compound after purification by semi-prep. HPLC (9.9 mg, 28%). Rf sm 0.25, Rf p 0.39 (hexane:EtOAc 8:2); LCMS (ESI+) [M+H]/z Calc'd 466, found 466. Anal. Calc'd C (69.65). H (4.98), N (15.04) S (6.89). Found: C (69.24), H (5.35), N (13.97) S (5.95).

Example 13

N-[3-(3-Styryl-1H-indazol-ylamino)-phenyl]-benzamide

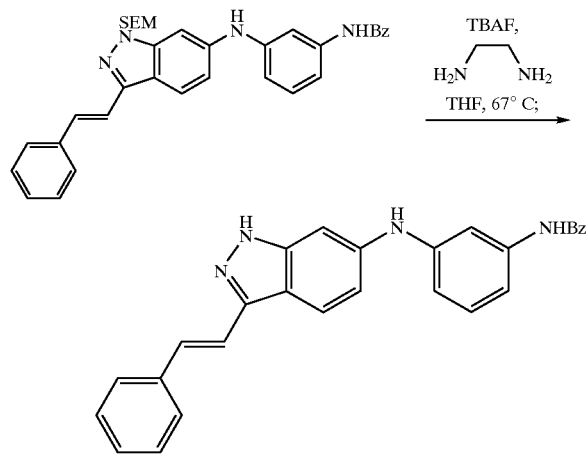

N-(3-(3-Styryl-1-[2-(trimethyl-silanyl)ethoxymethyl]-1H-indazol-6-amino]-phenyl)benzamide was converted to N-[3-(3-styryl-H-indazol-6-ylamino)-phenyl]-benzamide as described in Example 11. LCMS (ESI) [M+H]/z Calc'd 431, found 431. Anal. Calc'd: C, 78.12; H, 5.15; N, 13.01. Found: C, 77.06; H, 6.91; N, 9.88.

The starting material was prepared as follows:

(i)

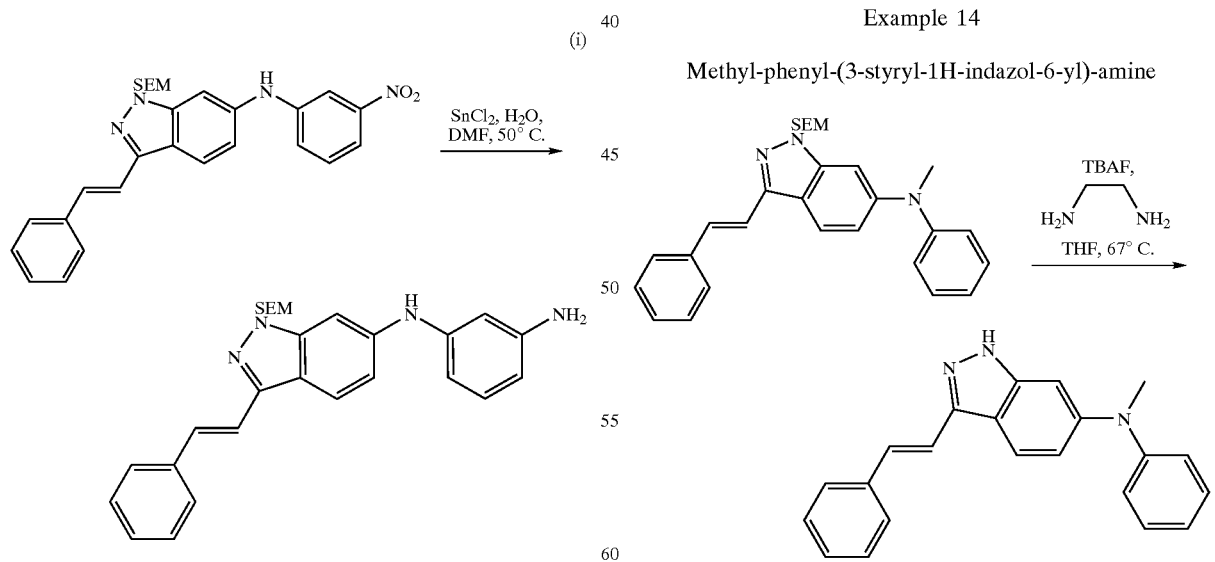

(3-Nitro-phenyl)-{3-styryl-1-[2-(trimethyl-silanyl)-ethoxymethyl]-1H-indazol-6-yl}-amine, prepared in Example 11, step (vi), was converted to N-{3-styryl-1-[2-(trimethyl-silanyl)-ethoxymethyl]-1H-indazol-6-yl}-benzene-1,3-diamine as described in Example 11, step (iv). LCMS (ESI) [M+H]/z Calc'd 457, found 457.

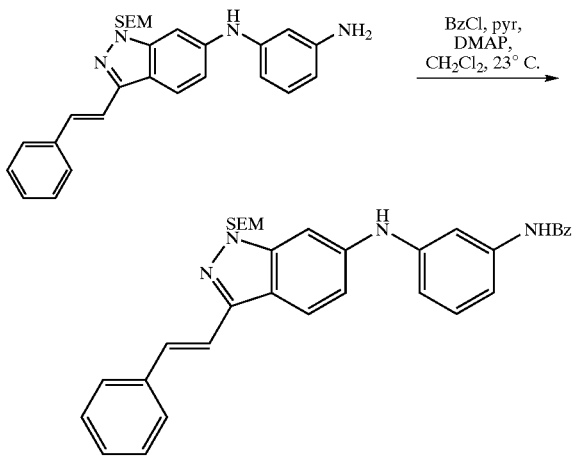

To a solution of N-{3-styryl-1-[2-(trimethyl-silanyl) ethoxymethyl]-1H-indazol-6-yl}-benzene-1,3-diamine (91 mg, 0.2 mmol) and pyridine (0.081 mL, 1.0 mmol) in CH$_2$Cl$_2$ (0.5 mL) cooled to −5° C. under an atmosphere of argon was added benzoyl chloride (0.028 mL, 0.24 mmol). After 0.5 h the reaction was quenched with saturated NaHCO$_3$(aq) then extracted 2×5 mL CH$_2$Cl$_2$. The pooled organic material was washed with brine (5 mL), dried with Na$_2$SO$_4$, decanted and concentrated under reduced pressure to give an oil. The crude material was purified by silica gel chromatography (eluting with hexane:EtOAc 3:2) to give N-(3-{3-Styryl-1-[2-(trimethyl-silanyl)-ethoxymethyl]-1H-indazol-6-ylamino}-phenyl)-benzamide (108 mg, 96% yield). Rf sm 0.35, Rf p 0.44 (ethyl acetate:hexane 1:1); FTIR (thin film) 3320, 2951, 2893, 1657, 1604, 1537, 1493, 1409, 1303, 1248, 1074 cm−1; LCMS (ESI) [M+H]/z Calc'd 561, Found 561. Anal. Calc'd: C, 72.82; H, 6.47; N, 9.99. Found: C, 72.33; H, 6.39; N, 9.81.

Example 14

Methyl-phenyl-(3-styryl-1H-indazol-6-yl)-amine

Methyl-phenyl-(3-styryl-1-[2-(trimethyl-silanyl) ethoxymethyl]-1H-indazol yl)-amine was converted to methyl-phenyl-(3-styryl-1H-indazol-6-yl)-amine as described in Example 11. MS (ESI) [M+H]/z Calc'd 326, found 326.

The starting material was made as follows:

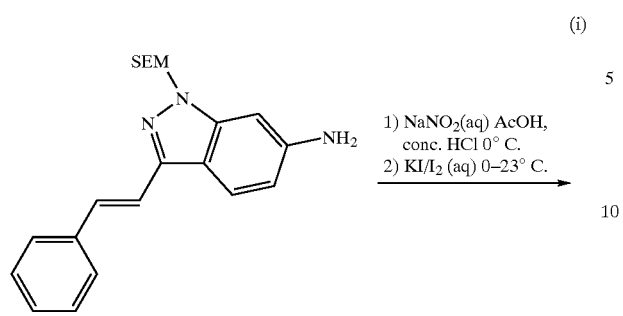

(i)

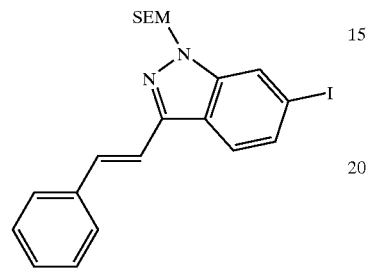

To a solution of 3-styryl-1-[2-(trimethyl-silanyl)-ethoxymethyl]-1H-indazol-6-ylamine (1.58 g, 4 mmol) in AcOH (14 mL), water (3 mL) and concentrated HCl (1.67 mL) cooled to 2° C. was added a solution of NaNO$_2$ (304 mg, 4.4 mmol) in water (05 mL) over 5 min. The resulting dark red solution was stirred at 2° C. for 0.5 h, then a solution of KI (797 mg, 4.8 mmol) and I2 (610 mg, 2.4 mmol) in water (1 mL) was added drop-wise so as to keep the internal temperature below 5° C. After 2 h at 2° C. the reaction was allowed to stir at 23° C. for 17 h. The reaction was quenched with 3 N NaOH (aq), diluted with EtOAc (50 mL) and H$_2$O (15 mL), the phases were separated and the aqueous was extracted 2×15 mL EtOAc. The pooled organic phase was washed 3×20 mL 5% NaHSO$_3$, brine (15 mL), dried with Na$_2$SO$_4$, decanted and concentrated under reduced pressure. The crude reaction was purified by silica gel chromatography (eluting with 1:1 hexane:EtOAc) to give 6-iodo-3-styryl-t-[2-(trimethyl-silanyl)-ethoxymethyl]-1H-indazole as a white solid (1.3 g, 68% yield). $^1$H NMR (300 MHz, CDCl$_3$) δ 8.03 (s, 1H), 7.79 (d, 1H, J=9.0 Hz), 7.30–7.60 (m, 8H), 5.73 (s, 2H), 3.63 (t, 2H, J=6.0 Hz), 0.96 (t, 2H, J=6.0 Hz), 0.0 (s, 9); $^{13}$C NMR (75 MHz, CDCl$_3$) δ 143.6, 142.4, 137.2, 132.1, 130.8, 129.0, 128.3, 126.8, 122.5, 122.4, 119.6, 119.5, 92.9, 78.1, 66.9, 18.0, −1.2. Anal. Calc'd: C, 52.94; H, 5.29; N, 5.88. Found: C, 52.66; H, 5.29; N, 5.74.

(ii)

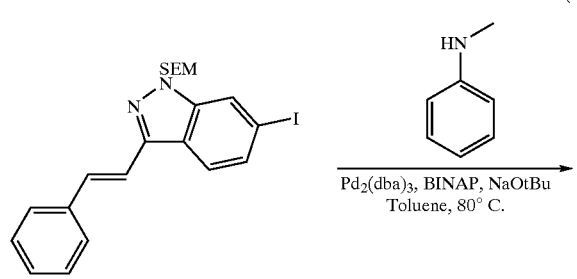

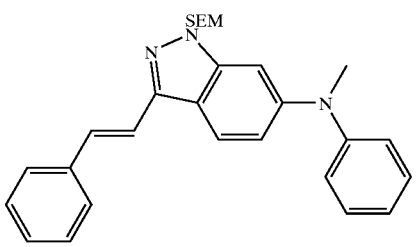

6-Iodo-3-styryl-1-[2-(trimethyl-silanyl)-ethoxymethyl]-1H-indazole was converted to methyl-phenyl-(3-styryl-1-[2-(trimethyl-silanyl)-ethoxymethyl]-1H-indazol-6-yl)-amine as described in Example 11, step (v). Rf sm 0.35 Rf p 0.13 (EtOAc:hexane 1:9); IR (KBr) 3031, 2951, 1625, 1595, 1498, 1449, 1326, 1303, 1248, 1212, 1076, 835, 694 cm$^{-1}$; MS (ESI) [M+H]/z Calc'd 456, Found 456.

Example 15

N-[3-(2-Benzo[1,3]dioxol-5-yl-vinyl)-1H-Indazol-6-yl]-N-methyl-benzene-1,3-diamine

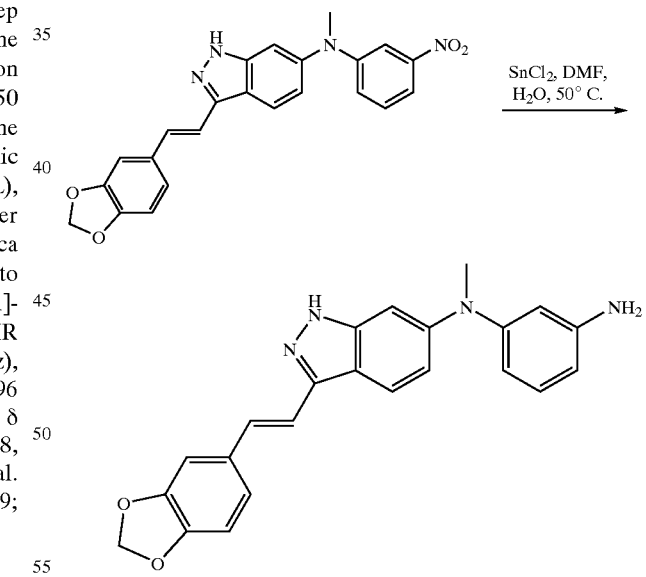

[3-(2-Benzo[1,3]dioxol-5-yl-vinyl)-1H-indazol-yl]-methyl-(3-nitro-phenyl) amine was converted to N-[3-(2-benzo[1,3]dioxol-5-yl-vinyl)-1H-indazol-6-yl]-N-methyl-benzene-1,3-diamine as described in Example 11, step (iv). LCMS (ESI) [M+H]/z Calc'd 385, found 385. Anal. Calc'd: C, 71.86; H, 5.24; N, 14.57. Found: C, 70.99; H, 5.60; N, 13.80.

The starting material was prepared as follows:

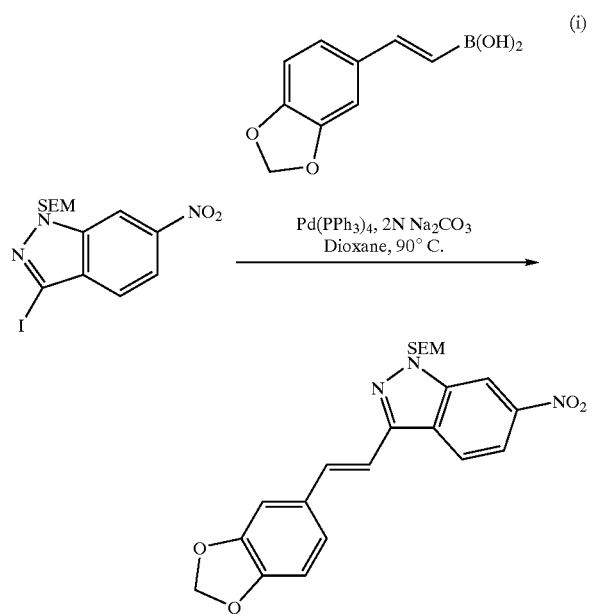

(i)

To a mixture of 6-nitro-3-iodo-[2-(trimethyl-silanyl)ethoxymethyl]-1H-indazole (4.2 g, 10 mmol), boronic acid (3.46 g, 15 mmol), and Pd(PPh$_3$)$_4$ (0.58 g, 0.5 mmol) at 23° C. under an atmosphere of argon was added 1,4-dioxane (38 mL) and 2N NaOH (aq) (12.5 mL, 25 mmol). The resulting mixture was heated to 90° C. After 2 h the reaction was diluted with EtOAc (100 mL) and water (70 mL), the phases were separated and the organic was extracted 2×100 mL EtOAc. The pooled organic phase was washed with brine (20 mL) then dried with Na$_2$SO$_4$, filtered and concentrated under reduced pressure. The crude mixture was purified by silica gel chromatography (eluting with 9:1 hexane:EtOAc) to give 3-(2-benzo[1,3]dioxol-5-yl-vinyl)-6-nitro-1-[2-(trimethyl-silanyl)ethoxymethyl]-1H-indazole as a yellow solid (4.15 g, 94% yield). FTIR (thin film) 2950, 2898, 1523, 1501, 1483, 1446, 1344, 1249, 1080, 1043, 927 cm$^1$; $^1$H NMR (300 MHz, CDCl$_3$) δ 8.56 (dd, 1H, J=0.68, 1.75 Hz), 8.14 (d, 1H, J=1.78 Hz), 8.13 (d, 1H, J=0.67 Hz), 7.50 (d, 1H, 16.53 Hz), 7.25 (d, 1H, 16.52 Hz), 7.18 (d, 1H, J=1.67 Hz), 7.07 (dd, 1H, J=1.65, 8.13 Hz), 6.88 (d, 1H, J=8.0 Hz), 6.05 (s, 2H), 5.84 (s, 2H), 3.66 (t, 2H, J=7.33 Hz), 0.97 (t, 2H, J=7.24 Hz), 0.0 (s, 9H); $^{13}$C NMR (75 MHz, CDCl$_3$) δ 148.5, 148.2, 147.0, 143.9, 140.1, 132.7, 131.3, 126.1, 122.3, 121.9, 116.7, 116.5, 108.7, 106.9, 105.7, 1015, 78.4, 67.2, 17.9, −1.3; LCMS (ESI) [M+H]/z Calc'd 531, found 531.

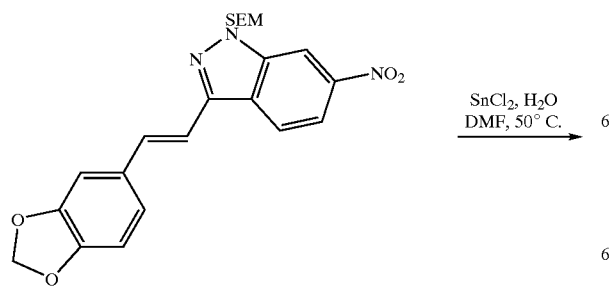

(ii)

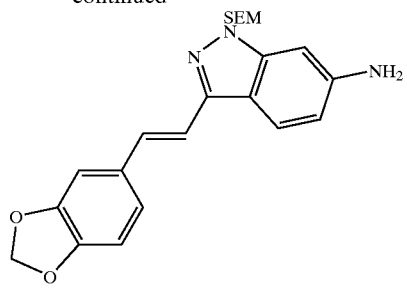

3-(2-Benzo[1,3]dioxol-5-yl-vinyl)-6-nitro-1-[2-(trimethyl-silanyl)-ethoxymethyl]-1H-indazole was converted to 3-(2-Benzo[1,3]dioxol-5-yl-vinyl)-1-[2-(trimethyl-silanyl)ethoxymethyl]-1H-indazol-6-ylamine as described in Example 11, step (iv). $^1$H NMR (300 MHz, CDCl$_3$) δ 7.73 (d, 1H, J=8.56 Hz), 7.52 (d, 1H, J=16.57 Hz), 7.18 (d, 1H, J=16.56 Hz), 7.10 (d, 1H, J=1.49 Hz), 6.98 (dd, 1H, J=1.52, 8.06 Hz), 6.80 (d, 1H, J=8.01 Hz), 6.68 (d, 1H, J=1.44 Hz), 6.63 (dd, 1H, J=1.86, 857 Hz), 5.95 (s, 2H), 5.59 (s, 2H), 3.59 (t, 2H, J=8.17 Hz), 0.91 (t, 2H, J=8.33 Hz), 0.04 (s, 9H); $^{13}$C NMR (75 MHz, CDCl$_3$) δ 148.3, 147.6, 146.4, 143.4, 143.0, 132.0, 130.8, 122.0, 121.7, 118.8, 116.5, 113.1, 108.5, 105.5, 101.3, 92.9, 77.6, 66.3, 17.9, −1.3; LCMS (ESI) [M+H]/z Calc'd 410, found 410.

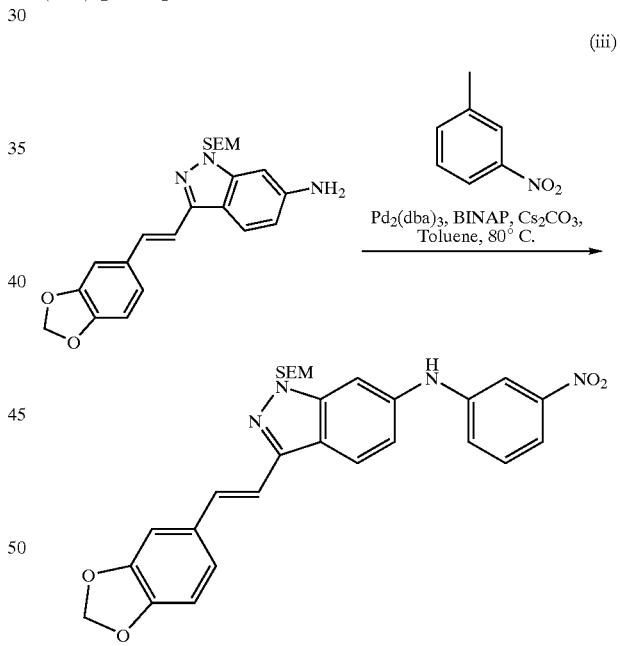

(iii)

3-(2-Benzo[1,3]dioxol-5-yl-vinyl)-1-[2-(trimethyl-silanyl)ethoxymethyl]-1H-indazol-6-ylamine was converted to {3-(2-Benzo[1,3]dioxol-5-yl-vinyl)-1-[2-(trimethyl-silanyl)-ethoxymethyl]-1H-indazol-6-yl}-(3-nitro-phenyl)-amine as described in Example 11, step (v). $^{13}$C NMR (75 MHz, CDCl$_3$) δ 150.8, 149.7, 149.1, 146.0, 144.8, 143.6, 142.1, 133.1, 132.7, 131.6, 124.0, 123.8, 123.1, 120.4, 119.5, 117.2, 116.8, 112.6, 109.9, 106.9, 102.6, 99.7, 79.1, 67.9, 19.2, 0.0; MS (FAB) [M+H]/z Calc'd 531, found 531. Anal. Calc'd: C, 63.38; H, 5.70; N, 10.56. Found: C, 63.49; H, 5.76; N, 10.42.

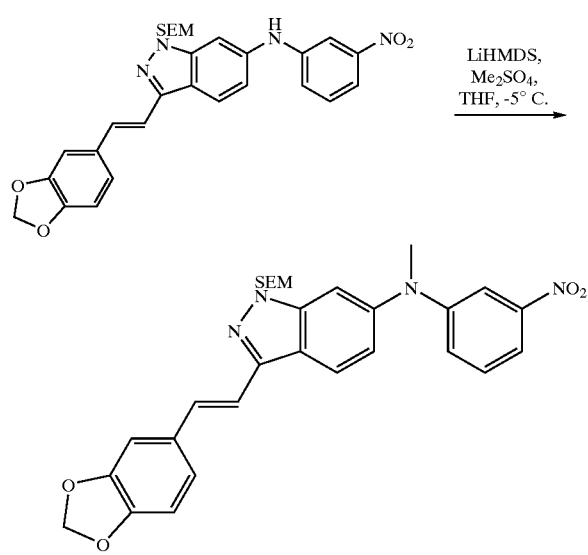

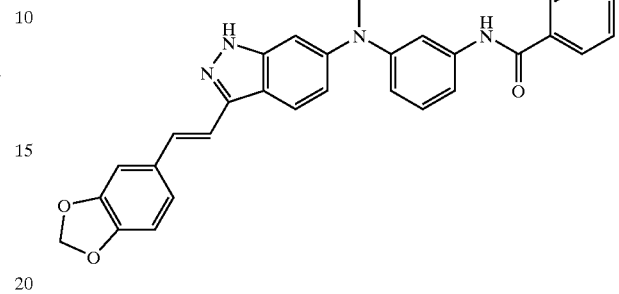

{3-(2-Benzo[1,3]dioxol-5-yl-vinyl)-1-[2-(trimethyl-silanyl)-ethoxymethyl]-1H-indazolyl-6-yl}-(3-nitro-phenyl) amine was converted to {3-(2-Benzo[1,3]dioxol-5-yl-vinyl)-1-[2-(trimethyl-silanyl)-ethoxymethyl]-1H-indazol-6-yl}-methyl(3-nitro-phenyl)-amine as described in Example 11, step (vi). FTIR (KBr) 2952, 2894, 1612, 1529, 1503, 1489, 1446, 1407, 1348, 1306, 1251, 1077, 1039 cm−1; $^{13}$C NMR (75 MHz, CDCl$_3$) δ 150.1, 149.5, 148.4, 147.8, 147.0, 143.5, 142.4, 131.8, 131.5, 129.8, 123.0, 122.49, 121.9, 120.1, 119.5, 118.2, 114.3, 11.3, 108.7, 105.7, 104.5, 101.4, 78.0, 66.8, 41.0, 17.9, −1.2; MS (FAB) [M+H]/z Calc'd 545, found 545. Anal. Calc'd: C, 63.95; H, 5.92; N. 10.29. Found: C, 62.63; H, 5.72; N, 9.62.

Example 16(a)

N-(3-{[3-(2-Benzo[1,3]dioxol-5-yl-vinyl)-1H-indazol-6-yl]-methyl-amino}-phenyl)-benzamide N-[3-(2-Benzo[1,3]dioxol-5-yl-vinyl)-1H-indazol-6-yl]-N-methyl-benzene-1,3-diamine (prepared as described in Example 15) was converted to N-(3-{[32-benzo[1,3]dioxol-5-yl-vinyl)1H-indazol-6-yl]-methyl-amino}-phenyl)-benzamide in the manner described in Example 12(a). LCMS (ESI) [M+H]/z Calc'd 489, Found 489. Anal. Calc'd: C, 73.76; H, 4.95; N, 11.47. Found: C, 73.19; H, 5.09; N, 11.20.

Example 16(b)

N-(3-{[3-(2-Benzo[1,3]dioxol-5-yl-vinyl)-1H-indazol-6-yl]-methyl-amino}-phenyl)-3-methyl-benzamide

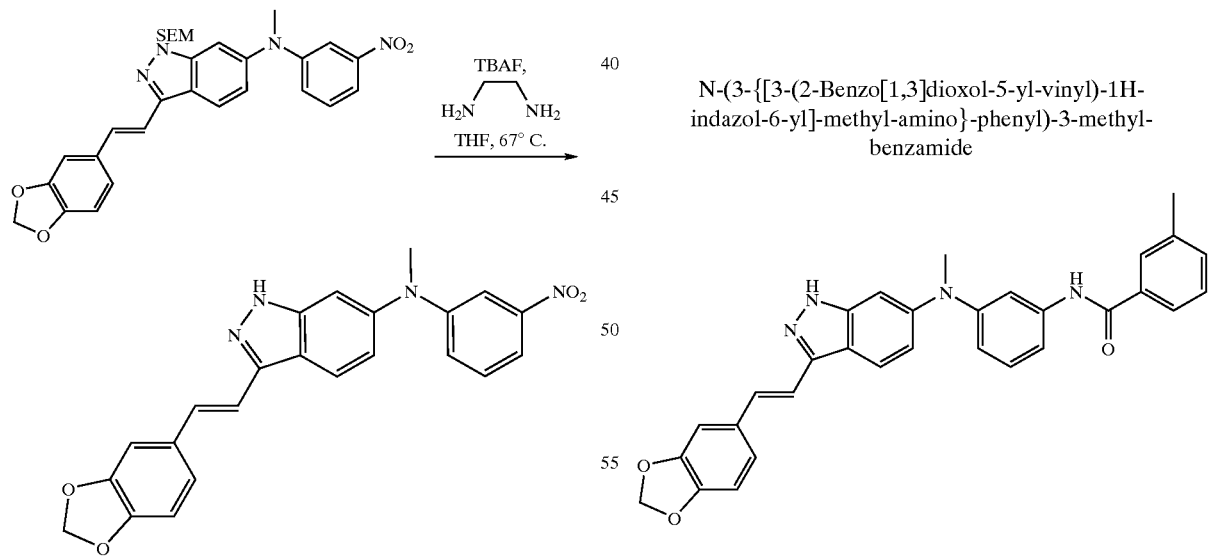

{3-(2-Benzo[1,3]dioxol-5-yl-vinyl)-1-[2-(trimethyl-silanyl)-ethoxymethyl]-1H-indazol-6-yl}-methyl-(3-nitro-phenyl)-amine was converted to [3-(2-Benzo[1,3]dioxol-5-yl-vinyl)1H-indazol-6-yl]-methyl-(3-nitro-phenyl)-amine as described in Example 11. LCMS (EST) [M+H]/z Calc'd 415, found 415. Anal. Calc'd: C, 66.66; H, 4.38; N, 13.52. Found: C, 66.56; H, 4.48; N, 13.35.

Example 16(b) was prepared in a similar manner to that described for Example 16(a) above, except that m-toluyl chloride was used instead of benzoyl chloride. LCMS (ESI) [M+H]/z Calc'd 504, found 504. Anal. Calc'd: C, 74.09; H, 5.21; N, 11.15. Found: C, 73.04; H, 5.84; N, 10.29.

Example 16(c)

N-(3-{[3-(2-Benzo[1,3]dioxol-5-yl-vinyl)-1H-indazol-6-yl]-methyl-amino}-phenyl)-3-dimethylamino-benzamide

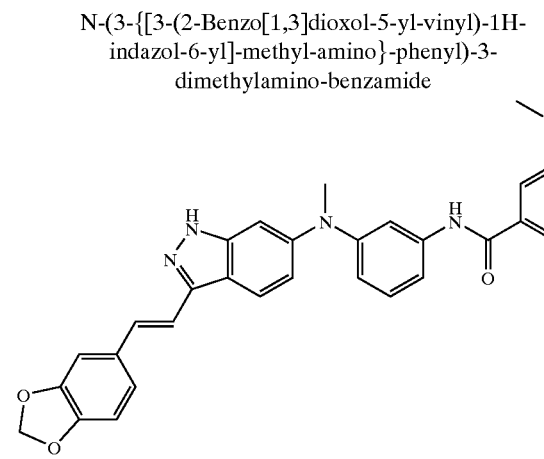

Example 16(c) was prepared in a similar manner to that described for Example 16(a), except that m-dimethylaminobenzoyl chloride was used instead of benzoyl chloride. LCMS (ESI) [M+H]/z Calc'd 532, found 532. Anal. Calc'd: C, 72.30; H, 550; N, 13.17. Found: C, 71.61; H, 5.80; N, 12.75.

Example 16(d)

N-(3-{[3-(2-Benzo[1,3]dioxol-5-yl-vinyl)-1H-indazol-6-yl]-methyl-amino}-phenyl)-3-trifluoromethyl-benzamide

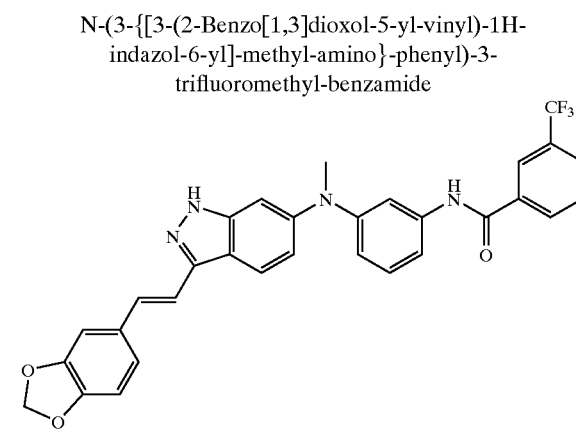

Example 16(d) was prepared in a similar manner to that described for Example 16(a), except that m-trifluoromethylbenzoyl chloride was used instead of benzoyl chloride. LCMS (ESI) [M+H]/z Calc'd 557, found 557. Anal. Calc'd: C, 66.90; H, 4.17; N, 10.07. Found: C, 66.64; H, 4.34; N, 9.82.

Example 16(e)

3-Acetyl-N-(3-{[3-(2-benzo[1,3]dioxol-5-yl-vinyl)-1H-indazol-6-yl]-methyl-amino}-phenyl)-benzamide

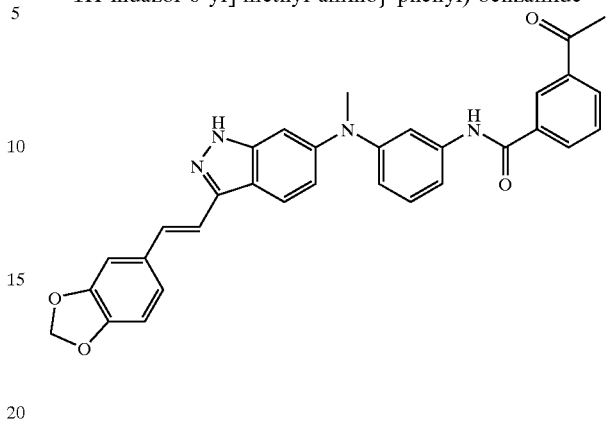

Example 16(e) was prepared in a similar manner to that described for Example 16(a), except that m-acetylbenzoyl chloride was used instead of benzoyl chloride. LCMS (ESI) [M+H]/z Calc'd 531, found 531. Anal. Calc'd: C, 72.44; H, 4.94; N, 10.56. Found: C, 55.51; H, 4.21; N, 7.58.

Example 16(f)

6-[N-(3-(4-tert-butyl-3-hydroxybenzamido)phenyl)-N-methylamino]-3-E-[(3,4-methylenedioxyphenyl)ethenyl]-1H-indazole

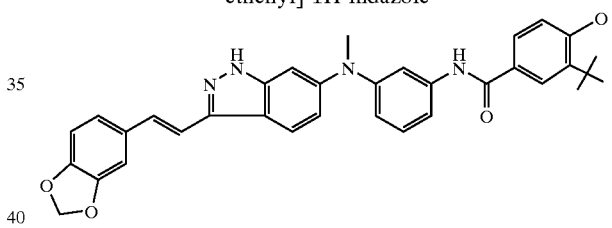

Example 16(f) was prepared in a similar manner to that described for Example 16(a), except that 3-tert-butyl-4-hydroxy-benzoic acid, HATU, and TEA were used instead of benzoyl chloride. $^1$H NMR (300 MHz, CD$_3$OD) δ 7.90 (d, 1H, J=8.91 Hz), 7.83 (d, 1H, J=2.29 Hz), 7.63 (dd, 1H, J=8.36 Hz, J=2.31 Hz), 7.54 (t, 1H, J=1.97 Hz), 7.25–7.43 (m, 4H), 7.14–7.20 (m, 2H), 7.06 (dd, 1H, J=8.11 Hz, J=1.55 Hz), 6.96 (dd, 1H, J=8.93 Hz, 1=1.97 Hz), 6.90 (m, 1H), 6.82 (t, 2H, J=8.18 Hz), 6.0 (s, 2H), 3.41 (s, 3H), 1.42 (s, 9H).

Example 17

Phenyl-(3-styryl-1H-indazol-6-yl)-methanone

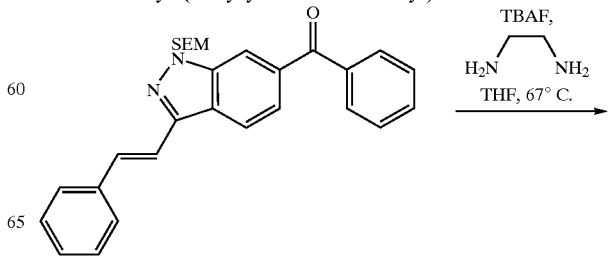

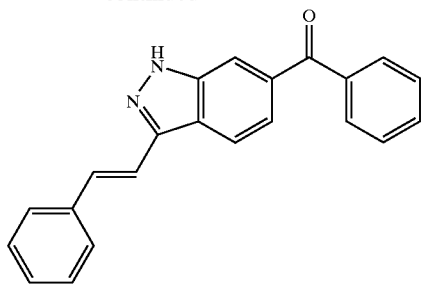

Phenyl-{3-styryl-1-[2-(trimethyl-silanyl)-ethoxymethyl]-1H-indazol-6-yl}-methanone was converted to phenyl-(3-styryl-1H-indazol-6-yl)-methanone as described in Example 11 (30 mg, 78%). MS (ESI) [M+H]/z Calc'd 325, found 325. Anal. Calc'd: C, 81.46; H, 4.97; N, 8.46. Found: C, 80.36; H, 5.16; N, 8.51.

The starting material was prepared as follows:

(i)

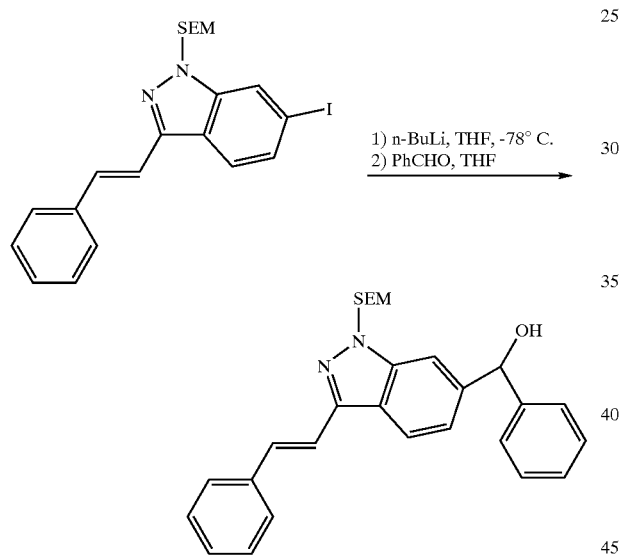

To a solution of 6-iodo-3-styryl-1-[2-(trimethyl-silanyl)-ethoxymethyl]-1H-indazole, prepared in Example 14, step (i), (143 mg, 0.3 mmol) in THF (1 mL) cooled to −78° C. under an atmosphere of argon was added n-BuLi (0.2 mL 0.315 mmol) dropwise. The resulting mixture was stirred at −78° C. for 30 min, then a solution of benzaldehyde (0.035 mL, 0.33 mmol) in THF (0.5 mL) was added rapidly via a cannula. After 0.5 h the reaction was quenched with saturated NH₄Cl (aq) and diluted with EtOAc (10 mL) and H₂O (3 mL). The phases were separated and the aqueous was extracted 2×10 mL EtOAc. The pooled EtOAc was washed with brine (5 mL), dried with Na₂SO₄, decanted and concentrated under reduced pressure. The crude mixture was purified by silica gel chromatography (eluting with hexane:EtOAc 4:1) to give phenyl-{3-styryl-1-[2-(trimethyl-silanyl)ethoxymethyl]-1H-indazol-6-yl 1-methanol (68 mg, 50% yield). Rf sm=0.72; Rf p=0.39 (7:3 hexane:EtOAc); FTIR (thin film) 3368, 2952, 2893, 1621, 1478, 1449, 1374, 1307, 1249, 1216, 1078, 960, 859, 835 cm⁻¹. MS (ESI) [M+H]/z Calc'd 457, found 457.

(ii)

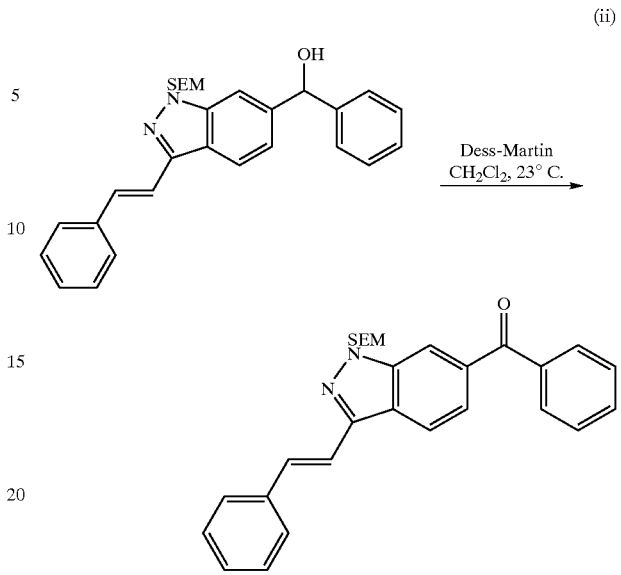

To a solution of phenyl-(3-styryl-1-[2-(trimethyl-silanyl)-ethoxymethyl]-1H-indazol-6-yl}-methanol (68 mg, 0.15 mmol) in dichloromethane (3 mL) at 23° C. under an atmosphere of argon was added periodinane (Dess-Martin reagent) (190 mg, 0.45 mmol). The resulting mixture was stirred at 23° C. for 1 hour. The solution was then diluted with hexane (3 mL) then filtered through Celite and concentrated under reduced pressure to a solid. The crude mixture was purified by silica gel chromatography (eluting with hexane:EtOAc 9:1) to give phenyl-(3-styryl-1-[2-(trimethyl-silanyl)-ethoxymethyl]-1H-indazol-6-yl]-methanone (54 mg, 79% yield). Rf sm=0.41, Rf p=0.63 (7:3 hexane:EtOAc); FTIR (thin film) 3059, 2952, 2894, 1659, 1474, 1448, 1307, 1249, 1078, 836, 649 cm⁻¹. MS (ESI) [M+H]/z Calc'd 455, found 455.

Example 18

(3-Amino-phenyl)-(3-styryl-1H-indazol-6-yl)-methanone

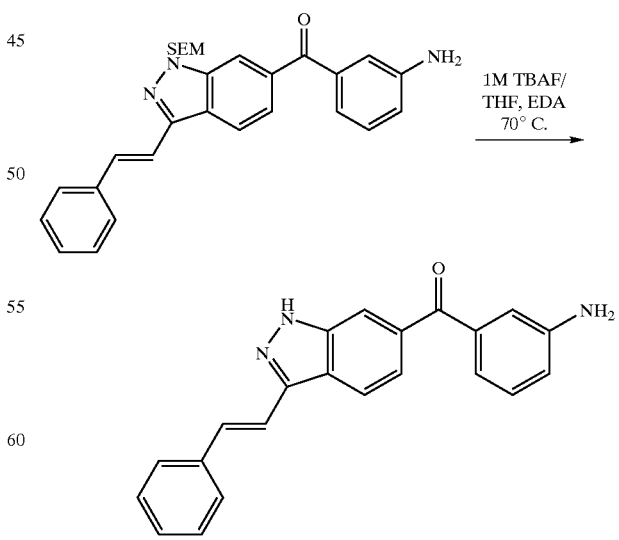

(3-Amino-phenyl)-{3-styryl-1-[2-(trimethyl-silanyl)ethoxymethyl]-1H-indazol-6-yl}-methanone was converted to (3-amino-phenyl)(3-styryl-1H-indazol-6 yl)-methanone as described in Example 11. $^1$H NMR (300 MHz, CDCl$_3$) δ 8.07 (dd, 1H, J=0.71, 8.50 Hz), 7.91 (s, 1H), 7.64 (dd, 1H, J=1.35, 8.48 Hz), 7.54–7.60 (m, 2H), 7.46 (d, 2H, J=12.84 Hz), 7.35–7.40 (m, 2H), 7.22–7.31 (m, 2H), 7.16–7.13 (m, 2H), 6.91 (ddd, 1H, J=1.08, 7.89 Hz). LCMS (ESI) [M+H]/z Calc'd 340, found 340.

The starting material was prepared as follows:

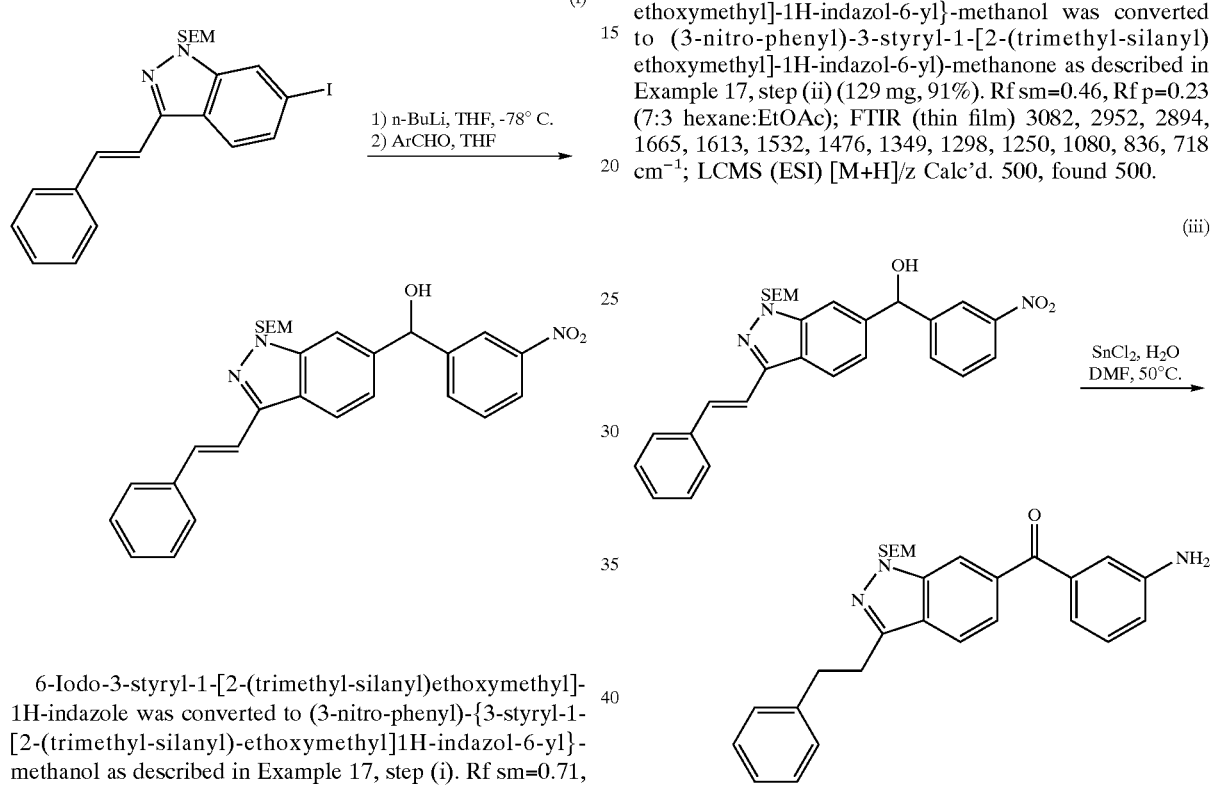

6-Iodo-3-styryl-1-[2-(trimethyl-silanyl)ethoxymethyl]-1H-indazole was converted to (3-nitro-phenyl)-{3-styryl-1-[2-(trimethyl-silanyl)-ethoxymethyl]1H-indazol-6-yl}-methanol as described in Example 17, step (i). Rf sm=0.71, Rf p=0.25 (7:3 hexane:EtOAc); FTIR (thin film) 3369, 3061, 2952, 2894, 2361, 1620, 1578, 1530, 1478, 1449, 1350, 1308, 1249, 1215, 1080, 961, 859 cm$^{-1}$; $^1$H NMR (300 MHz, CDCl$_3$) δ 835 (s, 1H), 8.14 (dd, 1H, J=1.34, 8.14 Hz), 7.99 (d, 1H, J=8.38 Hz), 7.76 (d, 1H, J=7.72 Hz), 7.68 (s, 1H), 7.59–7.30 (m, 8H), 7.21 (d, 1H, J=8.33 Hz), 6.09 (s, 1H), 5.73 (s, 2H), 3.61 (t, 2H, J=8.30 Hz), 090 (t, 2H, J=8.30 Hz), −0.06 (s, 9H). $^{13}$C NMR (75 MHz, CDCl$_3$) δ 148.5, 145.9, 143.4, 142.4, 141.3, 137.1, 132.7, 132.0, 129.5, 128.9, 128.2, 126.7, 122.6, 122.6, 121.8, 121.5, 120.8, 119.6, 107.8, 77.7, 75.4, 66.8, 17.8, −1.3. Anal. Calc'd: C, 67.04; H, 6.23; N, 8.38. Found: C, 66.93; H, 6.20; N, 8.41.

(3-Nitro-phenyl)-{3-styryl-1-[2-(trimethyl-silanyl)-ethoxymethyl]-1H-indazol-6-yl}-methanol was converted to (3-nitro-phenyl)-3-styryl-1-[2-(trimethyl-silanyl) ethoxymethyl]-1H-indazol-6-yl)-methanone as described in Example 17, step (ii) (129 mg, 91%). Rf sm=0.46, Rf p=0.23 (7:3 hexane:EtOAc); FTIR (thin film) 3082, 2952, 2894, 1665, 1613, 1532, 1476, 1349, 1298, 1250, 1080, 836, 718 cm$^{-1}$; LCMS (ESI) [M+H]/z Calc'd. 500, found 500.

(3-Nitrophenyl) (3-styryl-1-[2-(trimethyl-silanyl) ethoxymethyl]-1H-indazol-6-yl)-methanone was converted to (3-amino-phenyl)-{3-styryl-1-[2-(trimethyl-silanyl) ethoxymethyl]-1H-indazol-6-yl}-methanone as described in Example 11, step (iv) (102 mg, 84%). LCMS (ESI) [M+H]/z Calc'd 340, found 340.

Example 19(a)

N-[3-(3-Styryl-1H-indazole-6-carbonyl)-phenyl]-acetamide

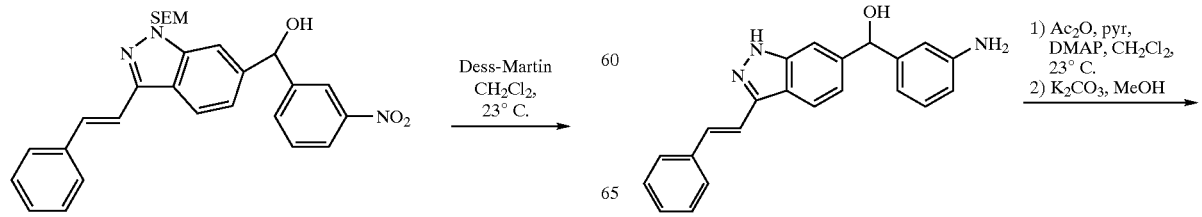

-continued

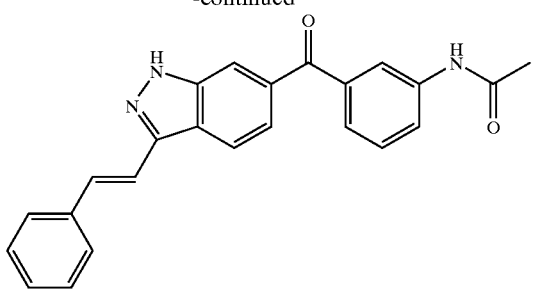

(3-Amino-phenyl)-(3-styryl-1H-indazol-6-yl)-methanone, prepared in Example 18, was converted to N-[3-(3-styryl-1H-indazole-6-carbonyl)-phenyl]-acetamide as described in Example 12(a) (12.2 mg, 78%). Rf sm=0.16, Rf p=0.35 (8:2 CH$_2$Cl$_2$:EtOAc); LCMS (ESI) [M+H]/z Calc'd 382, found 382. Anal. Calc'd: C, 75.57; H, 5.02; N, 11.02. Found: C, 74.32; H, 5.41; N, 10.54.

Example 19(b)

N-[3-(3-Styryl-1H-indazole-6-carbonyl)-phenyl]-benzamide

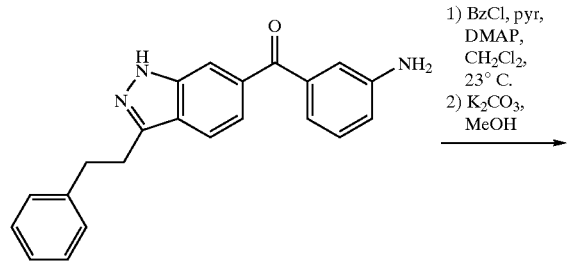

Example 19(b) was prepared in a similar manner to that described for Example 19(a), except that benzoyl chloride was used instead of acetic anhydride. $^1$H NMR (300 MHz, CDCl$_3$) δ 8.40 (s, 1H), 8.02 (d, 1H, J=8.49 Hz), 7.98 (d, 1H, J=1.01 Hz), 7.95 (s, 1H), 7.95 (s, 1H), 7.83–7.88 (m, 3H), 7.65 (dd, 1H, J=1.04, 8.48 Hz), 7.29–7.56 (m, 11 H). MS (ESI) [M+H]/z Calc'd 444, found 444. Anal. Calc'd: C, 78.54; H, 4.77; N, 9.47. Found: C, 78.01; H, 4.87; N, 9.32.

Example 19(c)

[3-(3-Styryl-1H-indazole-6-carbonyl)-phenyl]-carbamic acid benzyl ester

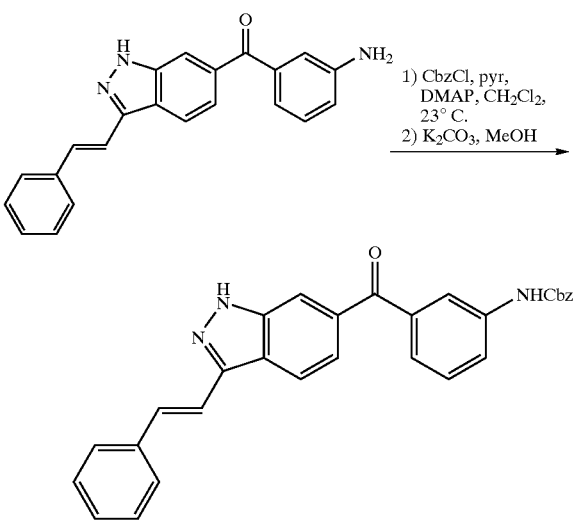

The title compound was prepared in a similar manner to that described for Example 19(a), except that carboxybenzyloxy chloride was used instead of acetic anhydride. $^1$H NMR (300 MHz, DMSO-d$_6$) δ 8.37 (d, 1H, J=8.48 Hz), 7.98 (s, 1H), 7.88 (s, 1H), 7.79 (s, 1H), 7.75 (d, 2H, J=7.44 Hz), 7.61 (d, 2H, J=1.81 Hz), 7.58 (s, 1H), 7.51 (t, 1H, J=7.79 Hz), 7.42 (t, 5H, J=6.56 Hz), 7.31–7.37 (m, 4H), 5.16 (s, 2H); LCMS (ESI) [M+H]/z Calc'd 474, found 474. Anal. Calc'd: C, 76.09; H, 4.90; N, 8.87. Found: C, 73.82; H. 4.93; N, 8.27.

Example 19(d)

5-Methyl-thiazole-2-carboxylic acid [3-(3-styryl-1H-indazole-6-carbonyl)phenyl]-amide

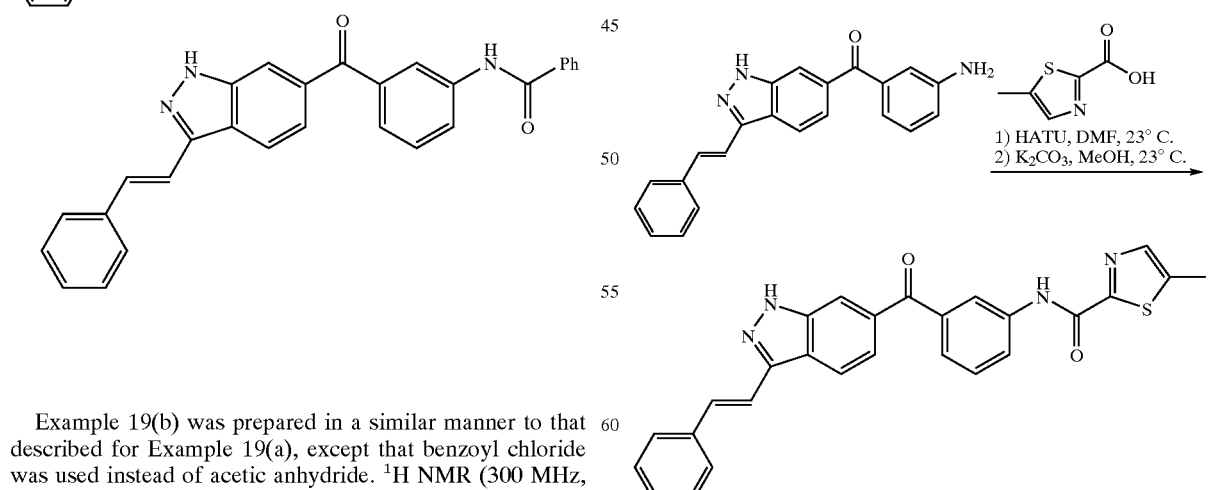

(3-Amino-phenyl)(3-styryl-H-indazol-6-yl)-methanone was converted to 5-methyl-thiazole-2-carboxylic acid [3-(3- styryl-H-indazole-6-carbonyl)-phenyl]-amide as described in Example 12(d) (9.9 mg, 28%). ¹H NMR (300 MHz, CDCl₃) δ 8.15 (d, 1H, J=8.49 Hz), 8.09 (t. 1H, J=1.86 Hz), 8.04 (dd, 1H, J=1.0, 7.98 Hz), 7.99 (s, 1H), 7.75 (dd, 1H. J=1.31, 8.47 Hz), 7.67 (s, 1H), 7.63 (d, 2H, J=7.30 Hz), 7.54–7.58 (m, 3H), 7.50 (s, 1H), 7.42 (t, 3H, J=8.09 Hz); LCMS (ESI) [M+H]/z Calc'd 465, found 465.

Example 19(e)

6-[3-(5-methylpyridin-3-ylcarboxamido)benzoyl]-E-styryl-1H-indazole

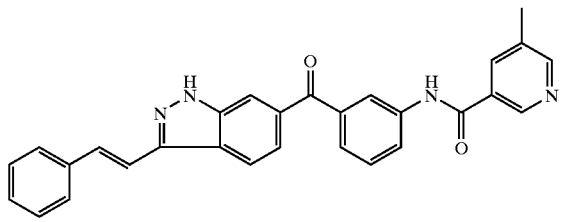

Example 19(e) was prepared in a similar manner to Example 19(d) except that 5-methyl-nicotinic acid was used instead of 5-methyl-thiazole-2-carboxylic acid. ¹H NMR (300 MHz, CDCl₃) δ 9.22 (s, 1H), 8.99 (d, 1H, J=0.59 Hz), 8.67 (s, 1H), 8.24 (s, 1H), 8.16 (d, 1H, J=8.32 Hz), 2.97 (dd, 1H, J=8.3 Hz, J=0.94 Hz), 7.72 (d, 1H, J 5=16.65 Hz), 7.64 (d, 2H, J=7.21 Hz), 7.19–7.47 (m, 8H), 6.95 (d, 1H, J=6.43 Hz), 2.49 (s, 3H). MS (ESI+) [M+H]/z Calc'd 459, found 459. Anal. Calc'd: C, 75.97. H, 4.84. N, 12.22. Found: C, 75.86. H, 4.94. N, 12.10.

Example 19(f)

6-[3-(indol-4-ylcarboxamido)benzoyl]-3-E-styryl-1H-indazole

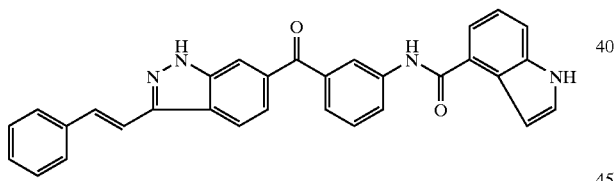

Example 19(f) was prepared in a similar manner to Example 19 (d) except 1H-Indole-4-carboxylic acid was used instead of 5-methyl-thiazole-2-carboxylic acid. LCMS (ESI+) [M+H]/z Calc'd 483, found 483. Anal. Calc'd: C, 77.16; H, 4.60; N, 11.61. Found: C, 76.15; H, 4.49; N, 11.31.

Example 19(g)

6-[3-(pyridin-2-ylacetamido)benzoyl]-3-E-styryl-1H-indazole

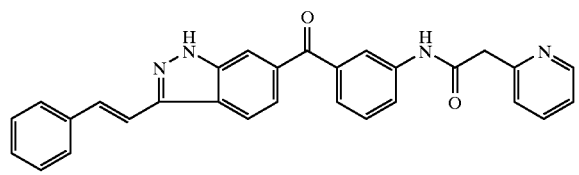

Example 19(g) was prepared in a similar manner to Example 19(d), except that, pyridin-2-yl-acetic acid was used instead. ¹H NMR (300 MHz, CDCl₃) δ 8.50 (dd, 1H, J=4.86 Hz, 3=0.91 Hz), 8.37 (d, 1H, J=8.51 Hz), 8.09 (s, 1H), 7.94 (d, 1H, J=7.89 Hz), 7.87 (s, 1H), 7.73–7.79 (m, 3H), 7.25–7.60 (m, 10H) 3.86 (s, 2H). MS (ESI) [M+H]/z Calc'd 459, found 459. Anal. Calc'd: C, 75.97. H, 4.84. N, 12.22. Found: C, 74.70. H, 4.83. N, 11.99.

Example 19(h)

6-[3-(2-methylpropionamido)benzoyl]-3-E-styryl-1H-indazole

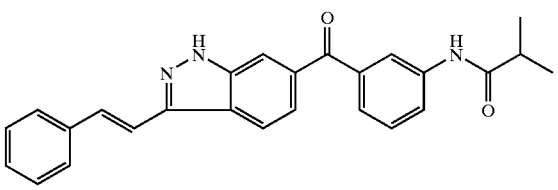

Example 19(h) was prepared in a similar manner to Example 19(a). Isobutyryl chloride was used instead of acetyl chloride. ¹H NMR (300 MHz, DMSO-d₆) δ 8.38 (d, 1H, J=8.13 Hz), 8.08 (t, 1H), 7.96 (s, H. J=7.8 Hz, J=1.91 Hz), 7.88 (s, 1H), 7.75 (d, 2H, J=7.25 Hz), 7.61 (d, 2H, 2.05 Hz), 7.40–7.58 (m, 5H), 7.31 (m, 1H), 2.60 (m, 1H, 1=6.82 Hz), 1.1 (d, 6H, J=6.82 Hz). (MS (ESI+) [M+Na]/z Calc'd 432, found 432. Anal. Calc'd: C, 76.26. H, 5.66. N, 10.26. Found: C, 75.14. H, 5.62. N, 10.08.

Example 19(i)

6[3-(2-acetamido-2-phenylacetamido)benzoyl]-3-E-styryl-1H-indazole

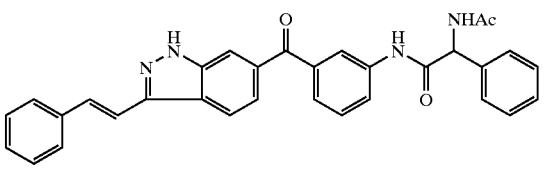

Example 19(i) was prepared in a similar manner to Example 19(d) except that acetylamino-2-phenyl-acetic acid was used instead of 5-methyl-thiazole-2-carboxylic acid. ¹H NMR (300 MHz, DMSO-d₆) δ 13.5 (s, 1H), 10.6 (s, 1H), 8.66 (d, 1H, J=7.66 Hz), 8.36 (d, 1H, 3=8.47 Hz), 8.07 (s, 1H), 7.92 (d, 1H, J=7.63 Hz), 7.86 (s, 1H), 7.75 (d, 2H, J=7.33 Hz), 7.29–7.60 (m, 13H), 5.61 (d, 1H, J=7.6 Hz), 1.92 (s, 3H). LCMS (ESI+) [M+H]/z Calc'd 515, found 515. Anal. Calc'd: C, 74.69. H, 5.09. N, 10.89. Found: C, 73.01. H. 5.01. N, 10.60.

Example 19(j)

6-[3-(pyridin-4-ylcarboxamido)benzoyl]-3-E-styryl-1H-indazole

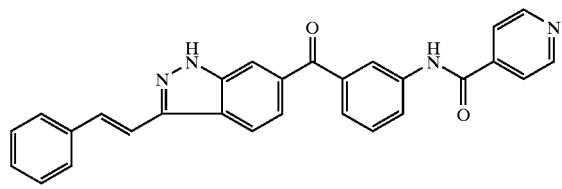

Example 19(j) was prepared in a similar manner to Example 19(d) except that isonicotinic acid was used instead of 5-methyl-thiazole-2-carboxylic acid. MS (ESI+) [M+Na]/z Calc'd 467, found 467. Anal. Calc'd: C, 75.66; H, 4.54; N, 12.60. Found: C, 74.17; H, 4.62; N, 12.31.

Example 19(k)

6-[3-(pyridin-2-ylcarboxamido)benzoyl]-3-E-styryl-1H-indazole

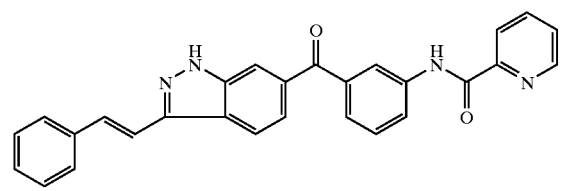

Example 19(k) was prepared in a similar manner to Example 19(d) except that pyridine-2-carboxylic acid was used instead of 5-methyl-thiazole-2-carboxylic acid. MS (ESI+) [M+Na]/z Calc'd 467, found 467. Anal. Calc'd: C, 75.66; H, 4.54; N, 12.60. Found: C, 74.17; H, 4.61; N, 12.44.

Example 19(l)

6-[3-(isoxazol-4-ylcarboxamido)benzoyl]-3-E-styryl-1H-indazole

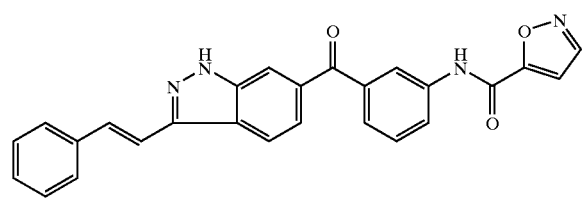

Example 19(l) was prepared in a similar manner to Example 19(d) except that isoxazole-5-carboxylic acid was used instead of 5-methyl-thiazole-2-carboxylic acid. MS (ESI+) [M+H]/z Calc'd 435, found 435. Anal. Calc'd: C, 71.88; H, 4.18; N, 12.90. Found: C, 71.36; H, 4.33; N, 12.47.

Example 19(m)

6-[3-(6-chloropyridin-2-ylcarboxamido)benzoyl]-3-E-styryl-1H-indazole

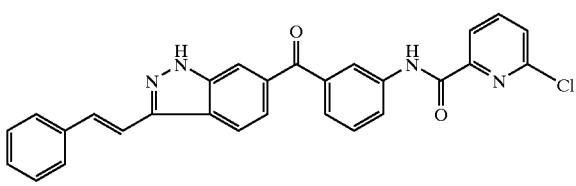

Example 19(m) was prepared in a similar manner to Example 19(d) except that 6-chloro-pyridine-2-carboxylic acid was used instead of 5-methyl-thiazole-2-carboxylic acid. MS (ESI+) [M+Nay/z Calc'd 501, found 501.

Example 19(n)

6-[3-(4-chloropyridin-2-ylcarboxamido)benzoyl]-3-E-styryl-1H-indazole

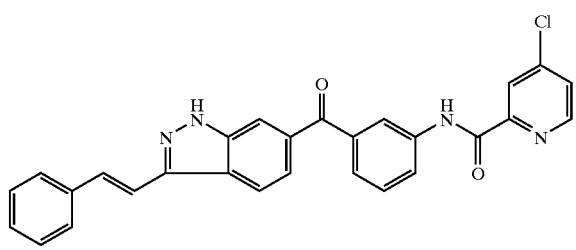

Example 19(n) was prepared in a similar manner to Example 19(d) except 4-, chloro-pyridine-2-carboxylic acid was used instead of 5-methyl-thiazole-2-carboxylic acid. MS (ESI+) [M+H]/z Calc'd 479, found 479. Anal. Calc'd: C, 70.22; H, 4.00; N, 11.70. Found: C, 70.07; H, 4.09; N, 11.64.

Example 19(o)

6-[3-(2-chloropyridin-4-ylcarboxamido)benzoyl]-3-E-styryl-1H-indazole

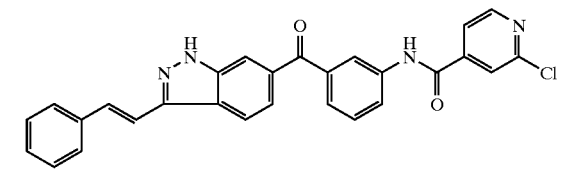

Example 19(o) was prepared in a similar manner to Example 19(d) except 2-chloro-isonicotinic acid was used instead of 5-methyl-thiazole-2-carboxylic acid. MS (ESI+) [M+H]/z Calc'd 479, found 479.

Example 19(p)

6-[3-(2-methylamino-2-phenylacetamido)benzoyl]-3-E-styryl-1H-indazole

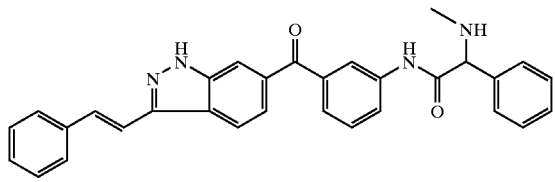

To a solution of 6[3-(2-(N-t-butoxycarbonyl-N-methylamino)-2-phenyl-acetamido)benzoyl]-3-E-styryl-1H-indazole (115 mg, 0.2 mmol) in CH$_2$Cl$_2$ (2 ml) cooled to 0° C. was added TFA (2 ml). After 40 min. the reaction mixture was quenched with saturated NaHCO$_3$ (aq), then extracted with CH$_2$Cl$_2$ (2×10 ml). The Organics were washed with brine, dried with Na$_2$SO$_4$, decanted and concentrated. Purification by silica gel chromatography (1:10 methanol-dichloromethane) gave 6[3-(2-methylamino-2-phenylacetamido)benzoyl]-3-E-styryl-1H-indazole (38 mg, 39%). MS (ESI+) [M+H]/z Calc'd 487, found 487. Anal. Calc'd: C, 76.52; H, 5.39; N, 11.51. Found: C, 74.99; H, 5.76; N, 10.89.

The starting material was prepared as described below:

(i) 6[3-(2-(N-1-butoxycarbonyl-N-methylamino)-2-phenyl-acetamido)benzoyl]-3-E-styryl-1H-indazole

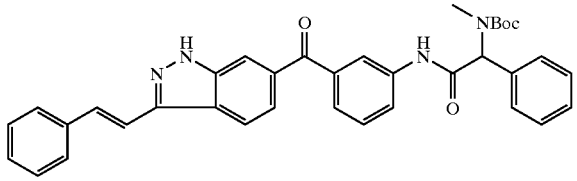

6-[3-(2-(N-t-butoxycarbonyl-N-methylamino)-2-phenyl-acetamido)benzoyl]-3-E-styryl-1H-indazole was prepared in a similar manner to Example 19(d) except that (t-butoxycarbonyl-methyl-amino)-phenyl-acetic acid was used instead of 5-methyl-thiazole-2-carboxylic acid. MS (ESI+) [M+H]/z Calc'd 587, found 587.

Example 20(a)

6-(3-Acetamido-phenylsulfanyl)-3-styryl-1H-indazole

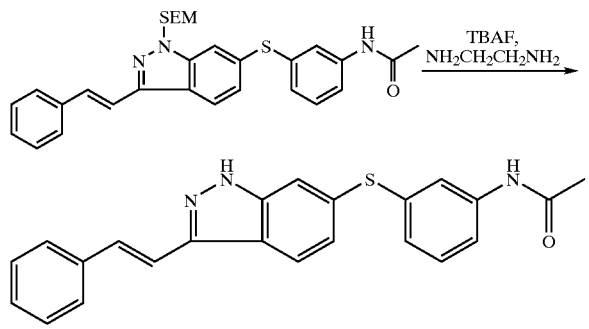

6-(3-Acetamido-phenylsulfanyl)$_3$-styryl-1-[2-(trimethyl-silanyl)-ethoxymethyl]-1H-indazole was converted to 6-(3-acetamido-phenylsulfanyl)-3-styryl-1H-indazole as described in Example 11 (30 mg, 81%): R$_f$ sm 0.65, p 0.35 (10% methanol in dichloromethane); $^1$H NMR (300 MHz, CDCl$_3$) δ 7.81 (d, 1H, J=8.5 Hz), 7.59 (bs, 1H), 7.48–7.0 (m, 13H), 1.98 (s, 3H); HRMS (FAB) [M+Na]/z Calc'd 408.1147, found 408.1156.

The starting material was prepared as follows:

(i)

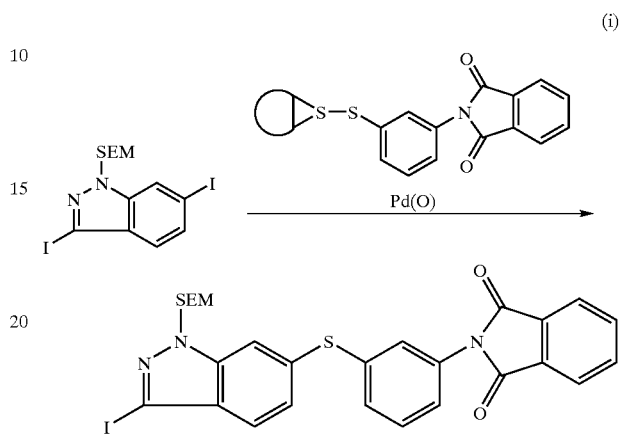

To the 9-BBN adduct of 3-phthalamido-thiophenol (1.4 equiv), which was prepared in situ as described below, was added 3,6-Diiodo-1-[2-(trimethyl-silanyl)-ethoxymethyl]-1H-indazole (250 mg, 0.5 mmol), Pd(dppf)Cl$_2$ (87 mg, 0.2 equiv) and potassium phosphate (339 mg, 1.6 mmol, 3.00 equiv) in DMF (3.0 mL). The reaction mixture was heated to 90° C. for 9 h. The mixture was cooled and partitioned between ethyl acetate and saturated sodium bicarbonate. The organic material was dried over sodium sulfate, decanted and concentrated. Purification by silica gel chromatography (2:8 ethyl acetate-hexane) gave 6-(3-phthalamido-phenylsulfanyl)-3-iodo-1H-indazole as an oil (159 mg, 50%): $^1$H NMR (300 MHz, CDCl$_3$) δ 7.93 (m, 2H), 7.79 (m, 2H), 7.62 (s, 1H), 7.5–7.3 (m, 5H), 7.22 (d, 1H), 5.68 (s, 2H), 3.55 (t, 2H, J=8.2 Hz), 0.87, (t, 2H, J=8.2 Hz), −0.06 (s, 9H); HRMS (FAB) (M+Cs]/z Calc'd 759.9563, found 759.9571.

The boron reagent was prepared as follows: In a 10 mL Schlenk flask 3-phthalamido-thiophenol was dried under high vacuum. To this was added a solution of 9-BBN (0.5 M in THF, 1.6 mL, 1.0 equiv). The mixture was heated to 55° C. for 2 h. The volatile material was removed under a stream of argon at 70° C. for 1.5 h. The residue was used without further manipulation.

(ii)

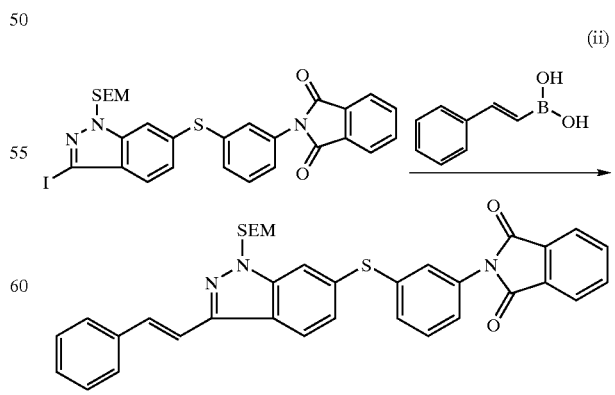

6-(3-Phthalamido-phenylsulfanyl)-3-iodo-1H-indazole was converted to 6-(3-phthalamido-phenylsulfanyl)-3- styryl-1H-indazole as described in Example 11, step (iii). $^1$H NMR (300 MHz, CDCl$_3$) δ 7.93 (m, 3H), 7.78 (m 2H), 7.7 (s, 1H), 7.58 (m, 2H), 7.47–7.26 (m, 10H), 5.71 (s, 2H), 3.59 (t, 2H, J=8.2 Hz), 0.89 (t, 2H, J=8.2 Hz), −0.06 (s, 9H); HRMS (FAB) [M+Cs]/z Calc'd 736.1066, found 736.1058.

(iii)

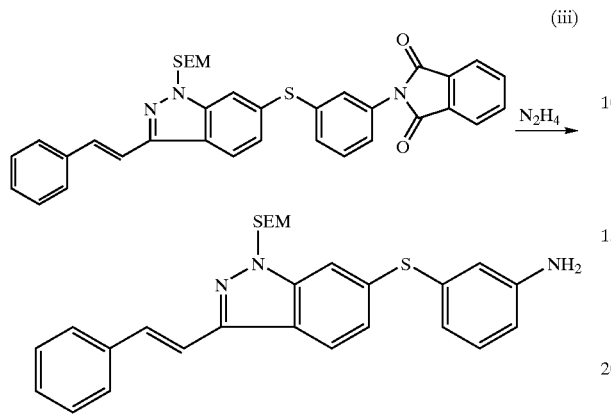

To a solution of 6-(3-phthalamidophenylsulfanyl)-3-styryl-1H-indazole (121 mg, 0.2 mmol) in ethanol (3.5 mL) was added hydrazine (63 μL, 2.0 mmol, 10 equiv). The reaction mixture was allowed to stir at 23° C. for 45 min and was diluted with saturated sodium bicarbonate and ethyl acetate. The organic material was dried over sodium sulfate, decanted and concentrated. Purification by silica gel chromatography (3:7 ethyl acetate-hexane) gave 6-(3-aminophenylsulfanyl)-3-styryl-1H-indazole as an oil (79 mg, 90%): $^1$H NMR (300 MHz, CDCl$_3$) δ 7.92 (d, 1H, J=8.5 Hz), 7.57 (m, 3H), 7.49 (d, 1H, J=16.8 Hz), 7.4–7.25 (m, 4H), 7.23 (dd, 1H, J=1.5, 8.5 Hz), 7.11 (t, 1H, J=7.9 Hz), 6.79 (m, 1H), 6.70 (t, 1H, J=1.9 Hz), 6.59 (m, 1H), 5.66 (s, 2H), 3.60 (bs, 2H), 3.59 (t, 2H, J=8.2 Hz), 0.90 (t, 2H, J=8.2 Hz), −0.05 (s, 9H); HRMS (FAB) [M+H]/z Calc'd 474.2035, found 474.2019.

(iv)

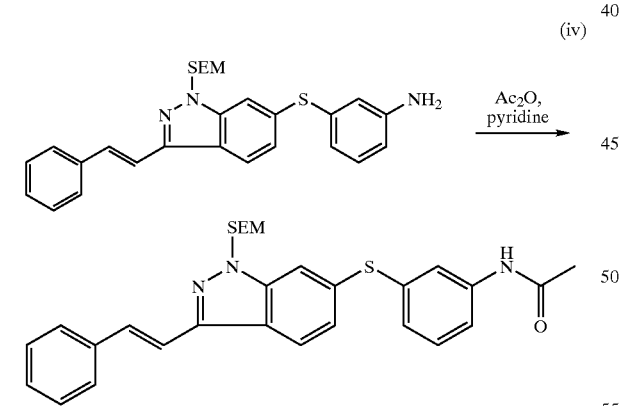

To a solution of 6-(3-aminophenylsulfanyl)-3-styryl-1H-indazole (43.7 mg, 0.10 mmol) in dichloromethane (0.5 mL) was added pyridine (81 μL, 1.0 mmol, 10 equiv), and acetic anhydride (47 μL 0.5 mmol, 5 equiv). The mixture was allowed to stir for 10 min at 23° C. The mixture was diluted with water and the product was extracted with 30% hexane in ethyl acetate. The organic material was washed with 5% citric acid and saturated sodium bicarbonate. The organic material was dried over sodium sulfate, decanted and concentrated. Purification by silica gel chromatography (3:7 ethyl acetate-hexane) gave 6-(3-acetamido-phenylsulfanyl)-3-styryl-1H-indazole as an oil (50 mg, 97%): R$_f$ sm 0.33, Rf p 0.18 (ethyl acetate-hexane 3:7); $^1$H NMR (300 MHz, CDCl$_3$) δ 7.94 (d, 1H), 7.65–7.1 (m, 13H), 5.70 (s, 2H), 3.62 (t, 2H, J=8.2 Hz), 2.18 (s, 3H), 0.93 (t, 2H, J=8.2 Hz), −0.05 (s, 9H). HRMS (FAB) [M+Cs]/z Calc'd 648.1117, found 648.1098.

Example 20(b)

6-(3-(Benzoylamido)-phenylsulfanyl)-3-styryl-1H-indazole

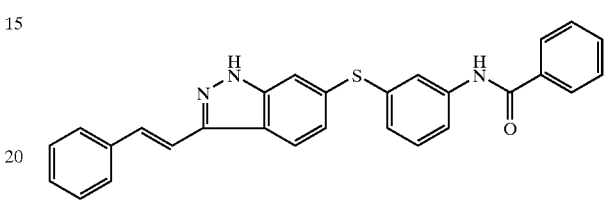

The title compound was prepared like Example 20(a), except that benzoyl chloride was used instead of acetic anhydride in step (iv). $^1$H NMR (300 MHz, CDCl$_3$) δ 8.03 (s, 1H), 7.73 (d, 1H, J=8.5 Hz), 7.63 (m, 2H), 7.47 (m, 1H), 7.42 (t, 1H, J=1.9 Hz), 7.37 (m, 3H), 7.31 (m, 1H), 7.28–6.98 (m, 9H); HRMS (FAB) [M+H]/z Calc'd 448.1484, found 448.1490.

Example 21

6-(1-(3-Aminophenyl)-vinyl)-3-styryl-1H-indazole

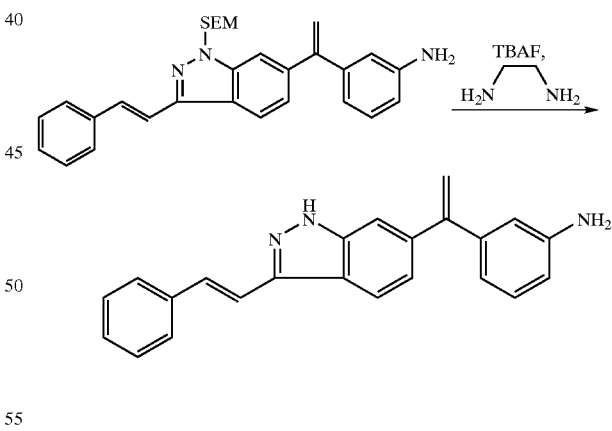

6-(1-(3-Aminophenyl)vinyl)-3-styryl-1-[2-(trimethyl-silanyl)-ethoxymethyl] 1H-indazole was converted to the tide compound as described for Example 11 (85 mg, 85%): R$_f$ sm 0.72, p 0.37 (ethyl acetate-hexane 1:1); FTIR (thin film) 3385, 3169, 2953, 1621, 1581, 1489, 1447, 1349, 1251, 1165, 1071, 959, 906, 870, 817 cm$^{-1}$; $^1$H NM (300 MHz, CDCl$_3$) δ 7.98 (d, 1H. J=8.5 Hz), 7.60 (m, 2H), 751 (s, 1H), 7.48 (s, 1H), 7.40 (m, 3H), 7.29 (m, 2H), 7.15 (m, 1H), 6.78 (m, 1H), 6.68 (m, 2H), 5.50 (s, 2H), 3.65 (bs, 2H); MS (ES) [M+H]/z Calc'd 338, found 338; MS (ES) [M−H]/z Calc'd 336, found 336.

The starting material was prepared as follows:

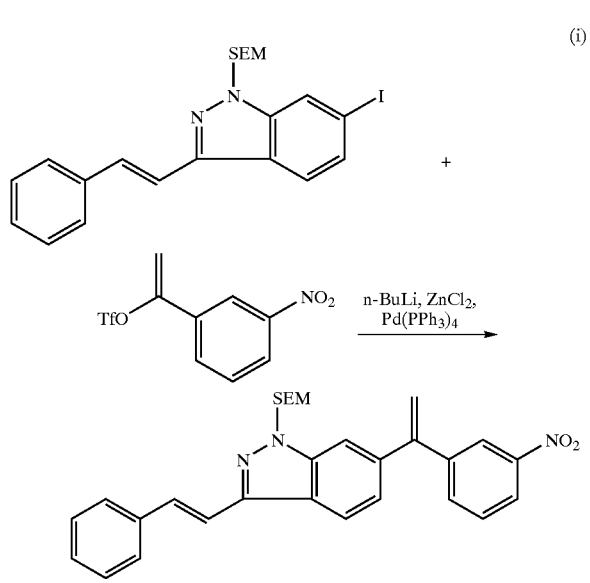

To a solution of 6-iodo-3-styryl-1-[2-(trimethyl-silanyl)-ethoxymethyl]-1H-indazole, prepared in Example 14, step (i), (330 mg, 0.693 mmol) in THF (3.0 mL) at −78° C. was added n-butyllithium (0.56 mL, 1.5 M, 1.2 equiv). After 20 min, this solution was then added to anhydrous zinc chloride (170 mg) and the mixture was warmed to 23° C. and stirred for 15 min. To this mixture was added 1-(3-nitro-phenyl) vinyltriflate (146 μL, 1.05 equiv) and Pd(PPh$_3$)$_4$ (40 mg, 0.05 equiv). This mixture was stirred for 30 min, was partitioned between ethyl acetate and saturated sodium bicarbonate and the organic layer was separated. The organic material was dried over sodium sulfate, decanted and concentrated under reduced pressure. Purification by silica gel chromatography (1:9 ethyl acetate-hexane) then a second column (1% ethyl acetate/benzene) gave 6-(1-(3-nitrophenyl)vinyl)-3-styryl-1-[2-(trimethyl-silanyl)-ethoxymethyl]-1H-indazole as an oil (180 mg, 52%): FTIR (thin film) 2951, 1616, 1530, 1477, 1448, 1348, 1305, 1248, 1217, 1077, 961, 913, 859 cm$^{-1}$; $^1$H NMR (300 MHz, CDCl$_3$) δ 8.26 (t, 1H, J=1.9 Hz), 8.21 (m, 1H), 8.00 (d, 1H, J=8.5 Hz), 7.69 (dt, 1H, J=1.4, 7.8), 7.62–7.28 (m, 9H), 7.19 (dd, 1H, J=1.4, 8.4 Hz), 5.72 (s, 3H), 5.69 (s, 1H), 3.60 (t, 2H, J=8.2 Hz), 0.89 (t, 2H, J=8.2 Hz), −0.05 (s, 9H); $^{13}$C NMR (75 MHz, CDCl$_3$) δ 149.9, 149.6, 144.7, 144.5, 142.8, 140.7, 138.6, 135.6, 133.1, 130.7, 130.2, 129.4, 128.0, 124.4, 124.2, 124.1, 123.8, 122.6, 121.2, 118.9, 111.0, 79.2, 68.0, 19.2, 0.0; HRMS (FAB) [M+Na]/z Calc'd 520.2031, found 520.2046.

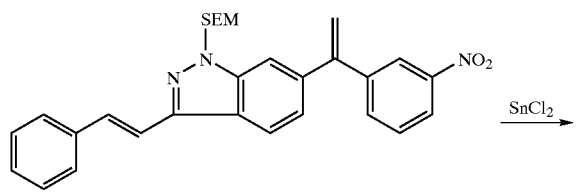

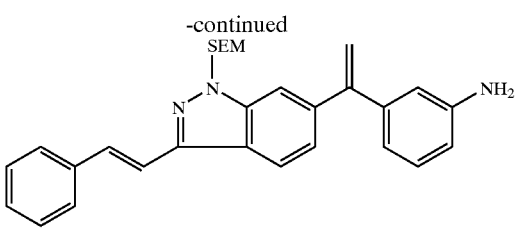

6-(1-(3-Nitrophenyl)-vinyl)-3-styryl-1-[2-(trimethyl-silanyl)-ethoxymethyl]-1H-indazole was converted to 6-(1-(3-aminophenyl)-vinyl)-3-styryl-1-[2-(trimethyl-silanyl)-ethoxymethyl]-1H-indazole as described in Example 11, step (iv) (140 mg, 95%): R$_f$ sm 0.59, p 0.46 (ethyl acetate-hexane 4:6); FTIR (thin film) 3460, 3366, 3223, 3084, 3028, 2952, 2894, 2246, 1616, 1601, 1581, 1489, 1474, 1448, 1359.1303, 1249, 1217, 1076, 961, 909, 860, 836, 733, 692 cm$^{-1}$; $^1$H NMR (300 MHz, CDCl$_3$) δ 7.96 (d, 1H, J=8.5 Hz), 7.59 (m, 3H), 7.50 (s, 1H), 7.46 (s, 1H), 7.40 (m, 2H), 7.30 (m, 1H), 7.25 (m, 1H), 7.14 (m, 1H), 6.77 (m, 1H), 6.68 (m, 2H); $^{13}$C NMR (75 MHz, CDCl$_3$) δ 151.6, 147.7, 144.6, 143.9, 142.8, 142.4, 138.6, 132.8, 130.6, 130.2, 129.3, 128.0, 124.4, 123.6, 121.9, 121.5, 120.2, 116.4, 116.1, 110.8, 79.0, 67.9, 19.2, 0.0; HRMS (FAB) [M+Na]/z Calc'd 490.2291, found 490.2302.

Example 22(a)

6-(1-(3-(5-Methyl-thiaxole-2-carboxoylamido) phenyl)-vinyl)-3-styryl-1N-indazole

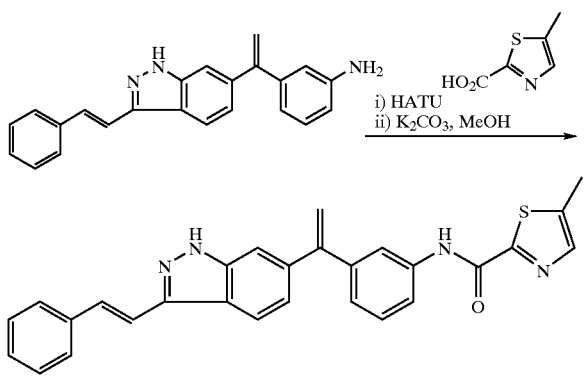

6-(1-(3-Aminophenyl)vinyl)-3-styryl-1H-indazole was converted to the title compound as described in Example 12(d) (20 mg, 72%): FTIR (thin film) 3271, 1673, 1605, 1585, 1538, 1486, 1428, 1349, 1304, 1090, 960, 907, 871 cm$^{-1}$; $^1$H NMR (300 MHz, CDCl$_3$) δ 10.7 (bs, 1H), 9.09 (s, 1H), 8.0 (d, 1H), 7.79 (m, 1H), 7.60 (m, 3H), 7.51 (m, 3H), 7.44–7.15 (m, 7H), 5.59 (s, 2H), 254 (s, 3H); $^{13}$C NMR (75 MHz, CDCl$_3$) δ 162.2, 157.9, 149.8, 144.4, 142.8, 142.2, 141.9, 141.5, 140.6, 137.63, 137.56, 131.6, 129.5, 129.1, 128.3, 126.9, 125.1, 122.6, 121.2, 120.9, 120.5, 120.2, 119.8, 116.1, 110.2, 12.8; HRMS (FAB) [M+H]/z Calc'd 463.1593, found 463,1582.

Example 22(b)

6-(1-(3-(Benzoylamido)phenyl)-vinyl)-3-styryl-1H-indazole

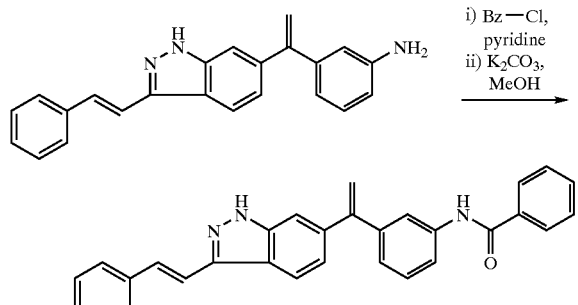

Example 22(b) was prepared in a similar manner to that described for Example 22(a), except that benzoyl chloride was used instead of 5-methyl-thiazole-2-carboxylic acid and HATU. FTIR (thin film) 3243, 1651, 1606, 1580, 1538, 1485, 1447, 1428, 1349, 1307, 1258, 1073, 959, 907 cm$^{-1}$; $^1$H NMR (300 MHz, CDCl$_3$) δ 9.09 (s, 1H), 7.99 (d, 1H, J=8.5 Hz), 7.78 (m, 1H), 7.60 (m, 3H), 7.51 (m, 3H), 7.43–7.15 (m, 10H), 556 (d, 2H, J=3.2 Hz); $^{13}$C NMR (75 MHz, CDCl$_3$) δ 166.5, 149.7, 144.3, 142.7, 142.1, 140.6, 138.1, 137.6, 135.0, 132.3, 131.6, 129.4, 129.1, 128.3, 127.4, 126.9, 125.0, 122.5, 120.9, 120.8, 120.6, 120.5, 115.9, 110.2; HRMS (FAB) [M+H]/z Calc'd 442.1919, found 442.1919.

Example 22(c)

6-(1-(3-Benzoylamido)phenyl)-vinyl)-3-styryl-1H-indazole

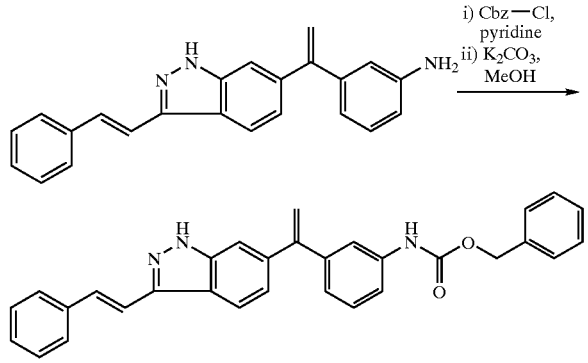

The title compound was prepared in a similar manner to that described for Example 22(a), except that carbobenzyloxy chloride was used instead of 5-methyl-thiazole-2-carboxylic acid and HATU. FTIR (thin film) 3305, 1712, 1606, 1586, 1537, 1487, 1445, 1348, 1216, 1059, 959, 908 cm$^{-1}$; $^1$H NMR (300 MHz, CDCl$_3$) δ 7.99 (d, 1H, J=8.5 Hz), 7.6–7.0 (m, 18H), 5.55 (s, 2H), 5.19 (s, 2H); $^{13}$C NMR (75 MHz, CDCl$_3$) δ 153.9, 149.8, 144.3, 142.7, 142.1, 140.7, 138.2, 137.6, 136.3, 131.7.129.4, 129.1, 129.0, 128.7, 128.7, 128.3, 126.9, 124.0, 122.6, 121.1, 120.8, 120.4, 115.9, 110.1, 67.4; HRMS (FAB) [M+H]/z Calc'd 472.025, found 472.2026.

Example 23

6-(1-(3-Acetamidophenyl)-vinyl)-3-styryl-1H-indazole

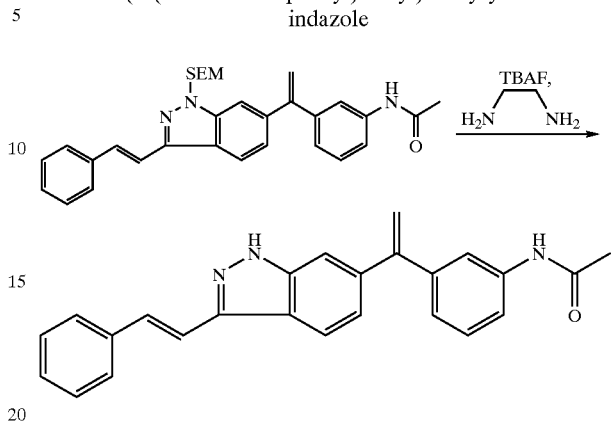

6-(1-(3-Acetamido-phenyl)-vinyl)-3-styryl-1-[2-trimethylsilanyl-ethoxymethyl]-1H-indazole was converted to 6-(1-(3-acetamido-phenyl)vinyl)-3-styryl-1H-indazole as described for Example 11: FTIR (thin film) 3252, 1667, 1606, 1557, 1486 cm$^{-1}$; $^1$H NMR (300 MHz, CDCl$_3$) δ 10.4 (bs, 1H), 7.91 (d, 1H, J=8.5 Hz), 7.5–7.0 (m, 13H), 5.47 (s, 2H), 2.10 (s, 3H); MS (ES) [M+H]/z Calc'd 380, found 380; [M−H]/z Calc'd 378, found 378.

The starting material was prepared as follows:

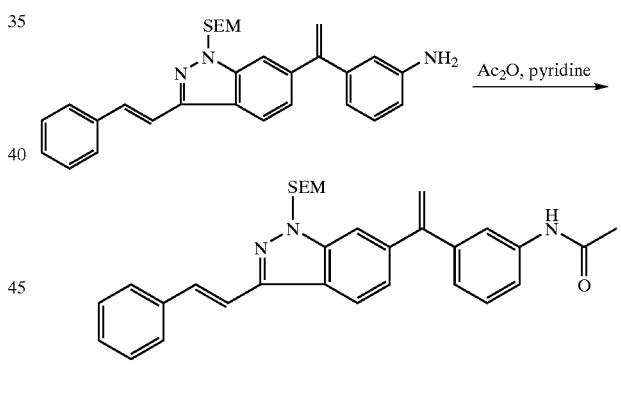

6-(1-(3-Aminophenyl)-vinyl)-3-styryl 1-[2-trimethylsilanyl-ethoxymethyl]-1H-indazole was converted to 6-(1-(3-acetamido-phenyl)-vinyl)-3-styryl-1-[2-trimethylsilanyl-ethoxymethyl]-1H-indazole as described for Example 12(a): R$_f$ sm 0.42, p 0.26 (ethyl acetate-hexane 4:6); FTIR (thin film) 3305, 3059, 2952, 1667, 1608, 1585, 1555, 1486, 1448, 1433, 1369, 1306, 1249, 1076, 912, 859, 836, 748, 693 cm$^{-1}$; $^1$H NMR (300 MHz, CDCl$_3$) δ 7.98 (d, 1H, J=8.5 Hz), 7.7–7.4 (m, 9H), 7.35 (m, 2H), 7.26 (dd, 1H, J=1.3, 8.4 Hz), 7.16 (bd, 1H, J=7.8 Hz), 5.75 (s, 2H), 5.62 (s, 1H), 5.61 (s, 1H), 3.66 (t, 2H, J=8.2 Hz), 2.16 (s, 3H), 0.98 (t, 2H, J=8.2 Hz), −0.02 (s, 9H); $^{13}$C NMR (75 MHz, CDCl$_3$) δ 169.8, 150.9, 144.6, 143.5, 142.8, 142.0, 139.4, 138.6, 132.9, 130.3, 129.3, 127.9, 125.6, 124.2, 123.7, 122.0, 121.3, 121.0, 117.1, 110.8, 68.0, 25.8, 19.1, 0.0; HRMS (FAB) [M+Na]/z Calc'd 532.2396, found 532.2410.

Example 24(a)

4-[3-(1-H-Benzoimidazol-2-yl)-1-H-indazol-6-yl]-2-methoxy-5-methyl-phenol

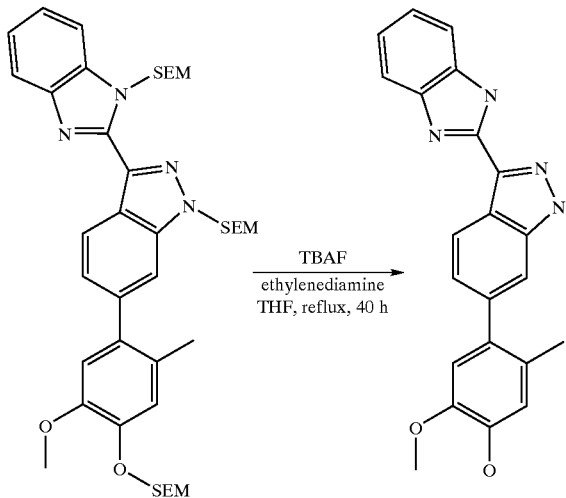

6-{5-Methoxy-2-methyl-4-[2-(trimethyl-silanyl)-ethoxymethoxy]-phenyl}-1-[2-(triethyl-silanyl)-ethoxymethyl]-3-{1-[2-(trimethyl-silanyl)ethoxymethyl]-1-H-benzamidazol-2-yl}-1-H-indazole (326 mg, 0.43 mmol) was stirred in a solution of TBAF (4.5 mL of 1 M in THF, which was concentrated in vacuo to 2.5 mL) and ethylenediamine (0.6 mL, 8.9 mmol) at reflux for 40 h. The reaction was diluted with ethyl acetate/THF (40 mL/5 mL) and washed with H$_2$O (20 mL) and brine (20 mL). Organics were dried (MgSO$_4$) and concentrated in vacuo. Purification by silica gel chromatography (60% THF/hexanes) and then precipitation from chloroform gave 108 mg (68%) of 4-[3-(1-H-benzoimidazol-2-yl)-1-H-indazol-4-yl]-2-methoxy-5-methyl-phenol as a white solid. $^1$H NMR (300 MHz, DMSO-d$_6$) δ 13.62 (s, 1H), 13.05 (br s, 1H), 9.01 (s, 1H), 8.50 (d, 1H, J=8.4 Hz), 7.62 (br s, 2H), 7.49 (s. 1H), 7.28–7.20 (m, 3H), 6.85 (s, 1H), 6.74 (s, 1 H), 3.77 (s, 3H), 2.15 (s, 3H). Anal. (C$_{22}$H$_{18}$N$_4$O$_2$ 1.3H$_2$O)C, H, N. Calculated: C, 67.10; H, 5.27; N, 14.23. Found: C, 67.30; H, 5.27; N, 14.11.

The starting materials were prepared as follows:

(i)

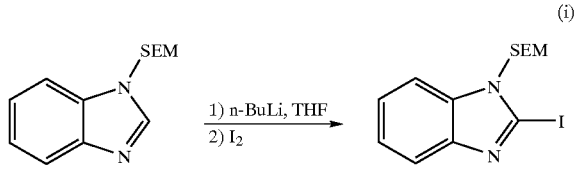

Preparation of 2-iodo-1-[2-(trimethyl-silanyl)-ethoxymethyl]-1H-benzoimidazole. A solution of 1-[2-(trimethyl-silanyl)-ethoxymethyl]-1H-benzoimidazole (5.029 g, 20.25 mmol) (see Witten et al., *J. Org. Chem.*, 51, 1891–1894 (1986)) in THF (50 mL) was cooled to −78° C. and added dropwise over 12 min via cannula to a flask containing n-butyllithium (2.5 M in hexanes, 12.2 mL) in THF (30 mL) at −78° C. under argon. After stirring for 25 min at −78° C., the flask was warmed to 0° C. for 10 min, then cooled again to −78° C. This solution was then added via cannula to a second flask containing iodine (25.7 g, 101 mmol) in THF (50 mL) at −78° C. Once the addition was complete (~5 min), the cooling bath was removed, and stirring was continued for 30 min. The reaction mixture was partitioned between ethyl acetate (500 mL) and water (100 mL). The organic layer was washed with saturated aqueous sodium metabisulfite (2×100 mL) to remove the dark iodine color, dried (MgSO$_4$), and concentrated in vacuo. Purification by flash chromatography (10% to 50% ethyl acetate/hexanes) yielded 4.79 g (63%) of pure 2-iodo-1-[2-(trimethyl-silanyl)ethoxymethyl]-1H-benzoimidazole as a yellow solid. $^1$H NMR (300 MHz, CDCl$_3$) δ 7.76–7.72 (m, 1H), 7.54–7.51 (m, 1H), 7.29–7.25 (m, 2H), 5.54 (s, 2H), 3.59 (t, 2H, J=8.1 Hz), 0.92 (t, 2H, J=8.1 Hz), −0.03 (s, 9H). Anal. (C$_{13}$H$_{19}$IN$_2$OS)C, H. Calculated: C, 41.71; H, 5.12; L 33.90; N, 7.48. Found: C, 41.90; H, 5.09; L 34.00; N, 7.37.

(ii)

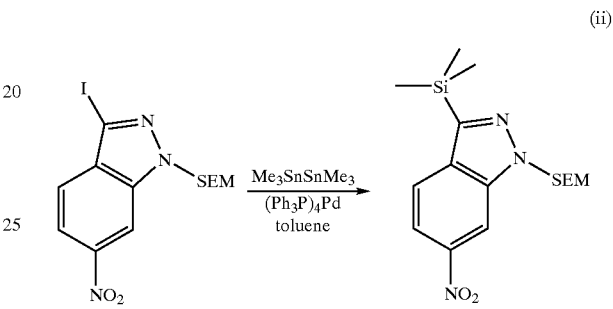

Preparation of 6-nitro-1-[2-(trimethyl-silanyl)-ethoxymethyl]-3-(trimethyl-stannanyl)-1-H-indazole: 3-Iodo-6-nitro-1-[2-(trimethyl-silanyl)-ethoxymethyl]-1-H-indazole (10.0 g, 23.9 mmol) and hexamethylditin (10.0 g, 30.5 mmol) were combined with dry toluene (45 mL) in a flask purged with argon. Tetrakis(triphenylphosphine)-palladium(0) (300 mg, 0.26 mmol) was added, and the reaction stirred at reflux under argon for 2.5 h. The reaction was cooled to 23° C. and diluted with ether (60 mL). Organics were washed with 0.1N HCl (20 mL) and brine (20 mL), dried (MgSO$_4$), and concentrated. Purification by silica gel chromatography (3% to 8% ether/hexanes) gave 7.70 g (71%) of 6-nitro-1-[2-(trimethyl-silanyl)-ethoxymethyl]-3-(trimethyl-stannanyl)-1-H-indazole as a faintly yellow solid. $^1$H NMR (300 MHz, CDCl$_3$) δ 8.53 (d, 1H, J=1.8 Hz), 8.03 (dd, 1H, J=8.7, 1.8 Hz), 7.81 (d, 1H, J=8.7 Hz), 5.84 (s, 2H), 3.58 (t, 2H, J=8.1 Hz), 0.90 (t, 2H, J=8.1 Hz), 0.50 (t, 9H, J=28.2 Hz), −0.05 (s, 9H). Anal. (C$_{16}$H$_{27}$N$_3$O$_3$SiSn) C, H, N. Calculated: C, 42.13; H, 5.97; N, 9.21. Found: C, 42.39; H, 6.01; N, 9.26.

(iii)

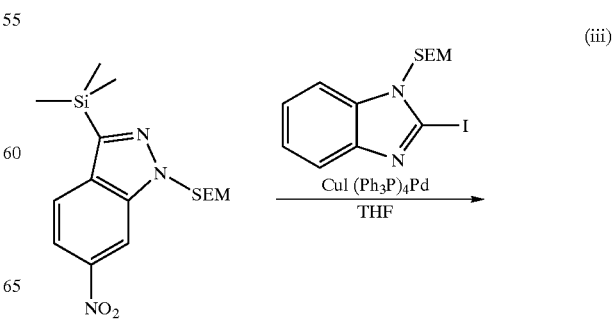

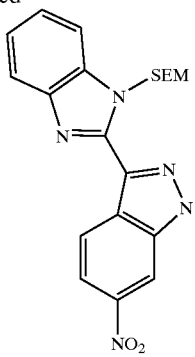

Preparation of 6-nitro-1-[2-(trimethyl-silanyl) ethoxymethyl]-3-{1-[2-(trimethyl-silanyl)-ethoxymethyl]-1-H-benzoimidazol-2-yl}-1-H-indazole: 6-Nitro-1-[2-(trimethyl-silanyl)-ethoxymethyl]-3-(trimethyl-stannanyl)-1-H-indazole (7.50 g, 16.4 mmol), 3-iodo-1-[2-(trimethyl-silanyl)-ethoxymethyl]-1-H-benzimidazole (6.50 g, 17.4 mmol), and copper(I) iodide (313 mg, 1.64 mmol) were combined with dry THF (150 mL) in a flask purged with argon. Tetrakis(triphenylphosphine)palladium(0) was added, and the reaction stirred at reflux under argon for 23 h. The reaction was cooled and adsorbed directly onto silica gel (~16 g). Purification by silica gel chromatography (4% to 15% ethyl acetate/hexanes) gave 7.28 g (82%) of 6-nitro-1-[2-(trimethyl-silanyl)-ethoxymethyl]-3-{1-[2-(trimethyl-silanyl)-ethoxymethyl]-1-H-benzoimidazol-2-yl}-1-H-indazole as a light yellow solid. $^1$H NMR (300 MHz, CDCl$_3$) a 8.91 (d, 1H, J=9.0 Hz), 8.59 (d, 1H, J=1.8 Hz), 8.22 (dd, 1H, J=8.7, 1.8 Hz), 7.92–7.89 (m, 1H), 7.667.62 (m, 1H), 7.40–7.36 (m, 2H), 6.24 (s, 2H), 5.90 (s, 2H), 3.68–3.59 (m, 4H), 0.94 (t, 2H, J=8.1 Hz), 0.86 (t, 2H, J=8.1 Hz), −0.04 (s, 9H), −0.15 (s, 9H). Anal. (C$_{26}$H$_{37}$N$_5$O$_4$Si$_2$) C, H. N. Calculated: C, 57.85; H, 6.91; N, 12.97. Found: C, 57.60; H, 6.81; N, 12.82.

(iv)

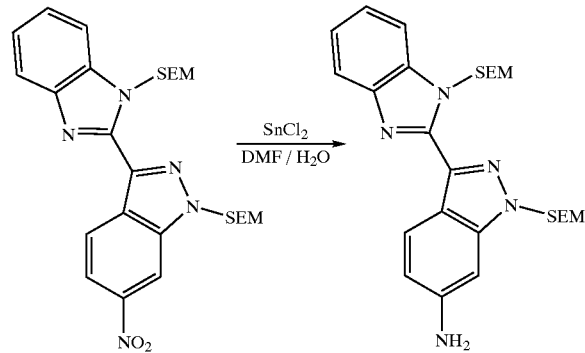

Preparation of 6-Amino-1-[2-(trimethyl-silanyl)-ethoxymethyl]-3-{1-[2-(trimethyl-silanyl)-ethoxymethyl]-1-H-benzoimidazol-2-yl}-1-H-indazole: Tin(II) chloride (12.0 g, 63.3 mmol) was added to a solution of 6-nitro-1-[2-(trimethyl-silanyl)ethoxymethyl]-3-{1-[2-(trimethyl-silanyl)-ethoxymethyl]-1-H-benzoimidazol-2-yl}-1-H-indazole (7.18 g, 13.3 mmol) in DMF/H$_2$O (160 mL/10 mL), and the reaction stirred at 50° C. for 2.5 h. The reaction was cooled to 0° C., and saturated sodium bicarbonate was added slowly, with mixing, until all frothing from quenching had subsided. The material was concentrated in vacuo and taken up in ether (100 mL). Insoluble material was removed by filtration and rinsed with ether (50 mL). The filtrate was washed with brine (50 mL), dried (Na$_2$SO$_4$), and concentrated in vacuo. Purification by silica gel chromatography (25% ethyl acetate/hexane) gave 6.05 g (89%) of 6-amino-1-[2-(trimethyl-silanyl)-ethoxymethyl]-3-{1-[2-(trimethyl-silanyl)ethoxymethyl]-1-H-benzoimidazol-2-yl}-1-H-indazole as a faintly yellow waxy solid. $^1$H NMR (300 MHz, CDCl$_3$) δ 8.40 (d, 1H, J=9.0 Hz), 7.89–7.86 (m, 1H), 7.63–7.60 (m, 1H), 7.35–7.31 (m, 2H), 6.78 (dd, 1H, J=8.7, 1.8 Hz), 6.75 (s, 1H), 6.25 (s, 2H), 5.69 (s, 2H), 3.93 (br s, 2H), 3.65–355 (m, 4H), 0.93 (t, 2H, J=8.1 Hz), 0.85 (t, 2H, J=8.1 Hz), −0.04 (s, 9H), −0.15 (s, 9H). Anal. (C$_{26}$H$_{39}$N$_5$O$_2$Si$_2$) C, H, N. Calculated: C, 61.26; H, 7.71; N. 13.74. Found: C, 61.18; H, 7.65; N, 13.82.

(v)

Preparation of 6-iodo-1-[2-(trimethyl-silanyl)-ethoxymethyl]-3-{1-[2-(trimethyl-silanyl)-ethoxymethyl]-1-H-benzoimidazol-2-yl}-1-H-indazole: A solution of 6-amino-1-[2-(trimethyl-silanyl)-ethoxymethyl]-3-{1-[2-(trimethyl-silanyl)ethoxymethyl]-1-H-benzoimidazol-2-yl}-1-H-indazole (500 mg, 0.98 mmol) in acetic acid (1.5 mL) was diluted with H$_2$O (1.0 mL) and stirred at 0° C. Concentrated HCl (250 e"-3 mmol) in H$_2$O (250 μL) was added. Sodium nitrate (90 mg, 1.3 mmol) in H$_2$O (300 μl) was added, and the reaction stirred for 8 min. Iodine (10 mg) and a solution of potassium iodide (250 mg, 1.3 mmol) in H$_2$O (250 μL) were added, and the frothing reaction stirred for 30 min at 23° C. The reaction was diluted with H$_2$O (25 mL) and extracted with ethyl acetate (2×20 mL). Organics were washed with saturated sodium metabisulfite solution (10 mL) and brine (10 mL), dried (Na$_2$SO$_4$), and concentrated in vacuo. Purification by silica gel chromatography (8% ethyl acetate/hexanes) gave 316 mg (52%) of 6-iodo-1-[2-(trimethyl-silanyl)ethoxymethyl]-3-{1-[2-(trimethyl-silanyl)ethoxymethyl]-1-H-benzoimidazol-2-yl}-1-H-indazole as a faintly yellow oil, which slowly crystallized to a white solid. $^1$H NMR (300 MHz, CDCl$_3$) δ 8.45 (d, 1H, J=9.0 Hz), 8.05 (s, 1H), 7.91–7.88 (m, 1H), 7.67–7.62 (m, 2H), 7.38–7.34 (m, 2H), 6.24 (s, 2H), 5.77 (s, 2H), 3.65–3.57 (m, 4H), 0.93 (t, 2H, J=8.1 Hz), 0.85 (t, 2H, J=8.1 Hz), −0.04 (s, 9H), −0.15 (s, 9H). Anal. ($C_{26}H_{37}N_4O_2Si_2$) C, H, N. Calculated: C, 50.31; H, 6.01; N, 9.03. Found: C, 50.55; H, 6.08; N, 9.00.

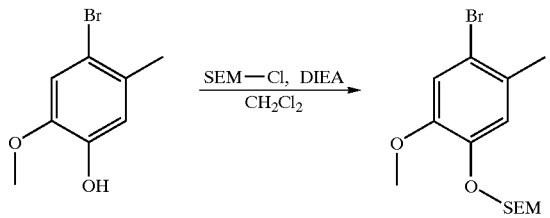

(vi)

Preparation of [2-(4-bromo-2-methoxy-5-methyl-phenoxymethoxy)ethyl]-trimethyl-silane: 4-Bromo-2-methoxy-5-methyl-phenol (see Chien-Hsun et al., *Syn. Lett.*, 12, 1351–1352 (1997)) was stirred in dry $CH_2Cl_2$ (100 mL) at 23° C. DIEA (6.05 mL, 34.6 mmol), and then 2-(trimethylsilyl)ethoxymethyl chloride (5.6 mL, 31.7 mmol) were added. After stirring for 1 h, the solution was washed with $H_2O$, 0.1 N HCl, $H_2O$, saturated $NaHCO_3$, and brine (25 mL each). Organics were dried ($Na_2SO_4$) and concentrated in vacuo. Purification by silica gel chromatography (6% ethyl acetate/hexanes) gave 9.06 g (91%) of [2-(4-bromo-2-methoxy-5-methyl-phenoxymethoxy)-ethyl]-trimethyl-silane as a clear oil. $^1$H NMR (300 MHz, $CDCl_3$) δ 7.06 (s, 1H), 7.02 (s, 1H), 5.24 (s, 2H), 3.84 (s, 3H), 3.79 (t, 2H, J=8.4 Hz), 2.31 (s, 3H), 0.96 (t, 2H, J=8.4 Hz), 0.01 (s, 9H).

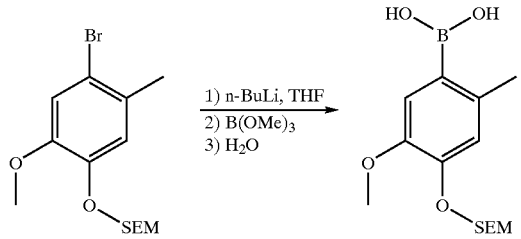

(vii)

Preparation of 5-methoxy-2-methyl-4[2-(trimethyl-silanyl)-ethoxymethoxy]-phenyl-boronic acid: [2-(4-Bromo-2-methoxy-5-methyl-phenoxymethoxy)-ethyl]-trimethyl-silane (2.6 g, 7.5 mmol) was stirred in dry THF (10 mL) at −78° C. under argon. n-Butyllithium (3.75 mL, 2.5 M in hexanes, 9.36 mmol) was added dropwise, and the reaction stirred for 30 min before it was transferred via cannula to a flask of trimethyl borate (8.4 mL, 75 mmol) in THF (15 mL), which was also stirring at −78° C. under argon. After addition was complete, the reaction stirred 30 min at −78° C. and then 30 min while warming to 0° C. It was then quenched with $H_2O$ (20 mL), acidified with 0.1 N HCl, and extracted with ethyl acetate (2×25 mL). Organics were washed with brine (20 mL), dried ($Na_2SO_4$), and concentrated in vacuo. Purification by silica gel chromatography (20% to 50% ethyl acetate/hexanes) gave 1.11 g (47%) of 5-methoxy-2-methyl-4-[2-(trimethyl-silanyl)-ethoxymethoxy]-phenyl-boronic acid as a white solid. $^1$H NMR (300 MHz, $CDCl_3$) δ 7.78 (s, 1H), 7.10 (s, 1H), 5.36 (s, 2H), 3.93 (s, 3H), 3.83 (t, 2H, J=8.4 Hz), 2.79 (s, 3H), 0.98 (t, 2H, J=8.4 Hz), 0.01 (s, 9H). Anal. ($C_{14}H_{25}BO_5Si$—$H_2O$)C, H. Calculated: C, 57.15; H, 7.88. Found: C, 56.89; H, 7.87.

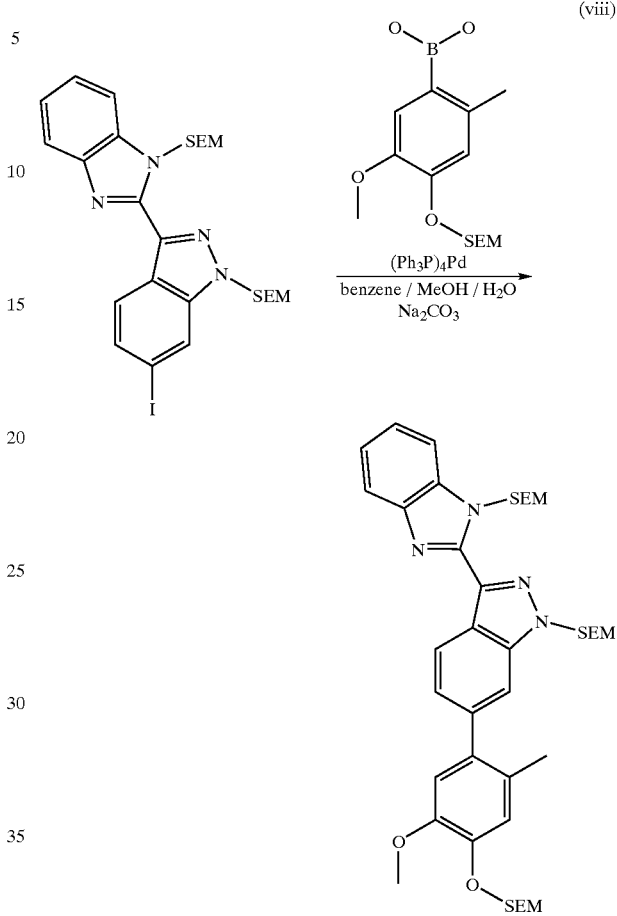

(viii)

Preparation of 6-{5-methoxy-2-methyl [2-(trimethyl-silanyl)-ethoxymethoxy]-phenyl}-1-[2-(trimethyl-silanyl)-ethoxymethyl]-3-{1-[2-(trimethyl-silanyl)ethoxymethyl]-1-H-benzamidazol-2-yl}-1-H-indazole. 6-Iodo 1-[2-(trimethyl-silanyl)ethoxymethyl]-3-{1-[2-(trimethyl-silanyl)-ethoxymethyl]-1-H-benzoimidazol-2-yl}-1-H-indazole (350 mg, 0.56 mmol), 5-methoxy-2-methyl-4[2-(triethyl-silanyl)ethoxymethoxy]-phenyl-boronic acid (211 mg, 0.68 mmol), and sodium carbonate (72 mg, 0.68 mmol) were stirred in a mixture of benzene (5 mL), $H_2O$ (330 μL), and methanol (1 mL) in a flask purged with argon. Tetrakis (triphenylphosphine)palladium(0) was added, and the reaction stirred at reflux under argon for 16 h. After cooling to 23° C., the reaction was diluted with ether (20 mL), washed with $H_2O$ (10 mL) and brine (10 mL), dried ($Na_2SO_4$), and concentrated in vacuo. Purification by silica gel chromatography (15% ethyl acetate/hexanes) gave 382 mg (89%) of 6-{5-methoxy-2-methyl-4-[2-(trimethyl-silanyl)-ethoxymethoxy]-phenyl}-1-[2-(trimethyl-silanyl)-ethoxymethyl]-3-{1-[2-(trimethyl-silanyl)ethoxymethyl]-1-H-benzamidazol-2-yl}-1-H-indazole as a white solid. $^1$H NMR (300 MHz, $CDCl_3$) δ 8.68 (d, 1H, J=8.4 Hz), 7.93–7.90 (m, 1H), 7.67–7.63 (m, 1H), 7.54 (s, 1H), 7.38–7.32 (m, 3H), 7.13 (s, 1H), 6.86 (s, 1H), 6.29 (s, 2H), 5.83 (s, 2H), 5.34 (s, 2H), 3.89 (s, 3H), 3.86 (t. 2H, J=8.4 Hz), 3.69–3.58 (m, 4H), 2.22 (s, 3H), 1.01 (t, 2H, J=8.4 Hz), 0.95–0.83 (m, 4H), 0.03 (s, 9H), 0.05 (s, 9H), −0.15 (s, 9H). Anal. ($C_{40}H_{60}N_4O_5Si_3$) C, H, N. Calculated: C, 63.12; H, 7.95; N, 7.36. Found: C, 63.22; H, 7.93; N, 7.46.

Example 24(b)

4-[3-(1-H-Benzoimidazol-2-yl)-1-H-indazol-6-yl]-3-methyl-phenol

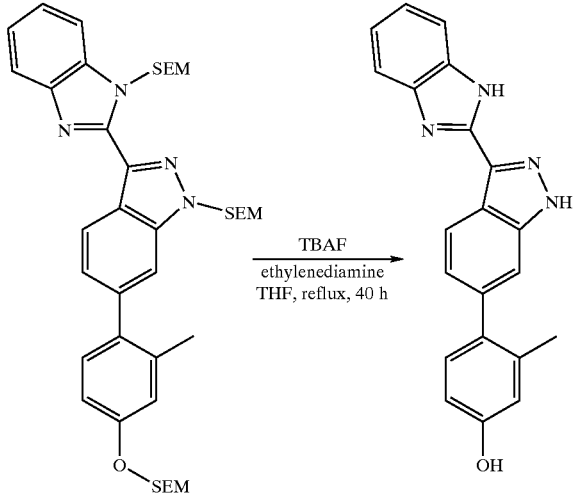

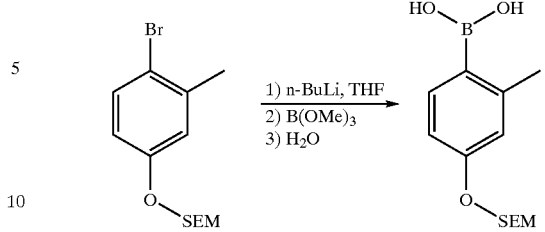

2-Methyl-4[2-(trimethyl-silanyl)ethoxymethoxy]-phenyl-boronic acid was prepared in 52% yield from [2-(4-bromo-3-methyl-phenoxymethoxy)-ethyl]-trimethyl-silane according to the procedure for 5-methoxy-2-methyl 4[2-(trimethyl-silanyl)ethoxymethoxy]-phenyl-boronic acid above. $^1$H NMR (300 MHz, CDCl$_3$) δ 8.15 (d, 1H, J=8.1 Hz), 6.98–6.92 (m, 2H), 5.29 (s, 2H), 3.78 (t, 2H, J=8.4 Hz), 2.78 (s, 3H), 0.98 (t, 2H, J=8.4 Hz), 0.01 (s, 9H). Anal. (C$_{13}$H$_{23}$BO$_4$Si —H$_2$O)C, H. Calculated: C, 59.10; H, 8.01. Found: C, 59.07; H, 8.08.

Example 24(c)

4-[3-(1-H-Benzoimidazol-2-yl)-1-H-indazol-6-yl]-2-chloro-5-methyl-phenol

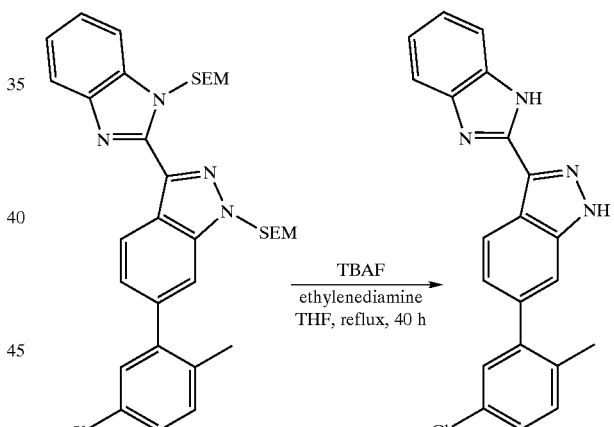

To prepare the title compound, the procedure described for Example 24(a) was followed, with 2-methyl-4-[2-(trimethyl-silanyl)ethoxymethoxy]-phenyl-boronic acid (prepared as described below) substituted for 5-methoxy-2-methyl 4[2-(trimethyl-silanyl)-ethoxymethoxy]-phenyl-boronic acid in step (viii). $^1$H NMR (300 MHz, DMSO-d$_6$) δ 13.60 (s, 1H), 12.99 (br s, 1H), 9.41 (s, 1H), 8.49 (d, 1H, J=8.4 Hz), 7.72 (br s, 1H), 7.52 (br s, 1H), 7.45 (s, 1H), 7.25–7.21 (m, 3H), 7.12 (d, 1H, J=8.1 Hz), 6.73–6.67 (m, 2H), 2.20 (s, 3H). Anal. (C$_{21}$H16N$_4$O.0.7H$_2$O) C, H. N. Calculated: C, 71.45; H, 4.97; N, 15.87. Found: C, 71.44; H, 4.96; N, 15.77.

2-Methyl-4[2-(triethyl-silanyl)ethoxymethoxy]-phenyl-boronic acid was prepared as follows:

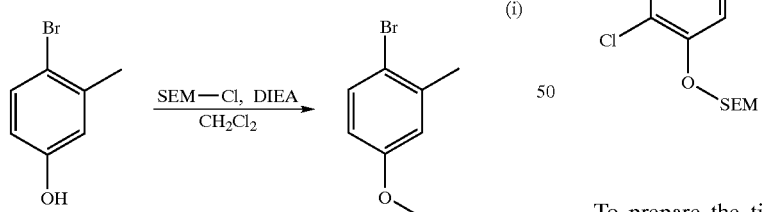

[2-(4-Bromo-3-methyl-phenoxymethoxy)-ethyl]-trimethyl-silane was prepared in 86% yield from 4-bromo-3-methyl-phenol according to the procedure for [2-(4-bromo-2-methoxy-5-methyl-phenoxymethoxy)-ethyl]-trimethyl-silane. $^1$H NMR (300 MHz, CDCl$_3$) δ 7.39 (d, 1H, J=8.7 Hz), 6.93 (d, 1H, J=2.7 Hz), 6.75 (dd, 1H, J=8.7, 2.7 Hz), 5.16 (s, 2H), 3.74 (t, 2H, J=8.4 Hz), 2.36 (s, 3H), 0.95 (t, 2H, J=8.4 Hz), 0.01 (s, 9H). Anal. (C$_{13}$H$_{21}$BrO$_2$Si) C, H. Calculated: C, 49.21; H, 6.67. Found: C, 49.33; H. 6.67.

To prepare the tide compound, 5-chloro-2-methyl-4-[2-(trimethyl-silanyl) ethoxymethoxy]-phenyl-boronic acid, prepared as described below, was substituted for 5-methoxy-2-methyl-4-[2(trimethyl-silanyl)ethoxymethoxy]-phenyl-boronic acid in the procedure described in Example 24(a), step (viii). $^1$H NMR (300 MHz, DMSO-d$_6$) δ 13.61 (s, 1H), 13.00 (br s, 1H), 10.22 (s, 1H), 8.51 (d, 1H, J=8.4 Hz), 7.64 (br s, 2H), 750 (s, 1H), 7.26–7.21 (m, 4H), 6.95 (s, 1H), 2.19 (s, 3H).

5-Chloro-2-methyl-4-[2-(trimethyl-silanyl) ethoxymethoxy]-phenyl-boronic acid was prepared as follows:

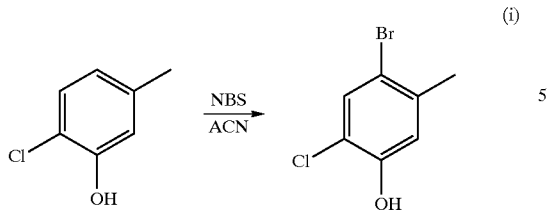

(i)

2-Chloro-5-methyl-phenol (6.68 g, 46.9 mmol) was stirred in acetonitrile (200 mL). N-Bromosuccinimide (8.5 g, 47.8 mmol) was added, and the reaction stirred for 45 min. The solution was concentrated in vacuo and redissolved in chloroform (100 mL). Organics were washed with saturated NaHCO$_3$ (50 mL) and brine (50 mL), dried (MgSO$_4$), and concentrated in vacuo. Purification by silica gel chromatography (8% ethyl acetate/hexanes) gave 7.98 g (77%) of 4-bromo-3-chloro-5-methyl-phenol as a clear oil. $^1$H NMR (300 MHz, CDCl$_3$) δ 7.47 (s, 1H), 6.91 (s, 1H), 5.52 (br s, 1H), 2.32 (s, 3H). Anal. (C$_7$H$_6$ClBrO 0.1H$_2$O)C, H. Calculated: C, 37.66; H. 2.80. Found: C, 37.57; H, 2.82.

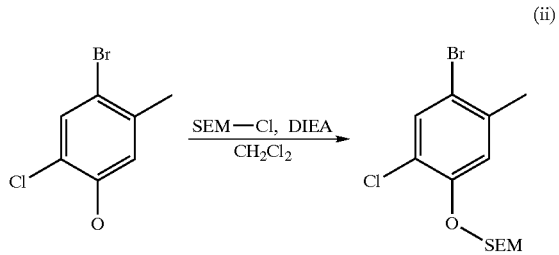

(ii)

[2-(4-Bromo-2-chloro-5-methyl-phenoxymethoxy)ethyl]-trimethyl-silane was prepared in 83% yield from 4-bromo-3-chloro-5-methyl-phenol according to the procedure for [2-(4-bromo-2-methoxy-5-methyl-phenoxymethoxy)-ethyl]-trimethyl-silane. $^1$H NMR (300 MHz, CDCl$_3$) δ 7.51 (s, 1H), 7.09 (s, 1H), 5.26 (s, 2H), 3.79 (t, 2H, J=8.4 Hz), 2.35 (s, 3H), 0.95 (t, 2H, 3=8.4 Hz), 0.02 (s, 9H). Anal. (C$_{13}$H$_{20}$ClBrO$_2$Si) C, H. Calculated: C, 44.39; H, 5.73. Found: C. 45.08; H, 5.91.

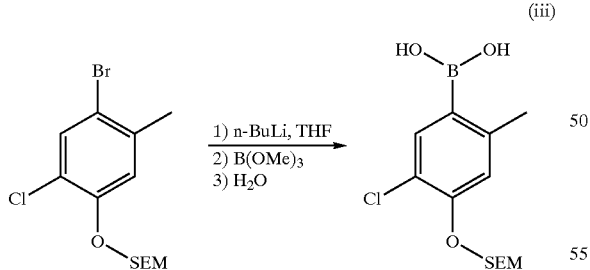

(iii)

5-Chloro-2-methyl-4-[2-(trimethyl-silanyl)-ethoxymethoxy]-phenyl-boronic acid was prepared in 54% yield from [2-(4-bromo-2-chloro-5-methyl-phenoxymethoxy)-ethyl]-trimethyl-silane according to the procedure for 5-methoxy-2-methyl-[2-(trimethyl-silanyl)-ethoxymethoxy]-phenyl-boronic acid. $^1$H NMR (300 MHz, CDCl$_3$) δ 8.11 (s. 1H), 7.09 (s, 1H), 5.37 (s, 2H), 3.84 (t, 2H, J=8.4 Hz), 2.76 (s, 3H), 0.98 (t, 2H, J=8.4 Hz), 0.01 (s, 9H). Anal. (C$_{13}$H$_{22}$BClO$_4$Si—H$_2$O)C, H. Calculated: C, 52.28; H, 6.75. Found: C, 51.98; H. 6.84.

Example 24(d)

3-1H-Benzoimidazol-2-yl-6-(4-hydroxy-2-methoxyphenyl)-1H-indazole

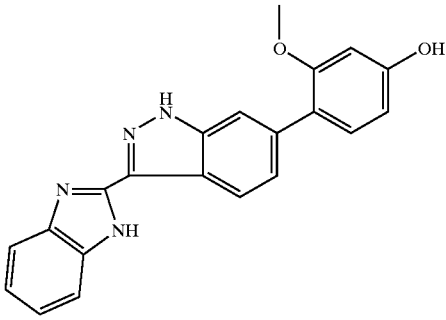

Example 24(d) was prepared in a similar manner to that described for Example 24(a), except that 4-bromo-3-methoxy-phenol, prepared as described by Carreno et. al., Syn. Let., 11, 124142 (1997), was used instead of 4-bromo-2-methoxy-5-methyl-phenol in step (vi). $^1$NMR (300 MHz, DMSO-d$_6$) δ 13.52 (s, 1H), 12.98 (s, 1H), 9.63 (s, 1H), 8.44 (d, 1H, J=8.4 Hz), 7.72 (d, 1H, J=6.9 Hz), 7.61 (s, 1H), 7.50 (d, 1H, J=6.9 Hz), 7.36(dd, 1H, J=8.4, 1.5 Hz), 7.18–7.22 (m, 3H), 6.55 (d, 1H, J=2.1 Hz), 6.48 (dd, 1H, J=8.1, 2.1 Hz), 3.74 (s, 3H). MS (ES) [m+H]/z calc'd 357, found 357; [m−H]z calc'd 355, found 355.

Example 24(e)

3-1H-Benzoimidazol-2-yl-6-(2-ethyl-4-hydroxyphenyl)-1H-indazole

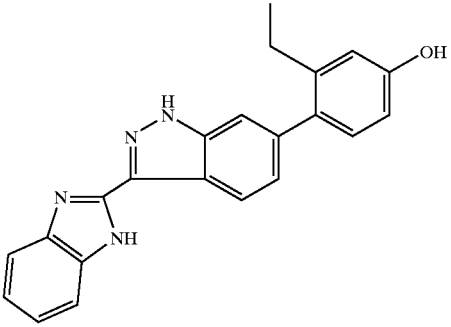

Example 24(e) was prepared in a similar manner to that described for Example 24(a), except that 4-bromo-3-ethyl-phenol, prepared in 80% yield according to the procedure described by Carreno et. al., Syn. Lett., 11, 1241–42 (1997) for the synthesis of 4-bromo-3-methyl-phenol, was used instead of 4-bromo-2-methoxy-5-methyl-phenol in step (vi). $^1$H NMR (300 MHz, DMSO-d$_6$) δ 13.66 (s, 1H), 13.02 (s, 1H), 9.43 (s, 1H), 8.49 (d, 1H, J=8.4 Hz), 7.72 (d, 1H, J=6.9 Hz), 7.53 (d, 1H, J=6.9 Hz), 7.44 (s, 1H), 7.18–7.25 (m, 3H), 7.06 (d, 1H, J=8.1 Hz), 6.75 (d, 1H, J=2.1 Hz), 6.66 (dd, 1H, J=8.1, 2.1 Hz), 250 (q, 2H, J=7.5 Hz), 1.04 (t, 3H, J=7.5 Hz). MS (ES) [m+H]/z calc'd 355, found 355; [m−H]/z calc'd 353, found 353.

Example 24(f)

3-1H-Benzoimidazol-2-yl-6-(2,4-dihydroxyphenyl)-1H-indazole

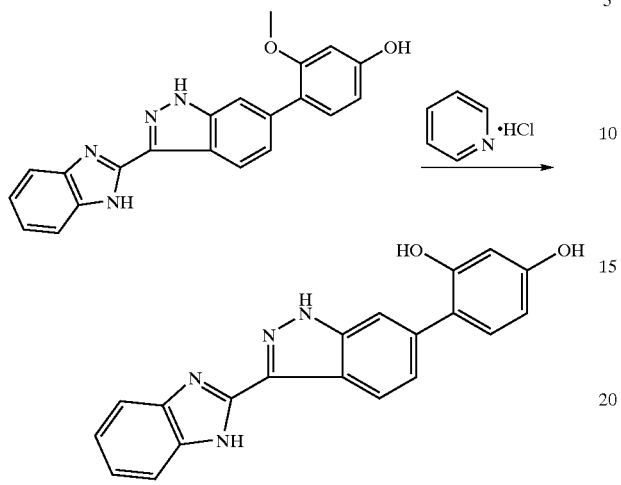

62-methoxy 4-hydroxyphenyl)-3-1H-benzoimidazol-2-yl-1H-indazole, prepared in example 24(d), (46 mg, 0.13 mmol) was heated in pyridinium chloride (0.5 g) at 180° C. for 2 h. The reaction was allowed to cool, and was quenched with sat. NaHCO$_3$ (15 mL) and extracted with EtOAc (2×20 mL). Organics were dried (Na$_2$SO$_4$) and concentrated in vacuo. Purification by silica gel chromatography (60% THF/hexanes) gave 26 mg (59%) of the title compound as a white solid. $^1$H NMR (300 MHz, DMSO-d$_6$) δ 13.49 (s, 1H), 12.94 (s, 1H), 9.49 (s, 1H), 9.39 (s, 1H), 8.43 (d, 1H, J=8.4 Hz), 7.71–7.74(m, 2H), 7.50(d, 1H, J=6.9 Hz), 7.43 (dd, 1H, J=8.4, 1.2 Hz), 7.16–7.23 (m, 3H), 6.45 (d, 1H, J=2.1 Hz), 6.35 (dd, 1H, J=8.4, 2.1 Hz). MS (ES) [m+H]/z calc'd 343, found 343; [m–H]/z calc'd 341, found 341.

Example 24(g)

3-1H-Benzoimidazol-2-yl-6-(2-phenoxy-4-hydroxyphenyl)-1H-indazole

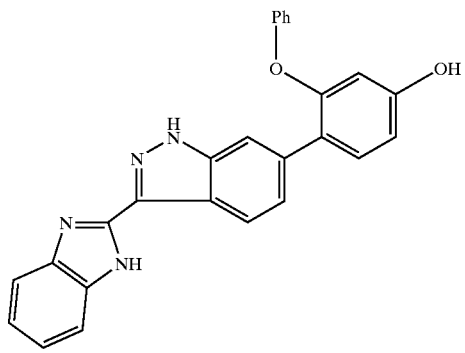

Example 24(g) was prepared in a similar manner to that described for Example 24(c), except that 3-phenoxy-phenol was used instead of 2-chloro-5-methyl-phenol in step (i). $^1$H NMR (300 MHz, DMSO-d$_6$) δ 13.54 (s, 1H), 12.95 (s, 1H), 9.78 (s, 1H), 8.43 (d, 1H, J=8.4 Hz), 7.67–7.72 (m, 2H), 7.49 (dd, 1H, J=6.3, 2.1 Hz), 7.43 (d, 2H, J=8.4 Hz), 7.33 (t, 2H, J=7.5 Hz), 7.17–7.22 (m, 2H), 6.96–7.07 (m, 3H), 6.72 (dd, 1H, J=8.4, 2.1 Hz), 6.40 (d, 1H, J=2.1 Hz). MS (ES) [m+H]/z calc'd 419, found 419; [m–H]/z calc'd 417, found 417.

Example 24(h)

3-1H-Benzoimidazol-2-yl-6-(2-(2-methoxyethyl)-4-hydroxyphenyl)-1H-indazole

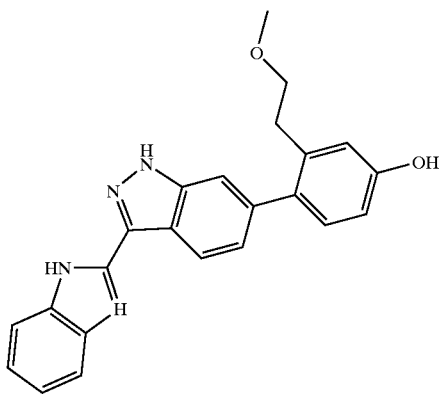

Example 24(h) was prepared in a similar manner to that described for Example 24(a), except that {2-[4-bromo-3-(2-methoxy-ethyl)-phenoxymethoxy]-ethyl}-trimethyl-silane, prepared as described below, was used instead of [24-bromo-2-methoxy-5-methyl-phenoxymethoxy)-ethyl]-trimethylsilane in step (vii). $^1$H NMR (300 MHz, DMSO-d$_6$) δ 13.60 (s, 1H), 13.01 (s, 1H), 9.44 (s, 1H), 8.49 (d, 1H, J=8.4 Hz), 7.73 (br s, 1H), 7.51 (br s, 1H), 7.46 (s, 1H), 7.21 (app d, 3H, J=8.1 Hz), 7.09 (d, 1H, J=8.1 Hz), 6.78 (d, 1H, J=2.4 Hz), 6.70 (dd, 1H, J=8.1, 2.4 Hz), 3.40 (t, 2H, J=7.2 Hz), 3.12 (s, 3H), 2.75 (t, 2H, J=7.2 Hz). MS (ES) [m+H]/z calc'd 385, found 385; [m–H]/z calc'd 383, found 383.

The starting material was prepared as follows:

(i)

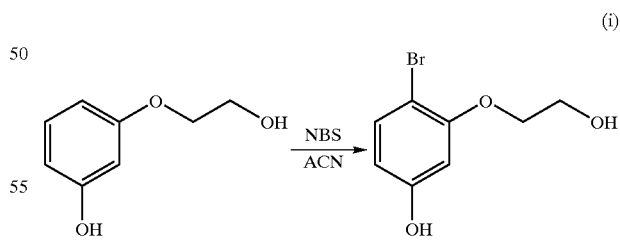

4-Bromo-3-(2-hydroxy-ethyl)-phenol was prepared in 88% yield by the substitution of 3-(2-hydroxy-ethyl)-phenol in the procedure described in Example 24(c), step (i). $^1$H NMR (300 MHz, CDCl$_3$) δ 9.56 (s, 1H), 7.29 (d, 1H, J=8.7 Hz), 6.74(d, 1H, J=3.0 Hz), 6.55 (dd, 1H, J=8.7, 3.0 Hz), 4.71 (t, 1H, J=5.4 Hz), 3.52–3.59 (m, 2H), 2.73 (t, 2H, J=7.2 Hz).

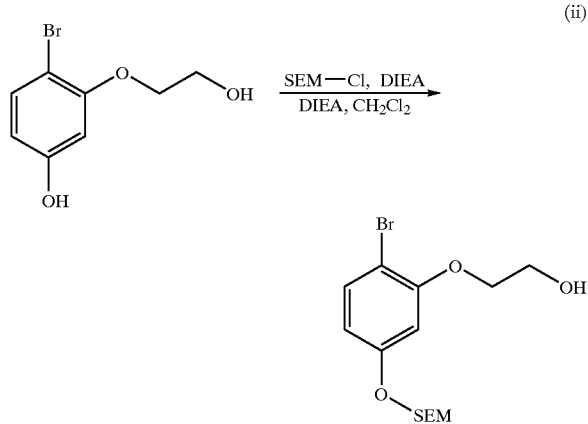

(ii)

Preparation of 2-[2-Bromo-5-(2-trimethylsilanyl-ethoxymethoxy)-phenyl] was prepared in 65% yield by the substitution of 4-bromo-3-(2-hydroxy-ethyl)-phenol in the procedure described in Example 24(a), step (vi). $^1$H NMR (300 MHz, CDCl$_3$) δ 7.43 (d, 1H, J=8.7 Hz), 6.97 (d, 1H, J=3.0 Hz), 6.82 (dd, 1H, J=8.7, 3.0 Hz), 5.19 (s, 2H), 3.88 (q, 2H, J=6.6 Hz), 3.74 (t, 2H, J=8.4 Hz), 2.99 (t, 2H, J=6.6 Hz), 1.42 (t, 1H, J=6.6 Hz), 0.94 (t, 2H, 1=8.4 Hz), −0.01 (s, 9H).

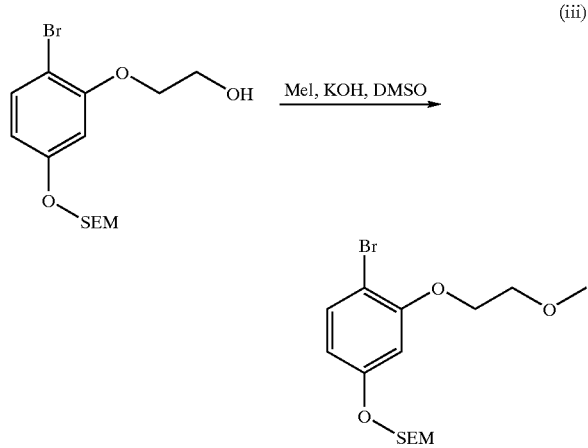

(iii)

{(2-[Bromo-3-(2-methoxy-ethyl)phenoxymethoxy]-ethyl}-trimethyl-silane: 2-[2-Bromo-5-(2-trimethylsilanyl-ethoxymethoxy)-phenyl]-ethanol (1.9 g, 6.0 mmol) was added to a solution of potassium hydroxide (1.35 g, 24 mmol) in DMSO (16 mL). Iodomethane (1.12 mL, 18 mmol) was added, and the solution stirred for 16 h. The reaction was diluted with water (50 mL) and extracted with ether (2×40 mL). Organics were washed with brine (40 mL), dried (Na$_2$SO$_4$) and concentrated in vacuo. Purification by silica gel chromatography (10% ether/hexanes) gave 1.28 g of (2-[4-bromo-3-(2-methoxy-ethyl)-phenoxymethoxy]-ethyl)-trimethyl-silane as a clear oil. $^1$H NMR (300 MHz, CDCl$_3$) δ 7.40 (d, 1H, J=8.7 Hz), 6.96 (d, 1H, J=3.0 Hz), 6.80 (dd, 1H, J=8.7, 3.0 Hz), 5.18 (s, 2H), 3.74 (t, 2H, J=8.4 Hz), 3.60 (t, 2H, J=7.2 Hz), 3.37 (s, 3H), 2.98 (t, 2H, J=7.2 Hz), 0.95 (t, 2H, J=8.4 Hz), −0.01 (s, 9H).

Example 24(i)

3-1H-Benzoimidazol-2-yl-(2-(2-hydroxyethyl)-4-hydroxyphenyl)-1H-indazole 3-1H-Benzoimidazol-2-yl-6-(2-(2-methoxyethyl)-4-hydroxyphenyl)-1H-indazole, from Example 24(i), (99 mg, 0.26 mmol) was dissolved in EtOAc (20 mL) and cooled to −78° C. under argon. Boron tribromide was added dropwise, and the reaction was allowed to stir while warming to r.t over 3 h. The solution was diluted with EtOAc (60 mL) and washed with sat NaHCO$_3$ and brine (20 mL each). Organics were dried (Na$_2$SO$_4$) and concentrated in vacuo. Purification by silica gel chromatography (THF) gave 56 mg (59%) of the title compound as a white solid. $^1$H NMR (300 MHz, DMSO-d$_6$) δ 13.60 (s, 1H), 13.01 (s, 1H), 9.41 (s, 1H), 8.49 (d, 1H, J=8.4 Hz), 7.71 (br s, 1H), 7.51 (br s, 1H), 7.46 (s, 1H), 7.21 (app d, 3H, J=8.1 Hz), 7.08 (d, 1H, J=8.4 Hz), 6.77 (d, 1H, J=2.1 Hz), 6.69 (dd, 1H. J=8.1, 2.1 Hz), 4.57 (br s, 1H), 3.46 (t, 2H, J=7.2 Hz), 2.68 (t, 2H, J=7.2 Hz). MS (ES) [m+H]/z calc'd 371, found 371; [m−H]/z calc'd 369, found 369.

Example 24(j)

3-1H-Benzoimidazol-2-yl-6-(2,6-dimethyl-4-hydroxyphenyl)-1H-indazole

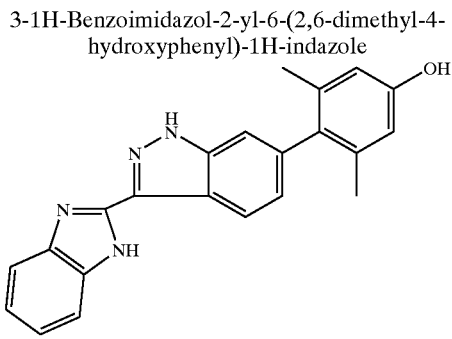

Example 24(j) was prepared in a similar manner to that described for Example 24(a), except that 4-bromo-3,5-dimethyl-phenol was used instead of 4-bromo-2-methoxy-5-methyl-phenol in step (vi). $^1$H NMR (300 MHz, DMSO-d$_6$) δ 13.57 (s, 1H), 12.99 (s, 1H), 9.22 (s, 1H), 8.52 (d, 1H, J=8.4 Hz), 7.72 (d, 1H, J=6.6 Hz), 7.51 (d, 1H, J=6.6 Hz), 7.31 (s, 1H), 7.16–7.25 (m. 2H), 7.02 (d, 1H, J=8.4 Hz), 6.55 (s, 2H), 1.93 (s, 6H). MS (ES) [m+H]/z calc'd 355, found 355; [m−H]/z calc'd 353, found 353.

Example 24(k)

3-1H-Benzoimidazol-2-yl-6-(2-methylsulfanyl-4-hydroxyphenyl)-1H-indazole

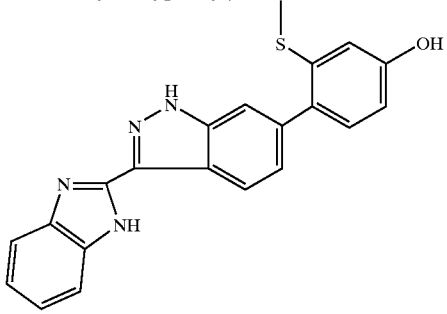

Example 24(k) was prepared in a similar manner to that described for Example 24(c), except that 3-methylsulfanyl-phenol, prepared as described below, was used instead of 2-chloro-5-methyl-phenol in step (i). $^1$H NMR (300 MHz, DMSO-$d_6$) δ 13.59 (s, 1H), 12.98 (s, 1H), 9.64 (s, 1H), 8.48 (d, 1H, J=8.4 Hz), 7.71 (br s, 1H), 7.52 (app s, 2H), 7.20–7.27 (m, 3H), 7.12 (d, 1H, J=8.4 Hz), 6.76 (d, 1H, J=2.1 Hz), 6.65 (dd, 1H, J=8.4, 2.1 Hz), 2.34 (s, 3H). MS (ES) [m+H]/z calc'd 373, found 373; [m−H]/z calc'd 371, found 371.

The starting material was prepared as follows:

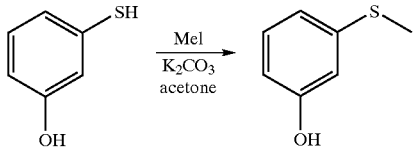

Preparation of 3-methylsulfanyl-phenol. 3-Hydroxythiophenol (5.0 g, 39.7 mmol) and potassium carbonate (6.03 g, 43.6 mmol) were stirred in acetone (80 mL) at 0° C. Iodomethane (2.5 mL, 40 mmol) was added dropwise, and the reaction stirred for 45 min. The solution was diluted with $H_2O$ (150 mL) and extracted with EtOAc (2×100 mL). Organics were washed with brine (100 mL), dried ($Na_2SO_4$) and concentrated in vacuo. Purification by silica gel chromatography (25% EtOAc/hexanes) 5.08 g (91%) of 3-methylsulfanyl-phenol as a clear oil. $^1$H NMR (300 MHz, CDCl$_3$) δ 7.15 (t, 1H, J=8.1 Hz), 6.82 (d, 1H, J=8.1 Hz), 6.74 (t, 1H, J=1.8 Hz), 6.60 (dd, 1H, J=8.1, 1.8 Hz), 4.86 (s, 1H), 2.47 (s, 3H).

Example 24(l)

3-1H-Benzoimidazol-2-yl-6-(2-(ethoxymethyl)-5-methoxy-4-hydroxy-phenyl)-1H-indazole

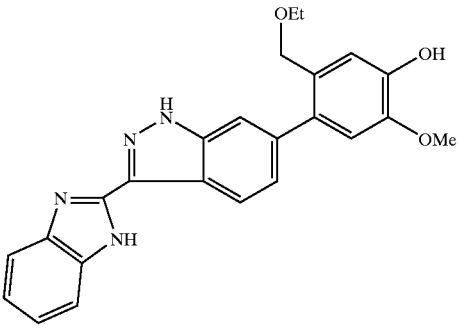

Example 24(l) was prepared in a similar manner to that described for Example 24(a), except that [2-(4-bromo-5-ethoxymethyl-2-methoxy-phenoxymethoxy)-ethyl]-trimethyl-silane, prepared as described below, was used instead of [2-(4-bromo-2-methoxy-5-methyl-phenoxymethoxy)-ethyl]-trimethylsilane in step (vii). $^1$H NMR (300 MHz, DMSO-$d_6$) δ 13.63 (s, 1H), 12.99 (s, 1H), 9.15 (s, 1H), 8.50 (d, 1H, J=8.4 Hz), 7.73 (dd, 1H, J=6.6, 2.1 Hz), 7.59 (s, 1H), 7.51 (dd, 1H, J=6.6, 2.1 Hz), 7.32 (d, 1H, J=8.4 Hz), 7.19–7.24 (m, 2H), 6.94 (s, 1H), 6.91 (s, 1H), 4.22 (s, 2H), 3.81 (s, 3H), 3.39 (q, 2H, J=6.9 Hz), 1.13 (t, 3H, J=6.9 Hz). MS (ES) [m+H]/z calc'd 415, found 415.

The starting material was prepared as follows:

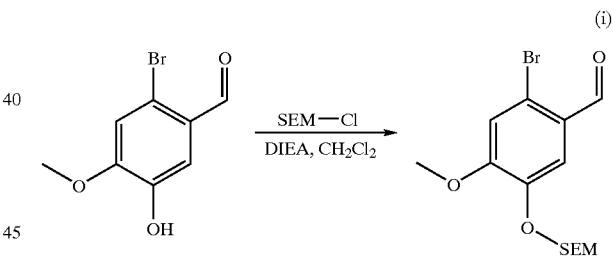

2-Bromo-4-methoxy-5-(2-trimethylsilanyl-ethoxymethoxy)-benzaldehyde was prepared in 79% yield by the substitution of 4-bromo-3-formyl-2-methoxy-phenol (Hazlet et. al., *J. Org. Chem.*, 27, 3253–55 (1962)) in the procedure described in Example 24(a), step(vi). $^1$H NMR (300 MHz, CDCl$_3$) δ 10.16 (s, 1H), 7.68 (s, 1H), 7.07 (s, 1H), 5.28 (s, 2H), 3.94 (s, 3H), 3.77 (t, 2H, J=8.4 Hz), 0.94 (t, 2H, J=8.4 Hz), −0.03 (s, 9H).

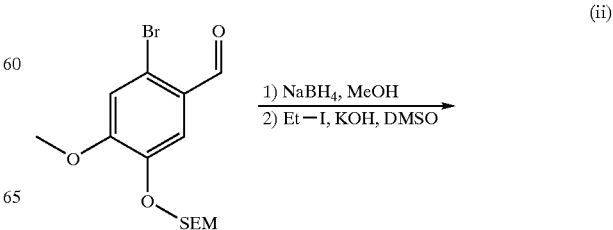

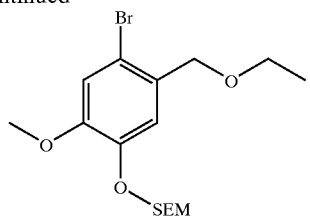

Preparation of [2-(4-Bromo-5-ethoxymethyl-2-methoxy-phenoxymethoxy)-ethyl]-trimethyl-silane: Sodium borohydride (275 mg, 7.2 mmol) was added in portions over 10 min to a solution of 2-bromo-4-methoxy-5-(2-trimethylsilanyl-ethoxymethoxy)-benzaldehyde (1.3 g, 3.6 mmol) in MeOH (20 mL) at 0° C. After 30 min, the reaction was diluted with H$_2$O (40 mL) and extracted with EtOAc (2×30 mL). Organics were washed with brine (30 mL), dried (Na$_2$SO$_4$) and concentrated in vacuo to give 1.31 g of [2-bromo-4-methoxy-5-(2-trimethylsilanyl-ethoxymethoxy)-phenyl]-methanol as a clear oil. $^1$H NMR (300 MHz, CDCl$_3$) δ 7.29 (s, 1H), 7.05 (s, 1H), 5.27 (s, 2H), 4.66 (d, 2H, J=6.6 Hz), 3.87 (s, 3H), 3.79 (t, 2H, J=8.4 Hz), 1.92 (t, 1H, J=6.6 Hz), 0.96 (t, 2H, J=8.4 Hz), 0.01 (s, 9H).

The crude benzyl alcohol was stirred with a solution of potassium hydroxide (800 mg, 14.4 mmol) in DMSO (8 mL). Iodoethane (580 mL, 7.2 mmol) was added, and the reaction stirred for 16 h before it was diluted with H$_2$O (30 mL) and extracted with ether (2×30 mL). Organics were washed with brine (20 mL), dried (Na$_2$SO$_4$) and concentrated in vacuo. Purification by silica gel chromatography (15% EtOAc/hexanes) gave 1.30 g (92%) of the title compound as a clear oil. $^1$H NMR (300 MHz, CDCl$_3$) δ 7.29 (s, 1H), 7.03 (s, 1H), 5.26 (s, 2H), 4.48 (s, 2H), 3.85 (s, 3H), 3.79 (t, 2H, J=8.4 Hz), 3.58 (q, 2H, J=6.9 Hz), 1.26 (t, 3H, J=6.9 Hz), 0.95 (t, 2H, J=8.4 Hz), −0.01 (s, 9H).

Example 24(m)

3-1H-Benzoimidaz 1-2-yl-6-(2-(hydroxymethyl)-4-ethoxy-5-methoxy-phenyl)-1H-indazole

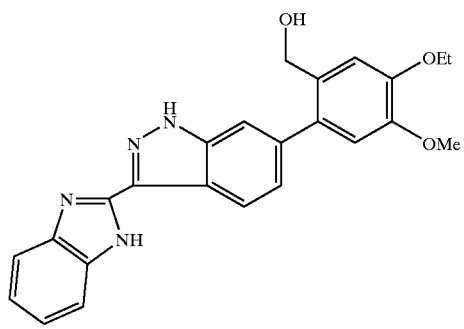

Example 24(m) was prepared in a similar manner to that described for Example 24(a), except that [2-(2-bromo-5-ethoxy 4-methoxy-benzyloxymethoxy)-ethyl]-trimethyl-silane, prepared as described below, was used instead of [2-(4-bromo-2-methoxy-5-methyl-phenoxymethoxy) ethyl]-trimethylsilane in step (vii). $^1$H NMR (300 MHz, DMSO-d$_6$) δ 13.64 (s, 1H), 13.00 (s, 1H), 8.50 (d, 1H, J=8.4 Hz), 7.73 (d, 1H, J=8.4 Hz), 7.62 (s, 1H), 7.52 (dd, 1H, J=6.0, 1.8 Hz), 7.32(dd, 1H, J=8.4, 1.2 Hz), 7.19–7.24 (m, 2H), 7.15 (s, 1H), 6.91 (s, 1H), 5.11 (t, 1H, J=5.1 Hz), 4.37 (d, 2H, J=5.1 Hz), 4.08 (q, 2H, J=6.9 Hz), 3.80 (s, 3H), 1.37 (t, 3H, J=6.9 Hz). MS (ES) [m+H]/z calc'd 415, found 415.

The starting material was prepared as follows:

(i)

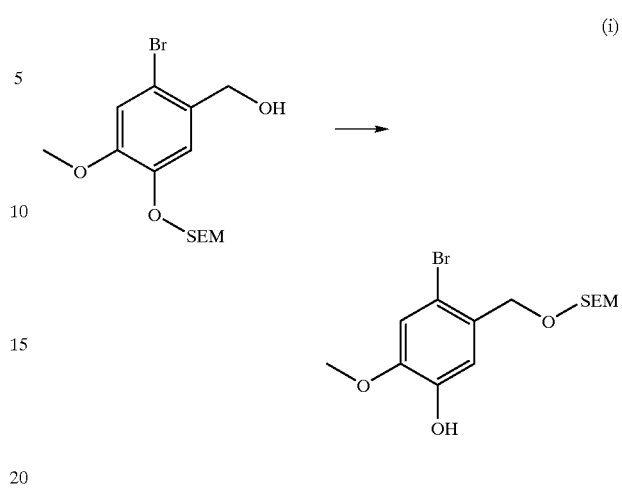

Preparation of 4-bromo-2-methoxy-5-(2-trimethylsilanyl-ethoxymethyl) phenol: [2-Bromo-4-methoxy-5-(2-trimethylsilanyl-ethoxmethoxy)-phenyl]-methanol, upon sitting for periods of over a week, underwent SEM-migration from the phenolic to the benzylic alcohol to yield the title compound. $^1$H NMR (300 MHz, CDCl$_3$) δ 7.04 (s, 1H), 7.01 (s, 1H), 5.54 (s, 1H), 4.77 (s, 2H), 4.57 (s, 2H), 3.88 (s, 3H), 3.68 (t, 2H, J=8.4 Hz), 0.97 (t, 2H, J=8.4 Hz), 0.02 (s, 9H).

(ii)

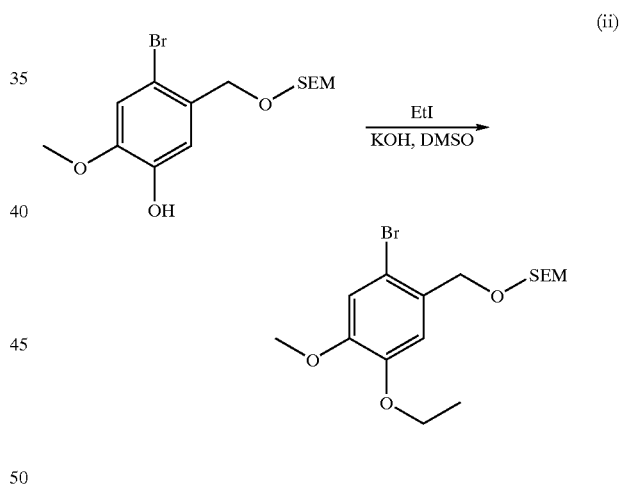

Preparation of [2-(2-bromo-5-ethoxy-4-methoxy-benzyloxymethoxy)-ethyl]-trimethyl-silane: 4-Bromo-2-methoxy-5-(2-trimethylsilanyl-ethoxymethyl)-phenol (1.28 g, 3.53 mmol) was stirred with a solution of potassium hydroxide (790 mg, 14.1 mmol) in DMSO (8 mL). Iodoethane (565 mL, 7.1 mmol) was added, and the reaction stirred for 16 h before it was diluted with H$_2$O (30 mL) and extracted with ether (2×30 mL). Organics were washed with brine (20 mL), dried (Na$_2$SO$_4$) and concentrated in vacuo. Purification by silica gel chromatography (15% EtOAc/hexanes) gave 1.26 g (91%) of the tide compound as a clear oil. $^1$H NMR (300 MHz, CDCl$_3$) δ 7.02 (s, 1H), 6.98 (s, 1H), 4.78 (s, 2H), 4.60 (s, 2H), 4.09 (q, 2H, J=6.6 Hz), 3.86 (s, 3H), 3.69 (t, 2H, J=8.4 Hz), 1.46 (t, 3H, J=6.6 Hz), 0.97 (t, 2H, J=8.4 Hz), 0.04 (s, 9H).

Example 24(n)

3-1H-Benzoimidazol-2-yl-6-(2-(hydroxymethyl)-5-methoxy-4-hydroxy-phenyl)-1H-indazole

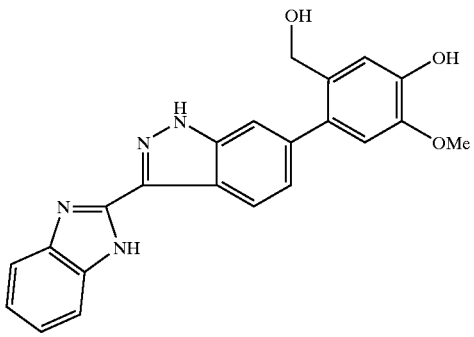

Example 24(n) was prepared in a similar manner to that described for Example 24(a), except that 6-[5-methoxy-2-hydroxymethyl-4-(2-trimethylsilanyl-ethoxymethoxy)-phenyl]-1-(2-trimethylsilanyl-ethoxymethyl)-3-[1-(2-trimethylsilanyl-ethoxymethyl)-1H-benzoimidazol-2-yl]-1H-indazole, prepared as described below, was used instead of 6-[5-methoxy-2-methyl(2-trimethylsilanyl-ethoxymethoxy)-phenyl]-1-(2-trimethylsilanyl-ethoxymethyl)-3-[1-(2-trimethylsilanyl-ethoxymethyl) 1H-benzoimidazol-2-yl]-1H-indazole. $^1$H NMR (300 Mz, DMSO-d$_6$) δ 13.59 (s, 1H), 12.95 (s, 1H), 9.05 (s, 1H), 8.49 (d, 1H, J=8.4 Hz), 7.72 (dd, 1H, J=6.3, 2.1 Hz), 7.60 (s, 1H), 7.51 (dd, 1H, J=6.3, 2.1 Hz), 7.31 (d, 1H, J=8.4 Hz), 7.20–7.24 (m, 2H), 7.02 (s, 1H), 6.87 (s, 1H), 5.02 (t, 1H, J=5.4 Hz), 4.32 (d, 2H, J=5.4 Hz), 3.80 (s, 3H). MS (ES) [m+H]/z calc'd 387, found 387; [m–H]/z calc'd 385, found 385.

The starting material was prepared as follows:

(i)

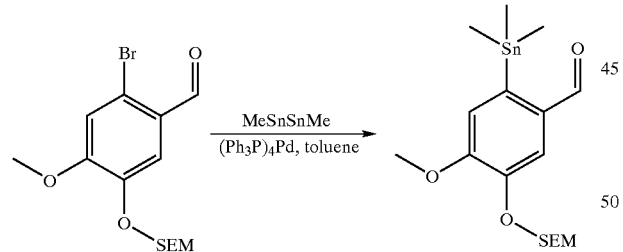

Preparation of 4-methoxy-5-(2-trimethylsilanyl-ethoxymethoxy)-2-trimethylstannanyl-benzaldehyde: 2-Bromo-4-methoxy-5-(2-trimethylsilanyl-ethoxymethoxy)-benzaldehyde (3.36 g, 9.3 mmol) and hexamethylditin (5.0 g, 15.3 mmol) were stirred in dry toluene (60 mL) in a flask purged with argon. Tetrakis(triphenylphosphine)palladium(0) (500 mg, 0.45 mmol) was added, and the reaction stirred at 100° C. for 23 h. The reaction was cooled and concentrated in vacuo. Purification by silica gel chromatography (5% EtOAc/hexanes) gave 2.77 g (67%) of 4-methoxy-5-(2-trimethylsilanyl-ethoxymethoxy)-2-trimethylstannanyl-benzaldehyde as a clear oil. $^1$H NMR (300 MHz, CDCl$_3$) δ 9.81 (dd, 1H, J=3.0, 0.9 Hz), 7.66 (t, 1H, J=6.6 Hz), 7.21 (t, 1H, J=9.0 Hz), 5.35 (s, 2H), 3.99 (s, 3H), 3.82 (t, 2H, J=8.4 Hz), 0.25 (t, 9H, J=26.7 Hz), 0.98 (t, 2H, J=8.4 Hz), −0.01 (s, 9H).

(ii)

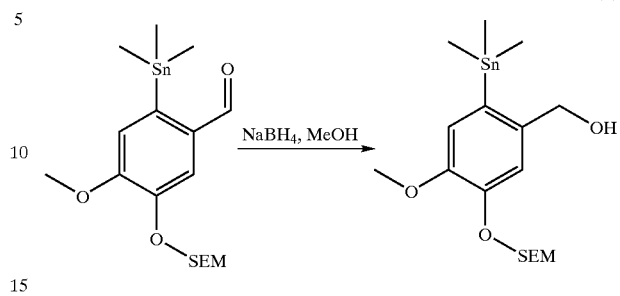

Preparation of [4-methoxy-5-(2-trimethylsilanyl-ethoxymethoxy)-2-trimethylstannanyl-phenyl]-methanol: 4-Methoxy-5-(2-trimethylsilanyl-ethoxymethoxy)-2-trimethylstannanyl-benzaldehyde (2.36 g, 5.3 mmol) was stirred in MeOH (30 mL) at 0° C. Sodium borohydride (400 mg, 10.6 mmol) was added, and the reaction stirred for 1 h. The solution was diluted with H$_2$O (60 mL), and extracted with EtOAc (2×50 mL). Organics were washed with brine (50 mL), dried (Na$_2$SO$_4$), and concentrated in vacuo to give 2.16 g (91%) of [4-methoxy-5-(2-trimethylsilanyl-ethoxymethoxy)-2-trimethylstannanyl-phenyl]-methanol as a clear oil. $^1$H NMR (300 MHz, CDCl$_3$) δ 7.18 (t, 1H, J=6.9 Hz), 7.03 (t, 1H, J=9.3 Hz), 5.27 (s, 2H), 4.58-4.63 (m, 2H), 3.89 (s, 3H), 3.80 (t, 2H, J=8.4 Hz), 1.53 (t, 1H, J=6.0 Hz), 0.96 (t, 2H, J=8.4 Hz), 0.31 (t, 9H, J=27.3 Hz), 0.01 (s, 9H).

(iii)

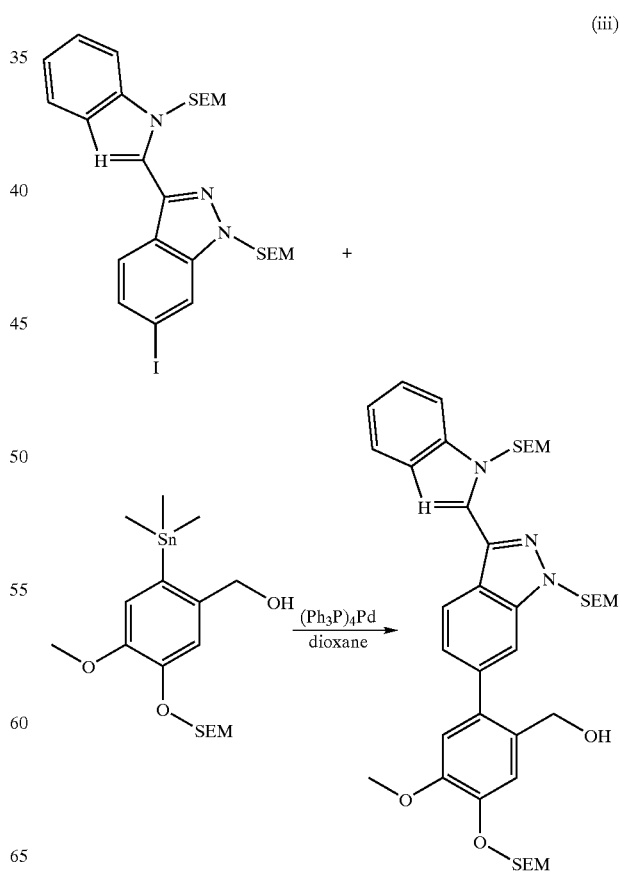

Preparation of 6-[5-methoxy-2-hydroxymethyl-4-(2-trimethylsilanyl-ethoxymethoxy)-phenyl]-1-(2-trimethylsilanyl-ethoxymethyl)-3-[1-(2-trimethylsilanyl-ethoxymethyl)-1H-benzoimidazol-2-yl]-1H-indazole: 6-Iodo-1-[2-(trimethyl-silanyl)-ethoxymethyl]-3-{1-[2-(trimethyl-silanyl)-ethoxymethyl]-1H-benzoimidazol-2-yl}-1H-indazole [Example 24(a), step (v)] (300 mg, 0.48 mmol) and [4-methoxy-5-(2-trimethylsilanyl-ethoxymethoxy)-2-trimethylstannanyl-phenyl]-methanol (282 mg, 0.63 mmol) were stirred in dioxane (8 mL) under argon at 98° C. for 16 h. The reaction was allowed to cool and was diluted with EtOAc. Organics were washed with sat NaHCO$_3$ and brine, dried (Na$_2$SO$_4$), and concentrated in vacuo. Purification by silica gel chromatography (20% EtOAc/hexanes) gave 224 mg (60%) of 6-[5-methoxy-2-hydroxymethyl-4-(2-trimethylsilanyl-ethoxymethoxy)-phenyl]-1-(2-trimethylsilanyl-ethoxymethyl)-3-[1-(2-trimethylsilanyl-ethoxymethyl)-1H-benzoimidazol-2-yl]-1H-indazol as a faint yellow oil. $^1$H NMR (300 MHz, CDCl$_3$) δ 8.70 (d, 1H, J=8.4 Hz), 7.89–7.92 (m, 1H), 7.63–7.66 (m, 2H), 7.34–7.41 (m, 4H), 6.91 (s, 1H), 6.29 (s, 2H), 5.83 (s, 2H), 5.36 (s, 2H), 4.55 (s, 2H), 3.78–3.92 (m, 5H), 3.59–3.70 (m, 4H), 0.83–1.04 (m, 6H), 0.03 (s, 9H); –0.04 (s, 9H), –0.13 (s, 9 Hz).

Example 24(o)

3-1H-Benzoimidazol-2-yl-6-(3-hydroxyphenyl)-1H-indazole

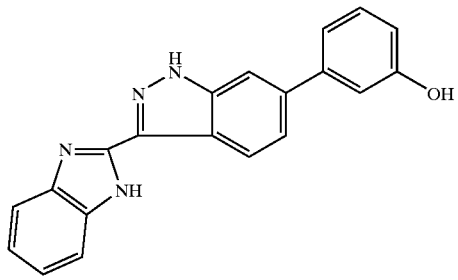

Example 24(o) was prepared in a similar manner to that described for Example 24(f), except that 6-(3-methoxyphenyl)-3-1H-benzoimidazol-2-yl-1H-indazole, prepared in a similar manner to that described for example 24(a) except that 3-methoxy-phenylboronic acid was used instead of 5-methoxy-2-methyl-4-[2-(trimethylsilanyl)-ethoxymethoxy]-phenylboronic acid in step (viii), was used instead of 6-(2-methoxy-4-hydroxyphenyl)-3-1H-benzoimidazol-2-yl-1H-indazole. $^1$H NMR (300 MHz, DMSO-d$_6$) δ 13.67 (s, 1H), 13.00 (s, 1H), 9.58 (s, 1H), 8.55 (d, 1H, J=8.4 Hz), 7.71–7.75 (m, 2H), 7.49–757 (m, 2H), 7.30 (t, 1H, J=7.8 Hz), 7.12–7.24 (m, 4H), 6.80 (dd, 1H, J=8.1, 1.5 Hz). MS (ES) [m+H]/z calc'd 327, found 327; [m–H]/z calc'd 325, found 325.

Example 24(p)

3-1H-Benzoimidazol-2-yl-6-(2-methoxy-3-hydroxyphenyl)-1H-indazole

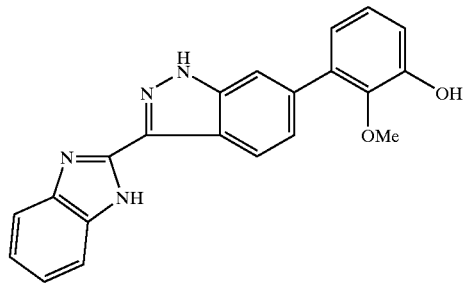

Example 24(p) was prepared in a similar manner to that described for Example 24(a), except that 3-bromo-2-methoxy-phenol, prepared as described by Aristoff et. al., Tet. Lett., 25, 3955–58 (1984) was used instead of 4-bromo-2-methoxy-5-methyl-phenol in step (vi). $^1$H NMR (300 MHz, DMSO-d$_6$) δ 13.60 (s, 1H), 12.97 (s, 1H), 9.37 (s, 1H), 8.52 (d, 1H, J=8.4 Hz), 7.69–7.74 (m, 2H), 7.51 (dd, 1H, J=7.8, 1.8 Hz), 7.43 (dd, 1H, J=8.4, 1.2 Hz), 7.19–7.24 (m, 2H), 7.02 (t, 1H, J=7.8 Hz), 6.85–6.93 (m, 2H), 3.50 (s, 3H). MS (ES) [m+H]/z calc'd 357, found 355, [m–H]/z calc'd 357, found 355.

Example 25(a)

3-(3H-Imidazo[4,5-c]pyridin-2-yl)-6-hydroxy-2-methoxyphenyl)-1H-indazole

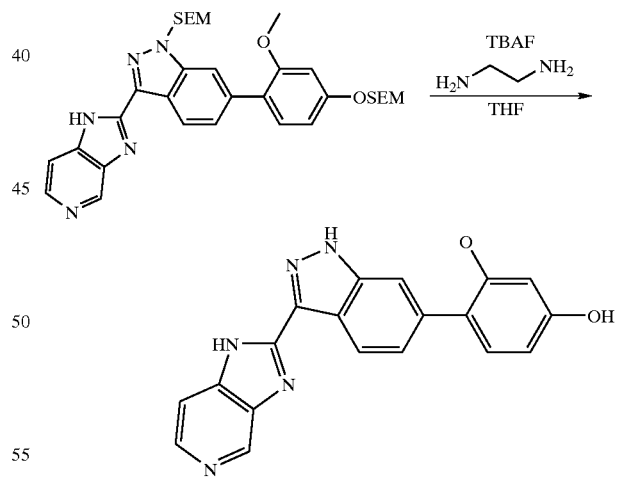

A solution of of 6-[5-methoxy-2-methyl-4-(2-trimethylsilanyl-ethoxymethoxy)phenyl]-1-(2-trimethylsilanyl-ethoxymethyl)-3-[3-(2-trimethylsilanyl-ethoxymethyl)-3H-imidazo[4,5-c]pyridin-2-yl]-1H-indazole (68 mg, 0.11 mmol) in TBAF (1 M in THF, 1.2 mL, 1.2 mmol) with ethylenediamine (150 mL, 2.2 mmol) was stirred at 68° C. for 48 h. The solution was concentrated in vacuo and purified by silica gel chromatography (2:1 EtOH/EtOAc). Precipitation from acetonitrile gave 21 mg (53%) of 3-(3H-imidazo[4,5]pyridin-2-yl)(4-hydroxy-2-methoxyphenyl)-1H-indazole as a white solid. $^1$H NMR (300 MHz, DMSO-$d_6$) δ 13.70 (s, 1H), 13.49 (br s, 1H), 9.62 (s, 1H), 9.01 (br s, 1H), 8.43 (d, 1H, J=8.7 Hz), 8.34 (d, 1H, J=5.7 Hz), 7.64 (s, 1H), 7.57 (br s, 1H), 7.39 (dd, 1H, J=8.7, 1.5 Hz), 7.21 (d, 1H, J=8.1 Hz), 6.55 (d, 1H, J=2.1 Hz), 6.49 (dd, 1H, J=8.1, 2.1 Hz), 3.74 (s, 3H). MS (ES) [m+H]/z calc'd 358, found 358; [m−H]/z calc'd 356, found 356.

The intermediates were prepared as follows:

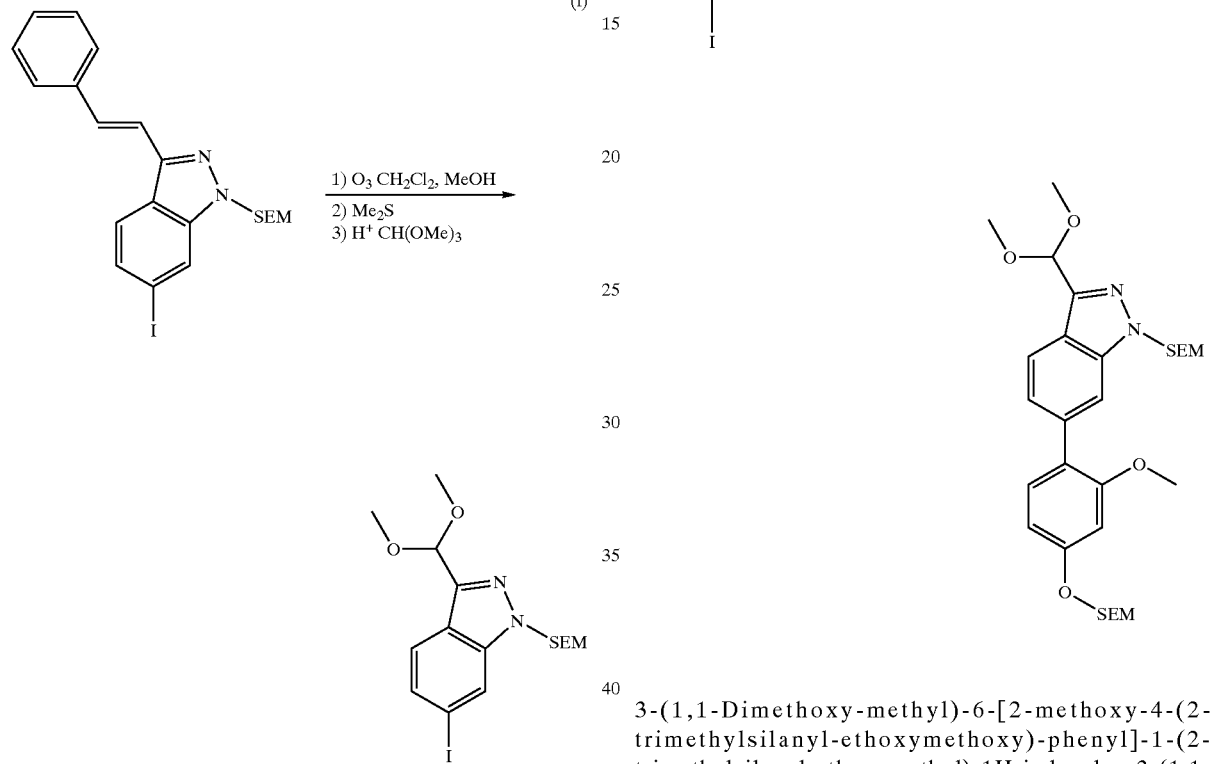

3-(1,1-Dimethoxy-methyl)-6-iodo-1-(2-trimethylsilanyl-ethoxymethyl)-1H-indazole. A solution of 6-iodo-3-styryl-1-[2-trimethyl-silanyl)-ethoxymethyl]-1H-indazole (Example 14, step (i)] (1.28 g, 2.69 mmol) in CH$_2$Cl$_2$ (40 mL)/MeOH (40 mL) was stirred at −78° C. The reaction was treated with ozone until a blue color persisted, and then was purged with argon. Methyl sulfide (4 mL) was added, and the reaction stirred 4 h while warming to r.t Concentration in vacuo gave a crude mixture of acetal and aldehyde, which was converted completely to the acetal by stirring in trimethyl orthoformate (10 mL) with Amberlyst 15(wet) acidic ion-exchange resin (0.8 g) for 1 h. The resin was removed by filtration, and the solution was concentrated in vacuo. Purification by silica gel chromatography gave 1.11 g (92%) of 3-(1,1-dimethoxy-methyl-6-iodo-1-(2-trimethylsilanyl-ethoxymethyl)-1H-indazole as a clear oil. $^1$H NMR (300 MHz, CDCl$_3$) δ 7.98 (s, 1H), 7.68 (d, 1H, J=8.4 Hz), 7.48 (dd, 1H, J=8.4, 1.2 Hz), 5.77 (s, 1H), 5.69 (s, 2H), 3.53 (t, 2H, J=8.4 Hz), 3.43 (s, 6H), 0.88 (t, 2H, J=8.4 Hz), −0.06 (s, 9H).

3-(1,1-Dimethoxy-methyl)-6-[2-methoxy-4-(2-trimethylsilanyl-ethoxymethoxy)-phenyl]-1-(2-trimethylsilanyl-ethoxymethyl)-1H-indazole. 3-(1,1-Dimethoxy-methyl)-6-iodo-1-(2-trimethylsilanyl-ethoxymethyl)-1H-indazole (1.06 g, 2.37 mmol), 2-methoxy-4-(trimethylsilanyl-ethoxymethoxy)phenylboronic acid (0.99 g, 3.32 mmol), and sodium carbonate (352 mg, 1.4 mmol) were stirred in a mixture of benzene (15 mL), MeOH (3 mL), and water (1 mL) in a flask purged with argon. Tetrakis(triphenylphosphine)palladium (0) (220 mg, 0.19 mmol) was added, and the reaction stirred at reflux for 16 h. The reaction was allowed to cool and was diluted with ether (70 mL). Organics were washed with H$_2$O and brine (30 mL each), dried (Na$_2$SO$_4$), and concentrated in vacuo. Purification by silica gel chromatography (15% EtOAc/hexanes) gave 1.12 g (82%) of 3-(1,1-dimethoxy-methyl)-6-[2-methoxy 4-(2-trimethylsilanyl-ethoxymethoxy)phenyl] 1-(2-trimethylsilanyl-ethoxymethyl)-1H-indazole as a faintly yellow oil. $^1$H NMR (300 MHz, CDCl$_3$) δ 7.91 (d, 1H, J=8.4 Hz), 7.64 (s, 1H), 7.37 (dd, 1H, J=8.4, 1.2 Hz), 7.29 (d, H, J=8.4 Hz), 6.71–6.77 (m, 2H), 5.82 (s, 1H), 5.75 (s, 2H), 5.28 (s, 2H), 3.77–3.83 (m, 5H), 3.57 (t, 2H, J=8.4 Hz), 3.46 (s, 6H), 1.00 (t, 2H, J=8.4 Hz), 0.88 (t, 2H, J=8.4 Hz), 0.03 (s, 9H), −0.05 (s, 9H).

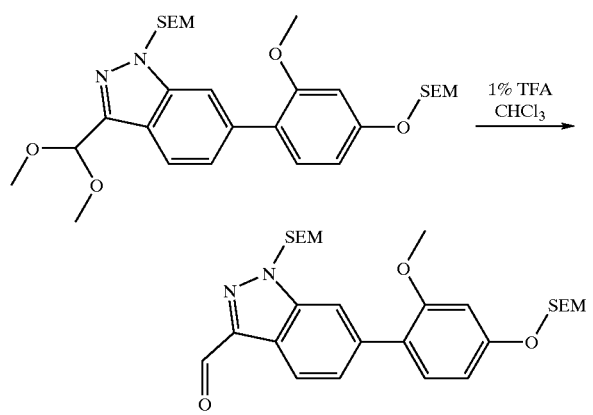

6-[2-Methoxy-4-(2-trimethylsilanyl-ethoxymethoxy)-phenyl]-1-(2-trimethylsilanyl-ethoxymethyl)-1H-indazole-3-carbaldehyde. 3-(1,1-Dimethoxy-methyl)-6-[2-methoxy-4-(2-trimethylsilanyl-ethoxymethoxy)-phenyl]-1-(2-trimethylsilanyl-ethoxymethyl)-1H-indazole (1.1 g, 1.92 mmol) was stirred in 1% TFA/CH$_2$Cl$_2$ (20 mL) for 1 h at rt Concentration in vacuo yielded 1.01 g (100%) of 6-[2-methoxy-4-(2-trimethylsilanyl-ethoxymethoxy)-phenyl]-1-(2-trimethylsilanyl-ethoxymethyl)-1H-indazole-3-carbaldehyde as a clear oil. $^1$H NMR (300 MHz, CDCl$_3$) δ 10.27 (s, 1H), 8.28 (d, 1H, J=8.4 Hz), 7.73 (s, 1H), 7.55 (dd, 1H, J=8.4, 1.2 Hz), 7.29 (d, 1H, J=8.4 Hz), 6.72–6.79 (m, 2H), 5.82 (s, 2H), 5.28 (s, 2H), 3.78–3.84 (m, 5H), 3.61 (t, 2H, J=8.1 Hz), 0.89–1.03 (m, 4H), 0.03 (s, 9H), −0.05 (s, 9H).

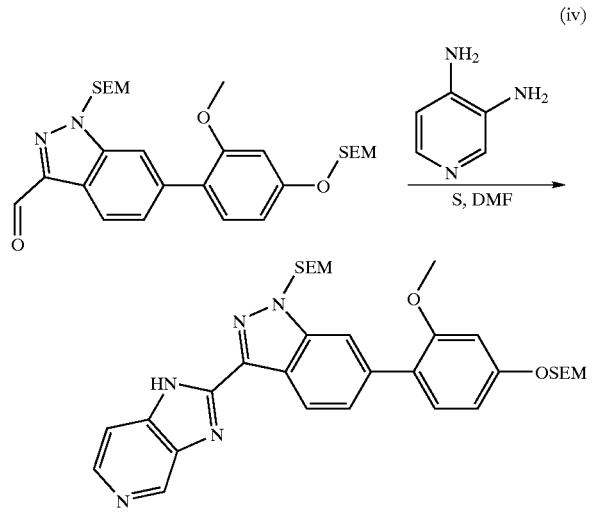

[5-methoxy-2-methyl-4-(2-trimethylsilanyl-ethoxymethoxy)-phenyl-1-(2-trimethylsilanyl-ethoxymethyl)-3-[3-(2-trimethylsilanyl-ethoxymethyl)-3H-imidazo[4,5-c]pyridin-2-yl]-1H-indazole. 6-[2-Methoxy 4-(2-trimethyl-silanyl-ethoxymethoxy)phenyl]-1-(2-trimethylsilanyl-ethoxymethyl)-1H-indazole-3-carbaldehyde (320 mg, 0.61 mmol), 3,4-diamino-pyridine (68 mg, 0.62 mmol), and sulfur (23 mg, 0.73 mmol) were combined in dry DMF (2 mL) and stirred at 90° C. for 16 h under argon. The reaction was allowed to cool and was diluted with EtOAc (20 mL). Organics were washed with sat. NaHCO$_3$ and brine (15 mL each), dried (Na$_2$SO$_4$), and concentrated in vacuo. Purification by silica gel chromatography (75% to 100% EtOAc/hexanes) gave 78 mg (21%) of 6-[5-methoxy-2-methyl-4-(2-trimethylsilanyl-ethoxymethoxy)phenyl]-1-(2-trimethylsilanyl-ethoxymethyl)-3-[3-(2-trimethylsilanyl-ethoxymethyl)-3H-imidazo[4,5-c]pyridin-2-yl]-1H-indazole as a white solid. $^1$H NMR (300 MHz, CDCl$_3$) δ 10.69 (br s, 1H), 9.21 (s, 1H), 8.63 (dd, 1H J=8.4, 0.3 Hz), 8.50 (d, 1H, J=5.4 Hz), 7.73 (s, 1H), 7.47 (br s, 1H), 7.57 (dd, 1H, J=8.7, 1.2 Hz), 7.33 (d, 1H, J=8.4 Hz), 6.746.80 (m, 2H), 5.80 (s, 2H), 5.29 (s, 2H), 3.78–3.85 (m, 5H), 3.63 (t, 2H, J=8.1 Hz), 0.89–1.04 (m, 4H), 0.04 (s, 9H), 0.06 (s, 9H).

Example 25(b)

3-[6-(2-morpholin-4-yl-ethylcarbamoyl)-1H-benzoimidazol-2-yl]-6-(2-methoxy-4-hydroxyphenyl)-1H-indazole

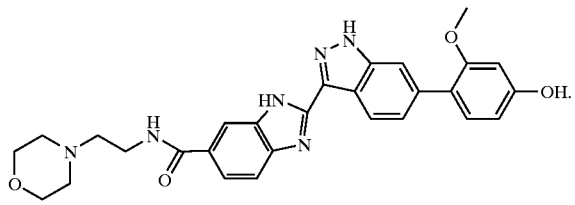

Example 25(b) was prepared in a similar manner to that described for Example 25(a), except that 3,4-diamino-N-(2-morpholin-1-yl-ethyl)-benzamide, prepared as described below, was used instead of 3,4-diaminopyridine in step (iv). $^1$H NMR (300 MHz, DMSO-d$_6$) δ 13.61 (s, 05H), 13.59 (s, 0.5H), 13.22 (s, 0.5H), 13.18 (s, 0.5H), 9.59 (s, if H), 8.35–8.46 (m, 2H), 8.27 (s, 0.5H), 8.02 (s, 0.5H), 7.71–7.79 (m, 1.5H), 7.63 (s, 1H), 7.53 (d, 0.5H, J=8.7 Hz), 7.38 (d, 1H, J=8.7 Hz), 7.21 (d, 1H, J=8.7 Hz), 6.55 (d, 1H, J=2.1 Hz), 6.49 (dd, 1H, J=8.4, 2.1 Hz), 3.75 (s, 3H), 3.58 (t, 4H, J=4.5 Hz), 3.42 (q, 2H, J=6.0 Hz), 2.43–2.51 (m, 6H). MS (ES) [m+H]/z calc'd 513, found 513; [m−H]/z calc'd 511, found 511.

3,4-Diamino-N-(2-morpholin-4-yl-ethyl)-benzamide was prepared as follows:

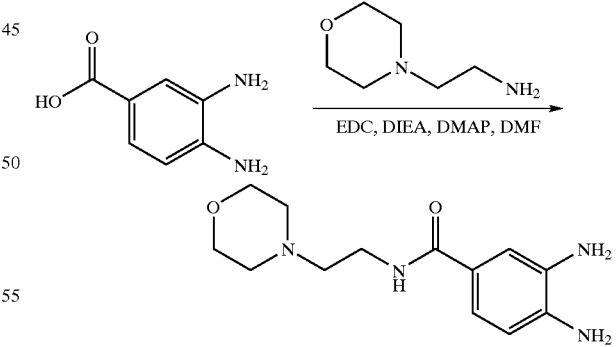

3,4-Diamino-N-(2-morpholin-4-yl-ethyl)-benzamide. 3,4-Diaminobenzoic acid (5 g, 32.9 mmol), 4-(2-aminoethyl) morpholine (5.2 mL, 39.4 mmol), triethylamine (9.2 mL, 66 mmol), and DMAP (0.40 g, 3.3 mmol) were combined in dry DMF (80 mL) at 0° C. EDC (9.45 g, 49.3 mmol) was added, and the reaction stirred for 24 h at r.t. Concentration in vacuo and purification by silica gel chromatography (10% MeOH/CH$_2$Cl$_2$ with 0.2% NH$_4$OH) gave 2.6 g (31%) of 3,4-diamino-N-(2-morpholin-4-yl-ethyl)-benzamide as a light brown solid. $^1$H NMR (300 MHz, DMSO-d$_6$) δ 7.72 (t, 1H, J=5.4 Hz), 7.02 (d, 1H, J=1.8 Hz), 6.92 (dd, 1H, J=8.1, 1.8 Hz), 6.46 (d, 1H, J=8.1 Hz), 4.89 (br s, 2H), 4.51 (br s, 2H), 3.55 (t, 4H, J=4.8 Hz), 3.29 (q, 2H, J=7.2 Hz), 2.36–2.43 (m, 6H).

Example 25(c)

3-[6-(4-methylpiperazin-1-yl)-1H-benzoimidazol-2-yl]-6-(2-methoxy-4-hydroxyphenyl)-1H-indazole

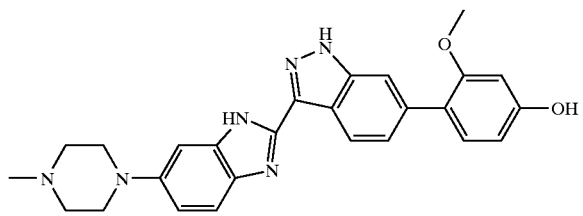

Example 25(c) was prepared in a similar manner to that described for Example 25(a), except 4-(4-methyl-piperazin-1-yl)benzene-1,2-diamine (Harapanhalli et al., *J. Med. Chem.*, 39, 4804–09 (1996)) was used instead of 3,4-diaminopyridine in step (iv). $^1$H NMR (300 MHz, DMSO-d$_6$) δ 13.51 (s, 0.33H), 13.38 (s, 0.67H), 12.66 (s, 0.33H), 12.59 (s, 0.67H), 9.58 (s, 1H), 8.42 (d, 0.33H, J=8.4 Hz), 8.41 (d, 0.67H, J=8.4 Hz), 7.59 (s, 1H), 7.55 (d, 0.67H, J=8.7 Hz), 7.31–7.37 (m, 1.33H), 7.20 (app d, 1.33H, J=8.4 Hz), 6.92–7.01 (m, 1.67H), 6.55 (d, 1H, J=1.5 Hz), 6.48 (dd, 1H, J=8.4, 2.1 Hz), 3.74 (s, 3H), 3.12 (br s, 4H), 2.50 (br s, 4H), 2.22 (s, 3H). MS (ES) [m+H]/z calc'd 455, found 455; [m−H]/z calc'd 453, found 453.

Example 25(d)

3-[4-(4-methylpiperazin-1-yl)-1H-benzoimidazol-2-yl]-6-(2-methoxy-4-hydroxyphenyl)-1H-indazole

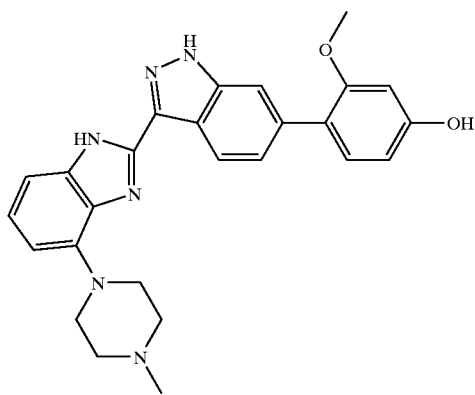

Example 25(d) was prepared in a similar manner to that described for Example 25(a), except 3-(4-methyl-piperazin-1-yl)-benzene-112-diamine (Harapanhalli et al., *J. Med. Chem.*, 39, 4804–09 (1996)), analogous to the 4-isomer preparation) was used instead of 3,4-diaminopyridine in step (iv). $^1$H NMR (300 MHz, DMSO-d$_6$) δ 13.41 (br s, 1H), 12.79 (br s, 1H), 9.60 (br s, 1H), 8.37 (d, 1H, J=8.4 Hz), 7.60 (s, 1H), 7.36 (dd, 1H, J=8.4, 1.2 Hz), 7.22 (d, 1H, J=8.4 Hz), 7.03–7.07 (m, 2H), 6.46–6.56 (m, 3H), 3.75 (s, 3H), 3.62 (br s, 4H), 2.62 (br s, 4H), 2.28 (s, 3H). MS (ES) [m+H]/z calc'd 455, found 455; [m−H]/z calc'd 453, found 453.

Example 25(e)

3-imidazol-2-yl-6-(2-methoxy-4-hydroxyphenyl)-1H-indazole

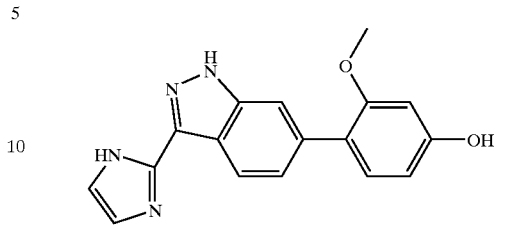

Example 25(e) was prepared in a similar manner to that described for Example 25(a), except 6-[5-methoxy-2-methyl-4-(2-trimethylsilanyl-ethoxymethoxy)-phenyl]-1-(2-trimethylsilanyl-ethoxymethyl)-3-imidazol-2-yl-1H-indazole was used instead of 6-[5-methoxy-2-methyl-4-(2-trimethylsilanyl-ethoxymethoxy)-phenyl]-1-(2-trimethylsilanyl-ethoxymethyl)-3-[3-(2-trimethylsilanyl-ethoxymethyl)-3H-imidazo[4,5-c]pyridin-2-yl]-1H-indazole. $^1$H NMR (300 MHz, DMSO-d$_6$) δ 13.10 (s, 1H), 12.59 (s, 1H), 9.56 (s, 1H), 8.27 (d, 1H, J=8.4 Hz), 7.53 (s, 1H), 7.25 (dd, 1H, J=8.4, 1.2 Hz), 7.13–7.20 (m, 3H), 6.54 (d, 1H, J=2.1 Hz), 6.47 (dd, 1H, J=8.4, 2.1 Hz), 3.73 (s, 3H). MS (ES) [m+H]/z calc'd 307, found 307.

The starting material was prepared as follows:

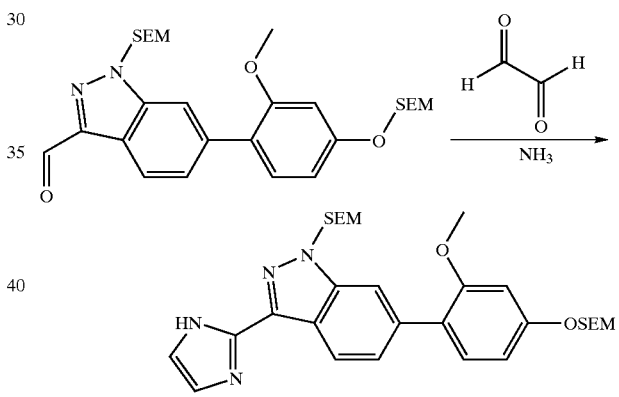

Glyoxal (40 wt % in H$_2$O, 0.4 mL, 3.5 mmol) was added dropwise to a solution of 420 mg (0.8 mmol) 6-[2-methoxy(2-trimethylsilanyl-ethoxymethoxy)phenyl]-1-2-trimethylsilanyl-ethoxymethyl)1H-indazole-3-carbaldehyde, from Example 25(a) step (iii), and 28% aqueous ammonia (0.6 mL) in THF (8 mL)/MeOH (8 mL), and the solution was stirred at r.t. for 16 h. The reaction was concentrated in vacuo and dissolved in CHCl$_3$ (50 mL). Organics were washed with H$_2$O and brine (25 mL each), dried (Na$_2$SO$_4$) and concentrated in vacuo. Purification by silica gel chromatography (40% EtOAc/hexanes) gave 120 mg (27%) of 6-[5-methoxy-2-methyl-4-(2-trimethylsilanyl-ethoxymethoxy)-phenyl]-1-(2-trimethylsilanyl-ethoxymethyl)-3-imidazol-2-yl-1H-indazole as a clear oil. $^1$H NMR (300 MHz, CDCl$_3$) δ 10.03 (s, 1H), 8.48 (d, 1H, J=8.4 Hz), 7.65 (s, 1H), 7.46 (dd, 1H, J=8.4, 1.5 Hz), 7.29–7.48 (m, 2H), 7.13 (d, 1H, J=1.5 Hz), 6.73–6.78 (m, 2H), 5.73 (s, 2H), 5.28 (s, 2H), 3.78–3.86 (m, 5H), 3.60 (t, 2H, J=8.4 Hz), 0.88–1.03 (m, 4H), 0.03 (s, 9H), −0.05 (s, 9H).

Example 25(f)

3-[4-(2-hydroxyethylsulfanyl)-1H-benzoimidazol-2-yl]-6-(2-methoxy-4-hydroxyphenyl)-1H-indazole

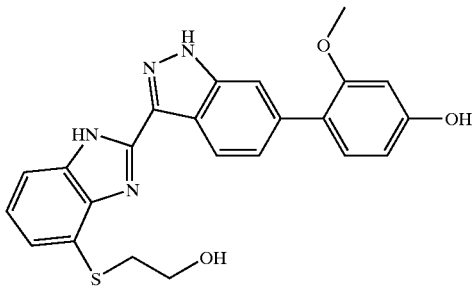

Example 25(f) was prepared in a similar manner to that described for Example 25(a), except that 2-(2,3-diaminophenylsulfanyl)-ethanol) was used instead of 3,4-diaminopyridine in step (iv). $^1$H NMR (300 MHz, DMSO-d$_6$) δ 13.51 (s, 1H), 13.02 (s, 1H), 9.59 (s, 1H), 8.45 (d, 1H, J=8.4 Hz), 7.61 (s, 1H), 7.32–7.40 (m, 2H), 7.11–7.23 (m, 3H), 6.55 (d, 1H, J=2.4 Hz), 6.48 (dd, 1H, J=8.1, 2.4 Hz), 4.96 (br s, 1H), 3.75 (s, 3H), 3.65 (br s, 2H), 3.33 (t, 2H, J=6.9 Hz). MS (ES) [m+Na]/z calc'd 455, found 455, [m–H]/z calc'd 431, found 431.

The starting material was prepared as follows:

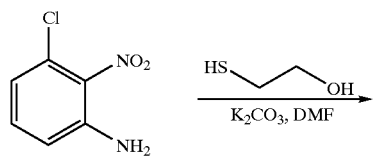

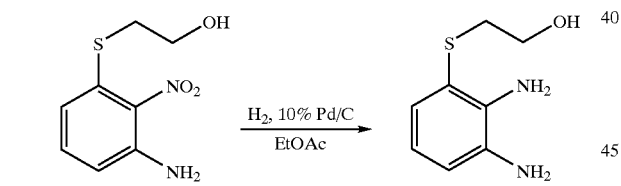

2-(3-Amino-2-nitro-phenylsulfanyl)ethanol. 3-Chloro-2-nitro-aniline (1.12 g, 6.5 mmol), 2-mercaptoethanol (0.60 ml, 8.6 mmol), and potassium carbonate (0.99 g, 7.1 mmol) were combined in dry DMF (15 ml) and stirred at 130° C. for 4 h. The solution was allowed to cool and was concentrated in vacuo. Purification by silica gel chromatography (70% EtOAc/hexanes) gave 1.29 g (93%) of 23-amino-2-nitro phenylsulfanyl)-ethanol as a bright red solid. $^1$H NMR (300 MHz, DMSO-d$_6$) δ 7.20 (t, 1H, J=8.1 Hz), 6.80 (s, 2H), 6.73 (dd, 1H, J=8.4, 0.9 Hz), 6.63 (dd, 1H, J=7.8, 1.2 Hz), 4.92 (t, 1H, J=6.0 Hz), 3.58 (q, 2H, J=6.0 Hz), 2.98 (t, 2H, J=6.0 Hz).

2-(2,3-Diamino-phenysulfanyl)-ethanol. 2-(3-Amino-2-nitrophenylsulfanyl) ethanol (1.02 g, 4.8 mmol) was reduced by hydrogenation using 45 psi of H$_2$ with 10% Pd-C (180 mg) in EtOAc (25 mL) for 6 h. After filtering through Celite, solvent was removed in vacuo. Purification by silica gel chromatography (EtOAc) gave 762 mg (87%) of 22,3-diamino-phenylsulfanyl)ethanol as a faintly yellow solid. $^1$H NMR (300 MHz, CDCl$_3$) δ 6.98 (dd, 1H, J=7.5, 1.5 Hz), 6.606.72 (m, 2H), 3.65 (t, 2H, J=5.7 Hz), 355 (br s, 5H), 2.91 (t, 2H, J=5.7 Hz). Example 25(g); 3-(5-methylcarbamoyl-1H-benzoimidazol-2-yl)-6-(2-methoxy-4 hydroxyphenyl)-1H-indazole

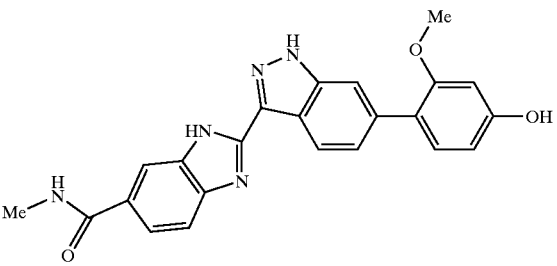

Example 25(g) was prepared in a similar manner to that described for Example 25(a), except 3,4-diamino-N-methyl-benzamide (Kumar, et. al. *J. Med. Chem*, 27, 1083–89 (1984)) was used instead of 3,4-diaminopyridine in step (iv). $^1$H NMR (300 MHz, DMSO-d$_6$) δ 13.59 (s, 0.5H), 13.55 (s, 0.5H), 13.21 (s, 0.5H), 13.14 (s, 0.5H), 9.60 (s, 1H), 8.38–9.46 (m, 2H), 8.26 (s, 0.5H), 8.03 (s, 0.5H), 7.71–7.79 (m, 1.5H), 7.63 (s, 1H), 7.52 (d, 0.5H, J=8.4 Hz), 7.35–7.40 (m, 1H), 7.21 (d, 1H, J=2.1 Hz), 6.55 (d, 1H, J=2.4 Hz), 6.49 (dd, 1H, J=8.4, 2.4 Hz), 3.75 (s, 3H), 2.82 (d, 1.5H, J=1.5 Hz). 2.81 (d, 1.5H, J=1.5 Hz). MS (ES) [m+H]/z calc'd 414, found 414, [m–H]/z calc'd 412, found 412.

Example 25(h)

3-(5-Dimethylamino-1H-benzoimidazol-2-yl)-6-(2-methoxy-4-hydroxy-phenyl)-1H-indazole

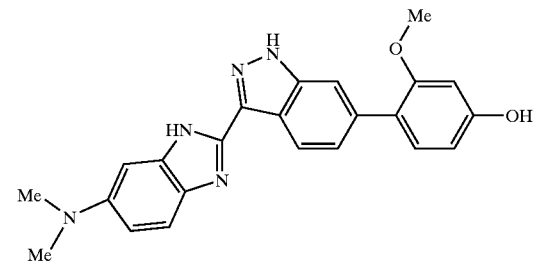

Example 25 (h) was prepared in a similar manner to that described for Example 25(a), except 3,4-diamino-N,N-dimethyl-aniline (Cazaux, et. al., *Can. J. Chem.*, 71, 1236–46 (1993)) was used instead of 3,4-diaminopyridine in step (iv). $^1$H NMR (300 MHz, DMSO-d$_6$) δ 13.36 (s, 1H), 12.51 (br s, 1H), 9.58 (s, 1H), 8.42 (d, 1H, J=8.4 Hz), 7.59 (s, 1H), 7.49 (br s, 1H), 7.33 (dd, 1H, J=8.4, 1.2 Hz), 7.20 (d, 1H, J=8.1 Hz), 6.87 (br d, 2H, J=8.1 Hz), 6.55 (d, 1H, J=2.1 Hz), 6.48 (dd, 1H, J=8.1, 2.1 Hz), 3.73 (s, 3H), 2.92 (s, 6H). MS (ES) [m+H]/z calc'd 400, found 400, [m–H]/z calc'd 398, found 398.

Example 25(i)

3-(5-Aminosulfonyl-1H-benzoimidazol-2-yl)-6-(2-methoxy-4-hydroxy-phenyl)-1H-indazole

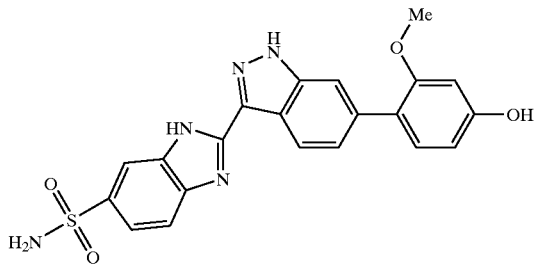

Example 25(i) was prepared in a similar manner to that described for Example 25(a), except 3,4-diaminobenzenesulfonamide was used instead of 3,4-diaminopyridine in step (iv). $^1$H NMR (300 MHz, DMSO-$d_6$) δ 13.67 (s, 0.5H), 13.64 (s, 0.5H), 13.39 (s, 0.5H), 13.35 (s, 0.5H), 9.60 (s, 1H), 8.43 (d, 1H, J=8.1 Hz), 8.18 (d, 0.5H, J=1.5 Hz), 7.99 (d, 0.5H, J=1.5 Hz), 7.86 (d, 0.5H, J=8.4 Hz), 7.62–7.72 (m, 2.5H), 7.29 (d, 1H, J=8.4 Hz), 7.20–7.28 (m, 3H), 6.55 (d, 1H. J=2.1 Hz), 6.49 (dd, 1H, J=8.4, 2.1 Hz), 3.75 (s, 3H). MS (ES) [m+H]/z calc'd 436, found 436, [m−H]/z calc'd 434, found 434.

Example 25(i)

3-(4-methylcarbamoyl-1H-benzolmidazol-2-yl)-6-(2-methoxy-4-hydroxy-phenyl)-1H-indazole

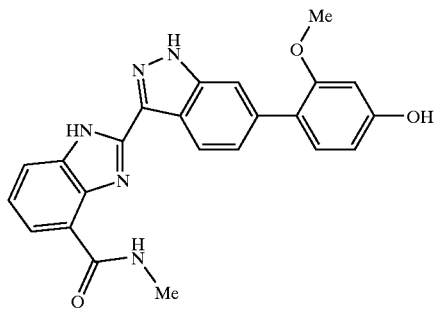

Example 25(i) was prepared in a similar manner to that described for Example 25(a), 2,3-diamino-N-methyl-benzamide was used instead of 3,4-diaminopyridine in step (iv). $^1$H NMR (300 MHz, DMSO-$d_6$)δ 13.71 (s, 1H), 13.46 (s, 1H), 9.85 (br d, 1H, J=4.8 Hz), 9.61 (s, 1H), 8.38 (d, 1H, J=8.4 Hz), 7.89 (dd, 1H, J=7.5, 1.2 Hz), 7.66–7.72 (m, 2H), 7.47 (dd, 1H, J=8.4, 1.2 Hz), 7.36(t, 1H, J=7.8 Hz), 7.23 (d, 1H, J=8.1 Hz), 6.56 (d, 1H, J=2.4 Hz), 6.50 (dd, 1H, J=8.4, 2.4 Hz), 3.76 (s, 3H), 3.10 (d, 3H, J=1.8 Hz). MS (ES) [m+H]l/z calc'd 414, found 414, [m−H]/z calc'd 412, found 412.

2,3-Diamino-N-methyl-benzamide was prepared as follows:

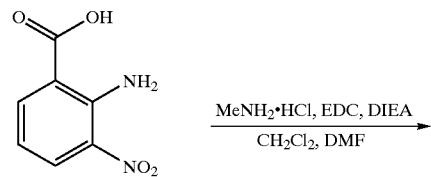

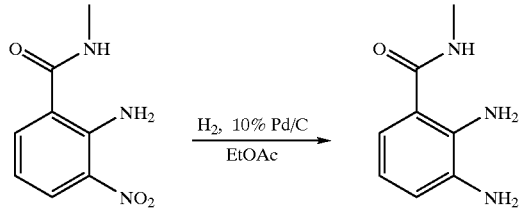

2-Amino-N-methyl-3-nitro-benzamide. 2-Amino-3-nitro-benzoic acid (1.8 g, 9.9 mmol) and methylamine hydrochloride (1.33 g, 19.8 mmol), were stirred in dry $CH_2CO_2$ (30 ml)/DMF (5 mL) at 0° C. EDC (2.83 g, 14.8 mmol) and DIEA (4.92 mL 27.7 mmol) were added, and the solution stirred 3 h while warming to r.t. The reaction was concentrated in vacuo and purified by silica gel chromatography (8% MeOH/CHCl$_3$) to give 1.42 g (74%) of 2-amino-N-methyl-3-nitro-benzamide as a yellow solid. $^1$H NMR (300 MHz, DMSO-$d_6$) δ 8.58 (br s, 1H), 8.23 (br s, 2H), 8.15 (dd, 1H, J=8.1, 1.8 Hz), 7.82 (dd, 1H, J=8.1, 1.8 Hz), 6.68 (t, 1H, J=8.1 Hz), 2.76 (d, 3H, J=4.5 Hz).

2,3-Diamino-N-methyl-benzamide. 2-Amino-N-methyl-3-nitro-benzamide (1.4 g, 7.2 mmol) was reduced by hydrogenation using 50 psi of $H_2$ with 10% Pd-C (250 mg) in EtOAc (25 mL) for 5 h. After filtering through Celite, solvent was removed in vacuo. Purification by silica gel chromatography (10% MeOH/CHCl$_3$) gave 1.08 mg (91%) of 2,3-diamino-N-methyl-benzamide as a faintly yellow solid. $^1$H NMR (300 MHz, CDCl$_3$) δ 6.87 (dd, 1H, J=7.8, 1.5 Hz), 6.76 (dd, 1H, J=7.8, 1.5 Hz), 6.59 (t, 1H, J=7.8 Hz), 6.14 (br s, 1H), 4.28 (br s, 4H), 2.95 (d, 3H, J=5.1 Hz).

Example 26

6-(4-Hydroxy-3-methoxyphenyl)-3-[E-2-(4-glycylamino-phenyl)-ethenyl]-1H-indazole

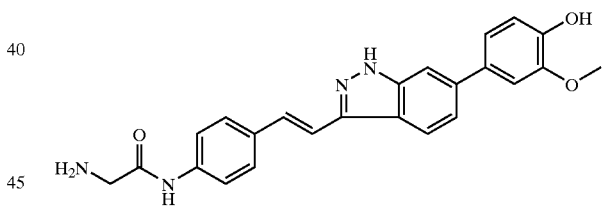

Example 26 was prepared from the starting material described below in a similar manner to that described for Example 1(a): $^1$H N (300 MHz, CDCl$_3$) δ 8.29 (d, 1H), 7.80 (m, 5H), 7.58 (m, 3H), 7.38 (s, H), 7.27 (d, 1H), 7.01 (d, 1H), 4.00 (s, 3H), 3.42 (s, 2H); LCMS (100% area) Rt=3.44 min, (pos) [M+H]/z Calc'd 415.1, found 415.2.

The starting material was prepared as follows:

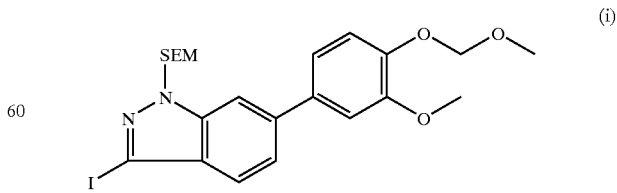

(i)

3-Iodo-6-(3-methoxy-4-methoxymethoxy-phenyl 1-[2-(trimethyl-silanyl) ethoxymethyl]-1H-indazole was prepared from the compound prepared in Example 1(a), step (v)

in a similar manner to that described for Example 10, step (ii): R$_f$ sm 0.11, p 0.43 (ethyl acetate-hexane 3:7); $^1$H NMR (300 MHz, CDCl$_3$) δ 7.71 (s, 1H), 7.55 (m, 2H), 7.33 (m, 1H), 7.20 (m, 2H), 5.82 (s, 2H), 5.33 (s, 2H), 4.02 (s, 3H), 3.64 (t, 2H), 3.59 (s, 3H), 0.95 (t, 2H), −0.03 (s, 9H).

(ii)

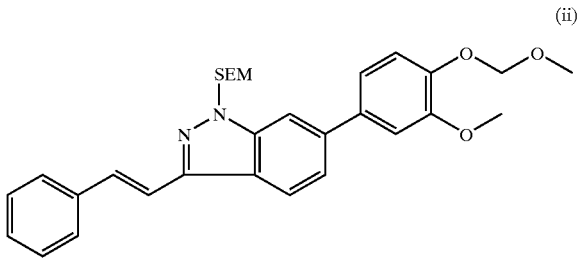

3-Styryl-6-(3-methoxy-4-methoxymethoxy-phenyl)-1-[2-(trimethyl-silanyl)-ethoxymethyl]-1H-indazole was prepared in a similar manner to that described for Example 11, step (iii): R$_f$ sm 0.41, p 0.35 (ethyl acetate-hexane 2:8); $^1$H NMR (300 MHz, CDCl$_3$) δ 8.12 (d, 1H), 7.73 (s, 1H), 7.62 (m, 2H), 7.51 (m, 2h), 7.46 (m, 2H), 7.38 (m, 1H), 7.30 (m, 4H), 5.85 (s, 2H), 5.38 (s, 2H), 4.03 (s, 3H), 3.70 (t, 2H), 3.62 (s, 3H), 0.98 (t, 2H), −0.02 (s, 9H).

(iii)

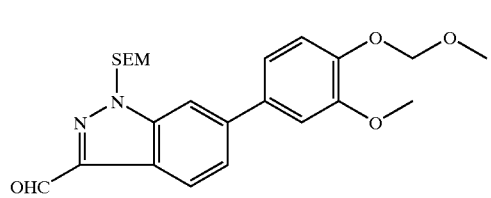

3-Carboxaldehyde-6-(3-methoxy-4-methoxymethoxy-phenyl)-1-[2-(trimethyl-silanyl)-ethoxymethyl]-1H-indazole was prepared in a similar manner to that described for Example 33(a), step (i): $^1$H NMR (300 MHz, CDCl$_3$) δ 10.33 (s, 1H), 8.34 (d, 1H), 7.82 (s, 1H), 7.65 (d, 1H), 7.25 (m, 3H), 5.90 (s, 2H), 5.36 (s, 2H), 4.02 (s; 3H), 3.67 (t, 2H), 3.51 (s, 3H), 0.98 (t, 2H), −0.02 (s, 9H).

(iv)

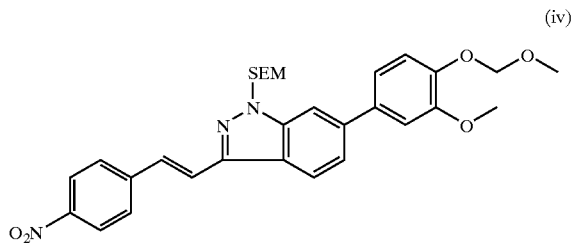

3-(4-Nitrostyryl)-6-(3-methoxy-4-methoxymethoxy-phenyl)-1-[2-(trimethyl-silanyl ethoxymethyl]-1H-indazole was prepared in a similar manner to that described for Example 33(a), step (ii) except that 4-nitrobenzyltriphenylphosphonium bromide and lithium hexamethyldisilazide were used instead of 2-picolyltriphenylphosphonium chloride-potassium hydride: LCMS (100% area) Rt=6.89 min, (pos) [M+H]/z Calc'd 562.4, found 562.4.

(v)

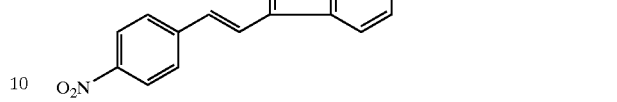

3-(4-Nitrostyryl)-6-(3-methoxy-4-methoxymethoxy-phenyl)-1H-indazole was prepared in a similar manner to that described for Example 11: FTIR (thin film) 3335, 3178, 2954, 1592, 1512, 1338, 1257, 1136, 1257, 1136, 987 cm$^{-1}$; $^1$H NMR (300 MHz, CDCl$_3$) δ 8.22 (d, 2H, J=8.8 Hz), 8.02 (d, 1H, J=8.5 Hz), 7.70 (d, 2H, J=8.8 Hz), 7.58 (m, 3H), 7.45 (dd, 1H, J=1.3, 8.5 Hz), 7.20 (m, 4H), 7.26 (s, 2H), 3.95 (s, 3H), 3.53 (s, 3H); LCMS (100% area) Rt=5.13 min, (pos) (M+H]/z Calc'd 432.1, found 432.1.

(vi)

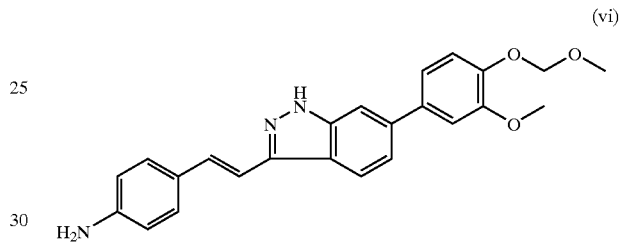

3-(4-aminostyryl)-6-(3-methoxy-4-methoxymethoxy-phenyl)-1H-indazole was prepared in a similar manner to that described for Example 11, step (iv): R$_f$ sm 0.39, p 0.26 (ethyl acetate-hexane 6:4); FTIR (thin film) 3366, 3210, 2954, 1608, 1517, 1465, 1412, 1259, 1157, 1077, 989, 912 cm$^{-1}$; $^1$H NMR (300 MHz, CDCl$_3$) δ 8.11 (d, 1H), 7.63 (s, 1H), 7.50–7.15 (m, 8H), 6.71 (d, 2H), 5.36 (s, 2H), 3.97 (s, 3H), 3.61 (s, 3H); LCMS (100% area) Rt=4.40 min, (pos) [M+H]/z Calc'd 402.2, found 402.2.

(vii)

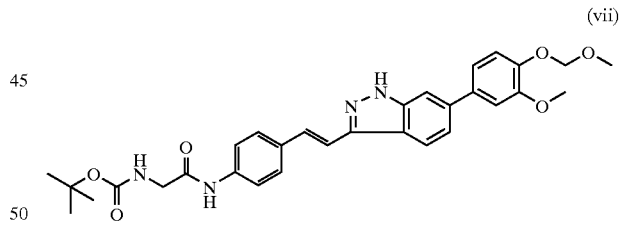

3-(4-aminostyryl)-4-(3-methoxy-4-methoxymethoxy-phenyl) 1H-indazole (90 mg, 0.224 mmol) was dissolved in dichloromethane (2 mL) and was treated with Boc-glycine (196 mg, 1.12 mmol, 5 equiv), DMAP (82 mg, 3 equiv) and HATU (426 mg, 5 equiv). The mixture was allowed to stir for 30 min. The mixture was partitioned between ethyl acetate and water. The organic material was concentrated, taken up in methanol (5 mL) and was treated with potassium carbonate (100 mg). The mixture was heated to 50° C. for 3 d. The resulting mix was again partitioned between ethyl acetate and water. The organic material was concentrated, and purified by silica (109 mg, 66%): R$_f$ sm 0.32, p 0.46 (ethyl acetate-hexane 6:4); $^1$H NMR (300 MHz, CDCl$_3$) δ 8.18 (bs, 1H), 8.03 (d, 1H, J=8.1 Hz), 7.56 (m, 5H), 7.40 (m, 3H), 7.20 (m, 3H), 5.29 (s, 2H), 5.20 (bs, 1H), 3.98 (s, 3H), 3.96 (d, 2H), 3.54 (s, 3H), 1.48 (s, 9H).

Example 27(a)

6-phenyl-3-E-styryl-1H-indazole

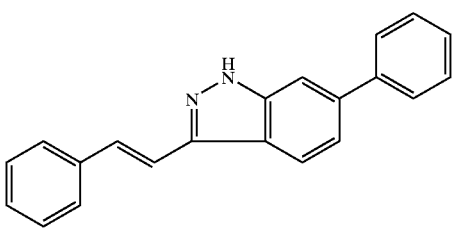

6-phenyl-3-styryl-11[2-(trimethyl-silanyl-ethoxymethyl]-1H-indazole (345 mg, 0.81 mmol) was treated with a solution of TBAF (16 ml of a 1 M solution in THF, 16 mmol), and ethylene diamine (0.53 ml, 8.1 mmol), and heated at 70° C. for 2 h. The solution was then poured into brine (200 ml), and extracted with ethyl acetate (3×30 ml). The organic layer was dried over $MgSO_4$, and concentrated under reduced pressure. Purification by silica gel chromatography gave 6-phenyl-3-E-styryl-1H-indazole as a white solid (80 mg, 34%): $^1$H N (300 MHz, $CDCl_3$) δ 8.10 (d, 1H, J=8.5 Hz); HRMS (FAB) [M+H]/z Calc'd 297.1392, found 297.1393. Anal. Calc'd, C (85.10), H (5.44), N (9.45). Found: C (85.10), H (5.46), N (9.43).

The starting material was prepared as follows:

(i)

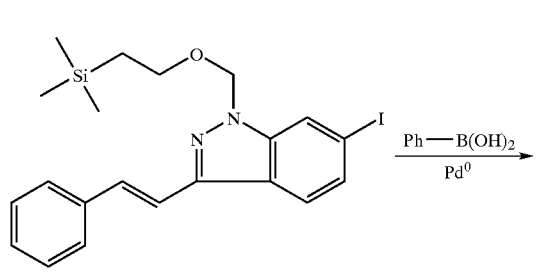

A solution of 476 mg (1.0 mmol) of 6-iodo-3-styryl-1-[2-(trimethyl-silanyl)ethoxymethyl]-1H— indazole, from Example 14 step (i), in dioxane (3 ml, degassed by sonication and bubbling argon), $Pd(PPh_3)_4$ (23 mg, 0.05 mmol), phenylboronic acid (302 mg, 2.5 mmol), and $Na_2CO_3$ (1.25 ml of a 2M aqueous solution, degassed as above) was heated at 90° C. for 2 h. The solution was then diluted with ethyl acetate (100 ml) and washed with brine (2×20 ml). The organic layer was dried over $MgSO_4$, and concentrated under reduced pressure. Purification by silica gel chromatography gave of 6-phenyl-3-styryl-1-[2-(trimethyl-silanyl) ethoxymethyl]-1H— indazole as a brown oil (345 mg, 81%). $^1$H NMR (300 MHz, $CDCl_3$) δ 8.09 (dd, 1H, J=8.5, 0.7 Hz), 7.75 (s, 1H), 7.70 (d, 1H, J=7.0 Hz), 7.647.58 (m. 2H), 7.56–7.51 (m, 2H), 7.50–7.45 (m, 2H), 7.45–7.36 (m, 4H), 7.34–7.27 (m, 1H), 5.80 (s, 2H), 3.73 (t, 2H, J=8.3 Hz), 1.12 (t, 2H, J=8.3 Hz).

Example 27(b)

6-(3-methoxyphenyl)-3-E-styryl-1H-indazole

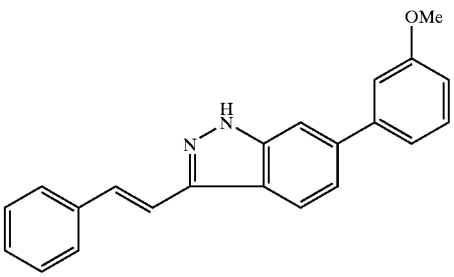

Example 27(b) was prepared in a similar manner to that described for Example 27(a), except that 3-methoxyphenylboronic acid was used instead of phenylboronic acid in step (i). $^1$H NMR (300 MHz, MeOH-$d_4$) δ 8.16 (d, 1H, J=8.4 Hz), 7.70 (s, 1H), 7.67–7.61 (m, 2H), 7.60–7.43 (m, 3H), 7.43–7.33 (m, 3H), 7.32–7.21 (m, 3H), 6.99–6.92 (m, 1H), 3.88 (s, 3H). HRMS (FAB) [M+Na]/z Calc'd 349.1317, found 349.1342. Analyzed with 0.1$H_2O$ Calc'd, C (80.50), H (5.59), N (855). Found: C (80.44), H (5.49), N (8.55).

Example 27(c)

6-(4-methoxyphenyl)-3-E-styryl-1H-indazole

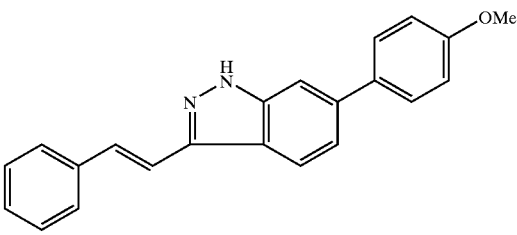

Example 27(b) was prepared in a similar manner to that described for Example 27(a), except that 4-methoxyphenylboronic acid was used instead of phenylboronic acid in step (i). $^1$H NMR (300 MHz, DMSO-$d_6$) δ 13.20 (s, 1H), 8.23 (d, 1H, J=8.4 Hz), 7.767.64 (m, 5H), 7.54 (s, 1H), 7.50–7.37 (m, 3H), 7.33–7.25 (m, 1H), 7.07 (d, 2H, J=8.8 Hz), 3.82 (s, 3H)HRMS (FAB) [M+H]/z Calc'd 327.1497, found 327.1502. Anal. Calc'd, C (80.96), H (5.56), N (8.58). Found: C (80.71), H (5.42), N (8.47).

Example 27(d)

6-naphth-1-yl-3-E-styryl-1H-indazole

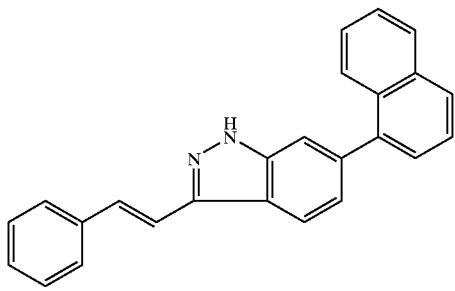

Example 27(d) was prepared in a similar manner to that described for Example 27(a), except that 1-naphthaleneboronic acid was used instead of phenylboronic acid in step (i) $^1$H NMR (300 MHz, DMSO-$d_6$) δ 10.11 (s, 1H), 8.45 (d, 1H. J=8.41), 7.97–7.87 (m, 3H), 7.66–7.37 (m, 13H), 7.35–7.28 (m, 1H). HRMS (FAB) [M+Na]/z Calc'd 369.1368, found 369.1359. Anal. Calc'd C (86.68), H (5.32), N (8.19). Found: C (86.52), H (5.32), N (8.19).

Example 27(e)

6-pyridin-3-yl-3-E-styryl-1H-indazole

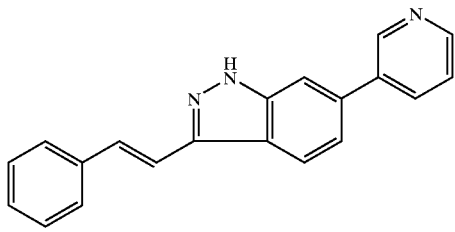

Example 27(e) was prepared in a similar manner to that described for Example 27(a), except that 3-pyridineboronic acid was used instead of phenylboronic acid in step (i). $^1$H NMR (300 MHz, MeOH-$d_4$) δ 8.97 (s, 1H), 8.63 (d, 1H, J=4.8 Hz), 8.30 (d, 1H, H=8.5 Hz), 8.27 (d, 1H, J=8.1 Hz), 7.86 (s, 1H), 7.72 (d, 2H, J=7.5 Hz), 7.69–7.56 (m, 4H), 7.54–7.42 (m, 2H), 7.40–7.32 (m, 1H). HRMS (FAB) [M+H]/z Calc'd 298.1344, found 298.1356. Analyzed with 0.25H$_2$O Calc'd, C (79.58), H (5.18), N (13.92). Found: C (79.53), H (5.16), N (13.80).

Example 27(f)

6-pyridin-4-yl-3-E-styryl-1H-indazole

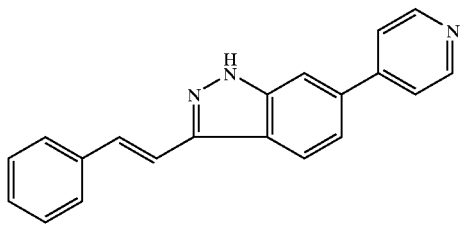

Example 27(f) was prepared in a similar manner to that described for Example 27(a), except that 4-pyridineboronic acid was used instead of phenylboronic acid in step (i). $^1$H NMR (300 MHz, MeOH-$d_4$) δ 8.69 (bs, 2H), 8.30 (d, 1H, J=8.5 Hz), 7.96 (s, 1H), 7.87 (d, 2H, H=5.6 Hz), 7.75–7.68 (m, 3H), 7.68–7.50 (m, 2H), 7.50–7.42 (m, 2H), 7.40–7.31 (m, 1H). HRMS (FAB) [M+H]/z Calc'd 298.1344, found 298.1357. Analyzed with 0.3H$_2$O Calc'd, C (79.34), H (5.19), N (13.88). Found: C (79.14), H (5.08), N (13.84).

Example 27(g)

6-indol-4-yl-3-E-styryl-1H-indazole

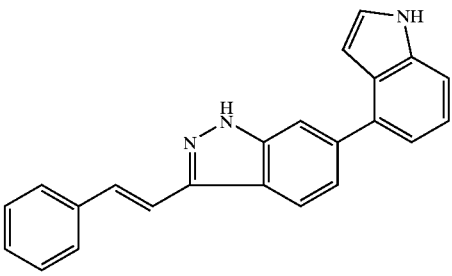

Example 27(g) was prepared in a similar manner to that described for Example 27(a), except that 4-indoleboronic acid was used instead of phenylboronic acid in step (i). $^1$H NMR (300 MHz, MeOH-$d_4$) δ 8.25 (d, 1H, J=8.5 Hz), 7.85 (s, 1H), 7.75–7.67 (m, 3H), 7.67–7.52 (m, 2H), 7.52–7.42 (m, 3H), 7.39–7.22 (m, 4H), 6.72 (d, 1H, J=3.2 Hz). HRMS (FAB) [M+H]/z Calc'd 336.1501, found 336.1506. Analyzed with 0.3H$_2$O Calc'd, C (78.97), H (5.36), N (12.01). Found: C (78.95), H (5.20), N (12.03).

Example 27(h)

6-[3-ethoxy-4-hydroxyphenyl]-3-E-styryl-1H-indazole

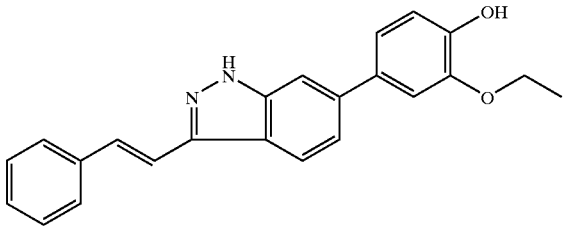

Example 27(h) was prepared in a similar manner to that described for Example 27(a), except that 3-ethoxy-4 -(2-trimethylsilanyl-ethoxymethoxy)benzene boronic acid was used instead of phenylboronic acid in step (i). $^1$H NMR (300 MHz, CDCl$_3$) δ 8.10 (d, 1H, J=8.7 Hz), 7.74 (s, 1H), 7.74–7.16 (m, 10H), 7.07 (d, 1H, J=8.15 Hz), 4.27 (q, 2H, J=14.0 Hz), 1.54 (t, 3H, J=14.0 Hz). HRMS (FAB) [M+H]/z Calc'd 357.1603, found 357.1611. Analyzed with 0.2H$_2$O, Calc'd, C (76.73), H (5.71), N (7.78). Found: C (76.72), H (5.91), N (7.63).

Starting material was prepared as follows:

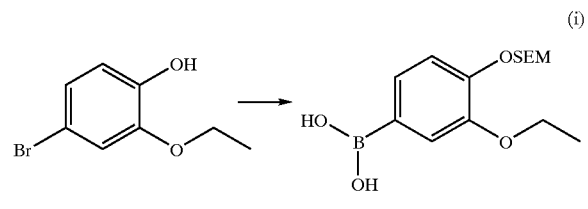

4-Bromo-2-ethoxy-phenol (Smith et al., Soc. Pl., 1877–78 (1992)) was converted to 3-ethoxy-4-(2-trimethylsilanyl-ethoxymethoxy)-benzene boronic acid in a manner similar to that described for Example 24(a) steps (vi)–(vii). $^1$H NMR (300 MHz, CDCl$_3$) δ 7.82 (d, 1H, J=8.0 Hz), 7.72 (s, 1H), 7.31 (d, 1H, J=8.1 Hz), 5.37 (s, 2H), 4.29 (q, 2H, J=14.0 Hz), 3.87 (t, 2H, J=16.8 Hz), 1.54 (t, 2H, J=14.0 Hz), 0.99 (t, 2H, J=16.8 Hz), 0.03 (s, 9H).

Example 27(i)

6-[3-(2-hydroxyethoxy)-4-hydroxyphenyl]-3-E-styryl-1H-indazole

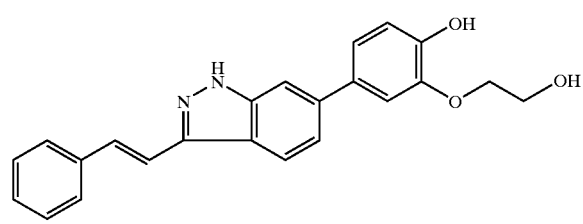

Example 27(i) was prepared in a similar manner to that described for Example 27(a), except that 3-[2-(trimethylsilanyl-ethoxymethoxy)ethoxy](2-trimethylsilanyl-ethoxymethoxy)-benzene boronic acid, prepared from 2-(2-hydroxy-ethoxy)-phenol (Yamaguchi et al., Bull. Chem. Soc. Jpn., 61, 2047–54 (1988)) in a similar manner to that described in Example 24(c) steps (i)–(iii) and was used instead of phenylboronic acid in step (i). $^1$H NMR (300 MHz, DMSO-d$_6$) δ 8.17 (d, 1H, J=8.7 Hz), 7.73–7.17 (m, 1H), 6.92 (d, 1H. 1=8.2 Hz), 4.13 (t, 2H, J=9.7 Hz), 3.8 (t, 2H, 1=9.7 Hz). HRMS (FAB) [M+H]/z Calc'd 373.1552, found 373.1563. Analyzed with 0.05 trifluoroacetic acid, Calc'd, C (73.37), H (5.35), N (7.41). Found: C (73.11), H (5.33), N (7.39).

Example 27(j)

6-(3,4-dimethoxyphenyl)-3-E-styryl-1H-indazole

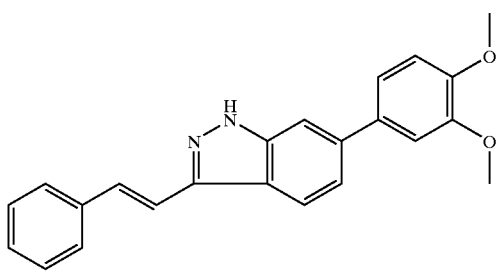

Example 27(j) was prepared in a similar manner to that described for Example 27(a), except that 3,4-dimethoxyphenylboronic acid was used instead of phenylboronic acid in step (i). $^1$H NMR (300 MHz, DMSO-d$_6$) δ 8.01 (d, 1H, J=8.1 Hz), 7.51–7.05 (m, 1H), 6.86 (d, 1H, J-4.0 Hz) 3.58 (s, 3H), 3.65 (s, 3H). HRMS (FAB) [M+H]/z Calc'd 357.1598, found 357.1508. Analyzed with 0.2H$_2$O, Calc'd, C (76.73), H (5.71), N (7.78). Found: C (76.45), H (5.70), N (7.68).

Example 27(k)

6-(2-methoxypyridin-5-yl)-3-E-styryl-1H-indazole

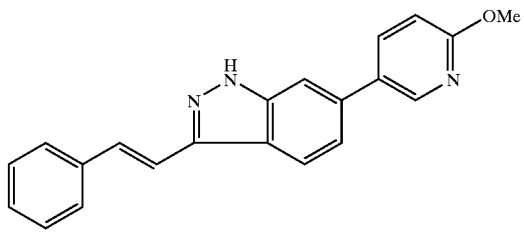

6-(22-methoxypyridin-5-yl)-3-(((E)-styryl)-1-(2-trimethylsilanyl-ethoxymethyl)-1H-indazole was converted to 6-(2-methoxypyridin-5-yl)-3-E-styryl-1H-indazole in a similar manner to that described for Example 27(a). $^1$H NMR (300 MHz, CDCl$_3$) □8.53 (d, 1H, J=2.1 Hz), 8.15 (d, 1H, J-9.2 Hz), 7.97 (dd, 1H, 1=2.6, 8.6 Hz), 7.79 (s, 1H), 7.74–7.34 (m, 8H), 6.94 (d, 1H, J=8.6 Hz). HRMS (FAB) [M+H]/z Calc'd 328.1450, found 328.1462. Anal. Calc'd, C (77.04), H (5.23), N (12.83). Found: C (77.00), H (5.28), N (12.65).

The starting material was prepared as follows:

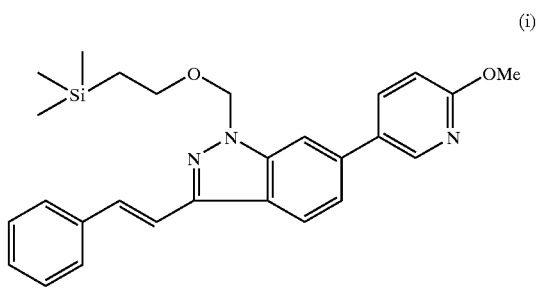

A solution of 5-bromo-2-methoxypyridine (2.00 g, 6.10 mmol), hexamethylditin (1.15 g, 6.10 mmol), and Pd(PPh$_3$)$_4$ (0.28 g, 0.24 mmol) in degassed dioxane (10 ml) was refluxed under for 16 h. 6-Iodo-3-((E)-styryl)-1-(2-trimethylsilanylthoxymethyl)-1H-indazole (2.90 g, 6.10 mmol) was added to above mixture, followed by Pd(PPh$_3$)$_4$ (0.35 g 0.31 mmol). The reaction mixture was refluxed for 16 h. The mixture was then diluted with ethyl acetate (150 ml), and washed with brine (30 ml). The organics were dried over MgSO$_4$, then concentrated under reduced pressure. Purification by silica gel chromatography gave 6-(2-methoxypyridin-5-yl)-3-((E)-styryl)-1-(2-trimethylsilanyl-ethoxymethyl)1H-indazole as a yellow solid (1.12 g, 40%). $^1$H NMR (300 MHz, CDCl$_3$) δ 8.51 (d, 1H, J=2.5 Hz), 8.50 (d, 1H, J=9.1 Hz), 7.93 (dd, 1H, J=2.5, 8.6 Hz), 7.69 (s, 1H), 7.69–7.28 (m, 8H), 6.89 (d, 1H, J=8.6 Hz), 5.83 (s, 2H), 4.03 (s, 3H), 3.64 (t, 2H, J=8.3 Hz), 0.93 (t, 2H, 1=8.3 Hz), –0.03 (s, 9H).

Example 28(a)

6-(3-hydroxyphenyl)-3-E-styryl-1H-indazole

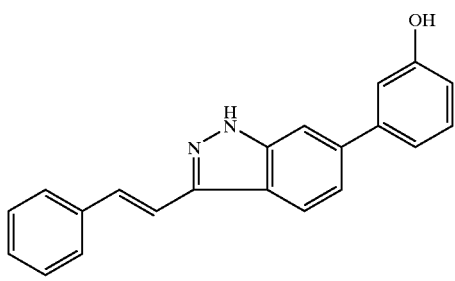

A solution of 100 mg (0.3 mmol) 63-methoxyphenyl)-3-E-styryl-1H-indazole, from Example 27(b), was cooled to −78° C. and treated with BBr$_3$ (1.8 ml of a 1M solution in CH$_2$Cl$_2$, 1.8 mmol). The resulting solution was held at −78° C. for 15 min, then warmed to 0° C., and held 3 h. A solution of saturated aqueous sodium bicarbonate was then added (10 ml), followed by ethyl acetate (50 ml). The organic layer was washed with brine (20 ml), then concentrated under reduced pressure. Purification by silica gel chromatography gave 6-(3-hydroxyphenyl)-3-E-styryl-1H-indazole as a white solid (55 mg, 59%). $^1$H NMR (300 MHz, MEOH-d$_4$) δ 8.16 (d, 1H, 1=8.5 Hz), 7.71–7.62 (m, 3H), 7.61–7.44 (m, 3H), 7.43–7.35 (m, 2H), 7.33–7.25 (m, 2H), 7.20–7.10 (m, 2H), 6.85–6.79 (m, 1H); δ 13.14 (s, 1H), 9.60 (s, 1H), 8.20 (d, 1H, 1=8.4 Hz), 7.73 (d, 2H, J=7.3), 7.64–7.52 (m, 5H), 7.47–7.37 (m, 3H), 7.33–7.25 (m, 1H), 6.89 (d, 2H, J=8.6 Hz).

Example 28(b)

6-(4-hydroxyphenyl)-3-E-styryl-1H-indazole

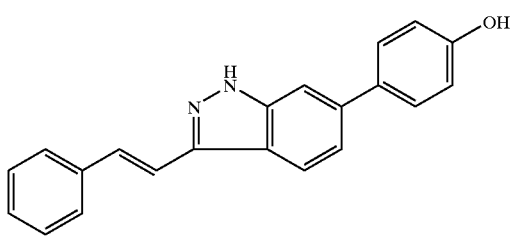

6-(4-methoxyphenyl)-3-E-styryl-1H-indazole, from Example 27(c), was converted to 6-(4-hydroxyphenyl)-3-E-styryl-1H-indazole in a similar manner to that described for Example 28(a). $^1$H NMR (300 MHz, DMSO-d$_6$) δ 13.14 (s, 1H), 9.60 (s, 1H), 8.20 (d, 1H, J=8.4 Hz), 7.73 (d, 2H, 3=7.3 Hz), 7.64–7.52 (m, 5H), 7.47–7.37 (m, 3H), 7.33–7.25 (m, 1H), 6.89 (d, 2H, J=8.6 Hz). HRMS (FAB) [M+Na]/z Calc'd 313.1341, found 313.1347. Analyzed with 0.5H$_2$O Calc'd, C (78.48), H (5.33), N (8.72). Found: C (78.35), H (5.26), N (8.49).

Example 28(c)

6-(2-hydroxypyridin-5-yl)-3-E-styryl-1H-indazole

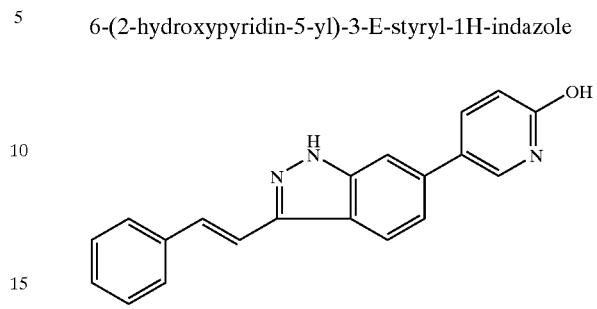

6-(2-Methoxypyridin-5-yl)-3-E-styryl-1H-indazole indazole, from Example 27(k), was converted to 6-(2-hydroxypyridin-5-yl)-3-E-styryl-1H-indazole in a similar manner to that described for Example 28(a). $^1$H NMR (300 MHz, DMSO-d$_6$) δ 8.22 (d, 1H, J=8.4 Hz), 7.96 (dd, 1H, J=2.6, 9.65 Hz), 7.81 (d, 1H, J=2.0 Hz), 7.74–7.30 (m, 9H), 6.50 (d, 1H, J=9.4 Hz). HRMS (FAB) [M+H]/z Calc'd 314.1293, found 314.1280. Analyzed with 0.1 trifluoroacetic acid, Calc'd, C (72.69), H (4.86), N (12.59). Found: C (72.77), H (4.81), N (12.65).

Example 28(d)

6-(3,4-dihydroxyphenyl)-3-E-styryl-1H-indazole

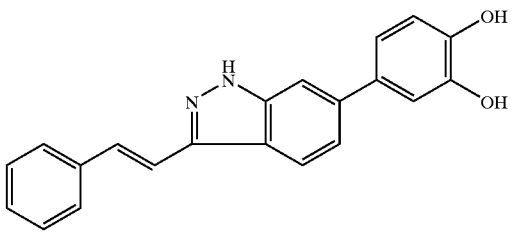

6-(3,4-Dimethoxyphenyl)-3-E-styryl-1H-indazole, from Example 27( ), was converted 6-(3,4-dihydroxyphenyl)-3-E-styryl-1H-indazole in a similar manner to that described for Example 28(a). $^1$H NMR (300 MHz, DMSO-d$_6$) δ 9.09 (br s, 1H), 9.07 (br s, 1H), 8.20 (d, 1H, J=85), 7.73 (d, 2H, J=7.5 Hz), 7.56 (d, 2H, J=10.1 Hz), 7.53 (s, 1H), 7.43–7.29 (m, 4H), 7.11 (s, 1H), 7.04 (d, 1H, J=8.2 Hz), 6.86 (d, 1H, J=8.2 Hz). HRMS (FAB) [M+H]/z Calc'd 329.1290, found 329.1274. Analyzed with 1.0H$_2$O, Calc'd, C (66.79), H (4.73), N (7.15). Found: C (66.54), H (4.56), N (7.36).

Example 29(a)

6-pyrid-4-yl-3-E-[2-(2,6-dichlorophenyl)ethenyl]-1H-indazole

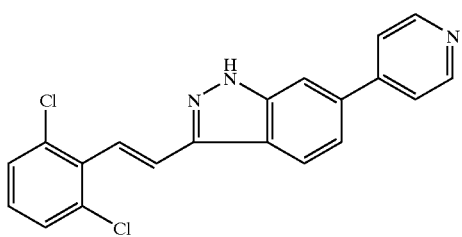

6-Pyrid-4-yl-3-E-[2-(2,6-dichlorophenyl)ethenyl]-1-(2-trimethylsilanyl-ethoxymethyl)-1H-indazole was converted to 6-pyrid-4-yl-3-E-[2-(2,6-dichlorophenyl)ethenyl]-1H-indazole in a similar manner to that described for Example 27(a). $^1$H NMR (300 MHz, CDCl$_3$) 513.55 (s, 1H), 8.68 (dd, 2H, J=4.6, 1.6 Hz), 8.21 (d, 1H, J=8.5 Hz), 7.96 (s, 1H), 7.81 (dd, 2H, J=4.5, 1.6 Hz), 7.66 (dd, 1H, J$_1$=8.5, 1.4 Hz), 7.58 (d, 2H, J=8.0 Hz), 7.51 (s, 2H), 7.39–7.32 (m, 1H). MS (FAB) [M+H]/z Calc'd 366, found 366. Analyzed with 0.7H$_2$O Calc'd, C (63.40), H (3.83), N (11.09). Found: C (63.63), H (3.75), N (10.83).

The starting material was prepared as follows:

(i)

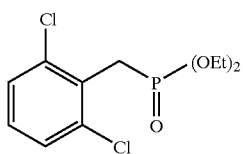

2,6-Dichlorobenzyl bromide (1.20 g, 5 mmol) was mixed with triethyl phosphite (1.66 g, 10 mmol) and heated at 150° C. for 2 h. The resulting mixture was then distilled at 160° C. under reduced pressure (10 mm Hg) to remove the excess triethyl phosphite. (2,6-Dichloro-benzyl)-phosphonic acid diethyl ester was obtained as a colorless liquid (1.46 g, 100%). $^1$H NMR (300 MHz, CDCl$_3$) δ 7.33–7.28 (m, 2H), 7.15–7.07 (m, 1H), 4.144.02 (m, 4H), 3.60 (d, 2H, J=22.4 Hz), 1.27 (t, 6H, J=7.0 Hz).

(ii)

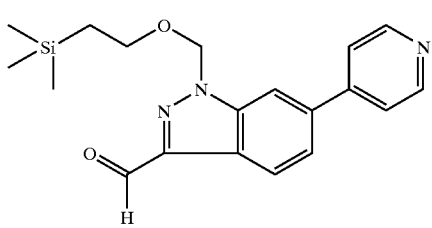

Ozone gas was bubbled through a solution of 6-pyrid-4-yl-3-E-styryl-1-(2-trimethylsilanyl-ethoxymethyl)-1H-indazole (2.13 g, 5.0 mmol) in THF (25 ml) and MeOH (25 ml) at −78° C. for 15 min. Argon was then bubbled through the solution for 10 min at −78° C. for 10 min, then dimethyl sulfide (1.46 ml, 20 mmol) was added. The solution was allowed to warm to rt, and held for 2 h. The solution was poured into brine (300 ml), then extracted with ethyl acetate (3×100 ml). The organics were dried over MgSO$_4$, then evaporated under reduced pressure. Purification by silica gel chromatography gave 6-pyridin-4-yl-1-(2-trimethylsilanyl-ethoxymethyl)-1H-indazole-3-carbaldehyde as a white solid (2.2 g, 75%). $^1$H NMR (300 MHz, CDCl$_3$) δ 10.39 (s, 1H), 8.75 (d, 2H, J=1.6 Hz), 8.45 (d, 1H, J=2.8 Hz), 7.91 (s, 1H), 7.75–7.66 (m, 3H), 5.90 (s, 2H), 3.63 (t, 2H, J=2.7 Hz), 0.93 (t, 2H, J=2.8 Hz), 0.00 (s, 9H).

(iii)

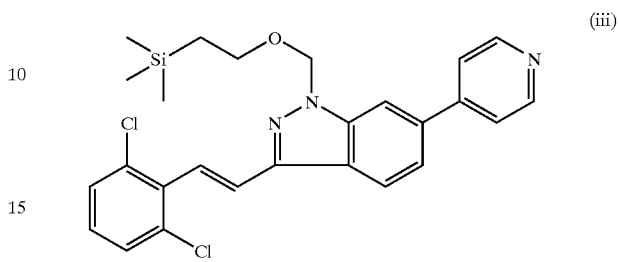

A solution of (2,6-dichlorobenzyl)phosphinic acid diethyl ester (582 mg, 2.0 mmol) in DMF (15 ml) was cooled to 0° C. and treated with NaH (160 mg of 60% in mineral oil, 4.0 mmol). The resulting solution was held at 0° C. for 30 min, then treated with 6 pyridin-4-yl-1-(2-trimethylsilanyl-ethoxymethyl)-1H-indazole-3-carbaldehyde (353 mg, 1.0 mmol). The resulting solution was allowed to warm to rt over 1 h, then held at rt 2 h. The solution was poured into brine (250 ml), then extracted with ethyl acetate (3×80 ml). The organics were dried over MgSO$_4$, then concentrated under reduced pressure. Purification by silica gel chromatography gave 6-pyrid-4-yl-3-E-[2-(2,6-dichlorophenyl)ethenyl]-1-(2-trimethylsilanyl-ethoxymethyl)-1H-indazole as a yellow oil (330 mg, 67%). $^1$H NMR (300 MHz, CDCl$_3$) δ 7.72 (dd, 2H, J=4.6, 1.5 Hz), 8.16 (d, 1H, J=8.5 Hz), 7.84 (s, 1H), 7.62 (ss, 2H, J=4.5, 1.6 Hz), 7.60 (s, 2H), 7.56 (dd, 1H, J=8.5, 1.5 Hz), 7.39 (d, 1H, J=8.1 Hz), 7.18–7.12 (m, 1H), 3.64 (t, 2H, J=8.3 Hz), 0.92 (t, 2H, J=8.3 Hz), 0.00 (s, 9H).

Example 29(b)

6-pyridyl-4-yl-3-E-[2-(3-methylphenyl)ethenyl]-1H-indazole

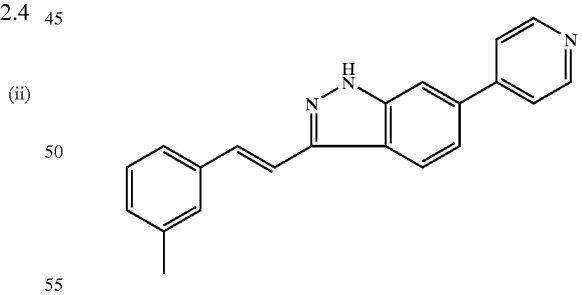

6-Pyridin-4-yl-1-(2-trimethylsilanyl-ethoxymethyl)-1H-indazole-3-carbaldehyde was converted to the desired product in a similar manner to that described for Example 29(a). $^1$H NMR (300 MHz, MeOH-d$_4$) 8.88 (d, 1H, J=6.7 Hz), 8.41–8.35 (m, 3H), 8.16 (s, 1H), 7.80 (dd, 1H, J=8.6, 1.6 Hz), 7.67–7.48 (m, 4H), 7.35 (t, 1H, J=7.6 Hz), 7.22–7.17 (m, 1H), 4.88 (s, 3H). MS (FAB) [M+H]/z Calc'd 312, found 312. Analyzed with 0.2H$_{20}$, 1.1 trifluoroacetic acid Calc'd, C (63.27), H (4.23), N (9.54). Found: C (63.08), H (4.18), N (9.80).

Example 29(c)

6-pyrid-4-yl-3-E-[2-(4-chlorophenyl)ethenyl]-1H-indazole

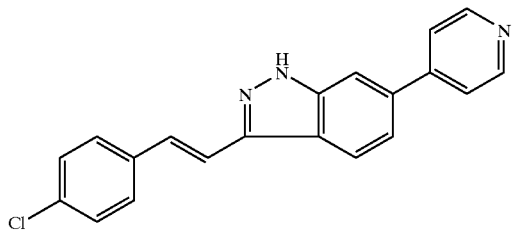

6-Pyridin-4-yl-1-(2-trimethylsilanyl-ethoxymethyl)-1H-indazole-3-carbaldehyde was converted to the desred product in a similar manner to that described for Example 29(a). $^1$H NMR (300 MHz, DMSO-d$_6$) δ 13.40 (s, 1H), 8.67 (dd, 2H, J=4.6, 1.6 Hz), 8.33 (d, 1H, J=8.5 Hz), 7.92 (s, 1H), 7.81 (dd, 2H, J=4.6, 1.6 Hz), 7.78 (d, 2H, J=8.5 Hz), 7.67–7.56 (m, 3H), 7.46 (d, 2H, J=8.5 Hz). Analyzed with 0.15H$_2$O, Calc'd, C (71.81), H (4.31), N (12.56). Found: C (71.85), H (4.26), N (12.48).

Example 29(d)

6-pyrid-4-yl-3-E-[2-(biphenyl-4-yl)ethenyl]-1H-indazole

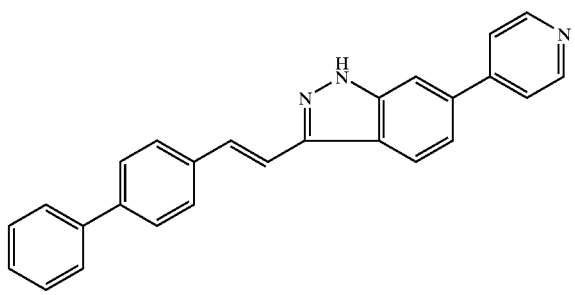

6-Pyridin-4-yl-1-(2-trimethylsilanyl-ethoxymethyl)-1H-indazole-3-carbaldehyde was converted to Example 29(d) in a similar manner to that described for Example 29(a). $^1$H NMR (300 MHz, DMSO-d$_6$) δ 13.40 (s, 1H), 8.68 (d, 2H, J=4.6, 1.5 Hz), 8.35 (d, 1H, J=8.5 Hz), 7.93 (s, 1H), 7.87–7.79 (m, 4H), 7.73 (d, 4H, J=8.1 Hz), 7.66–7.60 (m, 3H), 7.45 (m, 2H), 7.41–7.34 (m, 1H). MS (FAB) [M+H]/z Calc'd 374, found 374. Analyzed with 0.20H$_2$O Calc'd, C (82.82), H (5.19), N (11.15). Found: C (82.82), H (5.19), N (11.16).

Example 29(e)

6-pyridyl-4-yl-3-E-[2-(3-methoxyphenyl)ethenyl]-1H-indazole

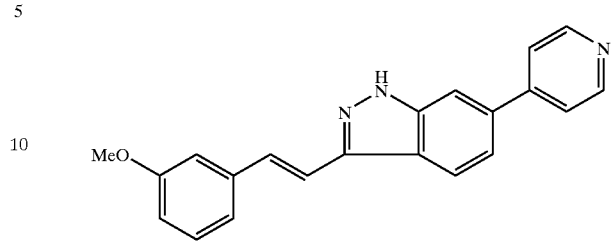

6-Pyridin-4-yl-1_(2-trimethylsilanyl-ethoxymethyl)-1H-indazole-3-carbaldehyde was converted to Example 29(e) in a similar manner to that described for Example $^2$9(a). $^1$H NMR (300 MHz, DMSO-d$_6$) δ 13.39 (s, 1H), 8.67 (d, 2H, J=5.3 Hz), 8.33 (d, 2H, J=8.5 Hz), 7.92 (s, 1H), 7.81 (dd, 2H, J=4.6, 1.5 Hz), 7.65–7.54 (m, 3H), 7.35–7.28 (m, 3H), 3.83 (s, 3H). MS (FAB) [M+H]/z Calc'd 328, found 328. Analyzed with 0.20H$_2$O Calc'd, C (76.20), H (5.30), N (12.70). Found: C (76.17), H (5.34), N (12.65).

Example 29(f)

6-pyrid-4-yl-3-E-[2-(pyrid-2-yl)ethenyl]-1H-indazole

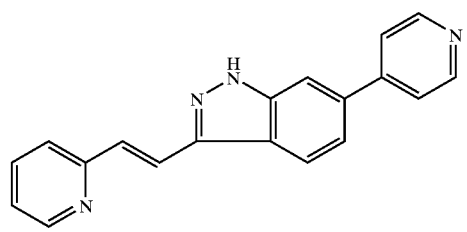

6-Pyridin-4-yl-1-(2-trimethylsilanyl-ethoxymethyl)-1H-indazole-3-carbaldehyde was converted to Example 29(f) in a similar manner to that described for Example 29(a). $^1$H NMR (300 MHz, DMSO-d$_6$) δ 8.68 (dd, 2H, J=4.5, 1.6 Hz), 8.62 (d, 1H, J=3.8 Hz), 8.33 (d, 1H, J=8.5 Hz), 7.99 (d, 1H, J=16.4 Hz), 7.94 (s, 1H), 7.86–7.78 (m, 3H), 7.73–7.57 (m, 3H), 7.32–7.26 (m, 1H). Analyzed with 0.05H$_2$O Calc'd, C (76.26), H (4.75), N (18.72). Found: C (76.22), H (4.79), N (18.76).

Example 29(g)

6-pyrid-4-yl-3-E-[2-(3-fluorophenyl)ethenyl]-1H-indazole

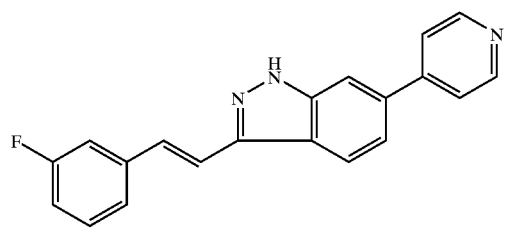

6-Pyridin-4-yl-1-(2-trimethylsilanyl-ethoxymethyl) 1H-indazole-3-carbaldehyde was converted to Example 29(g) in a similar manner to that described for Example 29(a). ¹H NMR (300 MHz, DMSO-d₆) δ 13.40 (s, 1H), 8.68 (dd, 2H, J=4.5, 1.6 Hz), 8.34 (d. 1H, J=8.4 Hz), 7.92 (s, 1H), 7.81 (dd, 2H, J1=4.5, 1.6 Hz), 7.74–7.52 (m, 5H), 7.49–7.40 (m, 1H), 7.1&7.07 (m, 1H). MS (FAB) [M+H]/z Calc'd 316, found 316. Anal. Calc'd, C (76.17), H (4.48), N (13.33). Found: C (76.07), H (4.53), N (13.36).

Example 29(h)

6-pyrid-4-yl-3-E-[2-(2-fluorophenyl)ethenyl]-1H-indazole

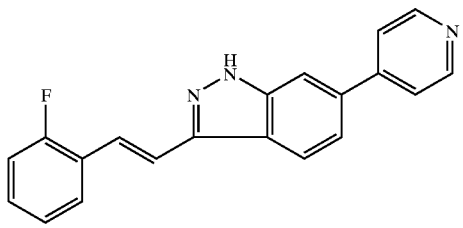

6-Pyridin-4-yl-1-(2-trimethylsilanyl-ethoxymethyl)-1H-indazole-3-carbaldehyde was converted to Example 29(h) in a similar manner to that described for Example 29(a). ¹H NMR (300 MHz, DMSO-d₆) δ 13.43 (s, 1H), 8.66 (dd, 2H, J=4.5, 1.6 Hz), 8.23 (d, 1H, 3=8.2 Hz), 7.98–7.90 (m, 2H), 7.80 (dd, 2H, J=4.5, 1.7 Hz), 7.73–7.54 (m, 3H), 7.40–7.31 (m, 1H), 7.30–7.21 (m, 2H). MS (FAB) [M+H]/z Calc'd 316, found 316. Anal. Calc'd, C (76.17), H (4.48), N (13.33). Found: C (76.12), H (4.51), N (13.29).

Example 29(i)

6-pyrid-4-yl-3-E-[2-(3-chlorophenyl)ethenyl]-1H-indazole

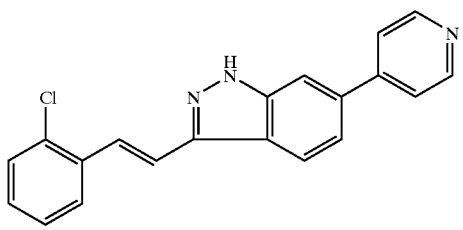

6-Pyridinyl-1-(2-trimethylsilanyl-ethoxymethyl)-1H-indazole-3-carbaldehyde was converted to Example 29(i) in a similar manner to that described for Example 29(a). ¹H NMR (300 MHz, DMSO-d₆) δ 13.42 (s, 1H), 8.68 (dd, 2H, J=4.5, 1.6 Hz), 8.35 (d, 1H, 3=8.1 Hz), 7.92 (s, 1H), 7.86 (s, 1H), 7.82 (dd, 2H, J=4.5, 1.7 Hz), 7.74–7.51 (m, 4H), 7.43 (t, 1H, J=7.8 Hz), 7.37–7.21 (m, 1H). MS (FAB) [M+H]/z Calc'd 332, found 332. Anal. Calc'd, C (72.40), H (4.25), N (12.67). Found: C (72.52), H (4.28), N (12.57).

Example 29(j)

6-pyrid-4-yl-3-E-[2-(2-methylthiazol-4-yl)ethenyl]-1H-indazole

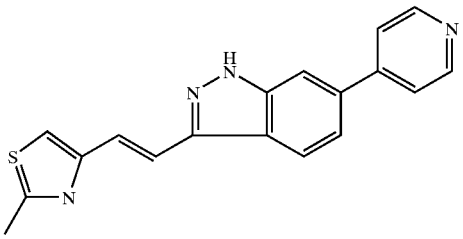

6-Pyridin-4-yl-1-(2-trimethylsilanyl-ethoxymethyl)-1H-indazole-3-carbaldehyde was converted to Example 29(j) in a similar manner to that described for Example 29(a). ¹H NMR (300 MHz, DMSO-d₆) δ 13.38 (s, 1H), 8.67 (dd, 2H, J=4.5, 1.6 Hz), 8.25 (d, 1H, J=8.5 Hz), 7.92 (s, 1H), 7.81 (dd, 2H, J=4.5, 1.6 Hz), 7.70–7.50 (m, 4H), 2.72 (s, 3H). MS (FAB) [M+H]/z Calc'd 319, found 319. Analyzed with 0.15 trifluoroacetic acid, Calc'd, C (65.51), H (4.25), N (16.70). Found: C (65.56), H (4.37), N 16.53).

Example 29(k)

6-pyrid-4-yl-3-E-[2-(naphthalen-2-yl)ethenyl]-1H-indazole

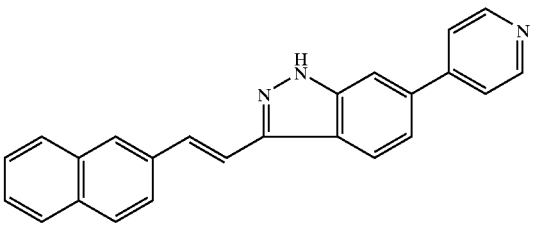

6-Pyridin-4-yl-1-(2-trimethylsilanyl-ethoxymethyl)-1H-indazole-3-carbaldehyde was converted to Example 29(k) in a similar manner to that described for Example 29(a). ¹H NMR (300 MHz, DMSO-d₆) δ 13.40 (s, 1H), 8.68 (dd, 2H, J=4.6, 1.4 Hz), 8.39 (d, 1H, J=8.5 Hz), 8.17 (s, 1H), 8.09–7.89 (m, 8H), 7.83 (dd, 2H, J=4.6, 1.6 Hz), 7.74 (s, 2H), 7.65 (dd, 1H, J=8.5, 1.4 Hz), 7.60–7.46 (m, 4H). MS (FAB) [M+H]/z Calc'd 348, found 348. Analyzed with 1.05 trifluoroacetic acid, Calc'd, C (67.10), H (3.89), N (9.00). Found: C (67.20), H (3.93), N (9.05).

Example 29(l)

6-pyrid-4-yl-3-E-[2-(2,3-difluorophenyl)ethenyl]-1H-indazole

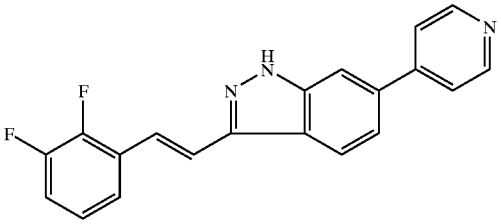

6-Pyridin-4-yl-1-(2-trimethylsilanyl-ethoxymethyl)-1H-indazole-3-carbaldehyde was converted to Example 29(1) in a similar manner to that described for Example 29(a). ¹H NMR (300 MHz, CDCl₃+MeOH-d₄) δ 8.68 (d, 2H, J=5.6 Hz,), 8.02 (d, 1H, J=85 Hz), 7.70 (s, 1H), 7.58 (dd, 2H, J-4.8, 1.5 Hz), 7.57–7.39 (m, 3H), 7.38–7.31 (m, 1H), 7.06–6.96 (m, 2H). MS (FAB) [M+H]/z Calc'd 334, found 334. Analyzed with 0.80H₂O, Calc'd, C (69.08), H (4.23), N (12.08). Found: C (68.77), H (3.93), N (11.85).

Example 29(m)

6-pyrid-4-yl-3-E-[2-(3,5-difluorophenyl)ethenyl]-1H-indazole

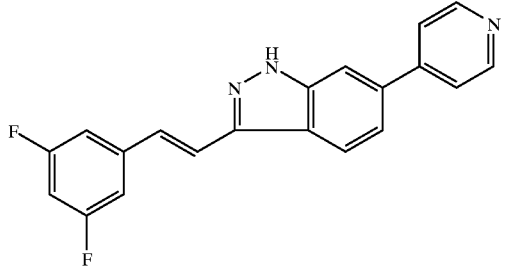

6-Pyridin-4-yl-1-(2-trimethylsilanyl-ethoxymethyl)-1H-indazole-3-carbaldehyde was converted to Example 29(m) in a similar manner to that described for Example 29(a). ¹H NMR (300 MHz, MeOH-d₄) δ 8.69 (d, 2H, J=6.3 Hz), 8.34 (d, 1H, J=8.5 Hz), 7.97 (s, 1H), 7.97 (d, 2H, J=6.3 Hz), 7.71 (d, 1H, J=10.0 Hz), 7.62 (s 1H), 7.60 (s, 1H), 7.36 (d, 1H, J=11.11), 6.95–6.89 (m, 1H). MS (ES) [M+H]/z Calc'd 334, found 334. Anal. Calc'd, C (72.06), H (3.93), N (12.61). Found: C (72.20), H (4.01), N (12.58).

Example 29(n)

6-pyrid-4-yl-3-E-[2-(biphenyl-3-yl)ethenyl]-1H-indazole

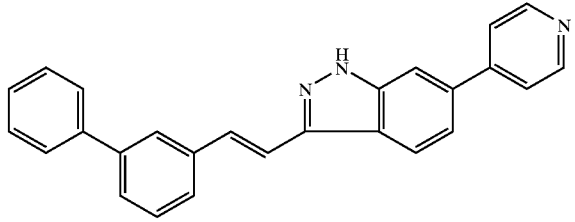

6-Pyridin-4-yl-1-(2-trimethylsilanyl-ethoxymethyl)-1H-indazole-3-carbaldehyde was converted to Example 29(n) in a similar manner to that described for Example 29(a). ¹H NMR (300 MHz, DMSO-d₆) δ 8.68 (d, 2H, J=6.1 Hz), 8.39 (d, 1H, J=8.5), 8.04 (s, 1H), 7.92 (s, 1H), 7.82 (d, 2H, J=6.2 Hz), 7.79–7.37 (m, 1 H). MS (ES) [M+H/z Calc'd 374, found 374. Anal. Calc'd, C (83.62), H (5.13), N (11.25). Found: C (83.47), H (5.08), N (11.32).

Example 29(o)

6-pyrid-4-yl-3-E-[2-(2,6-difluorophenyl)ethenyl]-1H-indazole

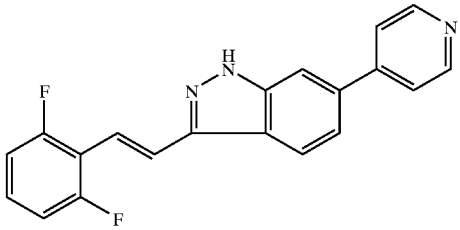

6-Pyridin-4-yl-1-(2-trimethylsilanyl-ethoxymethyl)-1H-indazole-3-carbaldehyde was converted to Example 29(o) in a similar manner to that described for Example 29(a). ¹H NMR (300 MHz, MeOH-d₄) δ 8.69 (d, 2H, J=6.3 Hz), 8.21 (d, 1H, J=8.6 Hz), 7.97 (s, 1H), 7.88 (d, 2H, J=6.3 Hz), 7.83 (d, 1H, 1–17.1 Hz), 7.71 (1H, J=8.6 Hz), 7.65 (d, 1H, J=17.1 Hz), 7.40–7.35 (m, 1H), 7.13–7.08 (m, 2H). MS (ES) [M+H]/z Calc'd 334, found 334. Analyzed with 0.1H₂O, Calc'd, C (71.67), H (3.97), N (12.54). Found: C (71.37), H (3.90), N (12.31).

Example 29(p)

6-pyrid 4-yl-3-E-[2-(3-trifluoromethoxyphenyl)ethenyl]-1H-indazole

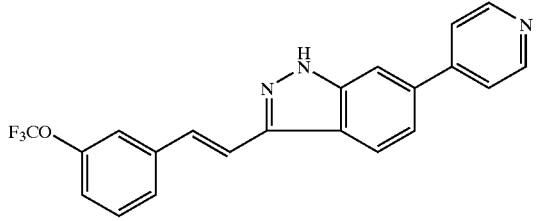

6-Pyridin-4-yl-1-(2-trimethylsilanyl-ethoxymethyl)-1H-indazole-3-carbaldehyde was converted to Example 29(p) in a similar manner to that described for Example 29(a). ¹H NMR (300 MHz, DMSO-d₆) δ 8.84 (d, 2H, 3=6.4 Hz), 8.43 (d, 1H, J=8.5 Hz), 8.19 (d, 2H, J=6.4 Hz), 8.07 (s, 1H), 7.81–7.27 (m, 5H), 7.78 (s, 1H). MS (ES) [M+H]/z Calc'd 382, found 382. Analyzed with 1.0 trifluoroacetic acid, Calc'd, C (55.76), H (3.05), N (8.48). Found: C (55.84), H (3.09), N (8.45).

Example 29(q)

6-pyrid-4-yl-3-E-[2-(benzimidazol-2-yl)ethenyl]-1H-indazole

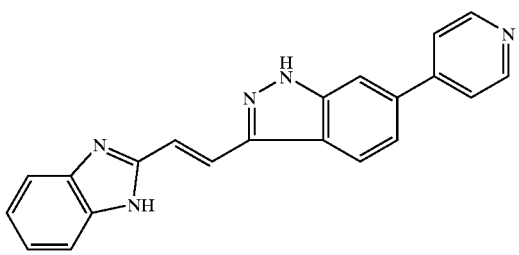

6-Pyridin-4-yl-1-(2-trimethylsilanyl-ethoxymethyl)-1H-indazole-3-carbaldehyde was converted to Example 29(q) in a similar manner to that described for Example 29(a). ¹H NMR (300 MHz, DMSO-d$_6$) δ 8.69 (d, 2H, J=6.1 Hz), 8.25 (d, 1H, J=8.5 Hz), 8.03 (d, 1H, J=16.7 Hz), 7.97 (s, 1H), 7.84 (d, 2H, J=6.2), 7.72 (d, 1H, J=8.5 Hz), 7.60–7.57 (m, 2H), 7.53 (d, 1H, J=16.7 Hz), 7.22–7.19 (m, 2H). MS (ES) [M+H]/z Calc'd 338, f338. Analyzed with 2.0 trifluoroacetic acid, 0.2H$_2$O, Calc'd, C (52.77), H (3.08), N (12.31). Found: C (52.59), H (3.17), N (12.18).

Example 29(r)

6-pyrid-4-yl-3-E-[2-(3,4-methylenedioxyphenyl)ethenyl]-1H-indazole

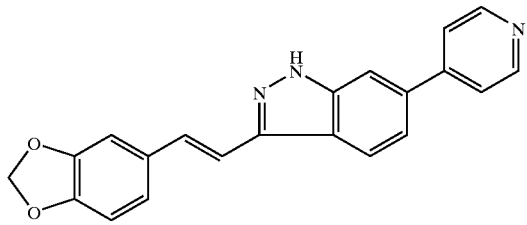

6-Pyridin-4-yl-1-(2-trimethylsilanyl-ethoxymethyl)-1H-indazole-3-carbaldehyde was converted to Example 29r in a similar manner to that described for Example 29(a). $^1$H NMR (300 MHz, DMSO-d$_6$) δ 8.67 (d, 2H, J=6.1 Hz), 8.30 (d, 1H, J=8.5 Hz), 7.89 (s, 1H), 7.81 (d, 2H, J=6.1 Hz), 7.61 (d, 1H, J=9.9 Hz), 7.46–7.42 (m, 3H), 7.18 (d, 1H, J=9.6 Hz), 6.95 (d, 1H, 8.0 Hz), 6.05 (s, 2H). MS (ES) [M+H]/z Calc'd 342, found 342. Anal. Calc'd, C (73.89), H (4.43), N (12.31). Found: C (73.74), H (4.52), N (12.40).

Example 29(s)

6-pyrid-4-yl-3-E-[2-(2,5-difluorophenyl)ethenyl]-1H-indazole

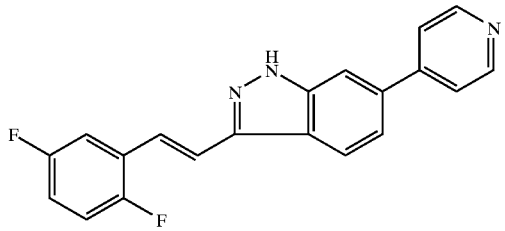

6-Pyridin-4-yl-1-(2-trimethylsilanyl-ethoxymethyl)-1H-indazole-3-carbaldehyde was converted to Example 29(s) in a similar manner to that described for Example 29(a). $^1$H NMR (300 MHz, MeOH-d$_4$) δ 8.53 (d, 2H, 1=6.0 Hz), 8.03 (d, 1H, J=8.5 Hz), 7.60 (d, 2H, 1=6.2 Hz), 7.56–7.35 (m, 3H), 7.34–7.26 (m, 1H), 7.03–6.93 (m, 1H), 6.90–6.81 (m, 1H). MS (ES) [M+H]/z Calc'd 334, found 334. Analyzed with 0.30H$_2$O, Calc'd, C (70.91), H (4.05), N (12.37). Found: C (70.97), H (4.17), N (12.37).

Example 29(t)

6-pyrid-4-yl-3-E-[2-(1H-pyrrol-2-yl)ethenyl]-1H-indazole

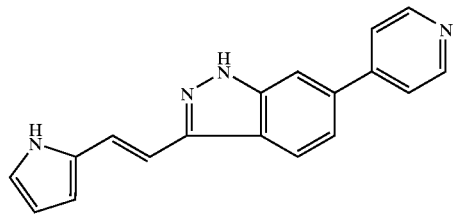

Pyridin-4-yl-1-(2-trimethylsilanyl-ethoxymethyl)-1H-indazole-3-carbaldehyde was converted to Example 29(t) in a similar manner to that described for Example 29(a). $^1$H NMR (300 MHz, MeOH-d$_4$) δ 8.60 (d, 2H, J=6.3 Hz), 8.13 (d, 1H, J=8.5 Hz), 7.86 (s<, 1H), 7.79 (d, 2H, J=6.2 Hz), 7.57 (dd, 1H, J1=8.5 Hz, J2=1.5 Hz), 7.40 (d, 1H, J=16.8 Hz), 7.09 (d, 1H, J=16.7 Hz), 6.87–6.82 (m, 1H), 6.40–6.35 (m, 1H), 6.16 (t, 1H, J=2.9 Hz). MS (ES) [M+H]l/z Calc'd 287, found 287. Analyzed with 0.5 ethyl acetate, 0.3 tetrahydrofuran, 0.1 hexanes, 0.1 ethylene diamine, Calc'd, C (72.07), H (6.21), N (16.05). Found: C (71.95), H (6.20), N (15.76).

The starting material was prepared as follows:

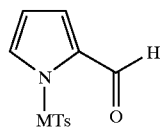

(i) A solution of 1H-pyrrole-2-carbaldehyde (9.5 g, 100 mmol) and THF (500 ml) was cooled with an ice bath. Bu$^t$ONa (19.2 g, 200 mmol) was added and reaction mixture was stirred at 0° C. for 1 h. MtsCl (32.7 g, 150 mmol) was then added. The reaction mixture was allowed to warm to rt and held for 2 h at rt. The solution was then treated with saturated aqueous NH$_4$Cl (100 ml) and the mixture was poured into brine (2 L). The mixture was extraced with EtOAc (3×300 ml). The combined organic layer was dried over MgSO$_4$ and concentrated under reduced pressure. The resulting oil was purified by silica gel chromatography to yield 1-(2,4,6-trimethyl-benzenesulfonyl)1H-pyrrole-2-carbaldehyde as a light yellow oil (15.7 g, 57%). $^1$H NMR (CDCl$_3$) δ 9.50 (s, 1H), 7.79–7.74 (m, 1H), 7.12 (dd, 1H, J=3.7, 1.8 Hz), 6.95 (s, 2H), 6.38 (t, 1H, J=3.4 Hz), 2.50 (s, 6H), 2.30 (s, 3H).

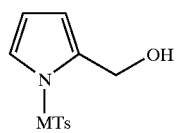

(ii) 1-(2,4,6-Trimethyl-benzenesulfonyl)-1H-pyrrole-2-carbaldehyde (2.77 g, 10 mmol) in THF (100 ml) was treated with LiBH$_4$ (0.44 g, 20 mmol) at rt. The resulting solution was held at rt for 1 h. MeOH (10 ml) was then added, and the resulting mixture mixture was poured into brine (600 ml), and extracted with EtOAc (3×200 ml).

The combined organic layer was dried over MgSO$_4$ and concentrated under reduced pressure. The resulting oil was then purified on silica gel column to yield [1-(2,4,6-Trimethyl-benzenesulfonyl)-1H-pyrrol-2-yl]-methanol as a light brown oil (2.43 g, 87%). $^1$H NMR (CDCl$_3$) δ 7.17 (dd, 1H, J=3.3, 1.8 Hz), 6.99 (s, 2H), 6.28–6.23 (m, 1H), 6.18 (t, 1H, J=3.3 Hz), 4.42 (s, 2H), 250 (s, 6H), 2.30 (s, 3H).

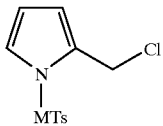

(iii) A solution of [1-(2, 4,6-Trimethyl-benzenesulfonyl 1H-pyrrol-2-yl]-methanol (1.4 g, 5.0 mmol) in CHCl$_3$ (25 ml) was cooled with an ice bath. SOCl$_2$ (1.1 ml, 15 mmol) was added slowly. The solution was allowed to warm to rt, and held an additional 45 min. The solution was then concentrated under reduced pressure. 2-Chloromethyl-1-(2, 4,6-trimethyl-benzenesulfonyl)1H-pyrrole was obtained as a brown solid (15 g, 100%). $^1$H NMR (CDCl$_3$) δ 7.28 (dd, 1H, J=3.3, 1.7 Hz), 6.98 (s, 2H), 6.38–6.34 (m, 1H), 6.19 (t, 1H, J=3.4 Hz), 4.58 (s, 2H), 2.50 (s, 6H), 2.30 (s, 3H).

Example 29(u)

6-pyrid-4-yl-3-E-[2-(3-methylcarbamoylmethoxyphenyl)ethenyl]-1H-indazole

6-Pyridin-4-yl-1-(2-trimethylsilanyl-ethoxymethyl)-1H-indazole-3-carbaldehyde was converted to Example 29(u) in a similar manner to that described for Example 29(a). $^1$H NMR (300 MHz, MeOH-d$_4$) δ 8.68 (d, 2H, J=5.9 Hz), 8.51 (br s, 1H), 8.37 (d, 1H, J=8.5 Hz), 8.19 (s, 1H), 7.93 (s, 1H), 7.87 (d, 1H, J=7.7 Hz), 7.85 (d, 2H, J=6.1 Hz), 7.62 (d, 1H, J=8.1 Hz), 7.65–7.63(m, 3H), 7.51 (t, 1H, J=7.6 Hz). MS (ES) [M+H]/z Calc'd 355, found 355. Analyzed with 0.4 trifluoroacetic acid, 0.50H$_2$O, Calc'd, C (69.67), H (4.98), N (14.26). Found: C (69.78), H (5.18), N (14.08).

Example 30(a)

6-[3-benzamidophenoxy]-3-E-[2-(thien-2-yl)ethenyl]-1H-indazole

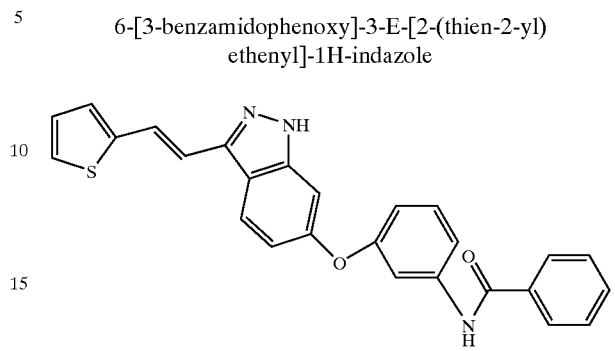

Example 30(a) was prepared in a manner similar to example 6(a) except that (E)-3-thiophen-2-yl-acryloyl chloride was used in place of 3-(4-chlorophenyl)acryloyl chloride in step (i). $^1$H NMR (DMSO-d$_6$) δ 13.05 (s, 1H), 10.33 (s, 1H), 8.19 (d, 1H, J=8.8 Hz), 7.92 (d, 2H, J=6.9 Hz), 7.70 (d, 1H, J=16.5 Hz), 7.65–7.49 (m, 6H), 7.40 (t, 1H, J=8.1 Hz), 7.35 (s, 1H, with fine splitting), 7.20 (d, 1H, J=16.5 Hz), 7.10 (m, 1H), 7.04 (s, 1H), 6.98 (d, 1H, J=8.8 Hz), 6.86 (s, 1H, J=9.8 Hz). Anal. Calc for C$_{26}$H$_{19}$N$_3$O$_2$S 0.6H$_2$O: C, 69.65; H, 4.54; N, 9.37; S, 7.15. Found: C, 69.77; H, 4.45; N, 9.52; S, 7.02.

Example 30(b)

6-[3-(1-acetylpiperidin-4-ylcarboxamido)phenoxy]-3-E-[2-(4-chlorophenyl)ethenyl]-1H-indazole

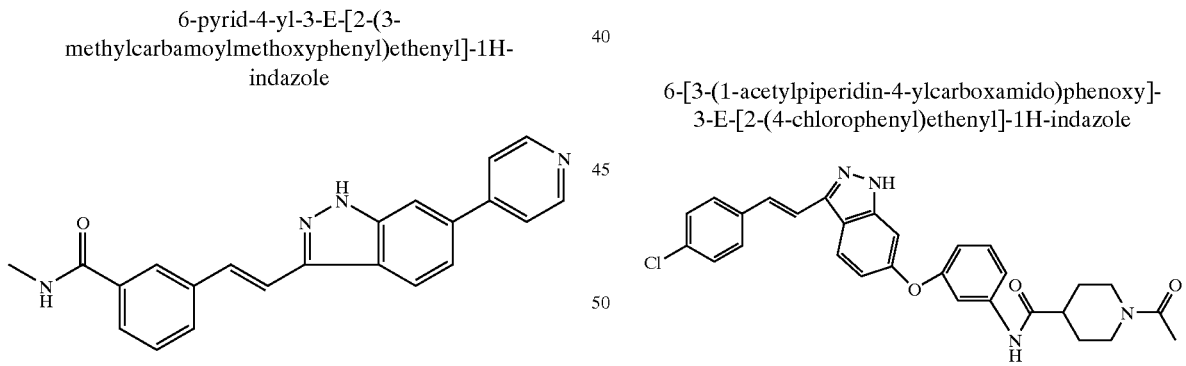

Example 30(b) was prepared in a similar manner to that described for 6(a) except that 1-acetyl-piperidine-4-carboxylic acid and HATU was used in place of benzoyl chloride in step(ii). $^1$H NMR (DMSO-d$_6$) (J=8.6 Hz) δ 7.76, (d, J=8.6 Hz), 7.53 (d, l=6.2 Hz), 7.46 (d, J=8.4 Hz), 7.37 (m, 3H), 7.01 (s, 1H, with fine splitting), 6.97 (d, J=8.8 Hz), 6.78 (d, J=7.7 Hz), 4.38 (m, 1H), 3.85 (m, 1H), 3.09–2.96 (m, 1H), 2.58 (m, 2H), 1.99 (s, 3H), 1.77 (m, 2H), 1.55 (m, 1H), 1.37 (m, 1H). Anal. Calc for C$_{29}$H$_{27}$ClN$_4$O$_3$.1.3H$_2$O: C, 64.69; H, 5.54; N, 10.41. Found: C, 64.64; H, 5.51; N, 10.23.

Example 30(c)

6-[3-benzamidophenoxy]-3-E-[2(fur-2-yl)ethenyl]-1H-indazole

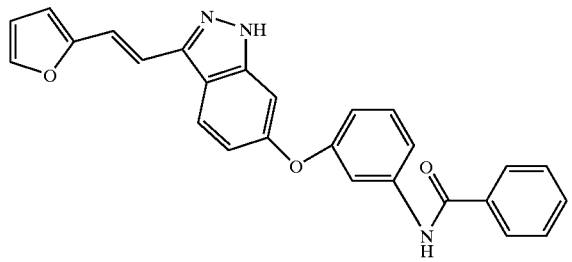

Example 30(c) was prepared in a manner similar to example 6(a) except that (E)-3-furan-2-yl-acryloyl chloride, prepared according to Collect, *Czech. Chem. Comm.*, 52, 409–24 (1987), was used in place of 3-(4-chlorophenyl)-acryloyl chloride in step (i). $^1$H NMR (DMSO-4) δ 13.00 (s, 1H), 10.32 (s, 1H), 8.14 (d, 1H, J=8.8 Hz), 7.91 (d, 2H, J=7.0 Hz), 7.73 (s, 1H), 7.70–7.51 (m, 5H), 7.40 (t, 1H, J=8.4 Hz), 7.30 (AB, 2H, J=16.7 Hz), 7.04 (s, 1H), 6.98 (d, 1H, J=8.7 Hz), 6.86 (d, 1H, J=8.0 Hz), 6.65 (s, 1H, with fine splitting), 6.60 (s, 1H, with fine splitting). Anal. Calc for $C_{26}H_{19}N_3O_2$ 0.7$H_2O$: C, 71.94; H, 4.74; N, 9.68. Found: C, 72.17; H, 4.83; N, 9.44.

Example 30(d)

6-[3-(indol-4-ylcarboxamido)phenoxy]-3-E-stryrylindazole

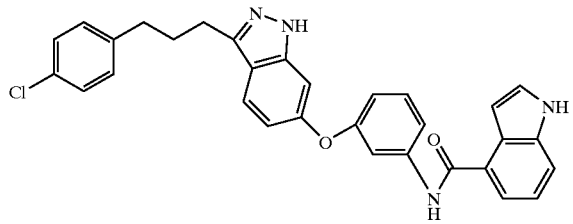

Example 30(d) was prepared in a similar manner to that described for Example 30(a) using 3-(styryl-1H-indazol-6-yloxy)phenylamine in place of 3-(3-styryl-4,5-dihydro-1H-indazol-6-yloxy)phenylamine and 1H-indole-4-carboxylic acid in place of benzoic acid in step (ii). $^1$H NMR (DMSO-$d_6$) δ 12.99 (s, 1H), 11.33 (s, 1H), 10.24 (s, 1H), 8.22 (d, 1H, J=8.7 Hz), 7.72–7.38 (m, 10H), 7.30 (d, 1H, J=7.1 Hz), 7.19 (m, 2H), 7.04 (m, 3H), 6.82 (m, 2H). Anal. Calc for $C_{30}H_{22}N_4O_2$ 0.6$H_2O$: C, 74.86; H. 4.86; N, 11.64. Found: C, 74.90; H, 5.01; N, 11.33.

Example 30(e)

6-[3-((1-Ethyl-3-methyl-1H-pyrazol-5-yl)carboxamido)phenoxyl]-3-E-stryrylindazole

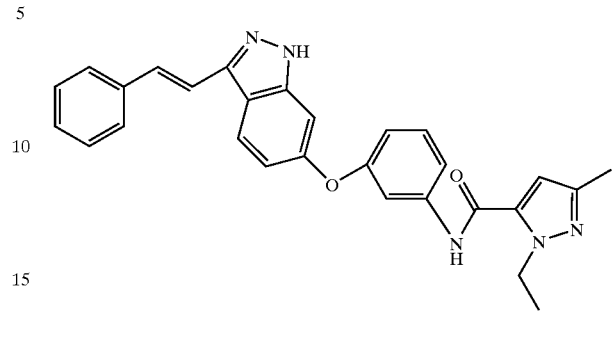

Example 30(e) was prepared in a similar manner to that described for Example 30(a) using 3-(styryl-1H-indazol-6-yloxy)-phenylamine in place of 3-(3-styryl-4,5-dihydro-1H-indazol-6-yloxy)phenylamine and 1-ethyl-3-methyl-1H-pyrazole-5-carboxylic acid in place of benzoic acid in step (ii).

Example 31(a)

6-[3-benzamidophenoxy]-3-E-[2-(pyridin-2-yl)ethenyl]-1H-indazole

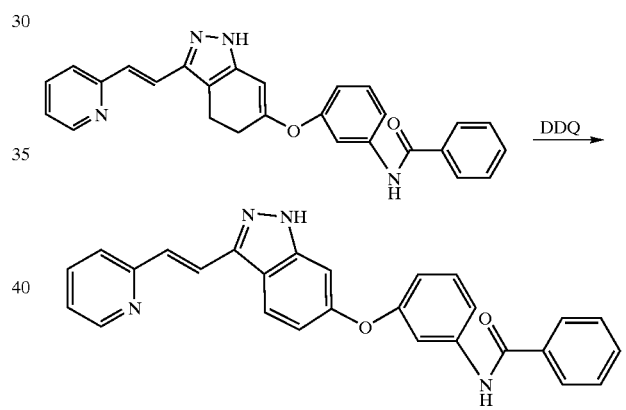

To a stirred solution of 6-[3-benzamidophenoxy]-3-E-[2-(pyridin-2-yl)ethenyl]-4,5-dihydro-1H-indazole (492 mg, 1.13 mmol) in 15 mL of 1,4-dioxane was added 386 mg (1.7 mmol) 2,3-dichloro-5,6-dicyano-1,4-benzoquinone (DDQ). The reaction mixture was stirred for 30 min at room temperature, then poured into sat NaHCO$_3$ solution and EtOAc. Layers were separated and the aqueous layer was re-extracted with EtOAc. The combined organic layers were washed sequentially with sat NaHCO$_3$ solution and sat NaCl solution, dried over MgSO$_4$ and conc. under reduced pressure. The residue was flash chromatographed on silica gel eluting CH$_2$Cl$_2$/EtOAc: MEOH (1:1:0.1). The oil obtained was triturated from EtOAc/hexanes to give the title compound as a tan solid (420 mg, 86%). $^1$H NMR (DMSO-$d_6$) δ 13.12 (s, 1H), 10.30 (s, 1H), 8.60 (d, 1H, J=3.8 Hz), 8.22 (d, 1H, J=8.8 Hz), 7.93 (m, 3H), 7.82 (t, 1H, J=7.7 Hz), 7.68–7.49 (m, 7H), 7.40 (t, 1H, J=8.1 Hz), 7.27 (m, 1H), 7.08 (s, 1H), 7.03 (s, 1H), 7.03 (d, 1H, J=8.7 Hz), 6.87 (d, 1H, J=8.1 Hz, with fine splitting). Anal. Calc for $C_{27}H_{20}N_4O_2$ 0.65 EtOAc: C, 72.59; H, 5.19; N, 11.44. Found: C, 72.34; H, 5.11; N, 11.82.

The starting material was prepared as follows:

step (i)

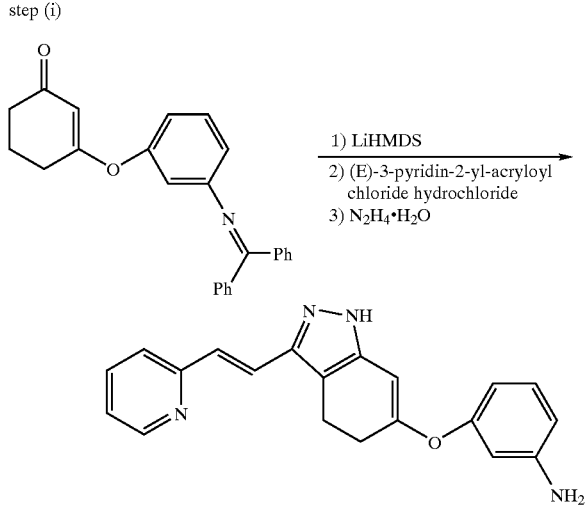

A solution of 3-[3-(benzhydrylidene-amino)-phenoxy]-cyclohex-2-enone (4.00 g, 10.9 mmol) in 20 mL of THF was added slowly to a ~78° C. solution of LiHMDS (36 mL of 10M solution in THF). Fifteen minutes after addition was complete, (E)-3-pyridin-2-yl-acryloyl chloride hydrochloride was added and stirring was continued at −78° C. for 30 min. The reaction was quenched with sat. NH$_4$Cl solution and extracted with EtOAc (3×). The combined organic layers were washed with sat NaCl solution, dried over MgSO$_4$ and conc. under reduced pressure. The residue was flash chromatographed on silica gel eluting Hexanes/EtOAc (2:1). The appropriate fractions were concentrated under reduced pressure and dissolved in EtOH/HOAc (1:1, 8 ml). To this solution at 80° C. was added hydrazine hydrate (3.4 ml, 70.0 mmol). After 15 min, all starting material was gone and the reaction mixture was cautiously poured into sat NaHCO$_3$ and extracted with EtOAc (2×). The combined organic layers were washed with sat NaCl solution, dried over MgSO$_4$ and conc. under reduced pressure. The residue was flash chromatographed on silica gel eluting CH$_2$Cl$_2$/MeOH (9:1) to give 6-(3-aminophenoxy)-3-E-[2-(pyridin-2-yl)ethenyl]4,5-dihydro-1H-indazole (676 mg, 19%). $^1$H NMR (DMSO-d$_6$) δ 12.51 (s, 1H), 8.57 (d, 1H, J=3.8 Hz), 7.78 (t, 1H, J=7.8 Hz), 7.51 (m, 2H), 7.25 (m, 1H), 7.05 (m, 2H), 6.35 (d, 1H, J=7.9 Hz, with fine splitting), 6.32 (t, 1H, J=2.1 Hz), 6.23 (d, 1H, J=7.9 Hz), 5.54 (s, 1H), 5.23 (s, 2H), 2.95 (t, 2H, J=8.2 Hz), 2.60 (t, 2H, J=8.2 Hz); MS [m+H]/z Calc'd 331. Found: 331. Anal. Calc for C$_{20}$H$_{18}$N$_4$O 0.15H$_2$O: C, 72.12; H, 5.54; N, 16.82. Found: C, 72.11; H, 5.55; N, 16.61.

step (ii)

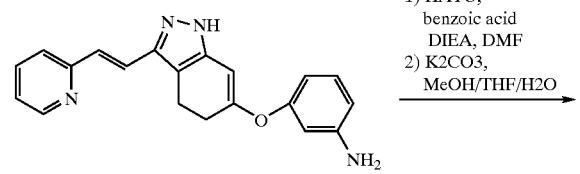

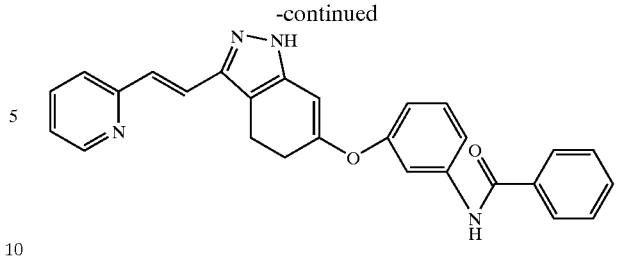

To a stirred solution of the dihydro aniline (350 mg, 1.06 mmol) and benzoic acid (776 mg, 6.36 mmol) in 15 mL of DMF, was added HATU (2.42 g, 6.36 mmol) and NEt$_3$ (1.8 ml, 12.71 mmol). The reaction mixture was heated at 50° C. for 1.5 hr, cooled and poured into ice/sat NaCl solution. The ppt was collected by vacuum filtration, washed with H$_2$O and air dried. To this filter cake dissolved in 10 mL of MeOH/THF (1:1), was added K$_2$CO$_3$ (650 mg) and 1 mL of H$_2$O. After 1 hr, the reaction mixture was poured into sat NaCl solution and extracted with EtOAc (2×). The combined organic layers were washed with sat NaCl solution, dried over MgSO$_4$ and conc. under reduced pressure. The residue was flash chromatographed on silica gel eluting CH$_2$Cl$_2$/EtOAc/MeOH (1:1:0.1) to give 6-[3-benzamidophenoxy]-3-E-[2-(pyridin-2-yl)ethenyl]4,5-dihydro-1H-indazole (333 mg, 72%). $^1$H NMR (DMSO-d$_6$) δ 12.58 (bs, 1H), 10.34 (s, 1H), 8.57 (d, 1H, J=3.8 Hz), 7.95 (d, 2H, J=6.8 Hz), 7.81–7.70 (m, 2H), 7.63–7.50 (m, 6H), 7.40 (t, 1H, J=8.1 Hz), 7.25 (m, 1H), 7.09 (d, 1H, J=16.3 Hz), 6.89 (d, 1H, J=8.0 Hz), 5.64 (s, 1H), 2.99 (t, 2H, J=8.1 Hz), 2.66 (t, 2H, J=8.1 Hz). Anal. Calc for C$_{27}$H$_{22}$N$_4$O$_2$ 0.1 CH$_2$Cl$_2$: C, 73.48; H, 5.05; N, 12.65. Found: C, 73.48; H, 5.05; N, 12.48.

Example 31(b)

6-[3((1,5-Dimethyl-1H-pyrazol-3-yl)carboxamido)phenoxy]-3-E-[2-(pyridin-2-yl)ethenyl]-1H-indazole

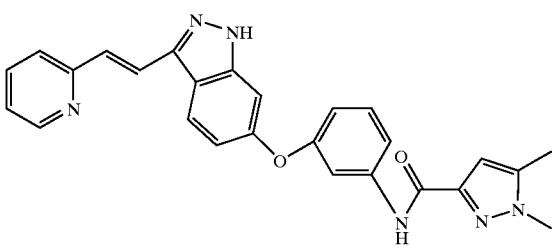

Example 31(b) was prepared in a similar manner to that described for Example 31(a) except that 1,5-dimethyl-1H-pyrazole-3 carboxylic acid was used in place of benzoic acid in step (ii). $^1$H NMR (DMSO-d$_6$) δ 13.13 (s, 1H), 10.07 (s, 1H), 8.60 (d, 1H, J=4.3 Hz), 8.21 (d, 1H, J=8.7 Hz), 7.93 (d, 1H, J=16.3 Hz), 7.82 (t, 1H, J=7.4 Hz), 7.69-(m, 3H), 7.56 (d, 1H, J=16.3 Hz), 7.32 (m, 2H), 7.05 (s, 1H), 7.01 (d, 1H, J=8.7 Hz), 6.80 (m, 1H), 6.52 (s, 1H), 3.81 (s, 3H) 2.29 (s, 3H). Anal. Calc for C$_6$H$_{22}$N$_6$O$_2$.0.1 CH$_2$Cl$_2$/0.1 hexanes: C, 6858; H, 5.09; N, 17.97. Found: C, 68.26; H, 5.25; N, 17.61.

Example 31(c)

6-[3-((5-methylsulfonylthien-2-yl)carboxamido)phenoxy]-3-E-[2-(pyridin-2-yl)ethenyl]-1H-indazole

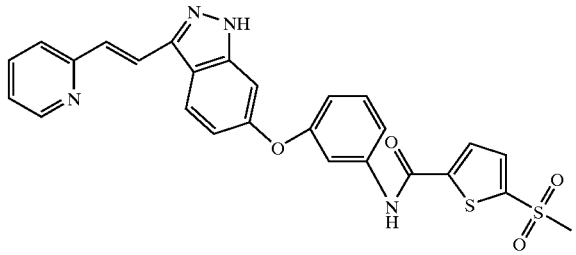

Example 31(c) was prepared in a similar manner to that described for Example 31(a) except that 5-methanesulfonyl-thiophene-2-carboxylic acid was used in place of benzoic acid in step (ii). $^1$H NMR (DMSO d) δ 13.17 (s, 1H), 10.58 (s, 1H), 8.61 (d, 1H, J=4.0 Hz), 8.24 (d, 1H, J=8.8 Hz), 8.05 (d, 1H, J=4.1 Hz), 7.97–7.79 (m, 3H), 7.68 (d, 1H, J=7.8 Hz), 7.60–7.48 (m, 3H), 7.43 (t, 1H, J=8.2 Hz), 7.28 (m, 1H), 7.10 (s, 1H, with fine splitting), 7.00 (d, 1H, J=8.7 Hz), 6.92 (d, 1H, J=8.1 Hz, with fine splitting), 3.41 (s, 3H). Anal. Calc for $C_{26}H_{20}N_4O_4S_2$ 0.4 EtOAc: C, 60.07; H, 4.24; N, 10.15; S, 11.62. Found: C, 60.22; H, 4.48; N. 10.05; S, 11.49.

Example 31(d)

6-[3-((1-Ethyl-3-methyl-1H-pyrazol-5-yl)carboxamido)phenoxy]-3-E-[2(pyridin-2-yl)ethenyl]-1H-indazole

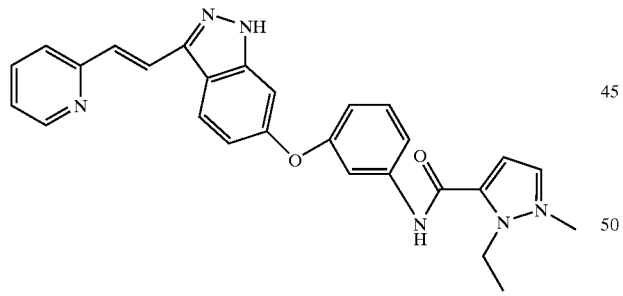

Example 31(d) was prepared in a similar manner to that described for Example 31(a) except that 1-ethyl-3-methyl-1H-pyrazole-5-carboxylic acid was used in place of benzoic acid in step (ii). $^1$H NMR (DMSO-d$_6$) δ 13.15 (s, 1H), 10.18 (s, 1H), 8.61 (d, 1H, J=3.7 Hz), 8.22 (d, 1H, 1=8.8 Hz), 7.94 (d, 1H, J=16.3 Hz), 7.82 (t, 1H, J=7.5 Hz), 7.67 (d, 1H, J=7.7 Hz), 7.55 (m, 3H), 7.40 (t, 1H, J=8.1 Hz), 7.28 (m, 1H), 7.06 (s, 1H), 7.01 (d, 1H, J=8.8 Hz), 6.89 (d, 1H, J=7.9 Hz), 6.78 (s, 1H), 4.38 (q, 2H, J=7.1 Hz), 2.19 (s, 3H), 1.29 (t, 3H, J=7.1 Hz). Anal. Calc for $C_2H_{24}N_6O_2$ 0.6 EtOAc: C, 68.25; H, 5.61; N, 16.24. Found: C, 68.28; H, 5.88; N, 16.01.

Example 31(e)

6-[3-(1-Methylimidazol-2-yl)carboxamido)phenoxy]-3-E-[2-(pyridin-2-yl)ethenyl]-1H-indazole

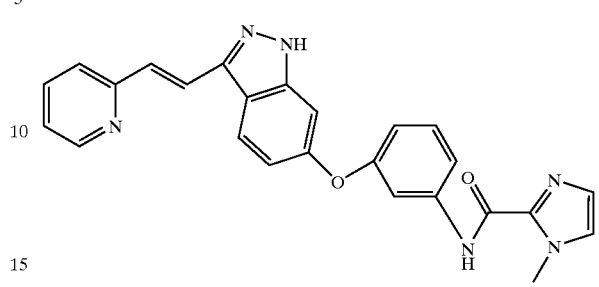

Example 31(e) was prepared in a similar manner to that described for Example 31(a) except that 1-methyl-1H-imidazole-2-carboxylic acid was used in place of benzoic acid in step (ii). $^1$H NMR (DMSO-d$_6$) δ 13.13 (s, 1H), 10.47 (s, 1H), 8.60 (d, 1H, J=3.9 Hz), 8.21 (d, 1H, J=8.7 Hz), 7.93 (d, 1H, J=16.3 Hz), 7.82 (t, 1H, J=7.6 Hz), 7.65 (m, 3H), 7.56 (d, 1H, J=16.3 Hz), 7.43 (s, 1H), 7.37 (t, 1H, J=8.1 Hz), 7.28 (m, 1H), 7.04 (m, 3H), 6.84 (d, 1H, J=7.7 Hz), 3.95 (s, 3H). Anal. Calc for $C_{25}H_{20}N_6O_2 \cdot 0.4H_2O$: C, 67.49; H, 4.80; N, 18.65. Found: C, 67.68; H. 4.73; N. 18.94.

Example 31(f)

6-[3-((1-Ethyl-3-methyl-1H-pyrazol-5-yl)carboxamido)phenoxy]-3-E-[2-(1,2-dimethyl-1H-imidazol-4-yl)ethenyl]-1H-indazole

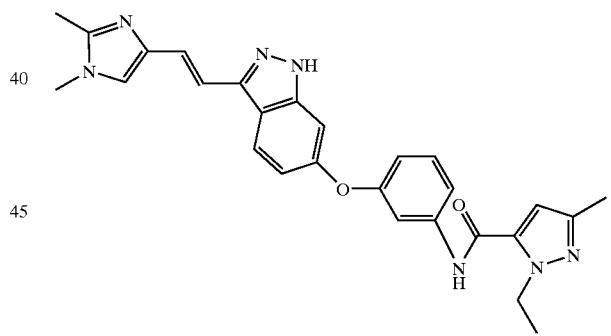

Example 31(f) was prepared in a similar manner to that described for Example 31(a) except that (E)-3-(1,2-dimethyl-H-imidazol-4-yl)acryloyl chloride hydrochloride was used in place of (E)-3-pyridin-2-yl-acryloyl chloride hydrochloride in step (i) and 1-ethyl-3-methyl-1H-pyrazole-5-carboxylic acid was used in place of benzoic acid in step (ii). $^1$H NMR (DMSO-d$_6$) & 12.82 (s, 1H), 10.17 (s, 1H), 8.05 (d, 1H, J=8.8 Hz), 7.58 (d, 1H, J=8.4 Hz), 7.48 (s, 1H), 7.38 (t, 1H, J=8.1 Hz), 7.25 (s, 2H), 7.20 (s, 1H), 7.01 (s, 1H), 6.92 (d, 1H, J=8.7 Hz), 6.85 (d, 1H, J=8.7 Hz), 6.78 (s, 1H), 4.37 (q, 2H, J=7.0 Hz), 3.56 (s, 3H), 2.31 (s, 3H), 2.19 (s, 3H), 1.29 (t, 3H, J=7.0 Hz). Anal. Calc for $C_{27}H_{27}N_7O_2$ 1.0H$_2$O.0.3 EtOAc: C, 64.39; H, 6.02; N, 18.64. Found; C, 64.52; H, 5.98; N, 18.52.

Example 32(a)

6-[3-benzamidophenoxy]-3-E-[2-(1H-imidazol-4-yl)ethenyl]-1H-indazole

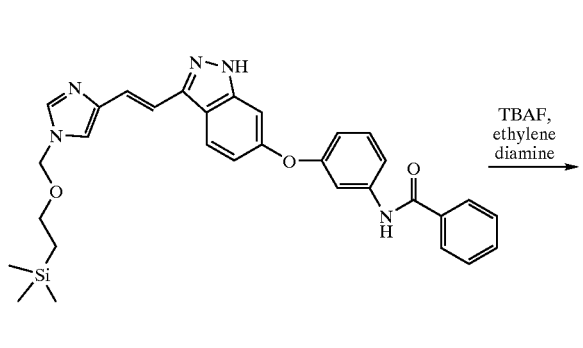

TBAF, ethylene diamine →

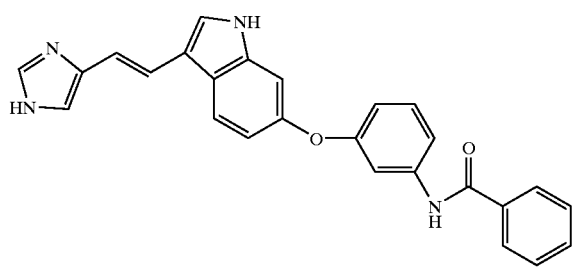

To a stirred solution of the 6-(3-benzamidophenoxy)-3-E-[2-(1-(2-trimethylsilanyl-ethoxy)-methyl-imidazol-4-yl)ethenyl]-1H-indazole compound (213 mg, 0.39 mmol) in 5 mL of THF was added 1.0 M TBAF in THF (6.0 ml, 6.0 mmol) and ethylenediamine (0.26 ml, 3.86 mmol). After heating at 70° C. for 18 h, the reaction mixture was cooled, diluted with EtOAc, and washed repeatedly with sat NaHCO$_3$ solution. The organic layer was dried over MgSO$_4$ and conc. under reduced pressure. The residue was flash chromatographed on silica gel eluting CH$_2$Cl$_2$:EtOAc:MeOH (1:1:0.2). The oil obtained was triturated from EtOAc/hexanes to give AG13853 (65 mg, 40%). $^1$H NMR (DMSO-d$_6$) δ 12.90 (s, 1H), 12.35 (s, 1H), 10.32 (s, 1H), 8.08 (d, 1H, J=8.7 Hz), 7.91 (d, 2H, J=6.8 Hz), 7.81 (s, 1H), 7.67.49 (m, 5H), 7.42–7.31 (m, 4H), 7.03 (s, 1H), 6.96 (d, 1H, J=8.7 Hz), 6.85 (d, 1H, J=8.1 Hz). Anal. Calc for C$_{25}$H$_{19}$N$_5$O$_2$.0.7H$_2$O.0.4 EtOAc: C, 68.07; H, 5.07; N, 14.92. Found: C, 67.93; H, 4.89; N, 15.06.

The starting material was prepared in a similar manner to that desribed for Example 31(a) except that (E)-3-{1-(2-trimethylsilanyl)-ethoxymethyl)-1H-imidazol-4-yl]-acryloyl chloride hydrochloride was used in place of (E)-3-pyridin-2-yl-acryloyl chloride hydrochloride in step (i).

Example 32(b)

6-[3-((1-Ethyl-3-methyl-1H-pyrazol-5-yl)carboxamido)phenoxy]-3-E-[2-(1H-imidazol-4-yl)ethenyl]-1H-indazole

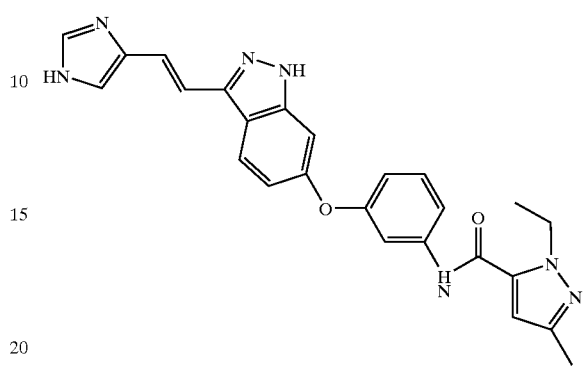

Example 32(b) was prepared in a similar manner to that described for Example 32(a) except that 1-ethyl-3-methyl-1H-pyrazole-5-carboxylic acid was used in place of benzoic acid in step (ii). $^1$H NMR (DMSO-d$_6$) δ 12.89 (s, 1H), 12.37 (s, 1H), 10.18 (s, 1H), 8.07 (d, 1H, J=8.9 Hz), 7.74 (s, 1H), 7.58 (d, 1H, J=8.3 Hz), 7.49 (s. 1H), 7.44–7.32 (m, 3H), 7.28 (s, 1H), 7.01 (s, 1H), 6.95 (d, 1H, J=8.9 Hz), 6.86 (d, 1H, J=8.6 Hz), 6.78 (s, 1H), 4.38 (q, 2H, J=7.1 Hz), 2.19 (s, 3H), 1.29 (t, 3H, J=, 7.1 Hz). Anal. Calc for C$_{25}$H$_{23}$N$_7$O$_2$.0.8H$_2$O.0.1 EtOAc: C, 63.99; H, 5.37; N, 20.57. Found: C, 63.72; H, 5.12; N, 20.25.

Example 32(c)

6-[3-((1-Ethyl-3-methyl-1H-pyrazol-5-yl)carboxamido)phenoxy]-3-E-[2-(2-methylimidazol-4-yl)ethenyl]-1H-indazole

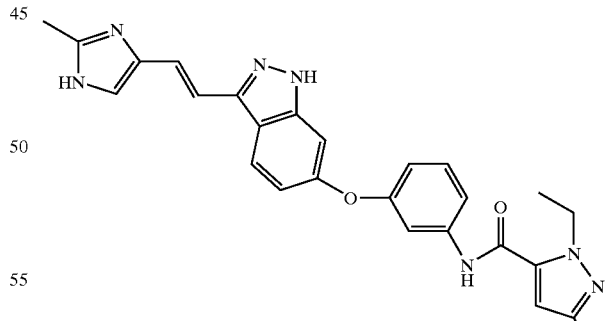

Example 32(c) was prepared in a simialr manner to that described for 32(b) except that (E)-3-[2-methyl-1-(2-trimethylsilanyl)ethoxymethyl)-1H-imidazol-4-yl]-acryloyl chloride hydrochloride was used in place of (E)-3-[1-(2-trimethylsilanyl)-ethoxymethyl)-1H-imidazol-4-yl]-acryloyl chloride hydrochloride in step (i). $^1$H NMR (DMSO-d6) δ 12.85 (bs, 1H), 11.80 (bs, 1H), 10.18 (s, 1H), 8.05 (d, 1H, J=8.7 Hz), 7.58 (d, 1H, J=8.4 Hz), 7.48 (s, 1H), 7.39 (t, 1H, J=8.2 Hz), 7.33–7.05 (m, 3H), 7.00 (s, 1H), 6.93 (d, 1H, J=8.7 Hz), 6.86 (d, 1H, J=8.2 Hz), 6.78 (s, 1H), 4.38 (q, 2H, J=7.1 Hz), 2.31 (s, 3H), 2.19 (s, 3H), 1.29 (t, 3H, J=7.1 Hz). Anal. Calc for $C_{26}H_{25}N_7O_2 \cdot 0.9H_2O \cdot 0.4$ EtOAc: C, 63.87; H, 5.83; N, 18.89. Found: C, 63.64; H, 5.76; N, 18.85.

Example 33(a)

6-[2-(methylcarbamoyl)phenylsulfanyl]-3-E-[2-(pyridin-2-yl)ethenyl]indazole

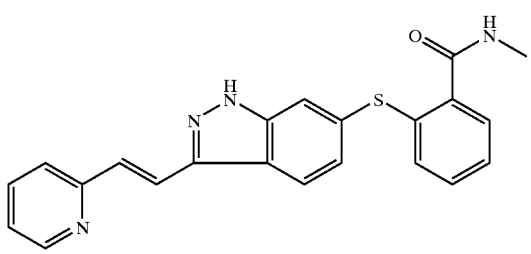

Example 33(a) was prepared from 6-[2-(methylcarbamoyl)phenylsulfanyl]-3-E-[2-(pyridin-2-yl)ethenyl]-1-[2-(trimethyl-silanyl)ethoxymethyl]-1H-indazole in a similar manner to that described for Example 11. $R_f$ sm 0.8, p 0.15 (ethyl acetate); $^1$H NMR (300 MHz, dmso-d6) δ 13.45 (s, 1H), 8.72 (d, 1H, J=3.9 Hz), 8.47 (m, 1H), 8.31 (d, 1H, J=8.5 Hz), 8.06 (d, 1H, J=16.4 Hz), 7.92 (dt, 1H, J=1.7, 7.6 Hz), 7.78 (d, 1H, J=7.8 Hz), 7.71 (s, 1H), 7.68 (d, 1H, J=16.5 Hz), 7.61 (dd, 1H, J=1.7, 7.2 Hz), 7.45–7.36 (m, 3H), 7.31 (d, 1H, J=8.5 Hz), 7.17 (m, 1H), 2.89 (d, 3H, J=4.6 Hz); $^{13}$C NMR (75 MHz, dmso-d6) δ 167.8, 154.8, 149.5, 141.9, 141.8, 137.0, 136.8, 135.4, 132.5, 130.2, 130.0, 129.2, 127.7, 126.1, 125.4, 123.5, 122.5, 122.4, 121.6, 120.2, 114.5; LCMS (100% area) Rt=3.5 min (pos) [M+H]/z Calc'd 387, found 387. Analyzed with $0.1H_2O$, 0.1 EtOAc Calc'd, C (67.78), H (4.82), N (14.11), S (8.08). Found: C (67.78), H (4.77), N (14.06), S (8.08).

The starting material was prepared as follows:

(i)

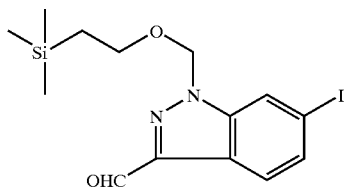

Under argon, 6-iodo-3-styryl-1-[2-(trimethyl-silanyl)-ethoxymethyl]-1H-indazole (30.0 g, 62.9 mmol) prepared in Example 14, step (i), was dissolved in dichloromethane (375 mL) and was cooled to −42° C. in an acetonitile-dry ice bath. Ozone was then bubbled through the mix (1 L/min, 60 V, 1.8 Amps) for 45 min. Standard indicators did not give a clear color change due to the solutions background color. To avoid over-oxidation, the reactions progress was monitored by TLC (1:9 EtOAc-Hex). The ozone addition was stopped and the flask was flushed with argon. Dimethyl sulfide (30 mL) was then added and the mixture was allowed to warm to 23° C. This mixture was stirred for 4 h and was concentrated under reduced pressure. The oil was placed under high vacuum for 16 h. The residue was dissolved in dichloromethane (15 mL) and was diluted with hexane (100 mL) to give some crystals (not desired product). The mixture was filtered and the filtrate was concentrated. The residue was dissolved in 8:2 Hex-EtOAc (250 mL), treated with 50 mL silica, filtered, and concentrated. 6 Iodo-3-carboxaldehyde-1-[2-(trimethyl-silanyl)ethoxymethyl]-1H-indazole formed as a yellow solid after 72 h under high vacuum (24.17 g, −95% pure by NMR, 91% yield): $R_f$ sm 0.34, p 0.29 (ethyl acetate-hexane 1:9); $^1$H NMR (300 MHz, CDCl₃) δ 10.25 (s, 1H), 8.09 (s, 1H), 8.05 (d, 1H), 7.80 (d, 1H), 5.88 (s, 2H), 3.71 (t, 2H), 0.93 (t, 2H), 0.0 (s, 9H).

(ii)

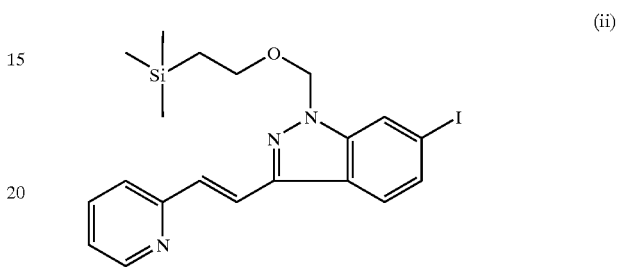

Iodo-3-carboxaldehyde-1-[2-(trimethyl-silanly)-ethoxymethyl]-1H-indazole (24.0 g, 59.7 mmol) was dissolved in THF (350 mL) and was cooled to −5° C. To this was added solid 2-picolyltriphenylphosphonium chloride-potassium hydride (45.7 g, 100 mmol, 1.68 equiv). The reaction mixture was allowed to stir for 45 min. To the mixture, was added 3N HCl (20 mL) followed by saturated aqueous sodium bicarbonate (50 mL) to give a pH of 6. Excess THF was removed under reduced pressure and the residue was partitioned between ethyl acetate and water. The organics were washed with saturated aqueous sodium bicarbonate, water and the organic layer was separated, dried over sodium sulfate, decanted and concentrated under reduced pressure. The residue was taken up in 1:9 ethyl acetate-hexane and was filtered. The filtrate was purified by silica gel chromatography (2 L silica, 20 to 30 to 50% ethyl acetate-hexane) to give 6-Iodo-3-E-[2-(pyridin-2-yl)ethenyl-1-[2-trimethyl-silanly)-ethoxymethyl]-1H-indazole (18.9 g, 66% yield): $R_f$ sm 0.52, p 0.25 (ethyl acetate-hexane 2:8); $^1$H NMR (300 MHz, CDCl₃) δ 8.64 (m, 1H), 8.00 (d, 1H, 3=0.7 Hz), 7.87 (d, 1H, J=16.4 Hz), 7.80 (d, 1H, J=8.5 Hz), 7.69 (td, 1H, J=7.7, 1.8 Hz), 7.55 (d, 1H, J=16.4 Hz), 7.55 (dd, 1H, J=8.5, 1.3 Hz), 7.47 (d, 1H, J=7.9 Hz), 7.18 (dd, 1H, J=1.1, 4.8 Hz), 5.70 (s, 2H), 359 (t, 2H, J=8.2 Hz), 0.90 (t, 2H, J=8.2 Hz), −0.04 (s, 9H); $^{13}$C NMR (75 MHz, CDCl₃) δ 156.8, 151.2, 144.2, 143.6, 138.0, 132.3, 132.2, 124.4, 124.0, 123.8, 123.7, 123.5, 120.7, 94.1, 79.4, 68.1, 19.17, 0.0.

(iii)

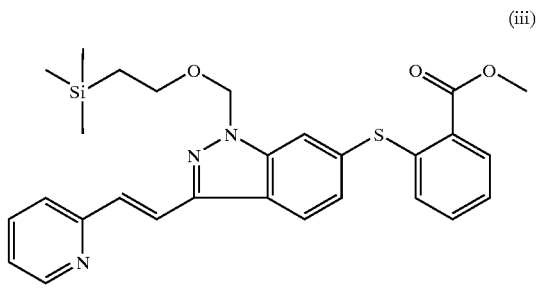

In a 200 mL round bottom flask was weighed cesium carbonate (13.7 g, 41.9 mmol, 2.5 equiv) and this salt was dried under high vacuum with a heat gun. The catalyst [Pd(dppf)Cl₂—CH₂Cl₂] (1.37 g, 1.68 mmol, 0.1 equiv) and 6-Iodo-3-E-[2-(pyridin-2-yl)ethenyl-1-[2-(trimethyl-silanly)-ethoxymethyl]-1H-indazole (8.0 g, 16.76 mmol) were then added and the mix was taken up in DMF (71 mL). To this mixture was added methyl thiosalicylate (4.62 mL, 33.5 mmol, 2.0 equiv) and the vessel was warmed to 85° C. for 4.5 h. This mixture was cooled to 23° C., was partitioned between ethyl acetate (350 mL) and 50%-saturated aqueous sodium bicarbonate (300 mL). The organics were washed with 10% sodium bisulfite (200 mL), brine and the organic layer was separated. The organic material was dried over sodium sulfate, decanted and concentrated under reduced pressure. Purification by silica gel chromatography (500 mL silica; 30 to 40 to 50% ethyl acetate-hexane) gave 6-[(2-methoxycarbonylphenyl)sulfanyl-3-E-[2-(pyridin-2-yl)ethenyl]-1-[2-(trimethyl-silanyl)ethoxymethyl]-1H-indazole (6.44 g, 74%): $R_f$ sm 0.52, p 0.19 (ethyl acetate-hexane 3:7); FTIR (thin film) 2950, 2887, 2356, 1713, 1585, 1464, 1433, 1250, 1076, 837 cm$^{-1}$; $^1$H NMR (300 MHz, CDCl₃) δ 8.70 (d, 1H), 8.12 (d, 1H), 8.04 (d, 1H), 7.99 (d, 1H, J=16.4 Hz), 7.90 (s, 1H), 7.88 (t, 1H), 7.76 (d, 1H, J=16.4 Hz), 7.62 (d, 1H), 7.55 (d, 1H), 7.30–7.15 (m, 3H), 6.92 (d, 1H), 5.80 (s, 2H), 4.01 (s, 3H), 3.78 (t, 2H), 0.96 (t, 2H), –0.03 (s, 9H); $^{13}$C NMR (75 MHz, CDCl₃) δ 168.3, 156.8, 151.2, 144.3, 144.2, 143.2, 138.0, 133.8, 133.6, 132.5, 132.4, 129.9, 129.3, 128.5, 126.0, 124.7, 124.6, 123.8, 123.5, 118.3, 79.4, 68.2, 53.7, 19.2, 0.0; LCMS (100% area) Rt=4.4 min, (pos) [M+H]/z Calc'd 518.2, found 518.2.

(iv)

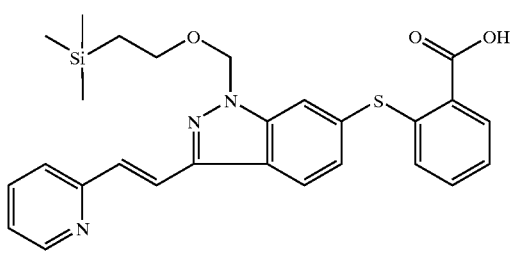

To 6-[(2-methoxycarbonylphenyl)sulfanyl]-3-E-[2-(pyridin-2-yl)ethenyl]-1-[2-(trimethyl-silanyl)ethoxymethyl]-1H-indazole (8.50 g, 16.4 mmol) was added THF (120 mL), methanol (120 ml), water (120 mL) and potassium carbonate (15.9 g, 115 mmol, 7.0 equiv). This mixture was heated to 67° C. and was stirred for 22 h. The mixture was cooled and the excess solvents were removed. The residue was partitioned between ethyl acetate (300 mL) and water (250 mL). The aqueous was acidified with 20% citric acid to pH 5 (~70 mL) and the aqueous was drained. The organic layer was washed with water (50 mL) and hexane (100 mL) was added to help precipitate the crystals that were forming in the ethyl acetate layer. The solid was filtered and dried to give 6-[(2-carboxyphenyl)sulfanyl]-3-E-[2-(pyridin-2-yl)ethenyl]-1-[2-(trimethyl-silanyl)ethoxymethyl]-1H-indazole (7.56 g, 91%): $R_f$ sm 0.67, p 0.41 (ethyl acetate-hexane 8:2); $^1$H NMR (300 MHz, CDCl₃) δ 8.60 (m, 1H), 8.10 (d, 1H, J=8.4 Hz), 8.04 (dd, 1H, J=1.7, 7.7 Hz), 7.85 (d, 1H, J=16.5 Hz), 7.83 (s, 1H), 7.70 (dt, 1H, J=1.7, 7.7 Hz), 7.59 (d, 1H, J=16.5 Hz), 7.52 (d, 1H, J=7.9 Hz), 7.38 (dd, 1H, J=1.3, 8.4 Hz), 7.22–7.10 (m, 3H), 6.80 (dd, 1H, J=1.0, 8.0 Hz), 3.59 (t, 2H, J=8.1 Hz), 0.85 (t, 2H, J=8.8.1 Hz), –0.1 (s, 9H).

(v)

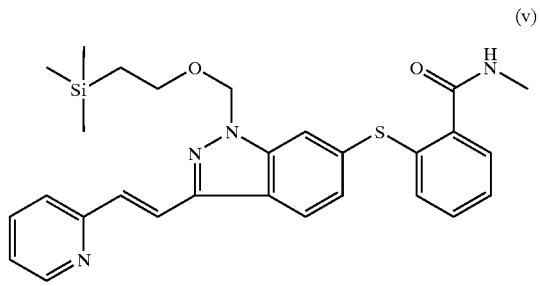

6-[(2-Carboxyphenyl)sulfanyl]-3-E-[2-(pyridin-2-yl)ethenyl-1-[2-(trimethyl-silanyl)-ethoxymethyl]-1H-indazole (820 mg, 1.63 mmol) was dissolved in DMF (5 mL) and was treated with methyl amine (2M in THF, 4.1 mL, 8.13 mmol, 50 equiv) and with HATU (929 mg, 2.44 mmol, 1.5 equiv). This mixture was stirred for 30 min, was partitioned between ethyl acetate and saturated aqueous sodium bicarbonate and the organic layer was separated. The organic material was dried over sodium sulfate, decanted and concentrated under reduced pressure. Purification by silica gel chromatography (50 mL silica; 60 to 70% ethyl acetate-hexane) gave 6-[2-(methylcarbamoyl)phenylsulfanyl]-3-E-[2(pyridin-2-yl)ethenyl]-1-[2-(trimethyl-silanyl)ethoxymethyl]-1H-indazole as a solid (795 mg, 94%): $R_f$ sm 0.35, p 0.23 (ethyl acetate-hexane 6:4); FTIR (thin film) 3306, 2951, 1643, 1606, 1587, 1563, 1469, 1433, 1410, 1303, 1249, 1217, 1075, 836 cm$^{-1}$; $^1$H NMR (300 MHz, CDCl₃) δ 8.70 (m, 1H), 8.06 (d, 1H, J=8.4 Hz), 7.94 (d, 1H, J=16.3 Hz), 7.74 (dt, 1H, J=1.8, 7.7 Hz), 7.70–7.60 (m, 3H), 752 (d, 1H, J=7.9 Hz), 7.35–7.20 (m, 5H), 6.45 (bs, 1H), 5.80 (s, 2H), 3.62 (t, 2H), 3.00 (d, 3H), 0.93 (t, 2H), –0.05 (s, 9H); $^{13}$C NMR (75 MHz, CDCl₃) δ 179.7, 169.9, 156.8, 151.1, 144.2, 143.0, 138.1, 136.1, 135.4, 133.2, 132.2, 132.1, 130.2, 1285, 127.2, 124.7, 124.1, 123.8, 123.5, 123.3, 114.9, 68.1, 28.2, 19.2, 0.00; LCMS (100% area) Rt=4.15 min, (pos) [M+H]/z Calc'd 517.2, found 517.2

Example 33(b)

6-[2-(2-methylquinol-6-ylcarbamoyl)phenylsulfanyl]-3-E-[2-(pyridin-2-yl)ethenyl]-1H-indazole

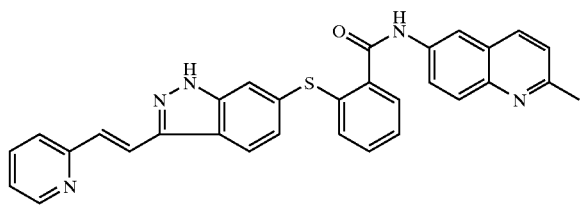

Example 33(b) was prepared in a similar manner to that described for Example 33(a) except that, in step (v), 6-amino-2-methylquinoline was used instead of methylamine: $^1$H NMR (300 MHz, CDCl₃) δ 10.2 (bs, 1H), 8.64 (m, 1H), 8.40 (s, 1H), 8.23 (s, 1H), 7.98–7.80 (m, 4H), 7.69 (dt, 1H, J=1.7, 7.7 Hz), 7.55–7.40 (m, 7H), 7.25–7.16 (m, 3H), 2.71 (s, 3H).

Example 33(c)

6-[2-(phenylcarbamoyl)phenylsulfanyl]-3-E-[2-(pyridin-2-yl)ethenyl]-1H-indazole

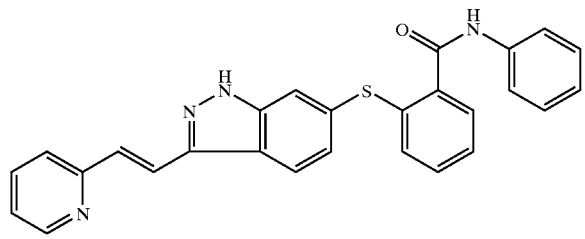

Example 33(c) was prepared in a similar manner to that described for Example 33(a) except that, in step (v), aniline was used instead of methyl amine: $^1$H NMR (300 MHz, dmso-d6) δ 13.35 (s, 1H), 10.53 (s, 1H), 8.67 (m, 1H), 8.22 (d, 1H, J=7.5 Hz), 7.99 (d, 1H, J=16.4 Hz), 7.85 (dt, 1H, J=1.8, 7.6 Hz), 7.80–7.55 (m, 5H), 7.45–7.10 (m, 9H); LCMS (100% area) Rt=3.86, (pos) [M+H]/z Calc'd 449.1, found 449.1. Analyzed with 0.41H$_2$O Calc'd, C (71.13), H (4.60), N (12.29), S (7.03). Found: C (71.04), H (4.62), N (12.31), S (7.01).

Example 33(d)

6-[2-(3-chlorophenylcarbamoyl)phenylsulfanyl]-3-E-[2-(pyridin-2-yl)ethenyl]-1H-indazole

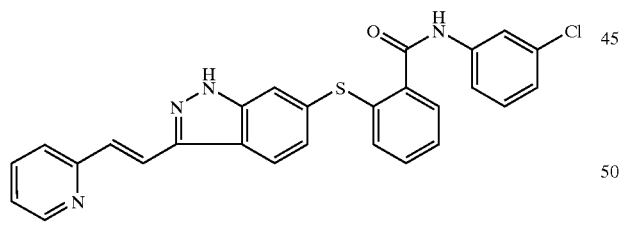

Example 33(d) was prepared in a similar manner to that described for Example 33(a) except that, in step (v), 3-chloroaniline was used instead of methyl amine: $^1$H NMR (300 MHz, CDCl$_3$) δ 8.53 (m, 1H), 7.92 (d, 1H, J=8.4 Hz), 7.77 (d, 1H, J=16.4 Hz), 7.68 (dt, 1H, J=1.7, 7.7 Hz), 7.64–7.56 (m, 2H), 7.51–7.43 (m, 3H), 7.35–7.28 (m, 4H), 7.19–7.12 (m, 3H), 7.02 (m, 1H); LCMS (100% area) Rt 3.98 min, (pos) [M+H]/z Calc'd 483.1, found 483.1. Analyzed with 0.3H$_2$O Calc'd, C (66.40), H (4.05), N (11.47), S (6.57). Found: C (66.36), H (4.08), N (11.49), S (6.55).

Example 33(e)

6-[2-(cyclopropylcarbamoyl)phenylsulfanyl]-3-E-[2-(pyridin-2-yl)ethenyl]-1H—1H-indazole

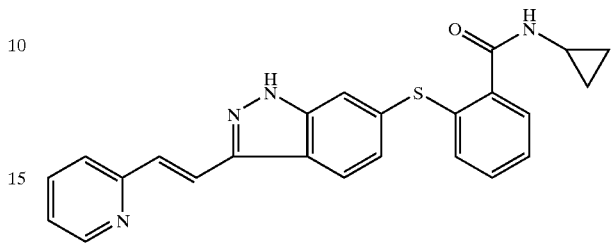

Example 33(e) was prepared in a similar manner to that described for Example 33(a) except that, in step (v), cyclopropylamine was used instead of methylamine: $^1$H NMR (300 MHz, dmso-d6) δ 13.45 (s, 1H), 8.73 (d, 1H, J=3.9 Hz), 8.56 (d, 1H, J=4.3 Hz), 8.31 (d, 1H, J=8.5 Hz), 8.08 (d, 1H, J=16.4 Hz), 7.91 (dt, 1H, J=1.7, 7.7 Hz), 7.78 (d, 1H, J=7.8 Hz), 7.70 (m, 2H), 7.57 (m, 1H,), 7.40 (m, 3H), 7.30 (d, 1H, J=8.4 Hz), 7.20 (d, 1H, J=7.8 Hz), 2.94 (m, 1H), 0.80 (m, 2H), 0.65 (m, 2H); LCMS (100% area) Rt 3.51 min, (pos) [M+H]/z Calc'd 413.1, found 413.1.

Example 33(f)

6-[2-(2,2,2-trifluoroethylcarbamoyl)phenylsulfanyl]-3-E-[2-pyridin-2-yl)ethenyl]-1H-indazole

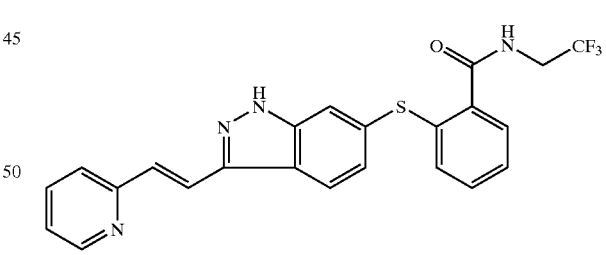

Example 33(f) was prepared in a similar manner to that described for Example 33(a) except that, in step (v), 2,2,2-trifluoroethylamine was used instead of methylamine: $^1$H NMR (300 MHz, dmso-d6) δ 13.5 (s, 1H), 9.29 (t, 1H, J=6.3 Hz), 8.74 (m, 1H), 8.37 (d, 1H, J=8.3 Hz), 8.10 (d, 1H, J=16.4 Hz), 7.94 (dt, 1H, J=1.8, 7.6 Hz), 7.80 (d, 1H, J=7.9 Hz), 7.75–7.65 (m, 3H), 7.55–7.40 (m, 3H), 7.33 (d, 1H), 7.22 (d, 1H), 4.22 (m, 2H); LCMS (100% area) Rt=3.70 min, (pos) [M+H]/z Calc'd 455.1, found 455.1.

Example 33(g)

6-[2-(carboxy)phenylsulfanyl]-3-E-[2-(pyridin-2-yl)ethenyl]-1H—1H-indazole, tetrabutylammonium salt

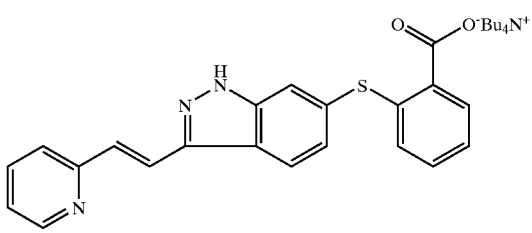

Example 33(g) was prepared in a similar manner to that described for Example 33(a) except that step (v) was omitted: $R_f$ sm 0.41, p 0.0 (ethyl acetate-hexane 8:2); $^1$H NMR (300 MHz, dmso-d6) δ 8.75 (m, 1H), 8.25 (d, 1H, J=8.6 Hz), 8.05 (d, 1H, 16.4 Hz), 7.88 (dt, 1H, J=1.8, 7.8 Hz), 7.83–7.60 (m, 4H), 7.33 (m, 2H), 7.16 (m, 2H), 6.70 (m, 1H), 3.30 (m, 8H), 1.70 (m, 8H), 1.42 (m, 8H), 1.05 (t, 12H); LCMS (100% area) Rt 3.24 (pos) [M+H (acid component only)]/z Calc'd 374.1, found 374.1. Analyzed with 0.1H$_2$O Calc'd, C (72.07), H (8.21). N (9.09), S (5.20). Found: C (72.04), H (8.29), N (9.06). S (5.12).

Example 33(h)

6-[2-(3-chlorophenylcarbamoyl)phenylsulfanyl]-3-Z-[2-(pyridin-2-yl)ethenyl]-1H-indazole

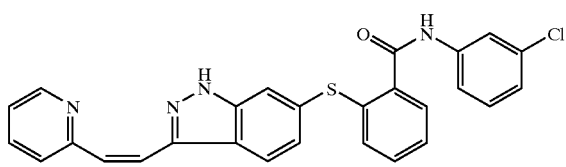

Example 33(h) was prepared in the same reaction as Example 33(d). It should be noted that, although this compound was isolated and characterized pure, it was found to isomerize to Example 33(d) under assay conditions. $^1$H NMR (300 MHz, CDCl$_3$) δ 8.82 (m, 1H), 8.31 (s, 1H), 7.86 (m, 2H), 7.77 (m, 2H), 7.61 (t, 1H, J=2.0 Hz), 7.46 (d, 1H, J=8.0 Hz), 7.33 (m, 5H), 7.21 (t, 1H, J=8.0 Hz), 7.13 (dd, 1H, J=1.5, 8.1 Hz), 7.08 (m, 1H), 6.98 (d, 1H, J=13.0 Hz), 6.66 (d, 1H, J=13.1 Hz); LCMS (100% area) Rt 4.40 min, (pos) [M+H]/z Calc'd 483.1, found 483.1. Analyzed with 0.3H$_2$O Calc'd, C (66.40), H (4.05), N (11.47), S (6.57). Found: C (66.36), H (4.08), N (11.49), S (6.55).

Example 34

6-[2-((RS-(trans-2-phenylcyclopropyl)carbamoyl)phenylsulfanyl]-3-E-[2-(pyridin-2-yl)ethenyl]-1H-indazole

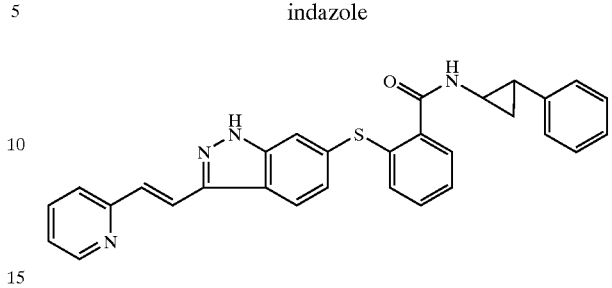

Example 33(g) was converted to Example 34 in a similar manner to that described for Example 33(a), step (v) except that trans-2-phenylcyclopropylamine was used instead of methylamine: FTIR (thin film) 1704, 1638, 1584, 1559, 1530, 1497, 1460, 1430, 1339, 1306, 1269, 1223, 1152, 1086, 1061, 966, 844 cm$^{-1}$; $^1$H NMR (300 MHz, CDCl$_3$) δ 13.3 (s. 1H), 8.71 (d, 1H, J=4.4 Hz), 8.61 (d, 1H, J=3.9 Hz), 8.20 (d, 1H, J=8.5 Hz), 7.96 (d, 1H, J=16.4 Hz), 7.81 (dt, 1H, J=1.7, 7.6 HZ), 7.66 (d, 1H, J=7.8 Hz), 7.59–7.50 (m, 3H), 7.37–7.25 (m, 5H), 7.21–7.08 (m, 5H), 3.01 (m. 1H), 2.03 (m, 1H), 1.25 (m, 2H); LCMS (100% area) Rt=3.72 min. (pos) [M+H]/z Calc'd 489.2, found 489.2. Analyzed with 0.6 MeOH, 0.16 CH$_2$Cl$_2$ Calc'd, C (70.86), H (5.17), N (10.75), S (6.15). Found: C (70.87), H (5.18), N (10.75), S (5.96).

Example 35(a)

6-[2(n-Propylcarbamoyl)phenylsulfanyl]-3-E-[2(pyridin-2-yl)ethenyl]-1H-indazole

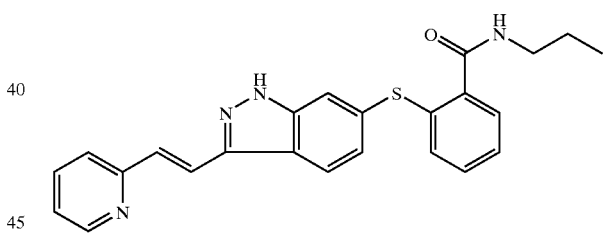

6-[2-(Pentafluorophenoxycarbonyl)phenylsulfanyl]-3-E-[2-(pyridin-2-yl)ethenyl)-1H—indazole (60 mg, 0.1112 mmol) was dissolved in DMF (0.8 mL), treated with n-propylamine (11 μL., 0.1335 mmol) and stiffed at room temperature. HPLC analysis after 15 minutes indicated that all staring material had been consumed. The reaction mixture was concentrated by high vacuum rotary evaporation, giving a solid. The solid was sonicated with CH$_2$Cl$_2$ giving a fine suspension, which was filtered, and rinsed with CH$_2$Cl$_2$ to provide 40 mg (87% yield) of the title compound. $^1$H NMR (DMSO-d$_6$) δ 13.31 (s, 1H), 8.60 (d, J=4.0 Hz, 1H), 8.41 (t, J=6.2 Hz, 1H), 8.19 (d, J=8.5 Hz, 1H), 7.94 (m, 3H), 7.81 (dt, J=1.7, 7.5 Hz, 1H), 7.66 (t, J=8.7 Hz, 1H), 7.56 (m, 2H), 7.47 (m, 1H), 7.30 (m, 3H), 7.18 (d, f=8.3 Hz, 1H), 3.20 (q, J=6.0 Hz, 2H), 1.55 (septet, J=5.9 Hz, 2H), 0.92 (t, J=6.0 Hz, 3H). Anal. Calcd. for C$_{24}$H$_{22}$N$_4$OS-(1.5H$_2$O, 0.8 DMF): C, 63.41; H, 6.17; N, 13.45; S, 6.41. Found: C, 63.37; H, 5.68; N, 13.44; S, 6.32.

The starting material was prepared as follows:

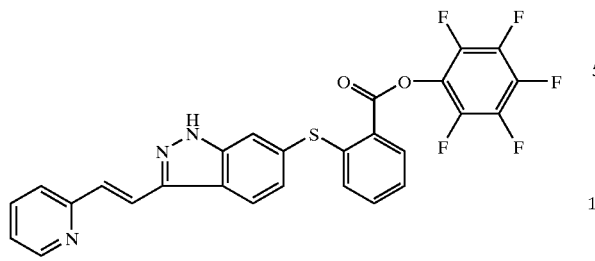

A solution of the tetrabutyl ammonium salt of 6-(2-carboxyphenylsulfanyl)-3-E-[2-(pyridin-2-yl)ethenyl]-1H-indazole) (615 mg, 1.0 mmol) dissolved in dry DMF (10.0 ml) was treated with pyridine (89 µL, 1.1 mmol), and pentafluorophenyl trifluoroacetate (206 µL, 1.2 eq), at room temperature, under an argon atmosphere. HPLC analysis after 45 minutes showed mostly unreacted carboxylic acid, so additional pyridine (89 µL, 1.1 mmol), and pentafluorophenyl trifluoroacetate (206 µL, 1.2 eq) were added. HPLC analysis 15 minutes later indicated that starting acid had been completely consumed. The reaction mixture was concentrated under high vacuum rotary evaporation, then triturated with $CH_2Cl_2$ (~1 mL) causing the formation of crystals, which were collected by filtration, rinsed with additional $CH_2Cl_2$, and dried. The mass of the bright yellow crystals was 336 mg. The remaining filtrate was concentrated and purified by flash chromatography (10% acetontrile/$CH_2Cl_2$ to 80% acetonitrile/$CH_2Cl_2$), yielding an additional 70 mg of solid. The total yield of 6-[2-(Pentafluorophenoxycarbonyl)phenylsulfanyl]-3-E-[2-(pyridin-2-yl)ethenyl]-1H-indazole was 406 mg, or 89%. $^1$H NMR ($CDCl_3$) δ 10.22 (1H, bs), 8.66 (1H, d, J=4.5 Hz), 8.28 (2H, dd, J=7.7, 1.5 Hz), 8.15 (1H, d, J=8.5 Hz), 7.97 (1H, d, J=16.2 Hz), 7.79 (1H, s), 7.15–7.75 (7H, m), 6.92 (1H, d, J=8.1 Hz).

Example 35(b)

6-[2-(i-Propylcarbamoyl)phenylsulfanyl]-3-E-[2-(pyridin-2-yl)ethenyl]-1H-indazole

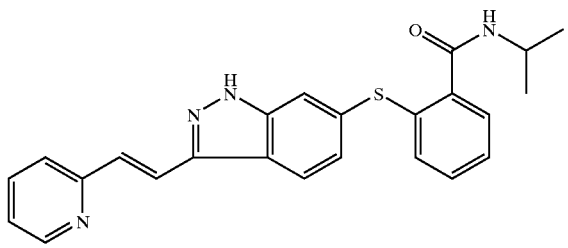

Example 35(b) was prepared in a similar manner to that described for Example 35(a) except that isopropylamine was used instead of n-propylamine. $^1$H NMR (DMSO-$d_6$) δ 13.30 (s, 1H), 8.60 (d, J=4.5 Hz, 1H), 8.26 (d, J=7.34 Hz, 1H), 8.19 (d, J=8.3 Hz, 1H), 7.94 (d, J=16.4 Hz, 1H), 7.80 (dt, J=1.7, 7.5 Hz, 1H), 7.66 (d, J=7.7 Hz, 1H), 7.56 (m, 2H), 7.45 (m, 1H), 7.30 (m, 3H), 7.18 (d, J=8.5 Hz, 1H), 7.08 (m, 1H), 4.04 (septet, J=7.4 Hz, 1H), 1.15 (d, J=6.6 Hz, 6H). Anal. Calcd. for $C_{24}H_{22}N_4OS$ 1.7$H_2O$: C, 64.75; H, 5.75; N, 12.59; S, 7.20. Found: C, 64.79; H, 5.36; N, 12.74; S, 7.08.

Example 35(c)

6-[2-(Cyclobutylcarbamoyl)phenylsulfanyl]-3-E-[2-(pyridin-2-yl)ethenyl]-1H-indazole

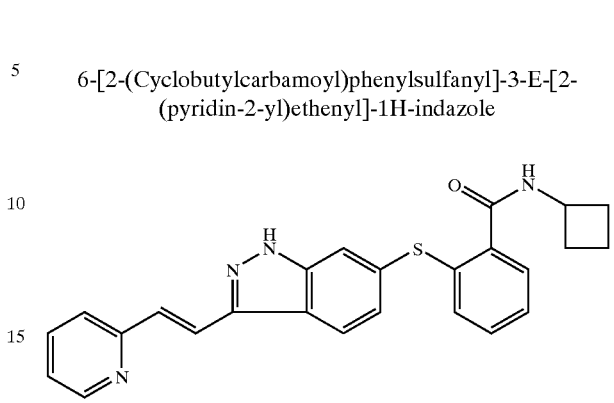

Example 35(c) was prepared in a similar manner to that described for Example 35(a) except that cyclobutylamine was used instead of n-propylamine. $^1$H NMR (DMSO-$d_6$) δ 13.31 (s, 1H), 8.62 (m, 2H), 8.19 (d, J=8.5 Hz, 1H), 7.94 (m, 2H), 7.80 (dt, J=1.7, 7.5 Hz, 1H), 7.65 (t, J=8.1 Hz, 1H), 7.56 (s, 1H), 7.47 (m, 1H), 7.30 (m, 3H), 7.17 (d, J=8.3 Hz, 1H), 4.36 (septet, J=8.1 Hz, 1H), 2.22 (m, 2H), 2.03 (m, 2H), 1.67 (m, 2H). Anal. Calcd. for $C_{25}H_{22}N_4OS.(0.5H_2O, 0.9 DMF)$: C, 66.36; H, 5.89; N, 13.69; S, 6.40. Found: C, 66.21; H, 5.78; N, 13.82; S, 6.36.

Example 35(d)

6-(2-Carbamoylphenylsulfanyl)-3-E-[2-(pyridin-2-yl)ethenyl]-1H-indazole

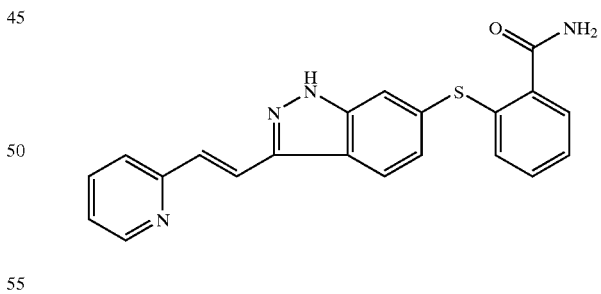

Example 35(d) was prepared in a similar manner to that described for Example 35(a) except that ammonia was used instead of n-propylamine. $^1$H NMR (DMSO-$d_6$) δ 8.60 (d, J=4.9 Hz, 1H), 8.21 (d, J=8.3 Hz, 1H), 7.94 (m, 3H), 7.81 (dt, J=1.7, 7.5 Hz, 1H), 7.60 (m, 4H), 7.48 (bs, 1H), 7.25 (m, 4H), 7.0 (m, 1H). Anal. Calcd. for $C_{21}H_{16}N_4OS.0.25H_2O$: C, 66.91; H, 4.41; N, 14.86; S, 8.51. Found: C, 66.99; H. 4.40; N, 15.10; S, 8.49.

Example 35(e)

6-[2-((1-methylpyrrol-2-ylhydrazido)carbonyl)phenylsulfanyl]-3-E-[2-(pyridin-2-yl)ethenyl]-1H-indazole

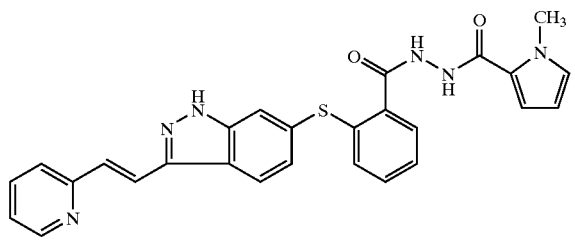

Example 35(e) was prepared in a similar manner to that described for Example 35(a) except that 1-methylpyrrol-2-ylhydrazide was used instead of n-propylamine. $^1$H NMR (DMSO-$d_6$) δ 13.34 (s, 1H), 10.25 (s, 1H), 10.05 (s, 1H), 8.60 (d, J=4.5 Hz, 1H), 8.22 (d, J=8.7 Hz, 1H), 7.95 (d, J=16.2 Hz, 1H), 7.81 (dt, J=1.7, 7.5 Hz, 1H), 7.66 (m, 3H), 7.57 (d, J=16.0 Hz, 1H), 7.43–7.18 (m, 4H), 7.07 (d, J=7.9 Hz, 1H), 7.00 (d, J=3.4 Hz, 2H), 6.07 (t, J=3.2 Hz, 1H), 3.88 (s, 3H). Anal. Calcd for $C_{27}H_{22}N_6O_2S \cdot 0.6\,H_2O$: C, 64.17; H, 4.63; N, 16.63; S, 6.34. Found: C, 64.24; H, 4.48; N. 16.56; S, 6.28.

Example 35(g)

6-[2-((4-Methoxybenzyl)methylcarbamoyl)phenylsulfanyl]-3-E-[2-(pyridin-2-yl)ethenyl]-1H-indazole Example 35(g) was prepared in a similar manner to that described for Example 35(a) except that 4-methoxybenzyl amine was used instead of n-propylamine. $^1$H NMR (DMSO-$d_6$)δ 13.31 (s, 1H), 8.90 (t, J=5.5 Hz, 1H), 8.60(d, J=4.2 Hz, 1H), 8.19 (d, J=8.3 Hz, 1H), 7.95 (d, J=16.3 Hz, 1H), 7.81 (dt, J=1.7, 7.5 Hz, 1H), 7.66 (d, J=7.9 Hz, 1H), 7.55 (m, 3H), 7.30 (m, 5H), 7.18 (d, J=8.5 Hz, 1H), 7.10 (d, J=8.3 Hz, 1H), 4.39 (d, J=6.0 Hz, 2H), 3.72 (s, 3H). Anal. Calcd. for $C_{29}H_{24}N_4O_2S \cdot 0.6H_2O$: C, 69.19; H, 5.05; N, 11.13; S, 6.37. Found: C, 69.12; H, 4.85; N, 11.24; S, 6.35.

Example 35(f)

6-[2-((2-fluorobenzyl)methylcarbamoyl)phenylsulfanyl]-3-E-[2-(pyridin-2-yl)ethenyl]-1H-indazole

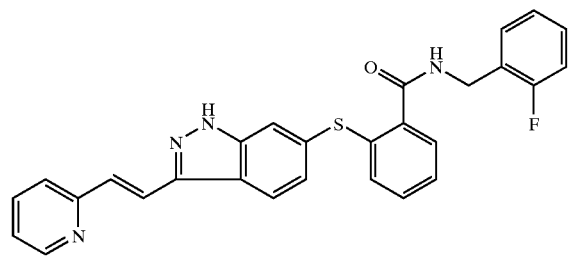

Example 35(f) was prepared in a similar manner to that described for Example 35(a) except that 2-fluorobenzyl amine was used instead of n-propylamine. $^1$H NMR (DMSO-$d_6$) δ 13.31 (s, 1H), 8.99(t, J=5.8 Hz, 1H), 8.61 (d, J=4.5 Hz, 1H), 8.19 (d, J=8.5 Hz, 1H), 7.94 (d, J=16.2 Hz, 1H), 7.81 (dt, J=1.7, 7.5 Hz, 1H), 7.66 (d, J=8.1 Hz, 1H), 7.56 (m, 3H), 7.47 (t, J=7.9 Hz, 1H), 7.31 (m, 4H), 7.15 (m, 4H), 4.51 (d, J=5.7 Hz, 2H). Anal. Calcd. for $C_{28}H_{21}FN_4OS \cdot 0.25H_2O$: C, 69.33; H, 4.47; N, 11.55; S, 6.61. Found: C, 69.32; H, 4.41; N, 11.58; S, 6.59.

Example 35(h)

6-[2-((5-Methylfur-2-yl)methylcarbamoyl)phenylsulfanyl]-3-E-[2-(pyridin-2-yl)ethenyl]-1H-indazole Example 35(h) was prepared in a similar manner to that described for Example 35(a) except that 5-methylfur-2-yl amine was used instead of n-propylamine. $^1$H NMR (DMSO-$d_6$) δ 13.31 (s, 1H), 8.88 (t, J=5.3 Hz, 1H), 8.60 (d, J=4.3 Hz, 1H), 8.19 (d, J=8.3 Hz, 1H), 7.95 (d, J=16.3 Hz, 1H), 7.81 (dt, J=1.7, 7.5 Hz, 1H), 7.66 (d, J=8.1 Hz, 1H), 7.54 (m, 3H), 7.30 (m, 4H), 7.18 (d, J=8.3 Hz, 1H), 7.06 (d, J=8.1 Hz, 3H). Anal. Calcd. for $C_{27}H_{22}N_4O_2S_{0.4}H_2O$: C, 68.45; H, 4.85; N, 11.83; S, 6.77. Found: C, 68.35; H, 4.80; N, 11.85; S, 6.68.

Example 35(i)

6-[2-(Benzyloxycarbamoyl)phenylsulfanyl]-3-E-[2-(pyridin-2-yl)ethenyl]-1H-indazole

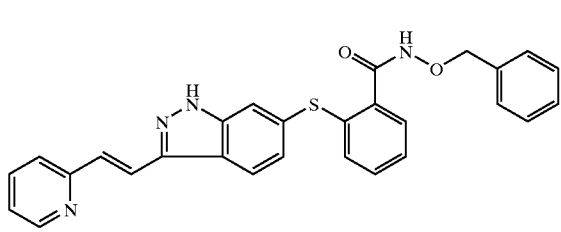

Example 35(i) was prepared in a similar manner to that described for Example 35(a) except that O-benzyl hydroxylamine was used instead of n-propylamine. $^1$H NMR (DMSO-d$_6$) δ 13.31 (s, 1H), 11.64 (s, 1H), 8.90 (t, J=5.5 Hz, 1H), 8.60 (d, J=4.1 Hz, 1H), 8.19 (d, J=8.3 Hz, 1H), 7.95 (d, J=16.3 Hz, 1H), 7.81 (dt, J=1.7, 7.5 Hz, 1H), 7.66 (d, J=7.9 Hz, 1H), 7.56 (m, 2H), 7.50–7.24 (m, 9H), 7.17 (t, J=8.5 Hz, 2H), 4.94 (s, 2H). Anal. Calcd. for C$_{28}$H$_{22}$N$_4$O$_2$S·0.8H$_2$O: C, 68.22; H, 4.83; N, 11.37; S, 6.50. Found: C, 68.08; H, 4.65; N, 11.41; S, 6.47.

Example 35(j)

6-[2-(Allyloxycarbamoyl)phenylsulfanyl]-3-E-[2-(pyridin-2-yl)ethenyl]-1H-indazole

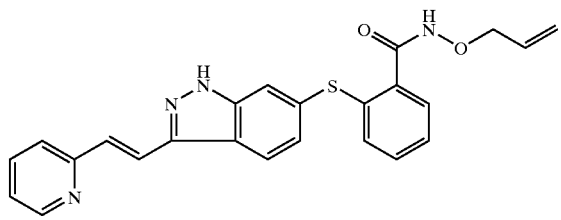

Example 35(j) was prepared in a similar manner to that described for Example 35(a) except that O-allyl hydroxylamine was used instead of n-propylamine. $^1$H NMR (DMSO-d$_6$) δ 13.32 (s, 1H), 11.56 (s, 1H), 8.60 (d, J=4.1 Hz, 1H), 8.19 (d, J=8.3 Hz, 1H), 7.95 (d, J=16.5 Hz, 1H), 7.81 (dt, J=1.7, 7.5 Hz, 1H), 7.66 (d, J=7.9 Hz, 1H), 7.56 (m, 2H), 7.48–7.24 (m, 5H), 7.16 (m, 2H), 6.00 (m, 1H), 5.37 (d, J=18.3 Hz, 1H), 5.27 (d, J=11.3 Hz, 1H), 4.42 (d, J=6.0 Hz, 1H). Anal. Calcd. for C$_{24}$H$_{20}$N$_4$O$_2$S·(0.2H$_2$O, 0.2CH$_2$Cl$_2$): C, 65.35; H, 4.96; N, 12.10; S, 6.92. Found: C, 65.24; H, 4.50; N, 12.56; S, 7.17.

Example 35(k)

6-[2-(Isopropoxycarbamoyl)phenylsulfanyl]-3-E-(2-(pyridin-2-yl)ethenyl]-1H-indazole

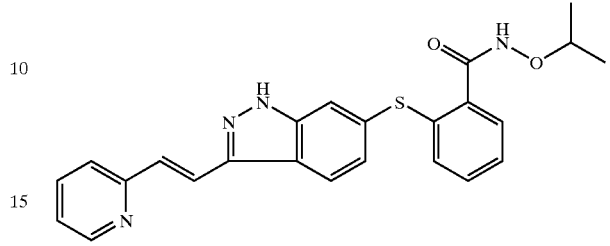

Example 35(k) was prepared in a similar manner to that described for Example 35(a) except that O-isopropyl hydroxylamine was used instead of n-propylamine. $^1$H NMR (DMSO-d$_6$) δ 13.30 (s, 1H), 11.33 (s, 1H), 8.60 (d, J=4.1 Hz, 1H), 8.19 (d, J=8.3 Hz, 1H), 7.95 (d, J=16.5 Hz, 1H), 7.81 (dt, J=1.7, 7.5 Hz, 1H), 7.66 (d, J=7.9 Hz, 1H), 7.55 (m, 2H), 7.48–7.24 (m, 4H), 7.17 (d, J=8.3 Hz, 2H), 4.12 (septet, J=5.7 Hz, 1H), 1.21 (d, J=6.2 Hz, 6H. Anal. Calcd. for C$_{24}$H$_{22}$N$_4$O$_2$S·(0.4H$_2$O, 0.7 CH$_2$Cl$_2$): C, 59.67; H, 4.91; N, 11.27; S, 6.45. Found: C, 59.61; H, 4.81; N, 11.42; S, 6.45.

Example 35(l)

6-[2-((4-Aminobenzyl)methylcarbamoyl)phenylsulfanyl]-3-E-[2-(pyridin-2-yl)ethenyl]-1H-indazole

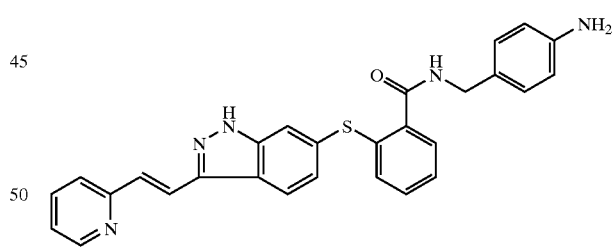

Example 35(l) was prepared in a similar manner to that described for Example 35(a) except that 4-aminobenzyl amine was used instead of n-propylamine. $^1$H NMR (DMSO-d$_6$) 513.31 (s, 1H), 8.78 (t, J=6.0 Hz, 1H), 8.60 (d, J=4.3 Hz, 1H), 8.19 (d, J=8.1 Hz, 1H), 7.95 (d, J=16.3 Hz, 1H), 7.85 (bs, 1H), 7.81 (dt, 1=1.7, 7.5 Hz. 1H), 7.66 (d, J=7.9 Hz, 1H), 7.59 (s, 1H), 7.51 (m, 2H), 7.30 (m, 3H), 7.19 (d, J=8.7 Hz, 1H), 7.05 (m, 3H), 6.56 (d, J=8.7 Hz, 1H), 6.51 (d, J=8.5 Hz, 2H), 4.29 (d, J=6.0 Hz, 2H). Anal. Calcd. for C$_{28}$H$_{23}$N$_5$OS·0.6 H$_2$O: C, 68.86; H, 4.99; N, 14.34; S, 6.57. Found: C, 68.83; N 4.80; N, 14.16; S. 6.52.

Example 35(m)

6-[2((Thien-2-ylhydrazido)carbonyl)phenylsulfanyl]-3-E-[2-(pyridin-2-yl)ethenyl]-1H-indazole

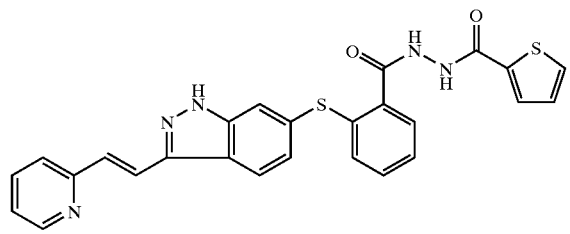

Example 35(m) was prepared in a similar manner to that described for Example 35(a) except that thien-2-ylhydrazide was used instead of n-propylamine. $^1$H NMR (DMSO-d$_6$) δ 13.49 (bs, 1H), 10.64 (s, 1H), 10.47 (s, 1H), 8.66 (d, J=4.0 Hz, 1H), 8.22 (d, J=8.5 Hz, 1H), 8.08–7.82 (m, 5H), 7.66 (m, 3H), 7.39 (m, 3H), 7.24 (m, 2H), 7.09 (d, J=8.1 Hz, 1H), 7.00 (d, J=3.4 Hz, 2H), 6.07 (t, J=3.2 Hz, 1H), 3.88 (s, 3H). Anal. Calcd. for C$_{26}$H$_{19}$N$_5$O$_2$S$_2$.1.5H$_2$O: C, 59.52; H, 4.23; N, 13.35; S, 12.22. Found: C, 59.56; H, 4.42; N, 13.33; S, 11.75.

Example 35(n)

6-[2-(N$^2$-(pyrid-2-ylhydrazino)carbonyl)phenylsulfanyl]-3-E-[2-(pyridin-2-yl)ethenyl]-1H-indazole

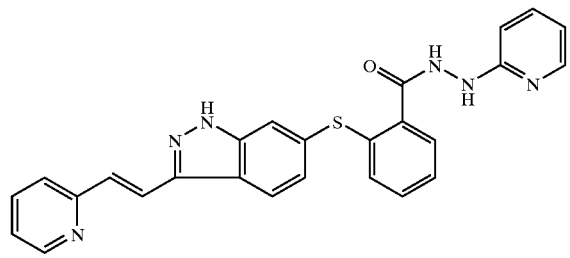

Example 35(n) was prepared in a similar manner to that described for Example 35(a) except that 2-hydrazinopyridine was used instead of n-propylamine. $^1$H NMR (DMSO-d$_6$) δ 13.31 (s, 1H), 10.30 (s, 1H), 8.60 (d, J=4.4 Hz, 1H), 8.48 (s, 1H), 8.21 (d, J=8.5 Hz, 1H), 8.09 (d, J=4.9 Hz, 1H), 7.94 (d, J=16.4 Hz, 1H), 7.81 (dt, J=1.7, 7.5 Hz, 1H), 7.67 (m, 1H), 7.62–7.47 (m, 3H), 7.40 (m, 2H), 7.31–7.12 (m, 3H), 6.73 (m, 2H). Anal. Calcd. for C$_{26}$H$_{20}$N$_6$OS.0.3 H$_2$O: C, 66.45; H, 4.42; N, 17.88; S, 6.82. Found: C, 66.33; H, 4.50; N, 17.78; S, 6.60.

Example 35(o)

6-[2-(N-Hydroxy-N-methylcarbamoyl)phenylsulfanyl]-3-E-[2-(pyridin-2-yl)ethenyl]-1H-indazole

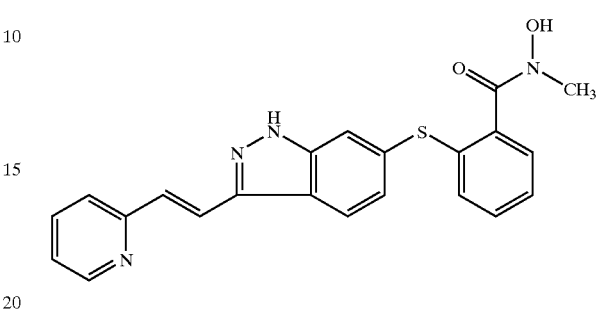

Example 35(o) was prepared in a similar manner to that described for Example 35(a) except that N-methyl hydroxylamine was used instead of n-propylamine. $^1$H NMR (DMSO-d$_6$) δ 13.24 (s, 1H), 9.94 (s, 1H), 8.60 (d, J=4.0 Hz, 1H), 8.14 (d, J=8.3 Hz, 1H), 7.92 (d, J=16.2 Hz, 1H), 7.80(dt, J=1.7, 7.5 Hz, 1H), 7.65 (t, J=8.5 Hz, 1H), 7.54 (d, J=16.5 Hz, 1H), 7.47–7.24 (m, 6H), 7.16 (d, J=8.5 Hz, 1H) 3.24 (bs, 1H). Anal. Calcd. for C$_{22}$H$_{18}$N$_4$O$_2$S.(0.5H$_2$O, 0.3 CH$_2$Cl$_2$): C, 61.29; H, 4.52; N, 12.82; S, 7.34. Found: C, 61.24; H, 4.33; N, 12.67; S, 7.34.

Example 35(p)

6-[2-((Pyrid-4-yl)methylcarbamoyl)phenylsulfanyl]-3-E-[2-(pyridin-2-yl)ethenyl]-1H-indazole

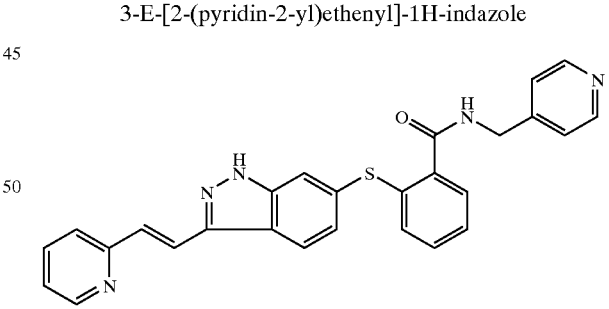

Example 35(p) was prepared in a similar manner to that described for Example 35(a) except that 4-aminomethyl pyridine was used instead of n-propylamine. $^1$H NMR (DMSO-d$_6$) δ 13.31 (bs, 1H), 9.07 (t, J=6.8 Hz, 1H), 8.60 (d, J=4.2 Hz, 1H), 8.48 (d, J=5.0 Hz, 1H), 8.19 (d, J=8.7 Hz, 1H), 7.95 (d, J=16.4 Hz, 1H), 7.80 (dt, J 1.7, 7.5 Hz, 1H), 7.68–7.52 (m, 3H), 7.42 (m, 2H), 7.39–7.31 (m, 3H), 7.27 (m, 1H), 7.20–7.10 (m, 2H), 4.48 (d, J=6.2 Hz, 2H).

Example 35(q)

6-[2-((2-Methylphenylhydrazido)carbonyl)phenylsulfanyl]-3-E-[2-(pyridin-2-yl)ethenyl]-1H-indazole

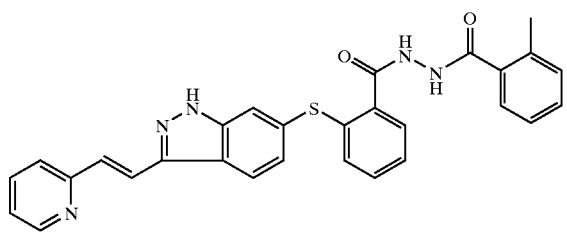

Example 35(q) was prepared in a similar manner to that described for Example 35(a) except that 2-methylphenyl hydrazide was used instead of n-propylamine. $^1$H NMR (DMSO-d$_6$) δ 13.43 (s, 1H), 10.45 (s, 1H), 10.28 (s, 1H), 8.64 (d, J=4.0 Hz, 1H), 8.22 (d, J=8.2 Hz, 1H), 8.01 (d J=16.6 Hz, 1H), 7.92 (m, 1H), 7.81 (m, 1H), 7.69 (m, 1H), 7.60 (d, J=16.4 Hz, 1H), 7.507.22 (m, 8H), 7.07 (d, J=7.7 Hz, 1H), 2.45 (s, 3H).

Example 35(r)

6-[2-(methoxycarbamoyl)phenylsulfanyl]-3-E-[2-(pyridin-2-yl)ethenyl]-1H-indazole

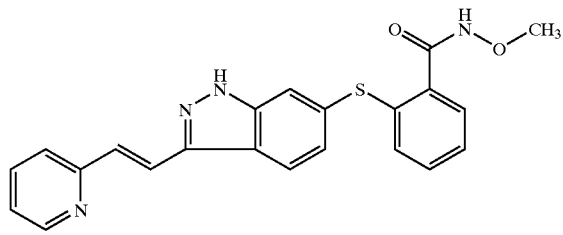

Example 35(r) was prepared in a similar mariner to that described for Example 35(a) except O-methyl hydroxylamine was used instead of n-propylamine. $^1$H NMR (DMSO-d$_6$) δ 13.32 (s, 1H), 11.60 (s, 1H), 8.60 (d, J=3.8 Hz, 1H), 8.19 (d, J=8.4 Hz, 1H), 7.95 (d, J=16.2 Hz, 1H), 7.81 (dt, J=1.7, 7.5 Hz, 1H), 7.66 (d, J=7.9 Hz, 1H), 7.56 (m, 2H), 7.47 (dd, J=7.4, 1.7 Hz, 1H), 7.43–7.24 (m, 3H), 7.17 (m, 2H), 3.72 (s, 3H). Anal. Calcd. for $C_{22}H_{18}N_4O_2S \cdot 0.6 \; CH_2Cl_2$: C, 59.86; H, 4.27; N, 12.36; S. 7.07. Found: C, 59.94; H, 4.40; N, 12.00; S, 6.80.

Example 35(s)

6-[2-((Cyclopropyl)methoxycarbamoyl)phenylsulfanyl]-3-E-[2-(pyridin-2-yl)ethenyl]-1H-indazole

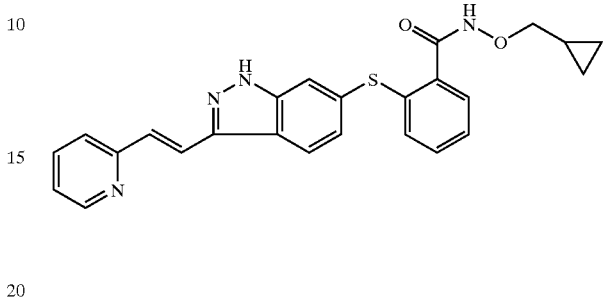

Example 35(s) was prepared in a similar manner to that described for Example 35(a) except that O-cyclopropyl hydroxylamine was used instead of n-propylamine. $^1$H NMR (DMSO-d$_6$) δ 13.38 (s, 1H), 11.51 (s, 1H), 8.64 (d, J=3.8 Hz, 1H), 8.18 (d, J=8.4 Hz, 1H), 8.00 (d, J=16.4 Hz, 1H), 7.86 (m, 2H), 7.63–752 (m, 2H), 7.49–7.29 (m, 4H), 7.17 (m, 2H), 3.70 (d, J=7.2 Hz, 1H), 1.10 (m, 1H), 0.53 (m, 2H), 0.27 (m, 2H). Anal. Calcd. for $C_{25}H_{22}N_4O_2S \; 1.6H_2O$: C, 63.70; H, 5.39; N, 11.89; S, 6.80. Found: C, 63.58; H, 4.95; N, 11.71; S, 6.66.

Example 35(t)

6-[2-(n-Propoxycarbamoyl)phenylsulfanyl]-3-E-[2-pyridin-2-yl)ethenyl]-1H-indazole

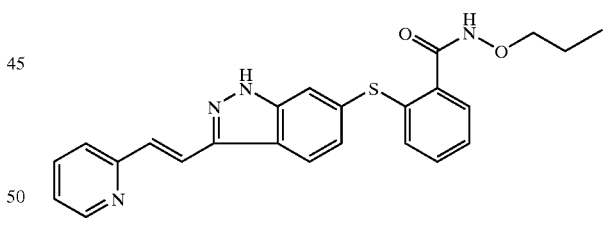

Example 35(t) was prepared in a similar manner to that described for Example 35(a) except that O-n-propyl hydroxylamine was used instead of n-propylamine. $^1$H NMR (DMSO-d$_6$) δ 13.31 (s, 1H), 11.48 (s, 1H), 8.60 (d, J=3.8 Hz, 1H), 8.19 (d, J=8.4 Hz, 1H), 7.95 (d, J=16.2 Hz, 1H), 7.81 (dt, J=1.7, 7.5 Hz, 1H), 7.66 (d, J=7.9 Hz, 1H), 7.60–7.52 (m, 2H), 7.49–7.24 (m, 4H), 7.17 (m, 2H), 3.84 (t, J=6.6 Hz, 2H), 1.62 (septet, J=6.4 Hz, 2H), 0.92 (t, J=6.1 Hz, 3H). Anal. Calcd. for $C_{24}H_{22}N_4O_2S \cdot (0.5H_2O, 0.25 \; CH_2Cl_2)$: C, 63.21; H, 5.14; N, 12.16; S, 6.96. Found: C, 63.15; H, 5.13; N, 12.17; S, 6.99.

Example 35(u)

6-[2-(Allylcarbamoyl)phenylsulfanyl]-3-E-[2-(pyridin-2-yl)ethenyl]-1H-indazole

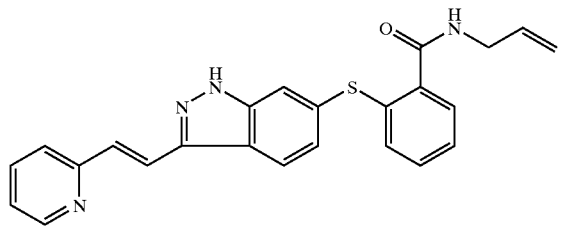

Example 35(u) was prepared in a similar manner to that described for Example 35(a) except that allylamine was used instead of n-propylamine. $^1$H NMR (DMSO-d$_6$) δ 13.31 (s, 1H), 8.60 (m, 2H), 8.19 (d, J=8.5 Hz, 1H), 7.93 (d, J=16.3 Hz, 3H), 7.79 (dt, J=1.7, 7.5 Hz, 1H), 7.64 (m, 1H), 7.60–7.48 (m, 3H), 7.37–7.23 (m, 3H), 7.17 (d, J=8.5 Hz, 1H), 7.07 (m, 1H), 5.87 (m, 1H), 5.25 (dq, J=17.33, 1.9 Hz, 1H), 5.09 (dq, J=10.2, 1.9 Hz, 1H), 3.87 (m, 2H). Anal. Calcd. for C$_{24}$H$_{20}$N$_4$OS·0.8 CH$_2$Cl$_2$: C, 62.00; H, 4.53; N, 11.66; S, 6.67. Found: C, 62.08; H, 4.73; N, 11.99; S, 6.66. MALDI FTMS (MH$^+$) Calc'd, 413.1431, found 413.1449.

Example 35(v)

6-[2-(Cyclopropylmethyl-carbamoyl)phenylsulfanyl]-3-E-[2-(pyridin-2-yl)ethenyl]-1H-indazole

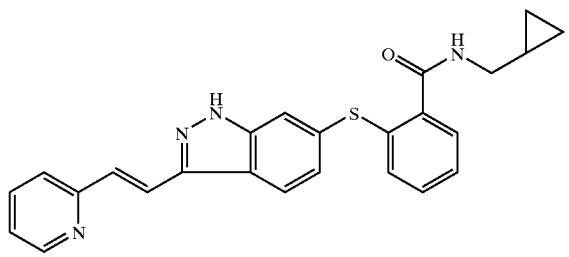

Example 35(v) was prepared in a similar manner to that described for Example 35(a) except that cyclopropylmethyl amine was used instead of n-propylamine. $^1$H NMR (DMSO-d$_6$) δ 13.30 (s, 1H), 8.60 (d, J=4.0 Hz, 1H), 8.48 (t, J=5.3 Hz, 1H), 8.17 (d, J=8.7 Hz, 1H), 7.90 (d, J=16.4 Hz, 1H), 7.80 (dt, J=1.7, 7.5 Hz, 1H), 7.67–7.45 (m, 4H), 7.33–7.23 (m, 3H), 7.18 (d, J=8.3 Hz, 1H), 7.06 (m, 1H), 3.13 (t, J=6.2 Hz, 2H), 1.00 (m, 1H), 0.41 (m, 1H), 0.24 (m, 1H). Anal. Calcd. for C$_{25}$H$_2$N$_4$OS·0.5 CH$_2$Cl$_2$: C, 65.30; H. 4.94; N, 11.95; S, 6.84. Found: C, 65.10; H. 4.93; N, 12.04; S, 6.82. MALDI FTMS (MH$^+$) Calc'd 427.1587, found 427.1605.

Example 35(w)

6-[2-(Cyanomethylcarbamoyl)phenylsulfanyl]-3-E-[2-(pyridin-2-yl)ethenyl]-1H-indazole

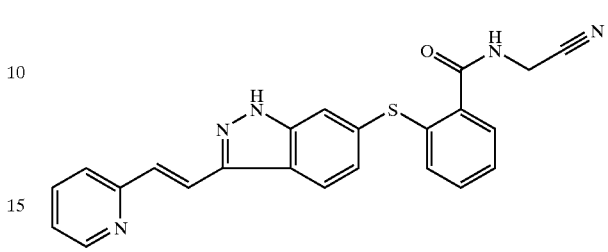

Example 35(w) was prepared in a similar manner to that described for Example 35(a) except that aminoacetonitrile was used instead of n-propylamine. $^1$H NMR (DMSO-d$_6$) δ 13.35 (s, 1H), 9.19 (t, J=5.3 Hz, 1H), 8.60 (d, J=4.8 Hz, 1H), 8.20 (d, J=8.7 Hz, 1H), 7.94 (d, J=16.4 Hz, 3H), 7.79 (dt, J=1.7, 7.5 Hz, 1H), 7.70–7.50 (m, 4H), 7.41–7.23 (m, 3H), 7.18 (d, J=8.5 Hz, 1H), 7.06 (d, J=6.6 Hz, 1H), 4.32 (d, J=5.5 Hz, 2H). MALDI FTMS (MH$^+$) Calc'd 412.1227, found 412.1215.

Example 35(x)

6-[2-(Ethylcarbamoyl)phenylsulfanyl]-3-E-[2-(pyridin-2-yl)ethenyl]-1H-indazole

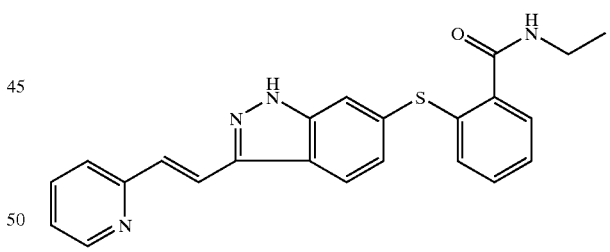

Example 35(x) was prepared in a similar manner to that described for Example 35(a) except that ethylamine was used instead of n-propylamine. $^1$H NMR (DMSO-d$_6$) δ 8.60 (d, J=4.0 Hz, 1H), 8.40 (t, J=6.2 Hz, 1H), 8.18 (d, J=8.5 Hz, 1H), 7.94 (m, 3H), 7.81 (dt, J=1.7, 7.5 Hz, 1H), 7.68–7.44 (m, 3H), 7.56 (m, 2H), 7.30 (m, 3H), 7.17 (dd, J=8.1, 1.8 Hz, 1H), 7.06 (m, 1H), 3.24 (m, 2H), 1.11 (t, J=7.0 Hz, 3H). Anal. Calcd. for C$_{23}$H$_{20}$N$_4$OS·(1.75H$_{20}$, 1.0 DMF): C, 61.82; H, 6.09; N, 13.87; S, 6.35. Found: C, 6158; H, 5.66; N, 13.96; S, 5.93. MALDI FIMS (MH$^+$) Calc'd 401.1431, found 401.1417.

Example 35(y)

6-[2-(Thiazol-2-ylcarbamoyl)phenylsulfanyl]-3-E-[2-(pyridin-2-yl)ethenyl]-1H-indazole

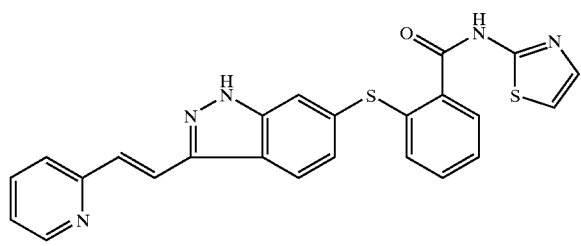

Example 35(y) was prepared in a similar manner to that described for Example 35(a) except that 2-aminothiazole was used instead of n-propylamine. $^1$H NMR (DMSO-d$_6$) δ 13.32 (s, 1H), 12.67 (s, 1H), 8.60 (d, J=4.1 Hz, 1H), 8.18 (d, J=85 Hz, 1H), 7.93 (d, J=16.3 Hz, 1H), 7.80 (dt, J=1.7, 7.5 Hz, 1H), 7.65 (d, J=7.9 Hz, 1H), 7.65 (d, J=8.3 Hz, 1H), 7.607.51 (m, 3H), 7.49–7.34 (m, 2H), 7.26 (m, 2H), 7.18 (m, 2H). Anal. Calcd. for C$_{24}$H$_{17}$N$_5$OS$_2$.0.75H$_2$O: C, 61.45; H, 3.98; N, 14.93; S, 13.67. Found: C, 61.35; H, 4.10; N, 14.96; S, 13.68.

Example 35(z)

6-[2-(2-(Ethoxy)ethylcarbamoyl)phenylsulfanyl]-3-E-[2-(pyridin-2-yl)ethenyl]-1H-indazole

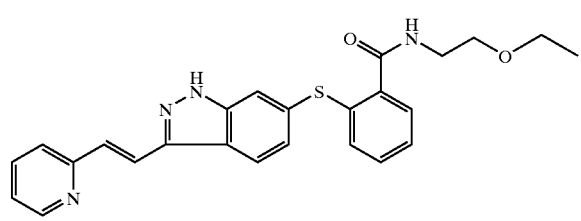

Example 35(z) was prepared in a similar manner to that described for Example 35(a) except that 2-ethoxyethyl amine was used instead of n-propylamine. $^1$H NMR (DMSO-d$_6$) δ 13.30 (s, 1H), 8.60 (d, J=4.0 Hz, 1H), 8.45 (t, J=6.2 Hz, 1H), 8.18 (d, J=8.5 Hz, 1H), 7.93 (m, 2H), 7.80 (dt, J=1.7, 7.5 Hz, 1H), 7.65 (d, J=7.7 Hz, 1H), 7.60–7.45 (m, 3H), 7.36–7.23 (m, 3H), 7.17 (d, J=8.3 Hz, 1H), 7.07 (m, 1H), 3.50 (m, 6H), 1.10 (d, J=7.0 Hz, 3H). Anal. Calcd. for C$_{25}$H$_{24}$N$_4$O$_2$S-0.5 CH$_2$Cl$_2$: C, 62.89; H, 5.17; N, 11.50; S, 6.58. Found: C, 62.45; H, 5.33; N, 11.25; S, 6.55.

Example 35(aa)

6-[2-((3-methoxybenzyl)methylcarbamoyl)phenylsulfanyl]-3-E-[2-(pyridin-2-yl)ethenyl]-1H-indazole

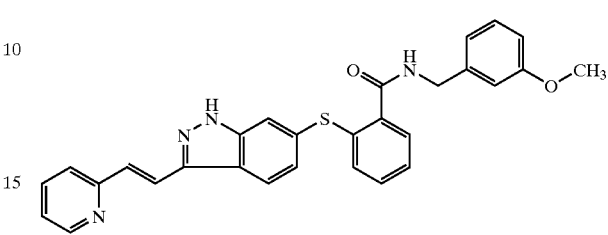

Example 35(aa) was prepared in a similar manner to that described for Example 35(a) except that 3-methoxybenzyl amine was used instead of n-propylamine. $^1$H NMR (DMSO-d$_6$) 13.30 (s, 1H), 8.97 (t, J=5.5 Hz, 1H), 8.60 (d, J=4.2 Hz, 1H), 8.18 (d, J=8.7 Hz, 1H), 7.93 (d, J=16.3 Hz, 1H), 7.80 (dt, J=1.7, 7.5 Hz, 1H), 7.65 (d, J=7.9 Hz, 1H), 7.60–7.51 (m, 3H), 7.38–7.15 (m, 5H), 7.08 (m, 1H), 6.94 (m, 2H), 6.80 (dd, J=8.1, 1.5 Hz, 1H), 4.44 (d, J=6.6 Hz, 2H), 3.71 (s, 3H). Anal. Calcd. for C$_{29}$H$_{24}$N$_4$O$_2$S.0.4H$_2$O: C, 60.25; H, 4.50; N, 17.57; S, 8.04. Found: C, 60.14; H, 4.47; N, 17.42; S, 8.00.

Example 35(bb)

6-[2-((fur-2-yl)methylcarbamoyl)phenylsulfanyl]-3-E-[2-(pyridin-2-yl)ethenyl]-1H-indazole

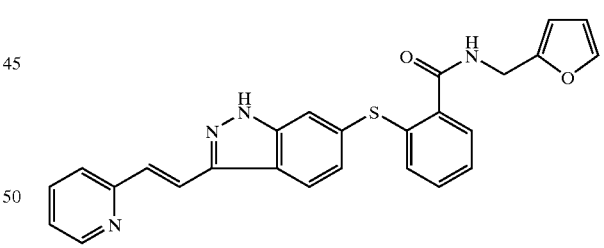

Example 35(bb) was prepared in a similar manner to that described for Example 35(a) except that 2-aminomethyl furan was used instead of n-propylamine. $^1$H NMR (DMSO-d$_6$) δ 13.31 (s, 1H), 8.93 (t, J=5.7 Hz, 1H), 8.60 (d, J=4.3 Hz, 1H), 8.19 (d, J=8.0 Hz, 1H), 7.93 (d, 1=16.5 Hz, 1H), 7.80 (dt, J=1.9, 7.4 Hz, 1H), 7.66 (d, J=7.7 Hz, 1H), 7.59–7.48 (m, 4H), 7.30 (m, 4H), 7.37–7.24 (m, 3H), 7.18 (d, J=9.2 Hz, 1H), 7.06 (d, J=8.1 Hz, 1H), 6.40 (m, 1H), 6.31 (mp, 1H), 4.44(d, J=5.3 Hz, 2H). Anal. Calcd. or C$_{26}$H$_{20}$N$_4$O$_2$S. (0.1H$_2$O, 0.75 CH$_2$Cl$_2$): C, 62.02; H, 4.22: N, 10.82; S. 6.19. Found: C, 61.58; H, 4.30; N, 10.55; S, 6.12.

Example 35(cc)

6-[2-(2-Propynylcarbamoyl)phenylsulfanyl]-3-E-[2-(pyridin-2-yl)ethenyl]-1H-indazole

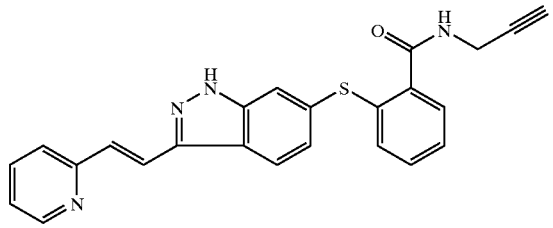

Example 35(cc) was prepared in a similar manner to that described for Example 35(a) except that propargylamine was used instead of propylamine (76%): $^1$H NMR (300 MHz, CDCl$_3$) δ 8.56 (m, 1H), 7.96 (d, 1H, J=8.6 Hz), 7.81 (d, 1H, 16.4 Hz), 7.68 (dt, 1H, J=1.8, 7.8 Hz), 7.6 (m, 1H), 7.52–7.45 (m, 3H), 7.3–7.23 (m, 3H), 7.16 (m, 2H), 4.10 (m, 2), 2.20 (t, 1H. J=2.6 Hz). LCMS (100% area) Rt=3.36 min, (pos) [M+H]/z Calc'd 411.1, found 411.1. Analyzed with 0.2H$_2$O, 0.17 DMF, 1.2 dichloromethane, Calc'd, C (58.44), H (4.19), N (11.05), S (6.07). Found: C (58.18), H (4.11), N (10.98), S (6.05).

Example 35(dd)

6-[2-(ethoxycarbamoyl)phenylsulfanyl]-3-E-[2-(pyridin-2-yl)ethenyl]-1H-indazole

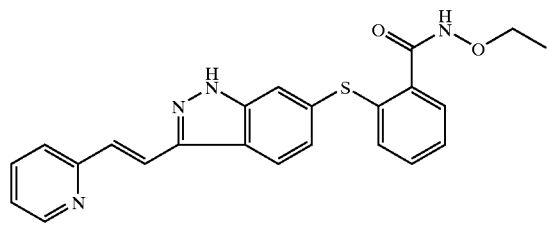

Example 35(dd) was prepared in a similar manner to that described for Example 35(a) except that ethoxyamine was used instead of propylamine: $^1$H NMR (300 MHz, CDCl$_3$) δ 11.60 (s, 1H), 8.71 (d, 1H, J=7.9 Hz), 8.30 (d, 1H, J=8.5 Hz), 8.05 (d, 1H, J=16.4 Hz), 7.91 (dt, 1H, J=1.7, 7.7 Hz), 7.76 (d, 1H, J=7.8 Hz), 7.67 (m, 2H), 7.56 (dd, 1H, J=1.8, 7.3 Hz), 7.52–7.36 (m, 3H), 7.28 (m, 2H)4.06 (q, 2H, j 7.0 Hz), 1.31 (t, 2H, J=7.0 Hz); LCMS (100% area) Rt=3.28 min, (pos) [M+H]/z Calc'd 417.1, found 417.1. Analyzed with 0.2H$_2$O Calc'd, C (65.53), H (4.98), N (13.05), S (7.48). Found: C (65.66), H (4.91), N (12.75), S (7.44).

Example 35(ee)

6-[2-(2-Methyl-2-propenylcarbamoyl)phenylsulfanyl]-3-E-[2-(pyridin-2-yl)ethenyl]-1H-indazole

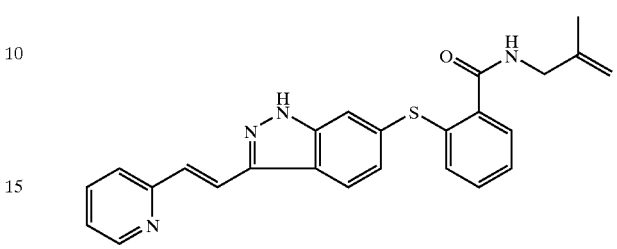

Example 35(ee) was prepared in a similar manner to that described for Example 35(a) except that 2-methylallylamine was used instead propylamine: $^1$H NMR (300 MHz, CDCl$_3$) δ 8.56 (m, 1H), 7.98 (d, 1H, J=85 Hz), 7.81 (d, 1H, J=16.4 Hz), 7.69 (dt, 1H, 3=1.7, 7.7 Hz), 7.60 (m, 1H), 7.53–7.42 (m, 3H), 7.32–7.24 (m, 3H), 7.16 (m, 2H), 6.72 (m, 1H), 4.89 (s. 1H), 4.81 (s, 1H), 3.90 (d, 2H, J=5.5 Hz), 1.71 (s, 3H). LCMS (100% area) Rt=3.37 min, (pos) [M+H]/z Calc'd 427.1, found 427.1. Analyzed with 0.7H$_2$O, 0.1 dichloromethane Calc'd, C (67.35), H (5.31), N (12.52), S (7.16). Found: C (67.55), H (5.39), N (12.35), S (7.15).

Example 35(ff)

6[2-((3-Fluorobenzyl)methylcarbamoyl)phenylsulfanyl]-3-E-[2-(pyridin-2-yl)ethenyl]-1H-indazole

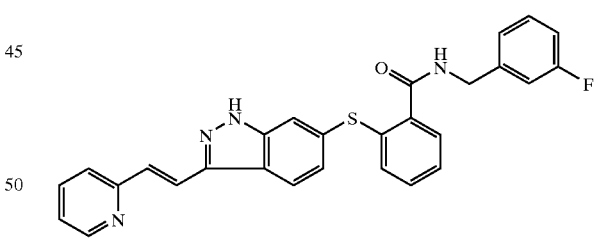

Example 35(ff) was prepared in a similar manner to that described for Example 35(a) except that 3-fluorobenzylamine was used instead propylamine: $^1$H NMR (300 MHz, CDCl$_3$) δ 8.60 (m, 1H), 7.97 (d, 1H, J=8.5 Hz), 7.86 (d, 1H, J=16.4 Hz), 7.70 (m, 2H), 7.51 (m, 2H), 7.33 (m, 4H), 7.18 (m, 2H), 7.11 (dd, 1H, J=1.6, 8.5 Hz), 6.95 (m, 3H), 4.51 (d, 2H, J=5.7 Hz); LCMS (100% area) Rt=3.55 min, (pos) [M+H]/z Calc'd 481.1, found 481.1. Analyzed with 0.7H$_2$O, 05 dichloromethane, Calc'd, C (63.91), H (4.40), N (10.46), S (5.99). Found: C (63.80), H (4.34), N (10.34), S (5.98).

Example 35(gg)

6-[2-(2-methylamino)ethylcarbamoyl)phenylsufanyl]-3-E-[2-(pyridin-2-yl)ethenyl]-1H-indazole

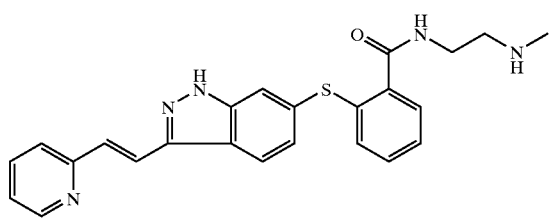

Example 35(gg) was prepared in a similar manner to that described for Example 35(a) except that N-methylethylenediamine was used instead of propylamine: $^1$H NMR (300 MHz, CDCl$_3$) δ 8.60 (m, 1H), 7.98 (d, 1H, J=8.5 Hz), 7.81 (d, 1H, J=16.4 Hz), 7.69 (dt, 1H, J=1.7, 7.7 Hz), 7.52 (m, 1H), 7.50–7.40 (m, 3H), 7.30–7.20 (m, 3H), 7.16 (m, 2H), 3.45 (t, 2H), 2.69 (t, 2H), 2.15 (bs, 3H); LCMS (100% area) Rt=3.16 min, (pos) [M+H]/z Calc'd 430.1, found 430.1. Analyzed with 0.2H$_2$O, 0.6 dichloromethane, 0.06 hex, Calc'd, C (61.28), H (5.24), N (14.31), S (6.55). Found: C (61.26), H (5.14), N (14.22), S (6.56).

Example 35(hh)

6-[2-(2-(Thien-2-yl)ethylcarbamoyl)phenylsulfanyl]-3-E-[2-(pyridin-2-yl)ethenyl]-1H-indazole

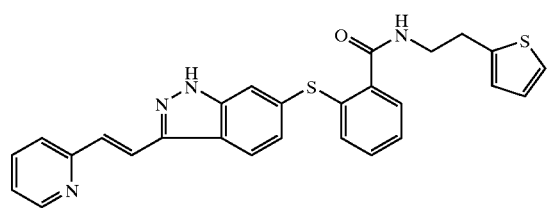

Example 35(hh) was prepared in a similar manner to that described for Example 35(a) except that 2-(2-aminoethyl)thiophene was used instead propylamine: $^1$H NMR (300 MHz, CDCl$_3$) δ 8.56 (m, 1H), 7.98 (d, 1H, J=8.5 Hz), 7.81 (d, 1H, J=16.4 Hz), 7.69 (dt, 1H, J=1.7, 7.7 Hz), 7.60 (m, 1H), 7.53–7.42 (m, 3H), 7.32–7.24 (m, 3H), 7.16 (m, 2H), 6.72 (m, 1H), 6.63 (m, 1H), 6.52 (m 1H), 3.45 (q, 2H), 3.00 (t, 2H). Analyzed with 0.5H$_2$O, 0.07 dichloromethane Calc'd, C (65.35), H (4.69), N (11.26), S (12.82). Found: C (65.49), H (4.80), N (11.21), S (12.77).

Example 35(ii)

6-[2-(aminocarbamoyl)phenylsulfanyl]-3-E-[2-(pyridin-2-yl)ethenyl]-1H-indazole

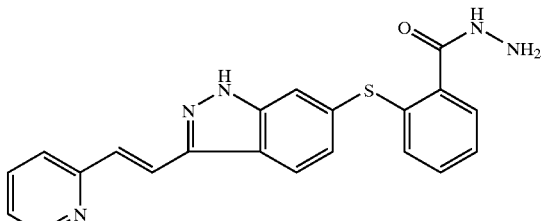

Example 35(ii) was prepared in a similar manner to that described for Example 35(a) except that hydrazine was used instead propylamine: $^1$H NMR (300 MHz, dmso-d6) □13.3 (s, 1H), 9.57 (s, 1H), 8.54 (d, 1H, J=3.9 z), 8.14 (d, 1H, J=8.5 Hz), 7.89 (d, 1H, J=16.4 Hz), 7.73 (dt, 1H, J=1.7, 7.6 Hz), 7.60 (d, 1H, J=7.9 Hz), 7.50 (m, 2H), 7.40 (dd, 1H, J=1.8, 7.1 Hz), 7.3–7.1 (m, 4H), 7.0 (m, 1H). LCMS (100% area) Rt=0.55 min, (pos) [M+H]l/z Calc'd 388.1, found 388.1. Analyzed with 0.1 DMF, 0.55 EtOAc, 0.12 Tol (NMR) and 0.15H$_2$O Calc'd, C (63.98), H (5.15), N (15.63), S (7.02). Found: C (63.99), H (5.07), N (15.75), S (6.89).

Examples 35(jj)–35(nn) can be prepared in a similar manner to that described for Example 35(a).

Example 35(jj)

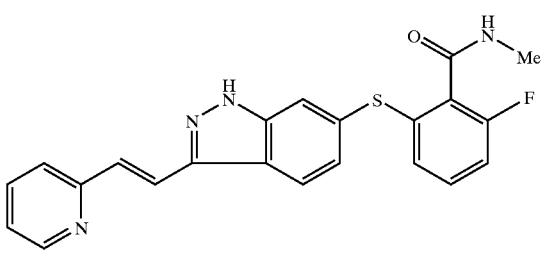

Example 35(kk)

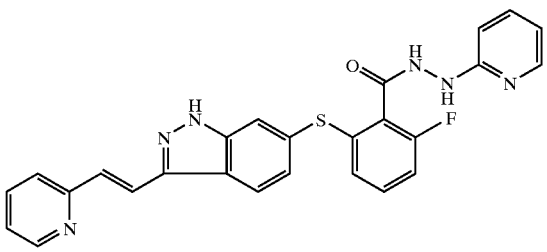

Example 35(ll)

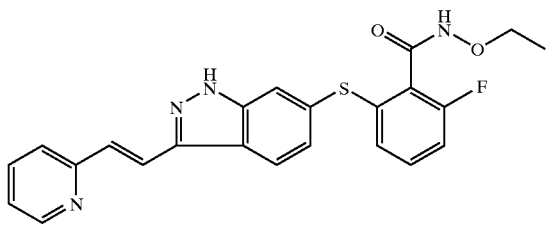

Example 35(mm)

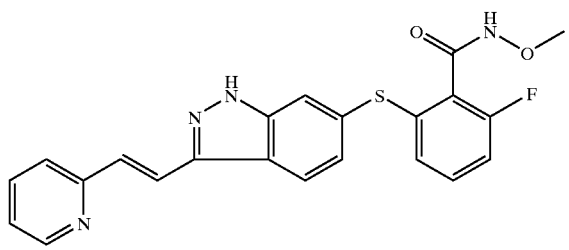

Example 35(nn)

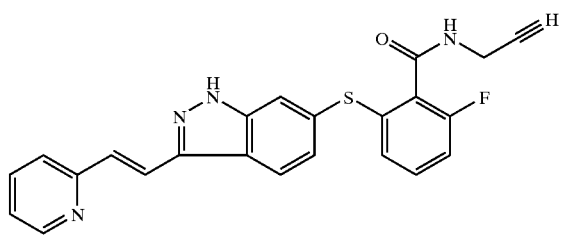

Example 36(a)

6-[2-(N²-(1-Methylimidazol-2-ylmethylidene)hydrazino)carbonyl)henylsulfanyl]-3-E-[2(pyridin-2-yl)ethenyl]-1H-indazole

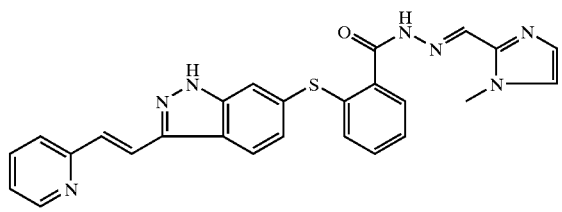

The compound prepared in Example 35(ii) (40 mg, 0.103 mmol) was treated with 1-methyl-2-imidazolecarboxaldehyde (29 mg, 0.258 mmol, 25 equiv) in ethanol to give Example 36(a): ¹H NMR (300 MHz, dmso-d6) δ 8.60 (m, 2H), 8.31 (s, 1H), 8.18 (d, 1H), 8.02 (d, 1H), 7.98 (d, 1H), 7.80 (m, 2H), 7.63 (m, 2H), 7.40 (m, 3H), 7.30 (m, 1H), 7.20 (m, 1H), 7.02 (m, 2H), 6.93 (s, 1H), 4.00 (s, 3H); LCMS (1100% area) Rt=4.0 min, (pos) [M+H]/z Calc'd 480.2, found 480.2. Analyzed with 1.45H₂O Calc'd, C (61.76), H (4.76), N (19.39), S (6.34). Found: C (61.78), H (4.67), N (19.34), S (6.39).

Example 36(b)

6-[2-(N²-(pyrid-2-ylmethylidene)hydrazino)carbonyl)-phenylsulfanyl]-3-E-[2-(pyridin-2-yl)ethenyl]-1H-indazole

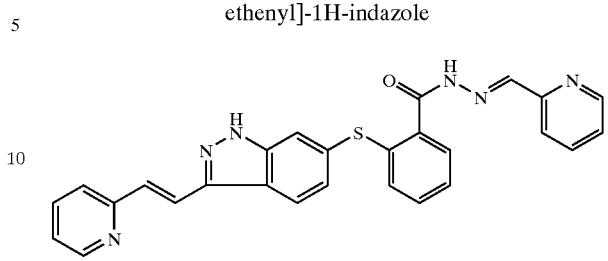

Example 36(b) prepared in a similar manner to that described for Example 36(a) except that 2-pyridylcarboxaldehyde was used instead of 1-methyl-2-imidazolecarboxaldehyde: ¹H NMR (300 MHz, CDCl₃) δ 8.57 (m, 2H), 8.45 (m, 2H), 8.22 (d, 1H), 8.10 (s, 1H), 7.93 (d, 1H), 7.83 (d, 1H), 7.8–7.1 (m, 1H); LCMS (100% area) Rt=4.0 min, (pos) [M+H]/z Calc'd 477.1, found 477.1. Analyzed with 0.85H₂O Calc'd, C (65.93), H (4.45), N (17.09), S (6.52). Found: C (66.02), H (4.42), N (16.95), S (6.38).

Example 36(c)

6-[2-(N²-(2,2,2-trifluroethylidene)hydrazino)carbonyl)phenylsulfanyl]-3-E-[2-(pyridin-2-yl)ethenyl]-1H-indazole

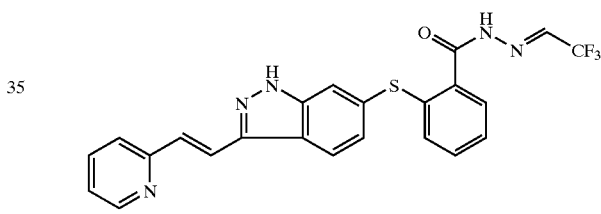

Example 36(c) was prepared in a similar manner to that described for Example 36(a) except that trifluoroacetaldehyde was used instead of 1-methyl-2-imidazolecarboxaldehyde: ¹H NMR (300 MHz, dmso-d6) δ 8.70 (m, 1H), 8.25 (m, 1H), 8.02 (d, 1H), 7.90 (dt, 1H), 7.80–7.20 (m, 10H). LCMS (100% area) Rt=5.64 min, (pos) [M+H]/z Calc'd 468.1, found 468.0. Analyzed with 0.75H₂O Calc'd, C (57.39), H (3.67), N (14.56), S (6.67). Found: C (57.44), H (3.67), N (14.56), S (6.67).

Example 37(a)

6-[6-fluoro-2-(ethoxycarbamoyl)phenylsulfanyl]-3-E-[2-(pyridin-2-yl)ethenyl]-1H-indazole

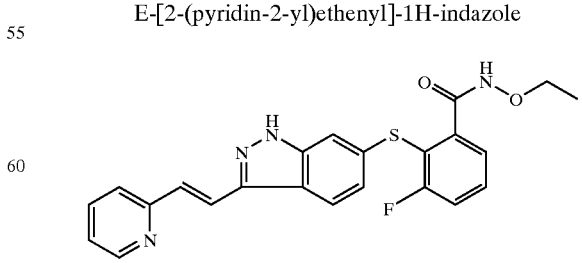

Example 37(a) was prepared in a similar manner to that described for Example 35(a) except that the starting material described below was employed and that ethoxyamine was used instead of propylamine: $^1$H NMR (300 MHz, CDCl$_3$) δ 8.59 (m, 1H), 8.08 (d, 1H), 7.88 (d, 1H, J=16.4 Hz), 7.79 (t, 1H), 7.65 (d, 1H), 7.60 (m, 1H), 7.50 (d, 1H, J=16.4 Hz), 7.40 (t, 1H), 7.36 (d, 1H), 7.28 (s, 1H), 7.23 (m, 1H), 7.10 (d, 1H), 3.90 (q, 2H), 1.19 (t, 3H). LCMS (100% area) Rt=4.85 min, (pos) [M+H]/z Calc'd 435.1, found 435.1, (neg) [M−H]/z Calc'd 433.1, found 433.1. Analyzed with 0.35H$_2$O, 0.07 EtOAc Calc'd, C (62.56), H (4.57), N (12.54), S (7.17). Found: C (62.61), H (4.55), N (12.49), S (7.11).

Starting material was prepared as follows:

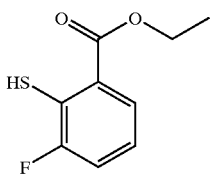

(i)

A solution of ethyl-2,3 difluorobenzoate (1.07 g, 5.75 mmol) in DMF (10 mL) was treated with sodium sulfide (896 mg, 11.5 mmol, 2.0 equiv) at 23° C. The mixture was stirred under argon for 10 h. The solution was diluted with ethyl acetate (50 mL) and water (50 mL) and 10% citric acid (5 mL). The organic layer was washed with saturated aqueous sodium bicarbonate, dried over sodium sulfate, decanted and concentrated under reduced pressure to give 3-Fluoro-2-mercapto-benzoic acid ethyl ester. $^1$H NMR (300 MHz, CDCl$_3$)δ7.71 (t, 1H), 7.38 (m, H), 7.12 (m, 1H), 4.41 (q, 2H), 1.40 (t, 3H); LCMS (100% area) Rt=4.53 min, (pos) [M+H]/z Calc'd 201.0, found 200.9.

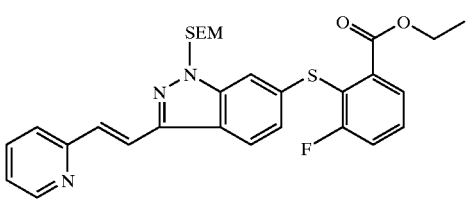

(ii)

The above thioether was prepared in a similar manner to that described for Example 33(a), step (iii) except that 3-Fluoro-2-mercapto-benzoic acid ethyl ester was used instead of thiosalicylate (320 mg, 39%): FTIR (thin film) 2952, 1727, 1607, 1586, 1564, 1469, 1433, 1366, 1292, 1249, 182, 1141, 1074, 836 cm$^{-1}$; $^1$H NMR (300 MHz, CDCl$_3$) δ 8.62 (m, 1H), 7.90 (d, 1H, J=8.6 Hz), 7.85 (d, 1H, 3=16.4 Hz), 7.67 (dt, 1H, J=1.8, 7.7 Hz), 757–7.38 (m, 5H), 7.23–7.10 (m, 3H), 5.65 (s, 2H), 4.34 (q, 2H, J=7.1 Hz), 3.56 (t, 2H, J=8.2 Hz), 1.30 (t, 3H, J=7.1 Hz), 0.88 (t, 2H, J=8.2 Hz), −0.06 (s, 9H); LCMS (100% area) Rt=4.44 min. (pos) [M+H]/z Calc'd 549.2, found 549.2.

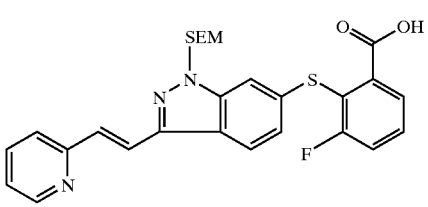

(iii)

The carboxylic acid above was prepared in a similar manner to that described for Example 33(a), step (iv) (303 mg, 99%): FTIR (thin film) 2953, 2496, 1715, 1643, 1607, 1567, 1470, 1434, 1300, 1250, 1221, 1075, 967, 932, 836 cm$^{-1}$; $^1$H NMR (300 MHz, CDCl$_3$) δ 8.81 (m, 1H), 7.87 (m, 2H), 7.79 (m, 3H), 7.65 (m, 2H), 7.56 (m, 1H), 4.40 (m, 1H), 7.30 (m, 1H), 7.00 (dd, 1H, J=1.4, 8.5 Hz), 5.58 (s, 2H), 3.59 (t, 2H, J=8.2 Hz), 0.93 (t, 2H, J=8.2 Hz), −0.01 (s, 9H). LCMS (100% area) Rt=10.47 min, (pos) [M+H]/z Calc'd 522.2, found 522.2.

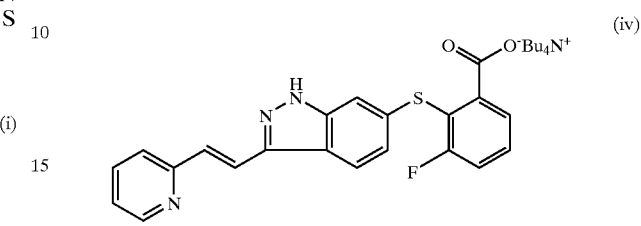

(iv)

The above salt was prepared in a similar manner to that described for Example 33(g): $^1$H NMR (300 MHz, dmso-d6) δ 13.2 (s, 1H), 8.68 (m, 1H), 8.12 (d, 1H, J=8.5 Hz), 7.98 (d, 1H, J J=16.4 Hz), 7.88 (dt, 1H, J=1.8, 7.6 Hz), 7.73 (d, 1H, J=7.9 Hz), 7.61 (d, 1H, J=16.4 Hz), 7.43–7.32 (m, 3H), 7.20 (m, 2H), 7.07 (t, 1H), 3.23 (m, 8H), 1.68 (m, 8H), 1.41 (m, 8H), 1.04 (t, 12H).

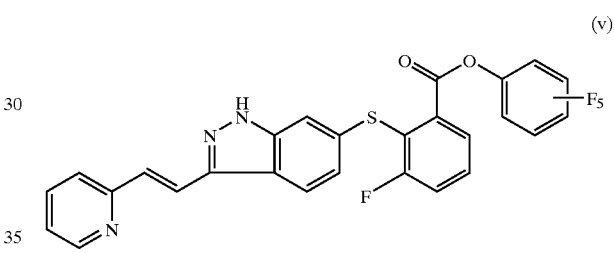

(v)

The above pentafluorophenyl ester was prepared in a similar manner to that described for Example 35(a), step (i): LCMS (100% area) Rt=10.53 min, (pos) [M+H]/z Calc'd 558.1, found 558.1.

Example 37(b)

6-[6-Fluoro-2-(cyclopropylcarbamoyl)phenylsulfanyl]-3-E-[2-(pyridin-2-yl)ethenyl]-1H-indazole

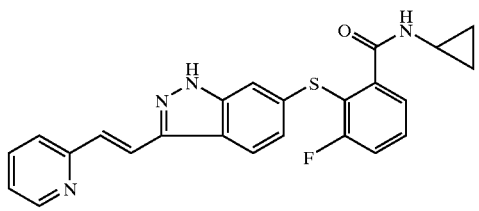

Example 37(b) was prepared in a similar manner to that described for Example 37(a) except that cyclopropylamine was used instead of ethoxyamine: $^1$H NMR (300 MHz, dmso-d6) δ 8.42 (m, 1H), 8.28 (d, 1H), 7.83 (d, 1H), 7.75 (m, 2H), 7.60 (m, 1H), 7.31 (m, 2H), 7.15 (m, 4H), 6.86 (d, 1H), 2.58 (m, 1H), 0.42 (m, 2H), 0.23 (m, 2H). LCMS (100% area) Rt=4.91 min. (pos) [M+H]/z Calc'd 431.1, found 431.1, (neg) M−H]/z Calc'd 429.1, found 429.2. Analyzed with 0.55H$_2$O Calc'd, C (65.46), H (4.60), N (12.72), S (7.28). Found: C (65.52), H (4.58), N (12.64), S (7.06).

Example 37(c)

6-[6-fluoro-2-(isopropoxycarbamoyl)phenylsulfanyl]-3-E-[2-(pyridin-2-yl)ethenyl]-1H-indazole

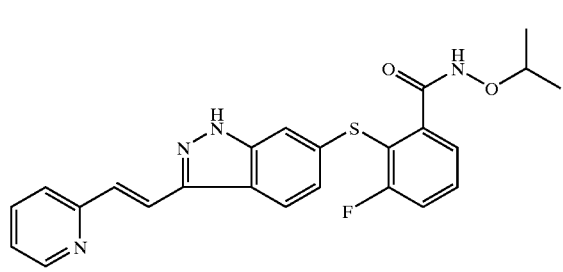

Example 37(c) was prepared in a similar manner to that described for Example 37(a) except that isopropoxyamine was used instead of ethoxyamine: ¹H NMR (300 MHz, CDCl₃) δ 9.50 (s, 1H), 8.47 (m, 1H), 7.72 (d, 1H), 7.68 (d, 1H, J=16.4 Hz), 7.54 (dt, 1H), 7.35 (m, 4H), 7.20 (m, 4H), 4.03 (m, 1H), 1.07 (d, 6H); LCMS (100% area) Rt=4.90 min, (pos) [M+H]/z Calc'd 449.1, found 449.1. Analyzed with 0.1 DMF, 0.3H₂O Calc'd, C (63.28), H (4.87), N (12.45), S (6.95). Found: C (63.22), H (4.84), N (12.37), S (6.91).

Example 37(d)

6-[6-fluoro-2-(methylcarbamoyl)phenylsulfanyl]-3-E-[2-(pyridin-2-yl)ethenyl]-1H-indazole

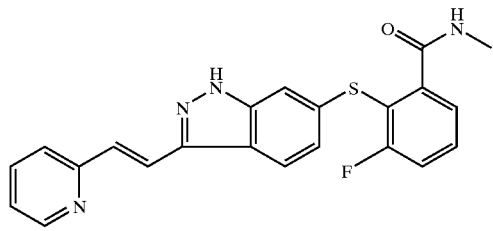

Example 37(d) was prepared in a similar manner to that described for Example 37(a) except that methylamine was used instead of ethoxyamine: ¹H NMR (300 MHz, dmso-d6) δ 8.37 (m, 1H), 8.18 (m, 1H), 7.87 (d, 1H), 7.67 (d, 1H, J=16.4 Hz), 7.59 (dt, 1H), 7.40 (d, H), 7.30 (m, 2H), 7.20 (m, 4H), 6.85 (d, 1H), 2.49 (d, 3H); LCMS (100% area) Rt=4.63 min, (pos) [M+H]/z Calc'd 405.1, found 405.2, (neg) [M−H]/z Calc'd 403.1, found 403.1. Analyzed with 0.2 DMF, 0.3 CH₂Cl₂ (nmr), 0.3H₂O Calc'd, C (61.13), H (4.39), N (13.07), S (7.13). Found: C (61.08), H (4.35), N (13.14), S (7.22).

Example 38(a)

6-[2-(2-Methylquinol-6-ylcarbamoyl)phenylsulfanyl]-3-E-(2-styryl)-1H-indazole

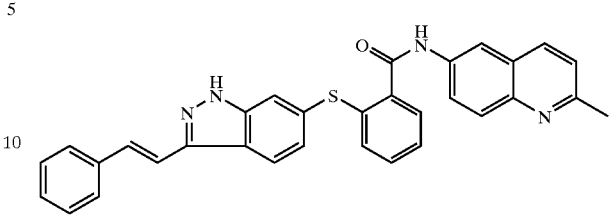

Example 38(a) was prepared in a similar manner to that described for Example 33(b) except that steps (i) and (ii) were omitted: ¹H NMR (300 MHz, CDCl₃) δ 8.58 (s, 1H), 8.13 (s, 1H), 7.80 (m, 3H), 7.67 (t, 1H), 7.43 (m, 2H), 7347.16 (m, 9H), 7.13 (d, 1H), 7.07 (d, 1H), 2.60 (s, 3H). LCMS (100% area) Rt=3.87 min, (pos) [M+H]/z Calc'd 513.1, found 513.2.

Example 38(b)

6-[2-((4-piperizin-1-yl-3-trifluoromethylphenyl)carbamoyl)phenylsulfanyl]-3-E-(2-styryl)-1H-indazole

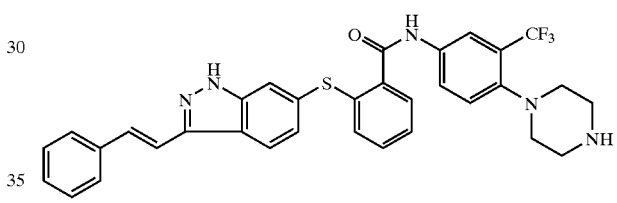

Example 38(b) was prepared in a similar manner to that described for Example 38(a) except that 3-trifluoromethyl-piperazin-1-yl-phenylamine was used instead of 6-amino-2-methylquinoline: ¹H NMR (300 MHz, CDCl₃) δ 8.75 (s, 1H), 7.95 (d, 1H), 7.77 (m, 2H), 7.69 (s, 1H), 7.55 (m, 3H), 7.40–7.25 (m, 9H), 7.20 (d, 1H), 3.00 (m, 4H), 2.83 (m, 4H). LCMS (100% area) Rt=3.94 min, (pos) [M+H]/z Calc'd 600.2, found 600.2. Analyzed with 0.1 hex (nmr), 1.4H₂O Calc'd, C (63.71), H (5.12), N (11.06), S (5.06). Found: C (63.67), H (5.06), N (10.98), S (5.00).

Example 39(a)

6-[2(Methylcarbamoyl)phenylamino]-3-E-[2-(pyridin-2-yl)ethenyl]-1H-indazole

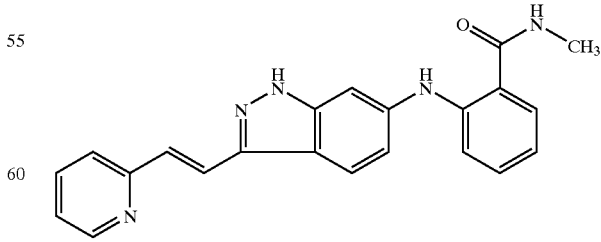

A solution of N-methyl-2-[3-((E)-2-pyridin-2-yl-vinyl)-1-(2-trimethylsilanyl-ethoxymethyl)-1H-indazol-6-ylamino]-benzamide (39 mg, 0.07820 mmol) (synthesis described below), ethylene diamine (21 μL, 0.3128 mmol), and 1M TBAF in THF (0.63 ml, 0.6256 mmol), was stirred in a 90° C. oil bath for 2 hr. The crude reaction mixture was diluted with ethyl acetate (50 mL), extracted 1M sodium bicarbonate solution (2×20 ml), brine (5×20 ml), dried magnesium sulfate, filtered, and concentrated to a solid. The solid was dissolved in THF, concentrated to an oil, then triturated with $CH_2Cl_2/Et_2O$, causing precipitation of a powder. The powder was collected by filtration, rinsed with $Et_2O$, and dried under high vacuum. Mass of collected solid was 20 mg (70% yield). $^1H$ NMR (DMSO d6) δ 12.91 (bs, 1H), 9.86 (s, 1H), 8.60 (d, J=4.0 Hz, 1H), 8.52 (m, 1H), 8.08 (d, J=8.5 Hz, 1H), 7.90 (d, J=16.4 Hz, 1H), 7.80 (dt, J=1.7, 7.5 Hz, 1H), 7.65 (d, J=7.9 Hz, 1H), 7.51 (d, J=16.1 Hz, 1H), 7.47–7.34 (m, 2H), 7.25 (m, 2H), 7.00 (d, J=9.6 Hz, 1H), 6.89 (t, J=7.0 Hz, 1H), 2.79 (d, J=4.7 Hz, 3H). Anal. Calcd. for $C_{22}H_{19}N_5O.0.5\ CH_2Cl_2$: C. 65.61; H, 4.89; N. 17.00. Found: C, 65.52; H, 5.08; N, 16.78.

The starting material was prepared as follows:

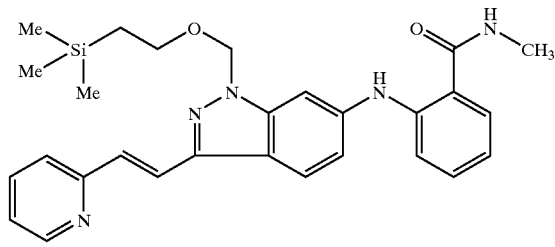

(i)

A solution of 191 mg (0.4 mmol) of 6-iodo-3-carboxaldehyde-1-[2-(trimethyl-silanly)-ethoxymethyl]-1H-indazole (from Example 33(a), step(ii)), methyl anthranilate (120.1 mg, 0.8 mmol). 2-(dicyclohexylphosphino) biphenyl (28 mg, 0.08 mmol), $Pd_2(dba)_3$ (18.4 mg, 0.02 mmol), $K_3PO_4$ (212.3 mg, 1.0 mmol), dissolved in dry DME (1.0 mL), was vacuum flushed with argon (3×), then stirred under an argon atmosphere for 3 d in an oil bath at 80° C. The crude mixture was filtered through a plug of $SiO_2$ eluted with ethyl acetate, then purified by "chromatotron" radial chromatography eluted with 25% $CH_3CN/CH_2Cl_2$. The mass of the fractions that were pure was 42 mg. An addition 120 mg of product that was ~90% pure was also collected. The total yield of N-methyl-2-[3-((E)-2-pyridin-2-yl-vinyl) 1-(2-trimethylsilanyl ethoxymethyl)-1H-indazol-6-ylamino)-benzamide was 162 mg or ~81%.

Example 39(b)

6-[2-(Prop-2-ynylcarbamoyl)phenylamino]-3-E-[2-(pyridin-2-yl)ethenyl]-1H-indazole

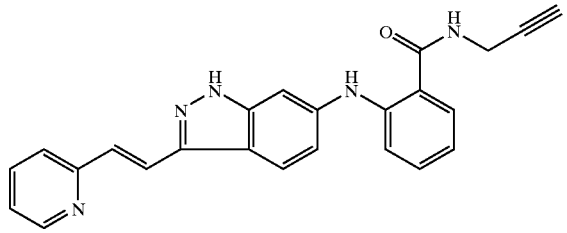

Example 39(b) was prepared in a similar manner to that described for Example 39(a) except that the propargylamine was used instead of methylamine. $^1H$ NMR (CDCl$_3$) δ 9.50 (s, i), 8.64 (d, J=4.5 Hz, 1H), 7.98 (d, J=8.9 Hz, 1H), 7.90 (d, J=16.4 Hz, 1H), 7.70 (dt, J=1.7, 7.5 Hz, 1H), 7.57 (d, J=16.3 Hz, 1H), 7.52–7.43 (m, 3H), 7.34 (dt, J=1.5, 7.2 Hz, 1H), 7.26 (m, 3H), 7.34 (ddd, J=1.0, 4.9, 7.5 Hz, 1H), 7.09 (dd, J=1.7, 9.0 Hz, 1H), 6.85 (dt, J=1.0, 7.0 Hz, 1H), 6.33 (bs, 1H), 4.24 (dd, J=2.6, 5.3 Hz, 2H), 2.30 (t, J=5.5 Hz, 1H). Anal. Calcd. for $C_{24}H_{19}N_5O.0.25\ CH_2Cl_2$: C, 70.24; H. 4.74; N. 16.89. Found: C, 70.72; H, 4.96; N, 16.55.

Example 40(a)

6-(3-Amino-benzoyl)-3-E-[2-(pyridin-2-yl)ethenyl]-1H-indazole

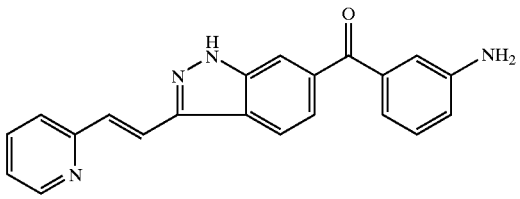

Example 40(a) was prepared in a similar manner to that described for Example 11. $^1H$ NMR (300 MHz, DMSO-d$_6$) δ 13.5 (s, 1H), 8.62 (d, 1H, J=3.86 Hz), 8.34 (d, 1H, J=8.5 Hz), 8.01 (dl 1H, J=16.36 Hz), 7.87 (s, 1H), 7.83 (td, 1H, J=7.69 Hz, J=1.81 Hz), 7.58–7.71 (m, 3H), 7.29 (qd, 1H, J=7.39 Hz, J=0.98 Hz), 7.21 (t, 1H, 3=7.77), 7.00 (t, 1H, J=1.86 Hz), 6.90 (dt, 1H, J=6.15 Hz, J=1.40 Hz), 6.86 (m, 1H). 5.40 (bs, 2H). MS (ESI+) [M+H]/z Calc'd 446, found 446. Calc'd: C, 74.10; H, 4.74; N, 16.46. Found: C, 72.72; H, 4.87; N, 16.02.

The starting material was prepared as follows:

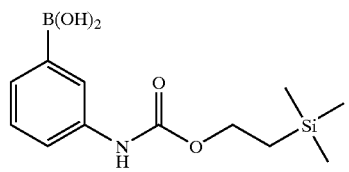

(i)

To m-amino-phenyl boronic acid (8.22 g, 60 mmol) in dimethyformamide (60 ml) at 23° C. under an atmosphere of argon was added triethylamine (10 ml, 72 mmol) and 4 (dimethylamino)pyridine (0.366 g, 3 mmol). The resulting solution was heated to 50° C. Carbonic acid 4-nitro-phenyl ester 2-trimethylsilanyl-ethyl ester (20.4 g, 72 mmol) was added in 5 by 4 g portions over 18 hours. After 44 h carbonic acid 4-nitro-phenyl ester 2-trimethylsilanyl-ethyl ester (3.4 g, 12 mmol) was added followed by triethylamine (1.7 ml, 12 mmol). After 63 h the reaction mixture was concentrated to an oil. Purification by silica gel chromatography eluting with 3-7 to 7-3 ethyl acetate-hexane gave (3-boronic acid-phenyl)carbamic acid 2-trimethylsilanyl-ethyl ester (8.12 g, 48%): $R_f$ sm 0.067, p 0.33 (ethyl acetate-hexane 1:1); $^1H$ NMR (300 MHz, CD$_3$OD) δ 7.64 (s, 1H), 7.49 (d, 1H, J=8.94 Hz), 7.26 (m, 2H), 4.23 (t, 2H, 3=8.28 Hz), 1.06 (t, 2H, J=8.21 Hz) 0.72 (s, 9H). MS (ES) [M+Na]/z Calc'd 304, found 304.

(ii)

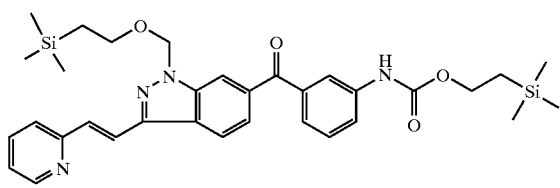

A mixture of 6-iodo-3-((E2-pyridin-2-yl-vinyl)-1-(2-trimethylsilanyl-ethoxymethyl)-1H-indazole (7.1 g, 14.8 mmol), (3-boronic acid-phenyl)-carbamic acid 2-trimethylsilanyl-ethyl ester (8.32 g, 29.6 mmol), dichlorobis(triphenylphosphine)-palladium(II) (312 mg, 0.44 mmol), potassium carbonate (6.13 g, 44.4 mmol) and triethylamine (2.1 ml, 14.8) in anisole (60 ml) was heated to 80° C. under an atmosphere of carbon monoxide. After 24 h more triethylamine (2.1 ml, 14.8 mmol) was added. After 33 hrs the reaction was determined to be complete by TLC analysis (ethyl acetate-hexane 7-3). The reaction mixture was cooled to 23° C., then diluted with saturated NaHCO$_3$ (aq) (40 ml) and ethyl acetate (300 ml). The phases were separated and the aqueous was extracted with ethyl acetate (2×100 mls). The pooled ethyl acetate was washed with brine (100 ml) and dried over Na$_2$SO$_4$, filtered and concentrated. Purification by silica gel chromatography gave (3-{1-[3-(2-Pyridin-2-yl-ethyl)-1)-1-(2-trimethylsilanyl-ethoxymethyl)-1H-indazol-6-yl]-methanoyl}-phenyl)-carbamic acid 2-trimethylsilanyl-ethyl ester as a yellow glass (7.22 g, 79%). $^1$H NMR (300 MHz. CDCl$_3$) δ 8.65 (d, 1H, J=3.93 Hz), 8.10 (d, 1H, J=8.54 Hz), 8.04 (s, 1H), 7.94 (d, 1H, J=16.33 Hz), 7.82 (s, 1H), 7.66–7.77 (m, 3H), 7.61 (d, 1H, J=16.35 Hz), 7.40–7.51 (m, 3H), 7.19 (m, 1H), 7.00 (s, 1H), 5.77 (s, 2H), 4.25 (t, 2H, J=6.93 Hz), 3.60 (t, 2H, J=8.10 Hz), 1.04 (t, 2H, J=6.79 Hz), 1.00 (t, 2H, J=8.13 Hz), 0.04 (s, 9H), 0.0 (s, 9H). MS (ESI+) [M+H]/z Calc'd 615, found 615.

Example 40(b)

6-(3-Amino-4-methyl-benzoyl)-3-E-[2-(pyridin-2-yl) ethenyl]-1H-indazole

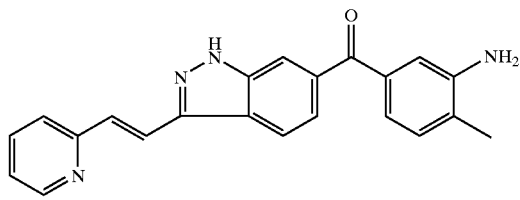

Example 40(b) was prepared in a similar manner to that of Example 40(a) except that in step (i) 4-methyl-3-amino-phenyl boronic acid, prepared as described below, was used in place of m-aminophenyl boronic acid. $^1$H NMR (DMSO-d$_6$) δ 13.6 (s, 1H), 8.62 (d, 1H, J=3.81 Hz), 8.33 (d, 1H, J=8.47 Hz), 8.01 (d, 1H, J=16.36 Hz), 7.85 (s, 1H), 7.82 (dd 1H, J=7.60 Hz, J=1.80 Hz), 7.70 (d, 1H, J=7.81 Hz), 7.63 (d, 1H, J=16.36 Hz), 7.57 (dd, 1H, J=8.47 Hz, J=1.2 Hz), 7.29 (m, 1H), 7.12 (d, 1H, J=7.82 Hz), 7.09 (d, 1H, J=1.64 Hz), 6.90 (dd, 1H, J=7.59 Hz, J=1.65 Hz), 5.16 (bs, 1H), 2.16 (s, 1H). MS (ESI) [M+H]/z Calc'd 355, Anal. Calc'd: C, 74.56; H, 5.12; N, 15.81. Found; C, 73.86; H, 5.25; N, 15.34.

The starting material was prepared as follows:

(i)

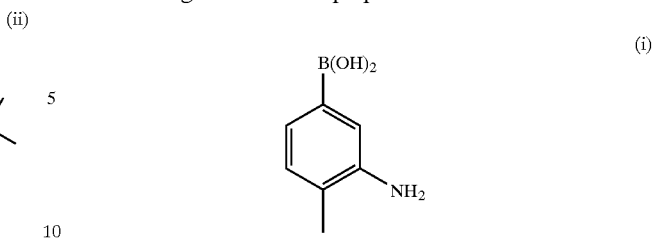

A mixture of 4-methyl-3-nitro-phenyl boronic acid (3.34 g, 18.45 mmol) and 10% Pd/C (334 mg) in MeOH (30 ml) was hydrogenated (1 atm) at 23° C. After 22 h the reaction mixture was filtered through celite and concentrated to give 3-amino-4-methyl phenyl boronic acid (2.53 g, 91%). $^1$H NMR (300 MHz, DMSO-d$_6$) δ 7.21 (s, 1H), 7.08 (d, 1H, J=7.5 Hz), 6.92 (d, 1H, J=7.46 Hz), 4.81 (bs, 2H), 2.09 (s, 3H). MS (ESI) [M+H]/z Calc'd 152, found 152.

Example 40(c)

6-(5-Amino-2,4-dimethyl-benzoyl)-3-E-[2-(pyridin-2-yl)ethenyl]-1H-indazole

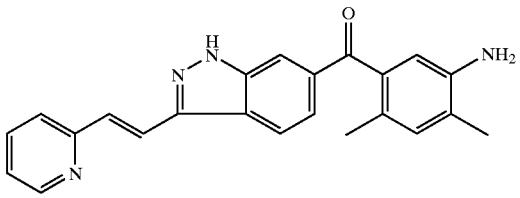

Example 40(c) was prepared in a similar manner to that of Example 40(a) except that in step (i) 2,4-dimethyl-3-amino-phenyl boronic acid (prepared as described below) was used in place of m-amino-phenyl boronic acid: $^1$H NMR (DMSO-d$_6$) δ 8.62 (d, 1H, J=3.78 Hz), 8.32 (d, 1H, J=8.48 Hz), 7.99 (d, 1H, J=16.35 Hz), 7.83 (td, 1H, J=7.68 Hz, J=1.8 Hz), 7.80 (s, 1H), 7.69 (d, 1H, J=7.80 Hz), 7.64 (dd, 1H, J=8.47 Hz, J=1.27 Hz), 7.62 (d, 1H, J=16.36 Hz), 7.29 (m, 1H), 6.94 (s, 1H), 6.64 (s, 1H), 4.87 (bs, 2H), 2.12 (s, 3H), 2.10 (s, 3H). LCMS (ESI+) [M+H]/z Calc'd 369, found 369. Anal. Calc'd: C, 74.98; H, 5.47; N, 15.21. Found: C, 73.85; H, 5.56; N, 14.49.

The starting material was prepared as follows:

(i)

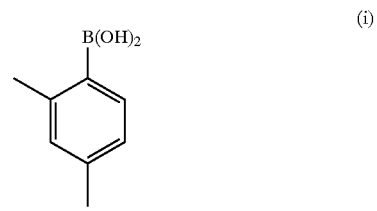

2,4-Diemthylphenyl boronic acid was made in a similar manner as that of Example 24(a), step (vii), except 2,4-dimethyl bromobenzene was used as starting material. $^1$H NMR (CD$_3$OD) δ 7.13 (d, 1H, J=7.43 Hz), 7.00 (s, 1H), 6.97 (d, 1H. J=7.49 Hz), 2.28 (s, 3H), 2.28 (s, 3H). LCMS (ESI+) [M+H]/z Calc'd 151, found 151.

(ii)

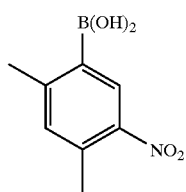

To fuming nitric acid (1 ml) cooled to −40° C. was added TFA (1 ml). The resulting mixture was allowed to warm slightly to −35° C. and 2,4-dimethyl phenyl boronic acid (150 mg, 1 mmol) was added in one portion. After 1 h, ice was added and the heterogenous mixture was filtered. The resulting solid was suspended in Et₂O and extracted with 3N NaOH (aq) (1 ml) then water (2 ml). The aqueous phase was acidified with 3N HCl (aq) (1 ml) and back extracted with EtOAc (3×5 ml). The pooled organics were washed with brine, dried with Na₂SO₄ decanted and concentrated to give 2,4-dimethyl-5-nitro-phenyl boronic acid (93 mg, 47%). LCMS (ESI+) [M+H]/z Calc'd 196, found 196.

(iii)

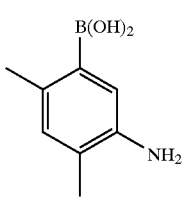

3-Amino-4,6-dimethylphenyl boronic acid was prepared in a similar as that described for Example 40(b), step (i). ¹H NMR (CD₃OD)δ 6.83 (s, 2H), 6.64 (s, 1H), 2.17 (s, 3H), 2.13 (s, 3H).

Example 41(a)

6-[3-((1-Ethyl-3-methyl-1H-pyrazol-5-yl)carboxamido)benzoyl]-3-E-[2-(pyridin-2-yl)ethenyl]-1H-indazole

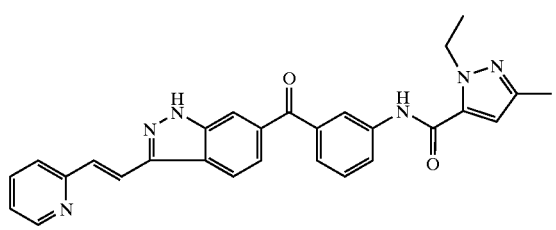

To a solution of 2-ethyl-5-methyl-2H-pyrazole-3-carboxylic acid (323 mg, 2.1 mmol, 2.1 equiv.) in DMF (5 ml) at 23° C. under argon was added diisopropylethylamine (365 μl, 2.1 mmol, 2.1 equiv.), HATU (798 mg, 2.1 mmol, 2.1 equiv.) and DMAP (cat.). To the resulting solution was added 6-(3-Amino-benzoyl)-3-E-(2-pyridin-2-yl)ethenyl)-1H-indazol (Example 40(a), 340 mg, 1 mmol, 1 equiv.). The reaction was followed by HPLC until all the starting analine was consumed ~2 h (this gave a mixture of mono and bis acylated compounds). The reaction mixture was quenched with saturated NaHCO₃, then diluted with water and extracted with ethylacetate. The pooled EtOAc was washed with water, brine, dried with Na₂SO₄, filtered and concentrated to an oil. The oil was dissolved in methanol (10 ml), K₂CO₃ (290 mg, 2.1 mmol, 2.1 equiv.) was added and the resulting mixture was stirred at 23° C. until the bis-acylated compound was consumed (~30 min.). The reaction mixture was concentrated to an oil, then partitioned between water and EtOAc. The organic phase was washed with brine, dried with Na₂SO₄, filtered and concentrated. Purification by silica gel chromatography (1:1–8:2 ethylacetate-dichloromethane) gave Example 41(a). ¹H NMR (300 MHz, DMSO-dd) 13.6 (s, 1H), 10.3 (s, 1H), 8.62 (d, 1H, J=3.88 Hz), 8.38 (d, 1H, J=851 Hz), 8.20 (s, 1H), 8.12 (td, 1H, J=7.58 Hz, =1.78 Hz), 8.02 (d, 1H, J=16.36 Hz), 7.93 (s, 1H), 7.83 (td, 1H, J=7.61 Hz, J=1.7 Hz), 7.70 (d, 1H, J=7.78 Hz), 7.65 (d, 1H, J=16.23 Hz), 7.65–7.53 (m, 3H), 7.30 (m, 1H), 4.43 (q, 2H, J=7.07 Hz), 2.21 (s, 3H), 1.31 (t, 3H, J=7.07 Hz). MS (ESI+) [M+H]/z Calc'd 477, found 477. Anal. Calc'd: C, 70.57; H, 5.08; N, 7.64. Found: C, 70.46; H, 5.11; N, 17.61.

Example 41(b)

6-[3-(pyridin-4-ylcarboxamido)benzoyl]-3-E-[2-(pyridin-2-yl(ethenyl]-1H-indazole

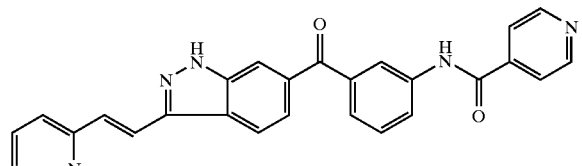

Example 41(b) was prepared in a similar manner to that described for Example 41 (a), except that isonicotinic acid was used instead of 2-ethyl-5-methyl-2H-pyrazole-3 arboxylic acid. ¹H NMR (300 MHz, CD₃OD) δ 8.74 (d, 2H, J=206.04 Hz), 8.56 (d, 1H, J=4.14 Hz), 8.27 (m, 2H), 8.05 (dt, 1H, J=7.97 Hz, J=1.64 Hz), 8.02 (s, 1H), 7.95 (d, 1H, J=16.55 Hz), 7.83–7.91 (m, 3H), 7.73 (m, 2H), 756–7.67 (m, 3H), 7.32 (m, 1H). MS (ESI+) [M+H]/z Calc'd 446, found 446. Anal. Calc'd: C, 72.80; H, 4.30; N, 15.72. Found: C, 7159; H, 4.43; N, 15.33.

Example 41(c)

6-(3-crotonylamidobenzoyl)-3-E-[2-(pyridin-2-yl)ethenyl]-1H-indazole

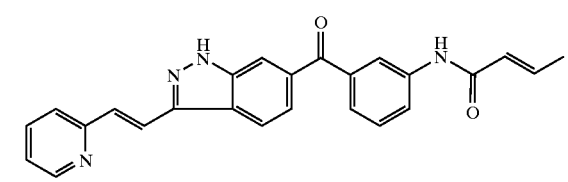

Example 41(c) was prepared in a similar manner to that described for Example 41(a), except that crotonic acid was used instead of 2-ethyl-5-methyl-2H-pyrazole-3-carboxylic acid. ¹H NMR (300 MHz, DMSO-d₄) δ 13.6 (s, 1H), 10.2 (s, 1H), 8.63 (d, 1H, J=3.81 Hz), 8.37 (d, 1H, J=8.49 Hz), 8.12 (s, 1H), 8.02 (d, 1H, J=16.34 Hz), 7.99 (d, 1H, J=7.88 Hz), 7.83 (td, 1H, J=7.67 Hz, 1=1.78 Hz), 7.70 (d, 1H, J=7.85 Hz), 7.65 (d. 1H, J=16.40 Hz), 7.63 (dd, 1H, J=8.43 Hz, J=1.23 Hz), 7.47–7.56 (m, 2H), 7.29 (qd. 1H, J=7.39 Hz, 1=0.99 Hz), 6.82 (m, 1H, J=6.9 Hz), 6.11 (dd, J=15.21 Hz, J=1.68 Hz), 1.87 (d, 3H, J=6.89 Hz). MS (ESI+) [M+H]/z Calc'd 409, found 409. Anal. Calc'd: C, 73.51; H, 4.94; N. 13.72. Found: C, 72.15; H. 4.97; N, 13.39.

Example 41(d)

6-[3-(indol-4-yl-carboxamido)benzoyl]-3-E-[2-(pyridin-2-yl)ethenyl]-1H-indazole

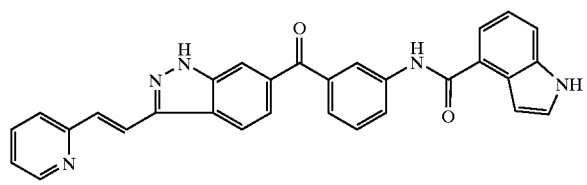

Example 41(d) was prepared in a similar manner to that described for Example 41 (a), except that 1H-Indole-4-carboxylic acid was used instead of 2-ethyl-S-methyl-2H-pyrazole-3-carboxylic acid. LCMS (ESI+) [M+H]/z Calc'd 484, found 484.

Example 41(e)

6-[3-((5-acetylthien-2-yl)carboxamido)benzoyl]-3-E-[2-(pyridin-2-yl)ethenyl]-1H-indazole

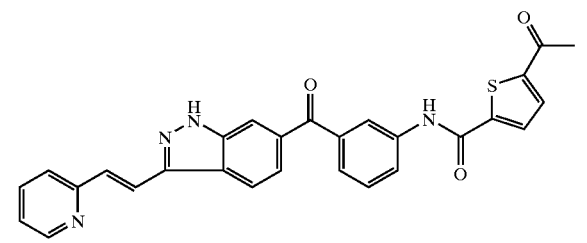

Example 41(e) was prepared in a similar manner to that described for Example 10.6 (s, 1H), 8.63 (d, 1H, J=3.83 Hz), 8.39 (d, 1H, J=8.51 Hz), 8.20 (s, 1H), 8.14 (dt, 1H, J=7.25 Hz, J=2.05 Hz), 8.07 (d, 1H, J=4.09 Hz), 8.02 (d, 1H, J=16.42 Hz), 8.00 (d, 1H, J=4.01 Hz), 7.94 (s, 1H), 7.83 (td, 1H, J=7.69 Hz, J=1.78 Hz), 7.59–7.65 (m, 5H), 7.30 (qd, 1H, J=7.40 Hz, J=0.96 Hz), 2.58 (s, 3H). MS (ESI+) [M+H]/z Calc'd 493, found 493. Anal. Calc'd: C, 68.28; H, 4.09; N, 11.37; S, 6.51. Found: C, 66.07; H, 4.34; N, 10.91; S, 6.14.

Example 41(f)

6-[3-(3,5-difluorophenylacetamido)benzoyl]-3-E-[2-(pyridin-2-yl)ethenyl]-1H-indazole

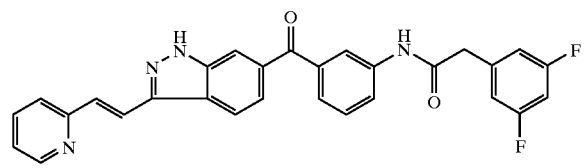

Example 41(f) was prepared in a similar manner to that described for Example 41 (a), except that (3,5-difluorophenyl)-acetic acid was used instead of 2-ethyl-5-methyl-2H-pyrazole-3-carboxylic acid. $^{1}$H NMR (300 MHz, DMSO d4) δ 13.6 (bs, 1H), 10.5 (s, 1H), 8.62 (d, 1H, J=4.02 Hz), 8.36 (d, 1H, J=8.51 Hz), 8.05 (s, 1H), 8.01 (d, 1H, J=16.38 Hz), 7.93 (d, 1H, J=7.88 Hz), 7.90 (s, 1H), 7.83 (td, 1H, J=7.61 Hz, 1=1.77 Hz), 7.70 (d, 1H, 1=7.85 Hz), 7.64 (d, 1H, J=16.33 Hz), 7.61 (dd, 1H, J=8.45 Hz, J=1.15 Hz), 7.48–7.57 (m, 2H), 7.15–7.31 (m, 5H), 3.77 (s, 2H). MS (ESI+) [M+H]/z Calc'd 495, found 495.

Example 41(g)

6-[3-((5-methyl-1H-pyrazol-3-yl)carboxamido)benzoyl]-3-E-[2-(pyridin-2-yl)ethenyl]-1H-indazole

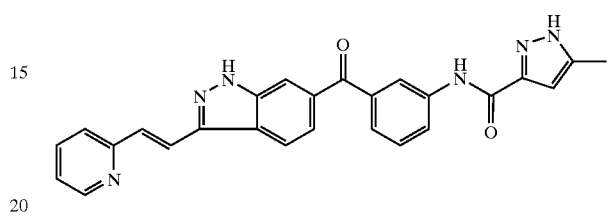

Example 41(g) was prepared in a similar manner to that described for Example 41(a), except that 5-methyl-2H-pyrazole-3-carboxylic acid was used in place of 2-ethyl-5-methyl-2H-pyrazole-3-carboxylic acid. $^{1}$H NMR (300 MHz, DMSO-d$_6$) δ 13.6 (bs, 1H), 13.0 (bs, 1H), 10.3 (bs, 1H), 8.63 (d, 1H, J=3.95 Hz), 8.37 (d, 1H, J=8.66 Hz), 8.36 (s, 1H), 8.16 (d, 1H, J=7.55 Hz), 8.02 (d, 1H, J=16.37 Hz), 7.93 (s, 1H), 7.83 (dt, 1H, J=7.61 Hz, J=1.73 Hz), 7.70 (d, 1H, J=7.82 Hz), 7.65 (d, 1H, J=16.36 Hz), 7.65 (dd, 1H, J=8.55 Hz, 1=1.12 Hz), 7.52 (m, 2H), 7.29 (m, 1H), 6.50 (s, 1H), 2.29 (s, 3H). MS (ESI+) [M+H]/z Calc'd 449, found 449. Anal. Calc'd: C, 69.63; H. 4.49; N, 18.74. Found: C, 68.53; H, 4.95; N, 17.47.

Example 41(h)

6-[3-((2-RS-trans-methylcyclopropyl)carboxamido)benzoyl]-3-E-[2-(pyridin-2-yl)ethenyl]-1H-indazole

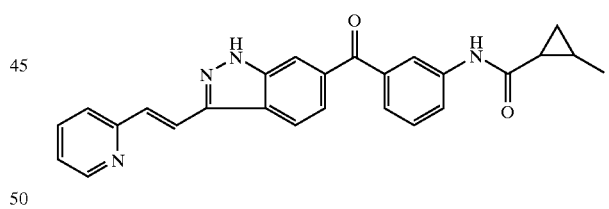

Example 41(h) was prepared in a similar manner to that described for Example 41(a), except that 2-Methyl-cyclopropanecarboxylic acid was used in place of 2-ethyl-5-methyl-2H-pyrazole-3-carboxylic acid. $R_f$ sm 0.32, $R_f$ p 0.42 (ethyl acetate-dichloromethane 8:2). $^{1}$H NMR (300 MHz, DMSO-d$_6$) δ 13.6 (s, 1H), 10.4 (s, 1H), 8.62 (dd, 1H, J=4.75 Hz, J=0.96 Hz), 8.36 (d, 1H, J=8.47 Hz), 8.06 (t, 1H, J=1.67 Hz), 8.01 (d, 1H, J=16.37 Hz), 7.90 (m, 2H), 7.83 (td, 1H, J=7.68 Hz, J=1.79 Hz), 7.70 (d, 1H. J=7.84 Hz), 7.64 (d, 1H, J=16.35 Hz), 7.61 (dd, 1H, J=8.47 Hz, J=1.32 Hz), 7.51 (t, 1H, J=7.69 Hz), 7.45 (dt, 1H, J=7.68 Hz, J=1.50 Hz), 729 (dq, 1H, J=7.41 Hz, J=1.04 Hz), 151 (m, 1H), 1.23 (m, 1H), 1.09 (d, 3H, J=5.93), 1.01 (m, TH), 0.65 (m, 1H). MS (ESI+) [M+H]/z Calc'd 423, found 423. Anal. Calc'd: C, 73.92; H, 5.25; N, 13.26. Found: C, 71.41; H, 5.56; N, 13.27.

Example 41(i)

6-[3-((1,5-dimethyl-1H-pyrazol-3-yl)carboxamido)
benzoyl]-3-E-[2-(pyridin-2-yl)ethenyl]-1H-indazole

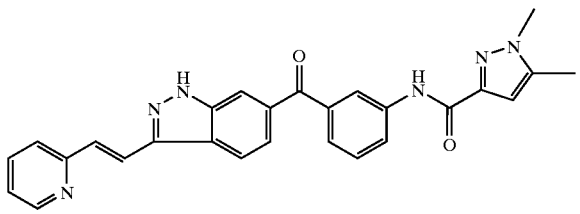

Example 41(i) was prepared in a similar manner to that described for Example 41(a), except that 1,5-dimethyl-1H-pyrazole-3-carboxylic acid was used in place of 2-ethyl-5-methyl-2H-pyrazole-3-carboxylic acid. $^1$H NMR (300 MHz, DMSO-d$_6$) δ 13.6 (s, 1H), 10.2 (s, 1H), 8.63 (d, 1H, J=3.87 Hz), 837 (d, 1H, J=8.49 Hz), 8.34 (d, 1H, 1=1.63 Hz), 8.16 (td, 1H, J=7.43 Hz, J=1.96 Hz), 8.02 (d, 1H, J=16.35 Hz), 7.92 (s, 1H), 7.83 (dt, 1H, J=7.68 Hz, 1=1.79 Hz), 7.70 (d, 1H, J=7.84 Hz), 7.65 (d, 1H, 1=16.35 Hz), 7.65 (dd, 1H, J=8.52 Hz, J=1.2 Hz), 7.52 (m, 2H), 7.29 (m, 1H), 655 (s, 1H), 3.83 (s, 3H), 2.30 (s, 3H). MS (ESI+) [M+H]/z Calc'd 463, found 463. Anal. Calc'd: C, 70.12; H, 4.79; N, 18.17. Found: C, 69.59; H. 4.88; N. 17.86.

Example 41(j)

6-[3-((3-methylpyridin-4-yl)carboxamido)benzoyl]-
3-E-[2-(pyridin-2-yl)ethenyl-1H-indazole

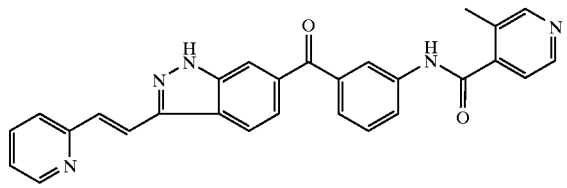

Example 41(j) was prepared in a similar manner to that described for Example 41(a), except that 3-methyl-isonicotinic acid was used in place of 2-ethyl-5-methyl-2H-pyrazole-3-carboxylic acid. $^1$H NMR (300 MHz, DMSO-d$_4$) δ 13.6 (s, 1H), 10.7 (s, 1H), 8.62 (dd, 1H, J=4.72 Hz, J=0.86 Hz), 8.57 (s, 1H), 8.55 (d, 1H, J=4.91 Hz), 8.37 (d, 1H, J=8.46 Hz), 8.20 (s, 1H), 8.07 (dt, 1H, J=7.27 Hz, J=1.99 Hz), 8.02 (d, 1H, J=16.37 Hz), 7.93 (s, 1H), 7.83 (td, 1H, J=7.69 Hz, 1=1.79 Hz), 7.70 (d, 1H, J=7.84 Hz), 7.64 (d, 1H, J=16.27 Hz), 7.55–7.65 (m, 3H), 7.48 (d, 1H, J=4.89 Hz), 7.30 (qd, 1H, J=7.39 Hz, J=1.02 Hz), 2.38 (s, 3H). MS (ESI+) [M+H]/z Calc'd 460, found 460.

Example 41(k)

6-[3-(cyclopropylcarboxamido)benzoyl]-3-E-[2-
(pyridin-2-yl)ethenyl]-1H-indazole

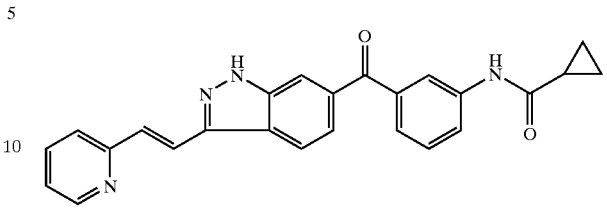

Example 41(k) was prepared in similar manner as Example 41(a) except that cyclopropane carboxylic acid used in place of 2-ethyl-5-methyl-2H-pyrazole-3-carboxylic acid. $^1$H NMR (CDCl$_3$/MeOD) δ 852 (d, 1H, J=3.9 Hz), 8.09 (d, 1H, J=8.5 Hz), 7.93 (s, 1H), 7.85–7.80 (m, 3H), 7.71–7.63 (m, 2H), 7.55–7.48 (m, 3H), 7.39 (1H, t, J=7.8 Hz), 7.16 (1H, qd, J=6.3, 1.5 Hz), 1.62–1.57 (m, 1H), 125–1.84 (m, 2H), 0.87–0.81 (m, 2H). HRMS (MALDI) C$_{25}$H$_{20}$N$_4$O$_2$ [M+H$^+$]/z Calc'd 409.1659, found 409.1660.

Example 41(l)

6-[3-((2-RS-trans-phenylcyclopropyl)carboxamido)
benzoyl]-3-E-[2-(pyridin-2-yl)ethenyl]-1H-indazole

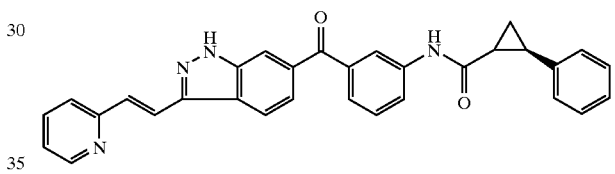

Example 41(l) was prepared in similar manner as Example 41(a) except that (1S,2S)-2-phenyl-cyclopropanecarboxylic acid used in place of 2-ethyl-5-methyl-2H-pyrazole-3-carboxylic acid. $^1$H NMR (CDCl$_3$/MeOD) δ 8.60 (d, 1H, J=4.2 Hz), 8.17 (d, 1H, J=8.4 Hz), 8.02 (s, 1H), 7.91 (t, 3H, J=8.1 Hz), 7.78–7.71 (m, 2H), 7.63–7.56 (s, 3H), 7.47 (t, 1H), 7.32–7.12 (m, 5H), 2.60–254 (n, 1H), 1.94–1.90 (m, 1H), 1.69 (q, 1H, J=4.8 Hz), 1.37–1.32 (m, 1H). HRMS C$_{31}$H$_{24}$N$_4$O$_2$ Calc'd (M+H$^+$)/z 485.1993, found 485.1995.

Example 41(m)

6-[3-((3-methylisoxazol-5-yl)carboxamido)benzoyl]-
3-E-[2-(pyridin-2-yl)ethenyl]-1H-indazole

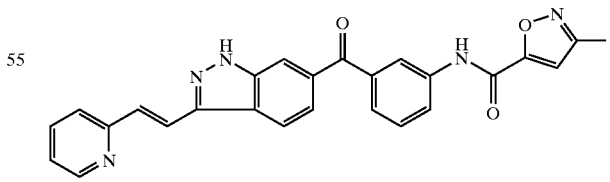

Example 41(m) was prepared in similar manner as Example 41 (a) except that 3-methyl-isoxazole-5-carboxylic acid used in place of 2-ethyl-5-methyl-2H-pyrazole-3-carboxylic acid. $^1$H NMR (DMSO-d$_6$) δ 10.95 (1H, s), 8.68 (1, d, J=4.2 Hz), 8.44 (d, 1H, J=8.7 Hz), 8.35 (s 1H), 8.21–8.18 (m, 1H,), 8.08 (d, 1H, J=16.2 Hz), 7.98 (s, 1H), 7.87 (td, 1H, J=7.5, 1.8 Hz), 7.76–7.64 (m, 6H), 7.37–7.33 (m, 1H), 6.72 (s, 1H), 3.36 (s, 3H). HRMS (MALDI) $C_{26}H_{19}N_5O_3$ [M+H$^+$]/z: Calc'd 450.1561, found 450.1570.

Example 41(n)

6-[3-((3-t-butyl-1-methyl-1H-pyrazol-5 yl)carboxamide)benzoyl]-3-E-[2-(pyridin-2-yl)ethenyl]-1H-indazole

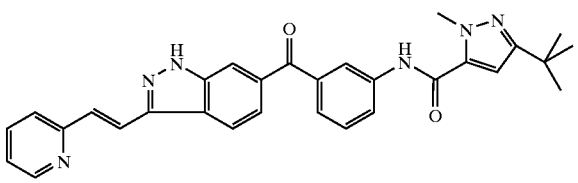

Example 41(n) was prepared in similar manner as Example 41 (a) except that 5-tert-butyl-2-Methyl-2H-pyrazole-3-carboxylic acid used in place of 2-ethyl-5-methyl-2H-pyrazole-3-carboxylic acid. $^1$H NMR (CDCl$_3$/MeOD) δ 8.59 (d, 1H, J=4.8 Hz), 8.14 (d, 1H, J=8.4 Hz), 8.08–8.04 (m, 1H,), 7.98–7.92 (m, 3H), 7.75 (td, 1H, J=7.8, 1.8 Hz), 7.68 (dd, 1H, J=8.4 Hz), 7.61–7.56 (m, 3H), 7.52 (t, 1H, J=8.70 Hz), 7.25–7.21 (m, 1H,), 6.75 (s, 1H,), 4.12 (s, 3H), 1.30 (s, 9H). HRMS (MALDI) $C_{30}H_{28}N_6O_2$[M+H$^+$]/z: Calc. 505.2347, found 505.2353.

Example 41(o)

6-[3-((5-chlorothien-2-yl)carboxamido)benzoyl]-3-E-[2-(pyridin-2-yl)ethenyl]-1H-indazole

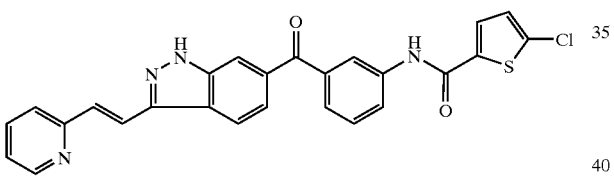

Example 41(o) was prepared in similar manner as Example 41(a) except that 5-chlorothiophene-2-carboxylic acid used in place of 2-ethyl-5-methyl-2H-pyrazole-3-carboxylic acid. $^1$H NMR (DMSO-d$_6$) δ 1058 (s, 1H,), 8.68 (d, 1H, J=4.2 Hz), 8.43 (d, 1H, J=8.5 Hz), 8.22 (s, 1H,), 8.15 (dt, 1H, J=7.5, 2.0 Hz), 8.08 (d, 1H, J=16.4 Hz), 8.007.98 (m, 3H), 7.88 (td, 1H, J=7.7, 1.9 Hz), 7.78–7.62 (m, 4H,), 7.33 (d, 2H, J=4.1 Hz). HRMS (MALDI) $C_{26}H_{17}N_4O_2ClS$ [M+H$^+$[/z: Calc. 485.0843, found 485.0853.

Example 41(p)

6-[3-((1,3-Dimethyl-1H-pyrazol-5-yl)carboxamido)benzoyl]-3-E-[2-(pyridin-2-yl)ethenyl]-1H-indazole

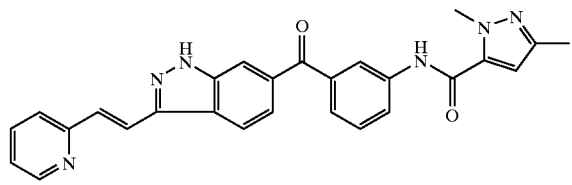

Example 41(p) was prepared in similar manner as Example 41(a) except that 2,5-dimethyl-2H-pyrazole-3-carboxylic acid used in place of 2-ethyl-5-methyl-2H-pyrazole-3 carboxylic acid. HPLC: R$_t$ 3.90 min (100% area). $^1$H NMR (CDCl$_3$) δ 852 (d, 1H, J=4.8 Hz), 8.10 (d, 1H, J=8.4 Hz), 7.98 (d, 1H, J=8.1 Hz), 7.93 (s, 1H,), 7.88–7.80 (m, 3H), 7.71–7.62 (m, 2H), 756–7.49 (m, 4H), 7.44 (t, 1H, J=7.8 Hz), 7.16 (dd, 1H, J=7.1, 4.8 Hz). HRMS (MALDI) $C_{27}H_{22}N_6O_2$.[M+H+]/z: Calc. 463.1877, found 465.1889.

Example 41(q)

6-[3-((2-chloro-6-methylpyridin-4-yl)carboxamido)benzoyl)-3-E-[2-(pyridin-2-yl)ethenyl]-1H-indazole

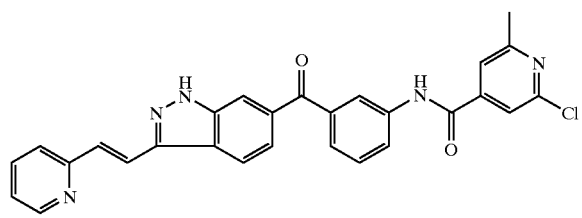

Example 41(q) was prepared in similar manner as Example 41(a) except that 2-chloro-6-methyl-isonicotinic acid used in place of 2-ethyl-5-methyl-2H-pyrazole-3-carboxylic acid. HPLC: R$_t$ 4.11 min. (100% area). $^1$H NMR (DMSO-d6) δ 10.77 (s, 1H), 8.68 (d, 1H, J=3.9 Hz), 8.44 (d, 1H, J=8.4 Hz), 8.28 (s, 1H), 8.21 (dt, 1H, J=6.9, 2.1 Hz), 8.08 (d, 1H, J=16.2 Hz), 7.98 (s, 1H), 7.92–7.64 (m, 9H), 7.35 (dd, 1H, J=6.6, 4.8 Hz), 2.61 (s, 3H).

Example 41(r)

6-[3-((1-n-propyl-3-methyl-1H-pyrazol-5-yl)carboxamido)benzoyl]-3-E-[2-(pyridin-2-yl)ethenyl]-1H-indazole

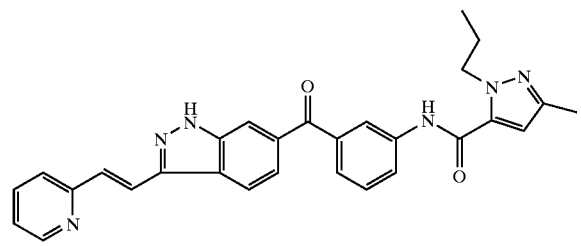

Example 41(r) was prepared in similar manner as Example 41(a) except that 5-methyl-2-propyl-2H-pyrazole-3-carboxylic acid used in place of 2-ethyl-5-methyl-2H-pyrazole-3-carboxylic acid. $^1$H NMR (DMSO-d$_6$) & 10.29 (s, 1H), 8.58 (d, 1H, J=3.9 Hz), 8.33 (d, 1H, J=8.4 Hz), 8.13 (s, 1H), 8.10 (dt, 1H, =5.4, 2.1 Hz), 7.96 (d, 1H, J=16.5 Hz), 7.87 (s, 1H), 7.78 (td, 1H, J=7.5, 1.5 Hz), 7.61–7.49 (m, 6H), 7.24 (dd, 1H, J=6.9, 1.8 Hz), 4.32 (t, 1H, J=6.90 Hz), 1.69 (q, 2H, J=7.2 Hz), 0.77 (t, 3H, 75 Hz). HRMS (MALDI) $C_{28}H_{20}ClN_5O_2$. [M+H$^+$]/z: Calc. 491.2190, found 491.2203.

Example 41(s)

6-[3-(4-t-butylbenzamido)benzoyl]-3-E-[2-(pyridin-2-yl)ethenyl]-1H-indazole

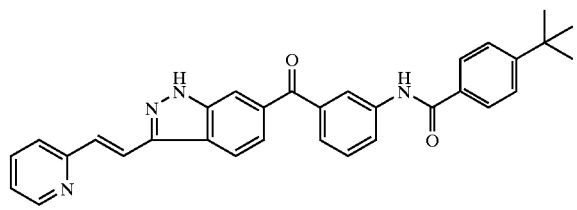

Example 41(s) was prepared in similar manner as Example 41(a) except that 4-tert-butyl-benzoic acid used in place of 2-ethyl-5-methyl-2H-pyrazole-3-carboxylic acid. HPLC: R, 4.67 min. (100% area). $^1$H NMR (DMSO-d$_6$) δ 10.45 (s, 1H), 8.44 (d, 1H, J=8.4 Hz), 8.32 (s, 1H), 8.22 (d, 1H, J=7.5 Hz), 8.07 (d, 1H, J=16.5 Hz), 7.99–7.95 (m, 3H), 7.88 (td, 1H, J=7.7, 1.5 Hz), 7.69–7.59 (m, 7H), 7.38 (dd, 1H. 13.5, 5.1 Hz), 1.36 (s, 9H).

Example 41(t)

6-[3((1-Allyl-3-methyl-1H-pyrazol-5-yl)carboxamido)benzoyl]3-E-[2-(pyridin-2-yl)ethenyl]-1H-indazole

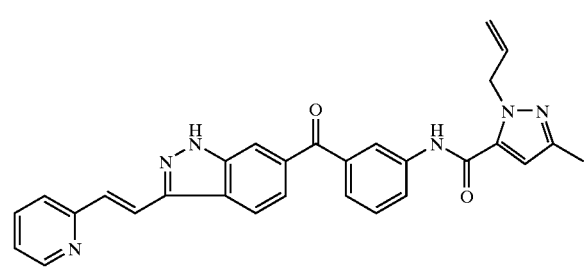

Example 41(t) was prepared in similar manner as Example 41(a) except that 2-allyl-5-methyl-2H-pyrazole-3-carboxylic acid used in place of 2-ethyl-5-methyl-2H-pyrazole-3-carboxylic acid. HPLC: R, 4.11 min. (100% area). $^1$H NMR (DMSO) δ 10.46 (s, 1H), 8.74 (t, 1H, J=5.1 Hz), 8.48 (d, 1H, J=8.4 Hz), 8.28 (s, 1H), 8.22 (t, 1H, J=5.4, 2.1 Hz), 8.15–8.01 (m, 3H), 7.39 (td, 1H, J=7.8, 1.8 Hz), 7.82–7.63 (m, 6H) 7.39 (td, 1H, J=7.7, 1.5 Hz), 6.146.02 (m, 1H), 5.22–5.03 (m, 4H), 2.38 (s, 3H). HRMS (MALDI) C$_{29}$H$_{24}$N$_6$O$_2$ (M+H$^+$)/z: Calc. 489.2034, found 489.2035.

Example 41(u)

6-[3-((2-chloro-6-methoxypyridin-4-yl)carboxamido)benzoyl]-3-E-[2-(pyridin-2-yl)ethenyl]-1H-indazole

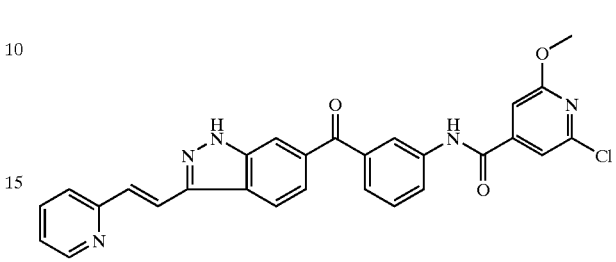

Example 41(u) was prepared in similar manner as Example 41(a) except that 2-chloro-6-methoxy-isonicotinic acid used in place of 2-ethyl-5-methyl-2H-pyrazole-3-carboxylic acid. HPLC R$_t$: 4.37 min. (100% area). $^1$H NMR (DMSO-d$_6$) δ 10.74 (s, 1H), 8.68 (d, 1H, J=3.6 Hz), 8.44 (d, 1H, J=8.4 Hz), 8.28 (s, 1H), 8.20 (td, 1H, 1=6.6, 2.4 Hz), 8.07 (d, 1H, 1=16.2 Hz), 7.98 (s, 1H), 7.89 (td, 1H, J=7.7, 1.8 Hz), 7.77–7.62 (m, 6H), 7.38 (s, 1H), 7.35 (dd, 1H, 1=6.9, 1.8 Hz), 3.98 (s, 3H).

Example 41(v)

6-[3-((3-Ethyl-1-methyl-1H-pyrazol-5-yl)carboxamido)benzoyl]-3-E-[2-(pyridin-2-yl)ethenyl]-1H-indazole

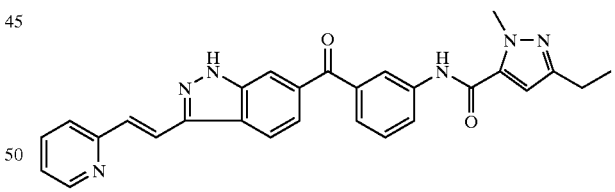

Example 41(v) was prepared in similar manner as Example 41(a) except that 5-ethyl-2-methyl-2H-pyrazole-3 carboxylic acid used in place of 2-ethyl-5-methyl-2H-pyrazole-3-carboxylic acid. R$_t$ 4.16 min. (100% area). $^1$H NMR (DMSO-d$_6$) δ 10.44 (s, 1H), 8.73 (d, 1H, =3.0 Hz), 8.78 (d, 1H, 8.7 Hz), 8.30 (s, 1H), 8.23 (d, 1H, J=6.9 Hz), 8.14–8.03 (m, 2H), 7.93 (t, 1H, 6.9 Hz), 7.82–7.63 (m, 6H), 7.40 (t, 1H, J=6.3 Hz), 7.01 (s, 1H), 4.12 (s, 1H), 2.68 (q, 21H, 7.8 Hz), 1.30 (t, 3H, J=7.5 Hz). HRMS (MALDI) C$_{28}$H$_{24}$N$_6$O$_2$ (M$^+$)/z: Calc. 477.2034, found 477.2054.

Example 41(w)

6-[3-((2-chloropyridin-4-yl)carboxamido)benzoyl]-3-E-[2-(pyridin-2-yl)ethenyl]-1H-indazole

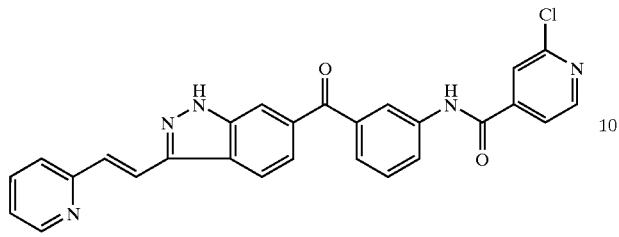

Example 41(w) was prepared in similar manner as Example 41(a) except that 2-chloro-isonicotinic acid used in place of 2-ethyl-5-methyl-2H-pyrazole-3-carboxylic acid. HPLC $R_t$: 3.99 min. (100% area). $^1$H NMR (DMSO-$d_6$) δ 10.88 (s, 1H), 7.33 (d, 2H, H=4.8 Hz), 8.49 (d, 1H, J=8.4 Hz), 8.33 (s, 12)), 8.26 (td, 1H, J=6.9, 3.0 Hz), 8.12–7.91 (m, 5H), 7.82–7.63 (m, 5H), 7.40 (t, 1H, =4.8 Hz).

Example 41(x)

6-[3((1-Isopropyl-3-methyl-1H-pyrazol-5-yl)carboxamido)benzoyl]-3-E-[2-(pyridin-2-yl)ethenyl]-1H-indazole

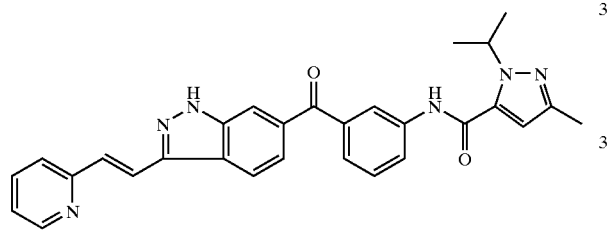

Example 41(x) was prepared in similar manner as Example 41(a) except that 2-isopropyl-5-methyl-2H-pyrazole-3-carboxylic acid used in place of 2-ethyl-5-methyl-2H-pyrazole-3-carboxylic acid. HPLC: $R_t$ 4.19 min. (100% area). $^1$H NMR (DMSO) δ 10.46 (s=1H), 8.72 (t, 1H, J=4.8 Hz), 8.48 (s, 1H, J=d9.0 Hz), 8.31 (s. 3H), 8.21 (td, (H, 3=9.6, 2.1 Hz), 8.15–7.98 (m, 2( ), 7.96–7.84 (m, 1H), 7.82–7.65 (m, 5H), 7.427.38 (m, 1H), 6.88 (s, 1H), 5.645.38 (m, 1H), 2.32 (s, 3H), 1.48 (d, 1H, J=6.6 Hz). HRMS (MALDI) $C_{19}H_{26}N_6O_2$ (M+H$^+$]/z; Calc. 491.2190, found 491.2194.

Example 41(y)

6-[3-(isopropoxycarbonylamino)benzoyl]-3-E-[pyridin-2-yl)ethenyl]-1H-indazole

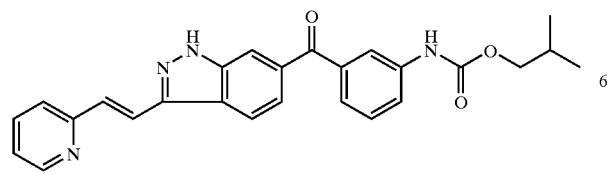

Example 41(y) was prepared in similar manner as Example 41(a) except that isopropyl chloroformate was used in place of 2-ethyl-5-methyl-2H-pyrazole-3-carboxylic acid. $^1$H NMR (DMSO-$d_6$) δ 9.97 (s, 1H), 8.72 (t, 2H, J=4.8 Hz), 8.47 (d, 1H, J=8.7 Hz), 8.347.96 (m, 3H), 8.01–7.87 (m, 2H), 7.82–7.69 (m, 2H), 7.52 (dt, 1H, J=7.5, 1.2 Hz), 7.42–7.36 (m, 2H), 3.68 (d, 2H, J=6.6 Hz), 2.02 (m, 1H), 1.02 (d, 6H. J=6.6 Hz). HRMS (MALDI) $C_{26}H_{24}N_4O_3$ M+H$^+$]/z: Calc' 441.1921, found 441.1937.

Example 41(z)

6-[3-((4-chloropyridin-2-yl)carboxamido)benzoyl]-3-E-[2-(pyridin-2-yl)ethenyl]-1H-indazole

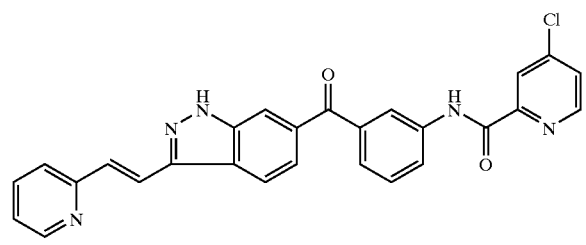

Example 41(z) was prepared in similar manner as Example 41(a) except that used 4-chloro-pyridine-2 arboxylic acid was used in place of 2-ethyl-5-methyl-2H-pyrazole-3-carboxylic acid. HPLC $R_1$: 4.40 min. (100% area). $^1$H NMR (DMSO-$d_6$) δ 10.99 (s, 1H), 8.72 (d, 1H, J=5.4 Hz), 8.63 (d, 1H, J=3.9 Hz), 8.44 (s, 1H), 8.38 (d, 1H, J=8.4 Hz), 8.25 (dt, 1H, 3=6.6, 2.4 Hz), 8.16 (d, 1H, J=1.8 Hz), 8.02 (d, 1H, J=16.2 Hz), 7.94 (s, 1H), 7.86–7.80 (m, 2H), 7.72–7.58 (m, 5H), 7.29 (dd, 1H, J=6.9, 6.0 Hz).

Example 41(aa)

6-[3-pyridin-2-ylcarboxamido)benzoyl]-3-E-[2-(pyridin-2-yl)ethenyl]-1H-imidazole

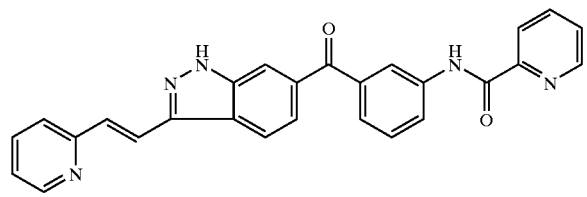

Example 41(aa) was prepared in a similar manner to that described for Example 41(a), except that pyridine-2-carboxylic acid was used instead of 2-ethyl-5-methyl-2H-pyrazole-3-carboxylic acid. $^1$H NMR (300 MHz, DMF-$d_6$) δ 10.9 (s, 1H), 8.74 (m, 1H), 8.63 (dd, 1H, J=4.78 Hz, 0.94 Hz), 8.46 (s, 1H), 8.38 (d, 1H. J 8.48 Hz), 8.25 (dt, 1H, J=7.17 Hz, 8=2.05 Hz), 8.16 (dt, 1H, J=7.738 Hz, J=1.04 Hz), 8.07 (td, 1H, J=7.56 Hz, J=1.67 Hz), 8.02 (d, 1H, J=16.28 Hz), 7.95 (s, 1H), 7.83 (td, 1H, J=7.65 Hz, 8=1.81 Hz), 7.22–7.66 (m, 47, 7.30 (qd, 1H, J=7.40 Hz, 3=1.02 Hz). MS (ESI+) [M+H]/z Calc'd 446, found 446.

Example 41(bb)

6-[3-(3-methoxybenzamido)benzoyl]-3-E-[2-pyridin-2-yl)ethenyl]-1H-indazole

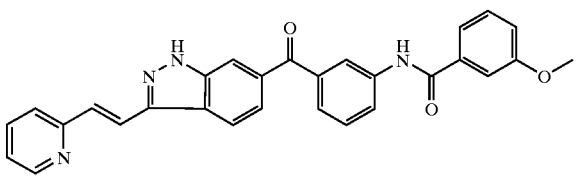

Example 41(bb) was prepared in similar manner as Example 41(a) except that 3-methoxybenzoic acid used in place of 2-ethyl-5-methyl-2H-pyrazole-3 carboxylic acid. ¹H NMR (DMSO-d₆) δ 10.50 (s, 1H,), 8.67 (d, 1H, J=3.9 Hz), 8.46 (d, 1H, J=8.7 Hz), 8.33 (s, 1H), 8.22 (dt, 1H, J=7.8, 1.8), 8.08 (d, 1H, J=15.0 Hz), 8.00 (s, 1H,), 7.78–7.54 (m, 8H), 7.51 (t, 1H, 7.8 Hz), 7.38–7.33 (m, 1H), 7.23 (dd, 1H, J=75, 1.5 Hz), 3.90 (s, 3H). HRMS (MALDI) $C_{29}H_{22}N_4O_3$. [M+H⁺]/z: Calc. 475.1765, found 475.1763.

Example 41(cc)

6-[3-(phenoxyamido)benzoyl]-3-E-[2-(pyridin-2-yl)ethenyl]-1H-indazole

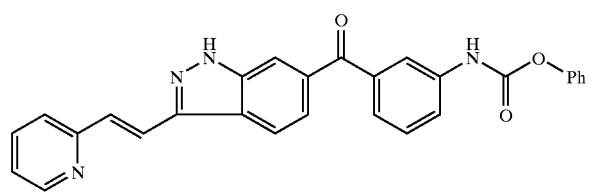

Example 41(cc) was prepared in a similar manner to that described for Example 41(a), except that phenyl chloroformate was used instead of 2-ethyl-5-methyl-2H-pyrazole-3-carboxylic acid. mp 212–217° C., ¹H NMR (300 MHz, DMSO-d₆) δ 13.63 (s, 1H), 1051 (s, 1H), 8.62 (d, I, J=4.3 Hz), 8.36 (d, 1H, J=8.6 Hz), 8.04–7.81 (m, 5H), 7.71–7.40 (m, 7H), 7.31–7.22 (m, 4H). ESIMS m/z 461 [M+H]⁺. Anal. calc'd for $C_{28}H_{20}N_4O_3 \times 0.3\ H_2O$ (465.9 g mol⁻¹): C, 72.18; H, 4.46; N, 11.33. Found: C, 72.41; H. 4.63; N, 11.57.

Example 41(dd)

6-[3-(3,3-dimethylacrylamido)benzoyl]-3-E-[2-(pyridin-2-yl)ethenyl]-1H-indazole

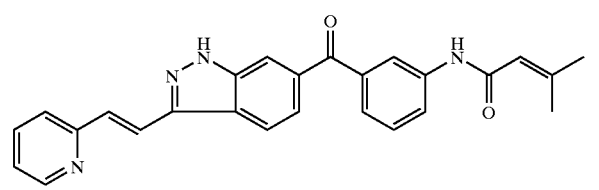

Example 41(dd) was prepared in a similar manner to that described for Example 41 (a), except that 3,3-dimethylacrylic acid was used instead of 2-ethyl-5-methyl-2H-pyrazole-3-carboxylic acid. ¹H NMR (300 MHz, DMSO-d₆) δ 13.6 (s, 1H), 10.2 (s, 1H), 8.63 (d, 1H, J=3.81 Hz), 8.37 (d, 1H, J=8.49 Hz), 8.12 (s, 1H), 8.02 (d, 1H, J=16.34 Hz), 7.99(d, 1H, J=7.88 Hz), 7.83 (td, 1H, J=7.67 Hz, 3=1.78 Hz), 7.70 (d, J H, =7.85 Hz), 7.63 (dd, 1H, J=8143 Hz, J 71.23 Hz), 747–7.56 (m, 2H), 7.29 (qd, 1H, J=7.39 Hz, J=0.99 Hz), 6.82 (m, 1H, J=6.9 Hz), 5.85 (s, 3H), 2.12 (s, 3H), 1.85 (s, 3H). MS (ESI+) [M+H]/z Calc'd 409, found 409. Anal. Calc'd for $C_{26}H_{22}N_4O_2 \times 0.33$ TBME: C, 7354; H, 5.80; N, 12.41. Found: C, 73.26; H, 5.76; N, 12.36.

Example 41(ee)

6-[3-(1-Ethyl-3-methyl-1H-pyrazol-5-yl)carboxamido)-4-methylbenzoyl]-3-E-[2-(pyridin-2-yl)ethenyl]-1H-indazole

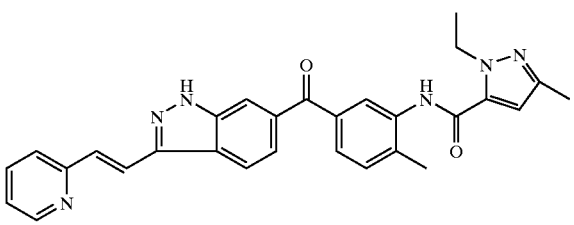

Example 41 (e) was prepared in similar manner as Example 41 (a) except that Example 40( ) was used in place of Example 40(a). ¹H NMR (DMSO-d₆) δ 13.6 (s, 1H), 9.94 (s, 1H), 8.62 (d, 1H, J=3.8 Hz), 8.36 (d, 1H, J=8.51 Hz), 8.01 (d, 1H, J=1636 Hz), 7.91 (s, 1H), 7.84 (dd, 1H, 3=7.66 Hz, J=1.74 Hz), 7.81 (s, 1H), 7.70 (d, 1H, J=7.9 Hz), 7.64 (d, 1H, J=16.5 Hz), 7.62 (m, 2H), 7.50 (d, 1H, J=7.83 Hz), 7.29 (m, 1H), 6.82 (s, 1H), 4.42 (qm 2H, J=7.06 Hz), 2.36 (s, 3H), 2.21 (s, 3H), 1.30 (t, 3H, 1=87.09 Hz). MS (ESI+) [M+H]/z Calc'd 491, found 491. Anal. Calc'd: C, 71.00; H. 5.34; N, 17.13. Found: C, 70.80; H, 5.38; N, 17.00.

Example 41(ff)

6-[3-((1-Allyl-3-methyl-1H-pyrazol-5-yl)carboxamido)-4-methylbenzoyl]-3-E-[2-(pyridin-2-yl)ethenyl]-1H-indazole

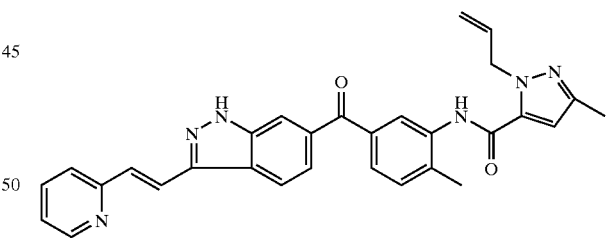

Example 41(ff) was prepared in a similar manner to that described for Example 41 (ee), except that 2-ally-5-methyl-2H-pyrazole-3-carboxylic acid was used in place of 2-ethyl-5-methyl-2H-pyrazole-3-carboxylic acid. ¹H NMR (DMSO-d₆) δ 13.6 (s, 1H), 9.98 (s, 1H), 8.62 (d, 1H, J=4.60 Hz), 8.36 (d, 1H, J=8.46 Hz), 8.01 (d, 1H, J=16.37 Hz), 7.91 (s, 1H), 7.83 (td, 1H, 3=7.69 Hz. 3=1.77 Hz), 7.78 (d, 1H, J=1.73), 7.70 (d. 1K, J=7.78 Hz), 759–7.70 (m, 3H), 7.50 (d, 1H, J=8.01 Hz), 7.29 (qd, 2H, J=7.46 Hz, 3=1.02 Hz), 6.86 (s, 1H), 5.95 (m, 1H), 4.93–5.10 (m, 4H), 2.34 (s, 3H), 2.22 (s, 3H). LCMS (EI+) [M+H]/z Calc'd 503, found 503. Anal. Calc'd: C. 71.70; H. 5.21; N, 16.72. Found: C, 70.98; H, 5.42; N, 15.94.

Example 41(gg)

6-(3-acetamido-4-methylbenzoyl)-3-E-[2-(pyridin-2-yl)ethenyl]-1H-indazole

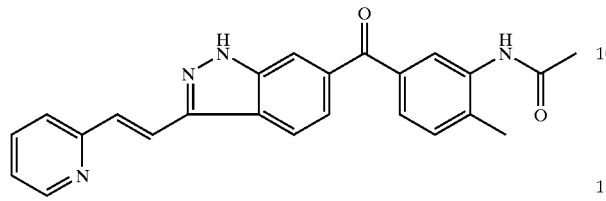

Example 41(g) was prepared in a similar manner to that described for Example 41 (ee), except that acetyl chloride was used in place of 2-ethyl-5-methyl-2H pyrazole-3-carboxylic acid. $^1$H NMR (CD$_3$OD) δ 8.57 (d, 1H, J=4.90 Hz), 8.13 (d, 1H, J=8.49 Hz), 7.99 (s, 1H), 7.95 (d, 1H, 3=16.53 Hz), 7.89 (d, 1H, J=1.46 Hz), 7.86 (td, 1H, J=7.64 Hz, 1=1.73 Hz), 7.73 (d, 1H, J=7.05 Hz), 7.62–7.69 (m, 2H), 7.65 (d, 1H, J=16.48 Hz), 7.44 (d, 1H, J=7.97 Hz), 7.32 (qd, 1H, J=7.44 Hz. J=1.03 Hz), 2.38 (s, 3H), 2.18 (s, 3H). LCMS (ESI+) [M+H]/z Calc'd 397, found 397. Anal. Calc'd: C, 72.71; H, 5.08; N, 14.13. Found: C, 72.29; H, 5.09; N, 13.98.

Example 41(hh)

6-[3-((1,3-Dimethyl-1H-pyrazol-5-yl)carboxamido)4-methylbenzoyl]-3-E-[2-(pyridin-2-yl)ethenyl]-1H-indazole

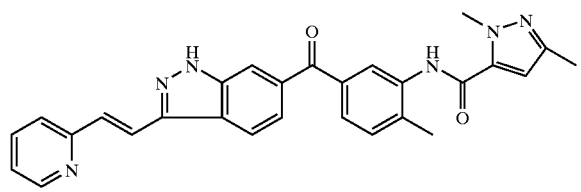

Example 41(hh) was prepared in a similar manner to that described for Example 41 (ee), except that 2,5-dimethyl-2H-pyrazole-3-carboxylic acid was used in place of 2-ethyl-5-methyl-2H-pyrazole-3-carboxylic acid. HPLC R$_t$: 3.92 min., (100% area). $^1$H NMR (DMSO) δ 10.02 (s, 1H), 8.74 (d, 1H, J=3.6 Hz), 8.49 (d, 1H, J=8.4 Hz), 8.13 (d, 1H, J=16.3 Hz), 8.03 (s, 1H), 7.96–7.93 (m, 2H), 7.84–7.72 (m, 4H), 7.63 (d, 1H, 8.1 Hz), 7.42 (dd, 1H, J=6.8, 1.5 Hz), 6.95 (s, 1H), 4.11 (s, 1H), 2.48 (s, 1H), 2.32 (s, 1H).

Example 41(ii)

6-[3-((1-n-propyl-3-methyl-1H-pyrazol-5-yl)carboxamido)-4-methylbenzoyl]-3-E-[2-(pyridin-2-yl)ethenyl]-1H-indazole

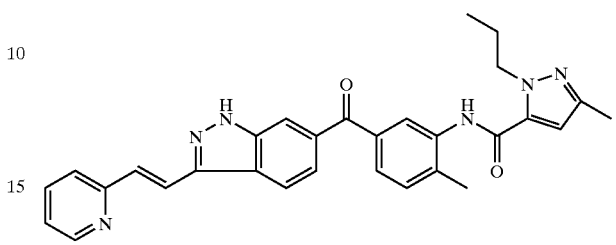

Example 41(ii) was prepared in a similar manner to that described for Example 41(ee), except that 5-methyl-2-propyl-2H-pyrazole-3-carboxylic acid was used in place of 2-ethyl-5-methyl-2H-pyrazole-3-carboxylic acid. HPLC: R, 4.16 min. (100% area). $^1$H NMR (DMSO-d$_6$) δ 10.29 (s, 1H), 8.58 (d, 1H, 3.9 Hz), 8.33 (d, 1H, J=8.4 Hz), 8.13 (s, 1H), 8.10 (dt, 1H, J=5.4, 2.1 Hz), 7.96 (d, 1H, J=16.5 Hz), 7.87 (s, 1H), 7.78 (td, 1H, J=7.5, 1.5 Hz), 7.61–7.49 (m, 6H), 7.24 (dd, 1H, J=6.9, 1.8 Hz), 4.32 (t, 2H, J=6.90 Hz), 2.58 (s, 3H), 2.22 (s, 3H) 1.69 (q, 2H, J=7.2 Hz), 0.77 (t, 3H, 7.5 Hz). HRMS (MALDI) C$_{30}$H$_{26}$N$_6$O$_2$ [M+H$^+$]/z: Calc. 505.2347, found 505.2343.

Example 41(jj)

6-[3-((3-Ethyl-1-methyl-1H-pyrazol-5-yl)carboxamido)-4-methylbenzoyl]-3-E-[2-(pyridin-2-yl)ethenyl]-1H-indazole

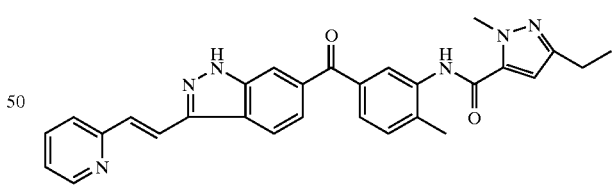

Example 41(jj) was prepared in a similar manner to that described for Example 41(ee), except that 5-ethyl-2-methyl-2H-pyrazole-3-carboxylic acid was used in place of 2-ethyl-5-methyl-2H-pyrazole-3-carboxylic acid. $^1$H NMR (DMSO-d$_6$) δ 10.78 (s, 1H), 9.43 (d, 1H, J=3.0 Hz), 9.15 (t, 1H, J=9.6 Hz), 8.82 (dd, 1H, J=16.4, 1.5 Hz), 8.72–8.61 (m, 2H), 8.52–8.30 (m, 4H), 8.10 (dd, 1H, J=6.9, 5.7), 7.93–7.89 (m, 1H), 7.72–7.69 (m, 1H), 4.85 (s, 3H), 3.39 (q, 2H, J=7.8 Hz), 3.17 (s, 3H), 2.10 (t, 3H, J=7.5 Hz). HRMS (MALDI) C$_{29}$H$_{26}$N$_6$O$_2$ (M+H$^+$) m/z: Calc. 491.2190, found 491.2211.

Example 41(kk)

6-[3((1-Isopropyl-3-methyl-1H-pyrazol-5-yl)carboxamido)-4-methylbenzoyl]-3-E-[2-(pyridin-2-yl)ethenyl]-1H-indazole

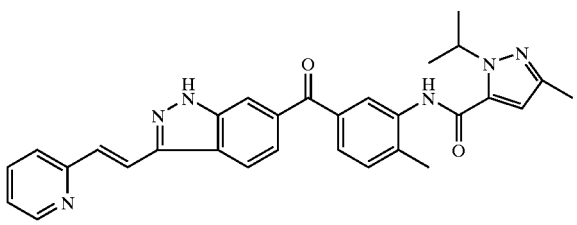

Example 41(kk) was prepared in a similar manner to that described for Example 41(ee), except that 2-isopropyl-5-methyl-2H-pyrazole-3-carboxylic acid was used in place of 2-ethyl-5-methyl-2H-pyrazole-3-carboxylic acid. HPLC: $R_t$ 4.11 min. (100% area). $^1$H NMR (DMSO-$d_6$) δ 9.99 (s, 1H), 8.68 (d, 1H, J=3.6 Hz), 8.42 (d, 1H, J=8.7 Hz), 8.07 (d, 1H, 3=16.4 Hz), 7.98 (s, 1H), 7.67–7.86 (m, 2H), 7.77–7.65 (m, 4H), 7.56 (d, 1H, J=7.8 Hz), 7.37–7.33 (m, 1H), 6.82 (s, 1H), 5.44–5.36 (m, 1H), 2.42 (s, 3H), 2.28 (s, 3H), 1.42 (d, 6H, J=6.6 Hz). Anal. ($C_{30}H_{28}N_6O_2 \cdot 0.2H_2O$) Calc'd: C, 5.63; N, 16.54. Found C, 7057; H, 5.70; N, 16.35.

Example 41(ll)

6-[2,4-dimethyl-5-((1-Ethyl-3-methyl-1H-pyrazol-5-yl)carboxamido)benzoyl]-3-E-[2-(pyridin-2-yl)ethenyl]-1H-indazole

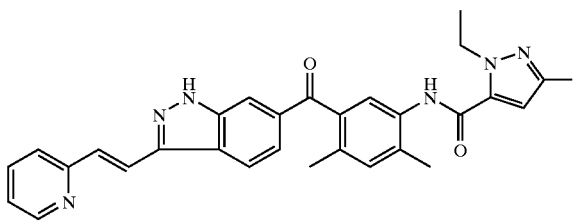

Example 41(ll) was prepared in similar manner as Example 41(a) except that Example 40(c) was used in place of Example 40(a). $^1$H NMR (DMSO-$d_6$) δ 13.6 (s, 1H), 9.82 (s, 1H), 8.63 (d, 1H, J=3.84 Hz), 8.35 (d, 1H, J=8.54 Hz), 8.00 (d, 1H, J=16.37 Hz), 7.83 (s, 1H), 7.83 (td, 1H., J=7.65 Hz, J=1.82 Hz), 7.69 (d, 1H, J=7.89 Hz), 7.65 (dd, 1H, J=8.52 Hz, J=1.36 Hz), 7.62 (d, 1H, J=16.34 Hz), 7.35 (s. 1H), 7.32 (s, 1H), 7.29 (q d, 1H, J=7.42 Hz, 0.09 Hz), 6.78 (s, 1H), 4.39 (q, 2H, J=7.15 Hz), 2.30 (s, 3H), 2.25 (s, 3H), 2.19 (s, 3H), 1.27 (t 3, 1H 7.15 Hz). LJMS (ESI+) [M+H]/z Calc'd 505, found 505.

Example 41(mm)

6-[2,4-dimethyl-5-((1,3-dimethyl-1H-pyrazol-5-yl)carboxamido)benzoyl]-3-E-[2-pyridin-2-yl)ethenyl]-1H-indazole

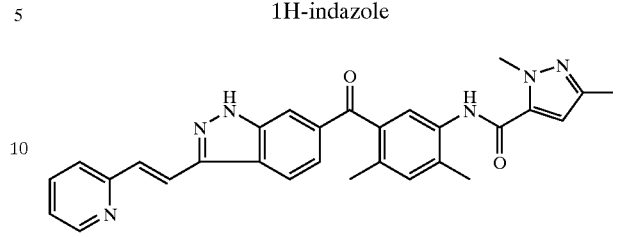

Example 41(mm) was prepared in a similar manner to that described for Example 41(ll), except that 2,5-dimethyl-2H-pyrazole-3-carboxylic acid was used in (S. 1H), 9.81 (S. 1H), 8.62 (d, 1H, 13.81 Hz), 8.35 (d, 1H, J=8.6 Hz), 8.00 (d, 1H, J=16.36 Hz), 7.83 (dt, 1H, J7.65 Hz, J=1.8 Hz), 7.8 (s, 1H), 7.69 (d, 1H, J=7.88 Hz), 7.65 (dd, 1H, J=8.53 Hz, J=1.36 Hz), 7.62 (d, 1H, J=16.35 Hz), 7.36 (s, 1H), 7.32 (s, 1H), 7.29 (qd, 1H, J=7.41 Hz, J=1.03 Hz), 6.79 (s, 1H), 3.96 (s, 3H), 2.30 (s, 3H), 2.25 (s, 3H), 2.18 (s, 3H). LCMS (ESI+) [M+H]/z Calc'd 491, found 491. Anal. Calc'd: C. 71.00; H, 5.34; N, 17.13. Found: C, 70.69; H. 5.57; N, 16.26.

Example 41(nn)

6-(5-acetamido-2,4-dimethylbenzoyl)-3-E-[2-(pyridin-2-yl)ethenyl]-1H-indazole

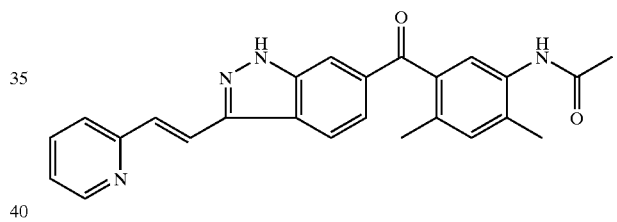

Example 41(nn) was prepared in a similar manner to that described for Example 41(ll), except that acetyl chloride was used in place of 2-ethyl-5-methyl-H-pyrazole-3-carboxylic acid. $^1$H NMR (DMSO-$d_6$) δ 13.6 (bs, 1H), 9.34 (s, 1H), 0.62 (d, 1H, 1=4.15 Hz), 8.33 (d, 1H, J=8.6 Hz), 7.86 (d, 1H, J=16.36 Hz), 7.83 (td, 1H, J=7.71 Hz, J=1.82 Hz), 7.81 (s, 1H), 7.69 (d, 1H, J=7.84 Hz), 7.64 (dd, 1H, J=1.38 Hz), 7.62 (d, 1H, J=16.46 Hz), 7.48 (s, H), 7.29 (qd, 1H, J=7.44 Hz, J=1.02 Hz), 7.24 (s, 1H), 2.27 (s, 3H), 2.23 (s, 3H), 2.02 (s, 3H). LCMS (ESI+) 1M+H]/z Calc'd 411, found 411.

Examples 41(oo)–41(lll) can be prepared in a similar manner to that described for Example 41(a).

Example 41(oo)

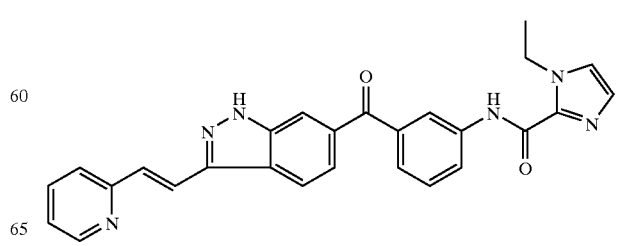

203
Example 41(pp)
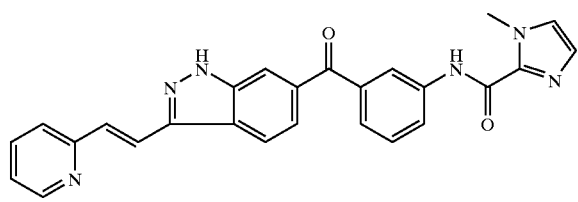
Example 41(qq)
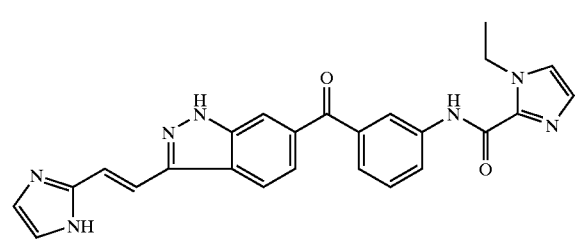
Example 41(rr)
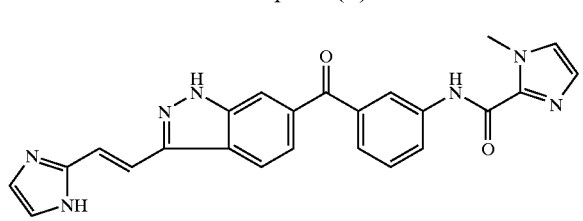
Example 41(ss)
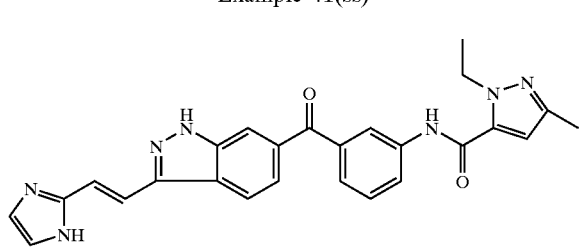
Example 41(tt)
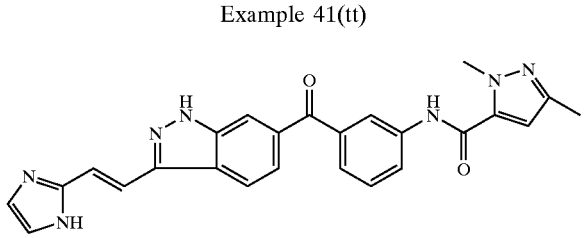
204
Example 41(uu)
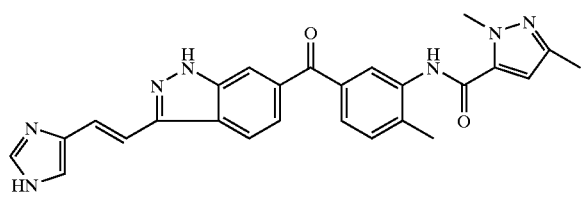
Example 41(vv)
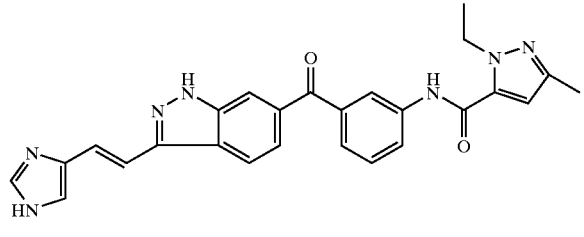
Example 41(ww)
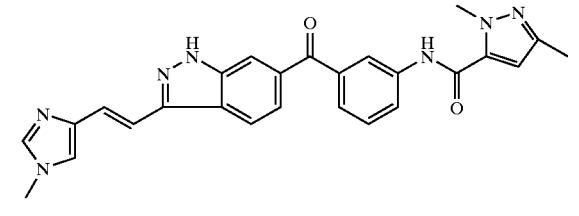
Example 41(xx)
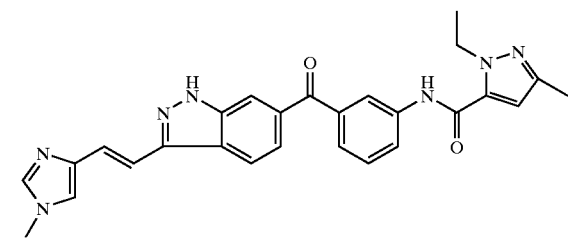
Example 41(yy)
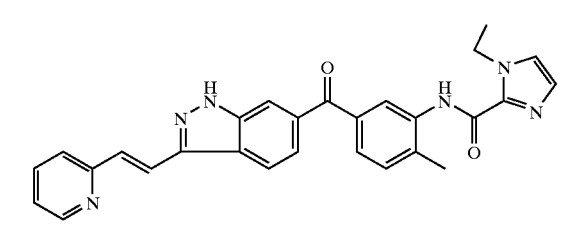

205
Example 41(zz)
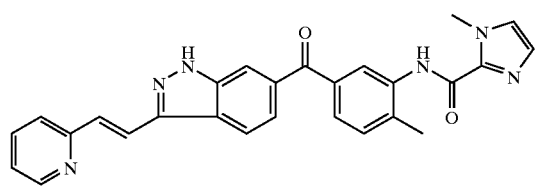
Example 41(aaa)
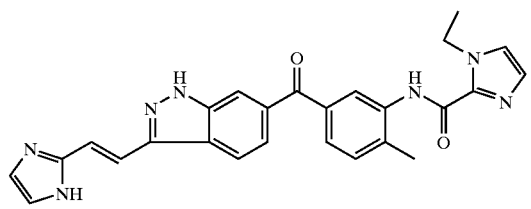
Example 41(bbb)
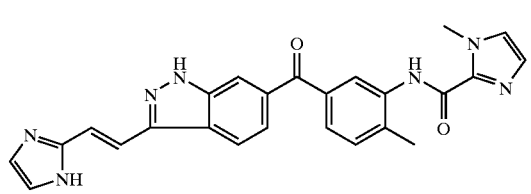
Example 41(ccc)
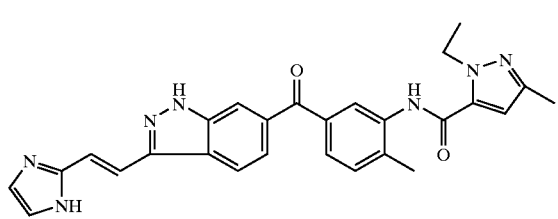
Example 41(ddd)
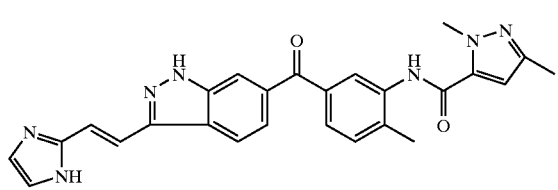
206
Example 41(eee)
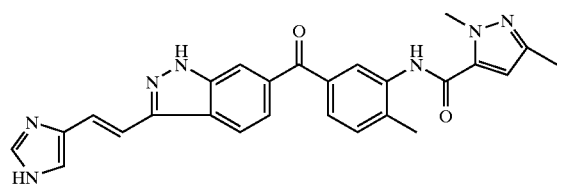
Example 41 (fff)
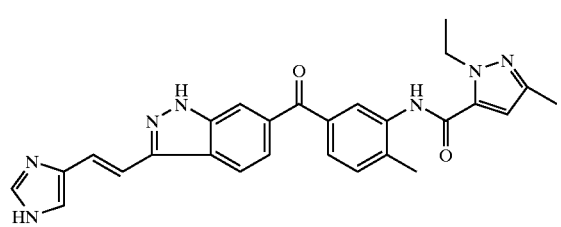
Example 41(ggg)
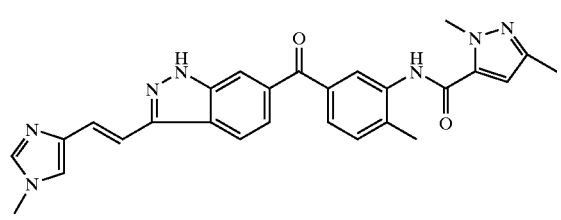
Example 41(hhh)
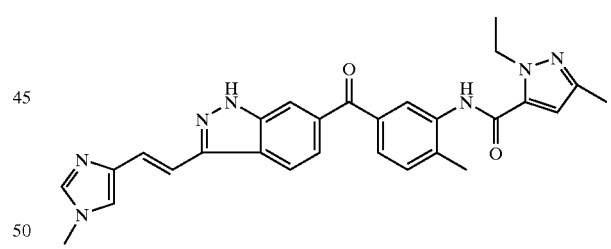
Example 41(iii)
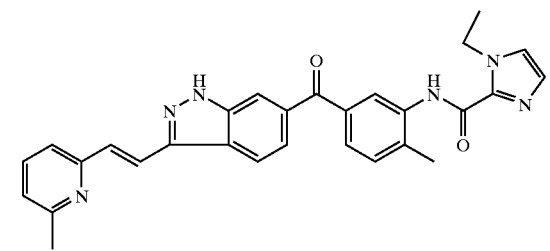

Example 41(jjj)

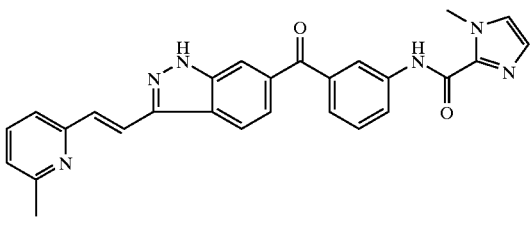

Example 41(kkk)

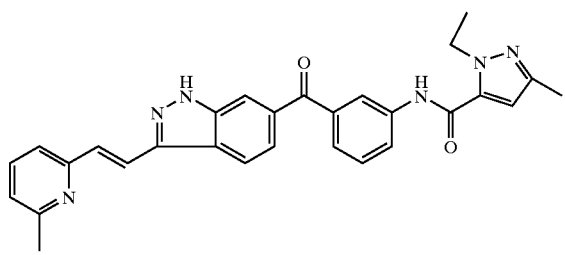

Example 41(lll)

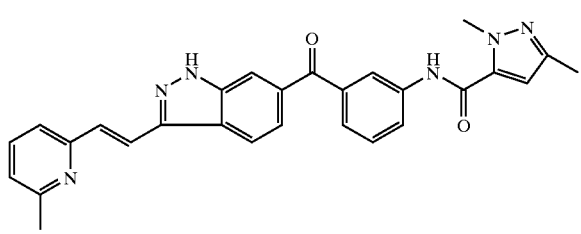

Example 42(a)

6-(3-Benzamidobenzoyl)-3-E-[2-(pyridin-2-yl)
ethenyl)-1H-indazole

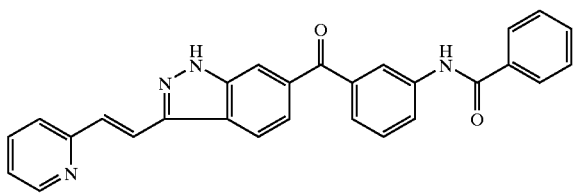

Example 42(a) was prepared from 6-(3-benzamidobenzoyl)-3-E-[2-(pyridin-2-yl)ethenyl]-1-(2-trimethylsilanyl-ethoxymethyl-1H-indazole in a similar manner as that of Example 12. (0.58 g, 80.6%). HPLC 4.13 min (98% area). $^1$H NMR (CDCl$_3$) δ 8.66 (d, 1H, J=4.1 Hz), 8.24 (d, 1H, J=8.5 Hz), 8.11–8.10 (m, 3H), 8.01–7.98 (m, 4H), 7.83 (t, 2H, J=7.1 Hz), 7.72–7.53 (m, 7H), 7.30 (qd, 1H, J=5.2, 1.1 Hz). HRMS (MALDI) C$_{28}$H$_{20}$N$_4$O$_2$. [M+H$^+$]/z: Calc. 445.1664, found 445.1659. Anal. (C$_{26}$H$_{11}$N$_5$O$_2$.0.2EtOAc): C, 75.87; H, 4.78; N, 12.39.

The starting material was prepared as follows:

(i)

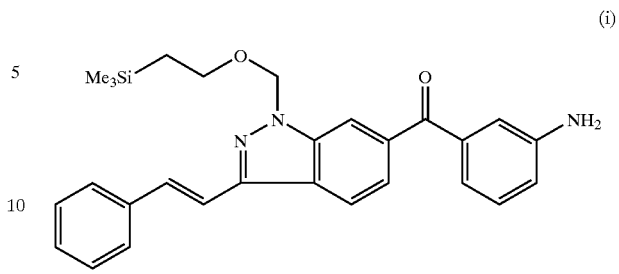

To a stirred solution of 6-iodo-3-((E)-styryl) 12-trimethylsilanyl-ethoxymethyl)1H-indazole (4.00 g, 8.40 mmol), from Example 14 step (i), in anisole (48 mL) under an argon atmosphere were added bis(triphenylphosphine) palladium dichloride (176 mg, 0.25 mmol), TBACI (288 mg, 1.0 mmol), 2-butanol (1.54 mL, 16.8 mmol) and potassium carbonate (3.48 g, 25.2 mmol). The resulting mixture was stirred under a carbon monoxide atmosphere at 80° C. for 100 h. After removal of the solvent by in vacuo concentration, the residue obtained was diluted with EtOAc (400 mL) and extracted with sat. NaCl (2×150 mL), sat. NaHCO$_3$ (2×50 mL) and water (2×50 mL) then organic layer filter through 20 mL of silica. The organic filtrate was then concentrated in vacuo, to give an amber oil. Purification by flash chromatography with hexane:EtOAc (7:3) provided 6-(3-aminobenzoyl)-3-((E)-styryl)-1-(2-trimethylsilanyl-ethoxymethyl)1H-indazole as an amber oil upon concentration (2.38 g, 61% yield). $^1$H NMR (CDCl$_3$) δ 8.84 (dd, 1H, J=8.70, 0.90 Hz), 8.02 (s, 1H), 7.77 (dd, 1H, J=8.40, 1.0 Hz), 7.62–7.59 (m, 2H), 7.40 (t, 2H, J=7.20 Hz), 7.38–7.24 (m, 4H), 7.22–7.19 (m, 3H), 6.98 (dq, 1H, J=8.30, 0.90 Hz), 3.83 (brs, 2H,), 3.61 (t, 2H, J=8.10 Hz), 0.91 (t, 2H, K=7.20 Hz), 0.17 (s, 9H).

(ii)

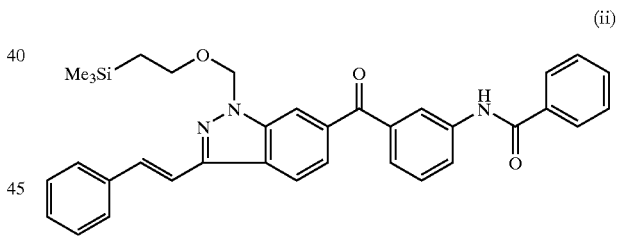

To a stirred solution of 6-(3-aminobenzoyl)-3-((E)-styryl)-112-trimethylsilanyl-ethoxymethyl)-1H-indazole (3.22 g, 6.87 mmol) in methylene chloride (10 mL) under an argon atmosphere was added benzoyl chloride (0.95 mL, 8.37 mmol) and pyridine (0.67 mL, 3.22 mmol). After 2 h the solution was diluted with 100 mL of EtOAc and washed with saturated NaCl (1×50 mL), citric acid (1M, 2.5 pH, 2×50 mL) and (50:50) NaHCO$_3$/water (2×50 mL). The organic layer was dried over Na$_2$SO$_4$ and filtered through 20 mL of silica The organic layer was concentrated in vacuo, to provide the product as a yellow solid. Purification using flash chromatography through silica eluting with hexane:EtOAc (7:3) afforded 6-(3-benzamidobenzoyl)-3-((E) styryl)-1-(2-trimethylsilanyl-ethoxymethyl)1H-indazole as a yellow foam (3.22 g, 85.1% yield). $^1$H NMR (CDCl$_3$) δ 8.19 (d, 1H, J=8.7 Hz), 8.16 (s, 1H,), 8.11–8.10 (m, 2H), 8.03–7.93 (m, 3H), 7.82(dd, 1H, J=8.4, 1.2 Hz), 7.70–7.67 (m, 3H), 7.647.54 (m, 5H), 7.48 (t, 2H, J=14.1 Hz) 7.39 (1H, d, J=7.2 Hz).

(iii)

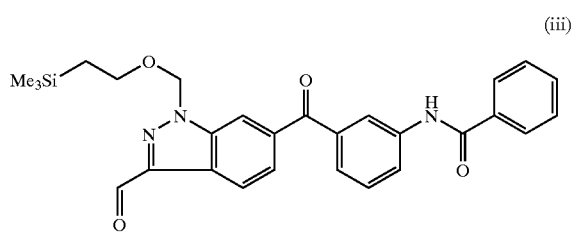

A stirred solution of 63-benzamidobenzoyl)-3-((E)-styryl)1-(2-trimethylsilanyl-ethoxy-methyl-1H-indazole (2.35 g, 4.07 mmol) in methylene chloride (45.6 mL) was cooled to −45° C. using acetonitrile/solid carbon dioxide bath. Ozone was then bubbled through the solution at a rate of 1.5 Lp)$_m$, 60 amps for 15 minutes. The reaction mixture was quenched with the addition of hydrogen sulfide (2.5 mL) and warmed to 25° C. Removal of methylene chloride was accomplished by in vacuo concentration. The residue was purified through silica eluting with hexane:EtOAc (7:3) afforded 63 benzamidobenzoyl)-1-(2-trimethylsilanyl-ethoxy-methyl)-1H-indazole-3-carboxaldehyde as an off-white foam (1.74 g, 85% yield). HPLC. 3.78 min (100% area); $^1$H NMR (DMSO-d$_6$) δ 10.77 (s, 1H), 10.42 (s, 1H), 8.468.39 (m, 2H), 8.31 (dt, 1H, J=6.0, 1.8 Hz), 8.19 (s, 1H,), 8.11–8.07 (m, 2H,), 7.91 (dd, 1H, J=6.0, 1.2 Hz), 7.70–7.64 (m, 5H), 5.81 (s, 2H) 3.68 (t, 2H, J=6.9 Hz), 0.98 (t, 2H, J=6.7 Hz), 0.02 (s, 9H).

(iv)

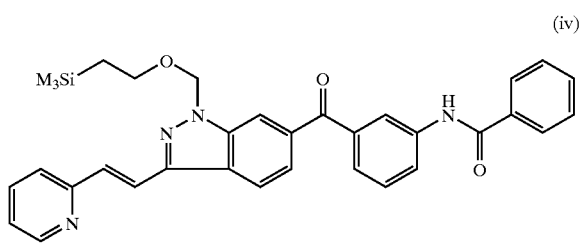

To a stirred solution of 2-picolytriphenyphosphonium chloride w/sodium hydride (2.23 g, 4.91 mmol) cooled to −78° C. was added 6-(3-benzamidobenzoyl)-1-(2-trimethylsilanyl-thoxy-methyl)-1H-indazole-3-carboxaldehyde (1.26 g, 2.46 mmol) in 5 mL of THF anhydrous under an argon purge and stirred for 1 h at 0° C. and quenched via CH$_3$COOH/MeOH (1:1, mL). The reaction mixture was diluted with 100 mL of EtOAc and partitioned between saturated NaCl (1×50 mL), and saturated NaHCO$_3$ (2×50 mL) then the organic layer dried over Na$_2$SO$_4$ and filter through 20 mL of silica plug (3:1 trans/cis mixture). Purification with a 4 mm silica rotor eluting with hexane/EtOAc (1:1) afford 63-benzamidobenzoyl)-3-E-[2-(pyridin-2-yl)ethenyl]-1-(2-trimethylsilanyl-ethoxymethyl)-1H-indazole after concentration as a yellow solid (1.05 g, 62%). $^1$H NMR (CDCl$_3$) δ 8.62 (d, 1H, 1=4.1 Hz), 8.22 (d, 1H, J=8.5 Hz), 8.11–8.10 (m, 3H), 8.01–7.98 (m, 4H), 7.83 (t, 2H, J=7.1 Hz), 7.72–7.53 (m, 7H), 7.30 (qd, 1H, J=5.2, 1.1 Hz), 5.81 (s, 2H) 3.68 (t, 2H, J=6.9 Hz), 0.98 (t, 2H, J=6.7 Hz), 0.02 (s, 9H).

Example 42(b)

6-(3-Benzamidobenzoyl)-3-(1H-benzoimidazol-2-yl)-1H-indazole

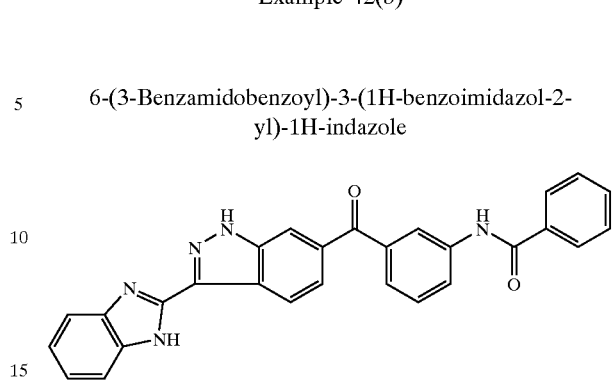

Example 42(b) was prepared in a similar manner to that described for Example 42(a) except that step (iv) was replaced by the following. To the aldehyde prepared in Example 42(a), step (iii) was added 1,2-diaminobenzene (0.011 g, 011 mmol), elemental sulfur (USP grade, 0.4 g, 0.1201 mmol), 2 mL of anhydrous DMF and the mix was warmed to 90° C. for 18 h, cooled to 25° C. The reaction mixture was diluted with 10 mL of ethyl acetate and was washed with saturated NaCl (1×10 mL), NaHCO$_3$ (1×10 Ml) and water 10 mL, dried over NaSO$_4$ and filter though a teflon filter 0.22 μM and concentrated to a amber oil. Purification by radial chromatography followed by precipitation from 2 mL of methylene chloride and hexane (2 mL) afforded intermediate as a white precipitated. $^1$H NMR (Acetone-d6) δ 8.81 (d, 1H, J=8.6), 8.308.25 (m, 2H), 8.11 (s, 1H), 8.02–7.99(m, 2H), 7.79 (td, 2H, J=12.2, 1.2 Hz), 7.63–7.47 (m, 7H), 7.28–7.40 (m, 2H). HRMS (MALDI) m/z C$_{28}$H$_{19}$N$_5$O$_2$ Calc. (M+H$^+$): 458.1617, found 458.1632.

Example 42(c)

6-(3-Benzamidobenzoyl)-3-E-[2-(2-methylthiazol-4-yl)ethenyl]-1H-indazole

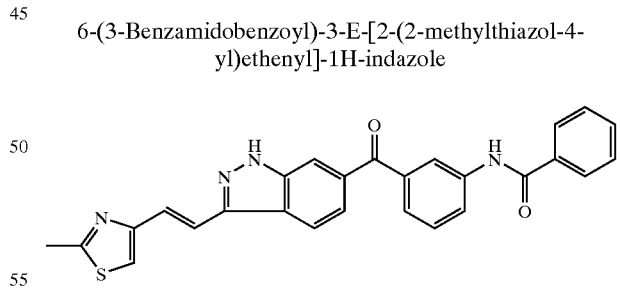

Example 42(c) was prepared in similar manner as 42(a) except 4-(2-methylthiazyl)-methyltriphenylphosphonium chloride was used in place of 2-picolytriphenyphosphonium chloride in step (iv). $^1$H NMR (DMSO) δ 8.11–8.01 (m, 4H), 7.92 (d, 2H, J=6.9 Hz), 7.76–7.71 (m, 2H), 7.65–7.62 (m, 1H), 7.567.48 (m, 5H,), 7.15 (s, 1H,), 2.81 (s, 3H). HRMS (MALDI) C$_{27}$H$_{20}$N$_4$O$_2$S (M+H$^+$]/z: Calc. (M+H$^+$) 465.1380, found 465.1373.

Example 42(d)

6-(3-benzamidobenzoyl)-3-(3H-imidazo[4,5-b]pyridin-2-yl)-1H-indazole

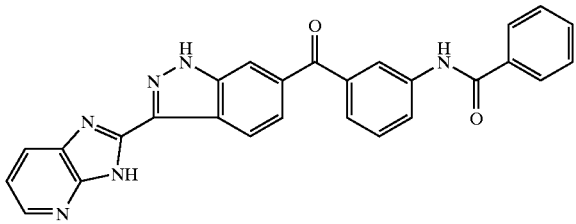

Example 42(d) was prepared in similar manner as 42(b) except 1,2-diamine-2-pyridine was used in place of 1,2-diaminebenzene. HPLC: 3.88 min (95% area); $^1$H NMR (DMSO-d$_6$) δ 10.62 (s, 1H), 8.83 (d, 1H, J=8.4 Hz), 8.53 (s, 1H), 8.43 (s, 1H), 8.32 (dt, 1H, J=6.9, 1.8 Hz), 8.15 (d, 1 h, J=12.9 Hz), 8.11–8.10 (m, 2H), 7.91 (d, 1H, J=9.0 Hz), 7.72–7.65 (m, 6H), 7.43 (dd, 1H, J=6.3, 4.8 Hz). HRMS (MALDI) m/z C$_{27}$H$_{18}$N$_6$O$_2$ Calc. (M+H$^+$): 459.1564, found 459.1558. Anal. (C$_{27}$H$_{18}$N$_6$O$_2$.0.4CH$_2$Cl$_2$): Calc. C, 66.83; H, 3.85; N, 17.07. Found: C, 66.93; H. 4.04, N, 16.68.

Example 42(e)

6-(3-benzamidobenzoyl)-3-E-[N-(4H-1,2,4-triazol-4-yl)iminomethyl]-1H-indazole

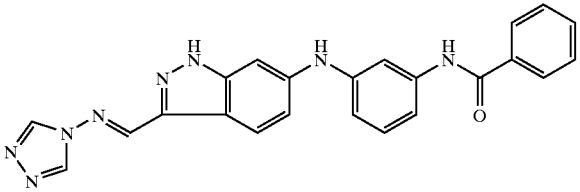

Example 42(e) was prepared in a similar manner as Example 42(a) except that 4-amino 1,2,4 triazole and PPTS were used at 80° C. in place of 2-picolytriphenyphosphonium chloride and potassium hydride at 23° C. HPLC R$_f$: 4.05 min (96% area); $^1$H NMR (DMSO-d$_6$) δ 10.58 (s, 1H), 9.53 (s, 1H), 9.40 (s, 2H), 8.56 (d, 1H, J=8.4 Hz), 8.38 (s, 1H), 8.26 (dt, 1H, J=7.2, 2.1 Hz), 8.13 (s, 1H), 8.08–8.05 (m, 2H), 7.73–7.67 (m, 5H). HRMS (MALDI) C$_{24}$H$_{17}$N$_7$O$_2$ [M+H$^+$]/z: Calc. 436.1516, found 436.1510. Anal. (C$_{24}$H$_{17}$N$_7$O$_2$.0.4hexane) Calc. C, 66.18; H, 4.67; N. 20.47. Found: C, 65.78; H, 4.87, N, 20.47.

Example 43

6-(3-Benzamidobenzoyl)-3-E-[2-(2-formamidophenyl)ethenyl]-1H-indazole

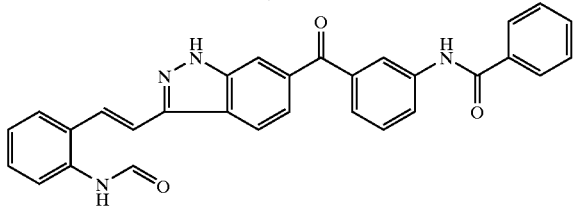

Example 43 was prepared from 6-(3-benzamidobenzoyl)-3-E-(2-formamidophenyl)ethenyl-1-(2-trimethylsilanyl-ethoxymethyl)-1H-indazole in a similar manner to that described for Example 11. 18 mg (36%). HPLC R$_f$: 4.19 min.

$^1$H NMR (CDCl$_3$) δ 8.43–7.92 (m, 6H), 7.68–7.49 (m, 4H) 7.39–7.36 (m, 3H), 7.32–7.21 (m, 2H), 7.09–7.00 (m, 2H), 6.91–6.84 (m, 1H). HRMS (MALDI) C$_{30}$H$_{22}$N$_4$O$_3$ [M+Na]/z; Calc. 509.1590, found 509.1580. Anal. (C$_{30}$H$_{22}$N$_4$O$_3$*0.3H$_2$O) Calc'd: C, 73.25; H, 4.63; N, 11.39. Found: C, 73.10; H, 4.58; N. 11.28.

Starting material was prepared as follows:

(i)

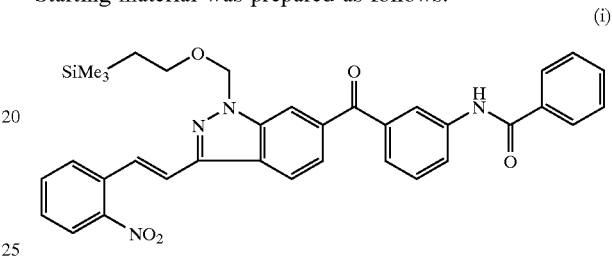

6-(3-Benzamidobenzoyl)-1-(2-trimethylsilanyl-ethoxymethyl)-1H-indazole-3-carboxaldehyde (prepared in Example 42(a), step (iii)) was converted to 6-(3-benzamidobenzoyl)-3-E-(2-nitrophenyl)ethenyl-1-(2-trimethylsilanyl-ethoxymethyl) 1H-indazole in similar manner to that of Example 42(a), step (iv) except that (2-nitrobenzyl)triphenylphosphonium bromide monohydrate was used in place 2-picolytriphenyphosphonium chloride (0.19 g, 79%). $^1$H NMR (CDCl$_3$) δ 8.15–7.93 (m, 5H), 7.89–7.86 (m, 3H), 7347.41 (m, 6H), 7.36–7.35 (m, 2H), 7.21–7.18 (m, 2H), 7.036.91 (m, 1H), 3.643.46 (m. 2H), 0.96–0.79 (m, 2H), –0.06(5, 91).

(ii)

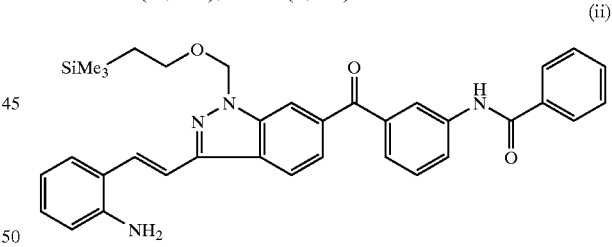

6-(3-Benzamidobenzoyl)-3-E-(2-nitrophenyl)ethenyl-1-(2-trimethylsilanyl-ethoxymethyl)-1H-indazole (0.19, 0.32 mmol) was dissolved in 3 mL of DMF, treated with SnCl$_2$ (0.26 g, 1.40 mmol) and water (0.037 mL, 1.87 mmol), and was stirred for 3 h at 50° C. The reaction was quenched at 25° C. with 0.5 mL of 3N NaOH and the precipitate was removed by filtration through celite. The solution was then partitioned between 50/50 saturated NaHCO$_3$/water (2×30 mL) and the organic layer was filtered through a silica plug to give 6-(3-benzamidobenzoyl)-3-E-(2-aminophenyl)ethenyl-1-(2-trimethylsilanyl-ethoxymethyl)1H-indazole as an amber oil (0.17 g, 92%). Product was used without further purification.

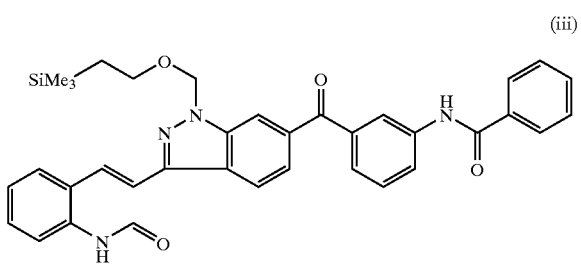

(iii)

6-(3-Benzamidobenzoyl)-3-E-(2-aminophenyl)ethenyl-1-(2-trimethylsilanyl-ethoxymethyl)-1H-indazole (0.17, 0.28 mmol) was dissolved in 3 mL of methylene chloride. To this was added formic acid pentafluorophenyl ester (0.12 g, 0.56 mmol) dropwise. After 3 h, the reaction mixture was diluted with 40 mL of EtOAc and was washed with 50/50 NaHCO$_3$ (2×30 mL) and the organic layer was filtered through a silica plug. The residue was purified by radial chromatography through silica eluting with hexane:EtOAc/CH$_2$Cl$_2$ (1:1:1) which afforded 6-(3-benzamidobenzoyl)-3-E-(2-formamidophenyl)ethenyl-1-(2-trimethylsilanyl-ethoxymethyl)-1H-indazole as a clear oil (63 mg, 40%). $^1$H NMR (CDCl$_3$) δ 8.48–8.36 (m, 1H), 8.207.84 (m, 4H), 7.61–7.52 (m, 5H), 7.41–7.32 (m, 4H), 7.26–7.01 (m, 4H), 6.82 (t, 1H, J=14.2 Hz), 3.48–3.23 (m, 2H), 0.95–0.87 (m, 2H), −0.05 (s, 9H).

Example 44

6-(3-Aminobenzoyl)-3-E-[N-(pyrrol-1-yl)iminomethyl]-1H-indazole

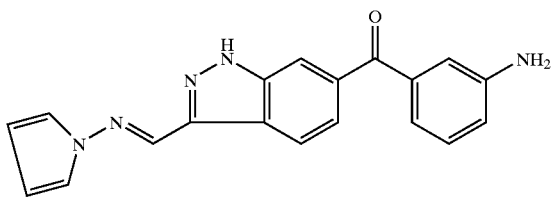

Example 44 was prepared from the starting material described below in a similar manner to that described for Example 12. R$_f$ sm 0.6, p 0.5 (ethyl acetate): $^1$H NMR (300 MHz, CDCl$_3$) δ 8.8 (s, 1H), 85 (d, 1H), 7.95 (s, 1H), 7.75 (d, 1H), 7.45–7.3 (m, 7H), 7.2 (m, 1H), 6.40 (s, 2H).
The starting material was prepared as follows:

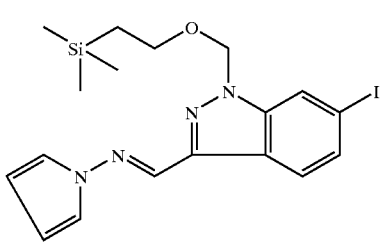

(i)

Aldehyde prepared in Example 33(a), step (i) (204 mg, 0.507 mmol) and 1-aminopyrrole (67 µL, 0.66 mmol, 1.3 equiv) were stirred together in toluene (2 mL). To this mix was added PPTS (1 mg) and the solution was heated to 80° C. for 1 h. The mixture was cooled and was partitioned between 2:8 ethyl acetate-hexane and water. The organic material was dried over sodium sulfate, decanted and concentrated under reduced pressure. The product was crystallized from dichloromethane (0.5 mL) and methanol (2 mL) (215.7 mg, 91%): $^1$H NMR (300 MHz, C$_6$D$_6$) δ 8.71 (s, 1H), 8.25 (d, 1H, J=8.5 Hz), 8.08 (s, 1H), 7.75 (d$_1$H, J=8.5 Hz), 6.35 (s, 2H), 5.85 (s, 2H).

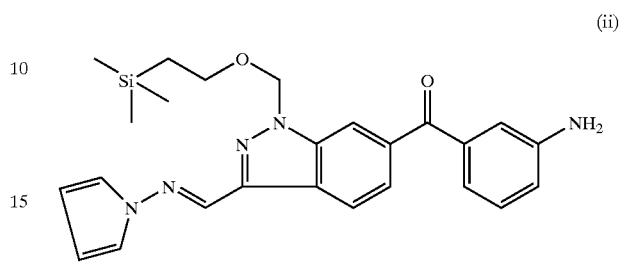

(ii)

A mixture of the above iodide (535 mg, 1.15 mmol, 1 equiv), 3-aminophenyl boronic acid (236 mg, 1.72 mmol, 1.5 equiv), PdCl$_2$(PPh$_3$)$_2$ (24 mg, 0.034 mg, 0.03 equiv), and potassium carbonate were taken up in anisole (6.7 mL) under carbon monoxide (1 atm). The mixture was heated to 80° C. for 14 h. The mix was cooled, partitioned between ethyl acetate and water. The organics were washed with saturated aqueous sodium bicarbonate, water and brine and the organic layer was separated. The organic material was dried over sodium sulfate, decanted and concentrated under reduced pressure. Purification by silica gel chromatography (50 mL silica: 2:8 to 3:7 ethyl acetate-hexane) gave product aniline as a solid (331 mg, 63%): R$_f$ sm 0.60, p 0.21 (ethyl acetate-hexane 3:7); $^1$H NMR (300 MHz, CDCl$_3$) δ 8.75 (s, 1H), 8.51 (d, 1H, J=8.4 Hz), 8.06 (s, 1H), 7.76 (dd, 2H, 7=1.3, 8.4 Hz), 7.26 (m, 31), 7.17 (m, 2H), 6.92 (m, 1H) 6.31 (t, 1H, J=2.3 Hz), 5.79 (s, 21), 3.84 (s, 21), 3.60 (t, 2H, 3=8.2 Hz), 0.91 (t, 2H, 3=8.2 Hz), −0.08 (s, 9H). LCMS 4.98 min (pos) [M+H]/z Calc'd 460, found 460.

Example 45(a)

6-[3-(Indol-4-ylcarboxamido)benzoyl]-3-E-[N-(pyrrol-1-yl)iminomethyl]-1H-indazole

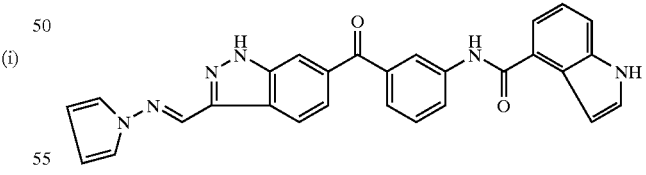

Example 45(a) was prepared from Example 44 in a similar manner to that described for Example 12(d), except that indole-4-carboxylic acid was used instead of 5-methylthiazole-2-carboxylic acid: R$_f$ sm 0.0, p 0.2 (ethyl acetate-benzene 1:3); $^1$H NMR (300 MHz, dmso-d6) δ 9.84 (s, 1H), 8.92 (s, 1H), 8.66 (s, 1H), 8.39 (d, 1H, 3=8.5 Hz), 8.02 (s, 1H), 7.86 (m, 2H), 7.66 (d, 1H, 8=8.5 Hz), 7.52–7.40 (m, 4H), 7.27–7.07 (m, 5H), 6.83 (s, 1H), 6.21 (s, 2H).

Example 45(a)

6-(3-Benzamidobenzoyl)-3-E-[N-(pyrrol-1-yl)iminomethyl]-1H-indazole

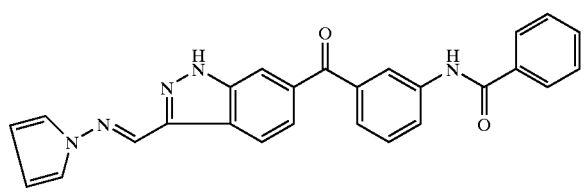

Example 45(b) was prepared from Example 44 in a similar manner to that described for Example 12(d), except that benzoyl chloride was used instead of 5-methyl-thiazole-2-carboxylic acid and HATU: $^1$H NMR (300 MHz, CDCl$_3$) δ 11.9 (bs, 1H), 8.70 (s, 1H), 8.43 (s, 1H), 8.39 (d, 1H, J=8.4 Hz), 7.99 (s, 1H), 7.9–7.8 (m, 4H), 7.65 (d, 1H, J=8.4 Hz), 7.48 (t, 2H, J=7.8 Hz), 7.42–7.35 (m, 3H), 7.20 (t, 2H, 2.2 Hz), 6.28 (t, 2H, J=2.2 Hz).

Example 46

6-[N-(3-aminophenyl)amino]-3-E-styryl-1H-indazole

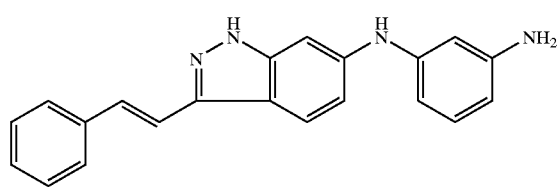

Example 46 was prepared from the starting material described below in a similar manner to that described for Example 13(i). $^1$H NMR (300 MHz, DMSO-d$_6$)° 12.6 (s, 1H), 8.07 (s, 1H), 7.97 (d, 1H, J=8.73 Hz), 7.69 (d, 1H, J=8.49 Hz), 7.40 (m, 4H), 7.28 (m, 1H), 7.06 (d, 1H, J=1.49 Hz), 6.44 (t, 1H, J=1.98 Hz), 6.34 (m, 1H), 6.14 (dd, 1H, J=7.88 Hz; J=1.26 Hz), 5.01 (bs, 2H).

(i)

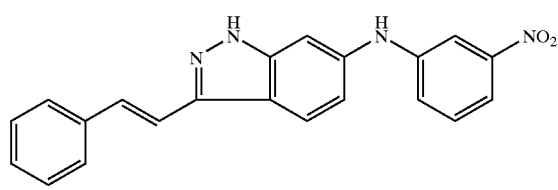

The compound prepared in Example 11, step (v), was converted to 6-[N-(3-nitrophenyl)amino]-3-E-styryl-H-indazole in a similar manner to that described for Example 12. $^1$H NMR (300 z CDCl$_3$) δ 8.0 (m, 2H), 7.77 (m, 1H), 7.64 (d, 2H, J=7.86 Hz), 7.41–7.56 (m, 6H), 7.3 (m, 2H), 7.08 (d, 2H, J=8.67 Hz). MS (ESI+) [M+H]/z Calc'd 357, found 357. Calc'd: C, 70.77; H, 4.53; N, 15.72. Found: C. 69.18; H, 4.51; N. 15.30.

Example 47

6-[N-(3-benzamido-4-fluorophenyl)amino]-3-E-styryl1H-indazole

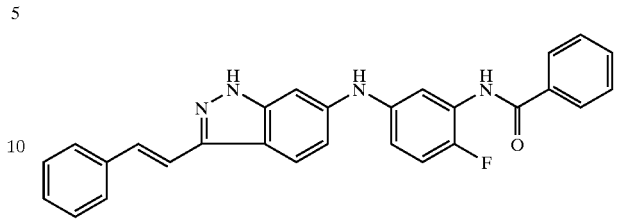

6-[N-(3-Benzamido-4-fluorophenyl)amino]-1-(2-trimethylsilanyl-ethoxymethyl-3-E-styryl1H-indazole was converted to Example 47 in a similar manner to that described for Example 11. $^1$H NMR (300 MHz, DMSO-d$_6$) δ 12. (s, 1H), 10.0 (s, 1H), 8.38 (bs, 1H), 8.02 (d, 1H, J=8.78), 7.98 (d, 2H, J=6.87 Hz), 7.69 (d, 2H, J=7.27 Hz), 7.48–7.61 (m, 4H), 7.45 (s, 2H), 7.40 (t, 2H, J=7.28 Hz), 7.53–7.30 (t, 2H, J=7.28 Hz), 7.53–7.30 m, 2H), &.07 (d, 1H, J=1.55 Hz), 7.03 (m, 1H), 6.95 (dd, 1H), J=8.79 Hz, J=1.85 Hz), MS (ESI+) [M+H]/z Calc'd 449, found 449. Anal. Calc'd: C, 74.98. H, 4.72. N, 12.193 Found: C, 74.29. H, 4.76. N, 12.12.

The starting material was prepared as follows:

(i)

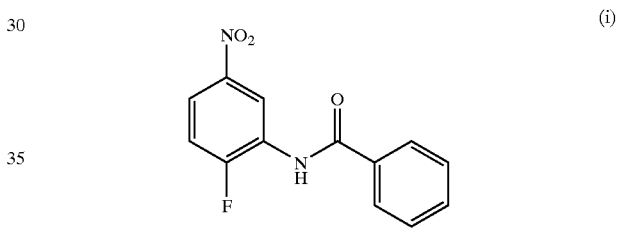

To a solution of 2-fluoro-5-nitro-phenylamine (3.12 g, 20 mmol) in dichloromethane (20 ml) at 23° C. under argon was added pyridine (1.94 ml, 24 mmol) and benzoyl chloride (2.8 ml, 24 mmol). After 45 minutes a white precipitate formed. The reaction mixture was concentrated in-vacuo then diluted with water and filtered to give a white solid which was re-suspended in MeOH and filtered again giving N-(2-fluoro-5-nitro-phenyl)-benzamide (4.86 g, 93%). H NMR (300 MHz. CDCl$_3$) δ 9.48 (dd, 1H. 3=6.8 Hz, J=2.81 Hz), 8.17 (bs, 1H), 8.03 (m, 1H), 7.92 (m, 2H), 7.52–7.65 (m, 3H), 7.31 (d, 1H, J=9.2 Hz).

(ii)

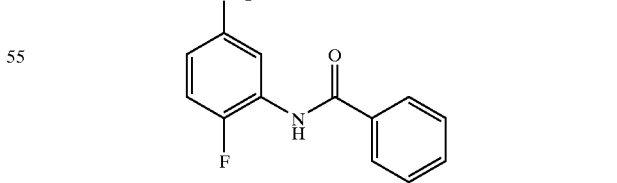

A mixture of N-(2-fluoro-5-nitro-phenyl)-benzamide (4.86 g. 18.7 mmol) and 10% Pd/C (486 mg) in a 1:1 mixture of THF-MeOH (80 ml) was hydrogenated at 23° C. After 2.5 h the reaction mixture was filtered through celite and concentrated to give N-(5-Amino-2-fluoro-phenyl)-benzamide (3.92 g, 91%). MS (ESI+) [M+H]/z Calc'd 231, found 231.

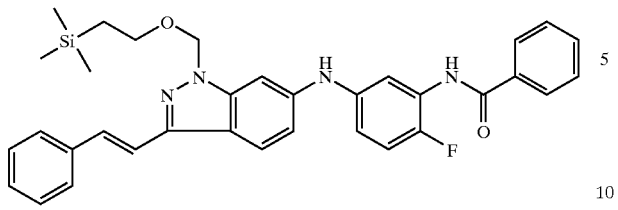

6-[N-(3-Benzamido-4-fluorophenyl)amino]-1-(2-trimethylsilanyl-ethoxymethyl-3-E-styryl 1H-indazole was prepared in a similar manner as Example 48(a), step (iii) except that N-(5-amino-2-fluorophenyl)benzamide, and the compound prepared in Example 14, step (i) were used as starting materials. $^1$H NMR (300 MHz, CDCl$_3$) δ 8.38 (dd, 1H, J=6.84 Hz, J=2.73 Hz), 8.09 (d, 1H, J=3.08 Hz), 7.86–7.91 (m, 3H), 7.48–7.61 (m, 5H), 7.28–7.45 (m, 4H), 7.19 (d, 1H, J=1.7 Hz), 7.08 (dd, 1H, J=10.48 Hz), 6.906.96 (n, 2H), 6.03 (bs, 1H), 5.66 (s, 2H), 3.62 (t, 2H, J=8.14 Hz), 0.91 (t, 2H, J=8.32 Hz), 0.0 (s, 9H). MS (ESI+) [M+H]/z Calc'd 579, found 579. Anal. Calc'd: C, 70.56. H, 6.10. N. 9.68. Found: C, 20.26. H, 6.08. N, 9.16.

Example 48(a)

6-[N-(5-((1-Ethyl-3-methyl-1H-pyrazol-5-yl)carboxamido)-2-fluoro-4-methylphenyl)amino]-3-E-[2-(pyridin-2-yl)ethenyl]-1H-indazole

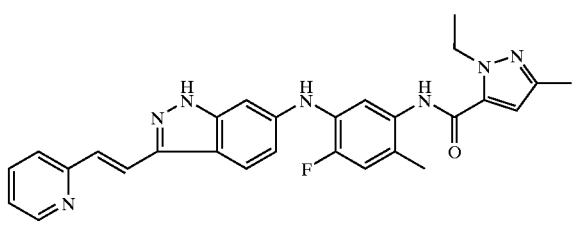

Example 48(a) was prepared in a similar manner as Example 41(a) from the starting material described below. $^1$H NMR (300 MHz, CD$_3$OD) δ 8.54 (d, 1H, J=4.8 Hz), 7.95 (d, 1H, J=9.49 Hz), 7.84 (td, 1H, 1=7.71 Hz, =1.78 Hz), 7.70 (d, 1H, J=7.95 Hz), 7.53 (d, 1H, J=16.59 Hz), 7.40 (d, 1H, J=7.92 Hz), 7.29 (qd, 1H, 1=7.45 Hz, J=1.07 Hz), 7.11 (d, 1H, 1=11.8), 7.03–7.06 (m, 2H), 6.71 (s, 1H), 4.50 (q, 2H, J=7.16 Hz), 2.27 (s, 3H), 2.26 (s, 3H), 1.38 (t, 3H, 1=7.11 Hz). MS (ESI+) [M+H]/z Calc'd 496, found 496. Anal. Calc'd: C, 67.86; H, 5.29; N, 19.79. Found: C, 66.24; H, 5.50; N, 18.61.

The starting material was prepared as follows:

(i)

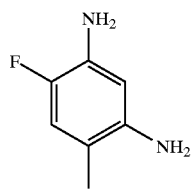

A mixture of 1-fluoro-5-methyl-2,4-dinitro-benzene (1.0 g, 5 mmol) and 10% Pd/C (200 mg) in MEOH (20 ml) was hydrogenated at 23° C. for 24 h. The reaction mixture was filtered through celite and concentrated. Purification by silica gel chromatography (1:1 ethyl acetate-hexane) gave 4-fluoro-6-methyl-benzene-1,3-diamine (613 mg, 87%).

(ii)

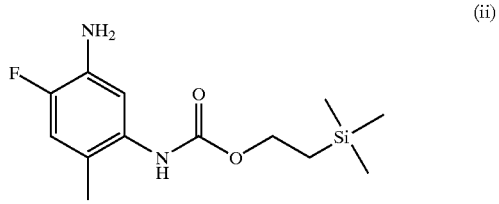

To a solution of carbonic acid 4-nitro-phenyl ester 2-trimethylsilanyl-ethyl ester (566 mg, 2 mmol) in DMF (4 ml) at 23° C. under an atmosphere of argon was added DMAP (12 mg. 0.1 mmol), DIEA (0.35 ml, 2 mmol) and 4-fluoro-6-methyl-benzene-1,3-diamine. The resulting solution was heated to 50° C. for 48 h. The reaction mixture was quenched with saturated NaHCO$_3$ (aq), extracted with EtOAc (3×20 ml). The EtOAc was removed in-vacuo, and the residue was re-dissolved in Et$_2$O then washed with 3 N NaOH (aq), water, brine, dried with Na$_2$SO$_4$, filtered and concentrated. Purification by silica gel chromatography (2:8–7:3 ethyl acetate-hexane) gave (5-amino-4-fluoro-2-methyl-phenyl)carbamic acid 2-trimethylsilanyl-ethyl ester (160 mg, 28%). MS (ESI+) [M+H]/z Calc'd 634, found 634.

(iii)

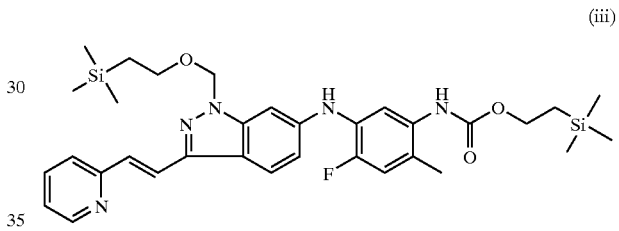

To a mixture of 6-Iodo-3-((E)-2-pyridin-2-yl-vinyl) 12-trimethylsilanyl-ethoxymethyl)1H-indazole (224 mg, 0.47 mmol), 5-amino-4-fluoro-2-methyl-phenyl)-carbamic acid 2-trimethylsilanyl-ethyl ester (160 mg, 0.56 mmol), Cs$_2$CO$_3$ (214 mg, 0.66 mmol), PdCl$_2$(PPh$_3$)$_2$ (5.4 mg, 0.0059 mmol) and BINAP (10 mg, 0.0176 mmol) under argon at 23° C. was added toluene (0.5 ml). The resulting mixture was heated to 80° C. for 16 h. The reaction mixture was cooled to 23° C. then diluted with water (20 ml) and extracted with EtOAc (3×50 ml). The organics were washed with water (30 ml), brine (30 ml), dried with Na$_2$SO$_4$ filtered and the concentrated to a foam. Silica gel column (3:7 ethyl acetate-hexane) provided (4-Fluoro-2-methyl-5-[3(E)-2-pyridin-2-yl-vinyl) 12-trimethylsilanyl-ethoxymethyl)-1H-indazol-6-ylamino]-phenyl)carbamic acid 2-trimethylsilanyl-ethyl ester (98 mg, 33%). TLC (7-3 hexane-ethyl acetate) Rfsm 0.42, Rfp 0.23. $^1$H NMR (CDCl$_3$) δ 8.64 (dd, 1H, J=4.79 Hz, J=0.86 Hz), 7.94 (d, 1H, J=8.71 Hz), 7.91 (bs, 1H), 7.86 (d, 1H, J=16.41 Hz), 7.69 (td, 1H, J=7.72 Hz, J=1.8 Hz), 7.55 (d, 1H, J=16.44 Hz), 7.49 (d, 1H, J=7.91 Hz), 7.17 (qd, 1H. J=7.44 Hz, J=0.98 Hz), 6.99 (dd, 1H, J=8.67 Hz, J=1.89 Hz), 6.93 (d, 1H, J=11.2 Hz), 6.25 (bs, 1H), 5.95 (d, 1H, J=1.97 Hz), 5.70 (s, 2H), 4.25 (t, 2H, J=8.53 Hz), 3.60 (t, 2H, J=8.24 Hz), 2.22 (s, 3H) 1.04 (t, 2H, J=8.54 Hz), 0.9 (t, 2H, J=8.25 Hz), 0.05 (s, 9H), 0.0 (s, 9H). $^{13}$C NMR (CDCl$_3$, 75 MHz) δ 156.0, 154.4, 149.8, 142.9, 142.8, 142.5, 136.6, 132.1, 130.1, 130.5, 128.7, 128.5, 124.3, 122.2, 122.0, 121.8, 118.2, 117.3, 117.0, 115.1, 95.2, 77.6, 77.4, 66.5, 63.7, 17.9, 17.2, −1.3. FTIR cm$^{-1}$: 3326, 2947, 1716, 1617, 1534, 1514, 1244, 1057. MS (ESI+) [M+H]/z Calc'd 634, found 634.

(iv)

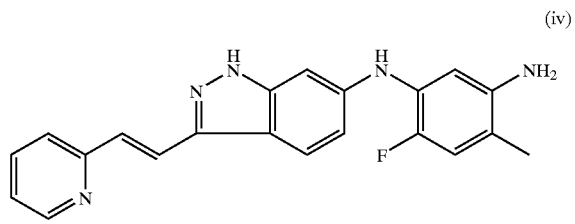

The above aniline was prepared in a similar manner as Example 11. $^1$H NMR (300 MHz, CD$_3$OD) δ 8.54 (m, 1H), 7.91 (dd, 1H, J=8.74 Hz, J=0.58 Hz), 7.83 (td, 1H, J=7.72 Hz, J=1.79 Hz), 7.80 (d, 1H, 3=16.52 Hz), 7.69 (d, 1H, J=7.98 Hz), 752 (d, 1H, J=1658 Hz), 7.29 (qd, 1H, J=7.43 Hz, J=1.07 Hz), 6.94–6.99 (m, 2H), 6.83 (d, 1H, J=11.98 Hz), 6.82 (d, 1H, J=7.49 Hz), 2.15 (s, 3H). MS (ESI+) [M+H]/z Calc'd 360, found 360.

Example 48(b)

6-[N-(5-((1,3-Dimethyl-1H-pyrazol-5-yl)carboxamido-2-fluoro-4-methylphenyl)amino]-3-E-[2-(pyridin-2-yl)ethenyl]-1H-indazole

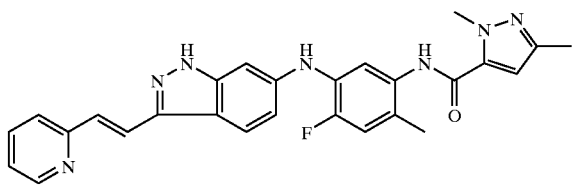

Example 48(b) was prepared in a similar manner as Example 48(a) except that 2,5-dimethyl-2H-pyrazole-3-carboxylic acid was used in place of 2-ethyl-5-methyl-2H-pyrazole-3 carboxylic acid. $^1$H NMR (300 MHz, DMSO-d$_6$) δ 12.8 (s, 1H), 9.71 (s, 1H), 859 (m, 1H), 8.11 (s, 1H), 8.00 (d, 1H, J=8.75 Hz), 7.87 (d, 1H, J=16.37 Hz), 7.80 (td, 1H, J=7.66 Hz, J=1.81 Hz), 7.64 (d, 1H, J=7.88 Hz), 7.49 (d, 1H, J=16.38 Hz), 7.34 (d, 1H, J=8.16 Hz), 7.26 (m, 1H), 7.21 (d, 1H, J=12.14 Hz), 6.97 (dd, 1H, J=8.76 Hz), 6.88 (s, 1H), 6.79 (s, 1H), 3.98 (s, 3H), 2.20 (s, 3H), 2.19 (s, 3H). MS (ESI+) [M+H]/z Calc'd 482, found 482. Anal. Calc'd: C, 67.35; H, 5.02; N, 20.36. Found: C, 66.83; H. 5.25; N, 19.68.

Example 49(a)

6[N-(3-((1,3-Dimethyl-1H-pyrazol-5-yl)carboxamido)-4-fluoro-phenyl)amino]-3-E-[2-pyridin-2-yl)ethenyl]-1H-indazole

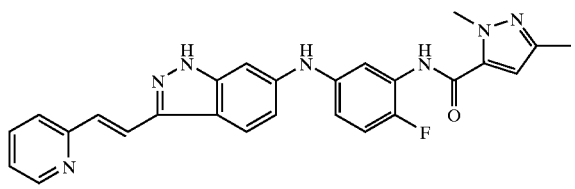

Example 49(a) was prepared in a similar manner as Example 48(a) except for the following: 2,5-Dimethyl-2H-pyrazole-3 arboxylic acid was used in place of 2-ethyl-5-methyl-2H-pyrazole-3-carboxylic acid; In step (iii), (5-Amino-2-fluoro-phenyl)-carbamic acid 2-trimethylsilanyl-ethyl ester, prepared as described below, was used instead of (5-amino-4-fluoro-2-methyl-phenyl)-carbamic acid 2-trimethylsilanyl-ethyl ester, DME was the solvent and biphenyl-2-yl-dicyclohexyl-phosphane was used as ligand. $^1$H NMR (300 MHz, CD$_3$OD) δ 12.7 (s, 1H), 9.94 (s, 1H), 8.48 (m, 1H), 8.40 (s, 1H), 8.02 (d, 1H, J=6.77 Hz), 7.87 (d, 1H, J=16.37 Hz), 7.80 (d, 1H, J=7.63 Hz, J=1.81 Hz), 7.64 (d, 1H, J=7.88 Hz), 7.49 (d, 1H, J=16.39 Hz), 7.42 (dd, 1H, J=6.65 Hz, J=2.68 Hz), 7.24 (m, 2H), 7.06 (m, 2H), 6.96 (dd, 1H, J=8.81 Hz, J=1.82 Hz), 6.85 (s, 1H), 4.0 (s, 3H), 2.20 (s, 3H). MS (ESI+) [M+H]/z Calc'd 468, found 468. Anal. Calc'd: C, 66.80; H, 4.74; N, 20.97. Found: C, 66.01; H, 4.72; N, 20.81.

(i)

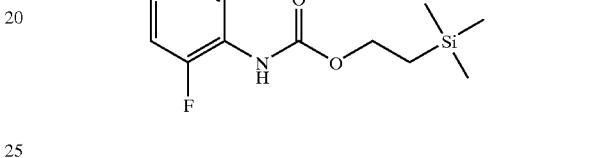

To a solution of 1-Fluoro-2-isocyanato-4-nitro-benzene (9.82 g, 54 mmol) in THF (40 ml) at 23° C. under an atmosphere of argon was added 2-Trimethylsilanyl-ethanol (7.72 ml, 54 mmol). The resulting mixture was stirred for 11 hours then heated to 50° C. for 2 hours. The reaction mixture was allowed to cool to 23° C. quenched with saturated NaHCO$_3$ (aq) and extracted with EtOAc (3×100 ml). The pooled ethyl acetate was washed with 1N HCl (aq) (2×90 ml) water (90 ml) and brine (90 ml), dried with Na$_2$SO$_4$, filtered and concentrated to a yellow solid. Silica gel chromatography (2:8 ethyl acetate-hexane) provided (2-Fluoro-5-nitro-phenyl)-carbamic acid 2-trimethylsilanyl-ethyl ester (12.3 g, 77%). $^1$H NMR (300 MHz, CDCl$_3$) δ 9.06 (dd, 1H, J=6.89 Hz, J=2.63 Hz), 7.89 (m 1H), 7.20 (m, 1H), 6.91 (bs, 1H), 4.31 (t, 2H, J=8.67 Hz), 1.06 (t, 2H, J=8.67 Hz), 0.05 (s, 9H). LCMS (ESI–) [M+H]/z Calc'd 299, found 299.

(ii)

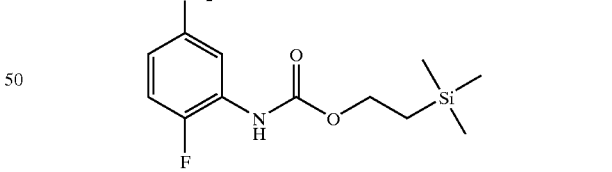

A mixture of (2-Fluoro-5-nitro-phenyl)-carbamic acid 2-trimethylsilanyl-ethyl ester (3.00 g, 10 mmol) and 10% Pd/C (300 mg) in methanol (30 ml) was hydrogenated at 23° C. The resulting mixture was stirred for 24 h. The reaction mixture was filtered through celite and concentrated to give (5-Amino-2-fluoro-phenyl)-carbamic acid 2-trimethylsilanyl-ethyl ester (2.62 g, 97%). $^1$H NMR (300 MHz, CDCl$_3$) δ 7.52 (m, 1H), 6.85 (dd, 1H, J=10.8 Hz, J=8.69 Hz), 6.73 (bs, 1H), 6.28 (m, 1H), 4.27 (t, 2H, J=8.57 Hz), 3.0–4.4 (bs, 2H), 1.06 (t, 2H, J=8.58 Hz), 0.07 (s, 9H).

Example 49(b)

6-[N-(3-((1,3-Dimethyl-1H-pyrazol-5-yl)carboxamido)-4-methylphenyl)amino]-3-E-[2-(pyridin-2-yl)ethenyl]-1H-indazole

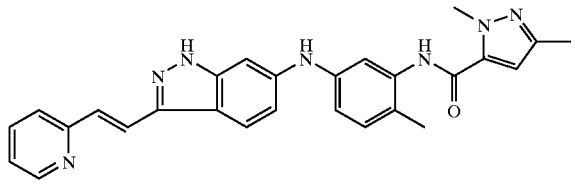

Example 49(b) was prepared in a similar manner to Example 49(a) except that 1-methyl-2-isocyanato-4-nitrobenzene was used instead of 1-Fluoro-2-isocyanato-4-nitrobenzene in step (i). $^1$H NMR (300 MHz. CDCl$_3$) δ 8.59 (m, 1H), 8.35 (s, 1H), 8.00 (d, 1H, J=8.73 Hz), 7.87 (d, 1H, J=16.38 Hz), 7.80 (td, 1H, J=7.66 Hz, J=1.85 Hz), 7.64 (d, 1H, J=7.85 Hz), 7.49 (d, 1H, J=16.35 Hz), 7.26 (m, 1H), 7.19 (m, 2H), 7.09 (d, 1H, J=1.48 Hz), 7.02 (dd, 1H, J=8.17 Hz, J=2.24 Hz), 6.97 (dd, 1H, J=8.79 Hz, J=1.80 Hz), 6.81 (bs, 1H), 4.00 (s, 3H), 2.20 (s, 3H), 2.18 (s, 3H). LCMS (ESI+) [M+H]/z Calc'd 464, found 464.

Example 49(c)

6-[N-(3-acetamido-4-fluorophenyl)amino]-3-E-[2-(pyridin-2-yl)ethenyl]-1H-indazole

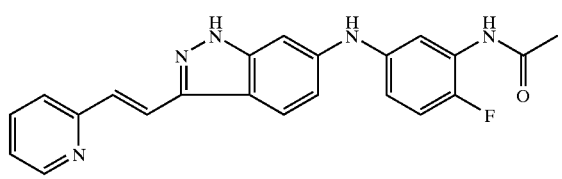

Example 49(c) was prepared in a similar manner to Example 49(a) except that acetic anhydride was used instead of 2,5-dimethyl-2H-pyrazole-3 carboxylic acid: $^1$H NMR (300 MHz, CD$_3$OD) δ 8.44 (m, 1H), 7.82 (d, 1H), 7.70 (m, 3H), 7.55 (d, 1H), 7.41 (d, 1H, J=16.4 Hz), 7.19 (m, 1H), 7.03 (s, 1H), 6.94 (m, 1H), 6.87 (m, 2H), 2.11 (s, 3H). LCMS (100% area) Rt=4.53 min, (pos) [M+H]/z Calc'd 388.4, found 388.4.

Examples 49(d)–49(x) can be prepared in a similar manner to that described for Example 49(a).

Example 49(d)

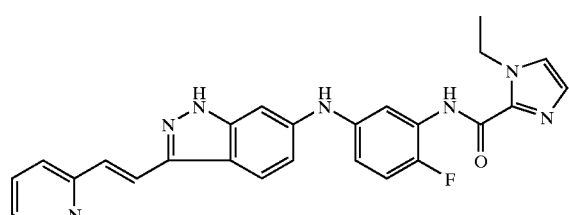

Example 49(e)

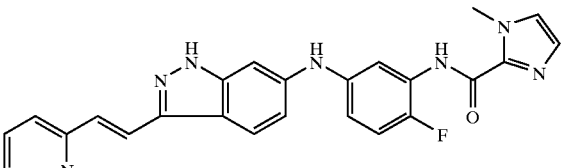

Example 49(f)

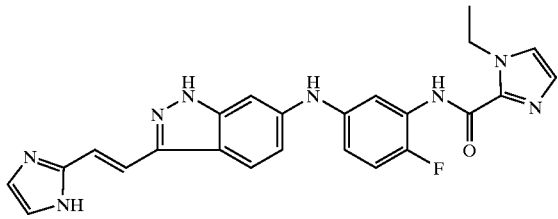

Example 49(g)

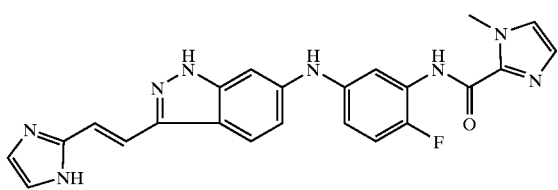

Example 49(h)

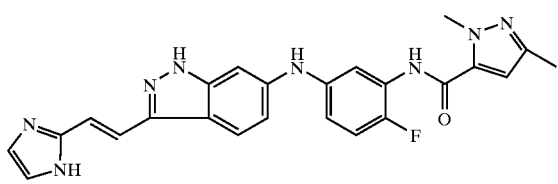

Example 49(i)

Example 49(j)
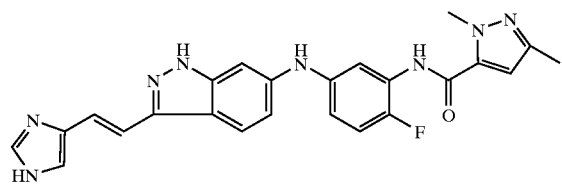
Example 49(O)
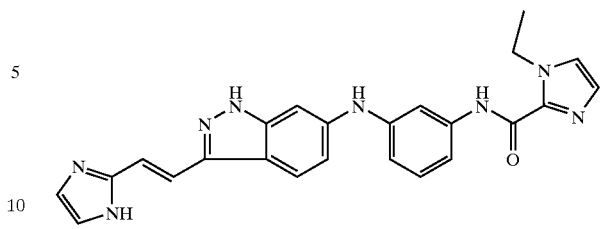
Example 49(k)
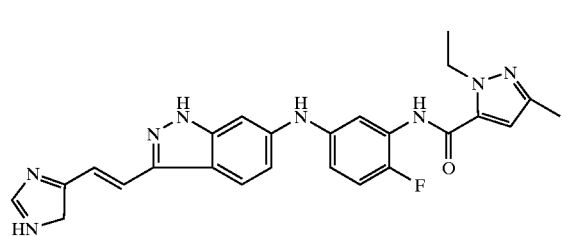
Example 49(p)
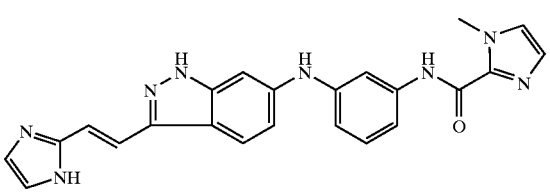
Example 49(l)
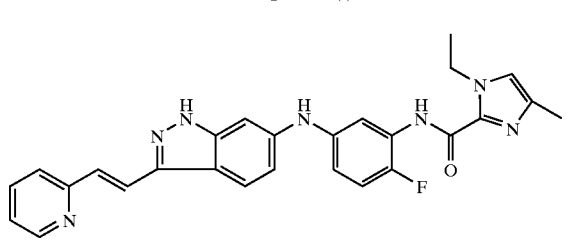
Example 49(q)
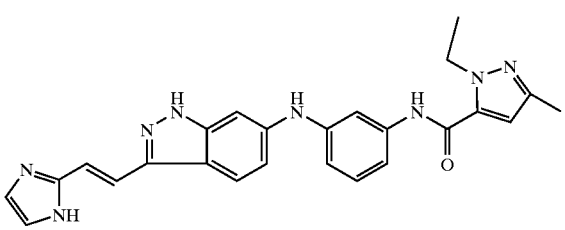
Example 49(m)
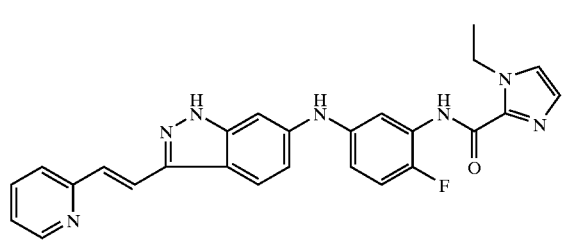
Example 49(r)
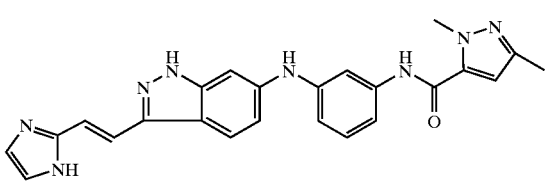
Example 49(n)
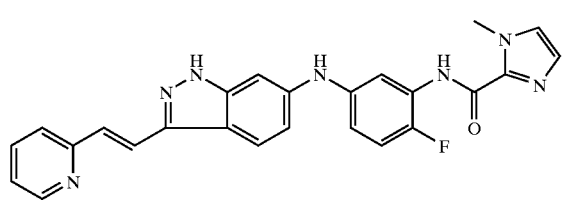
Example 49(s)
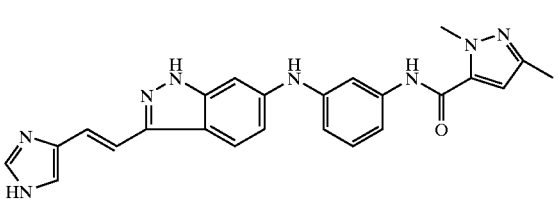

225

Example 49(t)

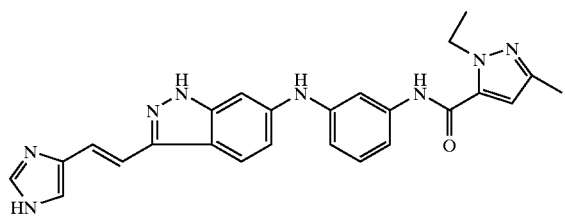

Example 49(u)

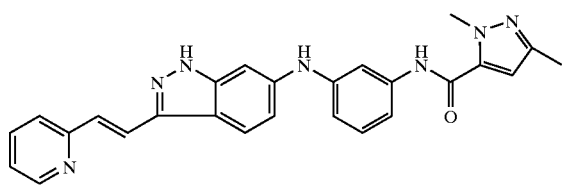

Example 49(v)

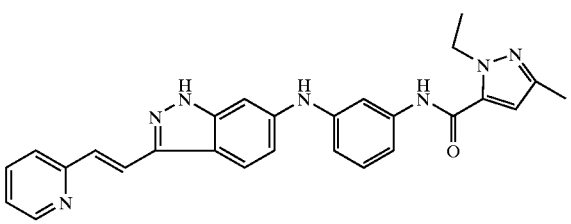

Example 49(w)

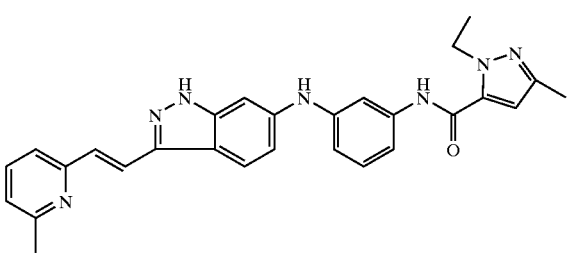

Example 49(x)

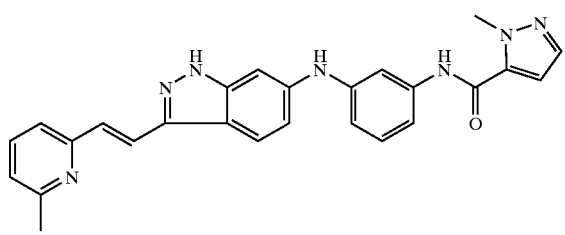

226

Example 50

6[3-(5-amino-2-fluorophenyl)carbamoyl-S-methyl-2-ethyl-2H-pyrazol-4-yl]-3-E-[2(pyridin-2-yl)ethenyl]-1H-indazole

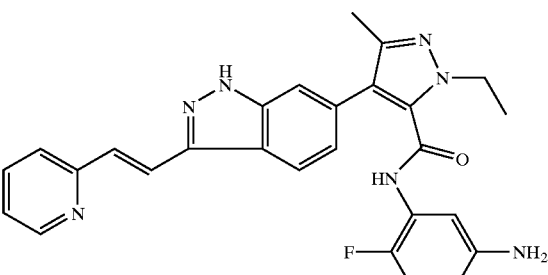

Example 50 was prepared from the starting material described below in a similar manner to that described for Example 11. MS (ESI+) [M+H]/z Calc'd 482, found 482. Calc'd: C, 67.35; H, 5.02; N, 20.36. Found: C, 66.70; H, 5.09; N, 19.95.

(i)

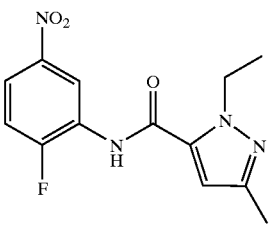

2-ethyl-5-methyl-2H-pyrazole-3-carboxylic acid (2-fluoro-5-nitro-phenyl)-amide was prepared in a similar manner as Example 47, step (i) except that 2-ethyl-5-methyl-2H-pyrazole-3-carboxylic acid and HATU were used instead of benzoyl chloride. MS (ESI+) [M+H]/z Calc'd 293, found 293.

(ii)

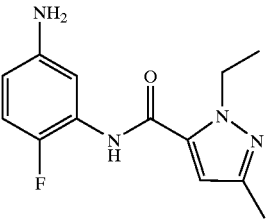

2-ethyl-5-methyl-2H-pyrazole-3-carboxylic acid (2-fluoro-5-nitro-phenyl)-amide was prepared in a similar manner as 40(b), step (i). MS (ESI+) [M+H]/z Calc'd 263, found 263.

(iii)

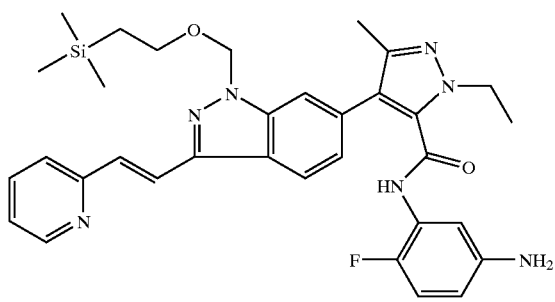

6-[3-(5-amino-2-fluorophenyl)carbamoyl-5-methyl-2-ethyl-2H-pyrazol-4-yl]-3-E-[2-pyridin-2-yl)ethenyl]-12-trimethylsilanyl-ethoxymethyl)-1H-indazole was prepared in a similar manner as Example 48(a), step (iii) except 2-Ethyl-5-methyl-2H pyrazole-3-carboxylic acid (5-amino-2-fluoro-phenyl)-amide was used as starting material. MS (ESI+) [M+H]/z Calc'd 612, found 612.

Example 51

6-pyrid-4-yl-3-E-(N-(pyrrol-1-yl)iminomethyl)-1H-indazole

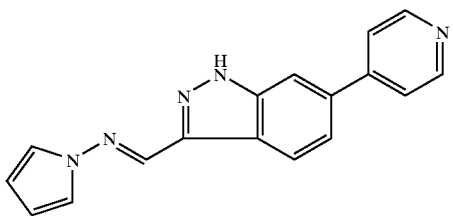

6-Pyrid-4-yl-3-E-(N-(pyrrol-1-yl)iminomethyl)-1-(2-trimethylsilanyl-ethoxymethyl)1H-indazole was converted to 6-pyrid-4-yl-3-E-(N-(pyrrol-1-yl)iminomethyl)1H-indazole in a similar manner to that described for Example 29(a). $^1$H NMR (300 MHz, CDCl$_3$) δ 8.76 (s, 1H), 8.67 (d, 2H, J=6.1 Hz), 8.53 (d, 1H, J=8.4 Hz), 7.74 (s, 1H), 7.61 (d, 2H, J=6.2 Hz), 7.54 (d, 1H, J=8.5 Hz), 7.27–7.25 (m, 2H), 6.31–6.29 (m, 2H). MS (ES) [M+H]/z Calc'd 288, found 288. Anal. Calc'd, C (71.07), H (4.56), N (24.37). Found: C (70.81), H (4.57), N (24.14).
The starting material was prepared as follows:

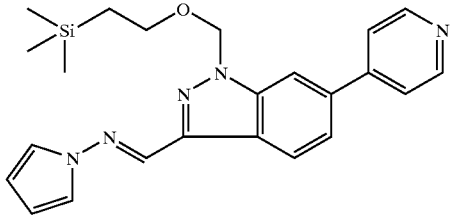

A solution of 6-pyridin-4-yl-1-(2-trimethylsilanyl-ethoxymethyl)-1H-indazole-3-carbaldehyde (208 mg, 0.59 mmol), N-aminopyrrole (145 mg, 1.76 mmol), and acetic acid (5.8 µl) in ethanol (1 ml) was held at 95° C. for 16 h. The solution was then evaporated under reduced pressure, and purified by silica gel chromatography to give 6-pyrid-4-yl-3-E-(N-(pyrrol-1-yl)iminomethyl)-1-(2-trimethylsilanyl-ethoxymethyl) 1H-indazole as an oil (140 mg, 57%). $^1$H NMR (300 MHz, CDCl$_3$) δ 9.08 (s, 1H), 8.71 (d, 2H, J=6.1 Hz), 8.46 (d, 1H, J=8.5 Hz), 8.34 (s, 1H), 7.85 (d, 2H, J=6.2 Hz), 7.80 (d, 1H, J=8.5 Hz), 7.56 (t, 2H, J=2.3 Hz), 6.25 (t, 2H, J=2.3 Hz), 5.93 (s, 1H), 5.74 (s, 2H), 3.64 (t, 2H, J=7.9 Hz), 0.86 (t, 2H, J=7.9 Hz), 0.00 (s, 9H).

Example 52(a)

6-(7-azaindazol-4-yl)-3-E-styryl-1H-indazole

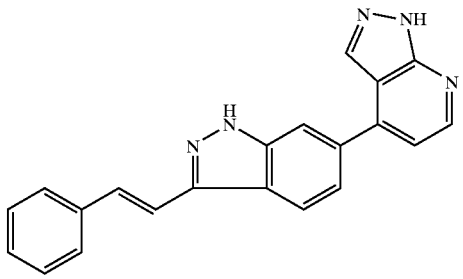

Sem-Example 52(a) was converted to Example 52(a) in a similar manner to that described for Example 27(a). $^1$H NMR (300 MHz, DMSO-d$_6$) δ 8.63 (d, 1H, J=4.8 Hz), 8.41 (d, 1H, J=8.5 Hz), 8.37 (s, 1H), 7.99 (s, 1H), 7.76 (d, 2H, J=7.3 Hz), 7.70 (d, 1H, J=8.5 Hz), 7.607.85 (m, 6H). HRMS (FAB) [M+H]/z Calc'd 338.1400, found 338.1389. Analyzed with 1.1 trifluoroacetic acid, Calc'd, C (60.21). H (3.51), N (15.13). Found: C (59.93), H (3.59), N (14.86).

The starting material was prepared as follows:

(i)

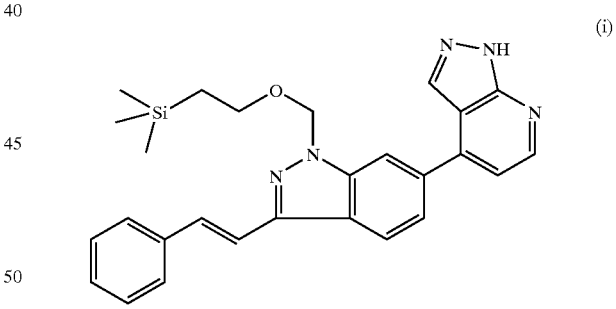

A solution of 3-styryl-1-(2-triethylsilanyl-ethoxymethyl)-6-trimethylstanny]-1H-indazole (1.0 g, 1.90 mmol), 1-(4-iodo-pyrazolo[3,4-b]pyridin-1-yl)-ethanone (0.56 g, 1.90 mmol), AsPh$_3$ (116 mg, 0.38 mmol), and Pd$_2$ dba$_3$ (87 mg, 0.09 mmol) in degassed dioxane (10 ml) was heated at 110° C. for 3 h. The solution was then diluted with ethyl acetate (50 ml), washed with brine (2×10 ml), dried over MgSO$_4$, and concentrated under reduced pressure. Purification by silica gel chromatography gave Example 52(a) as a white solid (412 mg, 46%). $^1$H NMR (300 MHz, CDCl$_3$) δ 8.82 (d, 1H, J=5.8 Hz), 8.52 (s, 1H), 8.29 (d, 1H, J=8.2 Hz), 8.05 (s, 1H), 7.73–7.32 (m, 10H), 5.86 (s, 2H), 3.69 (t, 2H, J=8.2 Hz), 0.97 (t, 2H, J=8.2 Hz), 0.03 (s, 9H).

(ii)

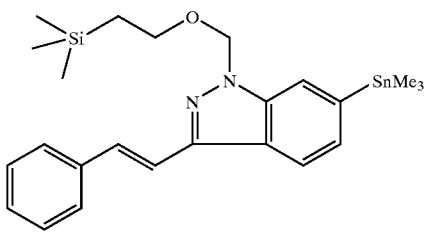

A solution of 6-iodo-3-styryl-1-(2-trimethylsilanyl-ethoxymethyl)-1H-indazole (2.90 g, 6.10 mmol), hexamethylditin (2.00 g, 6.12 mmol), and Pd(Ph$_3$)$_4$ (282 mg, 0.24 mmol) in degassed dioxane (10 ml) was heated at 110° C. for 3 h. The solution was then diluted with ethyl acetate (200 ml), washed with brine (2×21 ml), dried over MgSO$_4$, and evaporated under reduced pressure. Purification by silica gel chromatography gave 3-styryl-1-(2-trimethylsilanyl-ethoxymethyl)-6-trimethylstannyl-1H-indazole as a yellow oil (3 g, 96%). $^1$H NMR (300 MHz, CDCl$_3$) δ 8.02 (d, 1H, J=7.4 Hz), 7.71 (s, 1H), 7.71–7.29 (m, 8H), 5.77 (s, 2H), 3.65 (t, 2H, J=16.3 Hz), 0.95 (t, 2H, J=16.4 Hz), 0.38 (s, 9H), −0.03 (s, 9H).

(iii)

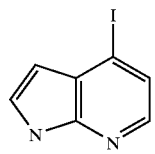

A mixture of 4-chloro-1H-pyrazolo[3,4-b]pyridine (820 mg, 5.30 mmol), sodium iodide (2.4 mg, 16.0 mmol), and acetyl chloride (0.8 ml) in acetonitrile (6 rid) was refluxed 8 h. The mixture was then treated with a 10% aqueous solution of NaCO$_3$ (10 ml), and a 10% aqueous solution of NaHSO$_3$ (10 ml), and held 10 min. The mixture was extracted with ethyl acetate (50 ml), and the organics were washed with brine (10 ml), dried over MgSO$_4$, and evaporated under reduced pressure. Purification by silica gel chromatography gave 12-(5-iodo-pyrazolo[3,4-b]pyridin 1-yl)ethanone as a brown solid (650 mg, 42%). $^1$H NMR (300 MHz, CDCl$_3$) δ 8.39 (d, 1H, J=5.0 Hz), 8.04 (s, 1H), 7.76 (d, 1H, J=5.0 Hz), 2.88 (s, 3H).

(iv)

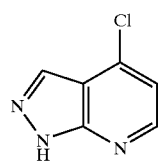

1,7-Dihydro-pyrazolo[3,4-b]pyridin-4-one (1.2 g, 8.8 mmol) (Dorn, H. et al., *Prakt. Chem.*, 324, 557–62 (1982)) in POCl$_3$ (15 ml) at 0° C. was treated with PCl$_5$ (2.5 mg, 0.01 mmol). The solution was allowed to warn to rt over 1 h, then heated to 90°c and held 3 h. The solution was concentrated under reduced pressure, then treated with ice and water (50 ml). The resulting mixture was extracted with ethyl acetate (100 ml), and the organic layer was washed with a saturated aqueous solution of sodium bicarbonate (30 ml). The organic layer was dried over MgSO$_4$, then evaporated under reduced pressure to give 4-chloro-1H-pyrazolo[3,4-b]pyridine as a yellow solid (820 mg, 60%). $^1$H NMR (300 MHz, CDCl$_3$) δ 8.57 (d, 1H, J=52 Hz), 8.25 (s, 1H), 7.28 (d, 1H, J=5.2 Hz).

Example 52(b)

6-(7-azaindol-4-yl)-3-E-styryl-1H-indazole

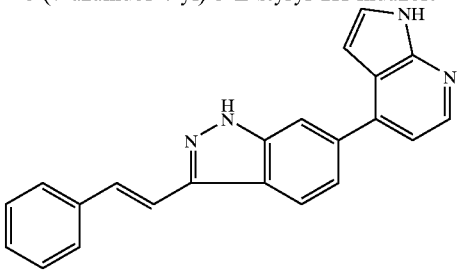

Sem-iodoindazole was converted to Example 52(b) in a similar manner to that described for Example 27(a). OH NMR (300 MHz, MeOH-d$_4$) δ 8.40 (d, 1H, J=5.3 Hz), 8.53 (d, 1H, J=8.6 Hz), 7.74–7.35 (m, 10H), 6.90 (s, 1H). HRMS (FAB) [M+H]/z Calc'd 337.1448, found 337.1457. Analyzed with 0.3H$_2$O, Calc'd, C (77.31), H (4.90), N (16.39). Found: C (77.51), H (4.88), N (16.27).
The starting material was prepared as follows:

(i)

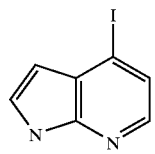

4-Chloro-1H-pyrrolo[2,3-b]pyridine (Clark, B. A. et al., *J. Chem. Soc. P*1, 2270–74 (1974)) was converted to 4-iodo-1H-pyrrolo[2,3-b]pyridine in a similar manner to that described for Example 52(a). 3H NMR (300 MHz, MeOH-d$_4$) δ 8.10 (m, 1H), 7.89 (d, 0.1H, J=5.0 Hz), 7.58 (m, 1H), 7.50 (d, 1H, J=5.0 Hz), 6.26 (br s, 1H).

Example 53(a)

3-(1H-benzoimidazol-2-yl)-N-(4-hydroxyphenyl)-1H-indazole-6-carboxamide

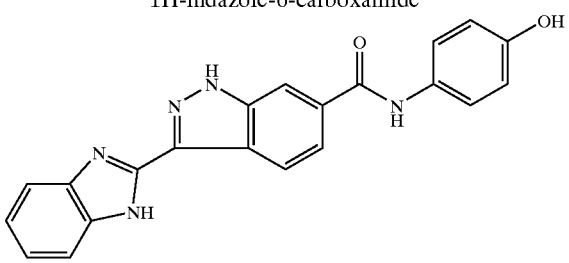

To a solution of 3-(1H-benzoimidazol-2-yl)-1H-indazole-6-carboxylic acid (208 mg, 0.7 mmol) in dry dimethylformamide (6 mL) was added 4-aminophenol (82 mg, 0.7 mmol) followed by HATU (312 mg, 0.8 mmol) and then triethylamine (20 drops) was added. The reaction was stirred overnight at room temperature. LC/MS showed desired product as major component. The solvent was removed by vacuum. The residue remaining was taken up in water and ethyl acetate. The layers were separated and the organic layer was concentrated under vacuum. The residue was dissolved in methanol (10 mL) and half of this solution was purified by HPLC using a gradient of 5% acetonitrile/water to 55% acetonitrile/water over 60 minutes with 0.1% trifluoroacetic acid in the water. The tide compound was isolated as a solid (20 mg). ¹H NMR (methanol-d₄) δ 6.87 (2H, d, 8.8 Hz), 7.55 (2H, d, 8.7 Hz), 7.61 (2H, m), 7.87 (2H, br s), 8.00 (1H, d, 8.4 Hz), 8.35 (1H, s), 8.52 (1H, d, 8.6 Hz). MS (APCI pos) 370.1.

The starting material was prepared as follows:

(i)

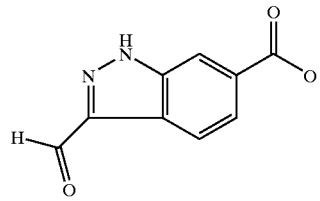

To 1H-indole-6-carboxylic acid (2.0 g, 12.42 mmol) in water (100 mL) was added NaNO₂ (856 g, 124.2 mmol). To this suspension was then slowly added dropwise via addition fuel 6N HCL (16 mL). The resulting slurry was allowed to stir at room temperature overnight The solid precipitate was filtered and washed with water (50 mL) to provide 2.35 g (100%) of 3-formyl-1H-indazole-5-carboxylic acid. ¹H NMR (DMSO-d₆) δ 14.46 (1H, s), 10.21 (1H, s), 8.26 (1H, s), 8.20 (1H, d, J=8.5 Hz), 7.90 (1H, d, J=8.3 Hz). MS (APCI positive) 205 (methyl ester).

(ii)

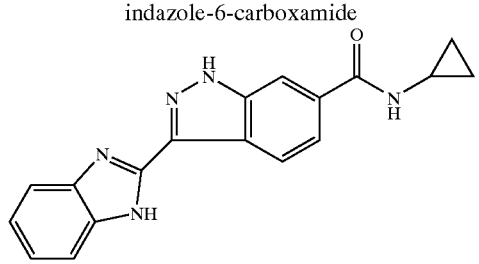

To 3-formyl-1H-indazole-6 carboxylic acid (2.35 g, 12.42 mmol) in DMF (60 mL) was added 1,2-phenylenediamine (12.42 mmol, 1.34 g) and sulfur powder (1.1 eq, 13.66 mmol). This mixture was then heated to reflux for 6 hours. The reaction was followed by TLC and LC-MS. After cooling, water (50 mL) was added to the reaction and the brown precipitate which formed was filtered and collected to provide 3.1 g (90%) of 3-(1H-benzoimidazol-2-yl)-1H-indazole-6-carboxylic acid. ¹H NMR (DMSO-d₆) δ 14.01 (1H, s), 8.58 (1H, d, J=8.5 Hz), 8.24 (1H, s), 7.87 (1H, d, l=8.7 Hz), 7.64 (2H, m), 7.25 (2H, m). MS (APCI positive) 279.

Example 53(b)

3-(1H-Benzoimidazol-2-yl)-N-cyclopropyl-1H-indazole-6-carboxamide

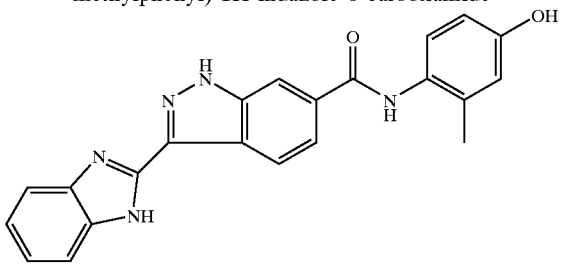

To 3-(1H-benzoimidazol-2-yl)-1H-indazole-6-carboxylic acid (200 mg, 0.719 mmol) in DMF (30 mL) was added cyclopropylamine (98 mg, 0.719 mmol), HATU (0.719 mmol, 273 mg), and triethylamine (0.726 mmol, 0.1 mL). This solution was allowed to stir at room temperature overnight The reaction was worked up via aqueous wash and extraction with ethyl acetate (3×50 mL). The organic layer was then dried with MgSO₄, filtered and concentrated to yield a dark oil. Flash column chromatography (30–70% Ethyl Acetate/Petroleum Ether) afforded the 3-(1H-benzoimidazol-2-yl)-N-cyclopropyl-1H-indazole-6-carboxamide as a yellow solid. (0.130 g, 57%) ¹H NMR (DMSO d) δ 13.88 (1H, s), 8.63 (1H, m), 8.51 (1H, d, J=8.5 Hz), 8.09 (1H, s), 7.75 (1H, d, J=8.7 Hz), 7.63 (2H, br s), 7.21 (2H, m), 2.89 (1H, m), 0.72 (2H, m), 0.63 (2H, m). MS (APCI positive) 318.1.

Example 53(c)

3-(1H-benzoimidazol-2-yl)-N-(4-hydroxy-3-methylphenyl)-1H-indazole-6-carboxamide

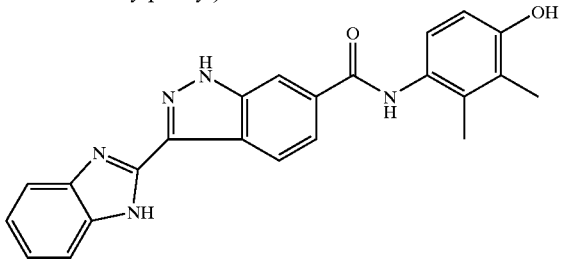

Example 53(c) was prepared in a similar manner to that described for Example 53(a), except 3-methyl-4-aminophenol was used in place of 4-aminophenol. ¹H NMR (DMSO-d₆) δ 8.59 (1H, d, J=8.3 Hz), 8.25 (1H, s), 7.89 (1H, dd, J=1.3, 8.5 Hz), 7.68 (211, br s), 7.28 (2H, m), 7.14 (1H, d, J=8.5 Hz), 6.74 (1H, s), 6.68 (2H, dd, J=3.0, 8.3 Hz). MS (APCI positive) 384.1.

Example 53(d)

3-(1H-benzoimidazol-2-yl)-N-(4-hydroxy-2,3-dimethylphenyl)-1H-indazole-6-carboxamide Example 53(d) was prepared in a similar manner to that described for Example 1553(a), except that 2,3-dimethylaminophenol was used in place of 4-aminophenol. ¹H NMR (DMSO-d₆) δ 9.93 (1H, s), 9.22 (1H, s), 8.56 (1H, d, J=8.5 Hz), 8.25 (1H, s), 7.90 (1H, d, J=8.5 Hz), 7.73 (1H, br s), 7.53 (1H, br s), 7.23 (2H, br s), 6.92 (1H, d, J=8.3 Hz), 6.68 (1H, d, J=8.5 Hz), 2.09 (6H, br s). MS (APCI positive) 398.4.

Example 53(e)

3-(1H-Benz imidaz 1-2-yl)-1H-indazole-6-carboxamide

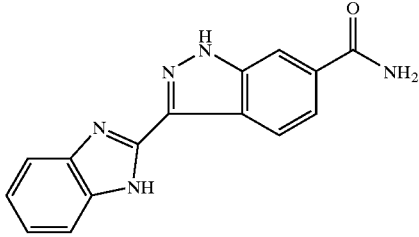

Example 53(e) was prepared in a similar manner to that described for Example 53(a), except that 1,1,1,3,3,3-hexamethyldisilazane was used in place of 4 aminophenol. $^1$H NMR (DMSO-d$_6$) 13.91 (1H, s), 13.04 (1H, s), 8.52 (1H, d, J=8.3 Hz), 8.20 (1H, br s), 8.15 (1H, s), 7.81 (1H, d. J=7.7 Hz), 7.75 (1H, d, J=6.6 Hz), 7.51 (2H, m), 7.21 (2H, m). MS (APCI positive) 278.1.

Example 53(f)

3-(1H-benzoimidazol-2-yl)-N-benzyloxy-1H-indazole-6-carboxamide

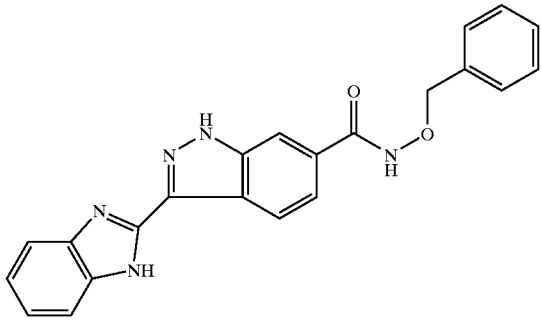

Example 53(f) was prepared in a similar manner to that described for Example 53(a) except that O-benzylhydroxylamine was used in place of 4-aminophenol. $^1$H NMR (DMSO-d$_6$) δ 13.94 (1H, s), 13.06 (1H, s), 11.97 (1H, s), 8.55 (1H, d, J=8.8 Hz), 8.02 (1H, s), 7.78 (1H, d, J=8.3 Hz), 7.52 (1H, d. J=8.3 Hz), 7.50 (3H, m), 7.40 (3H, m), 7.22 (2H, m), 4.97 (2H, s). MS (APCI positive) 384.2.

Example 53(g)

3-(1H-benzoimidaz 1-2-yl)-N-(3-fluoro-4-hydroxyphenyl)-1H-indazole-6-carboxamide

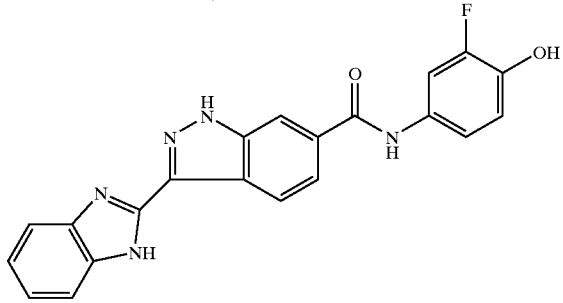

Example 53(g) was prepared in a similar manner to that described for Example 53(a) except that 3-fluoro-4-aminophenol was used in place of 4-aminophenol. $^1$H NMR (CH$_3$OD) δ 8.58 (1H, d, J=8.5 Hz), 8.20 (1H, s), 7.84 (1H, d, J=8.7 Hz), 7.68 (2H, br s), 7.63 (1H, dd, J=2.4, 13 Hz), 7.29 (3H, m), 6.92 (1H, t, J=9.2 Hz). MS (APCI positive) 388.3.

Example 54(a)

3-(5,6-Difluoro-1H-benzoimidazol-2-yl)-N-(4-hydroxyphenyl)-1H-indazole-6-carboxamide

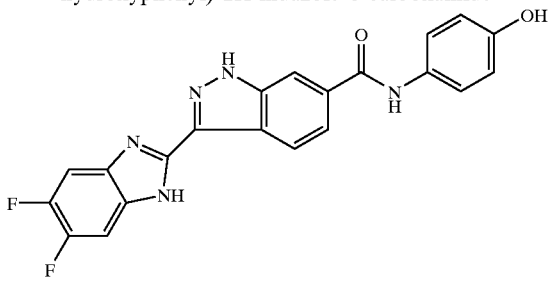

Using the same procedure as for the synthesis of 3-(1H-benzoimidazol-2-yl)-1H-indazole-6-carboxylic acid in Example 53(a), step (ii), N-(4-hydroxyphenyl)-3-formyl-1H-indazole-6-carboxamide and 4,5-difluoro 1,2-phenylenediamine gave 3-(5,6-difluoro-1H-benzoimidazol-2-yl)-N-(4-hydroxyphenyl)1H-indazole-6-carboxamide as a tan solid. $^1$H NMR (DMSO-d$_6$) δ 13.99 (1H, s), 13.27 (1H, s), 10.21 (1H, s), 9.25 (1H, s), 8.52 (1H, d, J=8.7 Hz), 8.21 (1H, s), 7.85 (1H, d, J=9.0 Hz), 7.80 (1H, t, J=9.8 Hz), 7.55 (2H, d, J=8.7 Hz), 7.47 (1H, t, J=9.8 Hz), 6.75 (2H, d, J=8.7 Hz). MS (APCI positive) 406.

The starting material was prepared as follows:

(i)

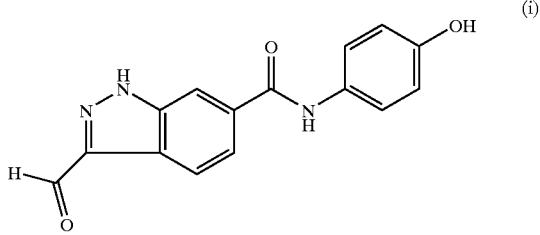

To a solution of 3-formyl-1H-indazole-6-carboxylic acid (1.6 g, 8.4 mmol) and 4 aminophenol (1.8 g, 16.8 mmol) in dry dimethylformamide (35 mL) was added HATU (3.8 g, 16.8 mmol) followed by triethylamine (1.4 mL, 10.1 mmol). The reaction was stirred at room and monitored by TLC and LC/MS. After two hours the reaction was complete. The solvent was removed by vacuum and the product was purified by flash column chromatography using ethyl acetate: petroleum ether 1:1 to pure ethyl acetate. N-(4-Hydroxyphenyl)-3-formyl-1H-indazole-6-carboxamide was isolated as a tan colored solid. $^1$H NMR (DMSO-d$_6$) δ 6.79 (2H, d, 8.9 Hz), 759 (2H, d, 8.9 Hz), 7.94 (1H, d, 9.8 Hz), 8.24 (1H, d, 8.2 Hz), 8.31 (1H, s), 9.31 (1H, br s), 10.27 (2H, s). MS (APCI pos) 282.1.

Example 54(b)

3-(5,6-Dichloro-1H-benzoimidazol-2-yl)-N-(4-hydroxyphenyl)-1H-indazole-6-carboxamide

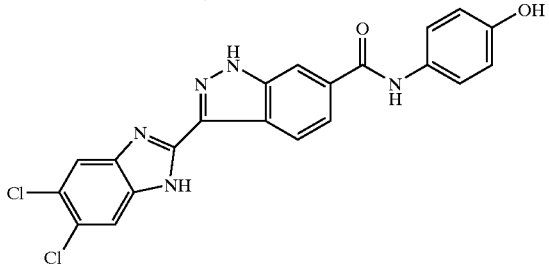

Example 54(b) was prepared in a similar manner to that described for Example 54(a), except that 4,5-dichloro-1,2-phenylenediamine was used in place of 4,5-difluoro-1,2-phenylenediamine. $^1$H NMR (DMSO-$d_6$) δ 14.08 (1H, s), 13.38 (1H, s), 10.22 (1H, s), 9.27 (1H, s), 8.52 (1H, d, J=8.7 Hz), 8.23 (1H, s), 8.02 (1H, s), 7.86 (1H, d, J=8.7 Hz), 7.70 (1H, s), 7.55 (2H, d, J=8.7 Hz), 6.75 (2H, d. J=8.7 Hz). MS (APCI positive) 438.

Example 54(c)

3-(5-Methoxy-1H-benzoimidazol-2-yl)-N-(4-hydroxyphenyl)-1H-indazole-6-carboxamide

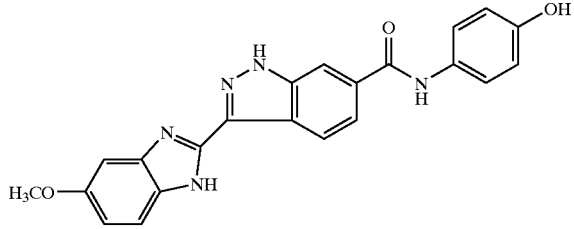

Example 54(c) was prepared in a similar manner to that described for Example 54(a), except that 4-methoxy-1,2-phenylenediamine was used in place of 4,5-difluoro-1,2-phenylenediamine. $^1$H NMR (DMSO-$d_6$) δ 13.76 (1H, s), 12.77 (1H, s), 10.13 (1H, s), 9.17 (1H, s), 8.45 (1H, d, J=8.3 Hz), 8.11 (1H, s), 7.75 (1H, d, J=8.6 Hz), 7.46 (2H, d, J=8.7 Hz), 7.32 (1H, d, J=8.3 Hz), 6.91 (1H, s), 6.77 (1H, m), 6.67 (2H, d, J=8.7 Hz), 3.72 (3H, s). MS (APCI positive) 400.

Example 54(d)

3-[1H-Naphtho(2,3-d)imidazol-2-yl]-N-(4-hydroxyphenyl)-1H-indazole-6-carboxamide

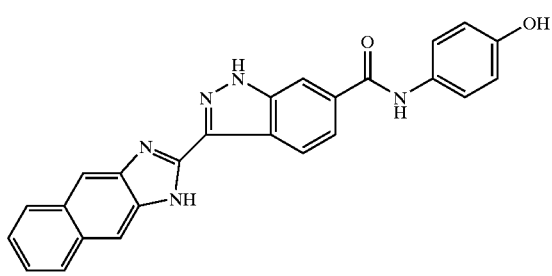

Example 54(d) was prepared in a similar manner to that described for Example 54(a), except that 2,3-naphthalenenediamine was used in place of 4,5-difluoro 1,2-phenylenediamine. $^1$H NMR (DMSO-$d_6$) δ 14.11 (1H, s), 13.10 (1H, s), 10.24 (1H, s), 9.27 (1H, s), 8.64 (1H, d, J=8.7 Hz), 8.28 (1H, s), 8.25 (1H, s), 7.97 (2H, m), 7.73 (1H, br s), 7.89 (1H, d, 3=8.6 Hz), 7.56 (2H, d, 3=8.7 Hz), 7.38 (2H, b), 6.76 (2H, d, J=8.7 Hz). MS (APCI positive) 420.

Example 54(e)

3-[1H-Naphtho(1,2-d)imidazol-2-yl]-N-(4-hydroxyphenyl)-1H-indazole-6-carboxamide

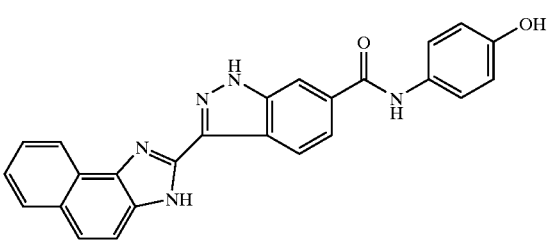

Example 54(e) was prepared in a similar manner to that described for Example 54(a), except that 1,2-naphthalenenediamine was used in place of 4,5-difluoro 1,2-phenylenediamine. $^1$H NMR (DMSO-$d_6$) δ 13.93 (1H, s), 13.38 (1H, s), 10.23 (1H, s), 9.27 (1H, s), 8.70 (2H, m), 8.22 (1H, s), 8.00 (1H, d, J=8.0 Hz), 7.87 (1H, m), 7.72 (3H, m), 7.57 (2H, d, J=8.7 Hz), 6.76 (2H, d, J=8.6 Hz). MS (APCI positive) 420.

Example 54(f)

3-(4,5-Dimethyl-1H-benzoimidazol-2-yl)-N-(4-hydroxyphenyl)-1H-indazole-6-carboxamide

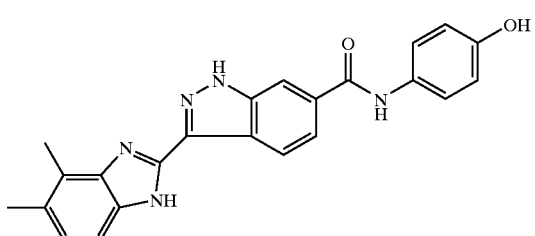

Example 54(f) was prepared in a similar manner to that described for Example 54(a), except that 3,4-dimethyl-1,2-phenylenediamine was used in place of 4,5-difluoro-1,2-phenylenediamine. $^1$H NMR (DMSO-$d_6$) δ 13.77 (1H, d, tautomers), 12.70 (1H, d, tautomers), 10.11 (1H, s), 9.16 (1H, s), 8.48 (1H, d, J=8.3 Hz), 8.09 (1H, s), 7.73 (1H, d, J=8.6 Hz), 7.47 (2H, d, J=8.7 Hz), 7.10 (1H, d, J=8.3 Hz), 6.93 (1H, d, J=8.3 Hz), 6.65 (2H, d, J=8.7 Hz), 2.49 (3H, s), 2.24 (3H, s). MS, (APCI positive) 398.4.

Example 54(g)

3-(5-tert-Butyl-1H-benzoimidazol-2-yl)-N-(4-hydroxyphenyl)-1H-indazole carboxamide

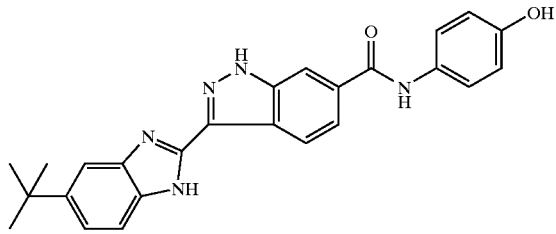

Example 54(g) was prepared in a similar manner to that described for Example 54(a), except that 4-tertbutyl-1,2-phenylenediamine was used in place of 4,5-difluoro 1,2-phenylenediamine. $^1$H NMR (acetone-d$_6$) δ 12.88 (1H, s), 9.47 (1H, s), 8.63 (1H, d, J=8.7 Hz), 8.18 (1H, s), 7.82 (1H, d, 3=8.3 Hz), 757 (4H, m), 7.26 (1H, d. J=8.4 Hz), 6.74 (1H, d, J=8.3 Hz), 1.31 (9H, s). MS (APCI positive) 426.

Example 54(h)

3-(5-Trifluoromethyl-1H-benzoimidazol-2-yl)-N-(4-hydroxyphenyl)-1H-indazole-6-carboxamide

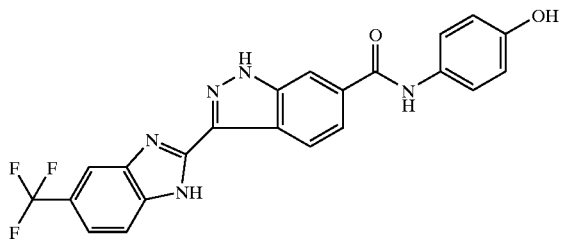

Example 54(h) was prepared in a similar manner to that described for Example 54(a), except that 4-trifluoromethyl-1,2-phenylenediamine was used in place of 4,5-difluoro-1,2-phenylenediamine. $^1$H NMR (methanol-di) δ 6.86 (2H, d, 8.9 Hz), 7.54 (2H, d, 8.9 Hz), 7.6 (1H, dd, 8.5 Hz), 7.83 (1H, d. 8.3 Hz), 7.89 (1H, dd, 8.6 Hz), 8.04 (1H, br s), 8.25 (1H, s), 8.61 (1H, d, 8.6 Hz). MS (APCI pos) 438.1.

Example 54(i)

3-(5-Fluoro-1H-benzoimidazol-2-yl)-N-(4-hydroxyphenyl)-1H-indazole-6-carboxamide

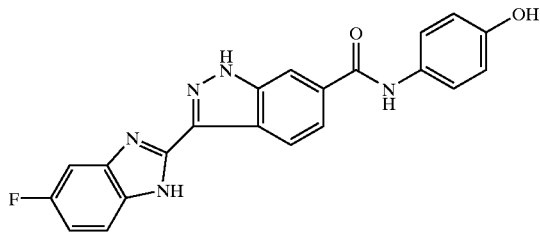

Example 54(i) was prepared in a similar manner to that described for Example 54(a), except that 4-fluoro-1,2-phenylenediamine was used in place of 4,5-difluoro 1.2-phenylenediamine. $^1$H NMR (acetone-d$_6$) δ 13.40 (1H, b), 12.47 (1H, b), 9.74 (1H, s), 8.67 (1H, d, J=8.6 Hz), 8.66 (1H, s), 8.29 (1H, s), 7.94 (1H, d, J=8.5 Hz), 7.67 (2H, J=8.4 Hz), 7.64 (1H, m), 7.40 (1H, m), 7.05 (1H, t, J=8.5 Hz), 6.83 (2H, d, J=8.4 Hz). MS (APCI pos) 388.

Example 54(j)

3-(5H-[1,3]dioxolo[4,5-f]benzoimidazol-6-yl)-N-(4-hydroxyphenyl)-1H-indazole-6-carboxamide

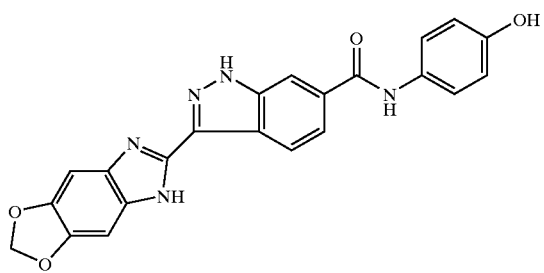

Example 54(j) was prepared in a similar manner to that described for Example 54(a), except that 4,5-methylenedioxy-1,2-phenylenediamine was used in place of 4,5-difluoro-1,2-phenylenediamine. $^1$H NMR (methanol-d$_4$) δ 6.85 (2H, d, 8.9 Hz), 7.15 (2H, s), 7.54 (2H, dl 8.9 Hz), 7.86 (1H, dd, 8.6 Hz), 8.23 (1H, s), 8.55 (1H, dd, 8.5 Hz). MS (APCI pos) 414.1.

Example 54(k)

3-(5,6-Dimethoxy-1H-benzoimidazol-2-yl)-N-(4-hydroxyphenyl)-1H-indazole-6-carboxamide

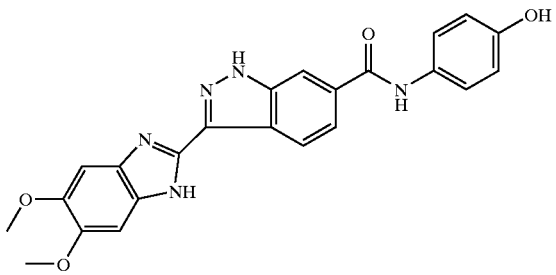

Example 54(k) was prepared in a similar manner to that described for Example 54(a), except that 4,5-dimethoxy-1,2-phenylenediamine was used in place of 4,5-difluoro-1,2-phenylenediamine. $^1$H NMR (methanol-d$_4$) δ 3.98 (6H, s), 6.85 (2H, d, 8.78 Hz), 7.29 (2H, br s), 7.54 (2H, d, 8.73 Hz), 7.86 (1H, d, 857 Hz), 8.24 (1H, s), 8.57 (1H, d, 858 Hz). MS (APCI pos) 430.1.

Example 54(l)

3-(5-Chloro-1H-benzoimidazol-2-yl)-N-(4-hydroxyphenyl)-1H-indazole-6-carboxamide

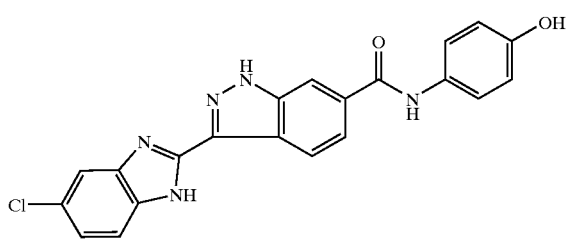

Example 54(l) was prepared in a similar manner to that described for Example 54(a), except that 4-chloro-1,2-phenylenediamine was used in place of 4,5-difluoro 1,2-phenylenediamine. $^1$H NMR (methanol-$d_4$) δ 8.62 (1H, d, J=8.6 Hz), 8.30 (1H, s), 7.90 (1H, dd, $J_1$=8.6 Hz, J2=1.3 Hz), 7.69 (b, 2H), 7.56 (2H, d, J=6.89 Hz), 7.33 (1H, dd, $J_1$=8.59, J2=1.97 Hz), 6.88 (2H, d, J=6.89 Hz). MS (APCI pos) 404.1.

Example 55

3-1H-Benzoimidazol-2-yl-6-pyridin-4-yl-1H-indazole

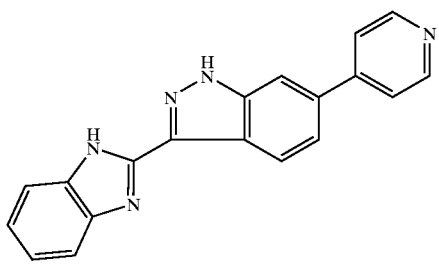

Sem-Example 55 was converted to Example 55 in a similar manner to that described for Example 27(a). $^1$H NMR (300 MHz, CDCl$_3$+MeOH-$d_4$+DMSO-$d_6$) δ 8.71–8.64 (m, 3H), 8.03 (s, 1H), 7.86 (dd, 2H, J=4.7.1.6 Hz), 7.77–7.72 (m, 3H), 7.32 (dd, 2H, J=6.0, 3.1 Hz). HRMS (]AB) [M+H]/z Calc'd 312.1244, found 312.1253. Analyzed with 1.40H$_2$O, Calc'd, C (67.80), H (4.73), N (20.81). Found: C (68.06), H (4.45), N (20.68).

The starting material was prepared as follows:

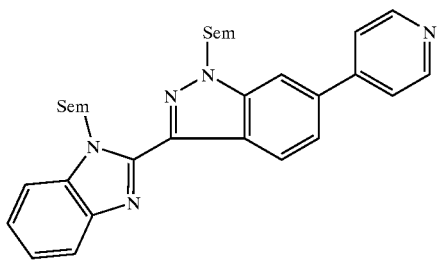

A solution of 6-pyridin-4-yl-1-(2-trimethylsilanyl-ethoxymethyl)-1H-indazole-3-carbaldehyde (0.70 g, 2.0 mmol), benzene-1,2-diamine (0.26 g, 2.4 mmol) and sulfur (77 mg, 2.4 mmol) in DMF (10 ml) was heated in an oil bath at 90° C. overnight. The resulting mixture was poured into brine (200 ml), then extracted with EtOAc (3×60 ml). The combined organic layer was dried over MgSO$_4$ and concentrated under reduced pressure. The resulting oil was purified by silica gel chromatography to yield 6-pyridin-4-yl-1-(2-trimethylsilanyl-ethoxymethyl)-3-[1-(2-trimethylsilanyl-ethoxymethyl)-1H-benzoimidazol-2-yl]-1H-indazole as a light brown oil (0.75 g, 65%). $^1$H NMR (CDCl$_3$) δ 8.82 (d, 1H, J=8.5 Hz), 8.73 (d, 1H, J=5.8 Hz), 7.947.89 (m, 2H), 7.87 (s, 1H), 7.69–7.62 (m, 4H), 7.407.34 (m, 2H), 3.703.49 (m, 4H), 0.94 (t, 2H, J=8.3 Hz), 0.67 (t, 2H, J=8.2 Hz), –0.03 (s, 9H), –0.13 (s, 9H).

Example 56

6-[3-(Propyn-3-ylcarbamoyl)benzoyl]-3-E-[2-(pyridin-2-yl)ethenyl]-1H-indazole

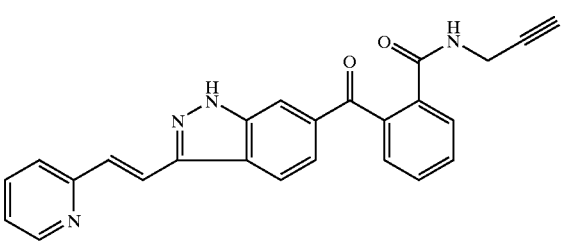

A solution of 2-{1-[3((E)-2-yl-2-vinyl)-1H-indazol-6-yl]-methanoyl}-benzoic acid (55.4 mg. 0.15 mmol) (synthesis described below), propargyl amine (15.4 μL. 0.225 mmol), and triethyl amine (41.8 μL 0.30 mmol), dissolved in DMF (1.5 hexafluorophosphate (62.7 mg, 0.165 mmol). After stirring for one hour the mixture was concentrated under high vacuum and purified by preparative C18 reverse phase column chromatography. The resulting 40 mg of product was further purified by "chromatotron" radial chromatography eluted with 25% CH$_3$CN/CH$_2$Cl$_2$, giving 16.5 mg of the product as a white solid (27% yield). $^1$H NMR (DMSO-$d_4$) δ 13.30 (s, 1H), 8.58 (d, J=5.00 Hz, 1H), 8.05 (d, J=8.29 Hz, 1H), 7.92 (d, J=16.2 Hz, 1H), 7.79. (m, 3H), 7.63 (d, J=8.25 Hz, 1H) 7.53 (m, 3H), 7.32 (s, 1H), 7.27 (m, 2H), 6.89 (d, J=8.48 Hz, 1H). Anal. Calcd. for C$_{25}$H$_1$N$_4$O20.5H$_2$O: C, 72.27; H, 4.61; N, 13.49. Found: C, 72.39; H, 4.62; N, 13.69.

(i)

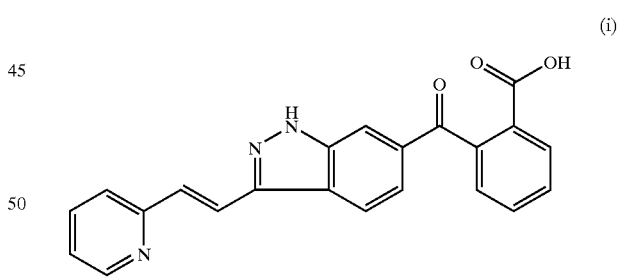

Synthesis of 2-{1-[3-(E)-2-Pyridin-2-yl-vinyl)-1H-indazol-6-yl]-methanoyl}-benzoic acid. A solution of 2-{1-[3-((E)-2-Pyridin-2-yl-vinyl)-1-(2-trimethylsilanyl-ethoxymethyl)-1H-indazol-6-yl]-methanoyl}-benzoic acid (402 mg, 0.805 mmol) (synthesis described below), ethylene diamine (215 μL, 3.22 mmol), and 1M TBAF in THF (6.44 ml, 6.44 mmol), was stirred in a 90° C. oil bath for 4 hr. The crude reaction mixture was quenched with acetic acid (386 μL, 6.44 mmol), diluted with ethyl acetate (100 mL), extracted 1M sodium bicarbonate solution (2×20 ml), brine (5×20 ml), dried magnesium sulfate, filtered, and concentrated to a 3 mL volume. The resulting crude material was purified by preparative C18 reverse phase column chromatography, giving 211 mg of the tide compound as a yellow solid (71% yield). $^1$H NMR (DMSO-d$_6$) δ 13.50 (bs, 1H), 8.68 (d, J=5.27 Hz, 1H), 8.29 (d, J=8.86 Hz, 1H), 8.13–7.90 (m, 4H), 7.81–7.43 (m, 7H).

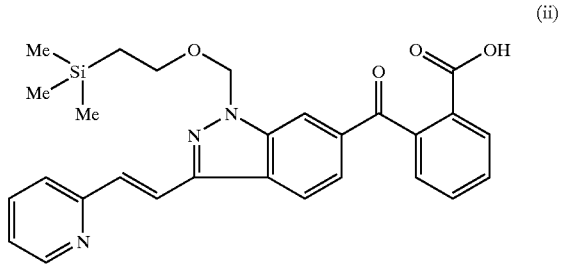

(ii)

Synthesis of 2-{1-[3-((E)-2-Pyridin-2-yl-vinyl)-1-(2-trimethylsilanyl-ethoxymethyl)-1H-indazol-6-yl]-methanoyl}-benzoic acid. A solution 6-iodoindazole (477 mg, 1.0 mmol) dissolved in THF (10 mL), at −100° C. was treated dropwise with 2.5 M n-butyl lithium in hexanes (440 μl, 1.10 mmol), stirred for 5 minutes at this temperature, then treated with a solution pthalic anhydride (222 mg, 1.5 mmol) in THF (1.0 mL). The resulting mixture was allowed to slowly warm to room temperature, where it was stripped of THF, diluted with ethyl acetate, extracted with 1 N citric acid, extracted with brine, dried over magnesium sulfate, and concentrated to an oil. The oil was triturated with methylene chloride, and diethyl ether, giving 484 mg (81% yield) of the tide compound as a white solid. $^1$H NMR (DMSO-d$_6$) δ 8.67 (d, J=5.09 Hz, 1H), 8.31 (d, J=8.85 Hz, 1H), 8.08–7.55 (m, 4H), 750–737 (m, 2H), 5.81 (s, 2H), 3.53 (t, J=8.10 Hz, 2H), 0.78 (t, J=8.15 Hz, 2H), 40.12 (s, 9H).

Example 57

6-[3-((1,3-dimethyl-1H-pyrazol-5-yl)carboxamido) phenoxy]-3-E-[2-(pyridin-2-yl)ethenyl]-1H-indazole

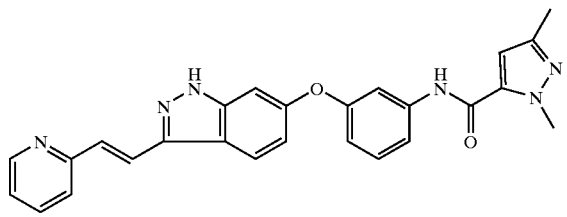

Example 57 was prepared in a similar manner to that of Example 58. $^1$H NMR (300 MHz, DMSO-d$_6$) δ 13.15 (s, 1H), 10.17 (s, 1H), 8.60 (d, 1H, J=4.2 Hz), 8.22 (d, 1H, J=8.7 Hz), 7.94 (d, 1H, J=16.4 Hz), 7.84 7.79 (m, 1H), 7.68–7.50 (m, 4H), 7.40 (t, 1H, J=8.1 Hz), 7.30–7.26 (m, 1H), 7.06 (s, 1H), 7.00 (dd, 1H, J=8.8, 1.9 Hz), 6.87 (dd, 1H, J=8.0, 1.9 Hz), 6.79 (s, 1H), 3.96 (s, 3H), 2.17 (s, 3H); ESIMS m/z 451 [M+H]$^+$. Anal. calcd for C$_{26}$H$_{22}$N$_6$O$_2$ ×0.5H$_2$O×0.4 hexanes (494.0 g/mol): C, 69.05; H. 5.84; N, 17.01. Found: C, 68.78; H, 5.55; N, 17.05.

Example 58

6-[3-((1-Ethyl-3-methyl-1H-pyrazol-5-yl) carboxamido)phenoxy]-3-E-[2-(1H-imidazol-2-yl) ethenyl]-1H-indazole

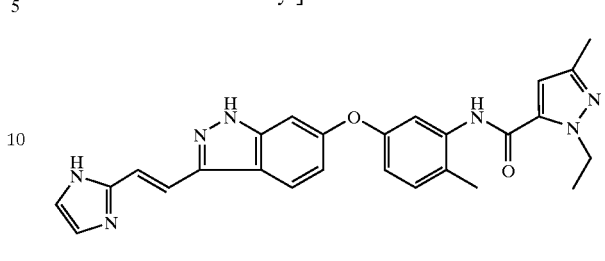

A solution of tetrabutylammonium fluoride (7.5 mL, 1.0 M in THF, 7.5 mmol, 15.0 eq) and 1,2-diaminoethane (0.33 mL, 5.0 mmol, 10 eq) was added to 2-ethyl-5-methyl-2H-pyrazole-3-carboxylic acid [2-methyl-5-(1-(2-trimethylsilanyl-ethoxymethyl)-3-{(E)-2-[1-(2-trimethylsilanyl-ethoxymethyl)-1H-imidazol-2-yl]-vinyl}-1H-indazol-6-yloxy)-phenyl]-amide (360 mg, 0.5 mmol, 1.0 eq) in 1,4-dioxane (5 mL) and the reaction mixture was heated to 90° C. for 18 hours. At the end of this time the reaction was concentrated under reduced pressure and the resultant orange oil was diluted with ethyl acetate (50 mL). The organic layer was vigorously washed with saturated sodium bicarbonate (5×50 mL), brine, dried over magnesium sulfate and concentrated under reduced pressure to give a yellow solid (287 mg). The crude product was purified by radial chromatography on silica gel using 5% methanol-chloroform with 0.1% ammonium hydroxide (R$_f$0.1) as the eluant to give 2-ethyl-5-methyl-2H-pyrazole-3-carboxylic acid (5-{3-[(E)-2-(1H-imidazol-2-yl)vinyl]-1H-indazol-6-yloxy}-2-methyl-phenyl)-amide (140 mg, 61%) as a light yellow solid: HPLC R$_t$=11.8 min.; TLC R$_f$=0.8 (10% methanol-chloroform with 0.1% ammonium hydroxide); $^1$H NMR (300 MHz, DMSO-d$_6$) δ 13.03 (s, 1H), 12.30 (br. s, 1H), 9.78 (s, 1H), 8.00 (d, 1H, J=8.6 Hz), 7.54 (d, 1H, J=16.8 Hz), 7.32 (d, 1H, J=8.5 Hz), 7.27 (d, 1H, J=16.9 Hz), 7.13–7.12 (m, 3H), 7.00–6.94 (m, 3H), 6.78 (s, 1H), 4.39 (q, 2H, J=7.1 Hz), 2.23 (s, 3H), 2.19 (s, 3H), 1.28 (t, 3H, J=7.1 Hz). Anal. calcd for C$_{26}$H$_2$N$_7$×0.5H$_2$O×0.4 hexanes (511.0 g/mol): C, 66.75; H, 6.23; N, 19.19. Found: C, 66.95; H, 6.25; N, 18.83.

The starting materials were prepared as follows:
(i) Preparation of 1-(2-trimethylsilanyl-ethoxymethyl)1H-imidazole

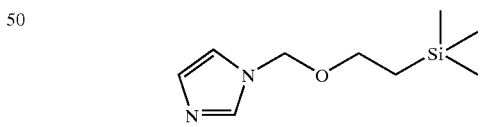

1H-Imidazole (2.0 g, 29.4 mmol, 1.0 eq) in THF (70 mL) was added to a 0° C. suspension of sodium hydride (1.5 g, 60% in mineral oil, 38.2 mmol, 1.3 eq) in TH (30 mL). After gas evolution ceased, the mixture was warmed to room temperature for 45 minutes and then recooled to 0° C. [2(Trimethylsilyl)ethoxy]methyl chloride (S. 4 mL, 30.2 mmol, 1.0 eq) was added, and the mixture was warmed to room temperature overnight. The reaction was quenched with saturated sodium bicarbonate, the THF removed under reduced pressure, and the resultant beige slurry extracted with ethyl acetate. The extracts were combined, washed with brine, dried over magnesium sulfate, filtered, and concentrated to give 6.9 g of an amber oil. The oil was purified by flash chromatography on silica gel using 2% methanol-chloroform as the eluant to give 1-(2-trimethylsilanyl-ethoxymethyl)-1H-imidazole as a light amber oil (4.7 g, 81%): TLC $R_f$=0.3 (5% methanol-chloroform); $^1$H NMR (300 MHz, DMSO-$d_6$) δ 7.77 (s, 1H), 726 (d, 1H, J=1.2 Hz), 6.93 (s, 1H), 5.32 (s, 2H), 3.45 (t, 2H, J=8.0 Hz), 0.83 (t, 2H, J=8.0 Hz), 0.05 (s, 9H); $^3$C NMR (75 MHz, DMSO-$d_6$) δ 137.9, 128.8, 119.6, 74.8, 65.1, 17.1, −1.4.

(ii) Preparation of [1-(2-trimethylsilanyl-ethoxymethyl)-1H-imidazol-2-yl]-methanol

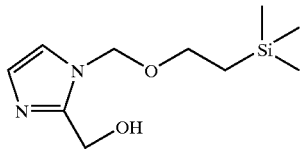

1-(2-Trimethylsilanyl-ethoxymethyl)-1H-imidazole (3.0 g, 15.4 mmol, 1.0 eq) was dissolved in THF (150 mL) and cooled to −78° C. n-BuLi (10.6 mL, 1.6 M in hexanes, 16.9 mmol, 1.1 eq) was added and the temperature was allowed to increase to −40° C. over 15 minutes. The light yellow solution was stirred for an additional 30 minutes at −40° C. then the anion was quenched with DMF (1.3 mL, 16.9 mmol, 1.1 eq). The reaction mixture was warmed to room temperature overnight then quenched with water. The solvent was removed and the mixture was extracted with dichloromethane. The organic layer was washed with water, dried with brine and magnesium sulfate, filtered and concentrated to give the crude product (3.5 g; TLC $R_f$=0.5 (5% methanol-chloroform). The proton NMR spectrum gives the aldehyde proton at 9.73 ppm (300 MHz, DMSO-$d_6$). The crude product was dissolved in methanol (15 mL), cooled to 0° C., and treated with sodium borohydride (1.2 g, 30.8 mmol, 2.0 eq). The reaction mixture was warmed to room temperature overnight. The solvent was removed and the crude product was diluted with chloroform, washed with water, dried with brine and magnesium sulfate, filtered and concentrated to give a clear oil (3.6 g). The oil was purified by flash chromatography on silica gel using 3–6% methanol-chloroform with 0.1% ammonium hydroxide as the eluant to give [1-(2-trimethylsilanyl-ethoxymethyl)-1H-imidazol-2-yl]-methanol as a white solid (1.4 g, 41% 2-steps); TLC $R_f$=0.4 (8% methanol-chloroform); $^1$H NMR (300 MHz, DMSO-$d_6$)δ 7.22(d, 1H, J=1.1 Hz), 6.81 (d, 1H, J=1.0 Hz), 5.36 (s, 2H), 5.31 (br, t, 1H, J=5.2 Hz), 4.50 (d, 2H, J=4.8 Hz), 3.48 (t, 2H, J=8.0 Hz), 0.83 (t, 2H, J=8.0 Hz), −0.05 (s, 9H); $^{13}$C NMR (75 MHz, DMSO-$d_6$) δ 148.9, 127.8, 122.5, 75.5, 66.5, 56.9, 18.5, 0.0.

(iii) Preparation of 2-chloromethyl-1-(2-trimethylsilanyl-ethoxymethyl)-1H-imidazole hydrochloride

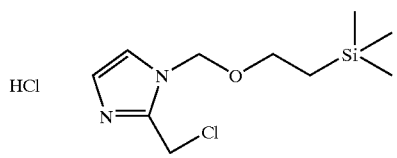

A solution of thionyl chloride (0.87 mL, 12.0 mmol, 3.0 eq) in chloroform (8 mL) was cooled to 0° C. and treated with a solution of [1-(2-trimethylsilanyl-ethoxymethyl)-1H-imidazol-2-yl]-methanol (0.92 g, 4.0 mmol, 1.0 eq) in chloroform (2 mL). The clear solution was stirred at 0° C. for 30 minutes and then at room temperature for 2 hours. The solvent was removed and the product was sequentially slurried and concentrated using chloroform, toluene and cyclohexane to give 2-chloromethyl-1-(2-trimethylsilanyl-ethoxymethyl)1H-imidazole hydrochloride as a beige solid (1.1 g, 97%): $^1$H NMR (300 MHz, DMSO-$d_6$) δ 7.85 (d, 1H, J=1.9 Hz), 7.70 (d, 1H, J=1.9 Hz), 5.62 (s, 2H), 5.14 (s, 2H), 3.57 (t, 2H, J=8.3 Hz), 0.90 (t, 2H, J=8.3 Hz), −0.02 (s, 9H); $^{13}$C NMR (75 MHz, DMSO-$d_6$) δ 142.1, 123.2, 120.2, 76.5, 66.8, 31.7, 17.3, −1.4.

(iv) Preparation of 3-amino-4-methyl-phenol

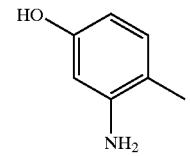

Black solid (95%); HPLC $R_t$=4.4 min.; $^1$H NMR (300 MHz, DMSO-$d_6$) δ 8.61 (s, 1H), 6.64 (d, 1H, J=8.1 Hz), 6.05 (d, 1H, J=2.4 Hz), 5.88 (dd, 1H, J=8.0, 2.4 Hz), 4.64 (br. s. 2H), 1.92 (s, 3H); $^{13}$C NMR (75 MHz, DMSO) δ 156.1, 147.2, 130.2, 111.7.103.3, 101.1, 16.6.

(v) Preparation of 3-(benzhydrylidene-amino)methyl-phenol

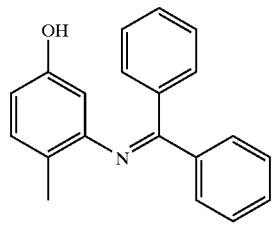

Yellow solid (49%); mp 106–108° C.; HPLC $R_f$=153 min.; TLC R=0.2(10% ethyl acetate-cyclohexane); $^1$H NMR (300 MHz, DMSO-$d_6$) δ 8.91 (s, 1H), 7.67–756 (m, 2H), 7.53–7.43 (m, 3H), 7.35–7.31 (m, 3H), 7.137.10 (m, 2H), 6.82 (d, 1H, J=8.3 Hz), 6.22 (dd, 1H, J=8.1, 2.5 Hz), 5.88 (d, 1H, J=2.5 Hz), 1.97 (s, 3H); $^{13}$C NMR (75 MHz, DMSO-d) δ 166.4, 155.2, 150.6, 138.9, 136.0, 130.8, 130.2, 128.7, 128.4, 128.2, 128.0, 117.3, 109.9, 106.2, 17.0.

(vi) Preparation of benzhydrylidene-{2-methyl-5-[3-((E)-styryl)-1-(2-trimethylsilanyl-ethoxymethyl)-1H-indazol-6-yloxy]-phenyl}-amine

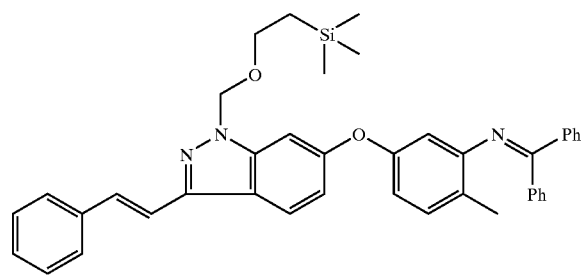

A round bottom flask was charged with potassium phosphate (5.5 g, 26.0 mmol, 2.0 eq), 3-(benzhydrylidene-amino)-4-methyl-phenol (3.9 g, 13.6 mmol 1.1 eq), 6-iodo-3-((E)-styryl)-1-(2-trimethylsilanyl-ethoxymethyl)1H-indazole (6.2 g, 13.0 mmol, 1.0 eq) and o-xylene (130 mL). The resultant slurry was degassed, purged with argon and treated with a mixture of tris(dibenzylideneacetone)dipalladium(0) (916 mg, 1.1 mmol, 8 mol %) and biphenyl-2-yl-di-tertbutyl-phosphane (656 mg, 2.2 mmol, 16 mol %). The flask was immersed in an oil bath and stirred at 100° C. for 18 hours. The black slurry was cooled to room temperature, filtered through celite and concentrated. The black oil was dissolved in chloroform, washed with water, brine, dried over magnesium sulfate, filtered and concentrated to give a black oil (12.1 g). The crude product was purified by flash chromatography on silica gel using 10–15% ether-cyclohexane as the eluant to give benzhydrylidene-[2-methyl-5-[3-((E)-styryl) (2-trimethylsilanyl-ethoxymethyl) 1H-indazol-6-yloxy]-phenyl)-amine as a yellow foam from ether (1.4 g, 16%): HPLC $R_t$=24.3 min.; TLC $R_f$=0.5 (20% ether-cyclohexane); $^1$H NMR (300 MHz, DMSO-$d_6$) δ 8.10 (d, 1H, J=8.8 Hz), 7.75–7.66 (m, 4H), 7.53–7.31 (m, 1H), 7.147.08 (m, 4H), 6.62 (dd, 1H, J=8.8, 2.0 Hz), 6.55 (dd, 1H, J=8.2, 2.5 Hz), 6.20 (d. 1H, 1=2.4 Hz), 5.64 (s, 2H), 3.51 (t, 2H, J=7.8 Hz), 2.12 (s, 3H), 0.78 (t, 2H, J=7.7 Hz), −0.14 (s, 9H).

(vii) Preparation of 2-methyl-5-[3-((E)-styryl)-1-(2-trimethylsilanyl-ethoxymethyl)-1H-indazol-6-yloxy]-phenylamine

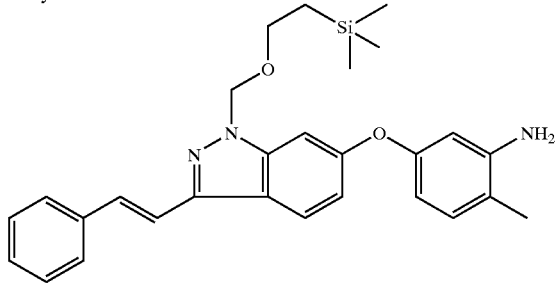

Amber oil (80%); HPLC $R_f$=21.0 min.; TLC $R_f$=0.4 (20% ethyl acetate-cyclohexane); $^1$H NMR (300 MHz, DMSO-4) δ 8.18 (d, 1H, J=8.8 Hz), 7.747.71 (m, 2H), 752 (s, 2H), 7.43–7.38 (m, 2H), 7.33–7.28 (m, 1H), 7.20 (d, 1H, J=2.0 Hz), 6.97–6.90 (m, 2H), 6.33 (d, 1H, J=2.4 Hz), 6.16 (dd, 1H, J=8.0, 2.5 Hz), 5.66 (s, 2H), 5.01 (br. s, 2H), 3.52 (t, 2H, J=8.0 Hz), 2.03 (s, 3H), 0.80 (t, 2H, J=8.0 Hz), −0.11 (s, 9H).

(viii) Preparation of 2-ethyl-5-methyl-2N-pyrazole-3-carboxylic acid (2-methyl-5-[3-((E)-styryl)-1-(2-trimethylsilanyl-ethoxymethyl)1H-indazol-6-yloxy]-phenyl}-amide

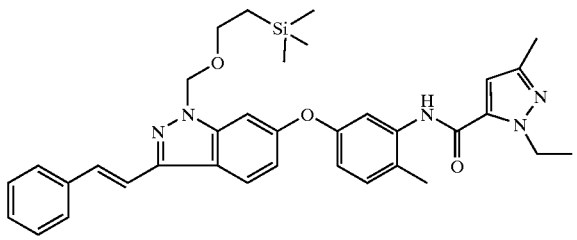

White foam (85%); HPLC $R_f$=21.5 min.; TLC $R_f$ 0.2 (20% ethyl acetate-cyclohexane); $^1$H NMR (300 MHz, DMSO-$d_6$) δ 9.75 (s, 1H), 8.24 (d, 1H, J=8.8 Hz), 7.747.72 (m, 2H), 7.53 (s, 2H), 7.43–7.38 (m, 2H), 7.347.28 (m, 3H), 7.12 (d, 1H, J=2.6 Hz), 7.00 (dd, 1H, J=8.8, 2.0 Hz), 6.92 (dd, 1H, J=8.3, 2.5 Hz), 6.78 (s, 1H), 5.69 (s, 2H), 4.40 (q, 2H, J=7.1 Hz), 3.53 (t, 2H, J=7.9 Hz), 2.22 (s, 3H), 2.19 (s, 3H), 1.27 (t, 3H, J=7.1 Hz), 0.78 (t, 2H, J=7.9 Hz), −0.15 (s, 9H).

(ix) Preparation of 2-ethyl-5-methyl-2H-pyrazole-3-carboxylic acid [5-[3-formyl-1-(2-trimethylsilanyl-ethoxymethyl)-1H-indazol-6-yloxy]-2-methyl-phenyl]-amide

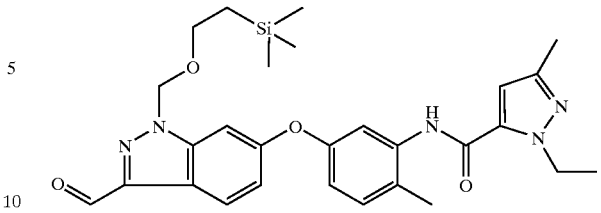

A solution of 2-ethyl-5-methyl-2H-pyrazole-3-carboxylic acid {2-methyl-5-[3-((E)-styryl)-1-(2-trimethylsilanyl-ethoxymethyl)-1H-indazol-6-yloxy]-phenyl}-amide (774 mg, 1.28 mmol, 1.0 eq) in 1,4-dioxane (8 mL) and water (2 mL) was treated with osmium tetraoxide (7 mg, 0.03 mmol, 0.02 eq). The solution was stirred for 5 minutes then treated with sodium periodate (822 mg, 3.84 mmol, 3.0 eq). The resultant thick tan slurry was stirred at room temperature overnight, poured into 15% $Na_2S_2O_3$ (100 mL) and extracted with ethyl acetate. The organic layer was washed with saturated sodium bicarbonate, brine, dried over magnesium sulfate, filtered and concentrated to give an amber oil (902 mg). The crude product was purified by radial chromatography on silica gel using 10–50% ethyl acetate-clohexane as the eluant to give 2-ethyl-5-methyl-2H-pyrazole-3-carboxylic acid (5-[3-formyl-1-(2-trimethylsilanyl-ethoxymethyl-1H-indazol-6-yloxy]-2-methyl-phenyl)-amide as a beige solid from ether (590 mg, 86%): HPLC $R_t$=18.9 min.; TLC $R_f$=0.2 (40% ethyl acetate-cyclohexane); $^1$H NMR (300 MHz, DMSO-$d_6$) δ 10.16 (s, 1H), 9.75 (s, 1H), 8.14 (d, 1H, J=8.8 Hz), 7.48 (d, 1H, J=1.8 Hz), 7.32 (d, 1H, J=85 Hz), 7.16–7.13 (m, 2H), 6.93 (dd, 1H, J=8.3, 2.6 Hz), 6.78 (s, 1H), 5.84(s, 2H), 4.39 (q, 2H, J=7.1 Hz), 355 (t, 2H, J=7.8 Hz), 2.23 (s, 3H), 2.19 (s, 3H), 1.27 (t, 3H, J=7.2 Hz), 0.79 (t, 2H, J=7.8 Hz), p. 15 (s, 9H).

(x) Preparation of 2-ethyl-5-methyl-2H-pyrazole-3 arboxylic acid [2-methyl-5-(1-(2-trimethylsilanyl-ethoxymethyl)-3-{(E)-2-[1-(2-trimethylsilanyl-ethoxymethyl)-1H-imidazol-2-yl]-vinyl}-1H-indazol-6-yloxy)-phenyl]-amide

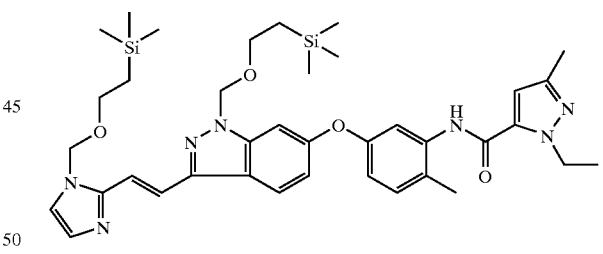

A solution of 2-chloromethyl-1-(2-trimethylsilanyl-ethoxymethyl)-1H-imidazole hydrochloride (344 mg, 1.22 mmol, 2.0 eq) in chloroform (20 TEL) was free based with saturated sodium bicarbonate. The organic layer was dried with brine and magnesium sulfate, filtered and concentrated to give an amber oil (301 mg, 100%). The resultant oil was dissolved in acetonitrile (12 mL), treated with triphenylphosphine (304 mg, 1.16 mmol, 1.9 eq) and warmed to 70° C. for 18 hours. The solvent was removed and the crude 12-trimethylsilanyl-ethoxymethyl)-2-[(triphenyl-$\lambda^5$-phosphanyl)-methyl]-1H-imidazole chloride was dissolved in THF (12 mL), cooled to −78° C., and treated with potassium tert-butoxide (1.2 mL, 1.0 M in THF, 1.22 mmol, 2.0 eq). After 15 minutes, 2-ethyl-5-methyl-2-pyrazole-3-carboxylic acid {5-[3-formyl-1-(2-trimethylsilanyl-ethoxymethyl) 1H-indazol-6-yloxy]-2-methyl-phenyl}- amide (325 mg, 0.61 mmol, 1.0 eq) in THF (1 mL) was added to the ylide at −78° C. The clear yellow solution was warmed to room temperature overnight, quenched with water and extracted with ethyl acetate. The organic layer was washed with brine, dried over magnesium sulfate, filtered and concentrated to give the crude product as an amber oil (1.0 g). The crude product was purified further by radial chromatography on silica gel using 0–5% methanol-chloroform as the eluant to give 2-ethyl-5-methyl-2H-pyrazole-3-carboxylic acid [2-methyl-5-(12-trimethylsilanyl-ethoxymethyl)-3-{(E)-2-[1-(2-trimethylsilanyl-ethoxymethyl)-1H-imidazol-2-yl]-vinyl}-1H-indazol-6-yloxy) phenyl]-amide as a tan solid upon standing overnight (390 mg, 88%). HPLC $R_t$=20.6 min.; TLC $R_f$=0.4 (4% methanol-dichloromethane); $^1$H NMR (300 MHz, DMSO-$d_6$) δ 9.75 (s, 1H), 8.14 (d, 1H, J=8.8 Hz), 7.64 (d, 1H, J=16.2 Hz), 7.42 (d, 1H, J=16.3 Hz), 7.39–7.35 (m, 3H), 7.30 (d, 1H, J=85 Hz), 7.12 (d, 1H, J=2.5 Hz), 7.03 (s, 1H), 6.99 (dd, 1H, J=8.8, 1.9 Hz), 6.78 (s, 1H), 5.70 (s, 2H), 5.55 (s, 2H), 4.40 (q, 2H, J=7.1 Hz), 3.55–3.48 (m, 4H), 2.22 (s, 3H), 2.19 (s, 3H), 1.27 (t, 3H, J=7.1 Hz), 0.84 (t, 2H, J=7.9 Hz), 0.77 (t, 2H, J=7.9 Hz), −0.11 (s, 9H), −0.15 (s. 9H).

Example 59(a)

6-[3-((1-Ethyl-3-methyl-1H-pyrazol-5-yl)carboxamido)benzoyl]-3-E-[2-(pyridin-2-yl)ethenyl]-1H-indazole hydrochloride

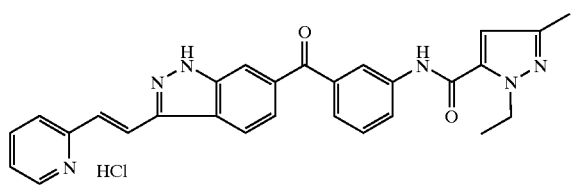

Example 41(a) (4.57 g, 9.59 mmol, 1 equiv) was taken up in methanol (96 mL) and was protected from light with aluminum foil. A second flask with methanol (20 mL) was treated with acetyl chloride (684 μL, 1.00 equiv) for 5 min. The acid solution was then added to the first mixture with several methanol washes (~20 mL). The volatile material was removed under reduced pressure and the residue was triturated with 1:1 ethyl acetate-hexane to give, after filtering and drying, a yellow powder (4.82 g, 98%): Analyzed with 1.0H$_2$O Calc'd, C (61.85), H (5.07), N (15.46). Found: C (61.15), H (5.15), N (15.38).

Example 59(b)

6-[3-((1,3-Dimethyl-1H-pyrazol-5-yl)carboxamido)benzoyl]-3-E-[2-(pyridin-2-yl)ethenyl]-1H-indazole hydrochloride

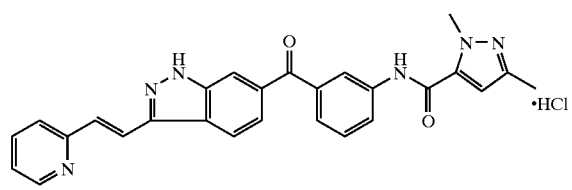

Example 59(b) was prepared in similar manner as Example 59(a) except that Example 41(p) was used in place of Example 41(a). HPLC: 3.92 min (100% area); $^1$H NMR (DMSO) δ 10.45 (s, 1H), 8.85 (d, 1H, J=4.8 Hz), 8.49 (d, 1H, J=8.7 Hz), 8.388.30 (m, 4H), 8.21 (dt, 1H, J=7.5, 2.1 Hz), 8.01(s, 1H), 7.907.79 (m, 2H), 7.72–7.64 (m, 3H), 6.70 (s, 1H), 4.10 (s, 31), 2.33 (s, 3H). Anal. (C$_{27}$H$_{20}$N$_4$O$_2$S.1.3H$_2$O, 0.2EtOAc): Calc. C, 62.15; H, 5.18; N, 15.64. Found C, 61.81; H, 5.01; N. 15.64.

Example 59(c)

6[N-(5-((1-Ethyl-3-methyl-1H-pyrazol-5-yl)carboxamido)-2-fluoro-4-methylphenyl)amino]-3-E-[2-(pyridin-2-yl]ethenyl]-1H-indazole hydrochloride

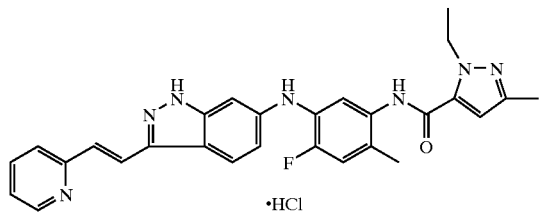

Example 59(c) was prepared in similar manner as Example 59(a) except that Example 48(a) was used in place of Example 41 (a). Anal. Calc'd: C, 63.21; H, 5.12; N. 18.43; Cl, 6.66. Found: C, 60.86; H, 5.38; N. 17.28: Cl, 6.52.

Example 59(d)

6-[N-(3-((1,3-Dimethyl-1H-pyrazol-5-yl)carboxamido)-4-fluoro-phenyl)amino]-3-E-[2-pyridin-2-yl)ethenyl]-1H-indazole hydrochloride

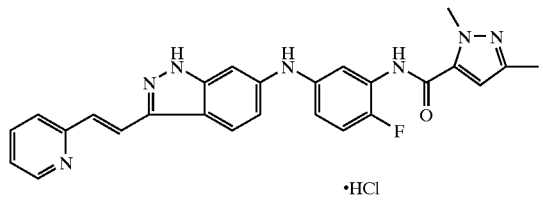

Example 59(d) was prepared in similar manner as Example 59(a) except that Example 49(a) was used in place of Example 41(a). $^1$H NMR (300 MHz, DMSO-$d_6$) δ: 13.2 (b, 1H), 9.97 (s, 1H), 8.75 (d, 1H, J=5.44 Hz), 8.51 (bs, 1H), 8.35 (m, 2H), 8.20 (d, 1H, J=16.59 Hz), 8.06 (d, 1H, J=8.81 Hz), 7.71 (d, 1H, J=16.59 Hz), 7.70 (m, 1H), 7.44 (dd, 1H, J=6.65 Hz, J=2.67 Hz), 7.24 (t, 1H, J=9.54 Hz), 7.12 (d, 1H, J=1.46 Hz), 7.05 (m, 2H), 6.86 (s, 1H), 4.0 (s, 3H), 3.84 (bs, 1H), 2.20 (s, 3H).

Example 59(e)

6-[3-((1-Ethyl-3-methyl-1H-pyrazol-5-yl)carboxamido)phenoxy]-3-E-[2-(pyridin-2-yl)ethenyl]-1H-indazole hydrochloride

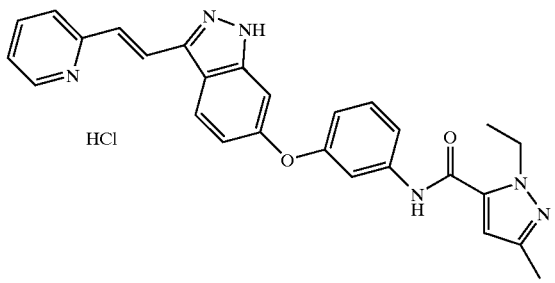

Example 59(e) was prepared in similar manner as Example 59(a) except that Example 31(d) was used in place of Example 41(a). $^1$H NMR (DMSO-4) δ 13.53 (s, 1H), 1023 (s, 1H) 8.78 (d, 1H, J=5.5 Hz), 8.30 (m, 4H), 7.80 (m, 2H), 7.59 (d, 1H, J=7.7 Hz), 755 (s, 1H), 7.41 (t, 1H, J=8.1 Hz), 7.11 (s, 2H), 6.88 (d, 1H, J=6.7 Hz), 6.81 (s, 1H), 4.38(q, 2H, J=7.0 Hz), 3.75 (bs, 1H), 2.19 (s, 3H), 1.29 (t, 3H, J=7.0 Hz). Anal. Calc for $C_{27}H_{25}ClN_6O_2 \cdot 1.7H_2O \cdot 0.1$ EtOAc: C, 60.89; H. 5.45; N, 1555. Found: C, 60.88; H, 551; N, 15.27.

Example 59(f)

6-[2-(methylcarbamoyl)phenylsulfanyl]-3-E-[2-(pyridin-2-yl)ethenyl]indazole hydrochloride

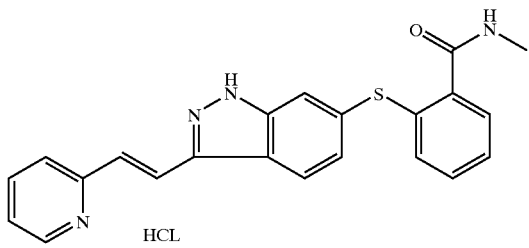

Example 59(f) was prepared in similar manner as Example 59(a) except that Example 33(a) was used in place of Example 41(a). Analyzed with $2.0H_2O$ Calc'd C, 57.58; H, 5.05; N, 12.21; Cl, 6.99. Found: C, 57.24; H, 5.048; N, 11.91: Cl, 6.63.

The exemplary compounds described above may be tested for their activity using the tests described below.

Biological Testing: Enzyme Assays

The stimulation of cell proliferation by growth factors such as VEFG, FGF, and others is dependent upon their induction of autophosphorylation of each of their respective receptor's tyrosine kinases. Therefore, the ability of a protein kinase inhibitor to block autophosphorylation can be measured by inhibition of the peptide substrates. To measure the protein kinase inhibition activity of the compounds, the following constructs were devised.

VEGF-R2 Construct for Assay: This construct determines the ability of a test compound to inhibit tyrosine kinase activity. A construct (VEGF-R2Δ50) of the cytosolic domain of human vascular endothelial growth factor receptor 2 (VEGF-R2) lacking the 50 central residues of the 68 residues of the kinase insert domain was expressed in a baculovirus/insect cell system. Of the 1356 residues of full-length VEGF-R2, VEGF-R2Δ507 contains residues 806939 and 990–1171, and also one point mutation (E990V) within the kinase insert domain relative to wild-type VEGF-R2. Autophosphorylation of the purified construct was performed by incubation of the enzyme at a concentration of 4 µM in the presence of 3 mM ATP and 40 mM $MgCl_2$ in 100 mM HEPES, pH 7.5, containing 5% glycerol and 5 mM DTT, at 4° C. for 2 h. After autophosphorylation, this construct has been shown to possess catalytic activity essentially equivalent to the wild-type autophosphorylated kinase domain construct. See Parast et al., *Biochemistry*, 37, 16788–16801 (1998).

FGF-R1 Construct for Assay: The intracellular kinase domain of human FGF-R1 was expressed using the baculovirus vector expression system starting from the endogenous methionine residue 456 to glutamate 766, according to the residue numbering system of Mohammadi et al., *Mol. Cell. Biol.,* 16, 977–989 (1996). In addition, the construct also has the following 3 amino acid substitutions: L457V, C488A, and C584S.

LCK Construct for Assay: The LCK tyrosine kinase was expressed in insect cells as an N-terminal deletion starting from amino acid residue 223 to the end of the protein at residue 509, with the following two amino acid substitutions at the N-terminus: P233M and C224D.

CHK1 Construct for Assay: C-terminally His-tagged full-length human CHK1 (FL-CHK1) was expressed using the baculovirus/insect cell system. It contains 6 histidine residues (6×His-tag) at the C-terminus of the 476 amino acid human CHK1. The protein was purified by conventional chromatographic techniques.

CDK2/Cyclin A Construct for Assay: CDK2 was purified using published methodology (Rosenblatt et al., *J. Mol. Biol.,* 230, 1317–1319 (1993)) from insect cells that had been infected with a baculovirus expression vector. Cyclin A was purified from *E. coli* cells expressing full-length recombinant cyclin A, and a truncated cyclin A construct was generated by limited proteolysis and purified as described previously (Jeffrey et al., *Nature,* 376, 313–320 (1995)).

CDK4/Cyclin D Construct for Assay: A complex of human CDK4 and cyclin D3, or a complex of cyclin D1 and a fusion protein of human CDK4 and glutathione-S-transferase (GST-CDK4), was purified using traditional biochemical chromatographic techniques from insect cells that had been co-infected with the corresponding baculovirus expression vectors.

FAK Construct for Assay. The catalytic domain of human FAK (FAKcd49) was expressed using the baculovirus vector expression system. The 280 amino acid domain expressed comprises residues methionine 409 to glutamate 689. One amino acid substitution exists P410 relative to the sequence assession number L13616 published by Whithey, G. S. et al., *DNA Cell Biol,* 9, 823–30 (1993). The protein was purified using classical chromatograph y techniques.

TIE-2 (TEK) Construct for Assay

The TIE-2 tyrosine kinase domain was expressed in insect cells as an N-terminal deletion starting from amino acid residue 774 to the end of the protein at residue 1124. This construct also carries a R774M mutation, which serves as the initiating methionine residue in translation.

VEGF-R2 Assay

Coupled Spectrophotometric (FLVK-P) Assay

The production of ADP from ATP that accompanies phosphoryl transfer was coupled to oxidation of NADH using phosphoenolpyruvate (PEP) and a system having pyruvate kinase (K) and lactic dehydrogenase (LDH). The oxidation of NADH was monitored by following the decrease of absorbance at 340 nm ($e_{340}$=6.22 cm$^{-1}$ mM$^{-1}$) using a Beckman DU 650 spectrophotometer. Assay conditions for phosphorylated VEGF-R2Δ50 (indicated as FLVK-P in the tables below) were the following: 1 mM PEP; 250 μM NADH; 50 units of LDH/mL; 20 units of PK/mL; 5 mM DTT; 5.1 mM poly($E_4Y_1$); 1 mM ATP; and 25 mM MgCl$_2$ in 200 mM HEPES, pH 7.5. Assay conditions for unphosphorylated VEGF-R2Δ50 (indicated as FLVK in the tables) were the following: 1 mM PEP; 250 μM NADH; 50 units of LDH/mL; 20 units of PK/mL; 5 mM DTT; 20 mM poly($E_4Y_1$); 3 mM ATP; and 60 mM MgCl$_2$ and 2 mM MnCl$_2$ in 200 mM HEPES, pH 7.5. Assays were initiated with 5 to 40 nM of enzyme. $K_i$ values were determined by measuring enzyme activity in the presence of varying concentrations of test compounds. The data were analyzed using Enzyme Kinetic and Kaleidagraph software.

ELISA Assay

Formation of phosphogastrin was monitored using biotinylated gastrin peptide (1–17) as substrate. Biotinylated phosphogastrin was immobilized using streptavidin coated 96-well microtiter plates followed by detection using anti-phosphotyrosine-antibody conjugated to horseradish peroxidase. The activity of horseradish peroxidase was monitored using 2,2'-azinodi-[3-ethylbenzathiazoline sulfonate(6)] diammonium salt (ABTS). Typical assay solutions contained: 2 μM biotinylated gastrin peptide; 5 mM DTT; 20 LM ATP; 26 mM MgCl$_2$; and 2 mM MnCl$_2$ in 200 mM HEPES, pH 7.5. The assay was initiated with 0.8 nM of phosphorylated VEGF-R2Δ50. Horseradish peroxidase activity was assayed using ABTS, 10 mM. The horseradish peroxidase reaction was quenched by addition of acid (H$_2$SO$_4$), followed by absorbance reading at 405 mm. $K_i$ values were determined by measuring enzyme activity in the presence of varying concentrations of test compounds. The data were analyzed using Enzyme Kinetic and Kaleidagraph software.

FGF-R Assay

The spectrophotometric assay was carried out as described above for VEGF-R2, except for the following changes in concentration: FGF-R=50 nM, ATP=2 nM, and poly(E4Y1)=15 mM.

LCK Assay

The spectrophotometric assay was carried out as described above for VEGF-R2, except for the following changes in concentration: LCK=60 nM, Mgcl$_2$=0 mM, poly (E4Y1)=20 mM.

CHK1 Assay

The production of ADP from ATP that accompanies phosphoryl transfer to the synthetic substrate peptide Syntide-2(PLARTLSVAGLPGKK) was coupled to oxidation of NADH using phosphoenolpyruvate (PEP) through the actions of pyruvate kinase (PK) and lactic dehydrogenase (LDH). The oxidation of NADH was monitored by following the decrease of absorbance at 340 nm ($\epsilon$340=6.22 cm$^{-1}$ mM$^{-1}$) using a BP8452 spectrophotometer. Typical reaction solutions contained: 4 mN PEP; 0.15 mM NADH; 28 units of LDH/mL; 16 units of PK/mL; 3 mM DTT; 0.125 mM Syntide-2; 0.15 mM ATP; 25 mM Mgcl$_2$ in 50 mM TRIS, pH 7.5; and 400 mM NaCl. Assays were initiated with 10 nM of FL-CHK1. $K_i$ values were determined by measuring initial enzyme activity in the presence of varying concentrations of test compounds. The data were analyzed using Enzyme Kinetic and Kaleidagraph software.

CDK2/Cyclin A and CDK4/Cyclin D Assays

Cyclin-dependent kinase activity was measured by quantifying the enzyme-catalyzed, time-dependent incorporation of radioactive phosphate from [$^{32}$P]ATP into a recombinant fragment of the retinoblastoma protein. Unless noted otherwise, assays were performed in 96-well plates in a total volume of 50 μL, in the presence of 10 mM HEPES (N-[2-hydroxyethyl]piperazine-N'-[2-ethanesulfonic acid]) (pH 7.4), 10 mM MgCl$_2$, 25 μM adenosine triphosphate (ATP), 1 mg/mL ovalbumin, 5 μg/mL leupeptin, 1 mM dithiothreitol, 10 mM β-glycerophosphate, 0.1 mM sodium vanadate, 1 mM sodium fluoride, 2.5 mM ethylene glycol-bis(β-aminoethyl ether)-N,N,N'N'-tetraacetic acid (EGTA), 2% (v/v) dimethylsulfoxide, and 0.03–0.2 μCi [$^{32}$P]ATP. The substrate (0.3–0.5 μg) was purified recombinant retinoblastoma protein fragment (Rb) (residues 386–928 of the native retinoblastoma protein; 62.3 kDa, containing the majority of the phosphorylation sites found in the native 106-kDa protein, as well as a tag of six histidine residues for ease of purification). Reactions were initiated with CDK2 (150 nM CDK2/Cyclin A complex) or CDK4 (50 nM CDK4/Cyclin D3 complex), incubated at 30° C., and terminated after 20 minutes (min.) by the addition of ethylenediaminetetraacetic acid (EDTA) to 250 mM. The phosphorylated substrate was then captured on a nitrocellulose membrane using a 96-well filtration manifold, and unincorporated radioactivity was removed by repeated washing with 0.85% phosphoric acid. Radioactivity was quantified by exposing the dried nitrocellulose membranes to a phosphorimager. Apparent $K_i$ values were measured by assaying enzyme activity in the presence of different compound concentrations and subtracting the background radioactivity measured in the absence of enzyme. The kinetic parameters (kcat, Km for ATP) were measured for each enzyme under the usual assay conditions by determining the dependence of initial rates on ATP concentration. The data were fit to an equation for competitive inhibition using Kaleidagraph (Synergy Software), or were fit to an equation for competitive tight-binding inhibition using the software KineTic (BioKin, Ltd.). Measured $K_i$ values for known inhibitors against CDK4 and CDK2 agreed with published IC$_{50}$ values. The specific activity of CDK4 was the same whether complexed to full-length cyclin D3 or the truncated Cyclin D3 construct; both complexes also yielded very similar $K_i$ values for selected inhibitors.

FAK Assay

FAK HTS utilized the fluorescence polarization assay provided by LJL Biosystems. The kinase reaction contained: 100 mM Hepes pH 7.5, 10 mM MgCl$_2$, 1 mM DTT, 1 mM ATP, and 1 mg/ml poly Glu-Tyr (4:1). The reaction is initiated by the addition of 5 nM FAKcd409. The reaction is terminated by the addition of EDTA followed by addition of fluor-labelled peptide and anti-phosphotyrosine antibody, both provided by LJL Biosystems. Inhibition results are read on a Analyst (LJL) detector.

TIE-2 Spectrophotometric Assay

The kinase-catalyzed production of ADP from ATP that accompanies phosphoryl transfer to the random copolymer poly(Glu$_4$Tyr) was coupled to the oxidation of NADH through the activities of pyruvate kinase (PK) and lactate dehydrogenase (LDH). NADH conversion to NAD$^+$ was monitored by the decrease in absorbance at 340 nm ($\epsilon$=6.22 cm$^{-1}$ mM$^{-1}$) using a Beckman DU650 spectrophotometer. Typical reaction solutions contained 1 mM phosphoenolpyruvate, 0.24 mM NADH, 40 mM MgCl$_2$, 5 mM DTT, 2.9 mg/mL poly(Glu$_4$Tyr), 0.5 mM ATP, 15 units/mL PK, 15 units/mL LDH in 100 mM HEPES, pH 7.5. Assays were initiated with the addition of 4 to 12 nM phosphorylated Tie-2 (aa 775–1122). Percent inhibition was determined in triplicate at a 1 μM level of inhibitor.

TIE-2 DELFIA Assay

Formation of phosphotyrosine was monitored using biotinylated p34cdc2 (aa6–20=KVEKIGEGTYGVVYK) peptide as substrate. Biotinylated peptide was immobilized using NeutrAvidin™ coated 96-well microtiter plates followed by detection using anti-phosphotyrosine-antibody (PY20) conjugated to europium NI chelate. Typical assay solutions contained: 1 µM biotinylated p34cdc2 peptide, 150 µM ATP, 5 mM MgCl$_2$, 1 mM DTT, 0.01% BSA, 5% glycerol, 2% DMSO, 25 mM HEPES pH 7.5. The assay was initiated in the NeutrAvidin plate with 50 nM of TIE2 intracellular domain. The kinase reaction was terminated with 50 mM EDTA. Plates were then washed, and europium antibody added. After incubation, they were again washed, and DELFIA™ Enhancement Solution added. Plates were read at standard Europium time-resolved settings (ex 340 nm, em 615 run, delay 400 µsec, window 400 µsec). Percent inhibition was calculated with reference to intraplate wells which had added DMSO rather than compound in DMSO, with background subtracted from both experimental and control with reference to an intraplate well which had EDTA added prior to addition of enzyme.

HUVEC Proliferation Assay

This assay determines the ability of a test compound to inhibit the growth factor-stimulated proliferation of human umbilical vein endothelial cells ("HUVEC"). HUVEC cells (passage 34, Clonetics, Corp.) were thawed into EGM2 culture medium (Clonetics Corp) in 175 flasks. Fresh EGM2 medium was added to the flasks 24 hours later. Four or five days later, cells were exposed to another culture medium (F12K medium supplemented with 10% fetal bovine serum (FBS), 60 µg/mL endothelial cell growth supplement (ECGS), and 0.1 mg/mL heparin). Exponentially-growing HUVEC cells were used in experiments thereafter. Ten to twelve thousand HUVEC cells were plated in 96-well dishes in 100 µl of rich, culture medium (described above). The cells were allowed to attach for 24 hours in this medium. The medium was then removed by aspiration and 105 µl of starvation media (F12K+1% FBS) was added to each well. After 24 hours, 15 µl of test agent dissolved in 1% DMSO in starvation medium or this vehicle alone was added into each treatment well; the final DMSO concentration was 0.1%. One hour later, 30 µl of VEGF (30 ng/mL) in starvation media was added to all wells except those containing untreated controls; the final VEGF concentration was 6 ng/mL. Cellular proliferation was quantified 72 hours later by MTT dye reduction, at which time cells were exposed for 4 hours MIT (Promega Corp.). Dye reduction was stopped by addition of a stop solution (Promega Corp.) and absorbance at 595 λ was determined on a 96-well spectrophotometer plate reader.

IC$_{50}$ values were calculated by curve-fitting the response of A$^{595}$ to various concentrations of the test agent; typically, seven concentrations separated by 0.5 log were employed, with triplicate wells at each concentration. For screening compound library plates, one or two concentrations (one well per concentration) were employed, and the % inhibition was calculated by the following formula:

% inhibition=(control-test)÷(control-starvation)

where control=A$^{595}$ when VEGF is present without test agent test=A$^{595}$ when VEGF is present with test agent starvation=A$^{595}$ when VEGF and test agent are both absent.

Cancer Cell Proliferation (MV522) Assay

The protocol for assessing cellular proliferation in cancer cells is similar to that used for assessments in HUVEC cells. Two thousand lung cancer cells (line MV522, acquired from American Tissue Cultural Collection) were seeded in growth media (RPMI1640 medium supplemented with 2 mM glutamine and 10% FBS). Cells are allowed to attach for 1 day prior to addition of test agents and/or vehicles. Cells are treated simultaneously with the same test agents used in the HUVEC assay. Cellular proliferation is quantified by MTT dye reduction assay 72 hours after exposure to test agents. The total length of the assay is 4 days vs. 5 for HUVEC cells because MV522 cells are not exposed to starvation medium.

Mouse PK Assay

The pharmacokinetics (e.g., absorption and elimination) of drugs in mice were analyzed using the following experiment Test compounds were formulated as a solution or suspension in a 30:70 (PEG 400: acidified H$_2$O) vehicle or as a suspension in 0.5% CMC. This was administered orally (p.o.) and intraperitoneally (i.p.) at variable doses to two distinct groups (n=4) of B6 female mice. Blood samples were collected via an orbital bleed at time points: 0 hour (pre-dose), 0.5 h, 1.0 h, 2.0 h, and 4.0 h, and 7.0 h post dose. Plasma was obtained from each sample by centrifugation at 2500 rpm for 5 min. Test compound was extracted from the plasma by an organic protein precipitation method. For each time bleed 50 µL of plasma was combined with 1.0 mL of acetonitrile, vortexed for 2 min. and then spun at 4000 rpm for 15 min. to precipitate the protein and extract out the test compound. Next, the acetonitrile supernatant (the extract containing test compound) was poured into new test tubes and evaporated on a hot plate (25° C.) under a steam of N$_2$ gas. To each tube containing the dried test compound extract 125 µL of mobile phase (60:40, 0.025 M NH$_4$H$_2$PO$_4$+2.5 mL/L TEA:acetonitrile) was added. The test compound was resuspended in the mobile phase by vortexing and more protein was removed by centrifugation at 4000 rpm for 5 min. Each sample was poured into an HPLC vial for test compound analysis on an Hewlett Packard 1100 series HPLC with UV detection. From each sample, 95 µL was injected onto a Phenomenex-Prodigy reverse phase C-18, 150×3.2 mm column and eluted with a 45–50% acetonitrile gradient run over 10 min. Test-compound plasma concentrations (µg/mL) were determined by a comparison to standard curve (peak area vs. conc. µg/mL) using known concentrations of test compound extracted from plasma samples in the manner described above. Along with the standards and unknowns, three groups (n=4) of quality controls (0.25 µg/mL, 1.5 µg/mL, and 7.5 µg/mL) were run to insure the consistency of the analysis. The standard curve had an R2>0.99 and the quality controls were all within 10% of their expected values. The quantitated test samples were plotted for visual display using Kalidagraph software and their pharmacokinetic parameters were determined using WIN NONLIN software. Example 1(a) provided the following results: 0.69 (Mouse pK, AUC, ip, µg-h/ml); 0.33 (Mouse pK, AUC, po, µg-h/ml).

Human Liver Microsome (HLM) Assay

Compound metabolism in human liver microsomes was measured by LC-MS analytical assay procedures as follows. First, human liver microsomes (HLM) were thawed and diluted to 5 mg/mL with cold 100 mM potassium phosphate (KPO4) buffer. Appropriate amounts of KPO4 buffer, NADPH-regenerating solution (containing B-NADP, glucose-6-phosphate, glucose-6-phosphate dehydrogenase, and MgCl$_2$), and HLM were preincubated in 13×100 mm glass tubes at 37 C. for 10 min. (3 tubes per test compound—triplicate). Test compound (5 FM final) was added to each tube to initiate reaction and was mixed by gentle vortexing, followed by incubation at 37° C. At t=0, 2 h, a 250-μL sample was removed from each incubation tube to separate 12×75 mm glass tubes containing 1 mL ice-cold acetonitrile with 0.05 μM reserpine. Samples were centrifuged at 4000 rpm for 20 min. to precipitate proteins and salt (Beckman Allegra 6KR, S/N ALK98D06, #634). Supernatant was transferred to new 12×75 mm glass tubes and evaporated by Speed-Vac centrifugal vacuum evaporator. Samples were reconstituted in 200 IAL 0.1% formic acid/acetonitrile (90/10) and vortexed vigorously to dissolve. The samples were then transferred to separate polypropylene microcentrifuge tubes and centrifuged at 14000×g for 10 min. (Fisher Micro 14, S/N M0017580). For each replicate (#1–3) at each timepoint (0 and 2 h), an aliquot sample of each test compound was combined into a single HPLC vial insert (6 total samples) for LC-MS analysis, which is described below.

The combined compound samples were injected into the LC-MS system, composed of a Hewlett-Packard HP1100 diode array HPLC and a Micromass Quattro II triple quadruple mass spectrometer operating in positive electrospray SIR mode (programmed to scan specifically for the molecular ion of each test compound. Each test compound peak was integrated at each timepoint. For each compound, peak area at each timepoint (n=3) was averaged, and this mean peak area at 2 h was divided by the average peak area at time 0 hour to obtain the percent test compound remaining at 2 h.

The results of the testing of the compounds using various assays are summarized in the table below, where a notation of "% @" indicates the percent inhibition at the stated concentration, "*" values represent Ki (nM) or % inhibition at a compound concentration of 1 μM for * or 50 nM for **, unless otherwise indicated. "NI" indicates no significant inhibition

TABLE 1

| Ex # | FLVK ** | FLVK-P** | Lck-P* | CHK-1* | FGF-P* | CDK2 * | CDK4 * | HUVEC IC50 (nM) | HUVEC + albumin IC50 (nM) | MV522 IC50 (μM) | % remain (HLM, 2 h) |
|---|---|---|---|---|---|---|---|---|---|---|---|
| 2(b) | 300 | 425 | | 549 | 228 μM | 2,200 | 8,000 | | | | |
| 2(c) | 2600 | | | | | 50 μM | 26 μM | | | | |
| 1(a) | 0.3 | 2 | 88 | 5.2 | 27 | 19 | 13 | 54 | | 0.35 | 98 |
| 3 | 6.6 | 65 | 37% | 4.8 | 112 | 16 | 23 | 930 | | 2.2 | |
| 8(a) | 3.2 | 23 | 43% | 530 | 42 | >100 μM | >100 μM | >1000 | | >10 | |
| 8(b) | 72 | | | 12% @ 50 μM | | | | | | | |
| 2(d) | 3.7 | | 43% | 91 | 68 | 53 | 53 | 450 | | 0.18 | |
| 1(c) | 1.4 | 4.7 | 46% | 78 | | 560 | 670 | >1000 | | >10 | |
| 2(a) | 40 | | | 61% @20 μM | | 610 | 1600 | >1000 | | 0.58 | |
| 1(b) | 2.2 | | | 1400 | | 4000 | 1300 | >1000 | | >10 | |
| 8(c) | 2.6 | 16 | 34% | >10,000 | | >100 μM | >100 μM | 280 | | >10 | |
| 9(a) | 2.4 | 16 | 162 | 400 | | | 1700 | 870 | | >10 | |
| 9(b) | 24 | | | 448 | | | | | | | |
| 2(e) | 40 | | | 5% @ 20 μM | | | | | | | |
| 10 | 9 | | | 9100 | | | | >700 | | >10 | |
| 20(a) | 29 | 12.7 | | | | | | 200 | | 9.4 | 52 |
| 20(b) | 1.6 | 8 | 23% | | 28% | | | 8.2 | | Ca. 10 | |
| 14 | 15 | | | 12% @25 μM | | | | | | | |
| 7 | 18 | | | 1,300 | | | | | | | |
| 17 | 11 | | | 532 | | | | | | | |
| 8(b) | 11 | | | 82,000 | | | | | | | |
| 4(a) | 0.65 | 1.4 | 68% | NI | 15.4 | NI | 19% | 3 | 30 | 6.3 | 35 |
| 23 | 1.6 | 2.1 | 12% | NI | 14% | NI | 17% | 9.5 | 106 | 5.7 | 74 |
| 21 | 4.6 | | | | | | | >700 | | | |
| 11 | 12 | | | | 34,000 | | | | | | |
| 22(b) | 0.63 | 1.2 | | | 21.5 | | | 4.8 | | 85 | |
| 22(a) | 0.22 | 0.2 | | | | | | 12 | | >10 | |
| 22(c) | 0.64 | | | | | | | 38 | | | |
| 4(b) | 2.7 | 1.9 | 13% @ 1 μM | | 4.9 | | | 25 | 205 | 3.2 | 63 |
| 12(a) | 1.8 | 6.9 | 17% | | 19 | | | 6 | 87 | 2.1 | 59 |
| 12(b) | 0.48 | 1.8 | 32% | | 31 | | | 4.8 | 44 | >10 | 29 |
| 18 | 12.5 | | | | | | | | | | |
| 19(b) | 0.49 | 6.6 | 58% | NI | 60% | NI | 11% | 2.9 | 27 | 4.3 | 137 |
| 19(a) | 13.8 | 6.8 | 16% @ 1 μM | | 92% | | | 44 | | | |
| 19(c) | | 5.9 | 50% | | 68% | | | 17 | | | |
| 12(c) | 1.6 | | | | | | | | | | |
| 19(d) | 0.72 | | 33% | | 39% | | | 6.8 | 34 | >10 | 36 |
| 5(a) | 0.03 | | 28% | | 10.4 | | | 12 | | 9.6 | |

TABLE 1-continued

| Ex # | FLVK ** | FLVK-P** | Lck-P* | CHK-1* | FGF-P* | CDK2 * | CDK4 * | HUVEC IC50 (nM) | HUVEC + albumin IC50 (nM) | MV522 IC50 (μM) | % remain (HLM, 2 h) |
|---|---|---|---|---|---|---|---|---|---|---|---|
| 12(d) | 0.39 | | 31% | | 61% | | | 8.1 | | >10 | 51 |
| 13 | 1.3 | | 61% | | 74% | | | 3.9 | 28 | >10 | 69 |
| 15 | | 15 | | | | | | | | | |
| 16(a) | 0.08 | | 28% | NI | 65% | NI | NI | 4.5 | 112 | 8 | 7* |
| 6(a) | 0.74 | | 33% | | 67% | | | 8.5 | 50 | 3.5 | 69* |
| 5(b) | 0.9 | | 78% | | 14 | | | 3.7 | 33 | 8.5 | |
| 16(b) | 0.34 | | 22% | | 73% | | | 4.7 | 140 | >10 | 50 |
| 16(c) | | 1.1 | | | | | | 100–1000 | | >10 | |
| 16(d) | 0.43 | | 33% | | 90% | | | 11 | | >10 | |
| 16( ) | 1.3 | | 8% | | 59% | | | 4.9 | 106 | >10 | 40 |
| 6(b) | | 0.15 | 81% | | 95% | | | 8 | 60 | 4 | 128 |
| 16(f) | | 2.8 | | | | | | >30 | | >10 | |
| 19(e) | | 20 | | | | | | >300 | | | |
| 30(a) | 1.7 | | 45% | 94% | | | | 1.6 | 22 | 5.7 | 64 |
| 19(f) | 0.18 | | 52% | | 58% | | | 2.3 | 16 | 3.9 | 98 |
| 46 | | 3.5 | | | | | | | | | |
| 19(g) | | | | | | | | | | | |
| 30(b) | | 2.2 | | | | | | 90 | | | |
| 19(q) | 0.86 | | 19% | | 59% | | | 18 | 1920 | | 90 |
| 30(c) | 0.83 | | 44% | | 82% | | | 2.5 | 21 | | 54 |
| 19(h) | | 5.9 | | | | | | 600 | | 7.9 | |
| 44 | | 9.6 | | | | | | >700 | | | |
| 38(a) | 0.22 | | 77% | | 74% | | | 4.5 | 20 | 10.7 | 72 |
| 45(b) | 99% | | 86% | | 79% | | | 1.9 | 11.5 | 4.4 | 97 |
| 45(a) | 0.062 | | | | | | | 3.1 | ca. 15 | 3.5 | 97 |
| 19(l) | | 4.7 | | | | | | >300 | | | |
| 42(a) | 0.046 | 79% | 53 | | 65 | | | 0.8 | 8 | 5.5 | 92 |
| 38(b) | | 72% | | | | | | 79 | | | |
| 19(j) | 0.33 | | 23% | | 44% | | | 2.2 | 50 | >10 | 66 |
| 42(b) | 0.35 | | 75% | | 27% | | | 2.1 | 29 | 2.1 | 81 |
| 19(k) | 100% | | 37% | | 41% | | | 2.6 | 28 | 4 | 58 |
| 33(b) | 0.66 | 76% | 63% | | 77% | | | 0.8 | 11.5 | 15 | 45 |
| 26 | | 1.1 | | 6.6 | | 3.2 | | | | | |
| 19(l) | 0.72 | | 36% | | 88% | | | 6.8 | 100 | 3.8 | |
| 19(m) | 0.68 | | 35% | | 23% | | | | 94 | >10 | 61 |
| 33(a) | 3.8 | 42% | 9% | 0 | 56 | 2% | 7% | 0.5 | 2.7 | >10 | 29 |
| 19(n) | 0.54 | | 26% | | 48% | | | 3.4 | 23 | 2.9 | |
| 33(c) | 0.28 | | 26% | | 76% | | | | 6.6 | >10 | 16 |
| 33(d) | 0.14 | | 55% | | 24 | | | | >300 | 8 | 22 |
| 40(a) | | 17.9 | | | | | | | | | |
| 41(aa) | 0.11 | | 49% | | 37% | | | 1 | 5.2 | >10 | 100 |
| 41(b) | 0.26 | | 24% | | 31% | | | 2 | 9.8 | >10 | 80 (UV) |
| 42(e) | 1.1 | | | | | | | | 95 | | |
| 42(d) | 1.7 | | | | | | | | 44 | >10 | |
| 43 | 2.6 | 56% | | | | | | | 24 | | 2 |
| 19(o) | 89% | | | | | | | | 20 | | |
| 41(c) | 0.22 | 83% | 36% | | 77% | | | 0.4 | 5.3 | | 68 |
| 41(d) | 0.093 | | | | | | | 0.9 | 6.4 | | |
| 41(a) | 0.03 | 94% | 50% | 0 | 20 | 0 | 6% | 0.48 | 4.4 | >10 | 96 |
| 19(p) | 1.5 | | | | | | | | | | |
| 41(e) | 0.22 | | 21% | | 31% | | | 0.15 | 5.6, 6.1 | | 22 |
| 41(f) | 0.11 | 84% | 65% | | 92% | | | 0.45 | 20 | | 59 |
| 41(g) | 0.1 | | 36% | | 95% | | | 0.9 | >10 | | 52 |
| 30(d) | 0.37 | | | | | | | | 3.8 | | |
| 30(e) | 0.37 | | 62% | | 92% | | | | 29 | | |
| 33(e) | 1.7 | 70% | 2% | | 68% | | | 0.46 | 5 | >10 | 54 |
| 33(f) | 8 | | | | | | | | 17 | | 31 |
| 41(h) | 90% | | 30% | | | | | 2 | 25 | | 8 |
| 47 | 0.25 | | 50% | | 88% | | | | | | |
| 31(a) | 0.29 | | 77%* | | 95% | | | 0.7 | 10 | | 58 |
| 41(l) | 0.04 | | 38%* | | 76% | | | 0.25 | 3.3 | | 48 |
| 35(u) | 79% | | | | | | | | 2.8 | | 27 |
| 32(a) | <0.1 | | 86%* | | 96% | | | 0.16 | 4.5 | | 2 |
| 41(k) | 2.95 | | 20% | | 49% | | | | 48 | | |
| 41(l) | 0.24 | | 63%* | | 66% | | | | 386 | | |
| 41(m) | 0.75 | | 40% | | 67% | | | | 23 | | 0 |
| 41(n) | 0.2 | | 66%* | | 87% | | | | 28 | | 70 |
| 31(b) | <0.1 | | 66% | | 97% | | | | 5.6 | | 2 |
| 41(o) | 0.05 | | 77% | | 74% | | | | 10 | | 94 |
| 31(c) | <0.1 | | 81% | | 98% | | | | 11.4 | | 87 |

TABLE 1-continued

| Ex # | FLVK** | FLVK-P** | Lck-P* | CHK-1* | FGF-P* | CDK2* | CDK4* | HUVEC IC50 (nM) | HUVEC + albumin IC50 (nM) | MV522 IC50 (μM) | % remain (HLM, 2 h) |
|---|---|---|---|---|---|---|---|---|---|---|---|
| 35(gg) | 23% | | | | | | | | >100 | | |
| 33(g) | 15% | | | | | | | | | | |
| 34 | 97% | | 78% | | 95% | | | | 15 | | 28 |
| 50 | | | | | | | | | | | |
| 35(v) | 72% | | 11% | | 59% | | | | 22 | | 26 |
| 35(w) | 59% | | | | | | | | 35 | | |
| 35(x) | 75% | | | | | | | | 2 | | 37 |
| 35(a) | 76% | | 12% | | 59% | | | | 2.1 | | 33 |
| 35(b) | 49% | | 12% | | 59% | | | | 35 | | |
| 35(c) | 76% | | 11% | | 42% | | | | 6.3 | | 17 |
| 41(p) | 0.06 | | 49% | 0 | 90 | 6% | 3% | 0.27 | 2.6 | >10 | 62 |
| 42(c) | 95% | | | | | | | | 1 to 3 | | |
| 41(dd) | 98% | | 50% | | 69% | | | | 5.8 | | 7 |
| 41(bb) | 99% | | 76% | | 88% | | | | 1 to 3 | | 110 |
| 35(y) | 99% | | 29% | | 82% | | | | 1 to 3 | | 7 |
| 35(d) | 76% | | | | | | | | >100 | | |
| 31(d) | 96% | | 52% | 0 | 14 | 5% | 9% | 1.3 | ca. 13 | 5.2 | 110 |
| 41(q) | 100% | | 53% | | 91% | | | | 2.7 | | |
| 35(e) | 99% | | 56% | | 69% | | | | 4.8 | >10 | 34 |
| 35(f) | 100% | | | | | | | | 8 | | 15 |
| 35(g) | 100% | | | | | | | | ca. 15 | | 53 |
| 35(h) | 100% | | | | | | | | 3.6 | | 9 |
| 35(i) | 100% | | | | | | | | 4.7 | | |
| 35(j) | 99% | | | | | | | | 1.5 | | 5 |
| 35(k) | 85% | | 6% | 0 | 34% | 8% | 7% | | 2.2 | >10 | 14 |
| 41(ee) | 0.13 | | 13% | 0 | 94% | 0 | 2% | 0.24 | 4.3, 2.7 | 9.4 | 47 |
| 35(z) | 95% | | | | | | | | 7.1 | | 2 |
| 35(aa) | 99% | | | | | | | | 5 | | 15 |
| 41(r) | 100% | | 55% | 0 | 92% | 0 | 5% | | 11 | | 83 |
| 41(cc) | 97% | | 41% | | 95% | | | | >100 | | |
| 35(l) | 90% | | | | | | | | 12 | | |
| 35(cc) | 89% | | 15% | 0 | 74% | 5% | 6% | 0.05 | 1.6 | | 31 |
| 35(ee) | 82% | | | | | | | | 3 | | 13 |
| 35(ff) | 0.11 | | 25% | | 75% | | | | 5.8 | | 31 |
| 35(dd) | 0.6 | | 17% | 0 | 75 | 7% | 8% | 0.18 | 2.9 | >10 | 26 |
| 35(bb) | 87% | | | | | | | | 4.1 | | 8 |
| 32(b) | 0.08 | | 70% | | 95% | | | | 21 | >10 | |
| 35(hh) | 100% | | 34% | | 73% | | | | 7 | | |
| 35(m) | 0.04 | | 61% | | 82% | | | | 35 | | |
| 48(a) | 0.37 | | 13% | 0 | 14 | 0 | 0 | | 8.8 | | 55 |
| 39(a) | 53% | | | | | | | 1.4 | ca. 50 | | 70 |
| 35(n) | 0.83 | | 58% | 23% | 92 | 4% | 10% | 0.11 | 11 | 5.1 | 47 |
| 41(s) | 0.23 | | 53% | | 86% | | | | | | |
| 35(o) | 39% | | 17% | | 44% | | | | >100 | | |
| 41(t) | 0.06 | | 51% | 0 | 85% | 1% | 2% | | 3.8 | | 87 |
| 32(c) | 0.27 | | 52% | | 96% | | | | >30 | | |
| 36(b) | 85% | | 22% | | 43% | | | | >30 | | |
| 37(d) | 26% | | 10% | | 38% | | | | >100 | | |
| 37(c) | 83% | | 12% | | 39% | | | | 12 | | 21 |
| 37(b) | 48% | | 8% | | 36% | | | | 30–100 | | |
| 59(a) | | | | | | | | | | | |
| 41(u) | 0.08 | | 54% | | 74% | | | | 7.9 | | |
| 41(hh) | 98% | | 13% | | 74% | | | | 3.9 | | 72 |
| 36(c) | 89% | | 28% | | 60% | | | | >30 | | |
| 36(a) | 87% | | 19% | | 38% | | | | 19 | | 58 |
| 35(p) | 62% | | 5% | | 11% | | | | >30 | | |
| 35(q) | 92% | | 42% | | 51% | | | | 18 | | |
| 40(b) | 89% | | 32% | | 92% | | | | | | |
| 41(ff) | 98% | | 15% | | 12 | | | | 5.6 | | 68 |
| 37(a) | 57% | | 6% | | 35% | | | | 15 | | 21 |
| 41(v) | 68%* | | 52% | | 68% | | | | 12 | | |
| 41(ii) | 57% | | 18% | | 11 | | | | 13 | | 85 |
| 35(r) | 0.11 | | 16% | | 20 | | | 0.36 | 2.3 | >10 | 51 |
| 35(s) | 60%* | | 18% | | 64% | | | | 4.6 | | 16 |
| 35(t) | 59%* | | 12% | | 63% | | | | 4 | | 7 |
| 41(ll) | 95% | | 14% | | 91% | | | | 23 | | |
| 41(w) | 97% | | 49% | | 67% | | | | ca. 10 | | |
| 41(x) | 98% | | 66% | | 3.4 | | | | 4.6 | | 100 |
| 41(mm) | 93% | | 6% | | 46% | | | 1.3 | 14.4 | | 94 |
| 41(jj) | 87% | | 19% | | 81% | | | | 21 | | |
| 41(y) | 98% | | 61% | | 86% | | | | 30– | | |

TABLE 1-continued

| Ex # | FLVK** | FLVK-P** | Lck-P* | CHK-1* | FGF-P* | CDK2* | CDK4* | HUVEC IC50 (nM) | HUVEC + albumin IC50 (nM) | MV522 IC50 (μM) | % remain (HLM, 2 h) |
|---|---|---|---|---|---|---|---|---|---|---|---|
| 31(e) | 0.02 | | 43% | | 62% | | | 100 | 6.2 | 8.6 | 49 |
| 40(c) | 24% | | 28% | | 59% | | | | | | |
| 41(gg) | 84% | | 27% | | 3.5 | | | | 9.5 | | 50 |
| 41(nn) | 57% | | 7% | | 91% | | | | >100 | | |
| 41(j) | 98% | | 16% | | 41% | | | | 7.7 | | |
| 48(b) | 97% | | 6% | | 77% | | | | ca. 8 | | |
| 41(z) | 100% | | 54% | | 74% | | | | 7.5 | | |
| 41(kk) | 100% | | 26% | | 97% | | | | 16 | | 63 |
| 39(b) | 2.8 | | 10% | | 50% | | | | >10 | | 67 |
| 31(f) | 97% | | 62% | | 99% | | | | >10 | | |
| 59(b) | | | | | | | | | | | |
| 49(a) | 0.04 | | 11% | | 79 | | | | ca. 4 | 8.4 | |
| 59(c) | | | | | | | | | | | |
| 49(b) | 98% | | 9% | | 80% | | | | ca. 10 | | |
| 56 | 5% | | | | | | | | | | |
| 35(ii) | 44% | | | | | | | | | | |
| 59(d) | | | | | | | | | | | |
| 57 | 100% | | 30% | | 89% | | | | | | |
| 59(e) | | | | | | | | | | | |
| 58 | 98% | | 19% | | 98% | | | | | | |

TABLE 2

| Ex # | CDK2* | CDK4* | CHK1* | FLVK-P* | Lck* | FGF* | HCT-116 IC50 (μM) |
|---|---|---|---|---|---|---|---|
| 24(a) | 0.017 | 0.0051 | 0.028 | 0.0983 | 67% | 72% | 0.23 |
| 24(b) | 0.021 | 0.0032 | 0.02 | 0.0331 | 96% | 88% | 0.37 |
| 24(c) | 0.0034 | 0.0015 | 0.044 | 0.0142 | 93% | 89% | 0.44 |
| 24(m) | 17% | 16% | NI @ 20 μM | | | | |
| 24(l) | 0.086 | 0.071 | 62% @ 20 μM | | | | 3.8 |
| 24(d) | 0.083 | 0.017 | 0.056 | 0.125 | 51% | 66% | 0.023 |
| 24(e) | 0.03 | 0.0044 | 75% | 52% | | | 0.15 |
| 24(f) | 0.0072 | 0.0074 | 97% | 89% | | | 1.5 |
| 24(g) | 0.13 | 0.029 | 1.67 | 0.194 | | | >5 |
| 24(o) | 0.029 | 0.2 | | | | | 2.2 |
| 24(h) | 0.054 | 0.053 | | | | | 3.6 |
| 24(i) | 0.055 | 0.013 | | | | | 1.7 |
| 24(j) | 2.1 | 0.32 | | | | | |
| 24(k) | 0.056 | 0.0072 | 81% | | 89% | 0.16 | 0.2 |
| 25(a) | 0.08 | 0.021 | 49% | | 44% | 62% | 0.051 |
| 24(n) | 0.035 | 0.019 | | | | | 1.5 |
| 25(b) | 0.112 | 0.048 | 83% | | 87% | 87% | 2.1 |
| 25(c) | 0.233 | 0.0155 | 90% | | | 96% | 0.25 |
| 25(d) | 0.16 | 0.098 | 87% | | 60% | 80% | |
| 25(e) | 0.477 | 0.181 | 16% | | 13% | 26% | |
| 25(f) | 0.39 | 1 | NI | | 58% | 56% | 0.098 |
| 25(g) | 0.08 | 0.021 | 21% | | 76% | 82% | 2 |
| 25(h) | 0.17 | 0.024 | 86% | | 87 | 91 | 0.32 |
| 25(l) | 0.021 | 0.02 | | | | | >5 |
| 24(p) | 0.089 | 0.092 | | | | | 0.44 |
| 25(j) | 0.079 | 0.016 | | | 70 | | 0.0083 |

*values represent Ki (μM) or % inhibition at a compound concentration of 1 μM, unless otherwise indicated.
NI indicates no significant inhibition

TABLE 3

| Example # | CHK-1* | CDK1* | CDK2* | CDK4* | FLVK* |
|---|---|---|---|---|---|
| 28(d) | 0.018 | 93% | 66% | 87% | |
| 27(j) | 15% @ 50 uM | | | | |
| 27(a) | 0.198 | NI @ 1 μM | NI @ 100 μM | 28% @ 5 μM | 71% |
| 27(b) | 28% @ 50 μM | | | | |
| 28(a) | 0.108 | 77% | 75% | 79% | 84% |
| 27(c) | 11% @ 5 μM | | | | |
| 28(b) | 0.0143 | | 97% | 98% | 96% |
| 27(d) | 14% @ 10 μM | | | | |
| 27(e) | 0.757 | | | | 34% |
| 27(l) | 0.227 | 85% | 73% | 92% | |
| 27(f) | 0.35 | 0.223 | 3.3 | 0.78 | 49% |
| 27(h) | 0.311 | 84% | | | |
| 27(k) | 24 | | | | |
| 28(c) | 1.14 | | | | 34% |
| 27(g) | 0.85 | | | | |
| 52(b) | 0.08 | 0.041 | 0.241 | 0.117 | 94% |
| 55 | 10 | | | | |
| 52(a) | 0.263 | 39% | | | 60% |
| 53(a) | 0.301 | 24 | 13% @ 5 μM | 28% @ 5 μM | |
| 29(b) | 0.138 | 0.9 | 3 | 3.9 | |
| 29(a) | NI @ 25 μM | | | | |
| 29(c) | 0.174 | 56% | 2.2 | 2 | |
| 29(d) | 10 | | | | |
| 29(e) | 0.074 | 0.593 | 1.4 | 2 | 33% |
| 29(f) | 0.418 | | | | |
| 51 | 0.087 | 0.146 | 84% | 79% | |
| 29(r) | 0.072 | 0.066 | 1.3 | 1.1 | |
| 29(g) | 0.068 | 0.39 | 1.4 | 1.1 | |
| 29(h) | 0.14 | 1.3 | 3 | 2.2 | |
| 54(d) | 0.68 | NI @ 1 μM | | | |
| 54(b) | 3.1 | | | | |
| 29(l) | 0.104 | 26% | 3.1 | 5 | |
| 53(d) | NI @ 100 μM | | | | |
| 54(e) | 0.342 | NI @ 1 μM | | | |
| 54(a) | 0.896 | 1% | | | |
| 53(c) | 1.1 | | | | |

TABLE 3-continued

| Example # | CHK-1* | CDK1* | CDK2* | CDK4* | FLVK* |
|---|---|---|---|---|---|
| 29(j) | 0.533 | 31% | | | |
| 29(q) | 11 | | | | 11% |
| 29(p) | 0.232 | 6% | | | |
| 53(b) | 1.4 | | | | |
| 29(k) | 1.3 | | | | |
| 54(f) | 2.9 | | | | |
| 54(c) | 0.125 | NI | | | |
| 54(g) | 0.195 | 3% | | | |
| 29(o) | 46 | | | | |
| 53(e) | 0.886 | 13% | | | |
| 29(l) | 1.4 | 7% | | | |
| 29(n) | 16 | | | | |
| 29(m) | 1 | 54% | | | |
| 53(f) | 7.3 | | | | |
| 54(h) | 1 | | | | |
| 29(s) | 11 | | | | |
| 54(j) | 0.424 | | | | |
| 54(i) | 0.461 | | | | |
| 29(t) | 0.072 | | | | |
| 29(u) | 0.151 | | | | |
| 53(g) | 1.5 | | | | |
| 54(l) | 0.99 | | | | |
| 54(k) | | | | | |

*values represent Ki ($\mu$M) or % inhibition at a compound concentration of 1 $\mu$M, unless otherwise indicated. NI indicates no significant inhibition Library Example I

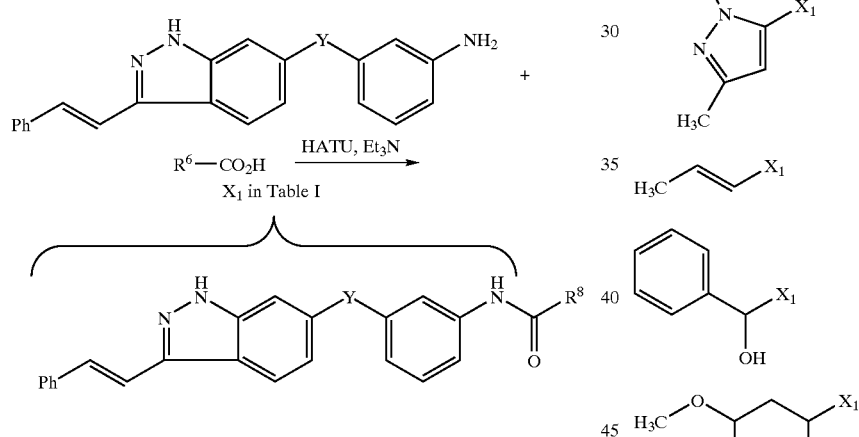

The three library building blocks ("amine templates") 6-(3-aminophenoxy)-3-E-styryl-1H-indazole (Y=O), 6-(3-aminobenzoyl)-3-E-styryl-1H-indazole (Y=CO), and 6-(3-aminophenyl)amino-3-E-styryl-1H-indazole (Y=NH) were prepared as described in Example 7, Example 18, and Example 46 respectively. 0.1 M solutions of the acid, the amine template, o-(7-azabenzotriazol-1-yl)-N,N,N',N'-tetra-methyluronium hexafluorophosphate and triethylamine were prepared separately in anhydrous DMF. To each tube in an array of 8×11 culture tubes (10×75 mm) was added 105 $\mu$L (0.0105 mmol) of a different acid. To this was added 100 $\mu$L (0.01 mmol) of the amine solution, 105 $\mu$L (0.0105 mmol) of the triethylamine solution followed by 105 $\mu$L (0.0105 mmol) of the o-(7-azabenzotriazol-1-yl)-N,N,N',N'-tetra-methyluronium hexafluorophosphate solution. The reactions were stirred in a heating block at 50° C. for 3 h. The reaction mixtures were transferred to a 1 mL 96-well plate using a liquid handler. The solvents were removed using the SpeedVac™ apparatus and the crude reaction mixtures were redissolved in DMSO to give a final theoretical concentration of 10 mM.

The compounds in the table were tested for inhibition of the proliferation of HUVEC at a nominal concentration of 10 nM, and the results are listed in Table I below, calculated from:

% inhibition=(control-treated)/(control-starvation)×100

Under these testing conditions, >50% inhibition is considered significant.

TABLE I

LIBRARY

| $R^8$ | Y = CO | Y = O | Y = NH |
|---|---|---|---|
| H₃C—CH=C(CH₃)—X₁ | 134 | 127 | 135 |
| 3-methylpyrazol-5-yl—X₁ | 124 | 145 | 118 |
| 1,3-dimethylpyrazol-5-yl—X₁ | 128 | 94 | 115 |
| H₃C—CH=CH—X₁ | 134 | 138 | 112 |
| Ph—CH(OH)—X₁ | 3 | 56 | 111 |
| 3-methoxycyclohexyl—X₁ | 30 | 91 | 109 |
| Ph—X₁ | 101 | 157 | 105 |
| 2H-pyran-2-one-5-yl—X₁ | −62 | 5 | 105 |
| 2-methylbenzyl—X₁ | 108 | 115 | 104 |
| H₂C=CH—CH₂—X₁ | 124 | 147 | 103 |

TABLE I-continued
LIBRARY
| R⁸ | Y = CO | Y = O | Y = NH |
|---|---|---|---|
| 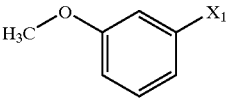 | 125 | 124 | 103 |
| 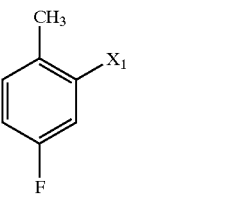 | 158 | 131 | 101 |
| 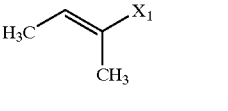 | 142 | 101 | 98 |
| 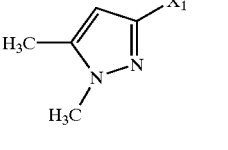 | 137 | 137 | 95 |
| 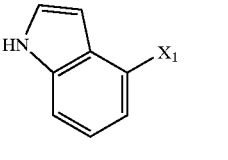 | 131 | 68 | 94 |
| 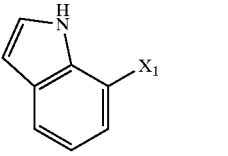 | 58 | 68 | 94 |
| 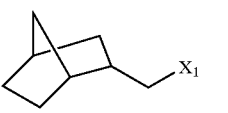 | 75 | 78 | 87 |
| 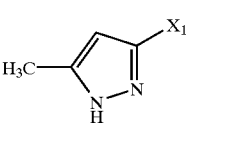 | 113 | 150 | 86 |
| 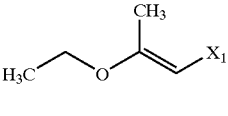 | 72 | 87 | 85 |
| 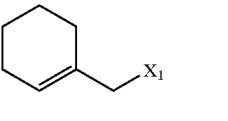 | 128 | 92 | 81 |
TABLE I-continued
LIBRARY
| R⁸ | Y = CO | Y = O | Y = NH |
|---|---|---|---|
| 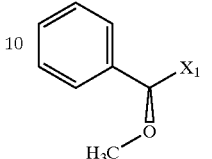 | 113 | 30 | 80 |
| 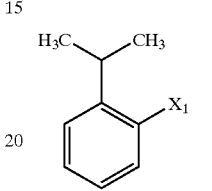 | 51 | 35 | 79 |
| 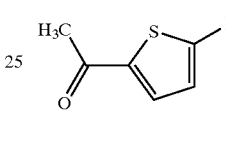 | 125 | 122 | 78 |
| 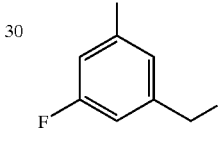 | 87 | 80 | 77 |
| 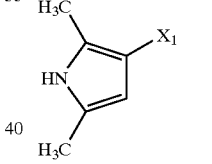 | 26 | 52 | 76 |
| 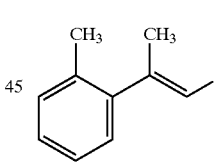 | 99 | 52 | 75 |
| 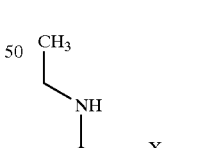 | 54 | 85 | 71 |
| 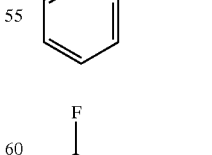 | 80 | 91 | 64 |

TABLE I-continued
LIBRARY
| R⁸ | Y = CO | Y = O | Y = NH |
|---|---|---|---|
| 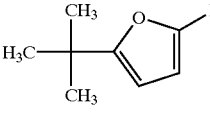 | 71 | 52 | 60 |
| 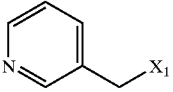 | 21 | 76 | 43 |
| 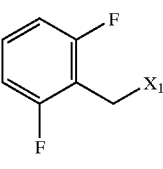 | 81 | 93 | 40 |
| 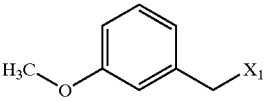 | 87 | 86 | 34 |
| 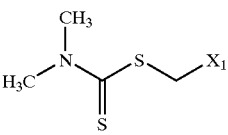 | 25 | 70 | 32 |
| 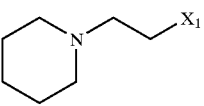 | 2 | 52 | 30 |
| 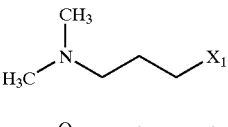 | 24 | 96 | 30 |
| 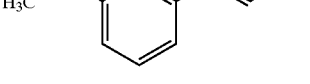 | 35 | 64 | 30 |
| 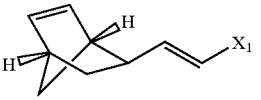 | 37 | 48 | 30 |
| 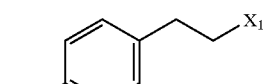 | 57 | 70 | 29 |
| 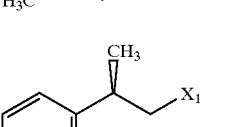 | 52 | 42 | 27 |
| 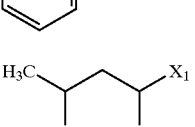 | 47 | 69 | 25 |
| 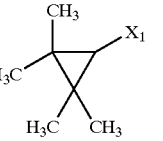 | 51 | 71 | 25 |
| 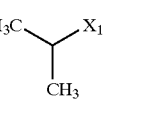 | 35 | 57 | 24 |
| 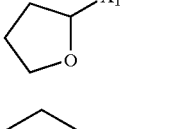 | 18 | 51 | 23 |
| 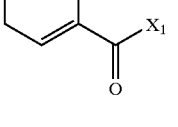 | 45 | 57 | 23 |
| 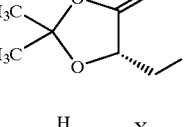 | 19 | 22 | 20 |
| 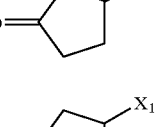 | 32 | 32 | 20 |
| 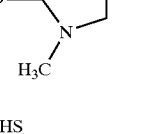 | 10 | 24 | 20 |
| 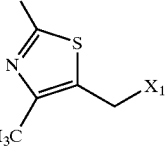 | 24 | 45 | 19 |
| 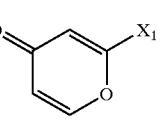 | −13 | 18 | 17 |
| 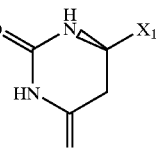 | −36 | −6 | 17 |

TABLE I-continued

LIBRARY

| R⁸ | Y = CO | Y = O | Y = NH |
|---|---|---|---|
| (dipropylamino-CH₂-X₁) | −2 | 25 | 17 |
| (2,2-dimethyl-3-(2-methylprop-1-enyl)cyclopropyl-X₁) | 3 | 24 | 16 |
| (5,5-dimethyl-2-oxotetrahydrofuran-4-yl-X₁) | 5 | 25 | 16 |
| (adamantyl-X₁) | −1 | 30 | 15 |
| (1-acetylpiperidin-4-yl-X₁) | 33 | 42 | 13 |
| (N-cyclopropylmethyl acrylamide-X₁) | 3 | 36 | 13 |
| (2,4-dioxotetrahydropyrimidin-6-yl-X₁) | 14 | 90 | 12 |
| (phenylacetyl-X₁) | −37 | 25 | 11 |
| (isovaleryl-X₁) | 81 | 64 | 11 |
| (2-methoxystyryl-X₁) | 47 | 17 | 10 |
| (3,3-dimethyl-2-hydroxybutyl-X₁) | 27 | 30 | 10 |
| (2,2,4,4-tetramethylcyclopentyl-X₁) | 5 | 23 | 7 |
| (2-oxoimidazolidin-4-yl-X₁) | 21 | 40 | 7 |
| (5-methylisoxazol-3-yl-X₁) | 50 | 112 | 6 |
| (2-methylcyclopropyl-X₁) | 96 | 134 | 6 |
| (bicyclo[2.2.2]octyl-X₁) | 42 | 13 | 6 |
| (3,4-dihydroxy-5-hydroxycyclohex-1-enyl-X₁) | −20 | 25 | 6 |
| (norbornenyl-X₁) | 44 | 82 | 5 |
| (3-methyl-2-hydroxybutyl-X₁) | 33 | 32 | 3 |

TABLE I-continued
LIBRARY
| R⁸ | Y = CO | Y = O | Y = NH |
|---|---|---|---|
| 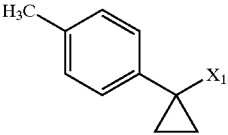 | 0 | 4 | 2 |
| 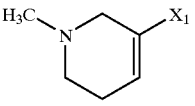 | 20 | 43 | 0 |
| 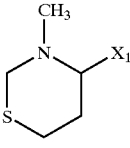 | 8 | 23 | 0 |
| 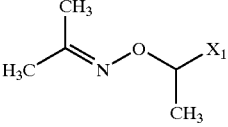 | 28 | 80 | −1 |
| 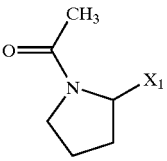 | 10 | 19 | −2 |
| 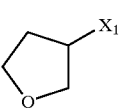 | 12 | 40 | −3 |
| 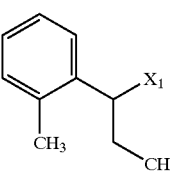 | 3 | 46 | −3 |
| 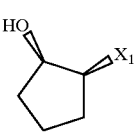 |  | 39 | −4 |
| 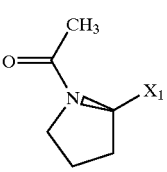 | 37 | 20 | −5 |
| 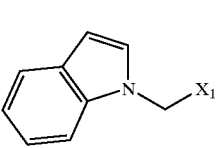 | −11 | 52 | −7 |
TABLE I-continued
LIBRARY
| R⁸ | Y = CO | Y = O | Y = NH |
|---|---|---|---|
| 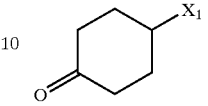 | 10 | 59 | −7 |
| 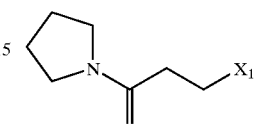 | 27 | 48 | −8 |
| 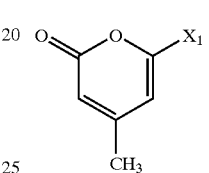 | 64 | 83 | −8 |
| 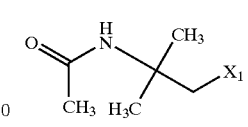 | 35 | 42 | −9 |
| 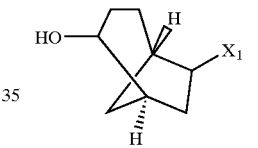 | 27 | 52 | −9 |
| 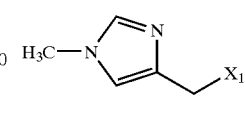 | 31 | 20 | −17 |
| 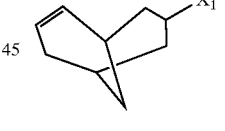 | 56 | 17 | −17 |
| 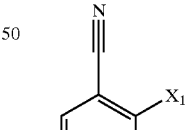 | −20 | 18 | −18 |
| 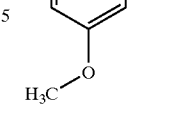 | 64 | 38 | −20 |

Library Example II
(a) When Y=S in Formula I

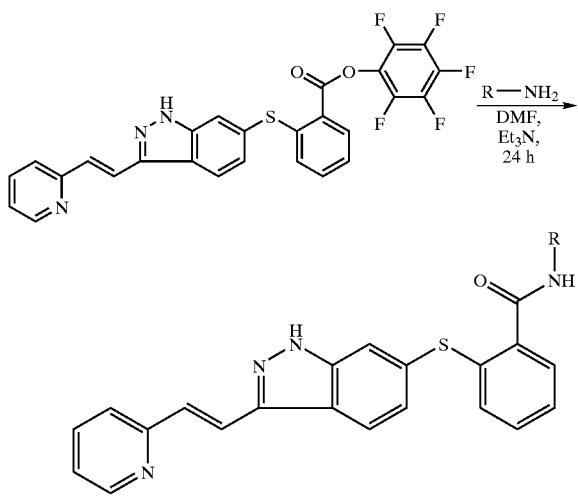

6-[2-(Pentafluorophenoxycarbonyl)phenylsulfanyl]-3-E-[2-(pyridin-2-yl)ethenyl]-1H-indazole (Y=S) was prepared as decribed in Example 35(a). Solutions of 261 amines (1.5 pmol), and Et$_3$N (0.1393 µL, 1.0 µmol), dissolved in DMF (15 µL), were distributed in to the wells of a 96-well plate. In cases where the amine was used as a hydrochloride salt, additional Et$_3$N (0.4179 µL, 3.0 µmol) was added to liberate the free base. Each of the wells was treated with a solution of pentafluorophenyl ester (0.5395 mg, 1.0 µmol) dissolved in DMF (30 µL), then agitated for 24 h at room temperature. The crude reaction mixtures were concentrated using a GeneVac™ apparatus, and then diluted with DMSO to a final concentration of 10 mM.

(b) When Y=NH in Formula I

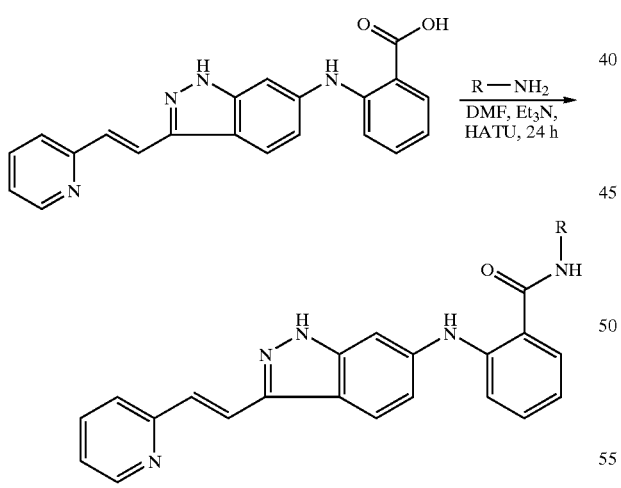

Solutions of 263 amines (2.0 µmol), and Et$_3$N (0.4181 µL, 3.0 µmol) were dissolved in DMF (20 µL) and distributed into the wells of a 96-well plate. In cases where the amine was used as a hydrochloride salt, additional Et$_3$N (0.5575 µL, 4.0 µmol) was added to liberate the free base. Each of the wells were treated with a solution of: 6-[2-carboxyphenyl-amino]-3-E-[2-(pyridin-2-yl)ethenyl]-1H-indazole (0.447 mg, 0.75 µmol) dissolved in DMF (20 µL), followed by a solution of HATU (0.570 mg, 1.5 µmol) dissolved in DMF (10 µL), and then agitated for 72 h at room temperature. The crude reaction mixtures were concentrated using a GeneVac™ apparatus, and then diluted with DMSO to a final concentration of 10 mM.

The compounds in the Library Table II were tested for inhibition of the proliferation of HUVEC at a nominal concentration of 0.5 and 2 nM for Y=S and the results are listed in below, as calculated from:

% inhibition=(control-treated)/(control-treated)/(control-starvation)×100

Under these testing conditions, >50% inhibition is considered significant

TABLE II

LIBRARY

| R$^1$ | 0.5 nM | 2 nM |
|---|---|---|
| ![structure] (phenyl-NH-CH2CH2-X1) | 19 | 89 |
| ![structure] (CH3-CH(OH)-CH2-X1) | 38 | 2 |
| ![structure] (dihydropyran-CH2-X1) | 37 | 16 |
| ![structure] (Et2N-CH2CH2-X1) | 39 | 15 |
| ![structure] (tetramethylpiperidine-NH-X1) | 35 | 10 |
| ![structure] (4-aminophenyl-CH2CH2-X1) | 32 | 31 |

TABLE II-continued

LIBRARY

| R¹ | 0.5 nM | 2 nM |
|---|---|---|
| morpholinopropyl (N-CH2CH2CH2-morpholine), X1 | 5 | 14 |
| isobutyl (H3C-CH(CH3)-CH2CH2-), X1 | 14 | 55 |
| tetrahydrofurfuryl (2-THF-CH2-), X1 | 23 | 44 |
| 2-oxopyrrolidin-1-yl propyl, X1 | 25 | 35 |
| (1-methylpyrrolidin-2-yl)ethyl, X1 | 30 | 23 |
| 3-piperidin-1-yl-propyl, X1 | 5 | 19 |
| benzyl (Ph-CH2-), X1 | 70 | 105 |
| 3-(2-methylpiperidin-1-yl)propyl, X1 | 25 | 15 |
| 4-benzylpiperidin-4-yl, X1 | 44 | 19 |
| 3-(dimethylamino)-2,2-dimethylpropyl, X1 | 38 | 5 |
| trans-4-hydroxycyclohexyl, X1 | 23 | 6 |
| 3-carboxypropyl (HOOC-CH2CH2-CH2-), X1 | 4 | 20 |
| 2-methoxyethyl (CH3-O-CH2CH2-), X1 | 21 | 60 |
| 2,2,2-trifluoroethyl (CF3-CH2-), X1 | 34 | 61 |
| 3-(imidazol-1-yl)propyl, X1 | 23 | 23 |

TABLE II-continued

LIBRARY

| R¹ | 0.5 nM | 2 nM |
|---|---|---|
| H₂N-SO₂-C₆H₄-CH₂CH₂-X₁ | 26 | 37 |
| H₃C-CH₂-N(CH₂CH₂CH₂CH₃)-CH₂CH₂-X₁ | 2 | 6 |
| (CH₃)₂N-C₆H₄-CH₂-X₁ | 32 | 24 |
| (HO)₂P(O)-CH₂-X₁ | 32 | 6 |
| HO-CH₂-CH(X₁)-CH₂-OH | 48 | 8 |
| H₂N-C₆H₄-CH₂-X₁ | 45 | 88 |
| HO-CH₂-C(X₁)(C(O)NH₂) | 17 | 4 |
| CH₃-X₁ | 8 | 21 |
| CH₃-C(O)-NH-CH₂CH₂-X₁ | 15 | 27 |

TABLE II-continued

LIBRARY

| R¹ | 0.5 nM | 2 nM |
|---|---|---|
| HO-CH₂-CH(X₁)-CH₂-(imidazole) | 22 | 24 |
| HO-CH₂-CH(X₁)-CH₂-CH₃ | 22 | 23 |
| HOOC-CH₂CH₂-CH₂-X₁ | 16 | 20 |
| HO-CH₂CH₂-O-CH₂CH₂-X₁ | 10 | 24 |
| morpholine-CH₂CH₂-X₁ | 28 | 22 |
| piperazine-CH₂CH₂-X₁ | 37 | 12 |
| pyridin-2-yl-CH₂CH₂-X₁ | 49 | 91 |
| pyrrolidine-CH₂CH₂-X₁ | 40 | 31 |

TABLE II-continued

LIBRARY

| R¹ | 0.5 nM | 2 nM |
|---|---|---|
| H₃C–O–CH₃ substituted propyl (CH₃CH(X₁)CH₂OCH₃) | 18 | 32 |
| 2-pyridylmethyl-X₁ | 6 | 43 |
| 3-pyridylmethyl-X₁ | 30 | 78 |
| 4-pyridylmethyl-X₁ | 34 | 58 |
| 2,3-dihydroxypropyl-X₁ | 22 | 20 |
| CH₃CH(X₁)CH₂OH | 19 | 28 |
| (CH₃)₂N-CH₂CH₂CH₂-X₁ | 6 | 1 |
| (CH₃)₂N-CH₂CH₂-X₁ | 20 | 10 |
| (CH₃)₂C(NH₂)CH₂-X₁ | 31 | 3 |

TABLE II-continued

LIBRARY

| R¹ | 0.5 nM | 2 nM |
|---|---|---|
| (H₃C-CH₂CH₂CH₂)₂N-CH₂CH₂CH₂-X₁ | 32 | 10 |
| (CH₃CH₂)₂N-CH₂CH₂CH₂-X₁ | 31 | −1 |
| H₂N-C(=O)-CH₂-X₁ | 6 | 4 |
| (CH₃)₂CH-CH₂-X₁ | 4 | 29 |
| 3-pyridyl-CH₂CH₂-X₁ | 23 | 61 |
| HO-CH₂CH₂-X₁ | 18 | 24 |
| H₂N-C(=O)-CH₂-CH(X₁)-C(=O)-NH₂ | 21 | 15 |
| CH₃-NH-C(=O)-CH₂-X₁ | −1 | 26 |

TABLE II-continued
| LIBRARY | | |
|---|---|---|
| R¹ | 0.5 nM | 2 nM |
| 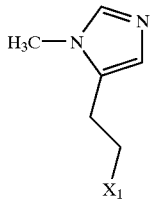 | −6 | 0 |
| 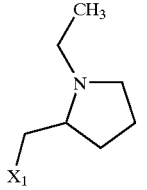 | 18 | 5 |
| 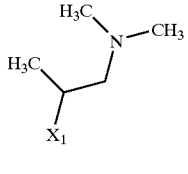 | 23 | 17 |
| 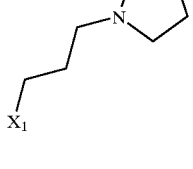 | 20 | 2 |
| 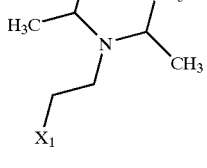 | 37 | 15 |
| 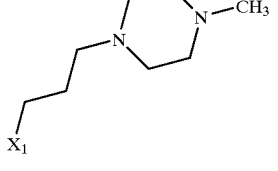 | 0 | 4 |
| 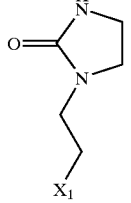 | 5 | 1 |
TABLE II-continued
| LIBRARY | | |
|---|---|---|
| R¹ | 0.5 nM | 2 nM |
| 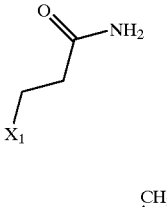 | 8 | 18 |
| 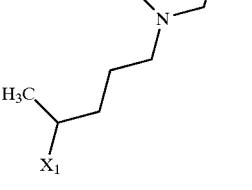 | 3 | 15 |
| 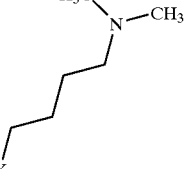 | 23 | 16 |
| 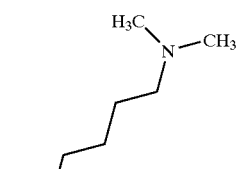 | 42 | 22 |
| 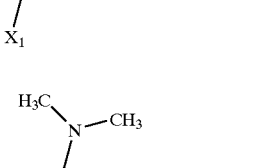 | −9 | 1 |
| 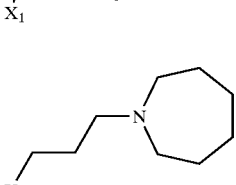 | 25 | −5 |
| 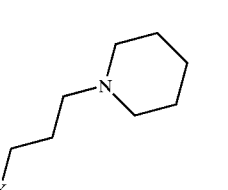 | 16 | 7 |

TABLE II-continued

LIBRARY

| R¹ | 0.5 nM | 2 nM |
|---|---|---|
| (3-oxothiolane-1,1-dioxide)-X₁ | 27 | 2 |
| HOOC-CH₂-NH-C(O)-CH₂-CH₂-X₁ | 49 | −9 |
| N≡C-CH₂-X₁ | 18 | 40 |
| (HO)(HO-N=)C-CH₂-X₁ | 5 | 9 |
| HOOC-CH₂-X₁ | 8 | 23 |
| HO-S(=O)₂-CH₂-CH₂-X₁ | 16 | 21 |
| CH₃-CH₂-CH(OH)-CH₂-X₁ | 13 | 23 |
| HO-CH₂-C(CH₃)₂-CH₂-X₁ | 8 | 22 |
| 1,2-diethyl-4-pyrazolidinyl-X₁ | 2 | −19 |
| 3-(N-ethyl-N-(3-methylphenyl)amino)ethyl-X₁ | 17 | 1 |
| H₂N-C(=NH)-CH₂-X₁ | 7 | −1 |
| (CH₃)₃C-CH₂-X₁ | 5 | −6 |
| 1-(hydroxymethyl)cyclohexyl-X₁ | 26 | −19 |
| 4-(2-imidazolyl)ethyl-X₁ (histamine-like) | 23 | −32 |
| HO-S(=O)₂-CH₂-X₁ | 2 | −3 |
| 3-(N-methyl-N-phenylamino)propyl-X₁ | 18 | 25 |

TABLE II-continued
LIBRARY
| R¹ | 0.5 nM | 2 nM |
|---|---|---|
| 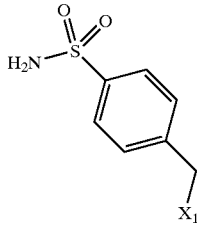 | 1 | 13 |
| 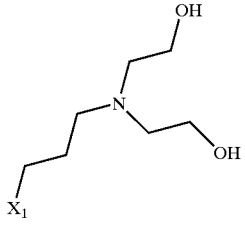 | 4 | 4 |
| 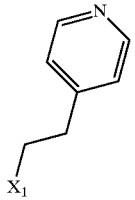 | 18 | 22 |
| H-X₁ | 9 | 30 |
|  | 7 | 25 |
| 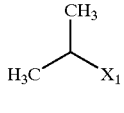 | 16 | 17 |
| 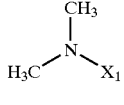 | 13 | 31 |
| 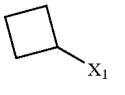 | 95 | 106 |
| 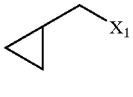 | 59 | 97 |
| 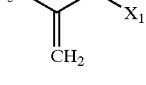 | 30 | 86 |
| 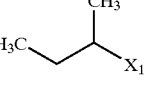 | 22 | 43 |
| 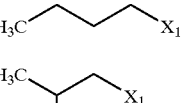 | 33 | 64 |
| 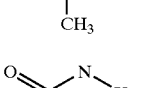 | 28 | 29 |
| 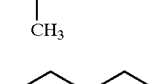 | 31 | 20 |
| 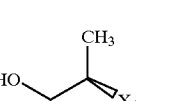 | 42 | 80 |
| 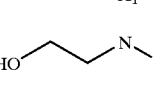 | 25 | 53 |
| 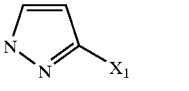 | 65 | 110 |
| 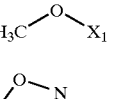 | 29 | 58 |
| 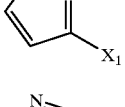 | 52 | 107 |
| 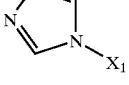 | 31 | 36 |
| 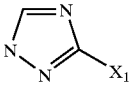 | 4 | 10 |
| 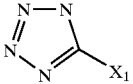 | 8 | 23 |
|  | 13 | 20 |
| HO⌒⌒N⌒X₁ | 33 | 18 |
| pyrazole-X₁ | 20 | 25 |
| H₃C—O—X₁ | 62 | 99 |
| isoxazole-X₁ | 6 | 16 |
| 1,2,4-triazole-X₁ | 17 | 13 |
| 1,2,4-triazole-X₁ | 19 | 22 |
| tetrazole-X₁ | 39 | 18 |

TABLE II-continued

LIBRARY

| R¹ | 0.5 nM | 2 nM |
|---|---|---|
| N≡C-CH₂CH₂-N(H)-X₁ | 44 | 5 |
| cyclopentyl-X₁ | 43 | 96 |
| (CH₃)₂CH-CH(CH₃)-X₁ | 19 | 55 |
| CH₃CH₂CH₂-CH(CH₃)-X₁ | 29 | 92 |
| H₃C-(CH₂)₄-X₁ | 49 | 109 |
| H₃C-CH₂-CH(CH₂CH₃)-X₁ | 25 | 14 |
| H₃C-CH₂-CH(CH₃)-CH₂-X₁ | 24 | 84 |
| (H₃C)₃C-CH₂-X₁ | 19 | 24 |
| (CH₃)₂CH-CH₂CH₂-X₁ | 47 | 107 |
| HO-(CH₂)₄-X₁ | 35 | 40 |
| H₃C-O-CH₂CH₂CH₂-X₁ | 26 | 31 |
| H₃C-CH₂-O-CH₂CH₂-X₁ | 53 | 75 |
| H₃C-O-C(=O)-N(H)-X₁ | 8 | 21 |
| 2-furyl-CH₂-X₁ | 70 | 112 |
| H₃C-CH₂-O-X₁ | 72 | 109 |

TABLE II-continued

LIBRARY

| R¹ | 0.5 nM | 2 nM |
|---|---|---|
| 3-methylisoxazol-5-yl-X₁ | 26 | 31 |
| 5-methylisoxazol-3-yl-X₁ | 28 | 14 |
| 3-amino-1,2,4-triazol-5-yl-X₁ | −6 | 41 |
| cyclohexyl-X₁ | 12 | 76 |
| thiazol-2-yl-X₁ | 33 | 94 |
| piperidin-1-yl-X₁ | 27 | 17 |
| 1,3,4-thiadiazol-2-yl-X₁ | 44 | 28 |
| (CH₃)₂CH-CH₂-CH(CH₃)-X₁ | 55 | 50 |
| H₃C-(CH₂)₅-X₁ | 21 | 90 |
| morpholin-4-yl-X₁ | 12 | 53 |
| tetrazol-5-yl-X₁ | 21 | 64 |
| 1,3-dioxolan-2-yl-CH₂-X₁ | 35 | 63 |
| (CH₃)₂CH-CH(CH₃)-CH(OH)-X₁ | 21 | −5 |

TABLE II-continued
LIBRARY
| R¹ | 0.5 nM | 2 nM |
|---|---|---|
| 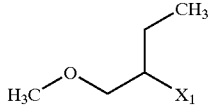 | 1 | 65 |
| 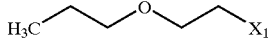 | 28 | 103 |
| 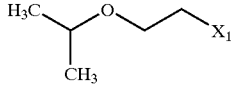 | 51 | 105 |
| 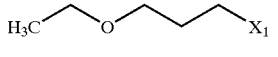 | 44 | 97 |
| 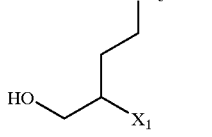 | 44 | 40 |
| 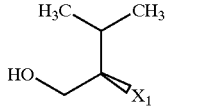 | 47 | −4 |
| 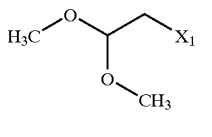 | 47 | 89 |
| 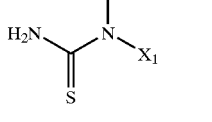 | 12 | 29 |
| 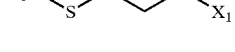 | 44 | 100 |
|  | 35 | 69 |
| 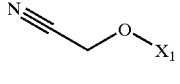 | 16 | 2 |
| 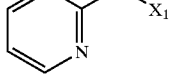 | 32 | 92 |
| 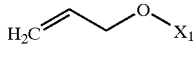 | 92 | 103 |
| 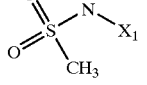 | 9 | 1 |
TABLE II-continued
LIBRARY
| R¹ | 0.5 nM | 2 nM |
|---|---|---|
| 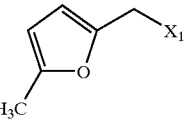 | 56 | 96 |
| 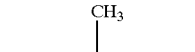 | 26 | 2 |
| 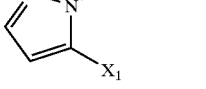 | 39 | 13 |
| 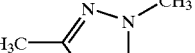 | 19 | 5 |
| 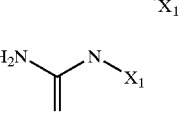 | 24 | 31 |
| 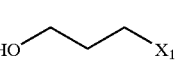 | 35 | 106 |
| 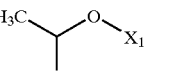 | 15 | 36 |
| 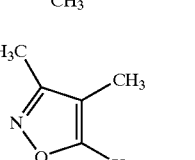 | 69 | 59 |
|  | −11 | 42 |
|  | 16 | 42 |
| 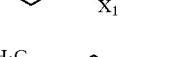 | 15 | 95 |
| 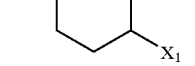 | 20 | 92 |

TABLE II-continued

LIBRARY

| R¹ | 0.5 nM | 2 nM |
|---|---|---|
| H₃C-N(piperazine)-N-X₁ (N-methylpiperazine) | 19 | −1 |
| branched heptyl (CH₃, H₃C-ethyl)-X₁ | 31 | 30 |
| 6-methylheptyl-X₁ | −1 | 14 |
| H₃C-(CH₂)₇-X₁ | 9 | 34 |
| H₃C-CH(CH₃)-CH₂-CH(CH₃)-X₁ branched | 6 | 44 |
| 4-heptyl-X₁ (H₃C-propyl, propyl) | 1 | 52 |
| 2,4-dimethyl-3-pentyl-X₁ | 18 | −2 |
| 4-oxo-4,5-dihydrothiazol-2-yl-X₁ | 9 | −9 |
| H₃C-(CH₂)₃-C(O)-NH-X₁ | 40 | 94 |
| 1,3-dioxolan-2-yl-CH₂CH₂-X₁ | 38 | 68 |
| 2-oxotetrahydrothiophen-3-yl-X₁ | 25 | 40 |

TABLE II-continued

LIBRARY

| R¹ | 0.5 nM | 2 nM |
|---|---|---|
| (CH₃)₂CH-O-CH₂CH₂CH₂-X₁ | 34 | 99 |
| 1-phenylethyl-X₁ | 30 | 94 |
| 2-methylbenzyl-X₁ | 24 | 99 |
| 3-methylbenzyl-X₁ | 19 | 101 |
| 4-methylbenzyl-X₁ | 20 | 92 |
| phenethyl-X₁ | 15 | 99 |
| N-methyl-N-phenyl-X₁ | 16 | 37 |
| pyrrolidin-1-yl-X₁ | 17 | 23 |
| PhCH₂-O-X₁ | 70 | 111 |
| pyrrol-2-yl-C(O)-NH-X₁ | 60 | 99 |
| 2-fluorobenzyl-X₁ | 75 | 114 |

TABLE II-continued
LIBRARY
| R¹ | 0.5 nM | 2 nM |
|---|---|---|
| 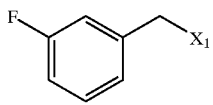 | 81 | 95 |
| 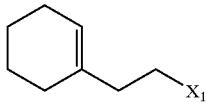 | 24 | 86 |
| 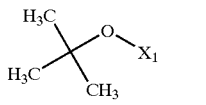 | −3 | 64 |
| 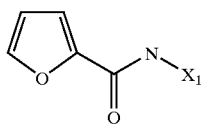 | 26 | 71 |
| 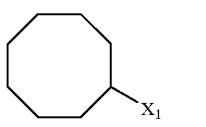 | 14 | 60 |
| 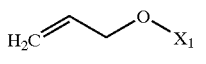 | 51 | 108 |
| 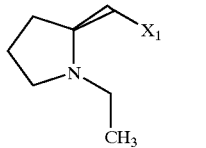 | 8 | 37 |
| 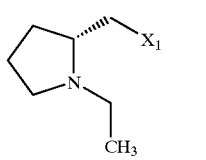 | 15 | 23 |
| 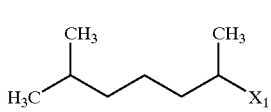 | 20 | 32 |
| 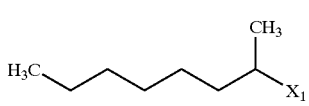 | 35 | 63 |
| 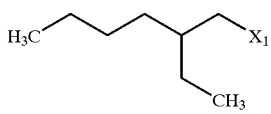 | 28 | 47 |
| 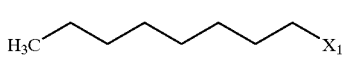 | 26 | 16 |
| 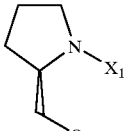 | 18 | 11 |
| 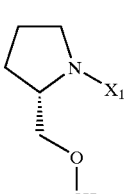 | 13 | 7 |
| 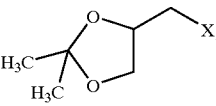 | 28 | 69 |
| 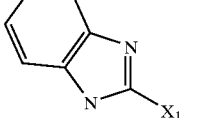 | 18 | 43 |
| 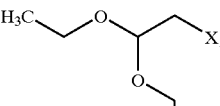 | 11 | 47 |
| 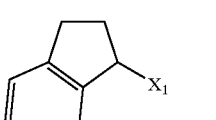 | 19 | 86 |
| 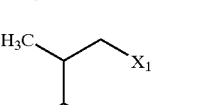 | 26 | 83 |
| 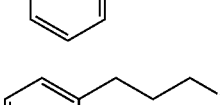 | 50 | 111 |
| 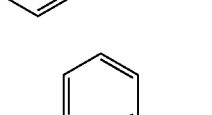 | 45 | 103 |
| 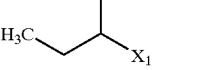 | | |

TABLE II-continued
LIBRARY
| R¹ | 0.5 nM | 2 nM |
|---|---|---|
| 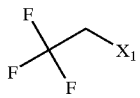 | 53 | 95 |
| 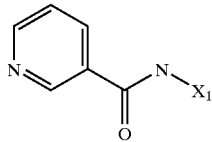 | 31 | 108 |
| 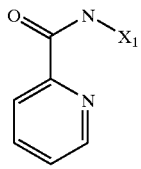 | 69 | 104 |
| 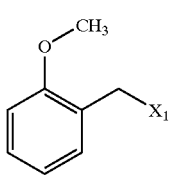 | 36 | 106 |
| 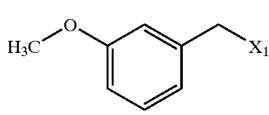 | 58 | 100 |
| 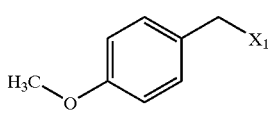 | 63 | 104 |
| 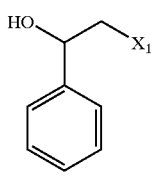 | 12 | 55 |
| 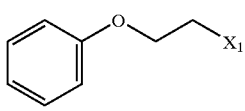 | 16 | 73 |
| 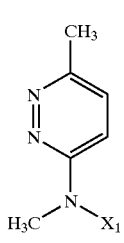 | 18 | −3 |
| 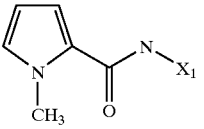 | 16 | 17 |
| 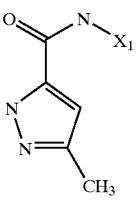 | 32 | 35 |
| 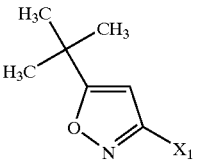 | 36 | 66 |
| 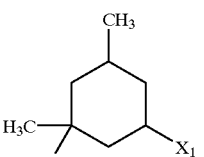 | 68 | 49 |
| 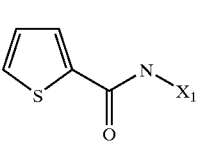 | 26 | 39 |
| 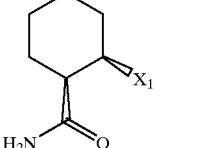 | 15 | 4 |
| 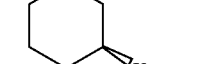 | 25 | 31 |
| 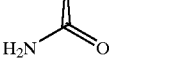 | 65 | 90 |
| 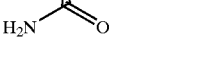 | 21 | 39 |

TABLE II-continued
LIBRARY
| R¹ | 0.5 nM | 2 nM |
|---|---|---|
| 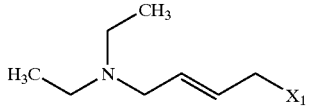 | 10 | 29 |
| 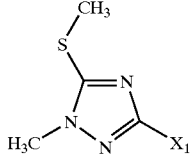 | 16 | 2 |
| 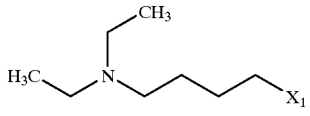 | 22 | 36 |
| 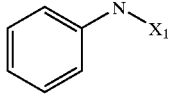 | 18 | 29 |
| 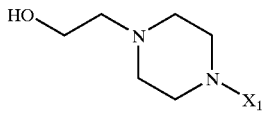 | 25 | 25 |
| 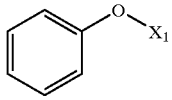 | 27 | 80 |
| 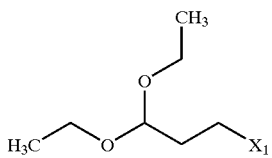 | 30 | 70 |
| 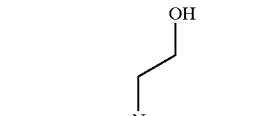 | 10 | 23 |
| 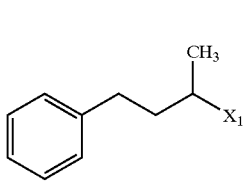 | 50 | 40 |
| 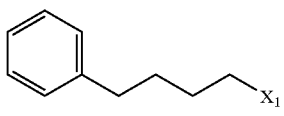 | 51 | 67 |
TABLE II-continued
LIBRARY
| R¹ | 0.5 nM | 2 nM |
|---|---|---|
| 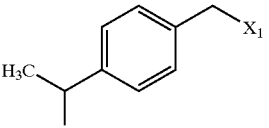 | 23 | 51 |
| 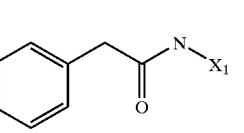 | 31 | 66 |
| 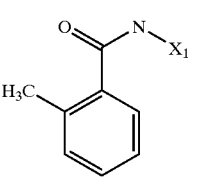 | 86 | 107 |
| 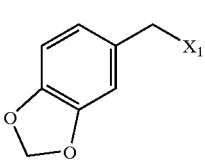 | 46 | 103 |
| 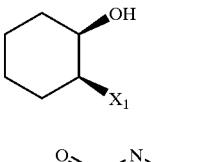 | 26 | 59 |
| 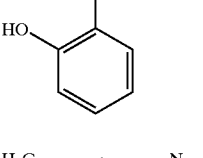 | 30 | 61 |
| 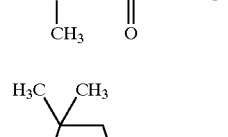 | 41 | 16 |
| 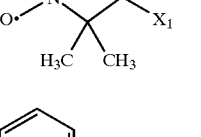 | 15 | 8 |
| 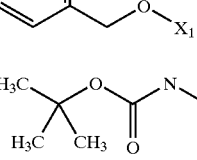 | 74 | 101 |
|  | 78 | 60 |

TABLE II-continued

LIBRARY

| R¹ | 0.5 nM | 2 nM |
|---|---|---|
| (cyclohexenyl-CH(X₁)-CH₂OH) | 58 | 37 |
| (triazolyl-C(CH₃)₂-C(O)-NH-X₁) | 34 | 90 |
| (dihydroimidazolyl-N-X₁) | 34 | 69 |
| (pyridin-2-yl-NH-X₁) | 19 | 35 |
| (morpholinyl-C(O)-CH₂-O-X₁) | 15 | −1 |
| (Ph₂CH-CH₂-X₁) | 11 | 15 |
| (azabicyclic-X₁) | 15 | −9 |
| (azaspiro-X₁) | 12 | |
| ((CH₃)₃N⁺-X₁) | 8 | |
| (CH₃-piperazinyl-X₁) | 38 | |
| (pyridinium-X₁) | 48 | |

Library Example III

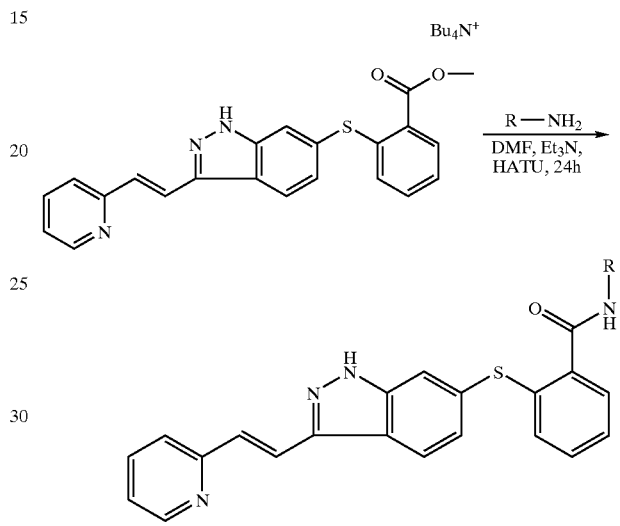

0.1 M solutions of the amines, triethylamine and 4-dimethylaminopyridine were prepared separately in anhydrous DMF and transferred to a glovebox. 0.1 M solution of 6-[2-carboxy)phenylsulfanyl]-3-E-[2-(pyridin-2-yl)ethenyl]-1H-indazole, Example 33(g), tetrabutylammonium salt and o-(7-azabenzotriazol-1-yl)-N,N,N',N'-tetramethyluronium hexafluorophosphate was prepared in the glovebox. To each tube in an array of 8×11 culture tubes (10×75 mm) in the golvebox was added 100 μL (0.01 mmol) of the different amine solutions followed by the addition of 100 μL (0.01 mmol) tetrabutylammonium2-{3-[(E)-2-(2-pyridinyl)ethyly]-1H-indazol-6-yl}sulfanyl)benzoate solution, 100 μL (0.01 mmol) of the triethylamine solution, 100 μL (0.01 mmol) of the 4-dimethylaminopyridine solution and 100 μL (0.01 mmol) of the o-(7-azabenzotriazol-1-yl)-N,N,N',N'-tetra-methyluronium hexafluorophosphate solution. The reactions were stirred in a heating block at 50° C. for 1 h. The reaction mixtures were transferred to a 1 mL 96-well plate using a liquid handler. The solvents were removed using the SpeedVac™ apparatus and the crude reaction mixtures were redissolved in DMSO to give a final theoretical concentration of 10 mM.

The compounds in the table were tested for inhibition of the proliferation of HUVEC at a nominal concentration of 0.5 nM, and the results are listed in Table m below, as calculated from:

% inhibition=(control-treated)/(control-starvation)×100

Under these testing conditions, >30% inhibition is considered significant.

TABLE III
| LIBRARY | |
|---|---|
| R | % inhibition |
| 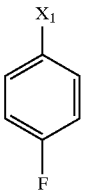 | −1 |
| 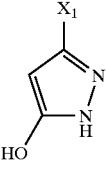 | −17 |
| 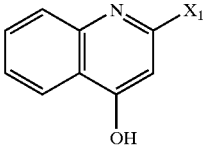 | 4 |
| 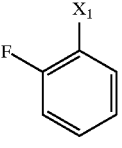 | 17 |
| 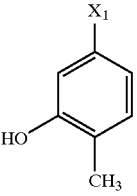 | 6 |
| 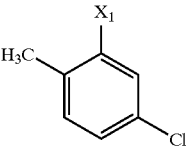 | 22 |
| 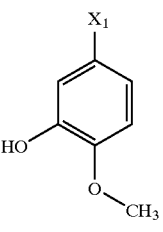 | −19 |
| 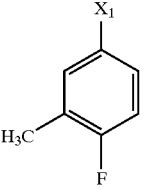 | 9 |
TABLE III-continued
| LIBRARY | |
|---|---|
| R | % inhibition |
| 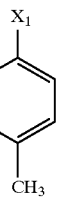 | 2 |
| 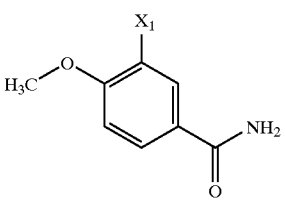 | 5 |
| 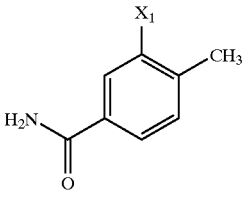 | 15 |
| 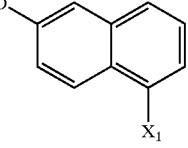 | −22 |
| 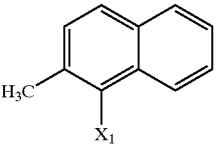 | −19 |
| 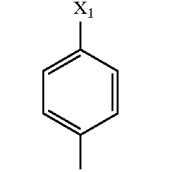 | −9 |
| 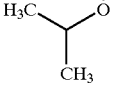 | −11 |

TABLE III-continued

LIBRARY

| R | % inhibition |
|---|---|
| 1,2,3,4-tetrahydronaphthalen-1-yl (X₁) | −17 |
| 2,3-dihydro-1H-inden-5-yl (X₁) | −6 |
| ethyl 1H-pyrazole-4-carboxylate, 3-yl (X₁) | −11 |
| 2-fluoro-5-methylphenyl (X₁) | −1 |
| 2-methyl-4-fluorophenyl (X₁) | 12 |
| 2-methyl-3-chlorophenyl (X₁) | 9 |
| 3-(ethoxycarbonyl)phenyl (X₁) | 7 |
| 3-(1-hydroxyethyl)phenyl (X₁) | −32 |
| 2-methyl-4-fluorophenyl (X₁) | −22 |
| 4-methylphenyl (X₁) | −15 |
| 4-butylphenyl (X₁) | −22 |
| 3,5-dimethylphenyl (X₁) | −4 |
| 4-methoxyphenyl (X₁) | 4 |
| 3-(acetamido)phenyl (X₁) | −29 |
| 7-hydroxynaphthalen-8-yl (X₁) | −6 |

TABLE III-continued
LIBRARY
| R | % inhibition |
|---|---|
| 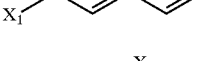 | −8 |
| 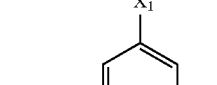 | 8 |
| 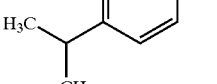 | 1 |
| 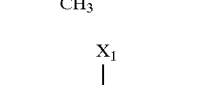 | −38 |
| 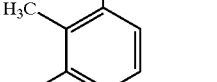 | −36 |
| 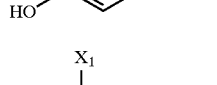 | −11 |
| 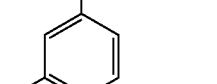 | −14 |
| 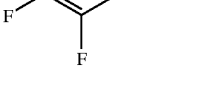 | −20 |
TABLE III-continued
LIBRARY
| R | % inhibition |
|---|---|
| 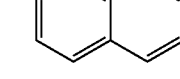 | −5 |
| 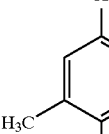 | −43 |
| 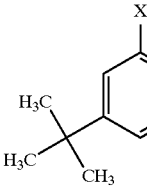 | −5 |
| 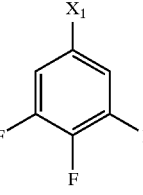 | 0 |
| 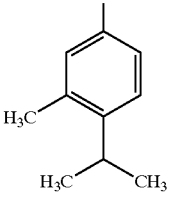 | 6 |
| 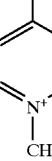 | 0 |
| 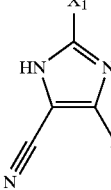 | −28 |

TABLE III-continued

LIBRARY

| R | % inhibition |
|---|---|
| (cyanoimidazole with X₁) | −13 |
| (tert-butyl pyrazole with X₁) | −21 |
| (hydroxyamidino imidazole with X₁) | −15 |
| (2,6-dichloropyridine with X₁) | 0 |
| (nitroso dihydroxypyrimidine with X₁) | −18 |
| (nitro thiazole with X₁) | −15 |
| (benzodioxane with X₁) | −1 |
| (3-fluorophenyl with X₁) | −11 |
| (quinoline with X₁) | 3 |
| (isopropoxyphenyl with X₁) | 1 |
| (methylthio thiadiazole with X₁) | −27 |
| (N-methyl cyclopropyl pyrazole with X₁) | −47 |
| (8-hydroxyquinoline with X₁) | 33 |
| (chloropyrazine with X₁) | 17 |
| (trifluoromethyl pyridine with X₁) | 20 |
| (chloro thiadiazole with X₁) | −29 |

TABLE III-continued

LIBRARY

| R | % inhibition |
|---|---|
| 2,6-diethylphenyl (X₁) | −17 |
| 2,6-diisopropylphenyl (X₁) | −7 |
| 5-methyl-1H-1,2,4-triazol-3-yl (X₁) | 0 |
| methyl 5-(X₁)furan-2-carboxylate | −1 |
| 1H-pyrazolo[3,4-d]pyrimidin-4-yl (X₁) | 4 |
| 6-hydroxy-1H-pyrazolo[3,4-d]pyrimidin-4-yl (X₁) | −43 |
| 3-propylphenyl (X₁) | −42 |

TABLE III-continued

LIBRARY

| R | % inhibition |
|---|---|
| 4-propylphenyl (X₁) | 22 |
| 4-pentylphenyl (X₁) | 13 |
| 4-(sec-butyl)phenyl (X₁) | 81 |
| 3-(1,3,4-oxadiazol-2-yl)phenyl (X₁) | −23 |
| 2,6-difluorophenyl (X₁) | −31 |
| 3-(1H-pyrazol-3-yl)phenyl (X₁) | −3 |

TABLE III-continued
LIBRARY
| R | % inhibition |
|---|---|
| 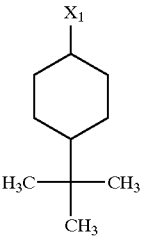 | 0 |
| 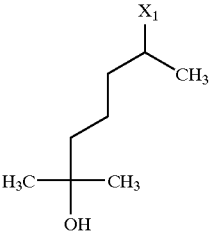 | 3 |
| 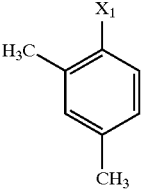 | 13 |
| 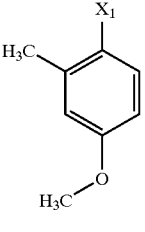 | 0 |
| 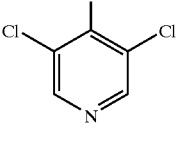 | −113 |
| 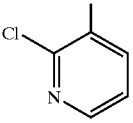 | 2 |
| 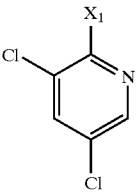 | 4 |
TABLE III-continued
LIBRARY
| R | % inhibition |
|---|---|
| 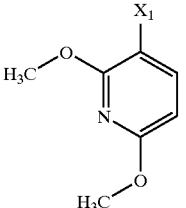 | 20 |
| 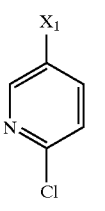 | 2 |
| 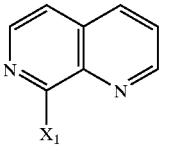 | −3 |
| 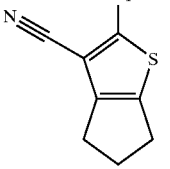 | −9 |
| 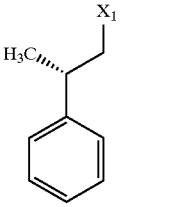 | −9 |
| 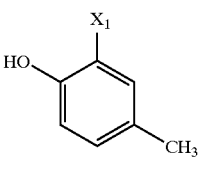 | −1 |
| 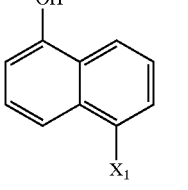 | 4 |

TABLE III-continued

| LIBRARY | |
|---|---|
| R | % inhibition |
| 2-methyl-4-hydroxyphenyl (X₁ on phenyl, H₃C ortho, OH para) | 12 |
| 4,4-dimethoxybutyl (X₁–CH₂CH₂CH₂–CH(OCH₃)₂) | 9 |
| 4-methylpyridin-2-yl (X₁ at 2, CH₃ at 4) | −6 |
| 5-carbamoylpyridin-2-yl (X₁ at 2, C(O)NH₂ at 5) | −2 |
| 3-acetylphenyl (X₁ meta to C(O)CH₃) | 5 |
| 4-acetylphenyl (X₁ para to C(O)CH₃) | 6 |
| quinolin-2-yl (X₁ at 2) | 18 |
| 4-ethylpyridin-2-yl (X₁ at 2, CH₂CH₃ at 4) | 20 |
| 3-ethyl-6-methylpyridin-2-yl | −23 |
| 6-ethylpyridin-2-yl | −12 |
| (S)-2-hydroxypropyl (X₁–CH₂–CH(OH)–CH₃) | 22 |
| 3-fluoro-4-methoxyphenyl | 9 |
| methyl 3-(X₁)pyrazine-2-carboxylate | 7 |
| ethyl 2-(X₁)benzoate | −4 |
| 2,3-dimethyl-4-hydroxyphenyl | 4 |

TABLE III-continued
LIBRARY
| R | % inhibition |
|---|---|
| 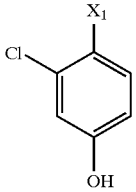 | 7 |
| 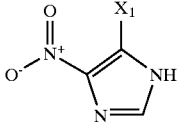 | 7 |
| 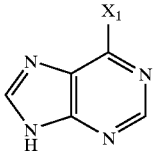 | 18 |
| 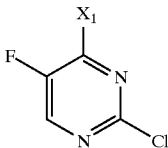 | 11 |
| 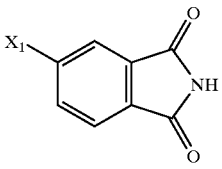 | −31 |
| 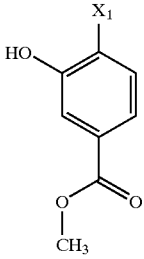 | −22 |
| 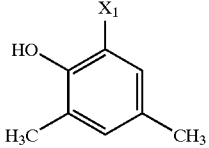 | −5 |
| 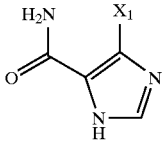 | −1 |
TABLE III-continued
LIBRARY
| R | % inhibition |
|---|---|
| 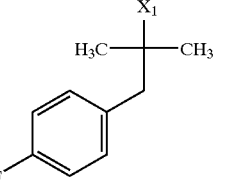 | −7 |
| 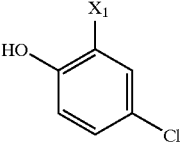 | −22 |
| 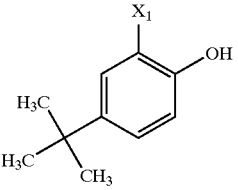 | −3 |
| 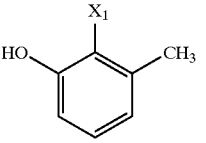 | 11 |
| 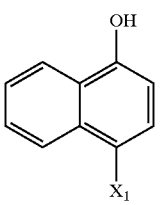 | 4 |
| 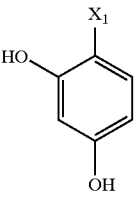 | 20 |
| 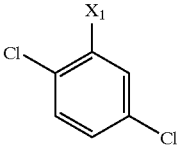 | 15 |
| 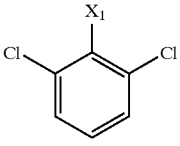 | −45 |

TABLE III-continued

LIBRARY

| R | % inhibition |
|---|---|
| (isopropyl, methyl phenyl with X₁) | −37 |
| (2,6-dimethyl phenyl with X₁) | −20 |
| (2-ethyl-6-methyl phenyl with X₁) | −4 |
| (tert-octyl with X₁) | 0 |
| (tert-amyl with X₁) | −29 |
| (2-chloro-4,6-dimethyl phenyl with X₁) | −26 |
| (adamantyl with X₁) | 3 |
| (2-methoxy-6-methyl phenyl with X₁) | 8 |
| (2-chloro-6-fluoro phenyl with X₁) | 12 |
| (tert-butyl 2-methyl-2-propanoate with X₁) | 6 |
| (2,6-dimethoxy phenyl with X₁) | −57 |
| (cumyl with X₁) | −25 |
| (2-isopropenyl phenyl with X₁) | −41 |
| (1-methyl benzimidazol-2-yl with X₁) | −21 |
| (5-tert-butyl-1,3,4-thiadiazol-2-yl with X₁) | −28 |
| (5-methyl-1,3,4-thiadiazol-2-yl with X₁) | −20 |

TABLE III-continued
LIBRARY
| R | % inhibition |
|---|---|
| 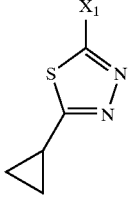 | −20 |
| 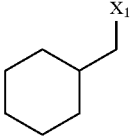 | 3 |
| 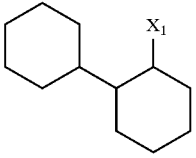 | 11 |
| 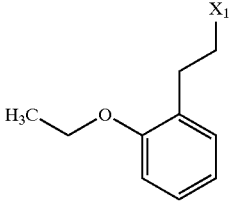 | 1 |
| 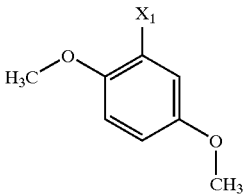 | −5 |
| 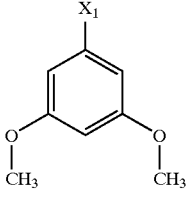 | −60 |
| 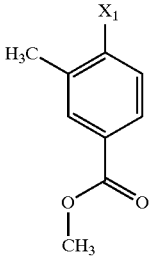 | −46 |
TABLE III-continued
LIBRARY
| R | % inhibition |
|---|---|
| 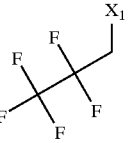 | −22 |
| 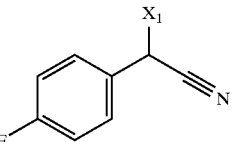 | −20 |
| 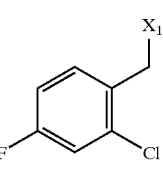 | −7 |
| 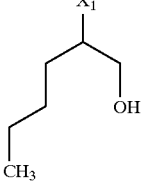 | −28 |
| 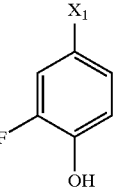 | −10 |
| 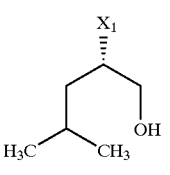 | −13 |
| 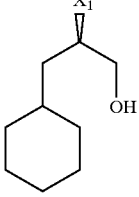 | 13 |
| 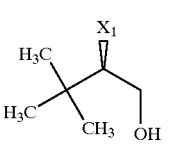 | −7 |

TABLE III-continued

LIBRARY

| R | % inhibition |
|---|---|
| 3-phenylphenyl (biphenyl) with X₁ | −13 |
| CH₃-S-CH₂CH₂-CH(X₁)-CH₂OH | −45 |
| H₃C-CH₂-C(=CH₂... )(X₁)-CH₂OH (with ethyl and methylene branches) | −40 |
| (CH₃)₂CH-CH₂-C(=X₁)-CH₂OH | −2 |
| CH₃CH₂-O-CH(OCH₂CH₃)-CH₂CH₂CH₂-X₁ (diethyl acetal) | −11 |
| HO-CH₂CH₂-S-CH₂CH₂-X₁ | −31 |
| 2-(isopropyl)phenyl-X₁ | −30 |

TABLE III-continued

LIBRARY

| R | % inhibition |
|---|---|
| CH₃-S-CH₂CH₂-C(=X₁)-CH₂OH | −11 |
| (CH₃)₂C(CH₂OH)(X₁) — neopentyl-type with HO- | −2 |
| CH₃-S-CH₂CH₂-X₁ | 18 |
| CH₃-CH₂-S-CH₂CH₂-X₁ | 7 |
| (CH₃CH₂CH₂CH₂)₂N-CH₂CH₂-X₁ (dibutylamino ethyl) | 1 |
| HO-N=C(OH)-CH(X₁)-CH₂CH₂CH₂CH₃ (hydroxamic acid type) | 0 |
| (CH₃O)₂CH-CH(CH₃)-X₁ (dimethyl acetal) | 0 |

TABLE III-continued

| LIBRARY | |
|---|---|
| R | % inhibition |
| 2,3,5-trifluorobenzyl (X₁-CH₂-Ar(F,F,F)) | 24 |
| C(CH₂OH)₃-X₁ (tris(hydroxymethyl)methyl) | 14 |
| C(CH₂OH)₂(CH₂CH₃)-X₁ | 61 |
| HON=C(OH)-CH(CH₃)CH₂CH₃ with X₁ | 9 |
| 6-quinolinyl (X₁) | 1 |
| 2-biphenyl (X₁) | 1 |
| 3-(trifluoromethyl)phenyl (X₁) | 4 |
| 5-isoquinolinyl (X₁) | 1 |
| 3,4-dichlorophenyl (X₁) | 8 |
| 3-chlorophenyl (X₁) | −15 |
| 4-chlorophenyl (X₁) | −12 |
| 4-hydroxyphenyl (X₁) | 52 |
| 4-(methylsulfonyl)phenyl (X₁) | 19 |
| 2-hydroxyphenyl (X₁) | 13 |
| 2-(1-pyrrolyl)phenyl (X₁) | −7 |
| 1-hydroxy-6-naphthyl (X₁) | −26 |
| 6-(1H-indazolyl) (X₁) | 7 |

TABLE III-continued
LIBRARY
| R | % inhibition |
|---|---|
| 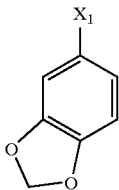 | 9 |
| 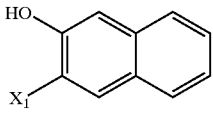 | 18 |
| 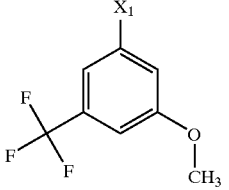 | 10 |
| 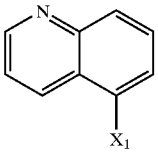 | −37 |
| 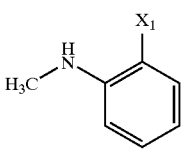 | −2 |
| 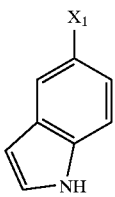 | 43 |
| 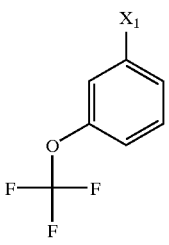 | 5 |
| 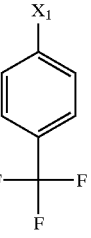 | 1 |
| 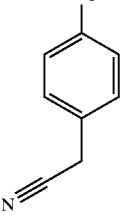 | −3 |
|  | −13 |
| 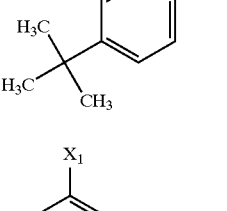 | −1 |
| 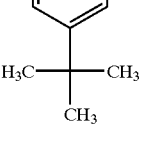 | −1 |
| 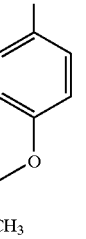 | 16 |

TABLE III-continued
LIBRARY
| R | % inhibition |
|---|---|
| 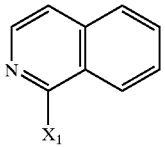 | 4 |
| 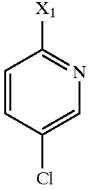 | −23 |
| 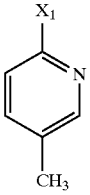 | −20 |
| 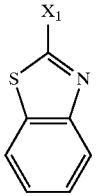 | −15 |
| 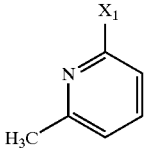 | 10 |
| 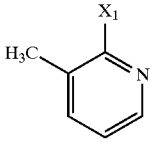 | −18 |
| 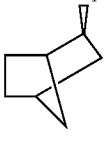 | −9 |
|  | 29 |
TABLE III-continued
LIBRARY
| R | % inhibition |
|---|---|
| 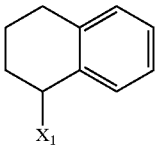 | 1 |
| 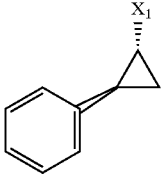 | 10 |
| 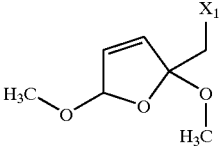 | 0 |
| 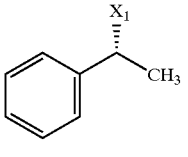 | 9 |
| 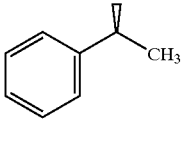 | −3 |
| 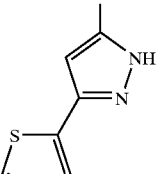 | −11 |
| 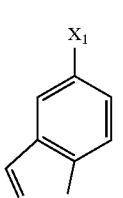 | 22 |
| 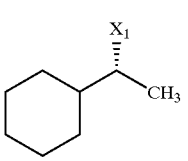 | 9 |

TABLE III-continued

| LIBRARY | |
|---|---|
| R | % inhibition |
| cyclopentyl-CH(X₁)-CH₂OH | −5 |
| (CH₃)₂CH-CH(X₁)-CH₂OH | −19 |
| indanone with X₁ and OH | −6 |
| cyclohexyl-CH(X₁)-CH₃ | −12 |
| Ph-C(OH)(H)-CH(X₁)-CH₂OH | −1 |
| benzotriazol-5-yl-X₁ | −7 |
| Ph-CH(OH)-CH₂-X₁ | 2 |
| Ph-C(=O)-CH₂-X₁, HO | −34 |
| 2,3-dihydro-1,4-benzodioxin-2-yl-CH₂-X₁ | −13 |
| 2,4-dimethoxyphenyl-CH₂-X₁ | 13 |
| 5-chloro-2-(hydroxymethyl)phenyl-X₁ | 48 |
| 2-thienyl-CH₂CH₂-X₁ | 36 |
| tetrahydrofuran-2-yl-CH₂-X₁ | −8 |
| tetrahydrofuran-2-yl-CH₂-X₁ | −11 |
| 3,4-dimethoxyphenyl-X₁ | 1 |
| 4-chloro-2-methoxyphenyl-X₁ | −4 |

TABLE III-continued

LIBRARY

| R | % inhibition |
|---|---|
| 4-methoxyphenethyl (X₁-CH₂CH₂-C₆H₄-OCH₃) | 10 |
| pyrazin-2-yl (X₁-) | −1 |
| naphthalen-1-yl (X₁-) | −33 |
| 3-chloro-4-hydroxyphenyl (X₁-C₆H₃(Cl)(OH)) | −19 |
| 4-butoxyphenyl (X₁-C₆H₄-O-CH₂CH₂CH₂CH₃) | −6 |
| 3-chloro-4-methoxyphenyl (X₁-C₆H₃(Cl)(OCH₃)) | 2 |

TABLE III-continued

LIBRARY

| R | % inhibition |
|---|---|
| 6-chloropyridazin-3-yl (X₁-) | −21 |
| 3-chloro-4-methylbenzyl (X₁-CH₂-C₆H₃(Cl)(CH₃)) | −16 |
| ethyl 4-benzoate (X₁-C₆H₄-C(O)-O-CH₂CH₃) | −25 |
| 4-(diethylamino)phenyl (X₁-C₆H₄-N(CH₂CH₃)₂) | −9 |
| 3-(hydroxymethyl)-4-methylphenyl (X₁-C₆H₃(CH₃)(CH₂OH)) | 1 |
| 3-fluorophenethyl (X₁-CH₂CH₂-C₆H₄-F) | 4 |

TABLE III-continued

LIBRARY

| R | % inhibition |
|---|---|
| 3,5-dimethoxybenzyl (H3CO, OCH3 on benzyl with X1) | 37 |
| H3C-O-(CH2)3-O-(CH2)3-X1 (butoxypropyl) | −12 |
| HO-(CH2)6-X1 | −20 |
| geranyl-type (CH3 branched dienyl) with X1 | −22 |
| 2-indanyl-X1 | 7 |
| 3,5-dichlorophenyl-X1 | −22 |

TABLE III-continued

LIBRARY

| R | % inhibition |
|---|---|
| 4-isopropylphenyl-X1 | −12 |
| 3,4-difluorobenzyl-X1 | 0 |
| 3,4-dimethylbenzyl-X1 | −6 |
| 2,3-dimethylbenzyl-X1 | 13 |
| 2-(4-methylphenyl)ethyl-X1 | −1 |
| 2-(4-ethylphenyl)ethyl-X1 | −11 |

TABLE III-continued

LIBRARY

| R | % inhibition |
|---|---|
| 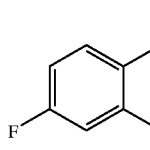 2,4-difluorobenzyl-X₁ | 11 |
| 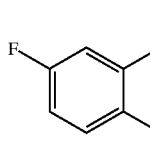 2,5-difluorobenzyl-X₁ | 15 |
| 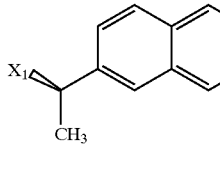 1-(naphthalen-2-yl)ethyl-X₁ | −8 |
| 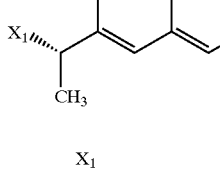 (R)-1-(naphthalen-2-yl)ethyl-X₁ | 1 |
| 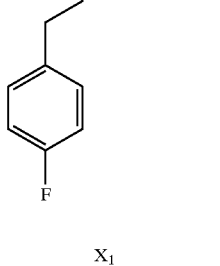 4-fluorophenethyl-X₁ | 3 |
|  propargyl-X₁ | 9 |
| 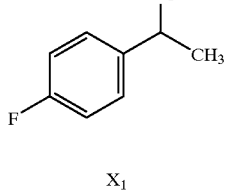 1-(4-fluorophenyl)ethyl-X₁ | 2 |
| 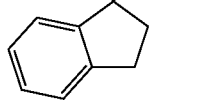 indan-1-yl-X₁ | 8 |

TABLE III-continued

LIBRARY

| R | % inhibition |
|---|---|
| indan-1-ylidene-X₁ | 15 |
| 1-(4-chlorophenyl)ethyl-X₁ | 14 |
| 2-phenylallyl-X₁ | 3 |
| pyridin-2-yl-X₁ | −31 |
| pyridin-3-yl-X₁ | −2 |
| phenyl-X₁ | 11 |
| 3-cyano-4,5-dimethylfuran-2-yl-X₁ | 13 |
| (1R,2S)-1,3-dihydroxy-1-phenylpropan-2-yl-X₁ | 10 |

TABLE III-continued
LIBRARY
| R | % inhibition |
|---|---|
| 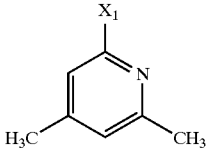 2,4-dimethylpyridine-X₁ | 3 |
| 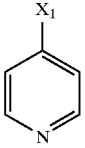 pyridin-3-yl-X₁ | 6 |
| 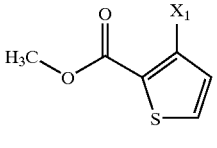 methyl 3-X₁-thiophene-2-carboxylate | 2 |
| 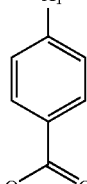 methyl 4-X₁-benzoate | −1 |
| 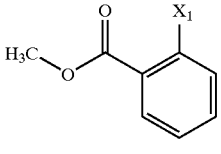 methyl 2-X₁-benzoate | 3 |
| 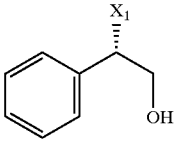 (R)-2-X₁-2-phenylethanol | 18 |
| 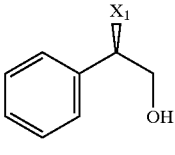 2-X₁-2-phenylethanol | −17 |
| 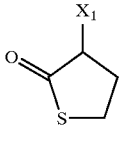 3-X₁-thiolan-2-one | −8 |
| 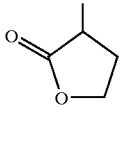 3-X₁-dihydrofuran-2-one | 3 |
| R | % inhibition |
|---|---|
| 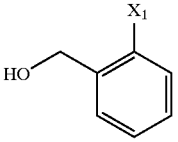 (2-X₁-phenyl)methanol | 0 |
| 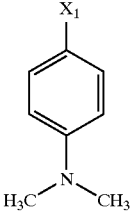 4-X₁-N,N-dimethylaniline | 18 |
| 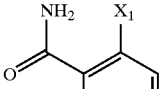 2-X₁-benzamide | 7 |
|  3-X₁-phenol | −6 |
| 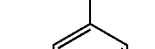 4-X₁-benzamide | 2 |
| 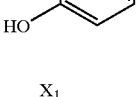 3-X₁-1,2,4-triazine | 3 |
| 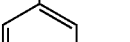 (3-X₁-phenyl)methanol | 14 |

TABLE III-continued
LIBRARY
| R | % inhibition |
|---|---|
| 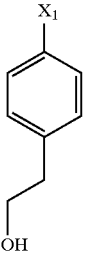 | 10 |
| 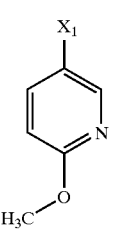 | −20 |
| 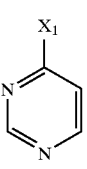 | −10 |
| 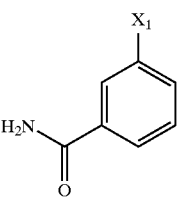 | 4 |
| 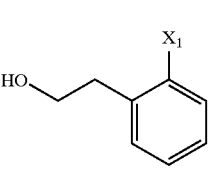 | 10 |
| 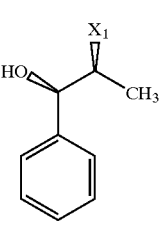 | 9 |
| 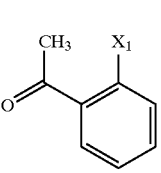 | −7 |
TABLE III-continued
LIBRARY
| R | % inhibition |
|---|---|
| 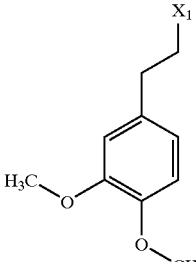 | −3 |
| 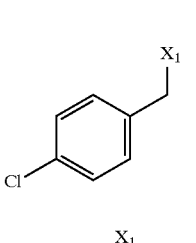 | 4 |
| 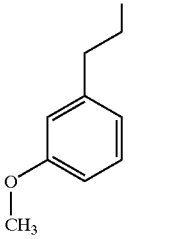 | 8 |
| 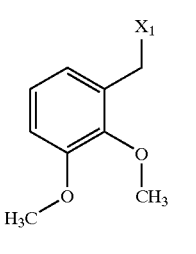 | 10 |
| 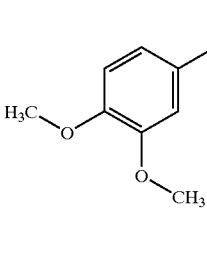 | 7 |
| 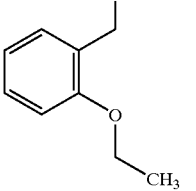 | −9 |

TABLE III-continued
LIBRARY
| R | % inhibition |
|---|---|
| 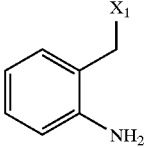 | 46 |
| 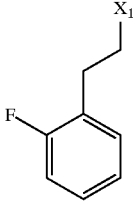 | 2 |
| 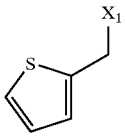 | 23 |
| 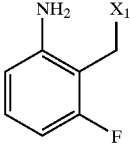 | 11 |
| 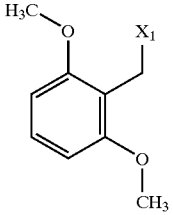 | −10 |
| 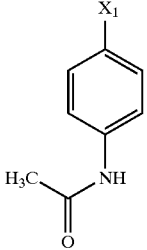 | −4 |
| 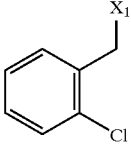 | 7 |
TABLE III-continued
LIBRARY
| R | % inhibition |
|---|---|
| 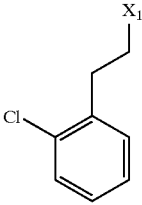 | 9 |
| 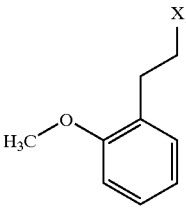 | 10 |
| 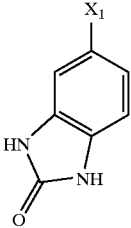 | 15 |
| 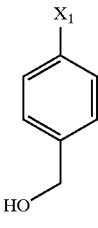 | −18 |
| 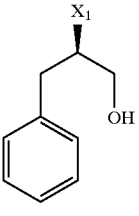 | −3 |
| 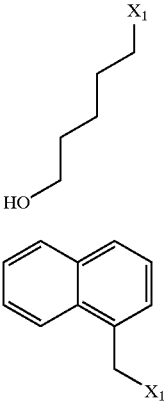 | −2 |
| 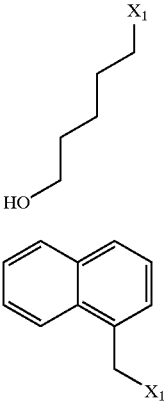 | 5 |

TABLE III-continued
LIBRARY
| R | % inhibition |
|---|---|
| 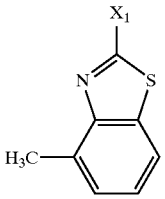 | −13 |
| 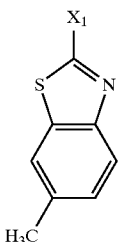 | −9 |
| 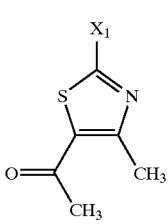 | −2 |
| 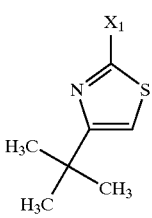 | −6 |
| 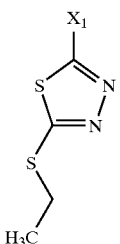 | 17 |
| 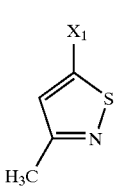 | 19 |
TABLE III-continued
LIBRARY
| R | % inhibition |
|---|---|
| 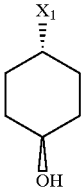 | 18 |
| 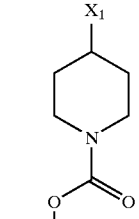 | −24 |
| 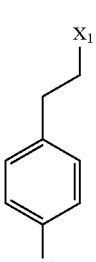 | 0 |
| 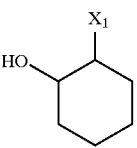 | −6 |
| 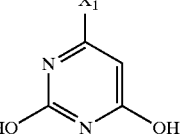 | 3 |
| 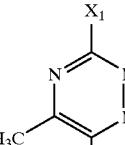 | −20 |
| 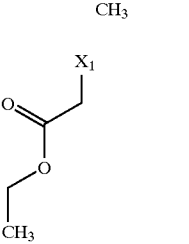 | −16 |

TABLE III-continued

| LIBRARY | |
|---|---|
| R | % inhibition |
| (norbornane with =CH-X₁ and two CH₃ groups) | −19 |
| (adamantane-CH₂-X₁) | 1 |
| HC≡C-C(cyclohexyl)(X₁) | 3 |
| 5-methyl-pyrazin-2-yl-CH₂-X₁ | 6 |
| indol-3-yl-CH₂CH₂-X₁ | 18 |
| HOCH₂-C(CH₃)(X₁)-CH₂OH | −18 |
| methyl 3-(X₁)-4-methylbenzoate | −9 |
| 1-hydroxycyclohexyl-CH₂-X₁ | 2 |
| 2,3-dihydrobenzofuran-5-yl-CH₂-X₁ | 14 |
| 2-(methylthio)phenyl-X₁ | −10 |
| 4-(methylthio)phenyl-X₁ | −7 |
| 3-hydroxypyridin-2-yl-X₁ | 4 |
| 3-methoxyphenyl-X₁ | 11 |
| 5-methyl-1H-pyrazol-3-yl-X₁ | 11 |
| 3-(methylthio)phenyl-X₁ | 8 |
| tert-butyl-X₁ | 23 |

TABLE III-continued

LIBRARY

| R | % inhibition |
|---|---|
| 1-naphthyl-CH(CH₃)-X₁ | 1 |
| 1-naphthyl-C(=X₁)-CH₃ | −20 |
| 3-chlorophenethyl-X₁ | 0 |
| 4-fluorobenzyl-X₁ | 57 |
| 3-chlorobenzyl-X₁ | 24 |
| PhCH₂-CH(X₁)-CH₂OH | 1 |
| 2,4,6-trimethylphenyl-X₁ | −10 |
| 2-methoxyphenyl-X₁ | −8 |
| 2-chlorophenyl-X₁ | −2 |
| 2-methylphenyl-X₁ | 5 |
| 3-methylphenyl-X₁ | 3 |

TABLE 4

[Structure: benzimidazole-indazole carboxamide core with R-NH-C(=O)- group]

| R | CHK-1 @ 20 μM |
|---|---|
| pyridin-3-yl-X₁ | 30.6 |
| phenyl-X₁ | 28.3 |
| HO-(CH₂)₃-X₁ | 22.5 |
| morpholino-CH₂CH₂-X₁ | 21.7 |
| pyridin-4-yl-X₁ | 40 |

TABLE 4-continued
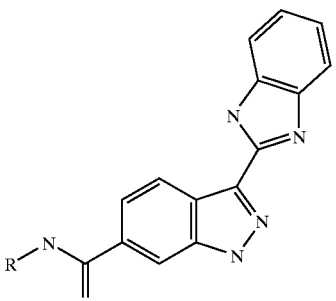
| R | CHK-1 @ 20 μM |
|---|---|
| 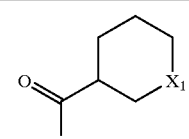 | 27.8 |
| 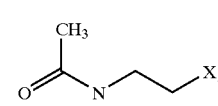 | 20.2 |
| 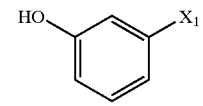 | 57.7 |
| 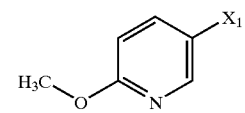 | 35.5 |
| 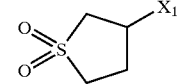 | 24.2 |
| 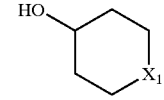 | 31.1 |
| 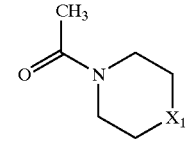 | 13.7 |
| 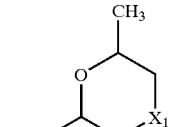 | 23.9 |
| 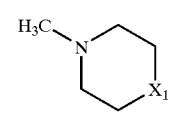 | 48.6 |
TABLE 4-continued
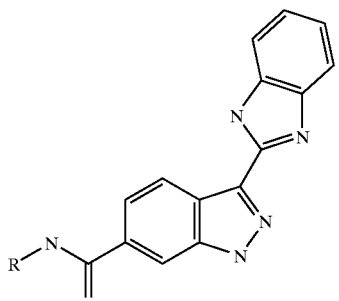
| R | CHK-1 @ 20 μM |
|---|---|
| 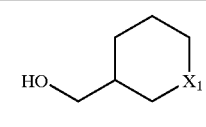 | 19.5 |
| 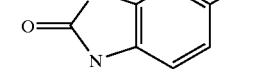 | 32.3 |
| 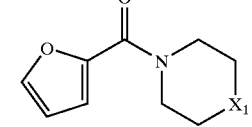 | 24.9 |
| 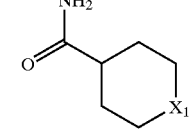 | 25.8 |
| 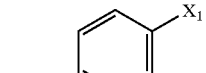 | 94.9 |
| 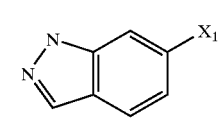 | 38.7 |
|  | 72 |
| 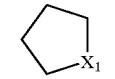 | 21.1 |
| 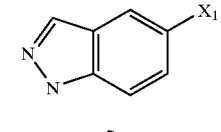 | 31.4 |
|  | 28.3 |

TABLE 4-continued

| R | CHK-1 @ 20 μM |
|---|---|
| (N-methyl piperazinone with X₁) | 28.5 |
| cyclohexyl-X₁ | 28.1 |
| allyl-piperazine-X₁ | 25.7 |
| 3-hydroxy-piperidine-X₁ | 23.9 |
| pyrazine-X₁ | 36.3 |
| morpholine-X₁ | 45.4 |
| HO-CH₂CH₂-X₁, CH₃-X₁ | 32.7 |
| ethyl piperidine-3-carboxylate-X₁ | 24.7 |
| CH₃-X₁, H₃C-X₁ | 52.7 |
| purine-X₁ | 38.6 |

| R | CHK-1 @ 20 μM |
|---|---|
| ethyl 3-X₁-butanoate | 23.6 |
| N≡C-CH₂-X₁, CH₃-X₁ | 39.8 |
| HO-CH₂-(4-tetrahydropyranyl)-X₁ | 28.1 |
| HO-CH₂CH₂-(4-tetrahydropyranyl)-X₁ | 33 |
| pyrazole-X₁ | 52.4 |
| 5-hydroxy-pyrazole-X₁ | 38.6 |
| 2-hydroxy-4-methoxyphenyl-X₁ | 32.3 |
| methyl 5-X₁-furan-2-carboxylate | 42.9 |
| 1-(2-pyridyl)-but-3-enyl-X₁ | 24.1 |

TABLE 4-continued

| R | CHK-1 @ 20 μM |
|---|---|
| H₃C-O-C(=O)-[benzene with OH and X₁] | 31.6 |

TABLE 5

| Example # | % Inhibition @ 1 μM | |
|---|---|---|
| | Tie2-P | FAK |
| 41(a) | 50 | 5 |
| 41(ee) | 41 | 7 |
| 41(p) | 49 | 9 |
| 41(r) | 56 | 5 |
| 41(t) | 51 | 9 |
| 48(a) | 52 | 11 |
| 31(d) | 46 | 6 |
| 33(a) | 35 | 12 |
| 35(k) | 55 | 7 |
| 35(dd) | 48 | 4 |
| 35(n) | 82 | 1 |
| 35(cc) | 47 | 7 |
| 1(a) | 95* | 69* |
| 3 | NI* | 26* |
| 8(a) | 55* | 3* |
| 2(d) | 90* | NI* |
| 8(c) | 31* | 15* |
| 9(b) | 88* | NI* |
| 10 | 20* | NI* |
| 17 | 50 | |
| 4(a) | 69 | |
| 11 | 40 | |
| 4(b) | 29 | |
| 2(c) | NI | |
| 22(a) | 8 | |

TABLE 5-continued

| Example # | % Inhibition @ 1 μM | |
|---|---|---|
| | Tie2-P | FAK |
| 23 | 5 | |
| 22(b) | NI | |
| 21 | 27 | |
| 12(a) | NI | |
| 19(a) | 18 | |
| 19(c) | NI | |
| 12(c) | 17 | |
| 19(d) | 15 | |
| 5(a) | 44 | |
| 16(a) | 10 | |
| 16(b) | 52 | |
| 24(a) | 91* | |
| 24(b) | 92* | |
| 24(c) | 94 | |
| 30(a) | 19 | |
| 8(d) | 10 | |

*compound tested at 10 μM
values in bold refer to spectrophotometric assay results; non-bolded values were obtained in a DELFIA assay Determination of Inhibitor Concentration in Mouse Plasma after Intraperitoneal and Oral Dosing The dosing solution consisted of the inhibitor dissolved in one of the following vehicles: either 30% or 60% aqueous polypropylene glycol solution with a molar equivalent of HCl in water, or 0.5% carboxymethylcellulose in water. The final concentration was normally 5 mg/ml with a dosing volume of 5 or 10 ml/kg. Taconic (Germantown, N.Y.) female mice were dosed as a function of compound mass per body mass, usually 50 or 25 mg/kg. Blood collection was via ocular bleed at 0.5, 1, 4 hr with the final time point, 7 hour, via intracardiac puncture. The blood was centrifuged to collect plasma, which was then stored at −80° C. until analysis. Samples were prepared for analysis using an internal standard and sodium hydroxide. After vortexing, ethyl acetate was added and mixed for 15–20 minutes at ambient temperature. Following centrifugation, the resulting organic layer was evaporated and subsequently reconstituted in acetonitrile and buffer. The samples were then analyzed via HPLC or LC-MS.

Compound levels were quantitated by generating a standard curve of known compound concentration in mouse plasma. Compound levels were plotted as a function of time and analyzed to provide area under the concentration curve (AUC ng*hr/ml), maximum concentration (Cmax ng/ml), minimum concentration (Cmin or 7 hour trough ng/ml), and terminal half-life (T½ hr). The results are shown in Table 6.

TABLE 6

| Example # | Route | Dose mg/kg | AUC$_{last}$ (ng*hr/ml) | Cmax (ng/ml) | Cmin (7 hr conc.) (ng/ml) | T$_{1/2 \beta}$ (hr) | Vehicle PEG400:H2O pH 2.3 |
|---|---|---|---|---|---|---|---|
| 1 (a) | IP | 50 | 691 | 283 | | 2.4 | 30:70 |
| 19 (b) | PO | 50 | NA | 30 | | ∞ | 60:40 |
| 19 (j) | IP | 25 | 23205 | 5764 | 456 | 1.6 | 60:40 |
| 19 (j) | PO | 50 | 5889 | 1937 | 63 | 1.2 | 60:40 |
| 19 (k) | IP | 25 | 428 | 149 | 15 | 2.2 | 60:40 |
| 19 (k) | PO | 50 | 19 | 8 | 4 | 2.2 | 60:40 |
| 31 (a) | IP | 25 | 47538 | 13018 | 1906 | 2.4 | 30:70 |
| 31 (a) | PO | 50 | 40863 | 14499 | 834 | 1.6 | 30:70 |
| 31 (b) | IP | 25 | >7037 | >2000 | 177 | 1.7 | 30:70 |

TABLE 6-continued

| Example # | Route | Dose mg/kg | AUC$_{last}$ (ng*hr/ml) | Cmax (ng/ml) | Cmin (7 hr conc.) (ng/ml) | T$_{1/2 \beta}$ (hr) | Vehicle PEG400:H2O pH 2.3 |
|---|---|---|---|---|---|---|---|
| 31 (b) | PO | 50 | 2071 | 1100 | 15 | 1.0 | 30:70 |
| 31 (d) | IP | 25 | 237784 | 64184 | 15073 | 5.3 | 30:70 |
| 31 (d) | PO | 10 | 49120 | 9740 | 2022 | 3.1 | 30:70 |
| 31 (d) | PO | 25 | 203860 | 50810 | 3801 | 1.9 | 30:70 |
| 31 (d) | PO | 50 | 430683 | 76915 | 42478 | 39.3 | 30:70 |
| 31 (e) | PO | 25 | >30339 | >5000 | 2952 | 13.1 | 30:70 |
| 31 (f) | PO | 25 | >244545 | >50000 | 9521 | 2.6 | 30:70 |
| 32 (a) | IP | 25 | >20554 | >4000 | 1273 | 3.7 | 30:70 |
| 32 (a) | PO | 50 | 4190 | 1746 | 40 | 1.1 | 30:70 |
| 32 (b) | PO | 25 | 490 | 179 | 18 | 2.1 | 30:70 |
| 32 (c) | PO | 25 | 388 | 161 | 10 | 2.4 | 30:70 |
| 33 (a) | IP | 25 | 13813 | 13794 | 54 | 1.1 | 30:70 |
| 33 (a) | PO | 100 |  | 3556 | 90 |  | 0.5% CMC |
| 33 (a) | PO | 25 |  | 721 | 66 |  | 0.5% CMC |
| 33 (a) | PO | 50 | 19067 | 23562 | 25 | 0.8 | 30:70 |
| 33 (b) | IP | 25 | 11245 | 1990 | 902 | 3.0 | 60:40 |
| 33 (b) | PO | 50 | 3925 | 1496 | 76 | 3.0 | 60:40 |
| 33 (c) | IP | 25 | 697 | 505 | 7 | 1.2 | 30:70 |
| 33 (c) | PO | 50 | 183 | 94 | 5 | 3.0 | 30:70 |
| 33 (d) | IP | 25 | 5080 | 1738 | 113 | 1.6 | 60:40 |
| 33 (d) | PO | 50 | 4744 | 1614 | 8 | 0.9 | 60:40 |
| 33 (e) | IP | 25 | 14323 | 9938 | 94 | 1.0 | 30:70 |
| 33 (e) | PO | 50 | 13290 | 9967 | 12 | 0.7 | 30:70 |
| 33 (f) | IP | 25 | 1887 | 1699 | 6 | 2.4 | 30:70 |
| 33 (f) | PO | 50 | 1436 | 1186 | 3 | 0.7 | 30:70 |
| 35 (a) | IP | 25 | 2032 | 2138 | 24 | 1.4 | 30:70 |
| 35 (a) | PO | 50 | 2445 | 1780 | 10 | 0.9 | 30:70 |
| 35 (aa) | PO | 25 | 4036 | 4168 | 106 | 2.1 | 30:70 |
| 35 (b) | IP | 25 | 2840 | 1509 | 12 | 0.8 | 30:70 |
| 35 (b) | PO | 50 | 4048 | 5595 | 13 | 0.8 | 30:70 |
| 35 (c) | IP | 25 | 9408 | 1976 | 465 | 3.2 | 30:70 |
| 35 (c) | PO | 50 | 4744 | 909 | 321 | 4.9 | 30:70 |
| 35 (cc) | IP | 25 | 2223 | 3183 | 6 | 1.4 | 30:70 |
| 35 (cc) | PO | 50 | 1718 | 1439 | 5 | 0.9 | 30:70 |
| 35 (dd) | IP | 25 | >23046 | >4000 | 1364 | 4.1 | 30:70 |
| 35 (dd) | PO | 25 | 1360 | 444 | 58 | 2.0 | 0.5% CMC |
| 35 (dd) | PO | 25 | >6521 | >4000 | 114 | 1.4 | 30:70 |
| 35 (e) | IP | 25 | 2409 | 1272 | 65 | 1.8 | 30:70 |
| 35 (e) | PO | 50 | 1503 | 1043 | 6 | 0.9 | 30:70 |
| 35 (ee) | IP | 25 | 546 | 579 | 2 | 1.5 | 30:70 |
| 35 (ee) | PO | 25 | 157 | 77 | 9 | 14.6 | 30:70 |
| 35 (f) | IP | 25 | 397 | 131 | 25 | 3.8 | 30:70 |
| 35 (f) | PO | 50 | 358 | 93 | 27 | 3.6 | 30:70 |
| 35 (ff) | IP | 25 | >6301 | >4000 | 72 | 1.7 | 30:70 |
| 35 (ff) | PO | 25 | Blq | Blq | blq | blq | 30:70 |
| 35 (g) | PO | 25 | 231 | 61 | 28 | 16.1 | 30:70 |
| 35 (h) | IP | 25 | 59 | 46 | 1 | 1.5 | 30:70 |
| 35 (h) | PO | 50 | 26 | 7 | 2 | * | 30:70 |
| 35 (hh) | PO | 25 | 292 | 221 | 5 | 1.7 | 30:70 |
| 35 (i) | PO | 25 |  |  |  |  | 30:70 |
| 35 (j) | IP | 25 | 9531 | 8606 | 52 | 1.3 | 30:70 |
| 35 (j) | PO | 50 | 1328 | 2176 | 5 | 4.5 | 30:70 |
| 35 (k) | IP | 25 | 2640 | 2189 | 35 | 1.4 | 30:70 |
| 35 (k) | PO | 50 | 5529 | 4524 | 33 | 1.4 | 30:70 |
| 35 (m) | IP | 25 | 226 | 58 | 17 | 4.0 | 30:70 |
| 35 (m) | PO | 25 | 10 | 7 | 0 | * | 30:70 |
| 35 (n) | PO | 25 | 4818 | 3545 | 55 | 1.4 | 30:70 |
| 35 (o) | PO | 25 | 683 | 486 | 3 | 1.0 | 30:70 |
| 35 (p) | PO | 25 | 1435 | 1958 | 5 | 1.3 | 30:70 |
| 35 (r) | PO | 25 | 4261 | 2601 | 67 | 1.3 | 30:70 |
| 35 (s) | PO | 25 | 7425 | 3371 | 86 | 2.2 | 30:70 |
| 35 (t) | PO | 25 | 3199 | 2801 | 41 | 1.1 | 30:70 |
| 35 (u) | PO | 25 |  |  |  |  | 30:70 |
| 35 (v) | IP | 25 | 4865 | 2215 | 16 | 0.9 | 30:70 |
| 35 (v) | PO | 50 | >2946 | >2000 | 26 | 1.0 | 30:70 |
| 35 (x) | IP | 25 | 951 | 781 | 48 | 3.2 | 30:70 |
| 35 (x) | PO | 50 | 3516 | 2313 | 16 | 0.9 | 30:70 |
| 35 (y) | IP | 25 | 159 | 135 | 2 | 1.2 | 30:70 |
| 35 (y) | PO | 50 | 58 | 45 | 1 | 1.2 | 30:70 |
| 35 (z) | IP | 25 | 837 | 556 | 22 | 1.8 | 30:70 |
| 35 (z) | PO | 50 | 1001 | 806 | 14 | 1.6 | 30:70 |
| 36 (a) | PO | 25 | 605 | 445 | 17 | 1.5 | 30:70 |
| 37 (a) | PO | 25 |  |  |  |  | 30:70 |
| 37 (c) | PO | 25 | 2419 | 2338 | 9 | 1.2 | 30:70 |
| 39 (a) | PO | 25 | >14848 | >4000 | 219 | 1.4 | 30:70 |

TABLE 6-continued

| Example # | Route | Dose mg/kg | $AUC_{last}$ (ng*hr/ml) | Cmax (ng/ml) | Cmin (7 hr conc.) (ng/ml) | $T_{1/2\,\beta}$ (hr) | Vehicle PEG400:H2O pH 2.3 |
|---|---|---|---|---|---|---|---|
| 39 (b) | PO | 25 | >30972 | >5000 | 3148 | 11.8 | 30:70 |
| 4 (a) | PO | 50 | NA | 50 | | NA | 60:40 |
| 41 (a) | IP | 25 | 92823 | 32202 | 3856 | 2.9 | 30:70 |
| 41 (a) | PO | 50 | 48998 | 18433 | 2462 | 3.4 | 30:70 |
| 41 (aa) | IP | 25 | 6659 | 2427 | 124 | 2.1 | 60:40 |
| 41 (aa) | PO | 50 | 289 | 259 | 5 | 0.9 | 60:40 |
| 41 (b) | IP | 25 | >5868 | >1000 | 412 | 4.7 | 60:40 |
| 41 (b) | PO | 50 | 759 | 532 | 6 | 1.1 | 60:40 |
| 41 (bb) | PO | 50 | 2178 | 596 | 75 | 2.0 | 30:70 |
| 41 (c) | IP | 25 | 3397 | 2068 | 57 | 1.7 | 60:40 |
| 41 (c) | PO | 50 | 3182 | 1296 | 104 | 2.6 | 60:40 |
| 41 (d) | IP | 25 | 10324 | 2787 | 573 | 2.8 | 60:40 |
| 41 (d) | PO | 50 | 7072 | 2954 | 150 | 1.5 | 60:40 |
| 41 (dd) | PO | 25 | 654 | 542 | 1 | 0.8 | 30:70 |
| 41 (e) | IP | 25 | 4900 | 1154 | 301 | 1.6 | 60:40 |
| 41 (e) | PO | 50 | 302 | 113 | 7 | 1.6 | 60:40 |
| 41 (ee) | IP | 25 | >28434 | >5000 | 1670 | 4.0 | 30:70 |
| 41 (ee) | PO | 50 | >25294 | >5000 | 1214 | 3.4 | 30:70 |
| 41 (ff) | PO | 25 | 9176 | 2784 | 410 | 2.0 | 30:70 |
| 41 (g) | IP | 25 | 1925 | 1583 | 0 | 0.3 | 60:40 |
| 41 (g) | PO | 50 | 508 | 842 | 1 | 0.7 | 60:40 |
| 41 (gg) | PO | 25 | 2692 | 2079 | 29 | 1.1 | 30:70 |
| 41 (h) | IP | 25 | 26911 | 16005 | 300 | 1.2 | 30:70 |
| 41 (h) | PO | 50 | 4677 | 4080 | 7 | 0.7 | 30:70 |
| 41 (hh) | PO | 25 | 5601 | 1526 | 405 | 7.9 | 30:70 |
| 41 (l) | IP | 25 | 1854 | 623 | 102 | 3.1 | 30:70 |
| 41 (l) | PO | 50 | 212 | 104 | 0 | 0.5 | 30:70 |
| 41 (ii) | PO | 25 | 7094 | 1826 | 346 | 2.3 | 30:70 |
| 41 (j) | PO | 25 | 1476 | 1008 | 17 | 1.3 | 30:70 |
| 41 (kk) | PO | 25 | 11612 | 3709 | 415 | 2.0 | 30:70 |
| 41 (m) | IP | 25 | 1864 | 501 | 54 | 2.3 | 30:70 |
| 41 (m) | PO | 50 | 9 | 5 | 0 | blq | 30:70 |
| 41 (mm) | PO | 25 | 2261 | 852 | 127 | 2.5 | 30:70 |
| 41 (n) | IP | 25 | 9408 | 1976 | 465 | 3.2 | 30:70 |
| 41 (n) | PO | 50 | 9066 | 2245 | 253 | 1.9 | 30:70 |
| 41 (o) | IP | 25 | >33750 | >5000 | >5000 | * | 30:70 |
| 41 (o) | PO | 50 | 14717 | 4776 | 427 | 1.7 | 30:70 |
| 41 (p) | IP | 25 | 4150 | 866 | 380 | 5.5 | 30:70 |
| 41 (q) | IP | 25 | >27000 | >4000 | >4000 | * | 30:70 |
| 41 (q) | PO | 25 | 8572 | 1901 | 457 | 5.2 | 30:70 |
| 41 (r) | IP | 25 | >23752 | >5000 | >5000 | * | 30:70 |
| 41 (r) | PO | 50 | >17789 | >5000 | >5000 | * | 30:70 |
| 41 (t) | PO | 25 | >22498 | >4000 | 1350 | 4.0 | 30:70 |
| 41 (u) | PO | 25 | 875 | 224 | 51 | 5.6 | 30:70 |
| 41 (v) | PO | 25 | 10949 | 2338 | 749 | 4.4 | 30:70 |
| 41 (x) | PO | 25 | 24174 | 4587 | 1268 | 4.2 | 30:70 |
| 41 (y) | PO | 25 | Blq | Blq | blq | blq | 30:70 |
| 42 (a) | IP | 25 | 19899 | 4027 | 1639 | 5.0 | 60:40 |
| 42 (a) | PO | 50 | 8384 | 3264 | 341 | 2.0 | 60:40 |
| 42 (b) | IP | 25 | 3207 | 953 | 211 | 3.0 | 60:40 |
| 42 (b) | PO | 50 | 4747 | 2589 | 46 | 3.0 | 60:40 |
| 42 (d) | IP | 25 | 1774 | 886 | 31 | 1.4 | 60:40 |
| 42 (d) | PO | 50 | 46 | 28 | 18 | BLQ | 60:40 |
| 45 (b) | IP | 25 | 11361 | 2636 | 1123 | 2.0 | 60:40 |
| 45 (b) | PO | 50 | 1636 | 427 | 102 | 3.0 | 60:40 |
| 47 | IP | 25 | 236 | 39 | 29 | 19.9 | 30:70 |
| 47 | PO | 50 | 327 | 84 | 25 | 3.4 | 30:70 |
| 59 (a) | PO | 25 | 50780 | 15878 | 1205 | 1.6 | 0.5% CMC |
| 48 (a) | IP | 25 | 27000 | 4000 | 4000 | * | 30:70 |
| 48 (a) | PO | 25 | 26636 | 4000 | 3857 | * | 30:70 |
| 48 (b) | PO | 25 | 2191 | 476 | 136 | 4 | 30:70 |
| 49 (a) | PO | 25 | 712 | 342 | 15 | | 30:70 |
| 49 (b) | PO | 25 | 33750 | 5000 | 5000 | | 30:70 |
| 5 (b) | PO | 10 | 61 | 12 | | 3.1 | 60:40 |
| 59 (a) | PO | 8 | 7707 | 2489 | 122 | 1.5 | 0.5% CMC |
| 59 (a) | PO | 40 | 57240 | 13798 | 1879 | 2.4 | 0.5% CMC |
| 59 (a) | PO | 200 | 156153 | 29975 | 12117 | 9.4 | 0.5% CMC |
| 59 (b) | PO | 50 | 276467 | 50000 | 26880 | | CMC |
| 59 (c) | PO | 25 | 327135 | 50000 | 43090 | | CMC |
| 59 (d) | PO | 8 | >24696 | >5000 | 1902 | | 0.5% CMC |
| 59 (d) | PO | 40 | >32297 | >5000 | 4135 | | 0.5% CMC |
| 59 (d) | PO | 200 | >12306 | >20000 | 12743 | | 0.5% CMC |
| 59 (e) | PO | 25 | 12510 | 28834 | 2135 | 21 | 0.5% CMC |

In Vivo Assay of Retinal Vascular Development in Neonatal Rats

The development of the retinal vascular in rats occurs from postnatal day 1 to postnatal day 14 (P1–P14). This process is dependent on the activity of VEGF (J. Stone, et al, *J. Neurosci.*, 15, 4738 (1995)). Previous work has demonstrated that VEGF also acts as a survival factor for the vessels of the retina during early vascular development (Alon, et. al, *Nat. Med.*, 1, 1024 (1995)). To assess the ability of specific compounds to inhibit the activity of VEGF in vivo, compounds were formulated in an appropriate vehicle, usually 50% polyethylene glycol, average molecular weight 400 daltons, and 50% solution of 300 mM sucrose in deionized water. Typically, two microliters (2 μl) of the drug solution was injected into the midvitreous of the eye of rat pups on postnatal day 8 or 9. Six days after the intravitreal injection, the animals were sacrificed and the retinas dissected free from the remaining ocular tissue. The isolated retinas were then subjected to a histochemical staining protocol that stains endothelial cells specifically (Lutty and McLeod, *Arch. Ophthalmol.*, 110, 267 (1992)), revealing the extent of vascularization within the tissue sample. The individual retinas are then flat-mount onto glass slides and examined to determine the extent of vascularization. Effective compounds inhibit the further development of the retinal vasculature and induce a regression of all but the largest vessels within the retina The amount of vessel regression was used to assess the relative potency of the compounds after in vivo administration. Vessel regression is graded on subjective scale of one to three pluses, with one plus being detectable regression judged to be approximately 25 percent or less, two pluses being judged to be approximately 25–75% regression and three pluses give to retinas with near total regression (approximately 75% or greater).

For more quantitative analysis of regression, images of ADPase-stained, flat-mounted retinas were captured with a digital camera attached to a dissecting microscope. Retinal images were then imported into an image analysis software (Image Pro Plus 4.0, Media Cybernetics, Silver Spring, Md.). The software was employed to determine the percentage of the area of the retina that contained stained vessels. This value for the experimental eye was compared to that measured for the vehicle injected, contralateral eye from the same animal. The reduction in the vascular area seen in the eye that received compound as compared to the vehicle-injected eye was then expressed as the "percent regression" for that sample. Percent regression values were averaged for groups of 5–8 animals.

In samples in which observation through the microscope indicated near total regression, a percent regression value of 65–70% was routinely measured. This was due to stain deposits within folds of retina, folds that were induced by the vehicle used for drug injection. The image analysis software interpreted these stain-containing folds as vessels. No attempt was made to correct for these folds since they varied from eye to eye. Thus, it should be noted that the percent regression values reported result from a conservative measurement that accurately rank orders compounds, but underestimates their absolute potency.

In Vivo Assay of Retinal Vascular Development in Neonatal Rat Model of Retinopathy of Prematurity A second model of VEGF dependent retinal neovascularization was employed to evaluate the activities of this series of compounds. In this model (Penn et. al, *Invest. Ophthalmol. Vis. Sci.*, 36, 2063, (1995)), rats pups (n=16) with their mother are placed in a computer controlled chamber that regulates the concentration of oxygen. The animals are exposed for 24 hours to a concentration of 50% oxygen followed by 24 hours at a concentration of 10% oxygen. This alternating cycle of hyperoxia followed by hypoxia is repeated 7 times after which the animals are removed to room air (P14). Compounds are administered via intravitreal injection upon removal to room air and the animals are sacrificed 6 days later (P20). The isolated retinas are then isolated, stained mounted and analyzed as detail above in the development model. The effectiveness was also graded as is described for the development model.

TABLE 7

| Example # | Model | Initial Evaluation | % Inhibition | Concen. (mg/ml) | Vehicle PEG/water |
|---|---|---|---|---|---|
| 16(e) | ROP | ++ | 36% | 5 | 70:30 |
| 16(e) | ROP | +++ | 54% | 10 | 70:30 |
| 16(e) | ROP | ++ | 37% | 5 | 70:30 |
| 16(e) | ROP | +/− | 16% | 1 | 70:30 |
| 19(b) | ROP | ++ | | 10 | 70:30 |
| 19(f) | P8 | +/++ | | 5 | 50:50 |
| 19(j) | ROP | +/− | | 10 | 70:30 |
| 19(j) | ROP | −− | | 1 | 70:30 |
| 19(k) | ROP | +/− | | 10 | 70:30 |
| 19(k) | ROP | −− | | 1 | 70:30 |
| 30(a) | ROP | ++ | | 10 | 70:30 |
| 30(a) | ROP | ++ | 48% | 10 | 70:30 |
| 31(a) | P8 | | 46% | 5 | 70:30 |
| 31(b) | P8 | | 32% | 5 | 50:50 |
| 31(c) | P8 | +/++ var | | 5 | 50:50 |
| 31(d) | P8 | | 12% | 5 | 50:50 |
| 31(e) | P8 | | 24% | 5 | 50:50 |
| 32(a) | P9 | | 20% | 5 | 50:50 |
| 33(b) | ROP | ++ | 55% | 10 | 70:30 |
| 33(b) | ROP | +/− | 14% | 1 | 70:30 |
| 33(b) | P6–P10 | | 37% | IP* | 70:30 |
| 33(e) | P8 | | 22% | 5 | 70:30 |
| 33(f) | P8 | | 20% | 5 | 50:50 |
| 35(a) | P8 | | 4% | 5 | 50:50 |
| 35(aa) | P8 | − | | 5 | 50:50 |
| 35(c) | P8 | | 0% | 5 | 50:50 |
| 35(cc) | P8 | +/++ | | 5 | 50:50 |
| 35(dd) | P8 | ++/+++ var | | 5 | 50:50 |
| 35(ee) | P8 | +/++ | | 5 | 50:50 |
| 35(h) | P8 | +/− | | 5 | 50:50 |
| 35(i) | P8 | +/++ | | 5 | 50:50 |
| 35(j) | P8 | | 7% | 5 | 50:50 |
| 35(k) | P8 | − | | 5 | 50:50 |
| 35(k) | P8 | ++ | | 5 | 50:50 |
| 35(v) | P8 | | 20% | 5 | 50:50 |
| 38(a) | ROP | +++ | 55% | 10 | 70:30 |
| 38(a) | ROP | + | 16% | 1 | 70:30 |
| 39(b) | P8 | | 9% | 5 | 50:50 |
| 4(a) | ROP | ++ | | 10 | 70:30 |
| 41(a) | ROP | +++ | 64% | 10 | 70:30 |
| 41(a) | P8 | | 0% | 0.5 | 50:50 |
| 41(a) | P8 | | 4% | 1 | 50:50 |
| 41(a) | P8 | ++/+++ | | 5 | 50:50 |
| 41(c) | ROP | +++ | 54% | 10 | 70:30 |
| 41(c) | ROP | +/− | 16% | 1 | 70:30 |
| 41(c) | P8 | ++ | | 5 | 50:50 |
| 41(d) | ROP | +++ | 59% | 10 | 70:30 |
| 41(d) | ROP | +/− | 0% | 1 | 70:30 |
| 41(e) | P8 | | 8% | 5 | 50:50 |
| 41(ee) | P8 | +/++ var | | 5 | 50:50 |
| 41(g) | P8 | | 37% | 5 | 50:50 |
| 41(h) | P8 | | 0% | 5 | 70:30 |
| 41(j) | P8 | +/++ | | 5 | 50:50 |
| 41(k) | P8 | | 1% | 5 | 50:50 |
| 41(l) | P8 | | 28% | 2.5 | 70:30 |
| 41(m) | P8 | | 10% | 5 | 50:50 |
| 41(mm) | P8 | + | | 5 | 50:50 |
| 41(n) | P8 | | 2% | 5 | 50:50 |
| 41(o) | P8 | | 2% | 5 | 50:50 |
| 41(p) | P8 | | 35% | 5 | 50:50 |
| 41(r) | P8 | +/++ var | | 5 | 50:50 |
| 42(a) | ROP | +++ | 23% | 10 | 70:30 |
| 42(a) | ROP | + | 1% | 1 | 70:30 |

TABLE 7-continued

| Example # | Model | Initial Evaluation | % Inhibition | Concen. (mg/ml) | Vehicle PEG/water |
|---|---|---|---|---|---|
| 42(a) | ROP | + | | 10 | 70:30 |
| 42(a) | P9 | | 55% | 10 | 70:30 |
| 42(a) | P6–P10 | | 61% | IP* | 70:30 |
| 42(a) | P8 | +/++ | | 5 | 50:50 |
| 42(b) | P9 | | 40% | 10 | 70:30 |
| 42(c) | P8 | | 36% | 5 | 50:50 |
| 45(b) | ROP | ++ | 60% | 10 | 70:30 |
| 45(b) | ROP | +/− | 25% | 1 | 70:30 |
| 49(a) | P8 | | 54% | 5 | 50:50 |
| 49(b) | P8 | | 5% | 5 | 50:50 |
| 5(b) | ROP | ++ | 45% | 5 | 70:30 |
| 59(a) | ROP | | 41% | 10 | 0.5% CMC |
| 59(a) | ROP | | 19% | 1 | 0.5% CMC |
| 6(a) | ROP | ++ | | 5 | 65:35 |
| 6(b) | ROP | ++ | | 10 | 70:30 |

Phosphorylase Kinase

Phosphorylase Kinase Construct for Assay.

The truncated catalytic subunit (gamma subunit) of phosphorylase kinase (amino acids 1–298) was expressed in *E. coli* and isolated from inclusion bodies. Phosphorylase kinase was then refolded and stored in glycerol at −20° C.

Phosphorylase Kinase Assay. In the assay, the purified catalytic subunit is used to phosphorylate phosphorylase b using radiolabled ATP. Briefly, 1.5 mg/mil of phosphorylase b is incubated with 10 nM phosphorylase kinase in 10 mM $MgCl_2$, 50 mM Hepes pH 7.4, at 37° C. The reaction is started with the addition of ATP to 100 uM and incubated for 15 min at 25° C. or 37° C. The reaction was terminated and proteins were precipitated by the addition of TCA to 10% final concentration. The precipitated proteins were isolated on a 96 well Millipore MADP NOB filter plate. The filter plate was then extensively washed with 20% TCA, and dried. Scintilation fluid was then added to the plate and incorporated radiolabel was counted on a Wallac microbeta counter. The % inhibition of phosphoryl transfer from ATP to phosphorylase b in the presence of 10 $\mu M$ of compound is shown in the Table 8 below.

TABLE 8

| Example # | % Inhibition @ 10 $\mu M$ |
|---|---|
| 52(b) | 92 |
| 27(f) | 90 |
| 27(a) | 37 |

The exemplary compounds described above may be formulated into pharmaceutical compositions according to the following general examples.

Example 1

Parenteral Composition

To prepare a parenteral pharmaceutical composition suitable for administration by injection, 100 mg of a water-soluble salt of a compound of Formula I is dissolved in DMSO and then mixed with 10 mL of 0.9% sterile saline. The mixture is incorporated into a dosage unit form suitable for administration by injection.

Example 2

Oral Composition

To prepare a pharmaceutical composition for oral delivery, 100 mg of a compound of Formula I is mixed with 750 mg of lactose. The mixture is incorporated into an oral dosage unit for, such as a hard gelatin capsule, which is suitable for oral administration.

Example 3

Intraocular Composition

To prepare a sustained-release pharmaceutical composition for intraocular delivery, a compound of Formula I is suspended in a neutral, isotonic solution of hyaluronic acid (1.5% conc.) in phosphate buffer (pH 7.4) to form a 1% suspension.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

What is claimed is:

1. A method to prepare a compound or a salt of formula I,

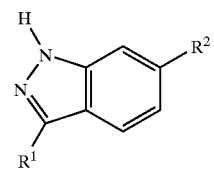

wherein $R^1$ is a substituted or unsubstituted aryl or heteroaryl, or a group of the formula $CH=CH-R^3$ or $CH=N-R^3$, where $R^3$ is a substituted or unsubstituted alkyl, cycloalkyl, heterocycloalkyl, aryl, or heteroaryl;

$R^2$ is Y—X, where Y is O, S, $C=CH_2$, C=O, S=O, $SO_2$, $CH_2$, $CHCH_3$, NH, or $N-C_1-C_8$ alkyl); X is

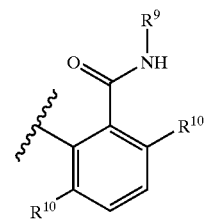

where $R^9$ is a substituted or unsubstituted alkyl, cycloalkyl, heterocycloalkyl, aryl, heteroaryl, alkoxyl, aryloxyl, cycloalkoxyl, NH—($C_1-C_8$ alkyl), NH-(aryl), NH-(heteroaryl), N=CH-(alkyl), NH(C=O)$R^{11}$, or $NH_2$, where $R^{11}$ is selected from hydrogen, substituted or unsubstituted alkyl, cycloalkyl, heterocycloalkyl, aryl, and heteroaryl; and $R^{10}$ is independently selected from hydrogen, halogen, and lower-alkyl;

the method comprising converting a compound of formula IX into a compound of formula X by a cross coupling reaction in the presence of a metal catalyst or a stoichiometric metal reagent:

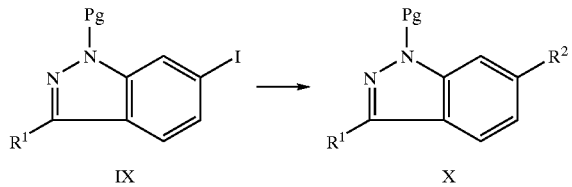

IX → X where Pg is a protecting group; and removing the protecting group to form the compound of formula I.

2. The method of claim 1, wherein the step of converting the compound of formula IX to the compound of formula X comprises:

(i) reacting the compound of formula IX with a nucleophilic $R^2$ compound in the presence of a metal catalyst; or (ii) treating the compound of formula IX with a stochiometric organometallic reagent in a halogen-metal exchange reaction to form a metal containing intermediate, and treating the intermediate with an electrophilic $R^2$ compound to form the compound of formula X.

3. The method of claim 1, wherein the Pg is 1-(2-trimethylsilanyl-ethoxymethyl).

4. The method of claim 2, wherein the nucleophilic $R^2$ compound is an $R^2$-boronic acid.

5. The method of claim 2, wherein the organometallic reagent is an organolithium compound.

6. The method of claim 1, wherein the compound of formula IX is prepared by treating the compound of formula VIII with an oxidizing reagent and a halogenating reagent:

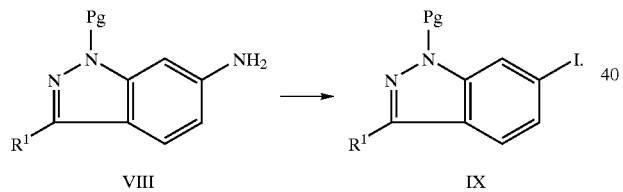

VIII → IX

7. The method of claim 6, wherein the oxidizing reagent is a nitrite compound.

8. The method of claim 6, wherein the compound of formula VIII is prepared from a compound of formula VII by reducing the nitro group of the compound of formula VII to the amino group of the compound of formula VIII

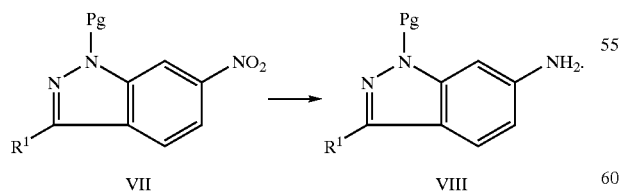

VII → VIII

9. The method of claim 8, wherein the step of reducing the nitro group is carried out in the presence of $SnCl_2$.

10. The method of claim 8, wherein the compound of formula VII is prepared from a compound of formula VI by a metal catalyzed cross coupling reaction

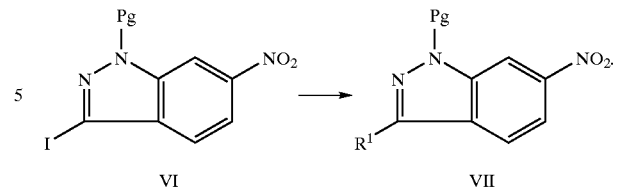

VI → VII

11. The method of claim 10, wherein the metal catalyzed cross coupling reaction is carried out in the presence of an $R^1$-organometallic reagent and a catalyst.

12. The method of claim 11, wherein the $R^1$-organometallic reagent is an $R^1$-boronic acid and the catalyst is a palladium catalyst.

13. The method of claim 10, wherein the compound of formula VI is prepared from a compound of formula V

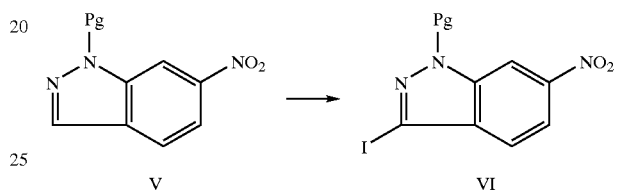

V → VI by a process that comprises: treating the compound of formula V with a strong base and an iodination reagent to form an intermediate; and subsequently treating the intermediate with a strong base and a Pg-halide.

14. The method of claim 13, wherein the Pg-halide is 1-(2-trimethylsilanyl-ethoxymethyl) chloride.

15. A method to prepare a compound or a salt of formula I,

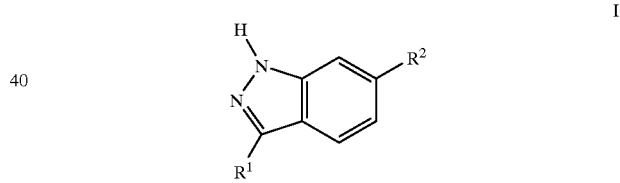

I wherein $R^1$ is a substituted or unsubstituted aryl or heteroaryl, or a group of the formula $CH=CH-R^3$ or $CH=N-R^3$, where $R^3$ is a substituted or unsubstituted alkyl, cycloalkyl, heterocycloalkyl, aryl, or heteroaryl;

$R^2$ is Y—X, where Y is O, S, $C=CH_2$, C=O, S=O, $SO_2$, $CH_2$, $CHCH_3$, NH, or N-($C_1$–$C_8$ alkyl); X is

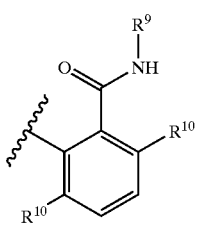

where $R^9$ is a substituted or unsubstituted alkyl, cycloalkyl, heterocycloalkyl, aryl, heteroaryl, alkoxyl, aryloxyl, cycloalkoxyl, NH—($C_1$–$C_8$ alkyl), NH-(aryl), NH-(heteroaryl), N=CH-(alkyl), NH(C=O)

$R^{11}$, or $NH_2$, where $R^{11}$ is selected from hydrogen, substituted or unsubstituted alkyl, cycloalkyl, heterocycloalkyl, aryl, and heteroaryl; and $R^{10}$ is independently selected from hydrogen, halogen, and lower-alkyl;

the method comprising converting a compound of formula XIV into a compound of formula XV by a metal catalyzed cross coupling reaction:

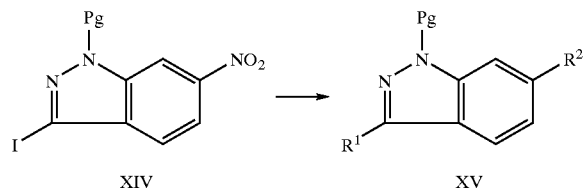

where Pg is a protecting group; and removing the protecting group to form the compound of formula I.

16. The method of claim 15, wherein the metal catalyzed cross coupling reaction is carried out by treating the compound of formula XIV with an $R^1$-organometallic reagent in the presence of a metal catalyst.

17. The method of claim 16, wherein the $R^1$-organometallic reagent is an $R^1$-boronic acid or an $R^1$—ZnCl, and the metal catalyst is a palladium catalyst.

18. The method of claim 15, wherein the compound of formula XIV is prepared from a compound of formula XIII by a metal catalyzed cross coupling reaction:

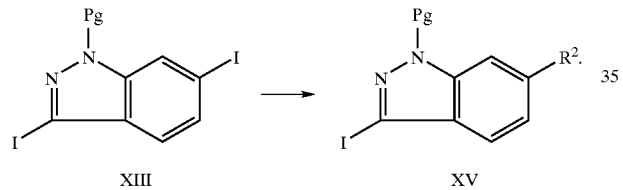

19. The method of claim 18, wherein the metal catalyzed cross coupling reaction is carried out by treating the compound of formula XIII with an $R^2$-organometallic reagent in the presence of a metal catalyst.

20. The method of claim 19, wherein the $R^2$-organometallic reagent is an $R^2$-boronic acid reagent, or a $R^2$—ZnCl reagent, and the metal catalyst is a palladium catalyst.

21. The method of claim 18, wherein the compound of formula XIII is prepared by reacting a compound of formula XII with a protecting group reagent:

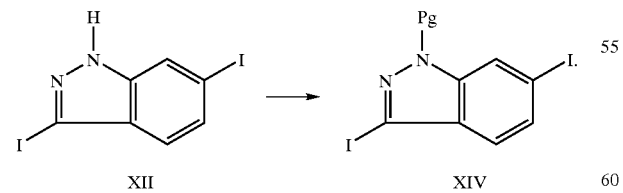

22. The method of claim 21, wherein the protecting group reagent is 1-(2-trimethylsilanyl-ethoxymethyl) chloride.

23. The method of claim 21, wherein the compound of formula XII is prepared from a compound of formula XI by an iodination reaction:

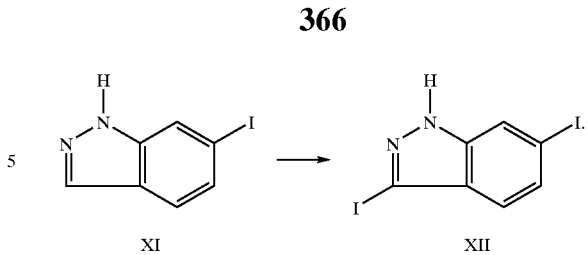

24. The method of claim 23, wherein the iodination reaction is carried out by treating the compound of formula XI with $I_2$ in the presence of a strong base.

25. A method to prepare a compound or a salt of formula I,

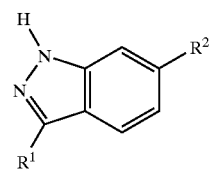

wherein $R^1$ is a substituted or unsubstituted aryl or heteroaryl, or a group of the formula $CH=CH—R^3$ or $CH=N—R^3$, where $R^3$ is a substituted or unsubstituted alkyl, cycloalkyl, heterocycloalkyl, aryl, or heteroaryl;

$R^2$ is Y—X, where Y is O, S, C=$CH_2$, C=O, S=O, $SO_2$, $CH_2$, $CHCH_3$, NH, or N-($C_1$-$C_8$ alkyl); X is

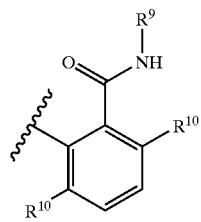

where $R^9$ is a substituted or unsubstituted alkyl, cycloalkyl, heterocycloalkyl, aryl, heteroaryl, alkoxyl, aryloxyl, cycloalkoxyl, NH-($C_1$-$C_8$ alkyl), NH-(aryl), NH-(heteroaryl), N=CH-(alkyl), NH(C=O)$R^{11}$, or $NH_2$, where $R^{11}$ is selected from hydrogen, substituted or unsubstituted alkyl, cycloalkyl, heterocycloalkyl, aryl, and heteroaryl; and $R^{10}$ is independently selected from hydrogen, halogen, and lower-alkyl;

the method comprising dehydrogenation of a compound of formula XVIII to form the compound of formula I:

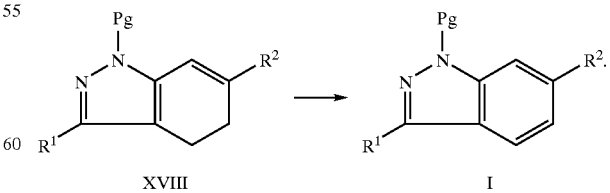

26. The method of claim 25, wherein the dehydrogenation reaction is carried out by treating the compound of formula XVIII with 2,3-dichloro-5,6-dicyano-1,4-benzoquinone (DDQ).

27. The method of claim 25, wherein the compound of formula XVIII is prepared by an annulation reaction of a 1,3-diketone compound of formula XVII:

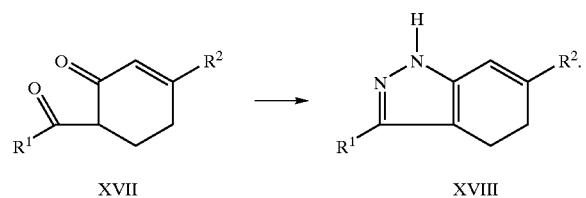

XVII          XVIII

28. The method of claim 27, wherein the annulation reaction is carried out in the presence of hydrazine.

29. The method of claim 27, wherein the compound of formula XVII is prepared from a compound of formula XVI by an acylation reaction:

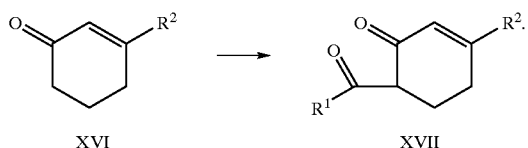

XVI          XVII

30. The method of claim 29, wherein the acylation reaction is carried out by treating a compound of formula XVI with a strong base and an acylation reagent LCO-$R^1$, where L is a leaving group.

31. The method of claim 29, wherein the compound of formula XVI is prepared from a compound of formula XV by a nucleophilic substitution reaction

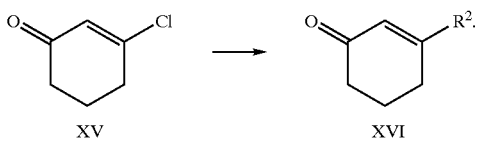

XV          XVI

32. The method of claim 31, wherein the nucleophilic substitution reaction is carried out by contacting the compound of formula XV with a strong base and a nucleophile $R^2$—H.

* * * * *